(12) United States Patent  (10) Patent No.: US 9,353,150 B2
Movassaghi et al.  (45) Date of Patent: May 31, 2016

(54) SUBSTITUTED PYRAZINO[1',2':1,5] PYRROLO[2,3-B]-INDOLE-1,4-DIONES FOR CANCER TREATMENT

(71) Applicants: Massachusetts Institute of Technology, Cambridge, MA (US); The Board of Trustees of the University of Illinois, Urbana, IL (US)

(72) Inventors: Mohammad Movassaghi, Arlington, MA (US); Justin Kim, Sunland, CA (US); Paul J. Hergenrother, Champaign, IL (US); Karen Morrison, West Sacramento, CA (US); Nicolas Boyer, Somerville, MA (US)

(73) Assignees: Massachusetts Institute of Technology, Cambridge, MA (US); The Board of Trustees of the University of Illinois, Urbana, IL (US)

( * ) Notice: Subject to any disclaimer, the term of this patent is extended or adjusted under 35 U.S.C. 154(b) by 57 days.

(21) Appl. No.: 14/096,158

(22) Filed: Dec. 4, 2013

(65) Prior Publication Data

US 2014/0187500 A1 Jul. 3, 2014

Related U.S. Application Data

(60) Provisional application No. 61/733,222, filed on Dec. 4, 2012, provisional application No. 61/823,714, filed on May 15, 2013, provisional application No. 61/868,173, filed on Aug. 21, 2013.

(51) Int. Cl.
| C07D 241/36 | (2006.01) |
| C07K 5/12 | (2006.01) |
| C07D 487/14 | (2006.01) |
| C07D 513/22 | (2006.01) |
| A61K 47/48 | (2006.01) |

(52) U.S. Cl.
CPC ............. *C07K 5/12* (2013.01); *A61K 47/48384* (2013.01); *C07D 487/14* (2013.01); *C07D 513/22* (2013.01)

(58) Field of Classification Search
CPC .................................................... C07D 241/36
USPC .................................. 544/343; 548/455, 518
See application file for complete search history.

(56) References Cited

U.S. PATENT DOCUMENTS 5,338,845 A 8/1994 Barrow et al.
6,147,076 A 11/2000 Danishefsky et al.

OTHER PUBLICATIONS

Li, et al. Journal of Natural Products, 75(5), 2012, 920-927.*
Cook et al., "Epidithiodiketopiperazines Block the Interaction between Hypoxia-inducible Factor-1α (HIF-1α) and p300 by a Zinc Ejection Mechanism," *J. Biol., Chem.*, 284(39):26831-26838 (2009).
Boyer, N. et al., Synthesis and Anticancer Activity of Epipolythiodiketopiperazine Alkaloids, Chem Sci., 4(4):1646-1657 (2013).
Coste, A. et al., Concise Total Synthesis of (+)-Bionectins A and C, Chem Sci., 4(8):3191-3197 (2013).
Kim, J. et al., Biogenetically inspired syntheses of alkaloid natural products, Chem Soc Rev., 38(11):3035-50 (2009).
Kim, J. et al., Concise total synthesis and stereochemical revision of (+)-naseseazines A and B: regioselective arylative dimerization of diketopiperazine alkaloids, J Am Chem Soc., 133(38):14940-3 (2011).
Kim, J. et al., General approach to epipolythiodiketopiperazine alkaloids: total synthesis of (+)-chaetocins A and C and (+)-12,12'-dideoxychetracin A, J Am Chem Soc., 132(41):14376-8 (2010).
Kim, J., et al., Total synthesis of (+)-11,11'-dideoxyverticillin A, Science, 324(5924):238-41 (2009).
Lathrop, S.P. et al., Radical-mediated dimerization and oxidation reactions for the synthesis of complex alkaloids, Chimia (Aarau), 66(6):389-93 (2012).
Dubey, R. et al., Direct organocatalytic coupling of carboxylated piperazine-2,5-diones with indoles through conjugate addition of carbon nucleophiles to indolenine intermediates, Tetrahedron Lett. 51(4):609-612 (2010).
PCT/ISA/206 for PCT/US2013/073062, 4 pages (Mar. 5, 2014).

* cited by examiner

*Primary Examiner* — Douglas M Willis
(74) *Attorney, Agent, or Firm* — McCarter & English, LLP; Elizabeth A. Hanley; Yu Lu

(57) ABSTRACT

The present application provides, among other things, a compound of Formula I-a and/or I-b,

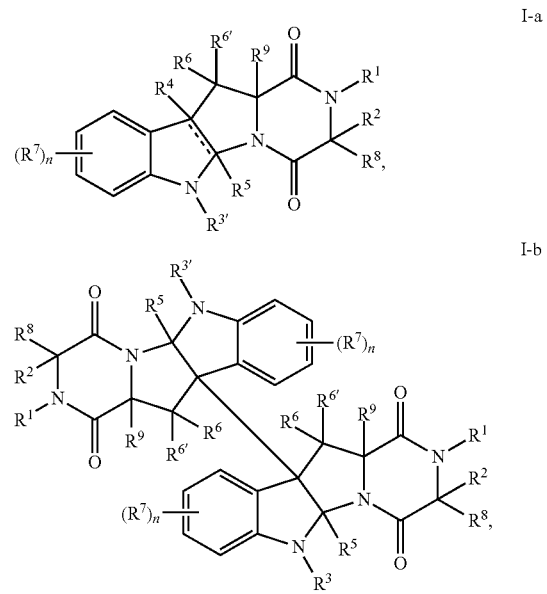

or a pharmaceutically acceptable salt thereof, wherein the variables are defined in the specification. The compounds of the invention are useful for treating various diseases including cancer.

11 Claims, 9 Drawing Sheets

SUBSTITUTED PYRAZINO[1',2':1,5] PYRROLO[2,3-B]-INDOLE-1,4-DIONES FOR CANCER TREATMENT

CROSS-REFERENCE TO RELATED APPLICATIONS

The present application claims priority to U.S. Provisional Application Ser. Nos. 61/733,222, filed Dec. 4, 2012, 61/823,714, filed May 15, 2013, and 61/868,173, filed Aug. 21, 2013, the entirety of each of which is incorporated herein by reference.

STATEMENT REGARDING FEDERALLY SPONSORED RESEARCH OR DEVELOPMENT

This invention was made with government support under Grant No. GM089732 awarded by the National Institutes of Health. The government has certain rights in the invention.

FIELD OF THE INVENTION

The present invention generally relates to, among other things, compounds, compositions and methods for treating diseases, for example, various cancers.

In accordance with 37 CFR 1.52(e)(5), a Sequence Listing in the form of a text file (entitled "Sequence Listing.txt," created on Feb. 26, 2014, and 1 kilobyte in size) is incorporated herein by reference in its entirety.

BACKGROUND

Epipolythiodiketopiperazine (ETP) alkaloids display a broad spectrum of biological activities ((a) T. W. Jordan and S. J. Cordiner, *Trends Pharmacol. Sci.*, 1987, 8, 144; (b) C.-S. Jiang and Y.-W. Guo, *Mini Rev. Med. Chem.*, 2011, 11, 728), including antibacterial (C.-J. Zheng, C.-J. Kim, K. S. Bae, Y.-H. Kim and W.-G. Kim, *J. Nat. Prod.*, 2006, 69, 1816), anticancer ((a) P. Waring and J. Beaver, *Gen. Pharmac.*, 1996, 27, 1311; (b) A. L. Kung, S. D. Zabludoff, D. S. France, S. J. Freedman, E. A. Tanner, A. Vieira, S. Cornell-Kennon, J. Lee, B. Wang, J. Wang, K. Memmert, H.-U. Naegeli, F. Petersen, M. J. Eck, K. W. Bair, A. W. Wood and D. M. Livingston, *Cancer Cell*, 2004, 6, 33; (c) D. M. Vigushin, N. Mirsaidi, G. Brooke, C. Sun, P. Pace, L. Inman, C. J. Moody and R. C. Coombes, *Med. Oncol.*, 2004, 21, 21; (d) D. Greiner, T. Bonaldi, R. Eskeland, E. Roemer and A. Imhof, *Nat. Chem. Biol.*, 2005, 1, 143; (e) M. Yanagihara, N. Sasaki-Takahashi, T. Sugahara, S. Yamamoto, M. Shinomi, I. Yamashita, M. Hayashida, B. Yamanoha, A. Numata, T. Yamori and T. Andoh, *Cancer Sci.*, 2005, 96, 816; (f) C. R. Isham, J. D. Tibodeau, W. Jin, R. Xu, M. M. Timm and K. C. Bible, *Blood*, 2007, 109, 2579; (g) Y. Chen, H. Guo, Z. Du, X.-Z. Liu, Y. Che and X. Ye, *Cell Prolif*, 2009, 42, 838; (h) Y.-M. Lee, J.-H. Lim, H. Yoon, Y.-S. Chun and J.-W. Park, *Hepatology*, 2011, 53, 171; (i) F. Liu, Q. Liu, D. Yang, W. B. Bollag, K. Robertson, P. Wu and K. Liu, *Cancer Res.*, 2011, 71, 6807; (j) K. Yano, M. Horinaka, T. Yoshida, T. Yasuda, H. Taniguchi, A. E. Goda, M. Wakada, S. Yoshikawa, T. Nakamura, A. Kawauchi, T. Miki and T. Sakai, *Int. J. Oncol.*, 2011, 38, 365; (k) N. Zhang, Y. Chen, R. Jiang, E. Li, X. Chen, Z. Xi, Y. Guo, X. Liu, Y. Zhou, Y. Che and X. Jiang, *Autophagy*, 2011, 7, 598; (l) H. Chaib, A. Nebbioso, T. Prebet, R. Castellano, S. Garbit, A. Restouin, N. Vey, L. Altucci and Y. Collette, *Leukemia*, 2012, 26, 662; (m) C. R. Isham, J. D. Tibodeau, A. R. Bossou, J. R. Merchan and K. C. Bible, *Br. J. Cancer*, 2012, 106, 314; (n) M. Takahashi, Y. Takemoto, T. Shimazu, H. Kawasaki, M. Tachibana, Y. Shinkai, M. Takagi, K. Shin-ya, Y. Igarashi, A. Ito and M. Yoshida, *J. Antiobiot.*, 2012, 65, 263; (o) C.-S. Jiang and Y.-W. Guo, *Mini Rev. Med. Chem.*, 2011, 11, 728), antiviral ((a) W. A. Rightsel, H. G. Schneider, B. J. Sloan, P. R. Graf, F. A. Miller, Q. R. Bartz, J. Ehrlich and G. J. Dixon, *Nature*, 1964, 204, 1333; P. A. Miller, K. P. Milstrey and P. W. Trown, *Science*, 1968, 159, 431), antiparasitic, antifungal ((a) J. J. Coleman, S. Ghosh, I. Okoli and E. Mylonakis, *PLoS ONE*, 2011, 6, e25321; (b) C. Speth, C. Kupfahl, K. Pfaller, M. Hagleitner, M. Deutinger, R. Würzner, I. Mohsenipour, C. Lass-Flörl and G. Rambach, *Mol. Immunol.*, 2011, 48, 2122), antimalarial, immunosuppressive, immunomodulatory ((a) A. Müllbacher, P. Waring, U. Tiwari-Palni and R. D. Eichner, *Molec. Immunol.*, 1986, 23, 231 (b) H. L. Pahl, B. Krauss, K. Schulze-Osthoff, T. Decker, E. B.-M. Traenckner, M. Vogt, C. Myers, T. Parks, P. Waring, A. Mühlbacher, A. P. Czernilofsky and P. A. Baeuerle, *J. Exp. Med.*, 1996, 183, 1829; (c) S, Nishida, L. S. Yoshida, T. Shimoyama, H. Nunoi, T. Kobayashi and S. Tsunawaki, *Infect. Immun.*, 2005, 73, 235; (d) P. Waring, R. D. Eichner and A. Müllbacher, *Med. Res. Rev.*, 1988, 8, 499; (e) P. Waring and J. Beaver, *Gen. Pharmac.*, 1996, 27, 1311), phytotoxic (M. Soledade, C. Pedras, G. Séguin-Swartz and S. R. Abrams, *Phytochem.*, 1990, 29, 777), nematicidal (J.-Y. Dong, H.-P. He, Y.-M. Shen and K.-Q. Zhang, *J. Nat. Prod.*, 2005, 68, 1510), antiplatelet (A. Bertling, S, Niemann, A. Uekötter, W. Fegeler, C. Lass-Flörl, C. von Eiffand B. E. Kehrel, *Thromb. Haemost.*, 2010, 104, 270), and anti-inflammatory effects (E. Iwasa, Y. Hamashima and M. Sodeoka, *Isr. J. Chem.*, 2011, 51, 420). Considerable synthetic efforts have been directed toward the synthesis of the ETP core and ETP-containing naturally occurring alkaloids; however, only a very limited number of compounds are accessible in very small amounts (P. Waring, R. D. Eichner and A. Müllbacher, *Med. Res. Rev.*, 1988, 8, 499; E. Iwasa, Y. Hamashima and M. Sodeoka, *Isr. J. Chem.*, 2011, 51, 420; for approaches to epipolythiodiketopiperazines, see: (a) P. W. Trown, *Biochem. Biophys. Res. Commun.*, 1968, 33, 402; (b) T. Hino and T. Sato, *Tetrahedron Lett.*, 1971, 12, 3127; (c) H. Poisel and U. Schmidt, *Chem. Ber.*, 1971, 104, 1714; (d) H. Poisel and U. Schmidt, *Chem. Ber.*, 1972, 105, 625; (e) E. Öhler, F. Tataruch and U. Schmidt, *Chem. Ber.*, 1973, 106, 396; (f) H. C. J. Ottenheijm, J. D. M. Herscheid, G. P. C. Kerkhoffand T. F. Spande, *J. Org. Chem.*, 1976, 41, 3433; (g) D. L. Coffen, D. A. Katonak, N. R. Nelson and F. D. Sancilio, *J. Org. Chem.*, 1977, 42, 948; (h) J. D. M. Herscheid, R. J. F. Nivard, M. W. Tijhuis, H. P. H. Scholten and H. C. J. Ottenheijm, *J. Org. Chem.*, 1980, 45, 1885; (i) R. M. Williams, R. W. Armstrong, L. K. Maruyama, J.-S. Dung and O. P. Anderson, *J. Am. Chem. Soc.*, 1985, 107, 3246; (j) C. J. Moody, A. M. Z. Slawin and D. Willows, *Org. Biomol. Chem.*, 2003, 1, 2716; (k) A. E. Aliev, S. T. Hilton, W. B. Motherwell and D. L. Selwood, *Tetrahedron Lett.*, 2006, 47, 2387; (l) L. E. Overman and T. Sato, *Org. Lett.*, 2007, 9, 5267; (m) N. W. Polaske, R. Dubey, G. S, Nichol and B. Olenyuk, *Tetrahedron: Asym.*, 2009, 20, 2742; (n) B. M. Ruff, S. Zhong, M. Nieger and S. Bräse, *Org. Biomol. Chem.*, 2012, 10, 935; (O) K. C. Nicolaou, D. Giguère, S. Totokotsopoulos and Y.-P. Sun, *Angew. Chem. Int. Ed.*, 2012, 51, 728; for selected epidithioketopiperazine total syntheses, see: (a) Y. Kishi, T. Fukuyama and S, Nakatsuka, *J. Am. Chem. Soc.*, 1973, 95, 6492; (b) Y. Kishi, S, Nakatsuka, T. Fukuyama and M. Havel, *J. Am. Chem. Soc.*, 1973, 95, 6493; (c) T. Fukuyama and Y. Kishi, *J. Am. Chem. Soc.*, 1976, 98, 6723; (d) R. M. Williams and W. H. Rastetter, *J. Org. Chem.*, 1980, 45, 2625; (e) G. F. Miknis and R. M. Williams, *J. Am. Chem. Soc.*, 1993, 115, 536; (f) E. Iwasa, Y. Hamashima, S. Fujishiro, E. Higuchi, A. Ito, M. Yoshida and M. Sodeoka, *J. Am. Chem. Soc.*, 2010, 132, 4078; (g) J. E. DeLorbe, S. Y. Jabri, S. M. Mennen, L. E. Overman and F.-L. Zhang, *J. Am. Chem. Soc.*, 2011, 133, 6549; (h) K. C. Nicolaou, S. Totokotsopoulos, D. Giguère, Y.-P. Sun and D. Sarlah, *J. Am. Chem. Soc.*, 2011, 133, 8150; (i) J. A. Codelli, A. L. A. Puchlopek and S. E. Reisman, *J. Am. Chem. Soc.*, 2012, 134, 1930; for our synthetic strategies relevant to epipolythiodiketopiperazines, see: (a) J. Kim, J. A. Ashenhurst and M. Movassaghi, *Science*, 2009, 324, 238; (b) J. Kim and M. Movassaghi, *J. Am. Chem. Soc.*, 2010, 132, 14376).

SUMMARY

Among other things, the present invention recognizes the need for biologically active compounds for treating various diseases. In some embodiments, the present invention provides a compound having the structure of formula I-a:

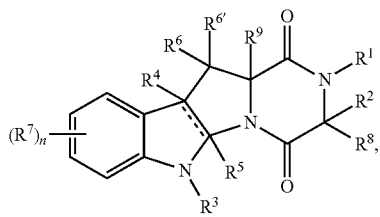

I-a or a pharmaceutically acceptable salt thereof, wherein the variables are described in detail, infra.

In some embodiments, the present invention provides a compound having the structure of formula I-b:

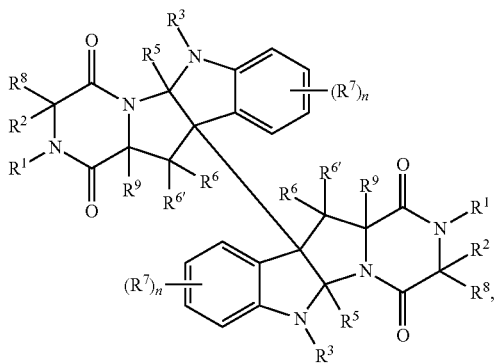

I-b or a pharmaceutically acceptable salt thereof, wherein the variables are described in detail, infra.

In some embodiments, the present invention provides drug-ligand conjugate compounds. In some embodiments, the present invention provides a compound having the structure of formula II:

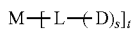

II or a pharmaceutically acceptable salt thereof, wherein the variables are described in detail, infra.

In some embodiments, the present invention provides a compound having the structure of formula II-a:

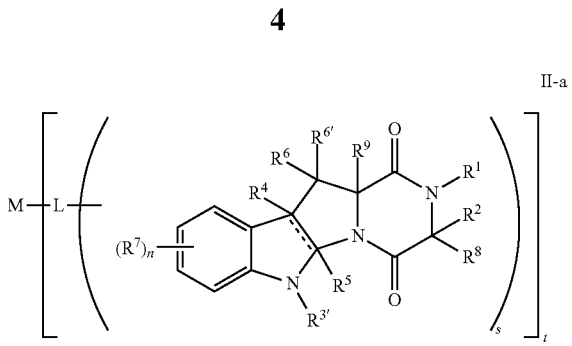

II-a or a pharmaceutically acceptable salt thereof, wherein the variables are described in detail, infra.

In some embodiments, the present invention provides a compound having the structure of formula II-b:

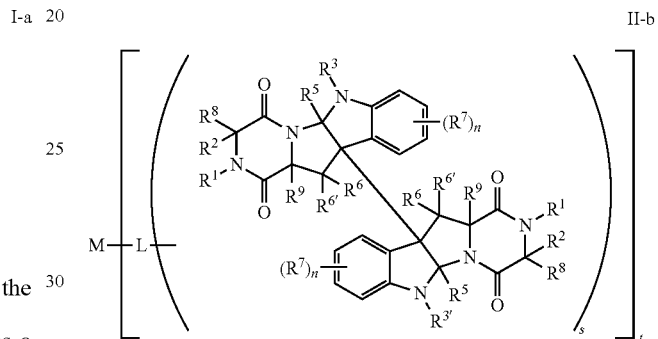

II-b or a pharmaceutically acceptable salt thereof, wherein the variables are described in detail, infra.

In some embodiments, the present invention provides a compound having the structure of formula III:

III or a pharmaceutically acceptable salt thereof, wherein the variables are described in detail, infra.

In some embodiments, the present invention recognizes the challenges for preparing ETP or thiodiketopiperazine alkaloids, or derivatives or analogs thereof. In some embodiments, the present invention provides a method for preparing ETP or thiodiketopiperazine alkaloids or a derivative thereof. In some embodiments, the present invention provides a method for preparing a provide compound. In some embodiments, the present invention provides new reagents for preparing ETP or thiodiketopiperazine alkaloids or derivatives or analogs thereof. In some embodiments, the present invention provides new reagents for preparing a provided compound. In some embodiments, a provided method and/or reagent provides unexpectedly high synthetic efficiency, for example, in terms of product yield and/or purity.

In some embodiments, the present invention provides a method for killing or inhibiting proliferation of cells comprising treating the cells with an amount of a provided compound, or a pharmaceutically acceptable salt thereof, being effective to kill or inhibit proliferation of the cells. In some embodiments, the cells are tumor cells or cancer cells. In some embodiments, the present invention provides a method of treating a disease, comprising administering to a subject in need an effective amount of a provided compound or a pharmaceutically acceptable salt thereof. In some embodiments, the present invention provides a method of treating a disease, comprising administering to a subject suffering therefrom or susceptible thereto an effective amount of a provided compound or pharmaceutically salt thereof. In some embodiments, a disease is a cancer, autoimmune disease or infectious disease. In some embodiments, a disease is cancer. In some embodiments, a disease is an autoimmune disease. In some embodiments, a disease is an infectious disease. In some embodiments, a provided compound is a compound of formula I-a. In some embodiments, a provided compound is a compound of formula I-b. In some embodiments, a provided compound is a compound of formula II. In some embodiments, a provided compound is a compound of formula III.

In some embodiments, the present invention provides methods of treating cancer. In some embodiments, the present invention provides a method of treating cancer in a subject suffering therefrom, comprising administering to the subject a therapeutically effective amount of a provided compound or pharmaceutically acceptable salt thereof. In some embodiments, a provided compound has the structure of formula I-a. In some embodiments, a provided compound has the structure of formula I-b. In some embodiments, a provided compound has the structure of formula II. In some embodiments, a provided compound has the structure of formula II-a. In some embodiments, a provided compound has the structure of formula II-b. In some embodiments, a provided compound has the structure of formula III.

DETAILED DESCRIPTION OF CERTAIN EMBODIMENTS

Figure 1:
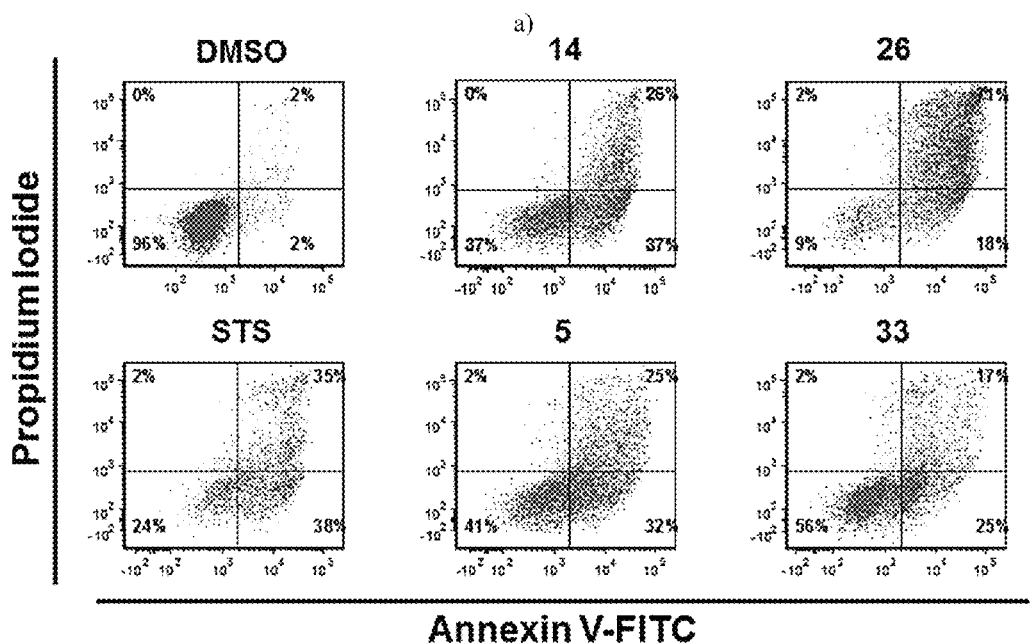
FIG. 1. ETP derivatives induce caspase-dependent apoptotic cell death, a) Analysis of phosphatidylserine exposure and propidium iodide inclusion at 24 hours in U-937 cells. Compounds were tested at 100-times their 72-hour $IC_{50}$ values [14 (20 nM), 5 (75 nM), 26 (250 nM), and 33 (500 nM)]. STS was used at 50 nM as a positive control for apoptosis. b) Western blot analysis of Pro-C3 and PARP-1 cleavage at 24 hours in U-937 cells using β-actin as loading control. Compounds were tested as above, with the exception of STS (100 nM); C3=caspase-3; ETP=epipolythiodiketopiperazine; FITC=fluorescein isothiocyanate; $IC_{50}$=half maximal inhibitory concentration; PARP=poly(ADP-ribose) polymerase 1; Pro-C3=procaspase-3; STS=staurosporine.
Figure 1:
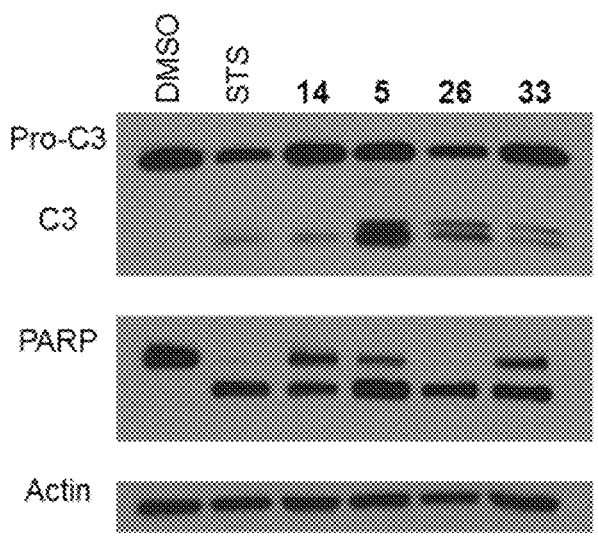

1. General Description of Certain Embodiments of the Invention

Among other things, the present invention recognizes the need for biologically active compounds for treating various diseases. In some embodiments, the present invention provides a compound having the structure of formula I-a:

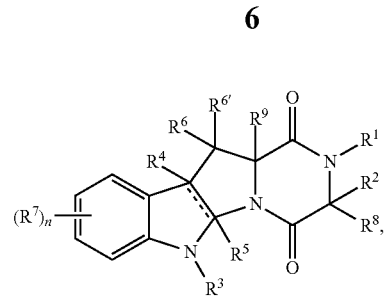

I-a or a pharmaceutically acceptable salt thereof, wherein:
⎓ is a single bond or a double bond, as valency permits;
$R^1$ is R, —C(O)R, —C(O)N(R)$_2$, —S(O)R, —S(O)$_2$R, —S(O)$_2$OR, —C(R)$_2$OR, or —S(O)$_2$N(R)$_2$;
each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:
two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur,
$R^2$ is R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or
$R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur,
each q is independently 0, 1, 2, 3, or 4;
$R^3$ is an electron-withdrawing group;
$R^4$ is absent when ⎓ is a double bond or is R or halogen;
$R^5$ is absent when ⎓ is a double bond or is hydrogen or an optionally substituted $C_{1-6}$ aliphatic group;
each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or
$R^6$ and $R^{6'}$ are taken together to form =O, =C(R)$_2$ or =NR;
n is 0, 1, 2, 3, or 4;
each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or:

two R⁷ are taken together with their intervening atoms to form an optionally substituted 4-7 membered ring having 0-2 heteroatoms independently selected from nitrogen, oxygen, or sulfur;

R⁸ is —(S)$_m$—R$^x$ wherein m is 1-3 and R$^x$ is R, —SR, —C(O)R, —C(O)OR, —C(O)N(R)$_2$, —C(S)R, —S(O)R, —S(O)$_2$R, or —S(O)$_2$N(R)$_2$; and R⁹ is —(S)$_p$—R$^y$ wherein p is 1-3 such that m+p is 2-4 and R$^y$ is R, —SR, —C(O)R, —C(O)OR, —C(O)N(R)$_2$, —C(S)R, —S(O)R, —S(O)$_2$R, or —S(O)$_2$N(R)$_2$; or R⁸ and R⁹ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

In some embodiments, the present invention provides a compound having the structure of formula I-b:

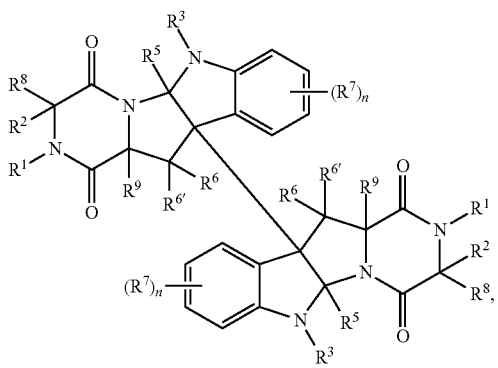

I-b or a pharmaceutically acceptable salt thereof, wherein:

each R¹ is independently R, —C(O)R, —C(O)N(R)$_2$, —S(O)R, —S(O)$_2$R, —S(O)$_2$OR, —C(R)$_2$OR, or —S(O)$_2$N(R)$_2$;

each R is independently hydrogen or an optionally substituted group selected from C$_{1-20}$ aliphatic, C$_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:

two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur, each R² is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or R¹ and R² are taken together with their intervening atoms to form an optionally substituted 4-7 membered heterocyclic ring having, in addition to the nitrogen atom to which R¹ is attached, 0-2 heteroatoms independently selected from oxygen, nitrogen or sulfur;

each q is independently 0, 1, 2, 3, or 4;

each R³ is independently an electron-withdrawing group;

each R⁵ is independently hydrogen or an optionally substituted C$_{1-6}$ aliphatic group;

each of R⁶ and R⁶' is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or R⁶ and R⁶' are taken together to form =O, =C(R)$_2$ or =NR;

each n is independently 0, 1, 2, 3, or 4;

each R⁷ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or two R⁷ are taken together with their intervening atoms to form an optionally substituted 4-7 membered ring having 0-2 heteroatoms independently selected from nitrogen, oxygen, or sulfur;

each R⁸ is independently —(S)$_m$—R$^x$ wherein m is 1-3 and R$^x$ is R, —SR, —C(O)R, —C(O)OR, —C(O)N(R)$_2$, —C(S)R, —S(O)R, —S(O)$_2$R, or —S(O)$_2$N(R)$_2$; and each R⁹ is independently —(S)$_p$—R$^y$ wherein p is 1-3 such that m+p is 2-4 and R$^y$ is R, —SR, —C(O)R, —C(O)OR, —C(O)N(R)$_2$, —C(S)R, —S(O)R, —S(O)$_2$R, or —S(O)$_2$N(R)$_2$; or R⁸ and R⁹ are taken together to form —S—, —(S)$_m$—[C(R)$_2$]$_q$—(S)$_p$—, —(S)$_m$—(S)$_p$—, (S)$_m$—C(O)—(S)$_p$—, —(S)$_m$—C(S)—(S)$_p$—, —(S)—S(O)—(S)$_p$—, or —(S)$_m$—S(O)$_2$—(S)$_p$—.

In some embodiments, the present invention provides drug-ligand conjugate compounds. In some embodiments, the present invention provides a compound having the structure of formula II:

II or a pharmaceutically acceptable salt thereof, wherein:

M is a cell-specific ligand unit;

each L is independently a linker unit;

each D independently has the structure of formula I-c or I-d,

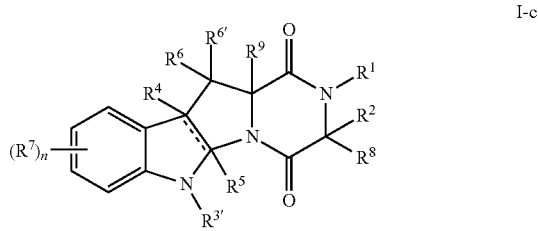

I-c

-continued

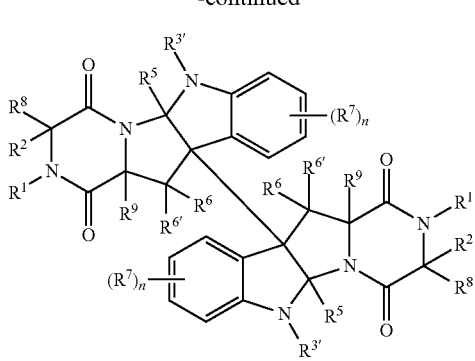

I-d or a pharmaceutically acceptable salt thereof, wherein:
each ⸺ is independently a single bond or a double bond, as valency permits;
each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;
each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:
two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur,
each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or
$R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur;
each q is independently 0, 1, 2, 3, or 4;
each $R^{3'}$ is independently R or an electron-withdrawing group;
each $R^4$ is independently absent when ⸺ is a double bond or is independently R or halogen;
each $R^5$ is independently absent when ⸺ is a double bond or is independently hydrogen or an optionally substituted C is aliphatic group;
each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form =O, =C(R)$_2$ or =NR;
each n is independently 0, 1, 2, 3, or 4;
each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or:
two $R^7$ are taken together with their intervening atoms to form an optionally substituted 4-7 membered ring having 0-2 heteroatoms independently selected from nitrogen, oxygen, or sulfur;
each $R^8$ is independently —(S)$_m$—$R^x$ wherein m is 1-3 and $R^x$ is R, —SR, —C(O)R, —C(O)OR, —C(O)N(R)$_2$, —C(S)R, —S(O)R, —S(O)$_2$R, or —S(O)$_2$N(R)$_2$; and
each $R^9$ is independently —(S)$_p$—$R^y$ wherein p is 1-3 such that m+p is 2-4 and $R^y$ is R, —SR, —C(O)R, —C(O)OR, —C(O)N(R)$_2$, —C(S)R, —S(O)R, —S(O)$_2$R, or —S(O)$_2$N(R)$_2$; or
$R^8$ and $R^9$ are taken together to form —S—, —(S)$_m$—[C(R)$_2$]$_q$—(S)$_p$—, —(S)$_m$—(S)$_p$, —(S)$_m$—C(O)—(S)$_p$—, —(S)$_p$—, —(S)$_m$—C(S)—(S)$_p$—, —(S)$_m$—S(O)—(S)$_p$—, or —(S)$_m$—S(O)$_2$—(S)$_p$—;
s is 1-10; and
t is 1-10.

In some embodiments, the present invention provides a compound having the structure of formula II-a:

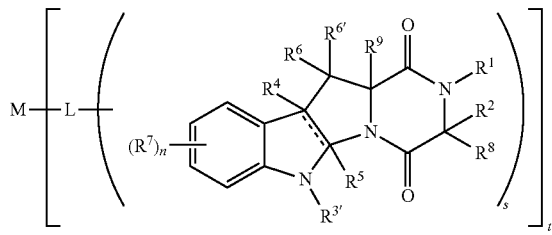

II-a or a pharmaceutically acceptable salt thereof, wherein each variable is independently as defined above and described herein.

In some embodiments, the present invention provides a compound having the structure of formula II-b:

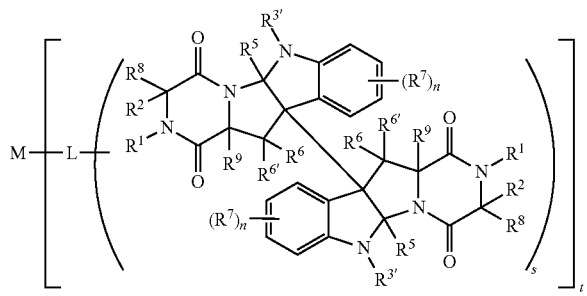

II-b or a pharmaceutically acceptable salt thereof, wherein each variable is independently as defined above and described herein.

In some embodiments, the present invention provides a compound having the structure of formula III:

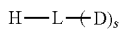

or a pharmaceutically acceptable salt thereof, wherein each variable is independently as defined above and described herein.

In some embodiments, the present invention provides a compound having the structure of formula III-a:

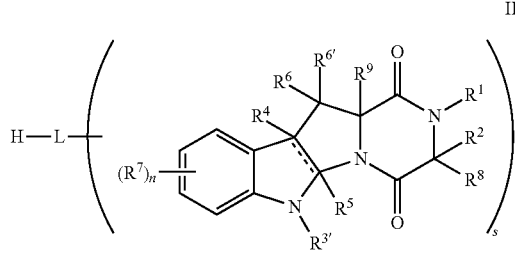

or a pharmaceutically acceptable salt thereof, wherein each variable is independently as defined above and described herein.

In some embodiments, the present invention provides a compound having the structure of formula III-b:

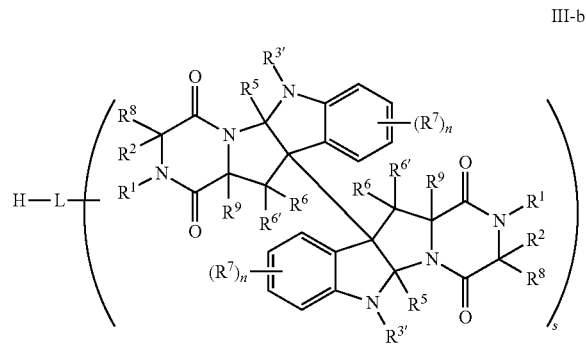

or a pharmaceutically acceptable salt thereof, wherein each variable is independently as defined above and described herein.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 93$^{rd}$ Ed. Additionally, general principles of organic chemistry are described in "Organic Chemistry", 2$^{nd}$ Ed, Thomas N. Sorrell, University Science Books, Sausalito: 2005, and "March's Advanced Organic Chemistry", 6$^{th}$ Ed., Smith, M. B. and March, J., John Wiley & Sons, New York: 2007, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation, but which is not aromatic (also referred to herein as "carbocycle," "cycloaliphatic" or "cycloalkyl"), that has, unless otherwise specified, a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic, bicyclic or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which at least one carbon atom, optionally with one or more attached hydrogen atoms, is replaced with a heteroatom (e.g., oxygen, nitrogen, sulfur, phosphorus, selenium, boron and the like). Examples of heteroalkyl groups include, but are not limited to, alkoxy, poly(ethylene glycol)-, alkyl-substituted amino, tetrahydrofuranyl, piperidinyl, morpholinyl, etc. In some embodiments, a heteroatom may be oxidized (e.g., —S(O)—, —S(O)$_2$—, —N(O)—, —P(O)— and the like).

The term "aryl" used alone or as part of a larger moiety as in "aralkyl," "aralkoxy," or "aryloxyalkyl," refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of boron, oxygen, sulfur, selenium, nitrogen, phosphorus, or silicon (including, any oxidized form of nitrogen, sulfur, selenium, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogen atoms of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —(CH$_2$)$_{0-4}$SR°; —(CH$_2$)$_{0-4}$S(O)R°; —O(CH$_2$)$_{0-4}$R°, —O—(CH$_2$)$_{0-4}$—C(O)OR°; —(CH$_2$)$_{0-4}$—CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°;

—$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —$SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$P(O)(OR°)R°$; —$P(O)(OR°)_2$; —$OP(O)R°_2$; —$OP(O)(OR°)R°$; —$OP(O)(OR°)_2$; —$PR°_2$; —$P(OR°)R°$; —$P(OR°)_2$; —$OPR°_2$; —$OP(OR°)R°$; —$OP(OR°)_2$; —$SiR°_3$; —$OSiR°_3$; —$SeR°$; —$(CH_2)_{0-4}SeSeR°$; —$B(R°)_2$; —$B(OR°)_2$; —$(C_{1-4}$ straight or branched alkylene)O—$N(R°)_2$; or —$(C_{1-4}$ straight or branched alkylene)C(O)O—$N(R°)_2$; wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —$O(haloR^•)$, —$CN$, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —$SSR^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a suitable carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^•$, -(haloR$^•$), —$OH$, —$OR^•$, —$O(haloR^•)$, —$CN$, —$C(O)OH$, —$C(O)OR^•$, —$NH_2$, —$NHR^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —$R^•$, -(haloR$^•$), —$OH$, —$OR^•$, —$O(haloR^•)$, —$CN$, —$C(O)OH$, —$C(O)OR^•$, —$NH_2$, —$NHR^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "chiral" is given its ordinary meaning in the art and refers to a molecule that is not superimposable with its mirror image, wherein the resulting non-superimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, the term "electron-withdrawing group" is given its ordinary meaning in the art and refers to an atom or group that draws electron density from a neighboring atom or group, usually by resonance and/or inductive effects. In some embodiments, an electron-withdrawing group withdraws electron density from an aromatic ring system by resonance and/or inductive effects. In some embodiments, an electron-withdrawing group withdraws electron density from an aromatic ring system by resonance and inductive effects. In some embodiments, an electron-withdrawing group lowers the electron density of an aromatic ring system such as phenyl. Exemplary electron-withdrawing groups are extensively described in the art, including but not limited to halogen, carbonyl moieties (e.g., aldehyde and ketone groups), —COOH and its derivatives (e.g., ester and amide moieties), protonated amines, quaternary ammonium groups, —CN, —$NO_2$, —S(O)— moieties, —P(O)— moieties and —S(O)$_2$-moieties. In some embodiments, an electron-withdrawing group comprises one or more —C(O)—, —C(=N—)—, —C(S)—, —S(O)—, —S(O)$_2$— or —P(O)— groups, and is connected to the rest of a molecule via one or more —C(O)—, —C(=N—)—, —C(S)—, —S(O)—, —S(O)$_2$— or —P(O)— groups. In some embodiments, an electron-withdrawing group is halogen. In some embodiments, an electron-withdrawing group is —F. In some embodiments, an electron-withdrawing group is —Cl. In some embodiments, an electron-withdrawing group is —Br. In some embodiments, an electron-withdrawing group is —I. In some embodiments, hydrogen is used as reference and regarded as having no effect.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable monoprotected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxycarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this invention. Such compounds are useful, for example, as analytical tools or probes in biological assays.

As used herein and in the claims, the singular forms "a", "an", and "the" include the plural reference unless the context clearly indicates otherwise. Thus, for example, a reference to "a compound" includes a plurality of such compounds.

As used herein, the term "in vitro" refers to events that occur in an artificial environment, e.g., in a test tube or reaction vessel, in cell culture, etc., rather than within an organism (e.g., animal, plant, and/or microbe).

As used herein, the term "in vivo" refers to events that occur within an organism (e.g., animal, plant, and/or microbe).

The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar, buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

A general, a "prodrug," as that term is used herein and as is understood in the art, is an entity that, when administered to an organism, is metabolized in the body to deliver an active (e.g., therapeutic or diagnostic) agent of interest. Typically, such metabolism involves removal of at least one "prodrug moiety" so that the active agent is formed. Various forms of "prodrugs" are known in the art. For examples of such prodrug moieties, see:

a) *Design of Prodrugs*, edited by H. Bundgaard, (Elsevier, 1985) and *Methods in Enzymology*, 42:309-396, edited by K. Widder, et al. (Academic Press, 1985);

b) *Prodrugs and Targeted Delivery*, edited by J. Rautio (Wiley, 2011);

c) *Prodrugs and Targeted Delivery*, edited by J. Rautio (Wiley, 2011);

d) A Textbook of Drug Design and Development, edited by Krogsgaard-Larsen;

e) Bundgaard, Chapter 5 "Design and Application of Prodrugs", by H. Bundgaard, p. 113-191 (1991);

f) Bundgaard, *Advanced Drug Delivery Reviews*, 8:1-38 (1992);

g) Bundgaard, et al., *Journal of Pharmaceutical Sciences*, 77:285 (1988); and h) Kakeya, et al., *Chem. Pharm. Bull.*, 32:692 (1984).

As with other compounds described herein, prodrugs may be provided in any of a variety of forms, e.g., crystal forms, salt forms etc. In some embodiments, prodrugs are provided as pharmaceutically acceptable salts thereof.

As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain l-amino acids, d-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, and/or susceptible to a disease, disorder, and/or condition. In some embodiments, a subject is human.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

An individual who is "suffering from" a disease, disorder, and/or condition has been diagnosed with and/or displays one or more symptoms of a disease, disorder, and/or condition An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The phrases "systemic administration," "administered systemically," "peripheral administration," and "administered peripherally" as used herein have their art-understood meaning referring to administration of a compound or composition such that it enters the recipient's system.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. The relevant intended purpose may be objective (i.e., measurable by some test or marker) or subjective (i.e., subject gives an indication of or feels an effect). In some embodiments, a therapeutically effective amount is an amount that, when administered to a population of subjects that meet certain clinical criteria for a disease or disorder (for example, as determined by symptoms manifested, disease progression/stage, genetic profile, etc.), a statistically significant therapeutic response is obtained among the population. A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts. Those of ordinary skill in the art will appreciate that in some embodiments of the invention, a unit dosage may be considered to contain an effective amount if it contains an amount appropriate for administration in the context of a dosage regimen correlated with a positive outcome.

3. Description of Certain Embodiments of the Invention

In some embodiments, the present invention provides a compound having the structure of formula I-a:

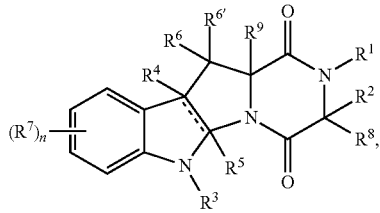

or a pharmaceutically acceptable salt thereof, wherein each variable is independently as described in classes and subclasses herein, both singly and in combination.

In some embodiments, the present invention provides a compound having the structure of formula I-b:

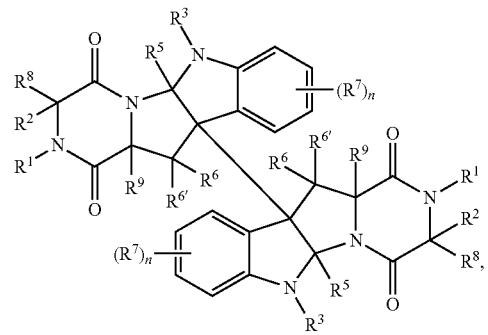

or a pharmaceutically acceptable salt thereof, wherein each variable is independently as described in classes and subclasses herein, both singly and in combination.

In some embodiments, the present invention provides drug-ligand conjugate compounds. In some embodiments, the present invention provides a compound having the structure of formula II:

$$M\mathrm{-\!\!\!-\!\!\!-}[L\mathrm{-\!\!\!-\!\!\!-}(D)_s]_t \qquad \text{II}$$

or a pharmaceutically acceptable salt thereof, wherein:
M is a cell-specific ligand unit;
each L is independently a linker unit;
each D independently has the structure of formula I-c or I-d,

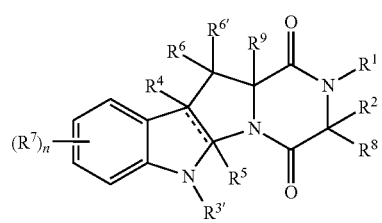

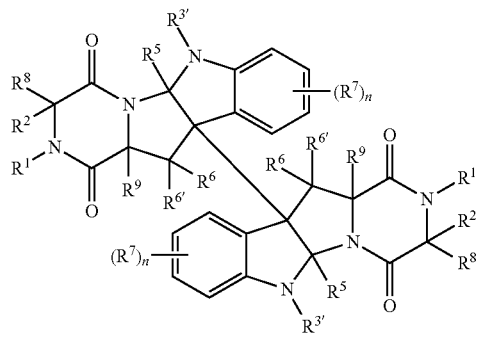

or a pharmaceutically acceptable salt thereof, wherein:
each 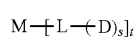 is independently a single bond or a double bond, as valency permits;
each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;
each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:

two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur, each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$; or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur;

each q is independently 0, 1, 2, 3, or 4;
each $R^{3'}$ is independently R or an electron-withdrawing group;
each $R^4$ is independently absent when ═ is a double bond or is independently R or halogen;
each $R^5$ is independently absent when ═ is a double bond or is independently hydrogen or an optionally substituted $C_{1-6}$ aliphatic group;
each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or
$R^6$ and $R^{6'}$ are taken together to form ═O, ═C(R)$_2$ or ═NR;
each n is independently 0, 1, 2, 3, or 4;
each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or
two $R^7$ are taken together with their intervening atoms to form an optionally substituted 4-7 membered ring having 0-2 heteroatoms independently selected from nitrogen, oxygen, or sulfur;
each $R^8$ is independently —(S)$_m$—$R^x$ wherein m is 1-3 and $R^x$ is R, —SR, —C(O)R, —C(O)OR, —C(O)N(R)$_2$, —C(S)R, —S(O)R, —S(O)$_2$R, or —S(O)$_2$N(R)$_2$; and
each $R^9$ is independently —(S)$_p$—$R^y$ wherein p is 1-3 such that m+p is 2-4 and $R^y$ is R, —SR, —C(O)R, —C(O)OR, —C(O)N(R)$_2$, —C(S)R, —S(O)R, —S(O)$_2$R, or —S(O)$_2$N(R)$_2$; or
$R^8$ and $R^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—;

s is 1-10; and
t is 1-10.

In some embodiments, the present invention provides a compound having the structure of formula II-a:

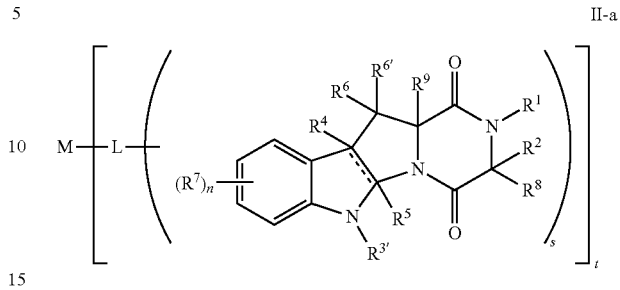

II-a or a pharmaceutically acceptable salt thereof, wherein each variable is independently as described in classes and subclasses herein, both singly and in combination.

In some embodiments, the present invention provides a compound having the structure of formula II-b:

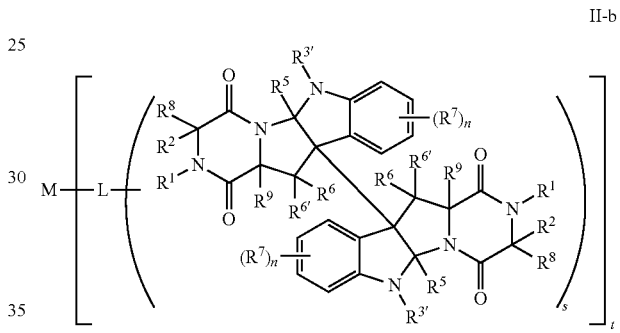

II-b or a pharmaceutically acceptable salt thereof, wherein each variable is independently as described in classes and subclasses herein, both singly and in combination.

In some embodiments, the present invention provides a compound having the structure of formula III:

III or a pharmaceutically acceptable salt thereof, wherein each variable is independently as described in classes and subclasses herein, both singly and in combination.

In some embodiments, the present invention provides a compound having the structure of formula III-a:

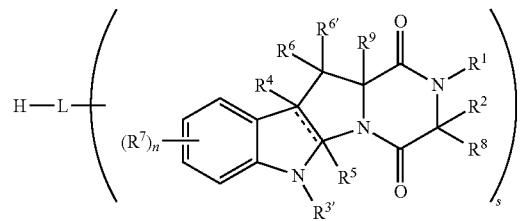

or a pharmaceutically acceptable salt thereof, wherein each variable is independently as described in classes and subclasses herein, both singly and in combination.

In some embodiments, the present invention provides a compound having the structure of formula III-b:

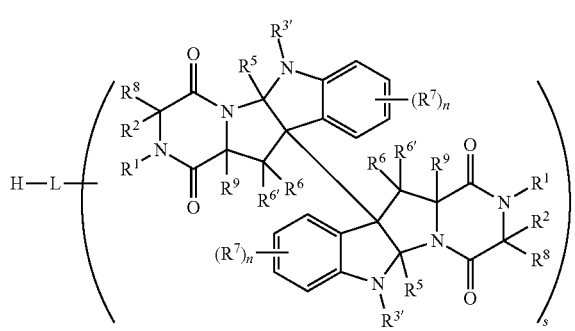

or a pharmaceutically acceptable salt thereof, wherein each variable is independently as described in classes and subclasses herein, both singly and in combination.

As generally defined above, ⸺ is a single bond or a double bond, as valency permits. In some embodiments, ⸺ is a single bond. In some embodiments, ⸺ is a double bond. In some embodiments, there are two or more ⸺ in a provided compound, and at least one ⸺ is a single bond, and at least one ⸺ is a double bond. In some other embodiments, there are two or more ⸺ in a provided compound, and each ⸺ is a single bond. In some other embodiments, there are two or more ⸺ in a provided compound, and each ⸺ is a double bond.

In some embodiments, ⸺ is a single bond, $R^4$ is R or halogen, and $R^5$ is hydrogen or an optionally substituted $C_{1-6}$ aliphatic. In some embodiments, ⸺ is a double bond, $R^4$ is absent and $R^5$ is absent.

As generally defined above, each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur. In some embodiments, each $R^1$ is independently R, —C(O)R, —C(O)N(R)$_2$, —S(O)R, —S(O)$_2$R, —S(O)$_2$OR, —CH$_2$OR, or —S(O)$_2$N(R)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur. In some embodiments, each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur. In some embodiments, $R^1$ is R, —C(O)R, —C(O)N(R)$_2$, —S(O)R, —S(O)$_2$R, —S(O)$_2$OR, or —S(O)$_2$N(R)$_2$. In some embodiments, $R^1$ is R. In some embodiments, $R^1$ is —C(O)R. In some embodiments, $R^1$ is —C(O)N(R)$_2$. In some embodiments, $R^1$ is —S(O)R. In some embodiments, $R^1$ is —S(O)$_2$R$^1$. In some embodiments, $R^1$ is —S(O)$_2$OR. In some embodiments, $R^1$ is —C(R)$_2$OR. In some embodiments, $R^1$ is —CH$_2$OR. In some embodiments, $R^1$ is —S(O)$_2$N(R)$_2$. In some embodiments, a provided compound has more than one $R^1$ groups. In some embodiments, each $R^1$ of a provided compound is the same. In some embodiments, at least one $R^1$ is different from the other $R^1$.

In some embodiments, $R^1$ is R. In some embodiments, $R^1$ is hydrogen. In some embodiments, $R^1$ is optionally substituted $C_{1-20}$ aliphatic. In some embodiments, $R^1$ is optionally substituted $C_{1-10}$ aliphatic. In some embodiments, $R^1$ is optionally substituted $C_{1-6}$ aliphatic. In some embodiments, $R^1$ is optionally substituted $C_{1-6}$ alkyl. In some embodiments, $R^1$ is optionally substituted hexyl, pentyl, butyl, propyl, ethyl or methyl. In some embodiments, $R^1$ is optionally substituted hexyl. In some embodiments, $R^1$ is optionally substituted pentyl. In some embodiments, $R^1$ is optionally substituted butyl. In some embodiments, $R^1$ is optionally substituted propyl. In some embodiments, $R^1$ is optionally substituted ethyl. In some embodiments, $R^1$ is optionally substituted methyl. In some embodiments, $R^1$ is hexyl. In some embodiments, $R^1$ is pentyl. In some embodiments, $R^1$ is butyl. In some embodiments, $R^1$ is propyl. In some embodiments, $R^1$ is ethyl. In some embodiments, $R^1$ is methyl. In some embodiments, $R^1$ is isopropyl. In some embodiments, $R^1$ is n-propyl. In some embodiments, $R^1$ is tert-butyl. In some embodiments, $R^1$ is sec-butyl. In some embodiments, $R^1$ is n-butyl. In some embodiments, $R^1$ is benzyloxymethyl. In some embodiments, $R^1$ is benzyl. In some embodiments, $R^1$ is allyl.

In some embodiments, $R^1$ is methyl, $R^3$ is other than hydrogen, Boc (tert-butyloxycarbonyl) and CF$_3$C(O)—. In some embodiments, $R^1$ is methyl, $R^3$ is other than hydrogen and CF$_3$C(O)—. In some embodiments, $R^1$ is methyl, $R^3$ is other than hydrogen. In some embodiments, $R^1$ is methyl, $R^3$ is other than hydrogen, Boc (tert-butyloxycarbonyl) and CF$_3$C(O)—. In some embodiments, $R^1$ is other than methyl.

Exemplary $R^1$ groups are depicted below.

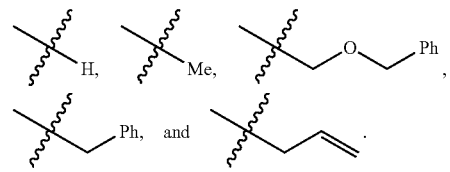

In some embodiments, in a provided compound of formula II, D is connected to L through $R^1$. In some embodiments, $R^1$ comprises an —OH, —NHR or —SH group for conjugation. In some embodiments, $R^1$ comprises an —OH group, and D is connected to L through the —OH group. In some embodiments, the —OH group reacts with a functional group in L or M to form, for example, an ether, ester, carbamate or carbonate ester. In some embodiments, $R^1$ comprises an amino group, and D is connected to L through the amino group. In some embodiments, $R^1$ comprises a —NH$_2$ group. In some embodiments, $R^1$ comprises a —NHR group. In some embodiments, the amino group reacts with a functional group in L or M to form, for example, an amine, imine, amide or carbamate. In some embodiments, $R^1$ comprises an —SH group, and D is connected to L through the —SH group. In some embodiments, the —SH group reacts with a functional group in L or M to form, for example, a disulfide, thioether or thioester.

As generally defined above, each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur, or two R⁷ are taken together with their intervening atoms to form an optionally substituted 4-7 membered ring having 0-2 heteroatoms independently selected from nitrogen, oxygen, or sulfur. In some embodiments, each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, or two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur.

In some embodiments, each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur. In some embodiments, R is hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur.

In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is benzyloxymethyl. In some embodiments, R is benzyl. In some embodiments, R is allyl. In some embodiments, R is not hydrogen. In some embodiments, R is not alkyl.

In some embodiments, R is optionally substituted $C_{1-20}$ heteroalkyl. In some embodiments, R is optionally substituted $C_{1-20}$ heteroalkyl having 1-6 heteroatoms independently selected from nitrogen, sulfur, phosphorus selenium, silicon or boron. In some embodiments, R is optionally substituted $C_{1-20}$ heteroalkyl having 1-6 heteroatoms independently selected from nitrogen, sulfur, phosphorus, selenium, silicon or boron, optionally including one or more oxidized forms of nitrogen, sulfur, phosphorus, selenium, silicon or boron. In some embodiments, R is optionally substituted $C_{1-20}$ heteroalkyl comprising 1-6 groups independently selected from

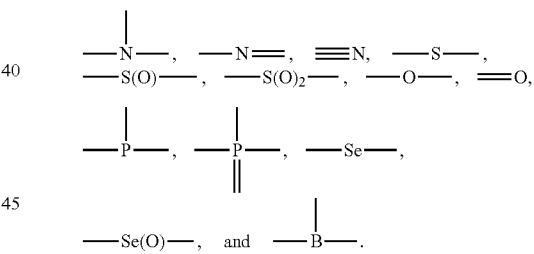

In some embodiments, R is not heteroalkyl. In some embodiments, R is methoxymethyl. In some embodiments, R is benzyloxymethyl.

In some embodiments, R is optionally substituted phenyl. In some embodiments, R is optionally substituted phenyl wherein one or more substituents are halogen. In some embodiments, R is optionally substituted phenyl wherein one or more substituents are —F. In some embodiments, R is optionally substituted phenyl wherein one or more substituents are —Cl. In some embodiments, R is optionally substituted phenyl wherein one or more substituents are —Br. In some embodiments, R is optionally substituted phenyl wherein one or more substituents are —I. In some embodiments, R is phenyl.

In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 8-14 membered bicyclic or polycyclic saturated, partially unsaturated or aryl ring. In some embodiments, R is an optionally substituted 8-14 membered bicyclic or polycyclic saturated ring. In some embodiments, R is an optionally substituted 8-14 membered bicyclic or polycyclic partially saturated ring. In some embodiments, R is an optionally substituted 8-14 membered bicyclic or polycyclic aryl ring. In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl. In some embodiments, R is optionally substituted anthracenyl. In some embodiments, R is optionally substituted 9-anthracenyl.

In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is optionally substituted phenyl. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is an optionally substituted 5-6 membered monocyclic heteroaryl ring having 1-4 heteroatoms independently selected from nitrogen, oxygen, or sulfur. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is an optionally substituted 8-10 membered bicyclic aryl ring. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is optionally substituted naphthyl. In some embodiments, R is optionally substituted biaryl wherein each aryl group is independently an optionally substituted group selected from phenyl, 5-6 membered monocyclic heteroaryl ring having 1-4 heteroatoms independently selected from nitrogen, oxygen, or sulfur, an 8-10 membered bicyclic aryl ring, or an 8-10 membered bicyclic heteroaryl ring having 1-5 heteroatoms independently selected from nitrogen, oxygen, or sulfur, and wherein at least one aryl group is an optionally substituted 8-10 membered bicyclic heteroaryl ring having 1-5 heteroatoms independently selected from nitrogen, oxygen, or sulfur. In some embodiments, R is optionally substituted biaryl wherein each aryl group is independently optionally substituted phenyl. In some embodiments, R is optionally substituted biaryl wherein each aryl group is independently optionally substituted phenyl, or an optionally substituted 5-6 membered monocyclic heteroaryl ring having 1-4 heteroatoms independently selected from nitrogen, oxygen. In some embodiments, R is optionally substituted biaryl wherein each aryl group is independently an optionally substituted 8-10 membered bicyclic aryl ring. In some embodiments, R is optionally substituted biaryl wherein one aryl group is optionally substituted naphthyl, and the other aryl group is independently an optionally substituted 8-10 membered bicyclic aryl ring. In some embodiments, R is optionally substituted biaryl wherein each aryl group is optionally substituted naphthyl. In some embodiments, R is optionally substituted biaryl wherein one aryl group is optionally substituted naphthyl, and the other aryl group is an optionally substituted 8-10 membered bicyclic heteroaryl ring having 1-5 heteroatoms independently selected from nitrogen, oxygen, or sulfur.

In some embodiments, R is an optionally substituted 5-6 membered monocyclic heteroaryl ring having 1-4 heteroatoms independently selected from nitrogen, oxygen, or sulfur. In some embodiments, R is a substituted 5-6 membered monocyclic heteroaryl ring having 1-4 heteroatoms independently selected from nitrogen, oxygen, or sulfur. In some embodiments, R is an unsubstituted 5-6 membered monocyclic heteroaryl ring having 1-4 heteroatoms independently selected from nitrogen, oxygen, or sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, or sulfur.

In some embodiments, R is an optionally substituted 5-membered monocyclic heteroaryl ring having one heteroatom selected from nitrogen, oxygen, or sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, or sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, or sulfur. Exemplary R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl.

In some embodiments, R is an optionally substituted 3-7 membered saturated or partially unsaturated heterocyclic ring having 1-3 heteroatoms independently selected from nitrogen, oxygen, or sulfur. In some embodiments, R is a substituted 3-7 membered saturated or partially unsaturated heterocyclic ring having 1-3 heteroatoms independently selected from nitrogen, oxygen, or sulfur. In some embodiments, R is an unsubstituted 3-7 membered saturated or partially unsaturated heterocyclic ring having 1-3 heteroatoms independently selected from nitrogen, oxygen, or sulfur.

In some embodiments, R is optionally substituted 3-membered heterocyclic ring having one heteroatom selected from nitrogen, oxygen or sulfur. Exemplary R groups include but are not limited to optionally substituted aziridinyl, thiiranyl or oxiranyl. In some embodiments, R is optionally substituted 4-membered heterocyclic ring having 1-3 heteroatoms independently selected from nitrogen, oxygen, or sulfur. Exemplary R groups include but are not limited to optionally substituted azetidinyl, oxetanyl, thietanyl, oxazetidinyl, thiazetidinyl, or diazetidinyl. In some embodiments, R is optionally substituted 5-membered heterocyclic ring having 1-3 heteroatoms independently selected from nitrogen, oxygen, or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, R is optionally substituted 6-membered heterocyclic ring having 1-3 heteroatoms independently selected from nitrogen, oxygen, or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, R is optionally substituted 7-membered heterocyclic ring having 1-3 heteroatoms independently selected from nitrogen, oxygen, or sulfur. Exemplary R groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, R is an optionally substituted 5-7 membered partially unsaturated monocyclic ring having 1-3 heteroatoms independently selected from nitrogen, oxygen, or sulfur. In certain embodiments, R is an optionally substituted 5-6 membered partially unsaturated monocyclic ring having 1-3 heteroatoms independently selected from nitrogen, oxygen, or sulfur. In certain embodiments, R is an optionally substituted 5-membered partially unsaturated monocyclic ring having 1-3 heteroatoms independently selected from nitrogen, oxygen, or sulfur. Exemplary R groups include but are not limited to optionally substituted dihydroimidazolyl, dihydrothiazolyl, dihydrooxazolyl, or oxazolinyl. In certain embodiments, R is an optionally substituted 6-membered partially unsaturated monocyclic ring having 1-3 heteroatoms independently selected from nitrogen, oxygen, or sulfur. Exemplary R groups include but are not limited to optionally substituted dihydropyridinyl, tetrahydropyridinyl, dihydropyrimidinyl, tetrahydropyrimidinyl, dihydropyrazinyl, tetrohydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, R is an optionally substituted 7-membered partially unsaturated monocyclic ring having 1-3 heteroatoms independently selected from nitrogen, oxygen, or sulfur. Exemplary R groups include but are not limited to optionally substituted azepiyl, oxepinyl, thiepinyl, diazepinyl, oxazepinyl, thiazepinyl, triazepinyl, oxadiazepinyl, thiadiazepinyl, dihydroazepiyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepiyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, R is an optionally substituted 7-14 membered bicyclic or polycyclic saturated or partially unsaturated heterocyclic ring having 1-5 heteroatoms independently selected from nitrogen, oxygen, or sulfur. In some embodiments, R is an optionally substituted 7-10 membered bicyclic saturated or partially unsaturated heterocyclic ring having 1-5 heteroatoms independently selected from nitrogen, oxygen, or sulfur. In some embodiments, R is optionally substituted indolinyl. In some embodiments, R is optionally substituted isoindolinyl. In some embodiments, R is optionally substituted 1,2,3,4-tetrahydroquinolinyl. In some embodiments, R is optionally substituted 1,2,3,4-tetrahydroisoquinolinyl. In some embodiments, R is an optionally substituted azabicyclo[3.2.1]octanyl.

In some embodiments, R is an optionally substituted 8-14 membered bicyclic or polycyclic heteroaryl ring having 1-5 heteroatoms independently selected from nitrogen, oxygen, or sulfur. In some embodiments, R is an optionally substituted 8-14 membered bicyclic or tricyclic heteroaryl ring having 1-5 heteroatoms independently selected from nitrogen, oxygen, or sulfur. In some embodiments, R is an 8-10 membered bicyclic heteroaryl ring having 1-5 heteroatoms independently selected from nitrogen, oxygen, or sulfur.

In some embodiments, R is an optionally substituted 5,6-fused heteroaryl ring having 1-5 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In some embodiments, R is an optionally substituted 5,6-fused heteroaryl ring having 1-3 heteroatoms independently selected from nitrogen, oxygen, or sulfur. In some embodiments, R is an optionally substituted 5,6-fused heteroaryl ring having two heteroatoms independently selected from nitrogen, oxygen, or sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, or sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, or sulfur. In some embodiments, R is an optionally substituted 5,6-fused heteroaryl ring having five heteroatoms independently selected from nitrogen, oxygen, or sulfur.

In some embodiments, R is an optionally substituted 5,6-fused heteroaryl ring having 1-5 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having one heteroatom independently selected from nitrogen, oxygen, or sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, or sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, or sulfur. In some embodiments, R is optionally substituted oxazolopyridyl, thiazolopyridinyl or imidazopyridinyl. In certain embodiments, R is an optionally substituted 5,6-fused heteroaryl ring having four heteroatoms independently selected from nitrogen, oxygen, or sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, or sulfur.

In certain embodiments, R is an optionally substituted 6,6-fused heteroaryl ring having 1-5 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having one heteroatom selected from nitrogen, oxygen, or sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, or sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, or sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, or sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, or sulfur.

In some embodiments, R is optionally substituted heterobiaryl wherein each heteroaryl group is independently an optionally substituted group selected from a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, R is optionally substituted heterobiaryl wherein each aryl group is an optionally substituted 8-10 membered bicyclic heteroaryl ring having 1-5 heteroatoms independently selected from nitrogen, oxygen, or sulfur.

In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur. In some embodiments, two R groups on the same atom are optionally taken together with the atom to which they are attached to form an optionally substituted 3-14 membered, saturated, partially unsaturated, or aryl ring having 0-4 heteroatoms independently selected from nitrogen, oxygen, or sulfur. In some embodiments, two R groups on the same carbon atom are optionally taken together with the carbon atom to form an optionally substituted 3-14 membered, saturated, partially unsaturated, or aryl ring having 0-4 heteroatoms independently selected from nitrogen, oxygen, or sulfur. In some embodiments, two R groups on the same nitrogen atom are optionally taken together with the nitrogen atom to form an optionally substituted 3-14 membered, saturated, partially unsaturated, or aryl ring having 1-5 heteroatoms independently selected from nitrogen, oxygen, or sulfur. In some embodiments, two R groups on the same sulfur atom are optionally taken together with the sulfur atom to form an optionally substituted 3-14 membered, saturated, partially unsaturated, or aryl ring having 1-5 heteroatoms independently selected from nitrogen, oxygen, or sulfur. In some embodiments, two R groups on the same oxygen atom are optionally taken together with the oxygen atom to form an optionally substituted 3-14 membered, saturated, partially unsaturated, or aryl ring having 1-5 heteroatoms independently selected from nitrogen, oxygen, or sulfur. In some embodiments, two R groups on the same phosphorus atom are optionally taken together with the phosphorus atom to form an optionally substituted 3-14 membered, monocyclic or bicyclic, saturated, partially unsaturated, or aryl ring having, in addition to the phosphorus atom, 0-4 heteroatoms independently selected from nitrogen, oxygen, or sulfur. In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur, wherein the two R groups are attached to two different atoms.

In some embodiments, two R groups are optionally taken together with their intervening atoms to form an optionally substituted 3-14 membered, saturated, partially unsaturated, or aryl ring having, in addition to the intervening atoms, 0-4 heteroatoms independently selected from nitrogen, oxygen, or sulfur. In some embodiments, two R groups are taken together to form an optionally substituted saturated ring. In some embodiments, two R groups are taken together to form an optionally substituted partially unsaturated ring. In some embodiments, two R groups are taken together to form an optionally substituted carbocyclic ring. In some embodiments, two R groups are taken together to form an optionally substituted aryl ring. In some embodiments, two R groups are taken together to form an optionally substituted phenyl ring. In some embodiments, two R groups are taken together to form an optionally substituted heterocyclic ring. In some embodiments, two R groups are taken together to form an optionally substituted heteroaryl ring.

In some embodiments, a ring formed by taking two R groups together is monocyclic, bicyclic or tricyclic. In some embodiments, a ring formed by taking two R groups together is monocyclic. In some embodiments, a ring formed by taking two R groups together is bicyclic. In some embodiments, a ring formed by taking two R groups together is monocyclic or bicyclic. In some embodiments, a ring formed by taking two R groups together is tricyclic. In some embodiments, a ring formed by taking two R groups together is monocyclic, bicyclic or tricyclic.

As generally defined above, each $R^2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$, or $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur. In some embodiments, $R^2$ is R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$. In some embodiments, $R^1$ and $R^2$ are taken together with their intervening atoms to form an optionally substituted 4-7 membered heterocyclic ring having, in addition to the nitrogen atom to which $R^1$ is attached, 0-2 heteroatoms independently selected from oxygen, nitrogen or sulfur.

In some embodiments, $R^2$ is R. In some embodiments, $R^2$ is hydrogen. In some embodiments, $R^2$ is optionally substituted $C_{1-20}$ aliphatic. In some embodiments, $R^2$ is optionally substituted $C_{1-15}$ aliphatic. In some embodiments, $R^2$ is optionally substituted $C_{1-10}$ aliphatic. In some embodiments, $R^2$ is optionally substituted $C_{1-6}$ aliphatic. In some embodiments, $R^2$ is optionally substituted $C_{1-6}$ alkyl. In some embodiments, $R^2$ is optionally substituted hexyl, pentyl, butyl, propyl, ethyl or methyl. In some embodiments, $R^2$ is optionally substituted hexyl. In some embodiments, $R^2$ is optionally substituted pentyl. In some embodiments, $R^2$ is optionally substituted butyl. In some embodiments, $R^2$ is optionally substituted propyl. In some embodiments, $R^2$ is optionally substituted ethyl. In some embodiments, $R^2$ is optionally substituted methyl. In some embodiments, $R^2$ is hexyl. In some embodiments, $R^2$ is pentyl. In some embodiments, $R^2$ is butyl. In some embodiments, $R^2$ is propyl. In some embodiments, $R^2$ is ethyl. In some embodiments, $R^2$ is methyl. In some embodiments, $R^2$ is isopropyl. In some embodiments, $R^2$ is n-propyl. In some embodiments, $R^2$ is tert-butyl. In some embodiments, $R^2$ is sec-butyl. In some embodiments, $R^2$ is n-butyl. In some embodiments, $R^2$ is benzyloxymethyl. In some embodiments, $R^2$ is benzyl.

In some embodiments, $R^2$ is optionally substituted $C_{1-20}$ heteroalkyl. In some embodiments, $R^2$ is optionally substituted $C_{1-20}$ heteroalkyl having 1-6 heteroatoms independently selected from nitrogen, sulfur, phosphorus selenium, silicon or boron. In some embodiments, $R^2$ is optionally substituted $C_{1-20}$ heteroalkyl having 1-6 heteroatoms independently selected from nitrogen, sulfur, phosphorus, selenium, silicon or boron, optionally including one or more oxidized forms of nitrogen, sulfur, phosphorus, selenium, silicon or boron.

In some embodiments, $R^2$ is —[C(R)$_2$]$_q$—OR. In some embodiments, $R^2$ is —CH$_2$OR. In some embodiments, $R^2$ is —[C(R)$_2$]$_q$—N(R)$_2$. In some embodiments, $R^2$ is —CH$_2$N(R)$_2$. In some embodiments, $R^2$ is —CH$_2$NHR. In some embodiments, $R^2$ is —[C(R)$_2$]$_q$—SR. In some embodiments, $R^2$ is —CH$_2$SR. In some embodiments, $R^2$ is —[C(R)$_2$]$_q$—OSi(R)$_3$. In some embodiments, $R^2$ is —CH$_2$OSi(R)$_3$. In some embodiments, $R^2$ is —[C(R)$_2$]$_q$—OC(O)R. In some embodiments, $R^2$ is —CH$_2$OC(O)R. In some embodiments, $R^2$ is —[C(R)$_2$]$_q$—OC(O)OR. In some embodiments, $R^2$ is —CH$_2$OC(O)OR. In some embodiments, $R^2$ is —[C(R)$_2$]$_q$—OC(O)N(R)$_2$. In some embodiments, $R^2$ is —CH$_2$OC(O)N(R)$_2$. In some embodiments, $R^2$ is —CH$_2$OC(O)NHR. In some embodiments, $R^2$ is —[C(R)$_2$]$_q$—OC(O)N(R)—SO$_2$R. In some embodiments, $R^2$ is —CH$_2$OC(O)N(R)—SO$_2$R. In some embodiments, $R^2$ is —CH$_2$OC(O)NHSO$_2$R. In some embodiments, $R^2$ is —[C(R)$_2$]$_q$—OP(OR)$_2$. In some embodiments, $R^2$ is —CH$_2$OP(OR)$_2$.

Exemplary R² groups are depicted below:

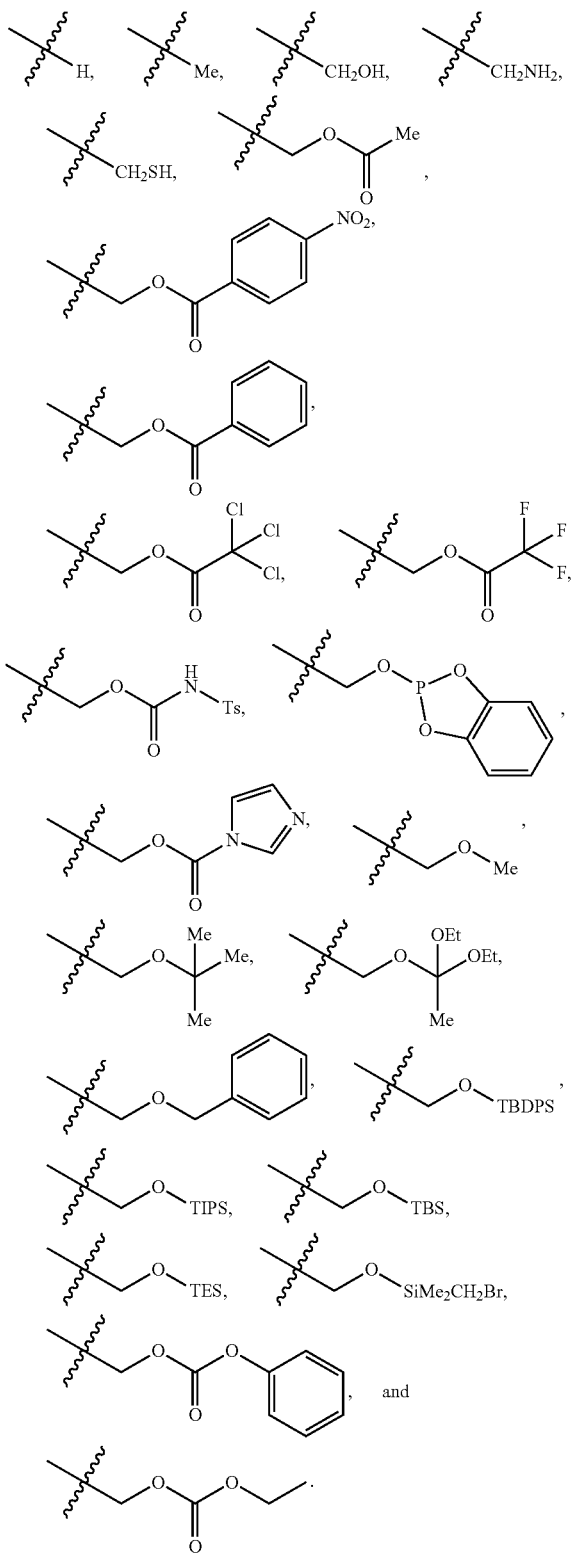

In some embodiments, R¹ and R² are taken together with their intervening atoms to form an optionally substituted 4-7 membered heterocyclic ring having, in addition to the nitrogen atom to which R¹ is attached, 0-2 heteroatoms independently selected from oxygen, nitrogen or sulfur. In some embodiments, R¹ and R² are taken together with their intervening atoms to form an optionally substituted 4-membered heterocyclic ring having, in addition to the nitrogen atom to which R¹ is attached, 0-2 heteroatoms independently selected from oxygen, nitrogen or sulfur. In some embodiments, R¹ and R² are taken together with their intervening atoms to form an optionally substituted 5-membered heterocyclic ring having, in addition to the nitrogen atom to which R¹ is attached, 0-2 heteroatoms independently selected from oxygen, nitrogen or sulfur. In some embodiments, R¹ and R² are taken together with their intervening atoms to form an optionally substituted 6-membered heterocyclic ring having, in addition to the nitrogen atom to which R¹ is attached, 0-2 heteroatoms independently selected from oxygen, nitrogen or sulfur. In some embodiments, R¹ and R² are taken together with their intervening atoms to form an optionally substituted 7-membered heterocyclic ring having, in addition to the nitrogen atom to which R¹ is attached, 0-2 heteroatoms independently selected from oxygen, nitrogen or sulfur. In some embodiments, R¹ and R² are taken together with their intervening atoms to form

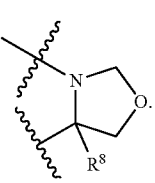

In some embodiments, R¹ and R² are taken together with their intervening atoms to form

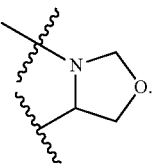 [SMILES: *C1COCN1*]

In some embodiments, R² comprises an —OH, —NHR or —SH group. In some embodiments, in a provided compound of formula II, D is connected to L through R². In some embodiments, R² comprises an —OH, —NHR or —SH group for conjugation. In some embodiments, R² comprises an —OH group, and D is connected to L through the —OH group. In some embodiments, R² is —CH₂OH. In some embodiments, the —OH group reacts with a functional group in L or M to form, for example, an ether, ester, carbamate or carbonate ester. In some embodiments, R² reacts with a functional group in L to form a carbonate ester. In some embodiments, R² comprises an amino group, and D is connected to L through the amino group. In some embodiments, R² comprises a —NHR group. In some embodiments, R² comprises a —NH₂ group. In some embodiments, R² is —CH₂NH₂. In some embodiments, the amino group reacts with a functional group in L or M to form, for example, an amine, imine, amide or carbamate. In some embodiments, R² comprises an —SH group, and D is connected to L through the —SH group. In some embodiments, the —SH group reacts with a functional group in L or M to form, for example, a disulfide, thioether or thioester.

In some embodiments, a provided compound of formula II has the structure of

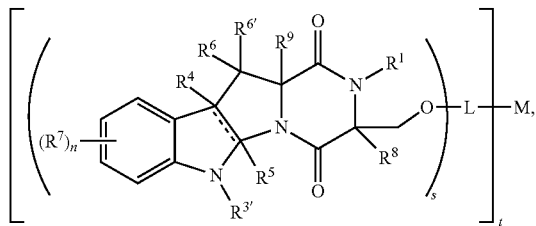

or a pharmaceutically acceptable salt thereof, wherein each variable is independently as described in classes and subclasses herein, both singly and in combination.

In some embodiments, a provided compound of formula II has the structure of

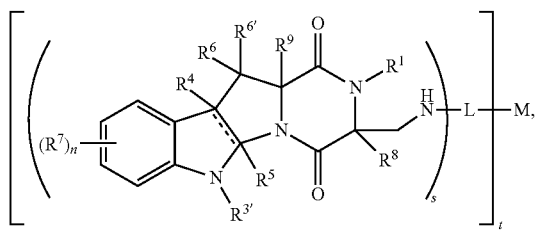

or a pharmaceutically acceptable salt thereof, wherein each variable is independently as described in classes and subclasses herein, both singly and in combination.

In some embodiments, a provided compound of formula II has the structure of

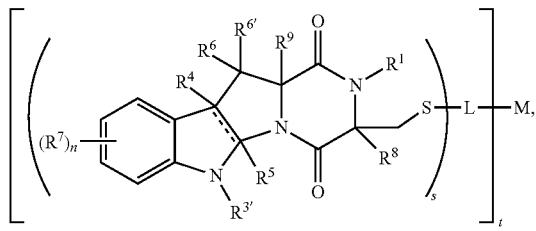

or a pharmaceutically acceptable salt thereof, wherein each variable is independently as described in classes and subclasses herein, both singly and in combination.

In some embodiments, a provided compound of formula II has the structure of

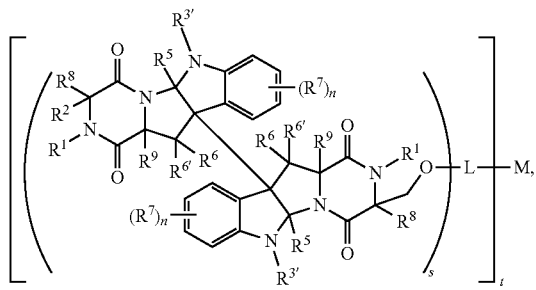

or a pharmaceutically acceptable salt thereof, wherein each variable is independently as described in classes and subclasses herein, both singly and in combination.

In some embodiments, a provided compound of formula II has the structure of

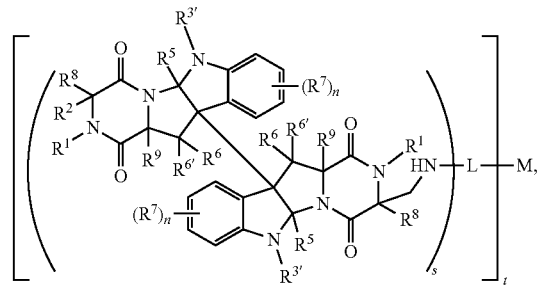

or a pharmaceutically acceptable salt thereof, wherein each variable is independently as described in classes and subclasses herein, both singly and in combination.

In some embodiments, a provided compound of formula II has the structure of

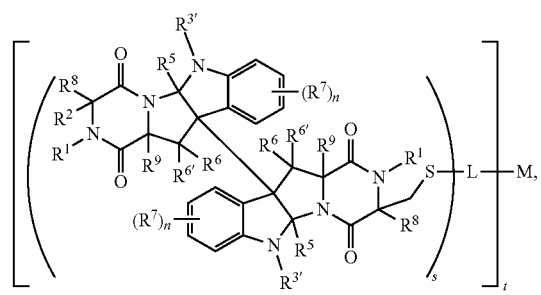

or a pharmaceutically acceptable salt thereof, wherein each variable is independently as described in classes and subclasses herein, both singly and in combination.

As generally defined above, each q is independently 0, 1, 2, 3 or 4. In some embodiments, q is 0. In some embodiments, q is 1. In some embodiments, q is 2. In some embodiments, q is 3. In some embodiments, q is 4.

In some embodiments, $R^3$ is an electron-withdrawing group. Exemplary electron-withdrawing groups are widely known in the art, for example, halogen, haloalkyl, carbonyl moieties (e.g., aldehyde and ketone groups), —COOH and its derivatives (e.g., ester and amide moieties), protonated amines, quaternary ammonium groups, —CN, —NO$_2$, —S(O)— moieties, and —S(O)$_2$— moieties. In some embodiments, an electron-withdrawing group comprises one or more —C(O)—, —C(=N—)—, —C(S)—, —S(O)—, —S(O)$_2$— or —P(O)— groups, and is connected to the rest of a provided compound via a —C(O)—, —C(=N—)—, —C(S)—, —S(O)—, —S(O)$_2$— or —P(O)— group. In some embodiments, an electron-withdrawing group is —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$. In some embodiments, an electron-withdrawing group is halogen. In some embodiments, an electron-withdrawing group is —F. In some embodiments, an electron-withdrawing group is —Cl. In some embodiments, an electron-withdrawing group is —Br. In some embodiments, an electron-withdrawing group is —I.

In some embodiments, an electron-withdrawing group is —CF$_3$. In some embodiments, an electron-withdrawing group is —C(O)R. In some embodiments, an electron-withdrawing group is —C(O)OR. In some embodiments, an electron-withdrawing group is —C(O)N(R)$_2$. In some embodiments, an electron-withdrawing group is —S(O)R. In some embodiments, an electron-withdrawing group is —S(O)$_2$R. In some embodiments, an electron-withdrawing group is —S(O)$_2$OR. In some embodiments, an electron-withdrawing group is —CN. In some embodiments, an electron-withdrawing group is protonated amine. In some embodiments, an electron-withdrawing group is —N$^+$(R)$_3$. In some embodiments, an electron-withdrawing group is —NO$_2$. In some embodiments, an electron-withdrawing group is —P(O)(R')$_2$, wherein each R$^1$ is independently R, —N(R)$_2$, —SR or —OR.

In some embodiments, R$^3$ is an electron-withdrawing group comprising one or more —C(O)—, —C(=N—)—, —C(S)—, —S(O)—, —S(O)$_2$— or —P(O)— groups, and is connected to the rest of a provided compound via a —C(O)—, —C(=N—)—, —C(S)—, —S(O)—, —S(O)$_2$— or —P(O)— group.

In some embodiments, R is an electronic-withdrawing group comprising a —S(O)$_2$— group, and is connected to the rest of the compound via a —S(O)$_2$— group. In some embodiments, R$^3$ is —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, or —S(O)$_2$N(R)$_2$. In some embodiments, R$^3$ is —S(O)$_2$R. In some embodiments, R$^3$ is —S(O)$_2$R, wherein R is other than phenyl. In some embodiments, R$^3$ is —S(O)$_2$—[C(R)$_2$]$_q$—R. In some embodiments, R$^3$ is —S(O)$_2$—[C(R)$_2$]$_q$—B(OR)$_2$. In some embodiments, R$^3$ is —S(O)$_2$—[C(R)$_2$]$_q$—Si(R)$_3$. In some embodiments, R$^3$ is —S(O)$_2$OR. In some embodiments, R$^3$ is —S(O)$_2$N(R)$_2$.

In some embodiments, R is an electronic-withdrawing group comprising a —S(O)— group, and is connected to the rest of the compound via a —S(O)— group. In some embodiments, R$^3$ is —S(O)R.

In some embodiments, R$^3$ is an electronic-withdrawing group comprising a —C(O)— group, and is connected to the rest of the compound via a —C(O)— group. In some embodiments, R$^3$ is —C(O)R, —C(O)OR, —C(O)N(R)$_2$, or —C(O)N(R)—OR. In some embodiments, R$^3$ is —C(O)R. In some embodiments, R$^3$ is —C(O)R, and R$^3$ is other than —C(O)CF$_3$. In some embodiments, R$^3$ is —C(O)OR. In some embodiments, R$^3$ is —C(O)N(R)$_2$. In some embodiments, R$^3$ is —C(O)N(R)—OR.

In some embodiments, R is an electronic-withdrawing group comprising a —C(=N—)— group, and is connected to the rest of the compound via a —C(=N—)— group. In some embodiments, R$^3$ is an electronic-withdrawing group comprising a —C(=NR)— group, and is connected to the rest of the compound via a —C(=NR)— group.

In some embodiments, R is an electronic-withdrawing group comprising a —P(O)— group, and is connected to the rest of the compound via a —P(O)— group. In some embodiments, R$^3$ is —P(O)(R'). In some embodiments, R is —P(O)(R)$_2$, —P(O)(OR)$_2$, or —P(O)[N(R)$_2$]$_2$. In some embodiments, R$^3$ is —P(O)(R)$_2$. In some embodiments, R$^3$ is —P(O)(OR)$_2$. In some embodiments, R$^3$ is —P(O)[N(R)$_2$]$_2$.

In some embodiments, R$^3$ is —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$.

In some embodiments, R$^3$ is other than —C(O)CF$_3$. In some embodiments, R$^3$ is other than tert-butyloxycarbonyl. In some embodiments, R$^3$ is other than —S(O)$_2$Ph. In some embodiments, R$^3$ is other than —C(O)CF$_3$ and tert-butyloxycarbonyl. In some embodiments, R$^3$ is other than —S(O)$_2$Ph and tert-butyloxycarbonyl. In some embodiments, R is other than —C(O)CF$_3$ and —S(O)$_2$Ph. In some embodiments, R$^3$ is other than —S(O)$_2$Ph, —C(O)CF$_3$ and tert-butyloxycarbonyl. In some embodiments, R$^3$ is other than —C(O)CF$_3$ when R$^1$ is —H or -Me. In some embodiments, R$^3$ is other than —C(O)CF$_3$ when R$^1$ is —H. In some embodiments, R$^3$ is other than —C(O)CF$_3$ when R$^1$ is -Me. In some embodiments, R$^3$ is other than tert-butyloxycarbonyl when R$^1$ is —H or -Me. In some embodiments, R$^3$ is other than tert-butyloxycarbonyl when R$^1$ is —H. In some embodiments, R$^3$ is other than tert-butyloxycarbonyl when R$^1$ is -Me. In some embodiments, R$^3$ is other than —S(O)$_2$Ph when R$^1$ is —H or -Me. In some embodiments, R$^3$ is other than —S(O)$_2$Ph when R$^1$ is —H. In some embodiments, R$^3$ is other than —S(O)$_2$Ph when R$^1$ is -Me. In some embodiments, R$^3$ is other than —C(O)CF$_3$ and tert-butyloxycarbonyl when R$^1$ is —H or -Me. In some embodiments, R$^3$ is other than —C(O)CF$_3$ and tert-butyloxycarbonyl when R$^1$ is —H. In some embodiments, R$^3$ is other than —C(O)CF$_3$ and tert-butyloxycarbonyl when R$^1$ is -Me. In some embodiments, R$^3$ is other than —C(O)CF$_3$ and —S(O)$_2$Ph when R$^1$ is —H or -Me. In some embodiments, R$^3$ is other than —C(O)CF$_3$ and —S(O)$_2$Ph when R$^1$ is —H. In some embodiments, R is other than —C(O)CF$_3$ and —S(O)$_2$Ph when R$^1$ is -Me. In some embodiments, R$^3$ is other than —S(O)$_2$Ph and tert-butyloxycarbonyl when R$^1$ is —H or -Me. In some embodiments, R$^3$ is other than —S(O)$_2$Ph and tert-butyloxycarbonyl when R$^1$ is —H. In some embodiments, R$^3$ is other than —S(O)$_2$Ph and tert-butyloxycarbonyl when R$^1$ is -Me. In some embodiments, R is other than —S(O)$_2$Ph, —C(O)CF$_3$ and tert-butyloxycarbonyl when R$^1$ is —H or -Me. In some embodiments, R$^1$ is other than —S(O)$_2$Ph, —C(O)CF$_3$ and tert-butyloxycarbonyl when R$^1$ is —H. In some embodiments, R$^3$ is other than —S(O)$_2$Ph, —C(O)CF$_3$ and tert-butyloxycarbonyl when R$^1$ is -Me.

Exemplary R$^3$ groups include:

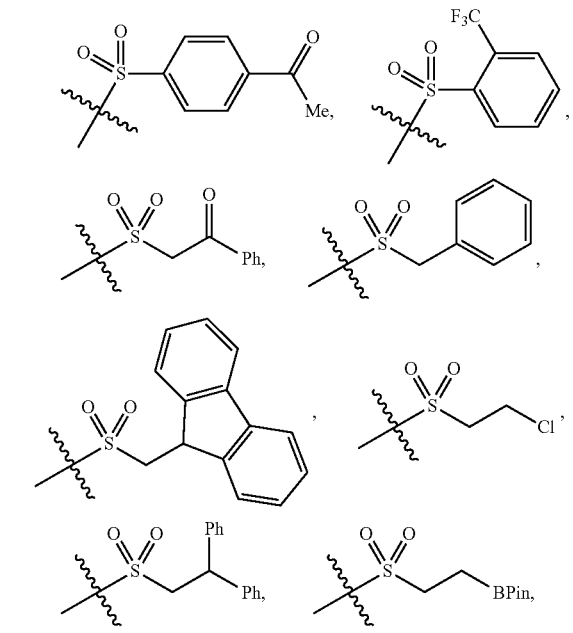

-continued

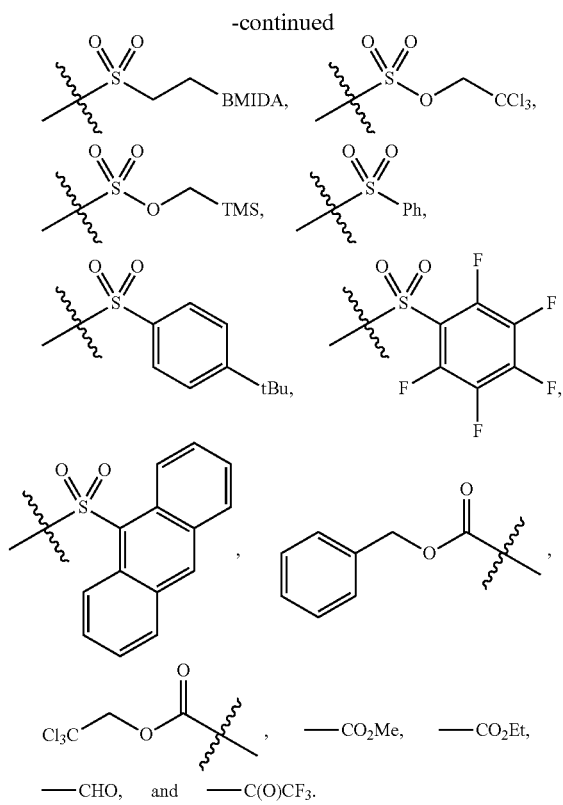

In some embodiments, each $R^{3'}$ is independently R or $R^3$. In some embodiments, each $R^{3'}$ is independently R, —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$.

In some embodiments, $R^{3'}$ is R. In some embodiments, $R^{3'}$ is hydrogen. In some embodiments, $R^{3'}$ is optionally substituted $C_{1-20}$ aliphatic. In some embodiments, $R^{3'}$ is optionally substituted $C_{1-15}$ aliphatic. In some embodiments, $R^{3'}$ is optionally substituted $C_{1-10}$ aliphatic. In some embodiments, $R^{3'}$ is optionally substituted $C_{1-6}$ aliphatic. In some embodiments, $R^{3'}$ is optionally substituted $C_{1-6}$ alkyl. In some embodiments, $R^{3'}$ is optionally substituted hexyl, pentyl, butyl, propyl, ethyl or methyl. In some embodiments, $R^{3'}$ is optionally substituted hexyl. In some embodiments, $R^{3'}$ is optionally substituted pentyl. In some embodiments, $R^{3'}$ is optionally substituted butyl. In some embodiments, $R^{3'}$ is optionally substituted propyl. In some embodiments, $R^{3'}$ is optionally substituted ethyl. In some embodiments, $R^{3'}$ is optionally substituted methyl. In some embodiments, $R^{3'}$ is hexyl. In some embodiments, $R^{3'}$ is pentyl. In some embodiments, $R^{3'}$ is butyl. In some embodiments, $R^{3'}$ is propyl. In some embodiments, $R^{3'}$ is ethyl. In some embodiments, $R^{3'}$ is methyl. In some embodiments, $R^{3'}$ is isopropyl. In some embodiments, $R^{3'}$ is n-propyl. In some embodiments, $R^{3'}$ is tert-butyl. In some embodiments, $R^{3'}$ is sec-butyl. In some embodiments, $R^{3'}$ is n-butyl.

In some embodiments, $R^{3'}$ is benzyloxymethyl. In some embodiments, $R^{3'}$ is benzyl. In some embodiments, $R^{3'}$ is other than hydrogen.

In some embodiments, $R^{3'}$ is optionally substituted $C_{1-20}$ heteroalkyl. In some embodiments, $R^{3'}$ is optionally substituted $C_{1-20}$ heteroalkyl having 1-6 heteroatoms independently selected from nitrogen, sulfur, phosphorus selenium, silicon or boron. In some embodiments, $R^{3'}$ is optionally substituted $C_{1-20}$ heteroalkyl having 1-6 heteroatoms independently selected from nitrogen, sulfur, phosphorus, selenium, silicon or boron, optionally including one or more oxidized forms of nitrogen, sulfur, phosphorus, selenium, silicon or boron.

In some embodiments, $R^{3'}$ is $R^3$. In some embodiments, $R^{3'}$ is —S(O)$_2$R, —S(O)$_2$—[C(R)$_2$]$_q$—R, —S(O)$_2$—[C(R)$_2$]$_q$—B(OR)$_2$, —S(O)$_2$—[C(R)$_2$]$_q$—Si(R)$_3$, —S(O)$_2$OR, —S(O)$_2$N(R)$_2$, —S(O)R, —C(O)R, —C(O)OR, —C(O)N(R)$_2$, —C(O)N(R)—OR, —P(O)(R)$_2$, —P(O)(OR)$_2$, or —P(O)[N(R)$_2$]$_2$. In some embodiments, $R^{3'}$ is —S(O)$_2$R. In some embodiments, $R^{3'}$ is —S(O)$_2$—[C(R)$_2$]$_q$—R. In some embodiments, $R^{3'}$ is —S(O)$_2$—[C(R)$_2$]$_q$—B(OR)$_2$. In some embodiments, $R^{3'}$ is —S(O)$_2$[C(R)$_2$]$_q$—Si(R)$_3$. In some embodiments, $R^{3'}$ is —S(O)$_2$OR. In some embodiments, $R^{3'}$ is —S(O)$_2$N(R)$_2$. In some embodiments, $R^{3'}$ is —S(O)R. In some embodiments, $R^{3'}$ is —C(O)R. In some embodiments, $R^{3'}$ is —C(O)OR. In some embodiments, $R^{3'}$ is —C(O)N(R)$_2$. In some embodiments, $R^{3'}$ is —C(O)N(R)—OR. In some embodiments, $R^{3'}$ is —P(O)(R)$_2$. In some embodiments, $R^{3'}$ is —P(O)(R)$_2$. In some embodiments, $R^{3'}$ is —P(O)(OR)$_2$. In some embodiments, $R^{3'}$ is —P(O)[N(R)$_2$].

In some embodiments, $R^{3'}$ is other than —C(O)CF$_3$. In some embodiments, $R^{3'}$ is other than tert-butyloxycarbonyl. In some embodiments, $R^{3'}$ is other than —S(O)$_2$Ph. In some embodiments, $R^{3'}$ is other than —C(O)CF$_3$ and tert-butyloxycarbonyl. In some embodiments, $R^{3'}$ is other than —S(O)$_2$Ph and tert-butyloxycarbonyl. In some embodiments, $R^{3'}$ is other than —C(O)CF$_3$ and —S(O)$_2$Ph. In some embodiments, $R^{3'}$ is other than —S(O)$_2$Ph, —C(O)CF$_3$ and tert-butyloxycarbonyl. In some embodiments, $R^{3'}$ is other than —C(O)CF$_3$ when $R^1$ is —H or -Me. In some embodiments, $R^{3'}$ is other than —C(O)CF$_3$ when $R^1$ is —H. In some embodiments, $R^{3'}$ is other than —C(O)CF$_3$ when $R^1$ is -Me. In some embodiments, $R^{3'}$ is other than tert-butyloxycarbonyl when $R^1$ is —H or -Me. In some embodiments, $R^{3'}$ is other than tert-butyloxycarbonyl when $R^1$ is —H. In some embodiments, $R^{3'}$ is other than tert-butyloxycarbonyl when $R^1$ is -Me. In some embodiments, $R^{3'}$ is other than —S(O)$_2$Ph when $R^1$ is —H or -Me. In some embodiments, $R^{3'}$ is other than —S(O)$_2$Ph when $R^1$ is —H. In some embodiments, $R^{3'}$ is other than —S(O)$_2$Ph when $R^1$ is -Me. In some embodiments, $R^{3'}$ is other than —C(O)CF$_3$ and tert-butyloxycarbonyl when $R^1$ is —H or -Me. In some embodiments, $R^{3'}$ is other than —C(O)CF$_3$ and tert-butyloxycarbonyl when $R^1$ is —H. In some embodiments, $R^{3'}$ is other than —C(O)CF$_3$ and tert-butyloxycarbonyl when $R^1$ is -Me. In some embodiments, $R^{3'}$ is other than —C(O)CF$_3$ and —S(O)$_2$Ph when $R^1$ is —H or -Me. In some embodiments, $R^{3'}$ is other than —C(O)CF$_3$ and —S(O)$_2$Ph when $R^1$ is —H. In some embodiments, $R^{3'}$ is other than —C(O)CF$_3$ and —S(O)$_2$Ph when $R^1$ is -Me. In some embodiments, $R^{3'}$ is other than —S(O)$_2$Ph and tert-butyloxycarbonyl when $R^1$ is —H or -Me. In some embodiments, $R^{3'}$ is other than —S(O)$_2$Ph and tert-butyloxycarbonyl when $R^1$ is —H. In some embodiments, $R^{3'}$ is other than —S(O)$_2$Ph and tert-butyloxycarbonyl when $R^1$ is -Me. In some embodiments, $R^{3'}$ is other than —S(O)$_2$Ph, —C(O)CF$_3$ and tert-butyloxycarbonyl when $R^1$ is —H or -Me. In some embodiments, $R^{3'}$ is other than —S(O)$_2$Ph, —C(O)CF$_3$ and tert-butyloxycarbonyl when $R^1$ is —H. In some embodiments, $R^{3'}$ is other than —S(O)$_2$Ph, —C(O)CF$_3$ and tert-butyloxycarbonyl when $R^1$ is -Me.

In some embodiments, $R^{3'}$ comprises an —OH, —NHR or —SH group. In some embodiments, in a provided compound of formula II, D is connected to L through $R^{3'}$. In some embodiments, $R^{3'}$ comprises an —OH, —NHR or —SH group for conjugation. In some embodiments, $R^{3'}$ comprises an —OH group, and D is connected to L through the —OH group. In some embodiments, the —OH group reacts with a functional group in L or M to form, for example, an ether, ester, carbamate or carbonate ester. In some embodiments, $R^{3'}$ reacts with a functional group in L to form a carbonate ester. In some embodiments, $R^{3'}$ comprises an amino group, and D is connected to L through the amino group. In some embodiments, $R^{3'}$ comprises a —NHR group. In some embodiments, $R^{3'}$ comprises a —NH$_2$ group. In some embodiments, the amino group reacts with a functional group in L or M to form, for example, an amine, imine, amide or carbamate. In some embodiments, $R^{3'}$ comprises an —SH group, and D is connected to L through the —SH group. In some embodiments, the —SH group reacts with a functional group in L or M to form, for example, a disulfide, thioether or thioester.

In some embodiments, $R^4$ is absent when $=$ is a double bond. In some other embodiments, $=$ is a single bond and $R^4$ is R or halogen.

In some embodiments, $R^4$ is R. In some embodiments, $R^4$ is hydrogen. In some embodiments, $R^4$ is an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^4$ is an optionally substituted $C_{1-20}$ aliphatic. In some embodiments, $R^4$ is an optionally substituted $C_{1-10}$ aliphatic. In some embodiments, $R^4$ is an optionally substituted $C_{1-6}$ aliphatic. In some embodiments, $R^4$ is optionally substituted $C_{1-6}$ alkyl. In some embodiments, $R^4$ is optionally substituted hexyl, pentyl, butyl, propyl, ethyl or methyl. In some embodiments, $R^4$ is optionally substituted hexyl. In some embodiments, $R^4$ is optionally substituted pentyl. In some embodiments, $R^4$ is optionally substituted butyl. In some embodiments, $R^4$ is optionally substituted propyl. In some embodiments, $R^4$ is optionally substituted ethyl. In some embodiments, $R^4$ is optionally substituted methyl. In some embodiments, $R^4$ is hexyl. In some embodiments, $R^4$ is pentyl. In some embodiments, $R^4$ is butyl. In some embodiments, $R^4$ is propyl. In some embodiments, $R^4$ is ethyl. In some embodiments, $R^4$ is methyl. In some embodiments, $R^4$ is isopropyl. In some embodiments, $R^4$ is n-propyl. In some embodiments, $R^4$ is tert-butyl. In some embodiments, $R^4$ is sec-butyl. In some embodiments, $R^4$ is n-butyl. In some embodiments, $R^4$ is benzyloxymethyl. In some embodiments, $R^4$ is benzyl. In some embodiments, $R^4$ is an optionally substituted $C_{1-6}$ alkyl. In some embodiments, $R^4$ is optionally substituted allyl. In some embodiments, $R^4$ is ally. In some embodiments, $R^4$ is styrenyl. In some embodiments, $R^4$ is other than hydrogen.

In some embodiments, $R^4$ is optionally substituted $C_{1-20}$ heteroalkyl. In some embodiments, $R^4$ is optionally substituted $C_{1-10}$ heteroalkyl. In some embodiments, $R^4$ is optionally substituted $C_{1-6}$ heteroalkyl.

In some embodiments, $R^4$ is optionally substituted phenyl. In some embodiments, $R^4$ is substituted phenyl. In some embodiments, $R^4$ is unsubstituted phenyl. In some embodiments, $R^4$ is p-MeOPh.

In some embodiments, $R^4$ is an optionally substituted 3-7 membered saturated or partially unsaturated carbocyclic ring. In some embodiments, $R^4$ is an optionally substituted 3-membered saturated ring. In some embodiments, $R^4$ is an optionally substituted 4-membered saturated or partially unsaturated carbocyclic ring. In some embodiments, $R^4$ is an optionally substituted 5-membered saturated or partially unsaturated carbocyclic ring. In some embodiments, $R^4$ is an optionally substituted 6-membered saturated or partially unsaturated carbocyclic ring. In some embodiments, $R^4$ is an optionally substituted 7-membered saturated or partially unsaturated carbocyclic ring.

In some embodiments, $R^4$ is an optionally substituted 8-14 membered bicyclic or polycyclic saturated, partially unsaturated or aryl ring. In some embodiments, $R^4$ is an optionally substituted an 8-14 membered bicyclic or polycyclic saturated ring. In some embodiments, $R^4$ is an optionally substituted 8-14 membered bicyclic or polycyclic partially unsaturated ring. In some embodiments, $R^4$ is an optionally substituted 8-14 membered bicyclic or polycyclic aryl ring. In some embodiments, $R^4$ is an optionally substituted 10-membered bicyclic aryl ring. In some embodiments, $R^4$ is an optionally substituted 14-membered tricyclic aryl ring.

In some embodiments, $R^4$ is an optionally substituted 5-6 membered monocyclic heteroaryl ring having 1-4 heteroatoms independently selected from nitrogen, oxygen, or sulfur. In some embodiments, $R^4$ is optionally substituted pyrrolyl. In some embodiments, $R^4$ is optionally substituted pyrrol-3-yl. In some embodiments, $R^4$ is N-TIPS-pyrrol-3-yl. In some embodiments, $R^4$ is pyrrol-3-yl.

In some embodiments, $R^4$ is an optionally substituted 3-7 membered saturated or partially unsaturated heterocyclic ring having 1-3 heteroatoms independently selected from nitrogen, oxygen, or sulfur. In some embodiments, $R^4$ is an optionally substituted 3-7 membered saturated heterocyclic ring having 1-3 heteroatoms independently selected from nitrogen, oxygen, or sulfur. In some embodiments, $R^4$ is an optionally substituted 3-7 membered partially unsaturated heterocyclic ring having 1-3 heteroatoms independently selected from nitrogen, oxygen, or sulfur.

In some embodiments, $R^4$ is an optionally substituted 8-14 membered bicyclic or polycyclic heteroaryl ring having 1-5 heteroatoms independently selected from nitrogen, oxygen, or sulfur. In some embodiments, $R^4$ is an optionally substituted 8-membered bicyclic or polycyclic heteroaryl ring having 1-5 heteroatoms independently selected from nitrogen, oxygen, or sulfur. In some embodiments, $R^4$ is an optionally substituted 8-membered bicyclic heteroaryl ring having 1-5 heteroatoms independently selected from nitrogen, oxygen, or sulfur. In some embodiments, $R^4$ is an optionally substituted 9-membered bicyclic or polycyclic heteroaryl ring having 1-5 heteroatoms independently selected from nitrogen, oxygen, or sulfur. In some embodiments, $R^4$ is an optionally substituted 9-membered bicyclic heteroaryl ring having 1-5 heteroatoms independently selected from nitrogen, oxygen, or sulfur. In some embodiments, $R^4$ is an optionally substituted 10-membered bicyclic or polycyclic heteroaryl ring having 1-5 heteroatoms independently selected from nitrogen, oxygen, or sulfur. In some embodiments, $R^4$ is an optionally substituted 10-membered bicyclic heteroaryl ring having 1-5 heteroatoms independently selected from nitrogen, oxygen, or sulfur. In some embodiments, $R^4$ is an optionally substituted 1-membered bicyclic or polycyclic heteroaryl ring having 1-5 heteroatoms independently selected from nitrogen, oxygen, or sulfur. In some embodiments, $R^4$ is an optionally substituted 11-membered tricyclic heteroaryl ring having 1-5 heteroatoms independently selected from nitrogen, oxygen, or sulfur. In some embodiments, $R^4$ is an optionally substituted 12-membered bicyclic or polycyclic heteroaryl ring having 1-5 heteroatoms independently selected from nitrogen, oxygen, or sulfur. In some embodiments, $R^4$ is an optionally substituted 12-membered tricyclic heteroaryl ring having 1-5 heteroatoms independently selected from nitrogen, oxygen, or sulfur. In some embodiments, $R^4$ is an optionally substituted 13-membered bicyclic or polycyclic heteroaryl ring having 1-5 heteroatoms independently selected from nitrogen, oxygen, or sulfur. In some embodiments, $R^4$ is an optionally substituted 13-membered tricyclic heteroaryl ring having 1-5 heteroatoms independently selected from nitrogen, oxygen, or sulfur. In some embodiments, $R^4$ is an optionally substituted 14-membered bicyclic or polycyclic heteroaryl ring having 1-5 heteroatoms independently selected from nitrogen, oxygen, or sulfur. In some embodiments, $R^4$ is an optionally substituted 14-membered tricyclic heteroaryl ring having 1-5 heteroatoms independently selected from nitrogen, oxygen, or sulfur. In some embodiments, $R^4$ some embodiments, $R^4$ is optionally substituted indolyl. In some embodiments, $R^4$ some embodiments, $R^4$ is optionally substituted indol-3-yl. In some embodiments, $R^4$ some embodiments, $R^4$ is indol-3-yl. In some embodiments, $R^4$ is

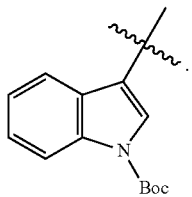 [SMILES: *c1cn(C(=O)OC(C)(C)C)c2ccccc12]

In some embodiments, $R^4$ is

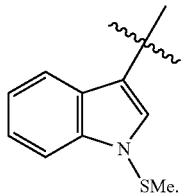 [SMILES: *c1cn(SC)c2ccccc12]

In some embodiments, $R^4$ is an optionally substituted group selected from phenyl, a 8-14 membered bicyclic or tricyclic aryl ring, a 5-6 membered monocyclic heteroaryl ring having 1-4 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur.

In some embodiments, $R^4$ is halogen. In some embodiments, $R^4$ is —F. In some embodiments, $R^4$ is —Cl. In some embodiments, $R^4$ is —Br. In some embodiments, $R^4$ is —I.

In some embodiments, $R^4$ comprises an —OH, —NHR or —SH group. In some embodiments, in a provided compound of formula II, D is connected to L through $R^4$. In some embodiments, $R^4$ comprises an —OH, —NHR or —SH group for conjugation. In some embodiments, $R^4$ comprises an —OH group, and D is connected to L through the —OH group. In some embodiments, the —OH group reacts with a functional group in L or M to form, for example, an ether, ester, carbamate or carbonate ester. In some embodiments, $R^4$ reacts with a functional group in L to form a carbonate ester. In some embodiments, $R^4$ comprises an amino group, and D is connected to L through the amino group. In some embodiments, $R^4$ comprises a —NHR group. In some embodiments, $R^4$ comprises a —NH$_2$ group. In some embodiments, the amino group reacts with a functional group in L or M to form, for example, an amine, imine, amide or carbamate. In some embodiments, $R^4$ comprises an —SH group, and D is connected to L through the —SH group. In some embodiments, the —SH group reacts with a functional group in L or M to form, for example, a disulfide, thioether or thioester.

In some embodiments, $R^5$ is absent when $=\!=\!=$ is a double bond.

In some embodiments, each $R^5$ is independently hydrogen or an optionally substituted $C_{1-6}$ aliphatic. In some embodiments, $R^5$ is hydrogen. In some embodiments, $R^5$ is optionally substituted $C_{1-6}$ aliphatic.

In some embodiments, $R^5$ comprises an —OH, —NHR or —SH group. In some embodiments, in a provided compound of formula II, D is connected to L through $R^5$. In some embodiments, $R^5$ comprises an —OH, —NHR or —SH group for conjugation. In some embodiments, $R^5$ comprises an —OH group, and D is connected to L through the —OH group. In some embodiments, the —OH group reacts with a functional group in L or M to form, for example, an ether, ester, carbamate or carbonate ester. In some embodiments, $R^5$ reacts with a functional group in L to form a carbonate ester. In some embodiments, $R^5$ comprises an amino group, and D is connected to L through the amino group. In some embodiments, $R^5$ comprises a —NHR group. In some embodiments, $R^5$ comprises a —NH$_2$ group. In some embodiments, the amino group reacts with a functional group in L or M to form, for example, an amine, imine, amide or carbamate. In some embodiments, $R^5$ comprises an —SH group, and D is connected to L through the —SH group. In some embodiments, the —SH group reacts with a functional group in L or M to form, for example, a disulfide, thioether or thioester.

As generally defined above, each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form =O, =C(R)$_2$ or =NR.

In some embodiments, each of $R^6$ and $R^{6'}$ is hydrogen. In some embodiments, each of $R^6$ and $R^{6'}$ is independently R.

In some embodiments, one of $R^6$ and $R^{6'}$ is hydrogen, and the other is R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$. In some embodiments, one of $R^6$ and $R^{6'}$ is hydrogen, and the other is R. In some embodiments, one of $R^6$ and $R^{6'}$ is hydrogen, and the other is halogen. In some embodiments, one of $R^6$ and $R^{6'}$ is hydrogen, and the other is —CN. In some embodiments, one of $R^6$ and $R^{6'}$ is hydrogen, and the other is —NO$_2$. In some embodiments, one of $R^6$ and $R^{6'}$ is hydrogen, and the other is —OR. In some embodiments, one of $R^6$ and $R^{6'}$ is hydrogen, and the other is —SR. In some embodiments, one of $R^6$ and $R^{6'}$ is hydrogen, and the other is —N(R)$_2$. In some embodiments, one of $R^6$ and $R^{6'}$ is hydrogen, and the other is —S(O)$_2$R. In some embodiments, one of $R^6$ and $R^{6'}$ is hydrogen, and the other is —S(O)$_2$N(R)$_2$. In some embodiments, one of $R^6$ and $R^{6'}$ is hydrogen, and the other is —S(O)R. In some embodiments, one of $R^6$ and $R^{6'}$ is hydrogen, and the other is —C(O)R. In some embodiments, one of $R^6$ and $R^{6'}$ is hydrogen, and the other is —C(O)OR. In some embodiments, one of $R^6$ and $R^{6'}$ is hydrogen, and the other is —C(O)N(R)$_2$. In some embodiments, one of $R^6$ and $R^{6'}$ is hydrogen, and the other is —C(O)N(R)—OR. In some embodiments, one of $R^6$ and $R^{6'}$ is hydrogen, and the other is —N(R)C(O)OR. In some embodiments, one of $R^6$ and $R^{6'}$ is hydrogen, and the other is —N(R)C(O)N(R)$_2$. In some embodiments, one of $R^6$ and $R^{6'}$ is hydrogen, and the other is —N(R)S(O)$_2$R. In some embodiments, one of $R^6$ and $R^{6'}$ is hydrogen, and the other is —OSi(R)$_3$. In some embodiments, one of $R^6$ and $R^{6'}$ is hydrogen, and the other is —OSi(R)$_3$, wherein one R is optionally substituted indolyl. In some embodiments, one of $R^6$ and $R^{6'}$ is hydrogen, and the other is —OSi(R)$_3$, wherein one R is optionally substituted indol-2-yl. In some embodiments, one of $R^6$ and $R^{6'}$ is hydrogen, and the other is —OSi(R)$_3$, wherein one R is optionally substituted

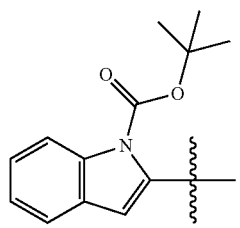

In some embodiments, one of $R^6$ and $R^{6'}$ is hydrogen, and the other is

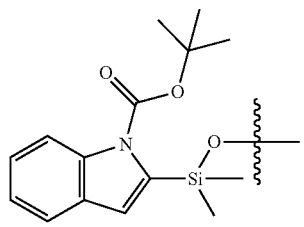

In some embodiments, $R^6$ and $R^{6'}$ are taken together to form =O, =C(R)$_2$ or =NR. In some embodiments, $R^6$ and $R^{6'}$ are taken together to form =O. In some embodiments, $R^6$ and $R^{6'}$ are taken together to form =C(R)$_2$. In some embodiments, $R^6$ and $R^{6'}$ are taken together to form =NR.

In some embodiments, $R^6$ is R. In some embodiments, $R^6$ is hydrogen. In some embodiments, $R^6$ is an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^6$ is halogen. In some embodiments, $R^6$ is —F. In some embodiments, $R^6$ is —Cl. In some embodiments, $R^6$ is —Br. In some embodiments, $R^6$ is —I.

In some embodiments, $R^6$ is —CN. In some embodiments, $R^6$ is —NO$_2$. In some embodiments, $R^6$ is —OR. In some embodiments, $R^6$ is —SR. In some embodiments, $R^6$ is —N(R)$_2$. In some embodiments, $R^6$ is —S(O)$_2$R. In some embodiments, $R^6$ is —S(O)$_2$N(R)$_2$. In some embodiments, $R^6$ is —S(O)R. In some embodiments, $R^6$ is —C(O)R. In some embodiments, $R^6$ is —C(O)OR. In some embodiments, $R^6$ is —C(O)N(R)$_2$. In some embodiments, $R^6$ is —C(O)N(R)—OR. In some embodiments, $R^6$ is —N(R)C(O)OR. In some embodiments, $R^6$ is —N(R)C(O)N(R)$_2$. In some embodiments, $R^6$ is —N(R)S(O)$_2$R. In some embodiments, $R^6$ is —OSi(R)$_3$. In some embodiments, $R^6$ is —OSi(R)$_3$, wherein one R is optionally substituted indolyl. In some embodiments, $R^6$ is —OSi(R)$_3$, wherein one R is optionally substituted indol-2-yl. In some embodiments, $R^6$ is —OSi(R)$_3$, wherein one R is

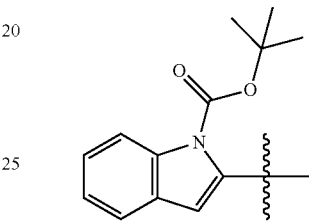

In some embodiments, $R^6$ is

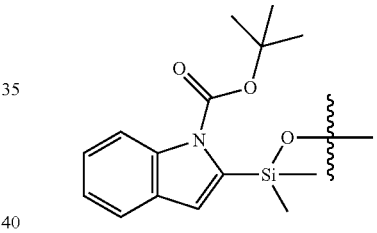

In some embodiments, $R^6$ is hydrogen, and $R^{6'}$ is R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$.

In some embodiments, $R^{6'}$ is R. In some embodiments, $R^{6'}$ is hydrogen. In some embodiments, $R^{6'}$ is an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^{6'}$ is halogen. In some embodiments, $R^{6'}$ is —F. In some embodiments, $R^{6'}$ is —Cl. In some embodiments, $R^{6'}$ is —Br. In some embodiments, $R^{6'}$ is —I.

In some embodiments, $R^{6'}$ is —CN. In some embodiments, $R^{6'}$ is —NO$_2$. In some embodiments, $R^{6'}$ is —OR. In some embodiments, $R^{6'}$ is —SR. In some embodiments, $R^{6'}$ is —N(R)$_2$. In some embodiments, $R^{6'}$ is —S(O)$_2$R. In some embodiments, $R^{6'}$ is —S(O)$_2$N(R)$_2$. In some embodiments, $R^{6'}$ is —S(O)R. In some embodiments, $R^{6'}$ is —C(O)R. In some embodiments, $R^{6'}$ is —C(O)OR. In some embodiments, $R^{6'}$ is —C(O)N(R)$_2$. In some embodiments, $R^{6'}$ is —C(O)N(R)—OR. In some embodiments, $R^{6'}$ is —N(R)C(O)OR. In some embodiments, $R^{6'}$ is —N(R)C(O)N(R)$_2$. In some embodiments, $R^{6'}$ is —N(R)S(O)$_2$R. In some embodiments, $R^{6'}$ is —OSi(R)$_3$. In some embodiments, $R^{6'}$ is —OSi(R)$_3$, wherein one R is optionally substituted indolyl. In some embodiments, $R^{6'}$ is —OSi(R)$_3$, wherein one R is optionally substituted indol-2-yl. In some embodiments, $R^{6'}$ is —OSi(R)$_3$, wherein one R is

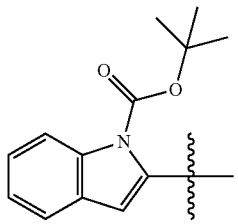

In some embodiments, $R^{6'}$ is

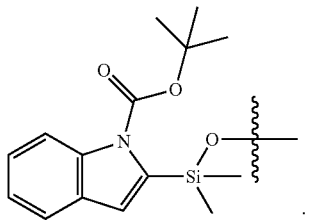 [SMILES: *O[Si](C)(C)c1cc2ccccc2n1C(=O)OC(C)(C)C]

In some embodiments, n is 0, 1, 2, 3 or 4. In some embodiments, n is 0. In some embodiments, n is 1-4. In some embodiments, n is 1. In some embodiments, n is 2. In some embodiments, n is 3. In some embodiments, n is 4.

In some embodiments, $R^6$ comprises an —OH, —NHR or —SH group. In some embodiments, in a provided compound of formula II, D is connected to L through $R^6$. In some embodiments, $R^6$ comprises an —OH, —NHR or —SH group for conjugation. In some embodiments, $R^6$ comprises an —OH group, and D is connected to L through the —OH group. In some embodiments, the —OH group reacts with a functional group in L or M to form, for example, an ether, ester, carbamate or carbonate ester. In some embodiments, $R^6$ reacts with a functional group in L to form a carbonate ester. In some embodiments, $R^6$ comprises an amino group, and D is connected to L through the amino group. In some embodiments, $R^6$ comprises a —NHR group. In some embodiments, $R^6$ comprises a —NH$_2$ group. In some embodiments, the amino group reacts with a functional group in L or M to form, for example, an amine, imine, amide or carbamate. In some embodiments, $R^6$ comprises an —SH group, and D is connected to L through the —SH group. In some embodiments, the —SH group reacts with a functional group in L or M to form, for example, a disulfide, thioether or thioester.

In some embodiments, $R^{6'}$ comprises an —OH, —NHR or —SH group. In some embodiments, in a provided compound of formula II, D is connected to L through $R^{6'}$. In some embodiments, $R^{6'}$ comprises an —OH, —NHR or —SH group for conjugation. In some embodiments, $R^{6'}$ comprises an —OH group, and D is connected to L through the —OH group. In some embodiments, the —OH group reacts with a functional group in L or M to form, for example, an ether, ester, carbamate or carbonate ester. In some embodiments, $R^{6'}$ reacts with a functional group in L to form a carbonate ester. In some embodiments, $R^{6'}$ comprises an amino group, and D is connected to L through the amino group. In some embodiments, $R^{6'}$ comprises a —NHR group. In some embodiments, $R^{6'}$ comprises a —NH$_2$ group. In some embodiments, the amino group reacts with a functional group in L or M to form, for example, an amine, imine, amide or carbamate. In some embodiments, $R^{6'}$ comprises an —SH group, and D is connected to L through the —SH group. In some embodiments, the —SH group reacts with a functional group in L or M to form, for example, a disulfide, thioether or thioester.

As generally defined above, each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$; or two $R^7$ are taken together with their intervening atoms to form an optionally substituted 4-7 membered ring having 0-2 heteroatoms independently selected from nitrogen, oxygen, or sulfur. In some embodiments, each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$. In some embodiments, two $R^7$ are taken together with their intervening atoms to form an optionally substituted 4-7 membered ring having 0-2 heteroatoms independently selected from nitrogen, oxygen, or sulfur.

In some embodiments, $R^7$ is R. In some embodiments, $R^7$ is hydrogen. In some embodiments, $R^7$ is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is halogen. In some embodiments, $R^7$ is —F. In some embodiments, $R^7$ is —Cl. In some embodiments, $R^7$ is —Br. In some embodiments, $R^7$ is —I.

In some embodiments, $R^7$ is —CN. In some embodiments, $R^7$ is —NO$_2$. In some embodiments, $R^7$ is —OR. In some embodiments, $R^7$ is —OSi(R)$_3$. In some embodiments, $R^7$ is —SR. In some embodiments, $R^7$ is —N(R)$_2$. In some embodiments, $R^7$ is —S(O)$_2$R. In some embodiments, $R^7$ is —S(O)$_2$OR. In some embodiments, $R^7$ is —S(O)$_2$N(R)$_2$. In some embodiments, $R^7$ is —S(O)R. In some embodiments, $R^7$ is —C(O)R. In some embodiments, $R^7$ is —C(O)OR. In some embodiments, $R^7$ is —C(O)N(R)$_2$. In some embodiments, $R^7$ is —C(O)N(R)—OR. In some embodiments, $R^7$ is —N(R)C(O)OR. In some embodiments, $R^7$ is —N(R)C(O)N (R)$_2$. In some embodiments, R$^7$ is —N(R)S(O)$_2$R. In some embodiments, R$^7$ is —P(R)$_2$. In some embodiments, R$^7$ is —P(OR)$_2$. In some embodiments, R$^7$ is —P(O)(R)$_2$. In some embodiments, R$^7$ is —P(O)(OR)$_2$. In some embodiments, R$^7$ is —P(O)[N(R)$_2$]$_2$. In some embodiments, R$^7$ is —B(R)$_2$. In some embodiments, R$^7$ is —B(OR)$_2$. In some embodiments, R$^7$ is —Si(R)$_3$.

In some embodiments, R$^7$ is an electron-withdrawing group. In some embodiments, R$^7$ is an electron-donating group.

In some embodiments, n is 1, 2, 3 or 4, and at least one R$^7$ is not hydrogen.

In some embodiments, R$^7$ comprises an —OH, —NHR or —SH group. In some embodiments, in a provided compound of formula II, D is connected to L through R$^7$. In some embodiments, R$^7$ comprises an —OH, —NHR or —SH group for conjugation. In some embodiments, R$^7$ comprises an —OH group, and D is connected to L through the —OH group. In some embodiments, the —OH group reacts with a functional group in L or M to form, for example, an ether, ester, carbamate or carbonate ester. In some embodiments, R$^7$ reacts with a functional group in L to form a carbonate ester. In some embodiments, R$^7$ comprises an amino group, and D is connected to L through the amino group. In some embodiments, R$^7$ comprises a —NHR group. In some embodiments, R$^7$ comprises a —NH$_2$ group. In some embodiments, the amino group reacts with a functional group in L or M to form, for example, an amine, imine, amide or carbamate. In some embodiments, R$^7$ comprises an —SH group, and D is connected to L through the —SH group. In some embodiments, the —SH group reacts with a functional group in L or M to form, for example, a disulfide, thioether or thioester.

As generally defined above, each R$^8$ is independently —(S)$_m$—R$^x$ wherein m is 1-3 and R$^x$ is R, —SR, —C(O)R, —C(O)OR, —C(O)N(R)$_2$, —C(S)R, —S(O)R, —S(O)$_2$R, or —S(O)$_2$N(R)$_2$, or R$^8$ and R$^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—. In some embodiments, each R$^8$ is independently —(S)$_m$—R$^x$ wherein m is 1-3 and R$^x$ is R, —SR, —C(O)R, —C(O)OR, —C(O)N(R)$_2$, —C(S)R, —S(O)R, —S(O)$_2$R, or —S(O)$_2$N(R)$_2$.

In some embodiments, m is 1. In some embodiments, m is 2-3. In some embodiments, m is 2. In some embodiments, m is 3.

In some embodiments, R$^8$ can be converted to —(S)$_m$—H or to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$— with R$^9$ when administered to a subject. In some embodiments, R$^8$ can be converted to —(S)$_m$—H or to form —(S)$_m$—(S)$_p$—, —(S)$_m$—C(O)—(S)$_p$—, —(S)$_m$—C(S)—(S)$_p$—, —(S)$_m$—S(O)—(S)$_p$—, or (S)$_m$—S(O)$_2$—(S)$_p$— with R$^9$ when administered to a subject.

In some embodiments, R$^x$ is R. In some embodiments, R$^8$ is —(S)$_m$—R. In some embodiments, R$^8$ is —(S)$_m$—R, wherein R$^8$ can be converted to —(S)$_m$—H or to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$— with R$^9$ when administered to a subject. In some embodiments, R$^8$ is —(S)$_m$—R, wherein R$^8$ can be converted to —(S)$_m$—H or to form —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$— with R$^9$ when administered to a subject. In some embodiments, R$^8$ is —SR. In some embodiments, R$^8$ is —S—S—R. In some embodiments, R$^8$ is —S—S—S—R. In some embodiments, R$^8$ is —(S)$_m$—R, wherein R is a cleavable group. In some embodiments, R is a cleavage group and when a provided compound is administered to a subject, —(S)$_m$—R is converted to —(S)$_m^-$. In some embodiments, R$^8$ is —(S)$_m$—R, wherein R is connected to —(S)$_m$— via a carbon atom, wherein the carbon atom is substituted with a divalent substituent. In some embodiments, R$^8$ is —(S)$_m$—R, wherein R is heteroalkyl. In some embodiments, R$^8$ is methyl. In some embodiments, R$^8$ is CPh$_3$. In some embodiments, R$^8$ is benzyl. In some embodiments, R$^8$ is acetyl. In some embodiments, R$^1$ is methoxymethyl. In some embodiments, R$^8$ is β-methoxyethoxymethyl.

In some embodiments, R$^x$ is —SR. In some embodiments, R$^x$ is —SMe. In some embodiments, R$^8$ is —(S)$_m$—SR. In some embodiments, R$^8$ is —S—SR. In some embodiments, R$^8$ is —S—S—SR. In some embodiments, R$^8$ is —S—S—S—SR.

In some embodiments, R$^x$ is —C(O)R. In some embodiments, R$^8$ is —(S)$_m$—C(O)R. In some embodiments, R$^8$ is —S—C(O)R. In some embodiments, R$^8$ is —S—S—C(O)R. In some embodiments, R$^8$ is —S—S—S—C(O)R. In some embodiments, R$^8$ is —(S)$_m$—C(O)R, where R is methyl. In some embodiments, R$^8$ is —(S)$_m$—C(O)R, where R is isopropyl.

In some embodiments, R$^x$ is —C(O)OR. In some embodiments, R$^8$ is —(S)$_m$—C(O)OR. In some embodiments, R$^8$ is —S—C(O)OR. In some embodiments, R$^8$ is —S—S—C(O)OR. In some embodiments, R$^8$ is —S—S—S—C(O)OR.

In some embodiments, R$^x$ is —C(O)N(R)$_2$. In some embodiments, R$^8$ is —(S)$_m$—C(O)N(R)$_2$. In some embodiments, R$^8$ is —S—C(O)N(R)$_2$. In some embodiments, R$^8$ is —S—S—C(O)N(R)$_2$. In some embodiments, R$^8$ is —S—S—S—C(O)N(R)$_2$.

In some embodiments, R$^x$ is —C(S)R. In some embodiments, R$^8$ is —(S)$_m$—C(S)R. In some embodiments, R$^8$ is —S—C(S)R. In some embodiments, R$^8$ is —S—S—C(S)R. In some embodiments, R$^8$ is —S—S—S—C(S)R.

In some embodiments, R$^x$ is —S(O)R. In some embodiments, R$^8$ is —(S)$_m$—S(O)R. In some embodiments, R$^8$ is —S—S(O)R. In some embodiments, R$^8$ is —S—S—S(O)R. In some embodiments, R$^8$ is —S—S—S—S(O)R.

In some embodiments, R$^x$ is —S(O)$_2$R. In some embodiments, R$^8$ is —(S)$_m$—S(O)$_2$R. In some embodiments, R$^8$ is —S—S(O)$_2$R. In some embodiments, R$^8$ is —S—S—S(O)$_2$R. In some embodiments, R$^8$ is —S—S—S—S(O)$_2$R.

In some embodiments, R$^x$ is —S(O)$_2$N(R)$_2$. In some embodiments, R$^8$ is —(S)$_m$—S(O)$_2$N(R)$_2$. In some embodiments, R$^8$ is —S—S(O)$_2$N(R)$_2$. In some embodiments, R$^8$ is —S—S—S(O)$_2$N(R)$_2$. In some embodiments, R$^8$ is —S—S—S—S(O)$_2$N(R)$_2$.

In some embodiments, R$^8$ comprises an —OH, —NHR or —SH group. In some embodiments, in a provided compound of formula II, D is connected to L through R$^8$. In some embodiments, R$^8$ comprises an —OH, —NHR or —SH group for conjugation. In some embodiments, R$^8$ comprises an —OH group, and D is connected to L through the —OH group. In some embodiments, the —OH group reacts with a functional group in L or M to form, for example, an ether, ester, carbamate or carbonate ester. In some embodiments, R$^8$ reacts with a functional group in L to form a carbonate ester. In some embodiments, R$^8$ comprises an amino group, and D is connected to L through the amino group. In some embodiments, R$^8$ comprises a —NHR group. In some embodiments, R$^8$ comprises a —NH$_2$ group. In some embodiments, the amino group reacts with a functional group in L or M to form, for example, an amine, imine, amide or carbamate. In some embodiments, R$^8$ comprises an —SH group, and D is connected to L through the —SH group. In some embodiments, the —SH group reacts with a functional group in L or M to form, for example, a disulfide, thioether or thioester.

As generally defined above, each $R^9$ is independently —$(S)_p$—$R^y$ wherein p is 1-3 such that m+p is 2-4 and $R^y$ is R, —SR, —C(O)R, —C(O)OR, —C(O)N(R)$_2$, —C(S)R, —S(O)R, —S(O)$_2$R, or —S(O)$_2$N(R)$_2$; or $R^8$ and $R^9$ are taken together to form —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$—. In some embodiments, $R^9$ is —$(S)_p$—$R^y$ wherein p is 1-3 such that m+p is 2-4 and $R^y$ is R, —SR, —C(O)R, —C(O)OR, —C(O)N(R)$_2$, —C(S)R, —S(O)R, —S(O)$_2$R, or —S(O)$_2$N(R)$_2$. In some embodiments, $R^8$ and $R^9$ are taken together to form —S—, —$(S)_m$—[C(R)$_2$]$_q$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$—. In some embodiments, $R^8$ and $R^9$ are taken together to form —S—, —$(S)_m$—C(R)$_2$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$—. In some embodiments, $R^8$ and $R^9$ are taken together to form —$(S)_m$—$(S)_p$—, —$(S)_m$—C(O)—$(S)_p$, —$(S)_m$—C(S)—$(S)_p$—, —$(S)_m$—S(O)—$(S)_p$—, or —$(S)_m$—S(O)$_2$—$(S)_p$—. In some embodiments, $R^8$ and $R^9$ are taken together to form —S—. In some embodiments, $R^8$ and $R^9$ are taken together to form —$(S)_m$—[C(R)$_2$]$_q$—$(S)_p$—. In some embodiments, $R^8$ and $R^9$ are taken together to form —$(S)_m$—C(R)$_2$—$(S)_p$—. In some embodiments, $R^8$ and $R^9$ are taken together to form —$(S)_m$—CH—$(S)_p$—. In some embodiments, $R^8$ and $R^9$ are taken together to form —S—CH$_2$—S—. In some embodiments, $R^8$ and $R^9$ are taken together to form —$(S)_m$—$(S)_p$—. In some embodiments, $R^8$ and $R^9$ are taken together to form —S—S—. In some embodiments, $R^8$ and $R^9$ are taken together to form —S—S—S—. In some embodiments, $R^8$ and $R^9$ are taken together to form —S—S—S—S—. In some embodiments, $R^8$ and $R^9$ are taken together to form —$(S)_m$—C(O)—$(S)_p$—. In some embodiments, $R^8$ and $R^9$ are taken together to form —S—C(O)—S—. In some embodiments, $R^8$ and $R^9$ are taken together to form —$(S)_m$—C(S)—$(S)_p$—. In some embodiments, $R^8$ and $R^9$ are taken together to form —S—C(S)—S—. In some embodiments, $R^8$ and $R^9$ are taken together to form —$(S)_m$—S(O)—$(S)_p$—. In some embodiments, $R^8$ and $R^9$ are taken together to form —S—S(O)—S—. In some embodiments, $R^8$ and $R^9$ are taken together to form —$(S)_m$—S(O)$_2$—$(S)_p$—. In some embodiments, $R^8$ and $R^9$ are taken together to form —S—S(O)$_2$—S—.

In some embodiments, p is 1. In some embodiments, p is 2-3. In some embodiments, p is 2. In some embodiments, p is 3.

In some embodiments, m+p is 2-4. In some embodiments, m+p is 3-4. In some embodiments, m+p is 2. In some embodiments, m+p is 3. In some embodiments, m+p is 4.

In some embodiments, $R^9$ can be converted to —$(S)_p$—H or to form —S—, —$(S)_m$—[C(R)$_2$]$_q$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$— with $R^8$ when administered to a subject. In some embodiments, $R^9$ can be converted to —$(S)_p$—H or to form —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$$(S)_p$— with $R^8$ when administered to a subject.

In some embodiments, $R^y$ is R. In some embodiments, $R^9$ is —$(S)_p$—R. In some embodiments, $R^9$ is —$(S)_p$—R, wherein $R^9$ can be converted to —$(S)_p$—H or to form —S—, —(S)—[C(R)$_2$]$_q$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$— with $R^8$ when administered to a subject. In some embodiments, $R^9$ is —$(S)_p$—R, wherein $R^9$ can be converted to —$(S)_p$—H or to form —$(S)_m$—$(S)_p$—, —$(S)_m$—C(O)—, —$(S)_m$—C(S)—$(S)_p$—, —$(S)_m$—S(O)—$(S)_p$—, or —$(S)_m$—S(O)$_2$—$(S)_p$— with $R^8$ when administered to a subject. In some embodiments, $R^9$ is —SR. In some embodiments, $R^9$ is —S—S—R. In some embodiments, $R^9$ is —S—S—S—R. In some embodiments, $R^9$ is —$(S)_p$—R, wherein R is a cleavable group. In some embodiments, R is a cleavage group and when a provided compound is administered to a subject, —$(S)_p$—R is converted to —$(S)_p$—. In some embodiments, $R^9$ is —$(S)_p$—R, wherein R is connected to —$(S)_m$— via a carbon atom, wherein the carbon atom is substituted with a divalent substituent. In some embodiments, $R^9$ is —$(S)_p$—R, wherein R is heteroalkyl. In some embodiments, $R^9$ is methyl. In some embodiments, $R^9$ is CPh$_3$. In some embodiments, $R^9$ is benzyl. In some embodiments, $R^9$ is acetyl. In some embodiments, $R^1$ is methoxymethyl. In some embodiments, $R^9$ is β-methoxyethoxymethyl.

In some embodiments, $R^y$ is —SR. In some embodiments, $R^y$ is —SMe. In some embodiments, $R^9$ is —$(S)_p$—SR. In some embodiments, $R^9$ is —S—SR. In some embodiments, $R^9$ is —S—S—SR. In some embodiments, $R^9$ is —S—S—S—SR.

In some embodiments, $R^y$ is —C(O)R. In some embodiments, $R^9$ is —$(S)_p$—C(O)R. In some embodiments, $R^9$ is —S—C(O)R. In some embodiments, $R^9$ is —S—S—C(O)R. In some embodiments, $R^9$ is —S—S—S—C(O)R. In some embodiments, $R^9$ is —$(S)_p$—C(O)R, where R is methyl. In some embodiments, $R^9$ is —$(S)_p$—C(O)R, where R is isopropyl.

In some embodiments, $R^y$ is —C(O)OR. In some embodiments, $R^9$ is —$(S)_m$—C(O)OR. In some embodiments, $R^9$ is —S—C(O)OR. In some embodiments, $R^9$ is —S—S—C(O)OR. In some embodiments, $R^9$ is —S—S—S—C(O)OR.

In some embodiments, $R^y$ is —C(O)N(R)$_2$. In some embodiments, $R^9$ is —$(S)_p$—C(O)N(R)$_2$. In some embodiments, $R^9$ is —S—C(O)N(R)$_2$. In some embodiments, $R^9$ is —S—S—C(O)N(R)$_2$. In some embodiments, $R^9$ is —S—S—S—C(O)N(R)$_2$.

In some embodiments, $R^y$ is —C(S)R. In some embodiments, $R^9$ is —$(S)_p$—C(S)R. In some embodiments, $R^9$ is —S—C(S)R. In some embodiments, $R^9$ is —S—S—C(S)R. In some embodiments, $R^9$ is —S—S—S—C(S)R.

In some embodiments, $R^y$ is —S(O)R. In some embodiments, $R^9$ is —$(S)_p$—S(O)R. In some embodiments, $R^9$ is —S—S(O)R. In some embodiments, $R^9$ is —S—S—S(O)R. In some embodiments, $R^9$ is —S—S—S—S(O)R.

In some embodiments, $R^y$ is —S(O)$_2$$R^y$. In some embodiments, $R^y$ is —$(S)_p$—S(O)$_2$R. In some embodiments, $R^9$ is —S—S(O)$_2$R. In some embodiments, $R^9$ is —S—S—S(O)$_2$R. In some embodiments, $R^9$ is —S—S—S—S(O)$_2$R.

In some embodiments, $R^y$ is —S(O)$_2$N(R)$_2$. In some embodiments, $R^9$ is —$(S)_p$—S(O)$_2$N(R)$_2$. In some embodiments, $R^9$ is —S—S(O)$_2$N(R)$_2$. In some embodiments, $R^9$ is —S—S—S(O)$_2$N(R)$_2$. In some embodiments, $R^9$ is —S—S—S—S(O)$_2$N(R)$_2$.

In some embodiments, $R^8$ is —$(S)_m$—$R^x$ wherein m is 1-3 and $R^x$ is —SR, —C(O)R, —C(O)OR, —C(O)N(R)$_2$, —C(S)R, —S(O)R, —S(O)$_2$R, or —S(O)$_2$N(R)$_2$; $R^9$ is —$(S)_p$—$R^y$ wherein p is 1-3 such that m+p is 2-4 and $R^y$ is —SR, —C(O)R, —C(O)OR, —C(O)N(R)$_2$, —C(S)R, —S(O)R, —S(O)$_2$R, or —S(O)$_2$N(R)$_2$; or $R^8$ and $R^9$ are taken together to form —S—, —$(S)_m$—[C(R)$_2$]$_q$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$—.

In some embodiments, $R^9$ comprises an —OH, —NHR or —SH group. In some embodiments, in a provided compound of formula II, D is connected to L through $R^9$. In some embodiments, $R^9$ comprises an —OH, —NHR or —SH group for conjugation. In some embodiments, $R^9$ comprises an —OH group, and D is connected to L through the —OH group. In some embodiments, the —OH group reacts with a functional group in L or M to form, for example, an ether, ester, carbamate or carbonate ester. In some embodiments, $R^9$ reacts with a functional group in L to form a carbonate ester. In some embodiments, $R^9$ comprises an amino group, and D is connected to L through the amino group. In some embodiments, $R^9$ comprises a —NHR group. In some embodiments, $R^9$ comprises a —NH$_2$ group. In some embodiments, the amino group reacts with a functional group in L or M to form, for example, an amine, imine, amide or carbamate. In some embodiments, $R^9$ comprises an —SH group, and D is connected to L through the —SH group. In some embodiments, the —SH group reacts with a functional group in L or M to form, for example, a disulfide, thioether or thioester.

In some embodiments, neither of $R^8$ and $R^9$ of a provided compound is on the α-face of the DKP. In some embodiments, $R^8$ and $R^9$ are on the same face of the hexahydropyrrolo[1,2-a]pyrazine-1,4-dione moiety as N1. In some embodiments, a provided compound is a prodrug. In some embodiments, each of $R^8$ and $R^9$ is independently —SR, wherein $R^8$ and $R^9$ can be readily converted into —(S)$_m$—(S)$_p$— when administered to a subject. In some embodiments, the present invention provides a method for optimizing an ETP or thiodiketopiperazine compound or a derivative or an analog thereof, comprising keeping the sulfur-containing groups on the same surface of the hexahydropyrrolo[1,2-a]pyrazine-1,4-dione moiety as N1.

As generally defined above, each D independently has the structure of formula I-c or I-d:

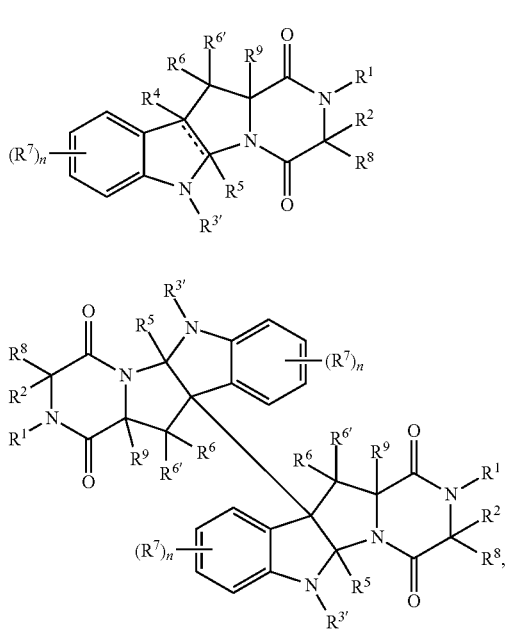

In some embodiments, D is a compound of formula I-c. In some embodiments, D is a compound of formula I-d. In some embodiments, D is a compound of formula I-a. In some embodiments, D is a compound of formula I-b. When D is a compound, it is understood that said compound is bonded to L. A compound as a D unit can bond to L through any suitable atom. In some embodiments, one or more of $R^1$, $R^2$, $R^3$, $R^{3'}$, $R^4$, $R^5$, $R^6$, $R^{6'}$, $R^7$, $R^8$ and $R^9$ groups are independently linked to L. In some embodiments, $R^1$ is linked to L. In some embodiments, $R^2$ is linked to L. In some embodiments, $R^3$ is linked to L. In some embodiments, $R^{3'}$ is linked to L. In some embodiments, $R^4$ is linked to L. In some embodiments, $R^5$ is linked to L. In some embodiments, $R^6$ is linked to L. In some embodiments, $R^{6'}$ is linked to L. In some embodiments, $R^7$ is linked to L. In some embodiments, $R^8$ is linked to L. In some embodiments, $R^9$ is linked to L. In some embodiments, D is linked to L through $R^2$ or $R^{3'}$. In some embodiments, D is linked to L through $R^2$ or $R^3$.

In some embodiments, t is 1-10. In some embodiments, t is 1-2. In some embodiments, t is 1-3. In some embodiments, t is 1-4. In some embodiments, t is 1-5. In some embodiments, t is 1-6. In some embodiments, t is 1-7. In some embodiments, t is 1-8. In some embodiments, t is 1-9. In some embodiments, t is 1-10. In some embodiments, t is 2-3. In some embodiments, t is 2-4. In some embodiments, t is 2-5. In some embodiments, t is 2-6. In some embodiments, t is 2-7. In some embodiments, t is 2-8. In some embodiments, t is 2-9. In some embodiments, t is 2-10. In some embodiments, t is 3-4. In some embodiments, t is 3-5. In some embodiments, t is 3-6. In some embodiments, t is 3-7. In some embodiments, t is 3-8. In some embodiments, t is 3-9. In some embodiments, t is 3-10. In some embodiments, t is 4-5. In some embodiments, t is 4-6. In some embodiments, t is 4-7. In some embodiments, t is 4-8. In some embodiments, t is 4-9. In some embodiments, t is 4-10. In some embodiments, t is 5-6. In some embodiments, t is 5-7. In some embodiments, t is 5-8. In some embodiments, t is 5-9. In some embodiments, t is 5-10. In some embodiments, t is 6-7. In some embodiments, t is 6-8. In some embodiments, t is 6-9. In some embodiments, t is 6-10. In some embodiments, t is 7-8. In some embodiments, t is 7-9. In some embodiments, t is 7-10. In some embodiments, t is 8-9. In some embodiments, t is 8-10. In some embodiments, t is 9-10. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10.

In some embodiments, t is greater than 1. In some embodiments, t is greater than one, and the D units attached to the same copy of M are the same. In some embodiments, t is greater than one, and all the D units attached to the same copy of M are not the same.

In some embodiments, s is 1-10. In some embodiments, s is 1-2. In some embodiments, s is 1-3. In some embodiments, s is 1-4. In some embodiments, s is 1-5. In some embodiments, s is 1-6. In some embodiments, s is 1-7. In some embodiments, s is 1-8. In some embodiments, s is 1-9. In some embodiments, s is 1-10. In some embodiments, s is 2-3. In some embodiments, s is 2-4. In some embodiments, s is 2-5. In some embodiments, s is 2-6. In some embodiments, s is 2-7. In some embodiments, s is 2-8. In some embodiments, s is 2-9. In some embodiments, s is 2-10. In some embodiments, s is 3-4. In some embodiments, s is 3-5. In some embodiments, s is 3-6. In some embodiments, s is 3-7. In some embodiments, s is 3-8. In some embodiments, s is 3-9. In some embodiments, s is 3-10. In some embodiments, s is 4-5. In some embodiments, s is 4-6. In some embodiments, s is 4-7. In some embodiments, s is 4-8. In some embodiments, s is 4-9. In some embodiments, s is 4-10. In some embodiments, s is 5-6. In some embodiments, s is 5-7. In some embodiments, s is 5-8. In some embodiments, s is 5-9. In some embodiments, s is 5-10. In some embodiments, s is 6-7. In some embodiments, s is 6-8. In some embodiments, s is 6-9. In some embodiments, s is 6-10. In some embodiments, s is 7-8. In some embodiments, s is 7-9. In some embodiments, s is 7-10. In some embodiments, s is 8-9. In some embodiments, s is 8-10. In some embodiments, s is 9-10. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10.

In some embodiments, s is greater than one, and the D units linked to the same copy of L are the same. In some embodiments, s is greater than one, and the D units linked to the same copy of L are not the same.

In some embodiments, s is smaller than 1. In some embodiments, s is 0.5. In some embodiments, a D unit is connected to two L units. In some embodiments, D has the structure of formula I-d, and is connected to two L units. In some embodiments, D has the structure of formula I-d, and each $R^2$ of D is independently connected to an L unit.

In some embodiments, molecules of formula II in a provided composition have different s or/and t values. In some embodiments, the s or/and t value for a composition is not an integer. In some embodiments, a composition is relatively homogenous, and s and t have narrower distributions than a relatively non-homogenous composition. In some embodiments, a composition is homogenous in that the s and t values for each molecule of formula II is the same.

In some embodiments, s=1. In some embodiments, a compound of formula II has the structure of formula II-c:

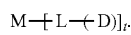

II-c

In some embodiments, a compound of formula II has the structure of formula II-d:

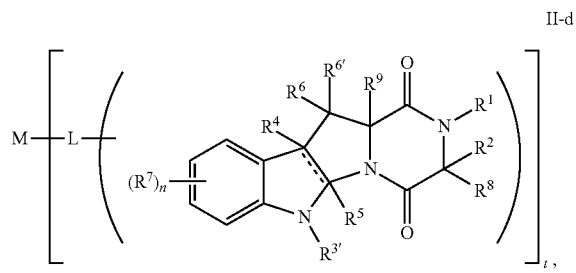

II-d or a pharmaceutically acceptable salt thereof, wherein each variable is independently as described in classes and subclasses herein, both singly and in combination.

In some embodiments, a compound of formula II has the structure of formula II-d:

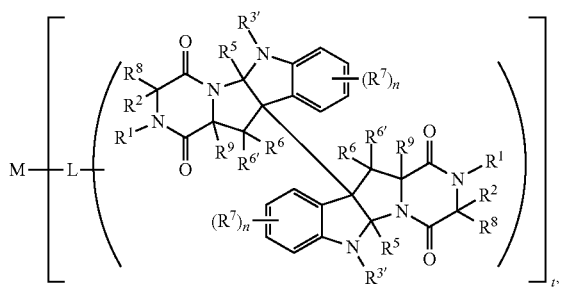

II-e or a pharmaceutically acceptable salt thereof, wherein each variable is independently as described in classes and subclasses herein, both singly and in combination.

In some embodiments, a compound of formula I has the structure of formula I-a-1.

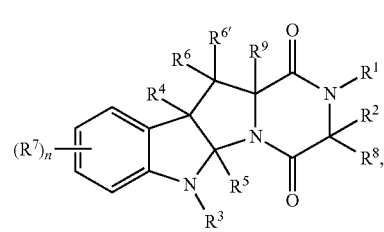

I-a-1 or a pharmaceutically acceptable salt thereof, wherein each variable is independently as described in classes and subclasses herein, both singly and in combination.

In some embodiments, a compound of formula I has the structure of formula I-a-2:

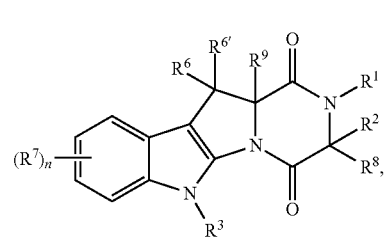

I-a-2 or a pharmaceutically acceptable salt thereof, wherein each variable is independently as described in classes and subclasses herein, both singly and in combination.

In some embodiments, a compound of formula I has the structure of formula I-a-3:

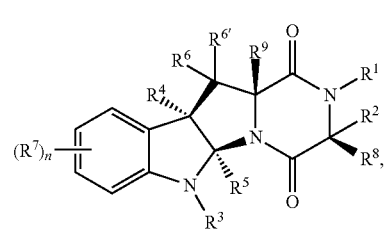

I-a-3 or a pharmaceutically acceptable salt thereof, wherein each variable is independently as described in classes and subclasses herein, both singly and in combination.

In some embodiments, a compound of formula I has the structure of formula I-a-4:

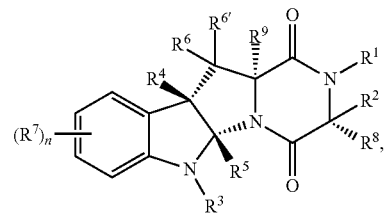

I-a-4 or a pharmaceutically acceptable salt thereof, wherein each variable is independently as described in classes and subclasses herein, both singly and in combination.

In some embodiments, a compound of formula I has the structure of formula I-a-5:

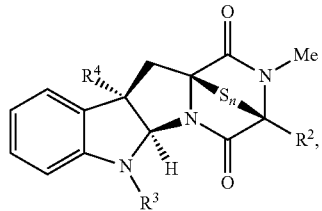

I-a-5 or a pharmaceutically acceptable salt thereof, wherein each variable is independently as defined above and described herein. In some embodiments, $R^2$ is —H or -Me; $R^3$ is —SO$_2$Ph, —H or —C(O)CF$_3$; $R^4$ is

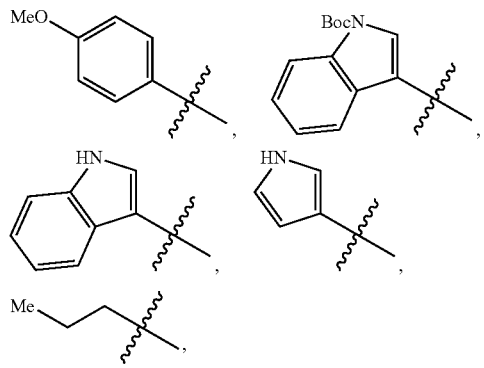

—F or —Br; and —S$_n$— is —S—S$_n$—S— wherein n is 0, 1, 2 or 3, —S—C(X)—S— wherein X is O or S, —S—, —SCH$_2$S—, or

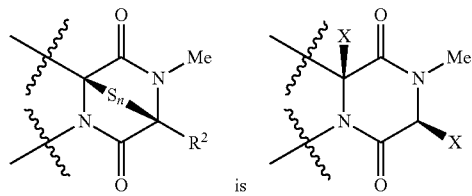

wherein X is —SBz, —S—C(O)R, —S—C(S)R or —S—SR. In some embodiments, $R^2$ is —H or -Me; $R^3$ is —SO$_2$Ph, —H or —C(O)CF$_3$; $R^4$ is

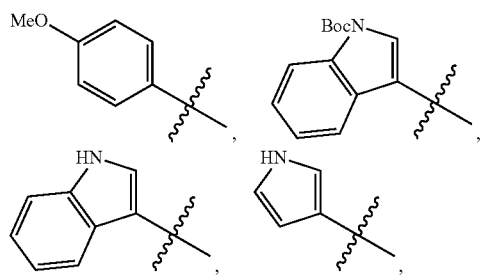

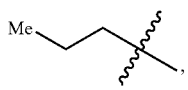

—F or —Br; and —S$_n$— is —S—S$_n$—S— wherein n is 0, 1, 2 or 3, —S—C(X)—S— wherein X is O or S, —S—, —SCH$_2$S—, or

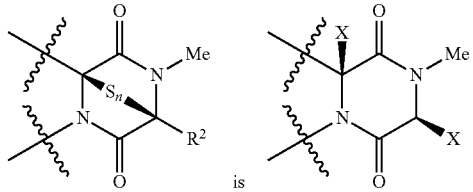

wherein X is —S—C(O)R, —S—C(S)R or —S—SR. In some embodiments, $R^2$ is —H or -Me; $R^3$ is —SO$_2$Ph, —H or —C(O)CF$_3$; $R^4$ is

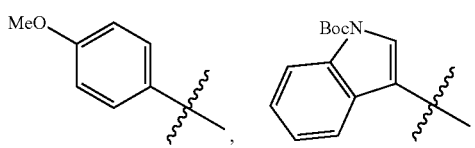

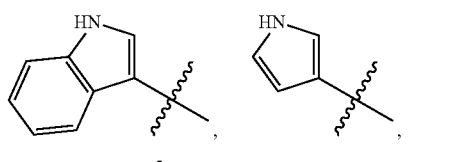

—F or —Br, and —S$_n$— is —S—S$_n$—S— wherein n is 0, 1, 2 or 3, —S—C(X)—S— wherein X is O or S, —S—, —SCH$_2$S—, or

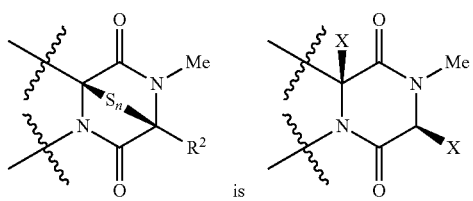

wherein X is —SAc or —S—SMe. In some embodiments, $R^2$ is —H or -Me; $R^3$ is —SO$_2$Ph; $R^4$ is

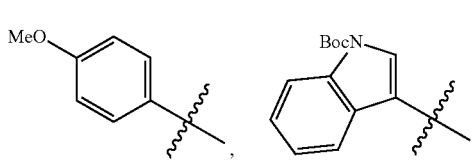

-continued

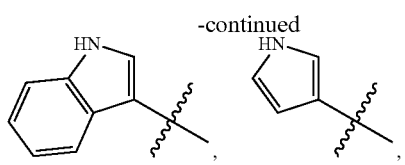
,

—F or —Br; and —$S_n$— is —S—$S_n$—S— wherein n is 0, 1, 2 or 3, —S—C(X)—S— wherein X is O or S, or

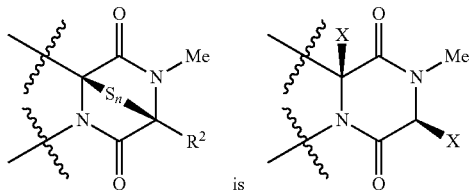
is wherein X is —SAc or —S—SMe.

In some embodiments, a compound of formula I has the structure of formula I-b-1:

I-b-1

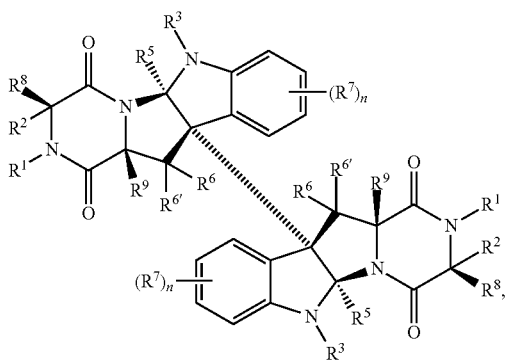

or a pharmaceutically acceptable salt thereof, wherein each variable is independently as described in classes and subclasses herein, both singly and in combination.

In some embodiments, a compound of formula I has the structure of formula I-b-2:

I-b-2

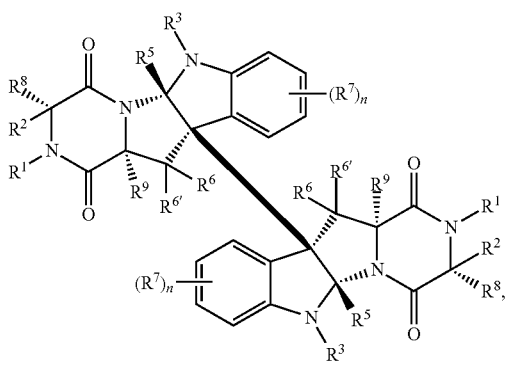

or a pharmaceutically acceptable salt thereof, wherein each variable is independently as described in classes and subclasses herein, both singly and in combination.

In some embodiments, a compound of formula I has the structure of formula I-b-3:

I-b-3

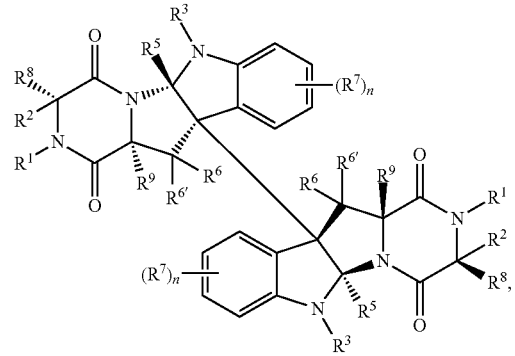

or a pharmaceutically acceptable salt thereof, wherein each variable is independently as described in classes and subclasses herein, both singly and in combination.

In some embodiments, a compound of formula I has the structure of formula I-b-4:

I-b-4

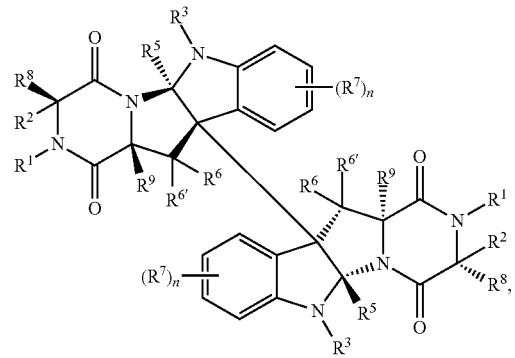

or a pharmaceutically acceptable salt thereof, wherein each variable is independently as described in classes and subclasses herein, both singly and in combination.

In some embodiments, a compound of formula I has the structure of formula I-b-5:

I-b-5

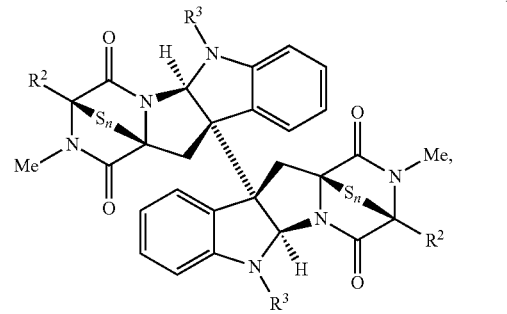

or a pharmaceutically acceptable salt thereof, wherein each variable is independently as defined above and described herein. In some embodiments, $R^2$ is -Me, —$CH_2OH$ or —$CH_2OAc$; $R^3$ is —$SO_2Ph$, —H or —$C(O)CF_3$; and —$S_n$— is —S—S$_n$—S— wherein n is 0, 1, 2 or 3, —S—C(X)—S— wherein X is O or S, —S—, —SCH$_2$S— or

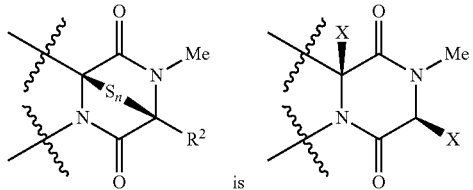 is wherein X is —SBz, —S—C(O)R, —S—C(S)—R, -or —S—SR. In some embodiments, R$^2$ is -Me, —CH$_2$OH or —CH$_2$OAc; R$^3$ is —SO$_2$Ph, —H or —C(O)CF$_3$; and —S$_n$— is —S—S$_n$—S— wherein n is 0, 1, 2 or 3, —S—C(X)—S— wherein X is O or S, —S—, —SCH$_2$S— or

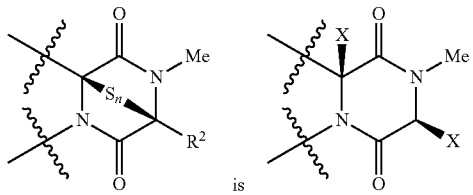 is wherein X is —S—C(O)R, —S—C(S)—R, -or —S—SR. In some embodiments, R$^2$ is -Me, —CH$_2$OH or —CH$_2$OAc; R$^3$ is —SO$_2$Ph, —H or —C(O)CF$_3$; and —S$_n$— is —S—S$_n$—S— wherein n is 0, 1, 2 or 3, —S—C(X)—S— wherein X is O or S, —S—, —SCH$_2$S—or

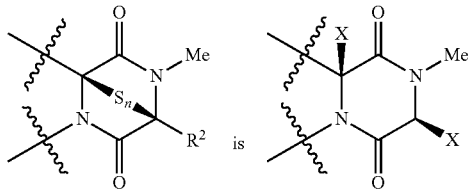 is wherein X is —SAc or —S—SMe. In some embodiments, R$^2$ is -Me, —CH$_2$OH or —CH$_2$OAc; R$^3$ is —SO$_2$Ph and —S$_n$— is —S—S$_n$—S— wherein n is 0, 1, 2 or 3, —S—C(X)—S— wherein X is O or S, or

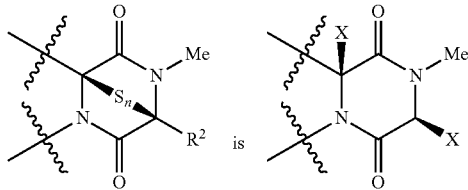

wherein X is —SAc or —S—SMe.

In some embodiments, D has the structure of formula I-c-1:

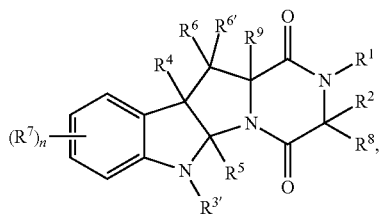

I-c-1 or a pharmaceutically acceptable salt thereof, wherein each variable is independently as described in classes and subclasses herein, both singly and in combination.

In some embodiments, D has the structure of formula I-c-2:

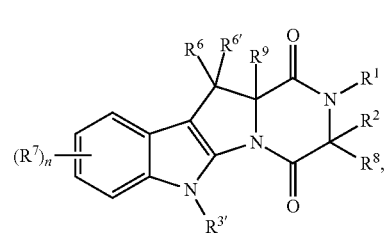

I-c-2 or a pharmaceutically acceptable salt thereof, wherein each variable is independently as described in classes and subclasses herein, both singly and in combination.

In some embodiments, D has the structure of formula I-c-3:

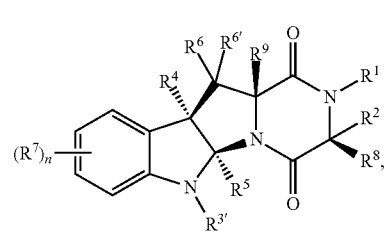

I-c-3 or a pharmaceutically acceptable salt thereof, wherein each variable is independently as described in classes and subclasses herein, both singly and in combination.

In some embodiments, a compound of formula I has the structure of formula I-c-4:

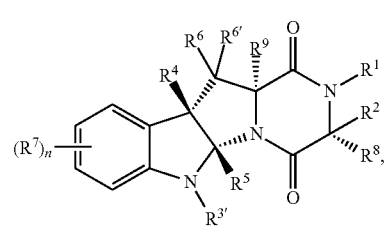

I-c-4 or a pharmaceutically acceptable salt thereof, wherein each variable is independently as described in classes and subclasses herein, both singly and in combination.

In some embodiments, D has the structure of formula I-d-1:

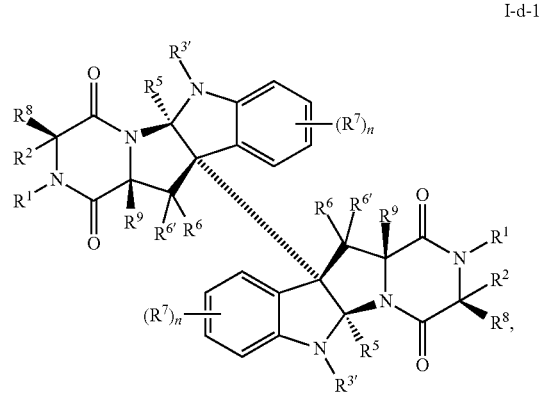

I-d-1 or a pharmaceutically acceptable salt thereof, wherein each variable is independently as described in classes and subclasses herein, both singly and in combination.

In some embodiments, a compound of formula I has the structure of formula I-d-2:

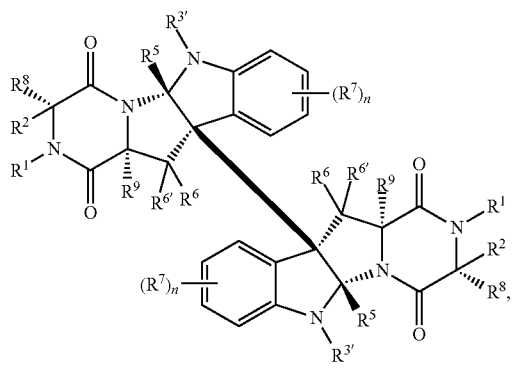

I-d-2 or a pharmaceutically acceptable salt thereof, wherein each variable is independently as described in classes and subclasses herein, both singly and in combination.

In some embodiments, a compound of formula I has the structure of formula I-d-3:

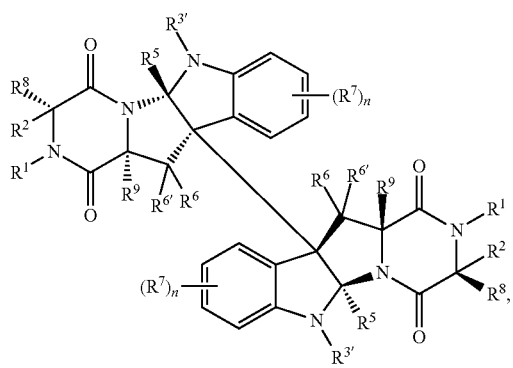

I-d-3 or a pharmaceutically acceptable salt thereof, wherein each variable is independently as described in classes and subclasses herein, both singly and in combination.

In some embodiments, a compound of formula I has the structure of formula I-d-4:

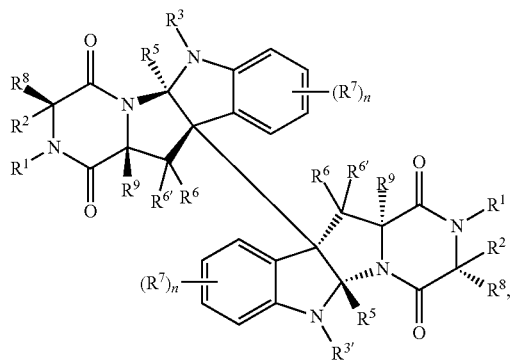

I-d-4 or a pharmaceutically acceptable salt thereof, wherein each variable is independently as described in classes and subclasses herein, both singly and in combination.

In some embodiments, D has the structure of formula I-a-1. In some embodiments, D has the structure of formula I-a-2. In some embodiments, D has the structure of formula I-a-3. In some embodiments, D has the structure of formula I-a-4. In some embodiments, D has the structure of formula I-a-5. In some embodiments, D has the structure of formula I-b-1. In some embodiments, D has the structure of formula I-b-2. In some embodiments, D has the structure of formula I-b-3. In some embodiments, D has the structure of formula I-b-4. In some embodiments, D has the structure of formula I-b-5.

In some embodiments, M is a cell-specific ligand unit. Exemplary cell-specific ligand unit are widely known in the art, including those described herein.

In some embodiments, M includes within its scope any unit of a Ligand ($L^L$) that, for example, binds or reactively associates or complexes with a receptor, antigen or other receptive moiety associated with a given target-cell population. In some embodiments, a Ligand is a molecule that binds to, complexes with, or reacts with a moiety of a cell population sought to be therapeutically or otherwise biologically modified. In some embodiments, the Ligand unit acts to deliver the drug unit (e.g., a compound of formulae I-c or I-d) to the particular target cell population with which the Ligand unit reacts. Such Ligands include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferring, or any other cell binding molecule or substance), nucleic acids and their derivatives and analogs. In some embodiments, a Ligand is modified from its corresponding natural form by, for example, amino acid mutations (including substitutions, deletions, insertions, etc), incorporation of unnatural building blocks (such as unnatural amino acids and unnatural nucleotides (e.g., those with unnatural bases, sugars, and/or internucleoside linkages)), chemical modifications, and/or conjugation with other small or macro molecules. In some embodiments, M comprises a reactive functional group such as an amine (—$NH_2$), aldehyde (—CHO), carboxyl (—COOH) or a sulfhydryl group (—SH), or can be modified to contain such a functional group. In some embodiments, M is coupled to the linker moiety of the conjugate by way of a free reactive sulfhydryl (—SH), amine (—$NH_2$), aldehyde (—CHO), ketone or carboxyl (—COOH) group or can be modified to contain such a sulfhydryl, amine, aldehyde, ketone or carboxyl group. In some embodiments, M is an antibody (Ab). In some embodiments, L is a covalent bond and M is directly connected to D. In some embodiments, L is not a covalent bond and M is connected to D through L.

In some embodiments, a Ligand unit can form a bond to a linker unit (L) via a carbon atom of the Ligand. In some embodiments, a Ligand unit can form a bond to a linker unit (L) via a heteroatom of the Ligand. Heteroatoms that may be present on a Ligand unit include sulfur (in some embodiments, from a sulfhydryl group of a Ligand), oxygen (in some embodiments, from a carbonyl, carboxyl or hydroxyl group of a Ligand) and nitrogen (in some embodiment, from a primary or secondary amino group of a Ligand). These heteroatoms can be present on the Ligand in the Ligand's natural state, for example a naturally-occurring antibody, or can be introduced into the Ligand via chemical modification.

In some embodiments, a Ligand has a sulfhydryl group and the Ligand bonds to the Linker unit via the sulfhydryl group's sulfur atom.

In yet some other embodiments, the Ligand has one or more lysine residues that can be chemically modified to introduce one or more sulfhydryl groups. The Ligand unit bonds to the Linker unit via the sulhydryl group's sulfur atom. The reagents that can be used to modify lysines include, but are not limited to, N-succinimidyl S-acetylthioacetate (SATA) and 2-Iminothiolane hydrochloride (Traut's Reagent).

In some embodiments, the Ligand can have one or more carbohydrate groups that can be chemically modified to have one or more sulfhydryl groups. The Ligand unit bonds to the Linker Unit, such as the Stretcher Unit, via the sulfhydryl group's sulfur atom.

In some embodiments, the Ligand can have one or more carbohydrate groups that can be oxidized to provide an aldehyde (—CHO) group (see, for e.g., Laguzza, et al., *J. Med. Chem.* 1989, 32(3), 548-55). The corresponding aldehyde can form a bond with a Reactive Site on a Stretcher. Reactive sites on a Stretcher that can react with a carbonyl group on a Ligand include, but are not limited to, hydrazine and hydroxylamine. Other protocols for the modification of proteins for the attachment or association to a compound of formulae I-c or I-d are described in Coligan et al., *Current Protocols in Protein Science*, vol. 2, John Wiley & Sons (2002).

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

In some embodiments, M is an antibody. In some embodiments, an antibody refers to any immunoglobulin, whether natural or wholly or partially synthetically produced. All derivatives thereof which maintain specific binding ability are also included. In some embodiments, an antibody also covers any protein having a binding domain which is homologous or largely homologous to an immunoglobulin-binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. In certain embodiments, an antibody may be a member of the IgG immunoglobulin class. In some embodiments, M is an antibody fragment or characteristic portion of an antibody, which refers to any derivative of an antibody which is less than full-length. In general, an antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. In some embodiments, a functional antibody fragment comprises at least about 50 amino acids. In some embodiments, a functional antibody fragment comprises at least about 200 amino acids. In some embodiments, an antibody may be a human antibody. In some embodiments, an antibody may be a humanized antibody. Exemplary antibody embodiments for M include intact monoclonal antibodies, polyclonal antibodies, multispecific antibodies (e.g., bispecific antibodies) formed from at least two intact antibodies, and antibody fragments, so long as they exhibit the desired biological activity.

Useful polyclonal antibodies as Ligand are, in some embodiments, heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Useful monoclonal antibodies as Ligand are, in some embodiments, homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture. These include, but are not limited to, the hybridoma technique originally described by Köhler and Milstein (1975, *Nature* 256, 495-497), the human B cell hybridoma technique (Kozbor et al., 1983, *Immunology Today* 4: 72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al., 1983, *Proc. Natl. Acad. Sci. USA*. 80, 7308-7312; Kozbor et al., 1983, *Immunology Today* 4, 72-79; and Olsson et al., 1982, *Meth. Enzymol.* 92, 3-16).

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690).

For further details for generating bispecific antibodies see, for example, Suresh et al., *Methods in Enzymology*, 1986, 121:210; Rodrigues et al., 1993, *J. of Immunology* 151:6954-6961; Carter et al., 1992, *Bio/Technology* 10: 163-167; Carter et al., 1995, *J. of Hematotherapy* 4:463-470; Merchant et al., 1998, *Nature Biotechnology* 16:677-681. Using such techniques, bispecific antibodies can be prepared for use in the treatment or prevention of disease as defined herein.

Bifunctional antibodies are also described, in European Patent Publication No. EPA 0 105 360. In some embodiments, hybrid or bifunctional antibodies can be derived either biologically, i.e., by cell fusion techniques, or chemically, especially with cross-linking agents or disulfide-bridge forming reagents, and may comprise whole antibodies and/or fragments thereof. Methods for obtaining such hybrid antibodies are disclosed for example, in International Publication WO 83/03679, and European Patent Publication No. EPA 0 217 577. Bifunctional antibodies include those biologically prepared from a "polydoma" or "quadroma" or which are synthetically prepared with cross-linking agents such as bis-(maleimido)-methyl ether ("BMME"), or with other cross-linking agents familiar to those skilled in the art.

An antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, for e.g., Kabat et al., 1991, *Sequences of Proteins of Immunological Interest*, Fifth Edition, National Institute of Health, Bethesda, Md.; Kabat E et al., 1980, *J. of Immunology* 125 (3):961-969).

Other useful antibodies include fragments of antibodies such as, but not limited to, $F(ab)_2$ fragments, which contain the variable region, the light chain constant region and the CH1 domain of the heavy chain can be produced by pepsin digestion of the antibody molecule, and Fab fragments, which can be generated by reducing the disulfide bridges of the $F(ab')_2$ fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), or any other molecule with the same specificity as the antibody.

In some embodiments, an antibody is an immunoglobulin antibody. In some embodiments, an immunoglobulin antibody recognizes a tumor-associated antigen.

In some embodiments, an antibody is a recombinant antibody, such as a chimeric and/or a humanized monoclonal antibodies, comprising both human and non-human portions, which can be made using standard recombinant DNA techniques. A chimeric antibody is a molecule in which different portions are derived from different animal species, such as those having a variable region derived from a murine monoclonal and human immunoglobulin constant regions. See, e.g., Cabilly et al., U.S. Pat. No. 4,816,567; and Boss et al., U.S. Pat. No. 4,816,397. Humanized antibodies are antibody molecules from non-human species having one or more complementarity determining regions (CDRs) from the non-human species and a framework region from a human immunoglobulin molecule. See, e.g., Queen, U.S. Pat. No. 5,585,089. Such chimeric and humanized monoclonal antibodies can be produced by recombinant DNA techniques known in the art, for example using methods described in International Publication No. WO 87/02671; European Patent Publication No. 184,187; European Patent Publication No. 171496; European Patent Publication No. 173494; International Publication No. WO 86/01533; U.S. Pat. No. 4,816,567; European Patent Publication No. 12,023; Berter et al, 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229: 1202-1207; Oi et al., 1986, *BioTechniques* 4:214; U.S. Pat. No. 5,225,539; Jones et al., 1986, *Nature* 321:552-525; Verhoeyan et al. (1988) *Science* 239:1534; and Beidler et al., 1988, *J. Immunol.* 141:4053-4060.

In some embodiments, completely human antibodies are desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. See, e.g., U.S. Pat. Nos. 5,625,126;

5,633,425; 5,569,825; 5,661,016; 5,545,806. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al. (1994) *Biotechnology* 12:899-903). Human antibodies can also be produced using various techniques known in the art, including phage display libraries (Hoogenboom and Winter, *J. Mol. Biol.*, 227:381 (1991); Marks et al., *J. Mol. Biol.*, 222:581 (1991); Quan, M. P. and Carter, P. 2002. *The rise of monoclonal antibodies as therapeutics.* In Anti-IgE and Allergic Disease, Jardieu, P. M. and Fick Jr., R. B, eds., Marcel Dekker, New York, N.Y., Chapter 20, pp. 427-469).

In other embodiments, an antibody is a fusion protein of an antibody, or a functionally active fragment thereof, for example in which the antibody is fused via a covalent bond (e.g., a peptide bond) at, for example, either the N-terminus or the C-terminus, to an amino acid sequence of another protein (or portion thereof, preferably at least 10, 20 or 50 amino acid portion of the protein) that is not the antibody. In some embodiments, the antibody or fragment thereof is covalently linked to the other protein at the N-terminus of the constant domain. In some embodiments, an antibody is a fusion protein comprising an albumin-binding peptide sequence (ABP).

In some embodiments, an antibody is conjugated to one or more polymer units. In some embodiments, a polymer unit is functionalized so that it is used for connection with -L-. In some embodiments, a polymer unit is functionalized in such a way that a controlled number of -L- and drug units (e.g., compounds of formula I-c or I-d) can be linked, therefore controlling the amount of a provided compound conjugated to an antibody molecule.

In some embodiments, antibodies include analogs and derivatives that are modified, e.g., by the covalent attachment of any type of molecule, by chemically modifying one or more amino acid residues, and/or by introducing one or more mutations, including substitutions, insertions and deletions, as long as such modifications permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, amino acid mutations, etc. Any of numerous chemical modifications can be carried out by known techniques, including, but not limited to specific chemical cleavage, acetylation, formylation, metabolic synthesis in the presence of tunicamycin, etc.

In some embodiments, an analog or derivative of an antibody, peptide or protein contains one or more unnatural amino acid residues. In some embodiments, an antibody, peptide or protein contains a controlled number of unnatural amino acid residues, which are used for conjugation to -L- and a provided compound, e.g., a compound of formula I-c or I-d, therefore controlling the number of copies of a provided compound conjugated to the antibody, peptide or protein molecule. In some embodiments, an antibody contains one unnatural amino acid residue for conjugation. In some embodiments, an antibody contains two unnatural amino acid residues for conjugation. In some embodiments, an antibody contains three unnatural amino acid residues for conjugation. In some embodiments, an antibody contains four unnatural amino acid residues for conjugation. In some embodiments, an antibody contains five unnatural amino acid residues for conjugation. In some embodiments, an antibody contains six unnatural amino acid residues for conjugation. In some embodiments, an antibody contains seven unnatural amino acid residues for conjugation. In some embodiments, an antibody contains eight unnatural amino acid residues for conjugation. In some embodiments, an antibody contains nine unnatural amino acid residues for conjugation. In some embodiments, an antibody contains ten unnatural amino acid residues for conjugation. Suitable unnatural amino acid residues and methods for their incorporation are widely known and practiced in the art. In some embodiments, an unnatural amino acid residue comprises an optionally substituted alkyl, heteroalkyl, alkenyl, alkynyl, cycloalkyl, aryl, heteroaryl or heterocyclyl group that is not found in natural amino acid residues. In some embodiments, an unnatural amino acid comprises at least one $-N_3$ group. In some embodiments, an unnatural amino acid comprises at least one alkenyl group. In some embodiments, an unnatural amino acid comprises at least one alkynyl group. In some embodiments, an unnatural amino acid comprises at least one ketone group. In some embodiments, an unnatural amino acid comprises at least one aldehyde group. In some embodiments, an unnatural amino acid residue is a p-acetylphenylalanine residue. In some embodiments, an unnatural amino acid residue is a formylglycine residue. Methods for conjugation through a $-N_3$, alkenyl, alkynyl, ketone and/or aldehyde are widely known and practiced in the art, including but not limited to click chemistry, metathesis and/or reactions with amines, alkoxyamines and hydrazides. Among other things, conjugation through functionalized unnatural amino acid residues provides control over both the number and placement of a provide compound (site-specific conjugation).

In some embodiments, M comprises at least one aldehyde or ketone group. In some embodiments, M comprises at least one aldehyde group. In some embodiments, M is coupled to the rest of a provided compound via reaction of the aldehyde or ketone group with an amine (e.g., reductive amination), a substituted hydrazine (e.g., forming a hydrazone), a hydrazide, or an alkoxyamine (e.g., forming oximes). In some embodiments, a coupling reaction comprises the use of N-substituted alkoxyamine, and an intramolecular transformation similar to a Pictet-Spengler reaction, for example:

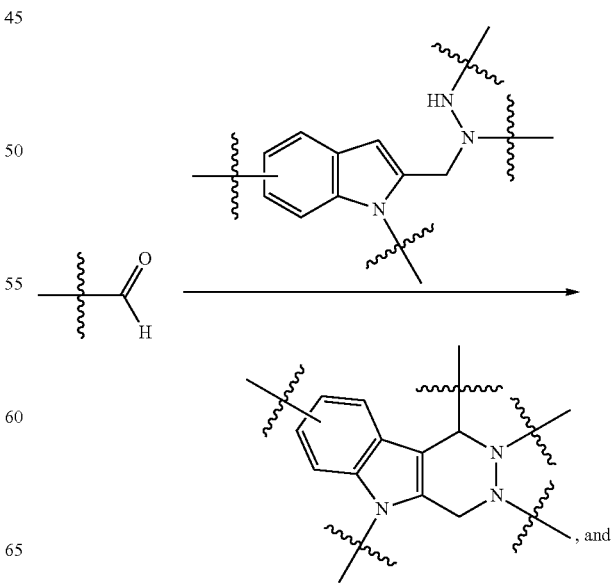

-continued

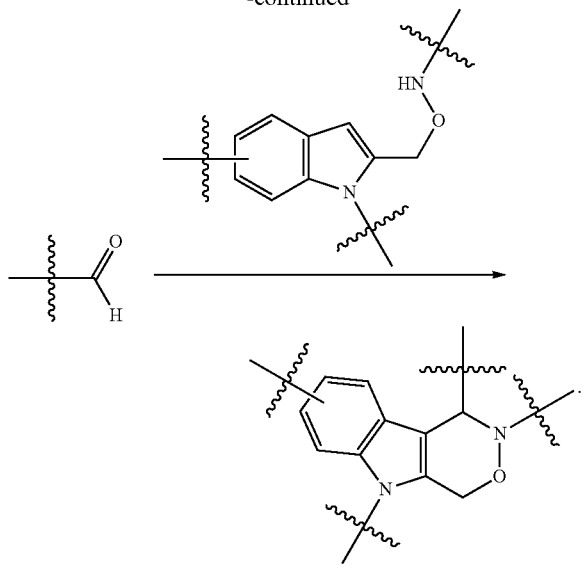

In some embodiments, an aldehyde group of M, or another type of reactive group of M that is used for linkage to L, is converted from another functional group. In some embodiments, an another functional group is within the side chain of a natural amino acid residue or an incorporated unnatural amino acid through, for example, a chemical or enzymatic transformation. In some embodiments, a transformation is an enzymatic transformation. In some embodiments, a transformation coverts a cysteine residue into a formylglycine residue. In some embodiments, such a transformation is promoted by a formylglycine-generation enzyme. Exemplary antibodies and the preparation and use thereof are described in US Patent Application Publication US 2010/0210543 and US 2012/0183566.

In some embodiments, an antibody is a cysteine engineered antibody. In some embodiments, a cysteine engineered antibody comprises one or more free cysteine amino acid, which is a cysteine amino acid residue which has been engineered into a parent antibody, has a thiol functional group (—SH), and is not paired as an intermolecular or intramolecular disulfide bridge. In some embodiments, a cysteine engineered antibody comprising a free cysteine amino acid having a thiol reactivity value in the range of 0.6 to 1.0 as defined in U.S. Pat. No. 7,855,275. Exemplary cysteine engineered antibodies are widely described in the art, including but not limited to those described in U.S. Pat. Nos. 7,855,275 and 7,521,541, the entirety of each of which is incorporated by reference herein. In some embodiments, a cysteine engineered antibody is site-specifically and efficiently coupled with a thiol-reactive reagent, such as a multifunctional linker reagent or a drug-linker intermediate (e.g., -L-(D)s, wherein D is a compound of I-c or I-d).

In some embodiments, M is a diabody, tribody, tetrabody, minibody or nanobody.

The antibodies include antibodies having modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631. Antibodies immunospecific for a cancer cell antigen can be obtained commercially, for example, from Genentech (San Francisco, Calif.) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In some embodiments, known antibodies for the treatment or prevention of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database, or a database like it, the literature publications, or by routine cloning and sequencing. Examples of antibodies available for the treatment of cancer include, but are not limited to, humanized anti-HER2 monoclonal antibody, HERCEPTIN® (trastuzumab; Genentech) for the treatment of patients with metastatic breast cancer, RITUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG$_{2a}$ antibody for the treatment of colorectal cancer, Cetuximab Erbitux (Imclone Systems Inc., NY) which is an anti-EGFR IgG chimeric antibody for the treatment of epidermal growth factor positive cancers, such as head and neck cancer, Vitaxin (MedImmune, Inc., MD) which is a humanized antibody for the treatment of sarcoma; Campath I/H (Leukosite, MA) which is a humanized IgG, antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, Calif.) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., Willner, D., Lasch, S. J., Henderson, A. J., Hofstead, S. J., Casazza, A. M., Firestone, R. A., Hellstrom, I., Hellstrom, K. E., "Cure of Xenografted Human Carcinomas by BR96-Doxorubicin Immunoconjugates" *Science* 1993, 261, 212-215), BR64 (Trail, P A, Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" *Cancer Research* 1997, 57, 100-105, mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" *Cancer Res.* 2000, 60, 3225-3231), mAbs against the CD70 antigen, such as 1F6 mAb and 2F2 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" *J. Immunol.*, 151, 5896-5906, 1993: Wahl et al., 2002 *Cancer Res.* 62(13):3736-42). Many other internalizing antibodies that bind to tumor associated antigens can be used and have been reviewed (Franke, A. E., Sievers, E. L., and Scheinberg, D. A., "Cell surface receptor-targeted therapy of acute myeloid leukemia: a review" *Cancer Biother Radiopharm.* 2000, 15, 459-76; Murray, J. L., "Monoclonal antibody treatment of solid tumors: a coming of age" *Semin Oncol.* 2000, 27, 64-70; Breitling, F., and Dubel, S., *Recombinant Antibodies*, John Wiley, and Sons, New York, 1998).

In certain embodiments, the antibody is Trastuzumab (full length, humanized anti-HER2 (MW 145167)), HerceptinF(ab)$_2$ (derived from anti-HER2 enzymatically (MW 100000)), 4D5 (full-length, murine antiHER2, from hybridoma), rhu4D5 (transiently expressed, full-length humanized antibody), rhuFab4D5 (recombinant humanized Fab (MW 47738)), 4D5Fc8 (full-length, murine antiHER2, with mutated FcRn binding domain), or Hg ("Hingeless" full-length humanized 4D5, with heavy chain hinge cysteines mutated to serines. Expressed in *E. coli* (therefore non-glycosylated). In certain embodiments, the antibody is not Trastuzumab (full length, humanized anti-HER2 (MW 145167)), HerceptinF(ab)$_2$ (derived from anti-HER2 enzymatically (MW 100000)), 4D5 (full-length, murine antiHER2, from hybridoma), rhu4D5 (transiently expressed, full-length humanized antibody), rhuFab4D5 (recombinant humanized Fab (MW 47738)), 4D5Fc8 (full-length, murine antiHER2, with mutated FcRn binding domain), or Hg ("Hingeless" full-length humanized 4D5, with heavy chain hinge cysteines mutated to serines. Expressed in *E. coli* (therefore non-glycosylated)).

In another specific embodiment, known antibodies for the treatment or prevention of an autoimmune disease are used in accordance with the compositions and methods of the invention. Antibodies immunospecific for an antigen of a cell that is responsible for producing autoimmune antibodies can be obtained from any organization (e.g., a university or a company) or produced by any method known to one of skill in the art such as, e.g., chemical synthesis or recombinant expression techniques. In another embodiment, useful antibodies are immunospecific for the treatment of autoimmune diseases include, but are not limited to, Anti-Nuclear Antibody; Anti-ds DNA; Anti-ss DNA, Anti-Cardiolipin Antibody IgM, IgG; Anti-Phospholipid Antibody IgM, IgG; Anti-SM Antibody; Anti-Mitochondrial Antibody; Thyroid Antibody; Microsomal Antibody; Thyroglobulin Antibody; Anti-SCL-70; Anti-Jo; Anti-U$_1$RNP; Anti-La/SSB; Anti SSA; Anti-SSB; Anti-Perital Cells Antibody; Anti-Histones; Anti-RNP; C-ANCA; P-ANCA; Anti centromere; Anti-Fibrillarin, and Anti-GBM Antibody. In some embodiments, an antibody is an anti-AGS16, anti-AGS5, anti-Nectin 4, anti-CA9, anti0mesothelin, anti-Cripto, anti-CD138, anti-CD70, anti-GPNMB, anti-CD56, anti-alpha integrin, anti-CD22, anti-PSMA, anti-Her2, anti-CD19, anti-DS6, anti-CD30, or anti-CD70 antibody.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In some embodiments, the Ligand binds to an activated lymphocyte that is associated with an autoimmune disease.

In some embodiments, useful Ligands immunospecific for a viral or a microbial antigen are monoclonal antibodies. The antibodies may be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful Ligands are those that are useful for the treatment or prevention of viral or microbial infection in accordance with the methods disclosed herein. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium,* and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

Transmembrane or otherwise tumor-associated polypeptides that are specifically expressed on the surface of one or more particular type(s) of cancer cell as compared to on one or more normal non-cancerous cell(s) were identified for cancer diagnosis and therapy. In some embodiments, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies as embodiments for M include, but are not limited to, antibodies against tumor-associated antigens (TAA). Such tumor-associated antigens are known in the art, and can be prepared for use in generating antibodies using methods and information which are well known in the art. Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. Examples of TAA include (1)-(36), but are not limited to TAA (1)-(36) listed below. Tumor-associated antigens targeted by antibodies include all amino acid sequence variants and isoforms possessing at least about 70%, 80%, 85%, 90%, or 95% sequence identity relative to the sequences identified in the corresponding sequences listed (1-36), or the sequences identified in the cited references, or which exhibit substantially the same biological properties or characteristics as a TAA having a sequence found in the cited references. In some embodiments, TAA having amino acid sequence variants exhibit substantially the same biological properties or characteristics as a TAA having the sequence found in the corresponding sequences below. For example, a TAA having a variant sequence generally is able to bind specifically to an antibody that binds specifically to the TAA with the corresponding sequence listed. The sequences and specifically recited herein are expressly incorporated by reference.

In some embodiments, an antibody binds to an ErbB receptor, and/or one or more of receptors (1)-(36):

(1) BMPR1B (bone morphogenetic protein receptor-type IB, Genbank accession no. NM_001203);

(2) E16 (LAT1, SLC7A5);

(3) STEAP1 (six transmembrane epithelial antigen of prostate);

(4) 0772P (CA125, MUC16);

(5) MPF (MPF, MSLN, SMR, megakaryocyte potentiating factor, mesothelin);

(6) Napi3b (NAPI-3B, NPTIIb, SLC34A2, solute carrier family 34 (sodium phosphate), member 2, type II sodium-dependent phosphate transporter 3b);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008016Rik, RIKEN cDNA 2700050C12, RIKEN cDNA 2700050C12 gene);

(9) ETBR (Endothelin type B receptor);

(10) MSG783 (RNF124, hypothetical protein FLJ20315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR(C3d/Epstein Barr virus receptor) or Hs.73792);

(15) CD79b (CD79B, CD790, IGb (immunoglobulin-associated beta), B29);

(16) FcRH2 (IFGP4, IRTA4, SPAP1A (SH2 domain containing phosphatase anchor protein Ia), SPAP1B, SPAP1C);

(17) HER2;

(18) NCA;

(19) MDP;

(20) IL20Rα;

(21) Brevican;

(22) EphB2R;
(23) ASLG659;
(24) PSCA;
(25) GEDA;
(26) BAFF-R (B cell-activating factor receptor, BLyS receptor 3, BR3;
(27) CD22 (B-cell receptor CD22-β isoform);
(28) CD79a (CD79A, CD79a, immunoglobulin-associated alpha, a B cell-specific protein that covalently interacts with Ig beta (CD79B) and forms a complex on the surface with IgM molecules, transduces a signal involved in B-cell differentiation);
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia);
(30) HLA-DOB (Beta subunit of MHC class II molecule (Ia antigen) that binds peptides and presents them to CD4+ T lymphocytes);
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability);
(32) CD72 (B-cell differentiation antigen CD72, Lyb-2);
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis);
(34) FcRH1 (Fc receptor-like protein 1, a putative receptor for the immunoglobulin Fc domain that contains C2 type Ig-like and ITAM domains, may have a role in B-lymphocyte differentiation);
(35) IRTA2 (Immunoglobulin superfamily receptor translocation associated 2, a putative immunoreceptor with possible roles in B cell development and lymphomagenesis; deregulation of the gene by translocation occurs in some B cell malignancies); and
(36) TENB2 (putative transmembrane proteoglycan, related to the EGF/heregulin family of growth factors and follistatin).

Other exemplary monoclonal antibodies which may recognize tumor associated antigen include:

| Antigen Site Recognized | Monoclonal Antibodies | Reference |
|---|---|---|
| Lung Tumors | KS1/4 | N. M. Varki, et al., Cancer Res, 44: 681, 1984 |
| | 534, F8; 604A9 | F. Cuttitta, et al., in: G. L. Wright (ed) Monoclonal Antibodies and Cancer, Marcel Dekker, Inc., NY., p. 161, 1984. |
| Squamous Lung | G1, LuCa2, LuCa3, LuCa4 | Kyoizumi et al., Cancer Res., 45: 3274, 1985. |
| Small Cell Lung Cancer | TFS-2 | Okabe et al., Cancer Res. 45: 1930, 1985. |
| Colon Cancer | 11.285.14 14.95.55 | G. Rowland, et al., Cancer Immunol. Immunother., 19: 1, 1985 |
| | NS-3a-22, NS-10 NS-19-9, NS-33a NS-52a, 17-1A Erbitux ® | Z. Steplewski, et al., Cancer Res., 41: 2723, 1981. |

-continued

| Antigen Site Recognized | Monoclonal Antibodies | Reference |
|---|---|---|
| Carcinoembryonic | MoAb 35 or ZCE025 | Acolla, R. S. et al., Proc. Natl. Acad. Sci., (USA), 77: 563, 1980. |
| Melanoma | 9.2.27 | T. F. Bumol and R. A. Reisfeld, Proc. Natl. Acad. Sci., (USA), 79: 1245, 1982. |
| p97 | 96.5 | K. E. Hellstrom, et al., Monoclonal Antibodies and Cancer, loc. cit. p. 31. |
| Antigen T65 | T101 | Boehringer-Mannheim, P. O. Box 50816, Indianapolis, IN 46250 |
| Ferritin | Antiferrin | Boehringer-Mannheim, P.O. Box 50816, Indianapolis, IN 46250 |
| | R24 | W. G. Dippold, et al., Proc. Natl. Acad. Sci. (USA), 77: 6114, 1980 |
| Neuroblastoma | P1 153/3 | R. H. Kennet and F. Gilbert, Science, 203: 1120, 1979. |
| | MIN 1 | J. T. Kemshead in Monoclonal Antibodies and Cancer, loc. cit. p. 49. |
| | UJ13A | Goldman et al., Pediatrics, 105: 252, 1984. |
| Glioma | BF7, GE2, CG12 | N. de Tribolet, et al., in Monoclonal Antibodies and Cancer, loc. cit. p. 81 |
| Ganglioside | L6 | I. Hellstrom et al. Proc. Natl Acad. Sci. (U.S.A) 83: 7059 (1986); U.S. Pat. Nos. 4,906,562, issued Mar. 6, 1990 and 4,935,495, issued Jun. 19, 1990. |
| | Chimeric L6 | U.S. Ser. No. 07/923,244, (abandoned) filed Oct. 27, 1986, equivalent to PCT Patent Publication, WO 88/03145, published May 5, 1988. |
| Lewis Y | BR64 | U.S. Ser. Nos. 07/289,635 (abandoned) filed Dec. 22, 1988, and U.S. Ser. No. 07/443,696 (now U.S. Pat. No. 5,242,824) Nov. 29, 1989, equivalent to European Patent Publication, EP A 0 375 562, published Jun. 27, 1990, |
| fucosylated Lewis Y | BR96, Chimeric BR96 | U.S. Ser. Nos. 07/374,947 (abandoned) filed Jun. 30, 1989, and U.S. Ser. No. 07/544,246 (abandoned) filed Jun. 26, 1990, equivalent to PCT Patent Publication, WO 91/00295, published Jan. 10, 1991. |
| Breast Cancer | B6.2, B72.3 | D. Colcher, et al., in Monoclonal Antibodies and Cancer. loc. cit. p. 121. |
| | Herceptin ® | Baselga et al., J. Clin. Oncol., 14: 737-744, 1996; U.S. Pat. No, 5,821,337 |
| | Mylotarg ® | |
| Osteogenic Sarcoma | 791T/48, 791T/36 | M. J. Embleton, ibid, p. 181 |
| Sarcoma | 791T/36 | |
| Leukemia | CALL 2 | C. T. Teng, et al., Lancet, 1: 01, 1982 |
| | anti-idiotype | R. A. Miller, et al., N. Eng. J. Med., 306: 517, 1982 |
| Ovarian Cancer | OC 125 | R C. Bast, et al., J. Clin. Invest., 68: 1331, 1981. |
| Prostate Cancer | D83.21, P6.2, Turp-27 | J. J. Starling, et al., in Monoclonal Antibodies and Cancer, loc. cit., p. 253 |
| Renal Cancer | A6H, D5D | P. H. Lange, et al., Surgery, 98: 143, 1985. |

-continued

| Antigen Site Recognized | Monoclonal Antibodies | Reference |
|---|---|---|
| Non-Hodgkins lymphoma | Rituxan® | |

In some embodiments, an antibody binds to one or more of the antigens listed below, or one or more of the antigens expressed by the tumor and/or tumor types listed below:

| Antigen category | Examples of antigens | Tumor types expressing antigen |
|---|---|---|
| Cluster of differentiation (CD) antigens | CD20 | non-Hodgkin lymphoma |
| | CD30 | Hodgkin lymphoma |
| | CD33 | Acute myelogenous leukemia |
| | CD52 | Chronic lymphocytic leukemia |
| Glycoproteins | EpCAM | Epithelial tumors (breast, colon, lung) |
| | CEA | Epithelial tumors (breast, colon, lung) |
| | gpA33 | Colorectal carcinoma |
| | Mucins | Epithelial tumors (breast, colon, lung, ovarian) |
| | TAG-72 | Epithelial tumors (breast, colon, lung) |
| | Carbonic anhydrase IX | Renal cell carcinoma |
| | PSMA | Prostate carcinoma |
| | Folate binding protein | Ovarian tumors |
| Glycolipids | Gangliosides (e.g., GD2, GD3, GM2) | Neuroectodermal tumors, some epithelial tumors |
| Carbohydrates | Lewis-Y[2] | Epithelial tumors (breast, colon, lung, prostate) |
| Vascular targets | VEGF | Tumor vasculature |
| | VEGFR | Epithelium-derived solid tumors |
| | αVβ3 | Tumor vasculature |
| | α5β1 | Tumor vasculature |
| Growth factors | ErbB1/EGFR | Glioma, lung, breast, colon, head and neck tumors |
| | ErbB2/HER2 | Breast, colon, lung, ovarian, prostate tumors |
| | ErbB3 | Breast, colon, lung, ovarian, prostate tumors |
| | c-MET | Epithelial tumors (breast, ovary, lung) |
| | IGF1R | Lung, breast, head and neck, prostate, thyroid, glioma |
| | EphA3 | Lung, kidney, colon, melanoma, glioma, hematological malignancies |
| | TRAIL-R1, TRAIL-R2 | Solid tumors (colon, lung, pancreas) and hematological malignancies |
| | RANKL | Prostate cancer and bone metastases |
| Stromal and extracellular matrix antigens | FAP | Epithelial tumors (colon, breast, lung, head and neck, pancreas) |
| | Tenascin | Glioma, epithelial tumors (breast, prostate) |

Exemplary tumor-associated antigens and specific antibodies thereto were also included in WO04/045516; WO03/000113; WO02/016429; WO02/16581; WO03/024392; WO04/016225; WO01/40309; and U.S. Provisional patent application Ser. No. 60/520,842.

Exemplary antibodies also include: Herceptin® (trastuzumab)=full length, humanized antiHER2 (MW 145167), Herceptin F(ab)₂=derived from antiHER2 enzymatically (MW 100000), 4D5=full-length, murine antiHER2, from hybridoma, rhu4D5=transiently expressed, full-length humanized antibody, rhuFab4D5=recombinant humanized Fab (MW 47738), 4D5Fc8=full-length, murine antiHER2, with mutated FcRn binding domain.

In some embodiments, an antibody specifically binds to a receptor encoded by an ErbB gene. In some embodiments, an antibody binds specifically to an ErbB receptor selected from EGFR, HER2, HER3 and HER4. In some embodiments, an antibody specifically binds to an extracellular domain of the HER2 receptor and inhibits the growth of tumor cells which overexpress HER2 receptor. In some embodiments, HERCEPTIN® (trastuzumab) selectively binds to the extracellular domain (ECD) of the human epidermal growth factor receptor 2 protein, HER2 (ErbB2) (U.S. Pat. No. 5,821,337; U.S. Pat. No. 6,054,297; U.S. Pat. No. 6,407,213; U.S. Pat. No. 6,639,055; Coussens et al (1985) Science 230:1132-9; Slamon, et al (1989) Science 244:707-12).

In some embodiments, an antibody is a monoclonal antibody, e.g. a murine monoclonal antibody, a chimeric antibody, or a humanized antibody. In some embodiments, a humanized antibody is huMAb4D5-1, huMAb4D5-2, huMAb4D5-3, huMAb4D5-4, huMAb4D5-5, huMAb4D5-6, huMAb4D5-7 or huMAb4D5-8 (Trastuzumab). The antibody may be an antibody fragment, e.g. a Fab fragment. In some embodiments, an antibody is hu4D5Fabv8.

As generally defined above, each L is independently a linker unit. In some embodiments, L is a covalent bond. In some embodiments, a linker unit is a chemical moiety comprising a covalent bond or a chain of atoms that covalently attaches an antibody to a drug moiety (D). In some embodiments, L is an optionally substituted bivalent $C_{1-50}$ aliphatic or heteroalkylene group, wherein one or more carbon atoms, optionally with one or more hydrogen atoms attached thereto, are optionally and independently replaced by —O—, =O, —N(R)—, =N—,

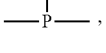

=N, —S—, =S, —S(O)—, —S(O)₂—, —S(O)₂N(R)—, —C(O)—, —OC(O)—, —OC(O)O—, —C(S)—, —C(O)N(R)—, —N(R)C(O)O—, N(R)C(O)N(R)—,

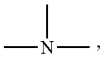 , 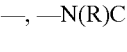 ,

—Se—, —Se(O)—,

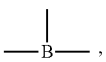 , an amino acid residue, or -Cy¹-, wherein each -Cy¹- is independently:
- a bivalent optionally substituted monocyclic ring independently selected from phenylene, a 3-8 membered saturated or partially unsaturated carbocyclylene, a 5-6 membered heteroarylene having 1-4 heteroatoms independently selected from nitrogen, oxygen, or sulfur, or a 3-8 membered saturated or partially unsaturated heterocyclylene having 1-4 heteroatoms independently selected from nitrogen, oxygen, or sulfur, or
- a bivalent optionally substituted bicyclic ring independently selected from an 8-10 membered arylene, a 7-10 membered saturated or partially unsaturated carbocyclylene, an 8-10 membered heteroarylene having 1-5 heteroatoms independently selected from nitrogen, oxygen, or sulfur, or a 7-10 membered saturated or partially unsaturated heterocyclylene having 1-5 heteroatoms selected from nitrogen, oxygen, or sulfur, or
- a bivalent optionally substituted tricyclic ring independently selected from 14 membered arylene, a 9-20 membered saturated or partially unsaturated carbocyclylene, a 9-14 membered heteroarylene having 1-8 heteroatoms independently selected from nitrogen, oxygen, or sulfur, or a 9-20 membered saturated or partially unsaturated heterocyclylene having 1-8 heteroatoms independently selected from nitrogen, oxygen, or sulfur; or
- a bivalent optionally substituted tetracyclic ring independently selected from a 16-18 membered arylene, an 11-30 membered saturated or partially unsaturated carbocyclylene, a 15-18 membered heteroarylene having 1-8 heteroatoms independently selected from nitrogen, oxygen, or sulfur, or an 11-30 membered saturated or partially unsaturated heterocyclylene having 1-12 heteroatoms independently selected from nitrogen, oxygen, or sulfur.

In some embodiments, -Cy¹- is a bivalent optionally substituted monocyclic ring.

In certain embodiments, -Cy¹- is bivalent optionally substituted phenylene.

In certain embodiments, -Cy¹- is a bivalent optionally substituted 3-8 membered saturated carbocyclylene. In certain embodiments, -Cy¹- is a bivalent optionally substituted 3-8 membered partially unsaturated carbocyclylene. In certain embodiments, -Cy¹- is a bivalent optionally substituted 5-6 membered saturated carbocyclylene. In certain embodiments, -Cy¹- is a bivalent optionally substituted 5-6 membered partially unsaturated carbocyclylene.

In certain embodiments, -Cy¹- is a bivalent optionally substituted 5 membered heteroarylene having 1-4 heteroatoms independently selected from nitrogen, oxygen, or sulfur.

In certain embodiments, -Cy¹- is a bivalent optionally substituted 5 membered heteroarylene having 1-2 heteroatoms independently selected from nitrogen, oxygen, or sulfur. In certain embodiments, -Cy¹- is a bivalent optionally substituted 6 membered heteroarylene having 1-4 heteroatoms independently selected from nitrogen, oxygen, or sulfur. In certain embodiments, —Cy¹- is a bivalent optionally substituted 6 membered heteroarylene having 1-2 heteroatoms independently selected from nitrogen, oxygen, or sulfur.

In certain embodiments, -Cy¹- is a bivalent optionally substituted 3-8 membered saturated heterocyclylene having 1-4 heteroatoms independently selected from nitrogen, oxygen, or sulfur. In certain embodiments, -Cy¹- is a bivalent optionally substituted 3-8 membered saturated heterocyclylene having 1-2 heteroatoms independently selected from nitrogen, oxygen, or sulfur. In certain embodiments, -Cy¹- is a bivalent optionally substituted 5-6 membered saturated heterocyclylene having 1-4 heteroatoms independently selected from nitrogen, oxygen, or sulfur. In certain embodiments, -Cy¹- is a bivalent optionally substituted 5-6 membered saturated heterocyclylene having 1-2 heteroatoms independently selected from nitrogen, oxygen, or sulfur. In certain embodiments, -Cy¹- is a bivalent optionally substituted 5 membered saturated heterocyclylene having 1-2 heteroatoms independently selected from nitrogen, oxygen, or sulfur. In certain embodiments, -Cy¹- is a bivalent optionally substituted 6 membered saturated heterocyclylene having 1-2 heteroatoms independently selected from nitrogen, oxygen, or sulfur.

In certain embodiments, -Cy¹- is a bivalent optionally substituted 3-8 membered partially unsaturated heterocyclylene having 1-4 heteroatoms independently selected from nitrogen, oxygen, or sulfur. In certain embodiments, -Cy¹- is a bivalent optionally substituted 3-8 membered partially unsaturated heterocyclylene having 1-2 heteroatoms independently selected from nitrogen, oxygen, or sulfur. In certain embodiments, -Cy¹- is a bivalent optionally substituted 5-6 membered partially unsaturated heterocyclylene having 1-4 heteroatoms independently selected from nitrogen, oxygen, or sulfur. In certain embodiments, -Cy¹- is a bivalent optionally substituted 5-6 membered partially unsaturated heterocyclylene having 1-2 heteroatoms independently selected from nitrogen, oxygen, or sulfur. In certain embodiments, —Cy¹- is a bivalent optionally substituted 5 membered partially unsaturated heterocyclylene having 1-2 heteroatoms independently selected from nitrogen, oxygen, or sulfur. In certain embodiments, -Cy¹- is a bivalent optionally substituted 6 membered partially unsaturated heterocyclylene having 1-2 heteroatoms independently selected from nitrogen, oxygen, or sulfur.

In some embodiments, -Cy¹- is bivalent optionally substituted naphthylene.

In some embodiments, -Cy¹- is a bivalent optionally substituted bicyclic 7-10 membered saturated carbocyclylene. In some embodiments, -Cy¹- is a bivalent optionally substituted bicyclic 7 membered saturated carbocyclylene. In some embodiments, -Cy¹- is a bivalent optionally substituted bicyclic 8 membered saturated carbocyclylene. In some embodiments, -Cy¹- is a bivalent optionally substituted bicyclic 9 membered saturated carbocyclylene. In some embodiments, -Cy¹- is a bivalent optionally substituted bicyclic 10 membered saturated carbocyclylene.

In some embodiments, -Cy¹- is a bivalent optionally substituted bicyclic 7-10 membered partially unsaturated carbocyclylene. In some embodiments, -Cy¹- is a bivalent optionally substituted bicyclic 7 membered partially unsaturated carbocyclylene. In some embodiments, -Cy¹- is a bivalent optionally substituted bicyclic 8 membered partially unsaturated carbocyclylene. In some embodiments, -Cy¹- is a bivalent optionally substituted bicyclic 9 membered partially unsaturated carbocyclylene. In some embodiments, -Cy¹- is a bivalent optionally substituted bicyclic 10 membered partially unsaturated carbocyclylene.

In some embodiments, -Cy¹- is a bivalent optionally substituted bicyclic 8-10 membered heteroarylene having 1-5 heteroatoms independently selected from nitrogen, oxygen, or sulfur. In some embodiments, -Cy¹- is a bivalent optionally substituted bicyclic 8-10 membered heteroarylene having 1-2 heteroatoms independently selected from nitrogen, oxygen, or sulfur. In some embodiments, -Cy¹- is a bivalent optionally substituted bicyclic 8 membered heteroarylene having 1-5 heteroatoms independently selected from nitrogen, oxygen, or sulfur. In some embodiments, -Cy¹- is a bivalent optionally substituted bicyclic 8 membered heteroarylene having 1-2 heteroatoms independently selected from nitrogen, oxygen, or sulfur. In some embodiments, -Cy$^1$- is a bivalent optionally substituted bicyclic 9 membered heteroarylene having 1-5 heteroatoms independently selected from nitrogen, oxygen, or sulfur. In some embodiments, -Cy$^1$- is a bivalent optionally substituted bicyclic 9 membered heteroarylene having 1-2 heteroatoms independently selected from nitrogen, oxygen, or sulfur. In some embodiments, -Cy$^1$- is a bivalent optionally substituted bicyclic 10 membered heteroarylene having 1-5 heteroatoms independently selected from nitrogen, oxygen, or sulfur. In some embodiments, -Cy$^1$- is a bivalent optionally substituted bicyclic 10 membered heteroarylene having 1-2 heteroatoms independently selected from nitrogen, oxygen, or sulfur.

In some embodiments, -Cy$^1$- is a bivalent optionally substituted bicyclic 7-10 membered saturated heterocyclylene having 1-5 heteroatoms selected from nitrogen, oxygen, or sulfur. In some embodiments, -Cy$^1$- is a bivalent optionally substituted bicyclic 7-10 membered saturated heterocyclylene having 1-2 heteroatoms selected from nitrogen, oxygen, or sulfur. In some embodiments, -Cy$^1$- is a bivalent optionally substituted bicyclic 7 membered saturated heterocyclylene having 1-5 heteroatoms selected from nitrogen, oxygen, or sulfur. In some embodiments, -Cy$^1$- is a bivalent optionally substituted bicyclic 7 membered saturated heterocyclylene having 1-2 heteroatoms selected from nitrogen, oxygen, or sulfur. In some embodiments, -Cy$^1$- is a bivalent optionally substituted bicyclic 8 membered saturated heterocyclylene having 1-5 heteroatoms selected from nitrogen, oxygen, or sulfur. In some embodiments, -Cy$^1$- is a bivalent optionally substituted bicyclic 8 membered saturated heterocyclylene having 1-2 heteroatoms selected from nitrogen, oxygen, or sulfur. In some embodiments, -Cy$^1$- is a bivalent optionally substituted bicyclic 9 membered saturated heterocyclylene having 1-5 heteroatoms selected from nitrogen, oxygen, or sulfur. In some embodiments, -Cy$^1$- is a bivalent optionally substituted bicyclic 9 membered saturated heterocyclylene having 1-2 heteroatoms selected from nitrogen, oxygen, or sulfur. In some embodiments, -Cy$^1$- is a bivalent optionally substituted bicyclic 10 membered saturated heterocyclylene having 1-5 heteroatoms selected from nitrogen, oxygen, or sulfur. In some embodiments, -Cy$^1$- is a bivalent optionally substituted bicyclic 10 membered saturated heterocyclylene having 1-2 heteroatoms selected from nitrogen, oxygen, or sulfur.

In some embodiments, -Cy$^1$- is a bivalent optionally substituted bicyclic 7-10 membered partially unsaturated heterocyclylene having 1-5 heteroatoms selected from nitrogen, oxygen, or sulfur. In some embodiments, -Cy$^1$- is a bivalent optionally substituted bicyclic 7-10 membered partially unsaturated heterocyclylene having 1-2 heteroatoms selected from nitrogen, oxygen, or sulfur. In some embodiments, -Cy$^1$- is a bivalent optionally substituted bicyclic 7 membered partially unsaturated heterocyclylene having 1-5 heteroatoms selected from nitrogen, oxygen, or sulfur. In some embodiments, -Cy$^1$- is a bivalent optionally substituted bicyclic 7 membered partially unsaturated heterocyclylene having 1-2 heteroatoms selected from nitrogen, oxygen, or sulfur. In some embodiments, -Cy$^1$- is a bivalent optionally substituted bicyclic 8 membered partially unsaturated heterocyclylene having 1-5 heteroatoms selected from nitrogen, oxygen, or sulfur. In some embodiments, -Cy$^1$- is a bivalent optionally substituted bicyclic 8 membered partially unsaturated heterocyclylene having 1-2 heteroatoms selected from nitrogen, oxygen, or sulfur. In some embodiments, -Cy$^1$- is a bivalent optionally substituted bicyclic 9 membered partially unsaturated heterocyclylene having 1-5 heteroatoms selected from nitrogen, oxygen, or sulfur. In some embodiments, -Cy$^1$- is a bivalent optionally substituted bicyclic 9 membered partially unsaturated heterocyclylene having 1-2 heteroatoms selected from nitrogen, oxygen, or sulfur. In some embodiments, -Cy$^1$- is a bivalent optionally substituted bicyclic 10 membered partially unsaturated heterocyclylene having 1-5 heteroatoms selected from nitrogen, oxygen, or sulfur. In some embodiments, -Cy$^1$- is a bivalent optionally substituted bicyclic 10 membered partially unsaturated heterocyclylene having 1-2 heteroatoms selected from nitrogen, oxygen, or sulfur.

In some embodiments, -Cy$^1$- is a bivalent optionally substituted tricyclic 14 membered arylene.

In some embodiments, -Cy$^1$- is a bivalent optionally substituted tricyclic 9-20 membered saturated carbocyclylene. In some embodiments, -Cy$^1$- is a bivalent optionally substituted tricyclic 10-20 membered saturated carbocyclylene. In some embodiments, -Cy$^1$- is a bivalent optionally substituted tricyclic 12-20 membered saturated carbocyclylene. In some embodiments, -Cy$^1$- is a bivalent optionally substituted tricyclic 12-18 membered saturated carbocyclylene. In some embodiments, -Cy$^1$- is a bivalent optionally substituted tricyclic 12-14 membered saturated carbocyclylene. In some embodiments, -Cy$^1$- is a bivalent optionally substituted tricyclic 14-16 membered saturated carbocyclylene. In some embodiments, -Cy$^1$- is a bivalent optionally substituted tricyclic 16-18 membered saturated carbocyclylene.

In some embodiments, -Cy$^1$- is a bivalent optionally substituted tricyclic 9-20 membered partially unsaturated carbocyclylene. In some embodiments, -Cy$^1$- is a bivalent optionally substituted tricyclic 10-20 membered partially unsaturated carbocyclylene. In some embodiments, -Cy$^1$- is a bivalent optionally substituted tricyclic 12-20 membered partially unsaturated carbocyclylene. In some embodiments, -Cy$^1$- is a bivalent optionally substituted tricyclic 12-18 membered partially unsaturated carbocyclylene. In some embodiments, -Cy$^1$- is a bivalent optionally substituted tricyclic 12-14 membered partially unsaturated carbocyclylene. In some embodiments, -Cy$^1$- is a bivalent optionally substituted tricyclic 14-16 membered partially unsaturated carbocyclylene. In some embodiments, -Cy$^1$- is a bivalent optionally substituted tricyclic 16-18 membered partially unsaturated carbocyclylene.

In some embodiments, -Cy$^1$- is a bivalent optionally substituted tricyclic 9-14 membered heteroarylene having 1-8 heteroatoms independently selected from nitrogen, oxygen, or sulfur. In some embodiments, -Cy$^1$- is a bivalent optionally substituted tricyclic 9-14 membered heteroarylene having 1-6 heteroatoms independently selected from nitrogen, oxygen, or sulfur. In some embodiments, -Cy$^1$- is a bivalent optionally substituted tricyclic 9-14 membered heteroarylene having 1-4 heteroatoms independently selected from nitrogen, oxygen, or sulfur. In some embodiments, -Cy$^1$- is a bivalent optionally substituted tricyclic 9-14 membered heteroarylene having 1-3 heteroatoms independently selected from nitrogen, oxygen, or sulfur. In some embodiments, -Cy$^1$- is a bivalent optionally substituted tricyclic 9-14 membered heteroarylene having 2-4 heteroatoms independently selected from nitrogen, oxygen, or sulfur. In some embodiments, -Cy$^1$- is a bivalent optionally substituted tricyclic 9-14 membered heteroarylene having 4-6 heteroatoms independently selected from nitrogen, oxygen, or sulfur.

In some embodiments, -Cy$^1$- is a bivalent optionally substituted tricyclic 10-14 membered heteroarylene having 1-8 heteroatoms independently selected from nitrogen, oxygen, or sulfur. In some embodiments, -Cy$^1$- is a bivalent optionally substituted tricyclic 10-14 membered heteroarylene having 1-6 heteroatoms independently selected from nitrogen, oxygen, or sulfur. In some embodiments, -Cy$^1$- is a bivalent optionally substituted tricyclic 10-14 membered heteroarylene having 1-4 heteroatoms independently selected from nitrogen, oxygen, or sulfur. In some embodiments, -Cy$^1$- is a bivalent optionally substituted tricyclic 10-14 membered heteroarylene having 1-3 heteroatoms independently selected from nitrogen, oxygen, or sulfur. In some embodiments, -Cy$^1$- is a bivalent optionally substituted tricyclic 10-14 membered heteroarylene having 2-4 heteroatoms independently selected from nitrogen, oxygen, or sulfur. In some embodiments, -Cy$^1$- is a bivalent optionally substituted tricyclic 10-14 membered heteroarylene having 4-6 heteroatoms independently selected from nitrogen, oxygen, or sulfur.

In some embodiments, -Cy$^1$- is a bivalent optionally substituted tricyclic 12-14 membered heteroarylene having 1-8 heteroatoms independently selected from nitrogen, oxygen, or sulfur. In some embodiments, -Cy$^1$- is a bivalent optionally substituted tricyclic 12-14 membered heteroarylene having 1-6 heteroatoms independently selected from nitrogen, oxygen, or sulfur. In some embodiments, -Cy$^1$- is a bivalent optionally substituted tricyclic 12-14 membered heteroarylene having 1-4 heteroatoms independently selected from nitrogen, oxygen, or sulfur. In some embodiments, -Cy$^1$- is a bivalent optionally substituted tricyclic 12-14 membered heteroarylene having 1-3 heteroatoms independently selected from nitrogen, oxygen, or sulfur. In some embodiments, -Cy$^1$- is a bivalent optionally substituted tricyclic 12-14 membered heteroarylene having 2-4 heteroatoms independently selected from nitrogen, oxygen, or sulfur. In some embodiments, -Cy$^1$- is a bivalent optionally substituted tricyclic 12-14 membered heteroarylene having 4-6 heteroatoms independently selected from nitrogen, oxygen, or sulfur.

In some embodiments, -Cy$^1$- is a bivalent optionally substituted tricyclic 9-20 membered saturated heterocyclylene having 1-8 heteroatoms independently selected from nitrogen, oxygen, or sulfur. In some embodiments, -Cy$^1$- is a bivalent optionally substituted tricyclic 9-20 membered saturated heterocyclylene having 1-6 heteroatoms independently selected from nitrogen, oxygen, or sulfur. In some embodiments, -Cy$^1$- is a bivalent optionally substituted tricyclic 9-20 membered saturated heterocyclylene having 1-4 heteroatoms independently selected from nitrogen, oxygen, or sulfur. In some embodiments, -Cy$^1$- is a bivalent optionally substituted tricyclic 9-20 membered saturated heterocyclylene having 1-3 heteroatoms independently selected from nitrogen, oxygen, or sulfur. In some embodiments, —Cy$^1$- is a bivalent optionally substituted tricyclic 9-20 membered saturated heterocyclylene having 2-4 heteroatoms independently selected from nitrogen, oxygen, or sulfur. In some embodiments, -Cy$^1$- is a bivalent optionally substituted tricyclic 9-20 membered saturated heterocyclylene having 4-6 heteroatoms independently selected from nitrogen, oxygen, or sulfur.

In some embodiments, -Cy$^1$- is a bivalent optionally substituted tricyclic 12-20 membered saturated heterocyclylene having 1-8 heteroatoms independently selected from nitrogen, oxygen, or sulfur. In some embodiments, -Cy$^1$- is a bivalent optionally substituted tricyclic 12-20 membered saturated heterocyclylene having 1-6 heteroatoms independently selected from nitrogen, oxygen, or sulfur. In some embodiments, -Cy$^1$- is a bivalent optionally substituted tricyclic 12-20 membered saturated heterocyclylene having 1-4 heteroatoms independently selected from nitrogen, oxygen, or sulfur. In some embodiments, -Cy$^1$- is a bivalent optionally substituted tricyclic 12-20 membered saturated heterocyclylene having 1-3 heteroatoms independently selected from nitrogen, oxygen, or sulfur. In some embodiments, —Cy$^1$- is a bivalent optionally substituted tricyclic 12-20 membered saturated heterocyclylene having 2-4 heteroatoms independently selected from nitrogen, oxygen, or sulfur. In some embodiments, -Cy$^1$- is a bivalent optionally substituted tricyclic 12-20 membered saturated heterocyclylene having 4-6 heteroatoms independently selected from nitrogen, oxygen, or sulfur.

In some embodiments, -Cy$^1$- is a bivalent optionally substituted tricyclic 12-18 membered saturated heterocyclylene having 1-8 heteroatoms independently selected from nitrogen, oxygen, or sulfur. In some embodiments, -Cy$^1$- is a bivalent optionally substituted tricyclic 12-18 membered saturated heterocyclylene having 1-6 heteroatoms independently selected from nitrogen, oxygen, or sulfur. In some embodiments, -Cy$^1$- is a bivalent optionally substituted tricyclic 12-18 membered saturated heterocyclylene having 1-4 heteroatoms independently selected from nitrogen, oxygen, or sulfur. In some embodiments, -Cy$^1$- is a bivalent optionally substituted tricyclic 12-18 membered saturated heterocyclylene having 1-3 heteroatoms independently selected from nitrogen, oxygen, or sulfur. In some embodiments, —Cy$^1$- is a bivalent optionally substituted tricyclic 12-18 membered saturated heterocyclylene having 2-4 heteroatoms independently selected from nitrogen, oxygen, or sulfur. In some embodiments, -Cy$^1$- is a bivalent optionally substituted tricyclic 12-18 membered saturated heterocyclylene having 4-6 heteroatoms independently selected from nitrogen, oxygen, or sulfur.

In some embodiments, -Cy$^1$- is a bivalent optionally substituted tricyclic 12-14 membered saturated heterocyclylene having 1-8 heteroatoms independently selected from nitrogen, oxygen, or sulfur. In some embodiments, -Cy$^1$- is a bivalent optionally substituted tricyclic 12-14 membered saturated heterocyclylene having 1-6 heteroatoms independently selected from nitrogen, oxygen, or sulfur. In some embodiments, -Cy$^1$- is a bivalent optionally substituted tricyclic 12-14 membered saturated heterocyclylene having 1-4 heteroatoms independently selected from nitrogen, oxygen, or sulfur. In some embodiments, -Cy$^1$- is a bivalent optionally substituted tricyclic 12-14 membered saturated heterocyclylene having 1-3 heteroatoms independently selected from nitrogen, oxygen, or sulfur. In some embodiments, —Cy$^1$- is a bivalent optionally substituted tricyclic 12-14 membered saturated heterocyclylene having 2-4 heteroatoms independently selected from nitrogen, oxygen, or sulfur. In some embodiments, -Cy$^1$- is a bivalent optionally substituted tricyclic 12-14 membered saturated heterocyclylene having 4-6 heteroatoms independently selected from nitrogen, oxygen, or sulfur.

In some embodiments, -Cy$^1$- is a bivalent optionally substituted tricyclic 14-16 membered saturated heterocyclylene having 1-8 heteroatoms independently selected from nitrogen, oxygen, or sulfur. In some embodiments, -Cy$^1$- is a bivalent optionally substituted tricyclic 14-16 membered saturated heterocyclylene having 1-6 heteroatoms independently selected from nitrogen, oxygen, or sulfur. In some embodiments, -Cy$^1$- is a bivalent optionally substituted tricyclic 14-16 membered saturated heterocyclylene having 1-4 heteroatoms independently selected from nitrogen, oxygen, or sulfur. In some embodiments, -Cy$^1$- is a bivalent optionally substituted tricyclic 14-16 membered saturated heterocyclylene having 1-3 heteroatoms independently selected from nitrogen, oxygen, or sulfur. In some embodiments, —Cy$^1$- is a bivalent optionally substituted tricyclic 14-16 membered saturated heterocyclylene having 2-4 heteroatoms independently selected from nitrogen, oxygen, or sulfur. In some embodiments, -Cy$^1$- is a bivalent optionally substituted tricyclic 14-16 membered saturated heterocyclylene having 4-6 heteroatoms independently selected from nitrogen, oxygen, or sulfur.

In some embodiments, -$Cy^1$- is a bivalent optionally substituted tricyclic 16-18 membered saturated heterocyclylene having 1-8 heteroatoms independently selected from nitrogen, oxygen, or sulfur. In some embodiments, -$Cy^1$- is a bivalent optionally substituted tricyclic 16-18 membered saturated heterocyclylene having 1-6 heteroatoms independently selected from nitrogen, oxygen, or sulfur. In some embodiments, -$Cy^1$- is a bivalent optionally substituted tricyclic 16-18 membered saturated heterocyclylene having 1-4 heteroatoms independently selected from nitrogen, oxygen, or sulfur. In some embodiments, -$Cy^1$- is a bivalent optionally substituted tricyclic 16-18 membered saturated heterocyclylene having 1-3 heteroatoms independently selected from nitrogen, oxygen, or sulfur. In some embodiments, —$Cy^1$- is a bivalent optionally substituted tricyclic 16-18 membered saturated heterocyclylene having 2-4 heteroatoms independently selected from nitrogen, oxygen, or sulfur. In some embodiments, -$Cy^1$- is a bivalent optionally substituted tricyclic 16-18 membered saturated heterocyclylene having 4-6 heteroatoms independently selected from nitrogen, oxygen, or sulfur.

In some embodiments, -$Cy^1$- is a bivalent optionally substituted tricyclic 9-20 membered partially unsaturated heterocyclylene having 1-8 heteroatoms independently selected from nitrogen, oxygen, or sulfur. In some embodiments, -$Cy^1$- is a bivalent optionally substituted tricyclic 9-20 membered partially unsaturated heterocyclylene having 1-6 heteroatoms independently selected from nitrogen, oxygen, or sulfur. In some embodiments, —$Cy^1$- is a bivalent optionally substituted tricyclic 9-20 membered partially unsaturated heterocyclylene having 1-4 heteroatoms independently selected from nitrogen, oxygen, or sulfur. In some embodiments, -$Cy^1$- is a bivalent optionally substituted tricyclic 9-20 membered partially unsaturated heterocyclylene having 1-3 heteroatoms independently selected from nitrogen, oxygen, or sulfur. In some embodiments, -$Cy^1$- is a bivalent optionally substituted tricyclic 9-20 membered partially unsaturated heterocyclylene having 2-4 heteroatoms independently selected from nitrogen, oxygen, or sulfur. In some embodiments, -$Cy^1$- is a bivalent optionally substituted tricyclic 9-20 membered partially unsaturated heterocyclylene having 4-6 heteroatoms independently selected from nitrogen, oxygen, or sulfur.

In some embodiments, -$Cy^1$- is a bivalent optionally substituted tricyclic 12-20 membered partially unsaturated heterocyclylene having 1-8 heteroatoms independently selected from nitrogen, oxygen, or sulfur. In some embodiments, -$Cy^1$- is a bivalent optionally substituted tricyclic 12-20 membered partially unsaturated heterocyclylene having 1-6 heteroatoms independently selected from nitrogen, oxygen, or sulfur. In some embodiments, —$Cy^1$- is a bivalent optionally substituted tricyclic 12-20 membered partially unsaturated heterocyclylene having 1-4 heteroatoms independently selected from nitrogen, oxygen, or sulfur. In some embodiments, -$Cy^1$- is a bivalent optionally substituted tricyclic 12-20 membered partially unsaturated heterocyclylene having 1-3 heteroatoms independently selected from nitrogen, oxygen, or sulfur. In some embodiments, -$Cy^1$- is a bivalent optionally substituted tricyclic 12-20 membered partially unsaturated heterocyclylene having 2-4 heteroatoms independently selected from nitrogen, oxygen, or sulfur. In some embodiments, -$Cy^1$- is a bivalent optionally substituted tricyclic 12-20 membered partially unsaturated heterocyclylene having 4-6 heteroatoms independently selected from nitrogen, oxygen, or sulfur.

In some embodiments, -$Cy^1$- is a bivalent optionally substituted tricyclic 12-18 membered partially unsaturated heterocyclylene having 1-8 heteroatoms independently selected from nitrogen, oxygen, or sulfur. In some embodiments, -$Cy^1$- is a bivalent optionally substituted tricyclic 12-18 membered partially unsaturated heterocyclylene having 1-6 heteroatoms independently selected from nitrogen, oxygen, or sulfur. In some embodiments, —$Cy^1$- is a bivalent optionally substituted tricyclic 12-18 membered partially unsaturated heterocyclylene having 1-4 heteroatoms independently selected from nitrogen, oxygen, or sulfur. In some embodiments, -$Cy^1$- is a bivalent optionally substituted tricyclic 12-18 membered partially unsaturated heterocyclylene having 1-3 heteroatoms independently selected from nitrogen, oxygen, or sulfur. In some embodiments, -$Cy^1$- is a bivalent optionally substituted tricyclic 12-18 membered partially unsaturated heterocyclylene having 2-4 heteroatoms independently selected from nitrogen, oxygen, or sulfur. In some embodiments, -$Cy^1$- is a bivalent optionally substituted tricyclic 12-18 membered partially unsaturated heterocyclylene having 4-6 heteroatoms independently selected from nitrogen, oxygen, or sulfur.

In some embodiments, -$Cy^1$- is a bivalent optionally substituted tricyclic 12-14 membered partially unsaturated heterocyclylene having 1-8 heteroatoms independently selected from nitrogen, oxygen, or sulfur. In some embodiments, -$Cy^1$- is a bivalent optionally substituted tricyclic 12-14 membered partially unsaturated heterocyclylene having 1-6 heteroatoms independently selected from nitrogen, oxygen, or sulfur. In some embodiments, —$Cy^1$- is a bivalent optionally substituted tricyclic 12-14 membered partially unsaturated heterocyclylene having 1-4 heteroatoms independently selected from nitrogen, oxygen, or sulfur. In some embodiments, -$Cy^1$- is a bivalent optionally substituted tricyclic 12-14 membered partially unsaturated heterocyclylene having 1-3 heteroatoms independently selected from nitrogen, oxygen, or sulfur. In some embodiments, -$Cy^1$- is a bivalent optionally substituted tricyclic 12-14 membered partially unsaturated heterocyclylene having 2-4 heteroatoms independently selected from nitrogen, oxygen, or sulfur. In some embodiments, -$Cy^1$- is a bivalent optionally substituted tricyclic 12-14 membered partially unsaturated heterocyclylene having 4-6 heteroatoms independently selected from nitrogen, oxygen, or sulfur.

In some embodiments, -$Cy^1$- is a bivalent optionally substituted tricyclic 14-16 membered partially unsaturated heterocyclylene having 1-8 heteroatoms independently selected from nitrogen, oxygen, or sulfur. In some embodiments, -$Cy^1$- is a bivalent optionally substituted tricyclic 14-16 membered partially unsaturated heterocyclylene having 1-6 heteroatoms independently selected from nitrogen, oxygen, or sulfur. In some embodiments, —$Cy^1$- is a bivalent optionally substituted tricyclic 14-16 membered partially unsaturated heterocyclylene having 1-4 heteroatoms independently selected from nitrogen, oxygen, or sulfur. In some embodiments, -$Cy^1$- is a bivalent optionally substituted tricyclic 14-16 membered partially unsaturated heterocyclylene having 1-3 heteroatoms independently selected from nitrogen, oxygen, or sulfur. In some embodiments, -$Cy^1$- is a bivalent optionally substituted tricyclic 14-16 membered partially unsaturated heterocyclylene having 2-4 heteroatoms independently selected from nitrogen, oxygen, or sulfur. In some embodiments, -$Cy^1$- is a bivalent optionally substituted tricyclic 14-16 membered partially unsaturated heterocyclylene having 4-6 heteroatoms independently selected from nitrogen, oxygen, or sulfur.

In some embodiments, -Cy$^1$- is a bivalent optionally substituted tricyclic 16-18 membered partially unsaturated heterocyclylene having 1-8 heteroatoms independently selected from nitrogen, oxygen, or sulfur. In some embodiments, -Cy$^1$- is a bivalent optionally substituted tricyclic 16-18 membered partially unsaturated heterocyclylene having 1-6 heteroatoms independently selected from nitrogen, oxygen, or sulfur. In some embodiments, —Cy$^1$- is a bivalent optionally substituted tricyclic 16-18 membered partially unsaturated heterocyclylene having 1-4 heteroatoms independently selected from nitrogen, oxygen, or sulfur. In some embodiments, -Cy$^1$- is a bivalent optionally substituted tricyclic 16-18 membered partially unsaturated heterocyclylene having 1-3 heteroatoms independently selected from nitrogen, oxygen, or sulfur. In some embodiments, -Cy$^1$- is a bivalent optionally substituted tricyclic 16-18 membered partially unsaturated heterocyclylene having 2-4 heteroatoms independently selected from nitrogen, oxygen, or sulfur. In some embodiments, -Cy$^1$- is a bivalent optionally substituted tricyclic 16-18 membered partially unsaturated heterocyclylene having 4-6 heteroatoms independently selected from nitrogen, oxygen, or sulfur.

In some embodiments, -Cy$^1$- is a bivalent optionally substituted tetracyclic 16-18 membered arylene.

In some embodiments, -Cy$^1$- is a bivalent optionally substituted tetracyclic 11-30 membered saturated carbocyclylene. In some embodiments, -Cy$^1$- is a bivalent optionally substituted tetracyclic 11-25 membered saturated carbocyclylene. In some embodiments, -Cy$^1$- is a bivalent optionally substituted tetracyclic 12-24 membered saturated carbocyclylene. In some embodiments, -Cy$^1$- is a bivalent optionally substituted tetracyclic 14-24 membered saturated carbocyclylene. In some embodiments, -Cy$^1$- is a bivalent optionally substituted tetracyclic 15-20 membered saturated carbocyclylene. In some embodiments, -Cy$^1$- is a bivalent optionally substituted tetracyclic 20-24 membered saturated carbocyclylene.

In some embodiments, -Cy$^1$- is a bivalent optionally substituted tetracyclic 11-30 membered partially unsaturated carbocyclylene. In some embodiments, -Cy$^1$- is a bivalent optionally substituted tetracyclic 11-25 membered partially unsaturated carbocyclylene. In some embodiments, -Cy$^1$- is a bivalent optionally substituted tetracyclic 12-24 membered partially unsaturated carbocyclylene. In some embodiments, -Cy$^1$- is a bivalent optionally substituted tetracyclic 14-24 membered partially unsaturated carbocyclylene. In some embodiments, -Cy$^1$- is a bivalent optionally substituted tetracyclic 15-20 membered partially unsaturated carbocyclylene. In some embodiments, -Cy$^1$- is a bivalent optionally substituted tetracyclic 20-24 membered partially unsaturated carbocyclylene.

In some embodiments, -Cy$^1$- is a bivalent optionally substituted tetracyclic 15-18 membered heteroarylene having 1-8 heteroatoms independently selected from nitrogen, oxygen, or sulfur. In some embodiments, -Cy$^1$- is a bivalent optionally substituted tetracyclic 15-18 membered heteroarylene having 1-6 heteroatoms independently selected from nitrogen, oxygen, or sulfur. In some embodiments, -Cy$^1$- is a bivalent optionally substituted tetracyclic 15-18 membered heteroarylene having 1-4 heteroatoms independently selected from nitrogen, oxygen, or sulfur. In some embodiments, -Cy$^1$- is a bivalent optionally substituted tetracyclic 15-18 membered heteroarylene having 1-3 heteroatoms independently selected from nitrogen, oxygen, or sulfur. In some embodiments, -Cy$^1$- is a bivalent optionally substituted tetracyclic 15-18 membered heteroarylene having 2-4 heteroatoms independently selected from nitrogen, oxygen, or sulfur. In some embodiments, -Cy$^1$- is a bivalent optionally substituted tetracyclic 15-18 membered heteroarylene having 4-8 heteroatoms independently selected from nitrogen, oxygen, or sulfur.

In certain embodiments, -Cy$^1$- is a bivalent optionally substituted tetracyclic 15-18 membered heteroarylene having 3 heteroatoms independently selected from nitrogen, oxygen, or sulfur. In certain embodiments, -Cy$^1$- is a bivalent optionally substituted tetracyclic 15 membered heteroarylene having 3 heteroatoms independently selected from nitrogen, oxygen, or sulfur. In certain embodiments, -Cy$^1$- is a bivalent tetracyclic 15 membered heteroarylene having 3 heteroatoms independently selected from nitrogen, oxygen, or sulfur, wherein -Cy$^1$- is substituted with at least two R groups. In certain embodiments, -Cy$^1$- is a bivalent tetracyclic 15 membered heteroarylene having 3 heteroatoms independently selected from oxygen and nitrogen, wherein -Cy$^1$- is substituted with at least two R groups, and wherein the at least two R groups are on adjacent atoms and are taken together with their intervening atoms to form an optionally substituted 3-8 membered saturated, partially unsaturated, or aryl ring having 0-4 heteroatoms independently selected from nitrogen, oxygen, or sulfur. In certain embodiments, —Cy$^1$- is a bivalent tetracyclic 15 membered heteroarylene having 3 heteroatoms independently selected from oxygen or nitrogen, wherein -Cy$^1$- is substituted with at least two R groups, and wherein the at least two R groups are on adjacent atoms and are taken together with their intervening atoms to form an optionally substituted 8 membered partially unsaturated ring having 1 heteroatom independently selected from nitrogen, oxygen, or sulfur. In certain embodiments, the one heteroatom of the above described optionally substituted 8 membered partially unsaturated ring is nitrogen.

In some embodiments, -Cy$^1$- is a bivalent optionally substituted tetracyclic 11-30 membered saturated heterocyclylene having 1-12 heteroatoms independently selected from nitrogen, oxygen, or sulfur. In some embodiments, -Cy$^1$- is a bivalent optionally substituted tetracyclic 11-30 membered saturated heterocyclylene having 1-10 heteroatoms independently selected from nitrogen, oxygen, or sulfur. In some embodiments, -Cy$^1$- is a bivalent optionally substituted tetracyclic 11-30 membered saturated heterocyclylene having 1-8 heteroatoms independently selected from nitrogen, oxygen, or sulfur. In some embodiments, -Cy$^1$- is a bivalent optionally substituted tetracyclic 11-30 membered saturated heterocyclylene having 1-6 heteroatoms independently selected from nitrogen, oxygen, or sulfur. In some embodiments, —Cy$^1$- is a bivalent optionally substituted tetracyclic 11-30 membered saturated heterocyclylene having 1-4 heteroatoms independently selected from nitrogen, oxygen, or sulfur. In some embodiments, -Cy$^1$- is a bivalent optionally substituted tetracyclic 11-30 membered saturated heterocyclylene having 1-3 heteroatoms independently selected from nitrogen, oxygen, or sulfur. In some embodiments, -Cy$^1$- is a bivalent optionally substituted tetracyclic 11-30 membered saturated heterocyclylene having 4-6 heteroatoms independently selected from nitrogen, oxygen, or sulfur. In some embodiments, -Cy$^1$- is a bivalent optionally substituted tetracyclic 11-30 membered saturated heterocyclylene having 4-8 heteroatoms independently selected from nitrogen, oxygen, or sulfur. In some embodiments, -Cy$^1$- is a bivalent optionally substituted tetracyclic 11-30 membered saturated heterocyclylene having 6-8 heteroatoms independently selected from nitrogen, oxygen, or sulfur.

In some embodiments, -Cy$^1$- is a bivalent optionally substituted tetracyclic 11-25 membered saturated heterocyclylene having 1-12 heteroatoms independently selected from nitrogen, oxygen, or sulfur. In some embodiments, -Cy$^1$- is a bivalent optionally substituted tetracyclic 11-25 membered saturated heterocyclylene having 1-10 heteroatoms independently selected from nitrogen, oxygen, or sulfur. In some embodiments, -Cy$^1$- is a bivalent optionally substituted tetracyclic 11-25 membered saturated heterocyclylene having 1-8 heteroatoms independently selected from nitrogen, oxygen, or sulfur. In some embodiments, -Cy$^1$- is a bivalent optionally substituted tetracyclic 11-25 membered saturated heterocyclylene having 1-6 heteroatoms independently selected from nitrogen, oxygen, or sulfur. In some embodiments, —Cy$^1$- is a bivalent optionally substituted tetracyclic 11-25 membered saturated heterocyclylene having 1-4 heteroatoms independently selected from nitrogen, oxygen, or sulfur. In some embodiments, -Cy$^1$- is a bivalent optionally substituted tetracyclic 11-25 membered saturated heterocyclylene having 1-3 heteroatoms independently selected from nitrogen, oxygen, or sulfur. In some embodiments, -Cy$^1$- is a bivalent optionally substituted tetracyclic 11-25 membered saturated heterocyclylene having 4-6 heteroatoms independently selected from nitrogen, oxygen, or sulfur. In some embodiments, -Cy$^1$- is a bivalent optionally substituted tetracyclic 11-25 membered saturated heterocyclylene having 4-8 heteroatoms independently selected from nitrogen, oxygen, or sulfur. In some embodiments, -Cy$^1$- is a bivalent optionally substituted tetracyclic 11-25 membered saturated heterocyclylene having 6-8 heteroatoms independently selected from nitrogen, oxygen, or sulfur.

In some embodiments, -Cy$^1$- is a bivalent optionally substituted tetracyclic 12-24 membered saturated heterocyclylene having 1-12 heteroatoms independently selected from nitrogen, oxygen, or sulfur. In some embodiments, -Cy$^1$- is a bivalent optionally substituted tetracyclic 12-24 membered saturated heterocyclylene having 1-10 heteroatoms independently selected from nitrogen, oxygen, or sulfur. In some embodiments, -Cy$^1$- is a bivalent optionally substituted tetracyclic 12-24 membered saturated heterocyclylene having 1-8 heteroatoms independently selected from nitrogen, oxygen, or sulfur. In some embodiments, -Cy$^1$- is a bivalent optionally substituted tetracyclic 12-24 membered saturated heterocyclylene having 1-6 heteroatoms independently selected from nitrogen, oxygen, or sulfur. In some embodiments, —Cy$^1$- is a bivalent optionally substituted tetracyclic 12-24 membered saturated heterocyclylene having 1-4 heteroatoms independently selected from nitrogen, oxygen, or sulfur. In some embodiments, -Cy$^1$- is a bivalent optionally substituted tetracyclic 12-24 membered saturated heterocyclylene having 1-3 heteroatoms independently selected from nitrogen, oxygen, or sulfur. In some embodiments, -Cy$^1$- is a bivalent optionally substituted tetracyclic 12-24 membered saturated heterocyclylene having 4-6 heteroatoms independently selected from nitrogen, oxygen, or sulfur. In some embodiments, -Cy$^1$- is a bivalent optionally substituted tetracyclic 12-24 membered saturated heterocyclylene having 4-8 heteroatoms independently selected from nitrogen, oxygen, or sulfur. In some embodiments, -Cy$^1$- is a bivalent optionally substituted tetracyclic 12-24 membered saturated heterocyclylene having 6-8 heteroatoms independently selected from nitrogen, oxygen, or sulfur.

In some embodiments, -Cy$^1$- is a bivalent optionally substituted tetracyclic 15-20 membered saturated heterocyclylene having 1-12 heteroatoms independently selected from nitrogen, oxygen, or sulfur. In some embodiments, -Cy$^1$- is a bivalent optionally substituted tetracyclic 15-20 membered saturated heterocyclylene having 1-10 heteroatoms independently selected from nitrogen, oxygen, or sulfur. In some embodiments, -Cy$^1$- is a bivalent optionally substituted tetracyclic 15-20 membered saturated heterocyclylene having 1-8 heteroatoms independently selected from nitrogen, oxygen, or sulfur. In some embodiments, -Cy$^1$- is a bivalent optionally substituted tetracyclic 15-20 membered saturated heterocyclylene having 1-6 heteroatoms independently selected from nitrogen, oxygen, or sulfur. In some embodiments, —Cy$^1$- is a bivalent optionally substituted tetracyclic 15-20 membered saturated heterocyclylene having 1-4 heteroatoms independently selected from nitrogen, oxygen, or sulfur. In some embodiments, -Cy$^1$- is a bivalent optionally substituted tetracyclic 15-20 membered saturated heterocyclylene having 1-3 heteroatoms independently selected from nitrogen, oxygen, or sulfur. In some embodiments, -Cy$^1$- is a bivalent optionally substituted tetracyclic 15-20 membered saturated heterocyclylene having 4-6 heteroatoms independently selected from nitrogen, oxygen, or sulfur. In some embodiments, -Cy$^1$- is a bivalent optionally substituted tetracyclic 15-20 membered saturated heterocyclylene having 4-8 heteroatoms independently selected from nitrogen, oxygen, or sulfur. In some embodiments, -Cy$^1$- is a bivalent optionally substituted tetracyclic 15-20 membered saturated heterocyclylene having 6-8 heteroatoms independently selected from nitrogen, oxygen, or sulfur.

In some embodiments, -Cy$^1$- is a bivalent optionally substituted tetracyclic 20-24 membered saturated heterocyclylene having 1-12 heteroatoms independently selected from nitrogen, oxygen, or sulfur. In some embodiments, -Cy$^1$- is a bivalent optionally substituted tetracyclic 20-24 membered saturated heterocyclylene having 1-10 heteroatoms independently selected from nitrogen, oxygen, or sulfur. In some embodiments, -Cy$^1$- is a bivalent optionally substituted tetracyclic 20-24 membered saturated heterocyclylene having 1-8 heteroatoms independently selected from nitrogen, oxygen, or sulfur. In some embodiments, -Cy$^1$- is a bivalent optionally substituted tetracyclic 20-24 membered saturated heterocyclylene having 1-6 heteroatoms independently selected from nitrogen, oxygen, or sulfur. In some embodiments, —Cy$^1$- is a bivalent optionally substituted tetracyclic 20-24 membered saturated heterocyclylene having 1-4 heteroatoms independently selected from nitrogen, oxygen, or sulfur. In some embodiments, -Cy$^1$- is a bivalent optionally substituted tetracyclic 20-24 membered saturated heterocyclylene having 1-3 heteroatoms independently selected from nitrogen, oxygen, or sulfur. In some embodiments, -Cy$^1$- is a bivalent optionally substituted tetracyclic 20-24 membered saturated heterocyclylene having 4-6 heteroatoms independently selected from nitrogen, oxygen, or sulfur. In some embodiments, -Cy$^1$- is a bivalent optionally substituted tetracyclic 20-24 membered saturated heterocyclylene having 4-8 heteroatoms independently selected from nitrogen, oxygen, or sulfur. In some embodiments, -Cy$^1$- is a bivalent optionally substituted tetracyclic 20-24 membered saturated heterocyclylene having 6-8 heteroatoms independently selected from nitrogen, oxygen, or sulfur.

In some embodiments, -Cy$^1$- is a bivalent optionally substituted tetracyclic 11-30 membered partially unsaturated heterocyclylene having 1-12 heteroatoms independently selected from nitrogen, oxygen, or sulfur. In some embodiments, -Cy$^1$- is a bivalent optionally substituted tetracyclic 11-30 membered partially unsaturated heterocyclylene having 1-10 heteroatoms independently selected from nitrogen, oxygen, or sulfur. In some embodiments, —Cy$^1$- is a bivalent optionally substituted tetracyclic 11-30 membered partially unsaturated heterocyclylene having 1-8 heteroatoms independently selected from nitrogen, oxygen, or sulfur. In some embodiments, -$Cy^1$- is a bivalent optionally substituted tetracyclic 11-30 membered partially unsaturated heterocyclylene having 1-6 heteroatoms independently selected from nitrogen, oxygen, or sulfur. In some embodiments, -$Cy^1$- is a bivalent optionally substituted tetracyclic 11-30 membered partially unsaturated heterocyclylene having 1-4 heteroatoms independently selected from nitrogen, oxygen, or sulfur. In some embodiments, -$Cy^1$- is a bivalent optionally substituted tetracyclic 11-30 membered partially unsaturated heterocyclylene having 1-3 heteroatoms independently selected from nitrogen, oxygen, or sulfur. In some embodiments, -$Cy^1$- is a bivalent optionally substituted tetracyclic 11-30 membered partially unsaturated heterocyclylene having 4-6 heteroatoms independently selected from nitrogen, oxygen, or sulfur. In some embodiments, -$Cy^1$- is a bivalent optionally substituted tetracyclic 11-30 membered partially unsaturated heterocyclylene having 4-8 heteroatoms independently selected from nitrogen, oxygen, or sulfur. In some embodiments, -$Cy^1$- is a bivalent optionally substituted tetracyclic 11-30 membered partially unsaturated heterocyclylene having 6-8 heteroatoms independently selected from nitrogen, oxygen, or sulfur.

In some embodiments, -$Cy^1$- is a bivalent optionally substituted tetracyclic 11-25 membered partially unsaturated heterocyclylene having 1-12 heteroatoms independently selected from nitrogen, oxygen, or sulfur. In some embodiments, -$Cy^1$- is a bivalent optionally substituted tetracyclic 11-25 membered partially unsaturated heterocyclylene having 1-10 heteroatoms independently selected from nitrogen, oxygen, or sulfur. In some embodiments, —$Cy^1$- is a bivalent optionally substituted tetracyclic 11-25 membered partially unsaturated heterocyclylene having 1-8 heteroatoms independently selected from nitrogen, oxygen, or sulfur. In some embodiments, -$Cy^1$- is a bivalent optionally substituted tetracyclic 11-25 membered partially unsaturated heterocyclylene having 1-6 heteroatoms independently selected from nitrogen, oxygen, or sulfur. In some embodiments, -$Cy^1$- is a bivalent optionally substituted tetracyclic 11-25 membered partially unsaturated heterocyclylene having 1-4 heteroatoms independently selected from nitrogen, oxygen, or sulfur. In some embodiments, -$Cy^1$- is a bivalent optionally substituted tetracyclic 11-25 membered partially unsaturated heterocyclylene having 1-3 heteroatoms independently selected from nitrogen, oxygen, or sulfur. In some embodiments, -$Cy^1$- is a bivalent optionally substituted tetracyclic 11-25 membered partially unsaturated heterocyclylene having 4-6 heteroatoms independently selected from nitrogen, oxygen, or sulfur. In some embodiments, -$Cy^1$- is a bivalent optionally substituted tetracyclic 11-25 membered partially unsaturated heterocyclylene having 4-8 heteroatoms independently selected from nitrogen, oxygen, or sulfur. In some embodiments, -$Cy^1$- is a bivalent optionally substituted tetracyclic 11-25 membered partially unsaturated heterocyclylene having 6-8 heteroatoms independently selected from nitrogen, oxygen, or sulfur.

In some embodiments, -$Cy^1$- is a bivalent optionally substituted tetracyclic 12-24 membered partially unsaturated heterocyclylene having 1-12 heteroatoms independently selected from nitrogen, oxygen, or sulfur. In some embodiments, -$Cy^1$- is a bivalent optionally substituted tetracyclic 12-24 membered partially unsaturated heterocyclylene having 1-10 heteroatoms independently selected from nitrogen, oxygen, or sulfur. In some embodiments, —$Cy^1$- is a bivalent optionally substituted tetracyclic 12-24 membered partially unsaturated heterocyclylene having 1-8 heteroatoms independently selected from nitrogen, oxygen, or sulfur. In some embodiments, -$Cy^1$- is a bivalent optionally substituted tetracyclic 12-24 membered partially unsaturated heterocyclylene having 1-6 heteroatoms independently selected from nitrogen, oxygen, or sulfur. In some embodiments, -$Cy^1$- is a bivalent optionally substituted tetracyclic 12-24 membered partially unsaturated heterocyclylene having 1-4 heteroatoms independently selected from nitrogen, oxygen, or sulfur. In some embodiments, -$Cy^1$- is a bivalent optionally substituted tetracyclic 12-24 membered partially unsaturated heterocyclylene having 1-3 heteroatoms independently selected from nitrogen, oxygen, or sulfur. In some embodiments, -$Cy^1$- is a bivalent optionally substituted tetracyclic 12-24 membered partially unsaturated heterocyclylene having 4-6 heteroatoms independently selected from nitrogen, oxygen, or sulfur. In some embodiments, -$Cy^1$- is a bivalent optionally substituted tetracyclic 12-24 membered partially unsaturated heterocyclylene having 4-8 heteroatoms independently selected from nitrogen, oxygen, or sulfur. In some embodiments, -$Cy^1$- is a bivalent optionally substituted tetracyclic 12-24 membered partially unsaturated heterocyclylene having 6-8 heteroatoms independently selected from nitrogen, oxygen, or sulfur.

In some embodiments, -$Cy^1$- is a bivalent optionally substituted tetracyclic 15-20 membered partially unsaturated heterocyclylene having 1-12 heteroatoms independently selected from nitrogen, oxygen, or sulfur. In some embodiments, -$Cy^1$- is a bivalent optionally substituted tetracyclic 15-20 membered partially unsaturated heterocyclylene having 1-10 heteroatoms independently selected from nitrogen, oxygen, or sulfur. In some embodiments, —$Cy^1$- is a bivalent optionally substituted tetracyclic 15-20 membered partially unsaturated heterocyclylene having 1-8 heteroatoms independently selected from nitrogen, oxygen, or sulfur. In some embodiments, -$Cy^1$- is a bivalent optionally substituted tetracyclic 15-20 membered partially unsaturated heterocyclylene having 1-6 heteroatoms independently selected from nitrogen, oxygen, or sulfur. In some embodiments, -$Cy^1$- is a bivalent optionally substituted tetracyclic 15-20 membered partially unsaturated heterocyclylene having 1-4 heteroatoms independently selected from nitrogen, oxygen, or sulfur. In some embodiments, -$Cy^1$- is a bivalent optionally substituted tetracyclic 15-20 membered partially unsaturated heterocyclylene having 1-3 heteroatoms independently selected from nitrogen, oxygen, or sulfur. In some embodiments, -$Cy^1$- is a bivalent optionally substituted tetracyclic 15-20 membered partially unsaturated heterocyclylene having 4-6 heteroatoms independently selected from nitrogen, oxygen, or sulfur. In some embodiments, -$Cy^1$- is a bivalent optionally substituted tetracyclic 15-20 membered partially unsaturated heterocyclylene having 4-8 heteroatoms independently selected from nitrogen, oxygen, or sulfur. In some embodiments, -$Cy^1$- is a bivalent optionally substituted tetracyclic 15-20 membered partially unsaturated heterocyclylene having 6-8 heteroatoms independently selected from nitrogen, oxygen, or sulfur.

In some embodiments, -$Cy^1$- is a bivalent optionally substituted tetracyclic 20-24 membered partially unsaturated heterocyclylene having 1-12 heteroatoms independently selected from nitrogen, oxygen, or sulfur. In some embodiments, -$Cy^1$- is a bivalent optionally substituted tetracyclic 20-24 membered partially unsaturated heterocyclylene having 1-10 heteroatoms independently selected from nitrogen, oxygen, or sulfur. In some embodiments, —$Cy^1$- is a bivalent optionally substituted tetracyclic 20-24 membered partially unsaturated heterocyclylene having 1-8 heteroatoms independently selected from nitrogen, oxygen, or sulfur. In some embodiments, -$Cy^1$- is a bivalent optionally substituted tetracyclic 20-24 membered partially unsaturated heterocyclylene having 1-6 heteroatoms independently selected from nitrogen, oxygen, or sulfur. In some embodiments, -$Cy^1$- is a bivalent optionally substituted tetracyclic 20-24 membered partially unsaturated heterocyclylene having 1-4 heteroatoms independently selected from nitrogen, oxygen, or sulfur. In some embodiments, -Cy$^1$- is a bivalent optionally substituted tetracyclic 20-24 membered partially unsaturated heterocyclylene having 1-3 heteroatoms independently selected from nitrogen, oxygen, or sulfur. In some embodiments, -Cy$^1$- is a bivalent optionally substituted tetracyclic 20-24 membered partially unsaturated heterocyclylene having 4-6 heteroatoms independently selected from nitrogen, oxygen, or sulfur. In some embodiments, -Cy$^1$- is a bivalent optionally substituted tetracyclic 20-24 membered partially unsaturated heterocyclylene having 4-8 heteroatoms independently selected from nitrogen, oxygen, or sulfur. In some embodiments, -Cy$^1$- is a bivalent optionally substituted tetracyclic 20-24 membered partially unsaturated heterocyclylene having 6-8 heteroatoms independently selected from nitrogen, oxygen, or sulfur.

In some embodiments, L is a covalent bond.

In some embodiments, a linker units include a divalent radical such as an alkyldiyl, an arylene, a heteroarylene, moieties such as: —[C(R)$_2$]$_n$O[C(R)$_2$]—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

In some embodiments, a linker unit (or linker, L) is a bifunctional or multifunctional moiety which can be used to link one or more Drug moieties (D) and an M unit, such as an antibody unit (Ab) to form antibody-drug conjugates (ADC) of formula II. Antibody-drug conjugates (ADC) can be conveniently prepared using a linker unit having reactive functionality for binding to the Drug and to the Antibody. In some embodiments, a cysteine thiol of M (e.g., a cysteine engineered antibody (Ab)), or a functional group of a modified or unnatural amino acid residue of M (e.g., an antibody), can form a bond with a functional group of a linker reagent, a drug moiety or drug-linker intermediate.

In some embodiments, a linker unit has a reactive site which has an electrophilic group that is reactive to a nucleophilic group of M. In some embodiments, a linker unit has a reactive site which has an electrophilic group that is reactive to a nucleophilic cysteine present on an antibody. The cysteine thiol of the antibody is reactive with an electrophilic group on a Linker and forms a covalent bond to a Linker. In some embodiments, a nucleophilic group is an amino group. Useful electrophilic groups include, but are not limited to, maleimide and haloacetamide groups.

In some embodiments, a linker unit has a reactive site which has a nucleophilic group that is reactive to an electrophilic group of M. In some embodiments, an electrophilic group of M is an aldehyde or ketone group. As described herein, in some embodiments, an aldehyde or ketone group is incorporated through, for example, inclusion of unnatural amino acids and/or chemical modifications (e.g., modification of an amino acid side, change, oxidation of carbohydrates of glycosylated proteins, etc).

In some embodiments, a linker unit L has the structure of:

-A$_a$-W$_w$—Y$_y$— wherein:
-A- is a Stretcher unit covalently attached to M;
a is 0 or 1;
each —W— is independently an Amino Acid unit;
w is independently an integer ranging from 0 to 12;
—Y— is a Spacer unit covalently attached to the drug moiety; and
y is 0, 1 or 2.

Stretcher Unit

The Stretcher unit (-A-), when present, is capable of linking an M unit, such as an antibody, to an amino acid unit (—W—) or a drug unit (D). In some embodiments, M has a nucleophilic group that forms a bond with an electrophilic functional group of a Stretcher unit. In some embodiments, M is an antibody, and a nucleophilic group, such as an amino or thiol group, forms a bond with an electrophilic functional group of a Stretcher unit. In some embodiments, M has an electrophilic group that forms a bond with a nucleophilic functional group of a Stretcher unit. In some embodiments, M is an antibody, and an electrophilic group, such as an aldehyde or ketone group, forms a bond with a nucleophilic functional group of a Stretcher unit, such as a thiol, amino, hydroxylamine, hydrazine or hydrazide group. In some embodiments, a nucleophilic group is —SH. In some embodiments, a nucleophilic group is —N(R)$_2$. In some embodiments, a nucleophilic group is a hydroxylamine group. In some embodiments, a nucleophilic group is a hydrazine group. In some embodiments, a nucleophilic group is a hydrazide group. In some embodiments, an electrophilic group is a ketone group. In some embodiments, an electrophilic group is an aldehyde group. In some embodiments, an electrophilic group comprises an unsaturated bond, such as a carbon-carbon double bond, a carbon-carbon triple bond, or a carbonyl group. In some embodiments, an electrophilic group is an unsaturated carbon-carbon bond conjugated to an electron-withdrawing group. In some embodiments, an electrophilic group is a carbon-carbon double bond conjugated to an electron-withdrawing group.

In some embodiments, a compound of formula II has the structure of formula L-IIIa or L-IIIb. In some embodiments, exemplary Stretcher units include those depicted in ADCs having the structure of Formulae L-IIIa and L-IIIb, wherein Ab is an antibody, —W—, —Y—, D, w and y are as defined above and described herein, and R$^{17}$ is an optionally substituted divalent radical selected from —(CH$_2$)$_r$—, C$_3$-C$_8$ carbocyclyl, —O—(CH$_2$)$_r$—, arylene, —(CH$_2$)$_r$ arylene, -arylene-(CH$_2$)$_r$—, —(CH$_2$)$_r$—$_3$-C$_8$ carbocyclyl, —C$_3$-C$_8$ carbocyclyl)-(CH$_2$)$_r$—, C$_3$-C$_8$ heterocyclyl, —(CH$_2$)$_r$—(C$_3$-C$_8$ heterocyclyl)-, —(C$_3$-C$_8$ heterocyclyl)-(CH$_2$)$_r$—, —(CH$_2$)$_r$C(O)NR$^b$(CH$_2$)$_r$, (CH$_2$CH$_2$O)$_r$, —(CH$_2$CH$_2$O)$_r$—CH, —(CH$_2$)$_r$C(O)NR$^b$(CH$_2$CH$_2$O)$_r$, —(CH$_2$)$_r$C(O)NR$^b$(CH$_2$CH$_2$O)$_r$—CH$_2$—, (CHCH$_2$O)C(O)NR$^b$(CH$_2$CH$_2$O)$_r$—, —(CH$_2$CH$_2$O)(C(O)NR$^b$(CH$_2$CH$_2$O)CH$_r$, and —(CH$_2$CH$_2$O)C(O)NR$^b$(CH$_2$)$_r$—; wherein R$^b$ is H, C$_1$-C$_6$ alkyl, phenyl, or benzyl; and r is independently an integer ranging from 1-10.

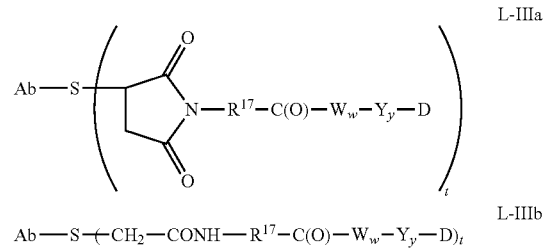

In some embodiments, arylene includes divalent aromatic hydrocarbon radicals of 6-20 carbon atoms derived by the removal of two hydrogen atoms from a parent aromatic ring system. Typical arylene groups include, but are not limited to, radicals derived from benzene, substituted benzene, naphthalene, anthracene, biphenyl, and the like.

In some embodiments, heterocyclyl groups include a ring system in which one or more ring atoms is a heteroatom, e.g. nitrogen, oxygen, and sulfur. In some embodiments, a heterocyclic radical comprises 1 to 20 carbon atoms and 1 to 3 heteroatoms selected from N, O, P, and S. In some embodiments, a heterocyclic group may be an optionally substituted monocyclic group having 3 to 7 ring members (2 to 6 carbon atoms and 1 to 3 heteroatoms selected from N, O, P, and S) or a bicyclic group having 7 to 10 ring members (4 to 9 carbon atoms and 1 to 3 heteroatoms selected from N, O, P, and S), for example: a bicyclo[4,5], [5,5], or [6,6] system. In some embodiments, a heterocyclic group is derived from an exemplary heterocyclic compounds described in Paquette, Leo A.; "Principles of Modem Heterocyclic Chemistry" (W. A. Benjamin, New York, 1968) (for example, Chapters 1, 3, 4, 6, 7, and 9); "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocyclic groups include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

In some embodiments, carbocyclyl groups include a saturated or unsaturated ring having 3 to 7 carbon atoms as a monocyclic or 7 to 12 carbon atoms as a bicyclic group. In some embodiments, monocyclic carbocyclic groups have 3 to 6 ring atoms, or 5 or 6 ring atoms. In some embodiments, bicyclic carbocyclic groups have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocyclic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

In some embodiments, a Stretcher unit is that of formula L-IIIa, and is derived from maleimido-caproyl (MC) wherein $R^{17}$ is —(CH$_2$)$_2$—:

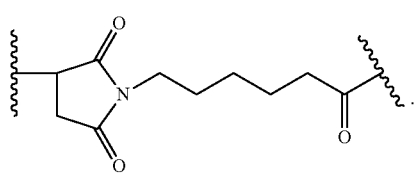

MC

In some embodiments, a Stretcher unit is that of formula L-IIIa, and is derived from maleimido-propanoyl (MP) wherein $R^{17}$ is —(CH$_2$)$_2$—:

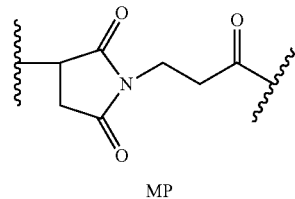

MP

In some embodiments, a Stretcher unit is that of formula L-IIIa wherein $R^{17}$ is —(CH$_2$CH$_2$O)$_r$—CH$_2$— and r is 2:

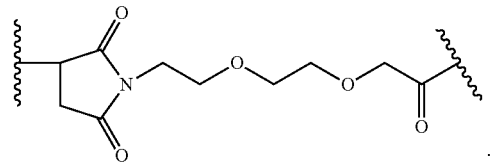 [SMILES: *C(=O)COCCOCCN1C(=O)CC(*)C1=O]

In some embodiments, a Stretcher unit is that of formula L-IIIa wherein $R^{17}$ is —(CH$_2$)$_r$C(O)NR$^b$(CH$_2$CH$_2$O)$_r$—CH$_2$— wherein R$^b$ is H and each r is 2:

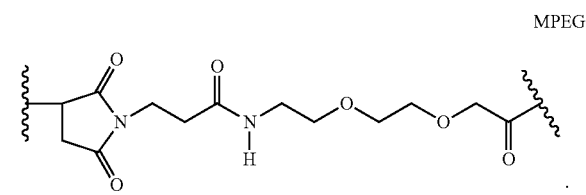 [SMILES: *C(=O)COCCOCCNC(=O)CCN1C(=O)CC(*)C1=O]

MPEG

In some embodiments, a Stretcher unit is that of formula L-IIIb wherein $R^{17}$ is —(CH$_2$)$_5$—:

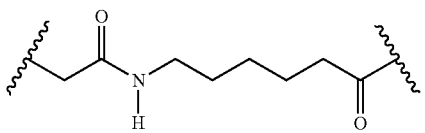

In some other embodiments, a Stretcher unit is linked to M, e.g., an Antibody unit via a disulfide bond between a sulfur atom of an Antibody unit and a sulfur atom of the Stretcher unit. An exemplary Stretcher unit is depicted in a compound of formula II having the structure of formula L-IV, wherein R, Ab-, —W—, —Y—, -D, w and y are as defined above and described herein.

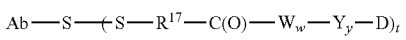

L-IV

Ab—S—(S—R$^{17}$—C(O)—W$_w$—Y$_y$—D)$_t$

In some embodiments, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Exemplary Stretcher units are depicted in a compound of formula II having the structure of formula L-Va and L-Vb, wherein R, Ab-, —W—, —Y—, -D, w and y are as defined above and described herein.

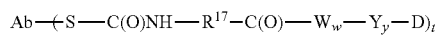

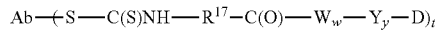

In some embodiments, a linker unit is a dendritic type or polymeric linker for covalent attachment of more than one drug moiety through a branching, multifunctional linker moiety to an antibody (for example, Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990;). In some embodiments, a linker unit is dendritic. In some embodiments, a linker unit is polymeric. In some embodiments, dendritic or polymeric linkers can increase the molar ratio of drug to antibody, i.e. loading, which is related to the potency of the ADC. In some embodiments, a dendritic or polymeric linker unit provides favorable conditions for conjugation of a drug unit and a linker unit. In some embodiments, a drug unit is first coupled to a dendritic or polymeric linker unit, followed by coupling of the linker unit with M. In some embodiments, a first coupling between a drug unit and a dendritic or polymeric linker unit can be conducted in organic solvents or mixtures thereof that may not be friendly to an M unit such as a protein (e.g., an antibody).

Exemplary dendritic linker reagents are depicted below. In some embodiments, up to nine nucleophilic drug moiety reagents can be conjugated by reaction with the chloroethyl nitrogen mustard functional groups. It is understood that the number of drug moiety reagents that can be conjugated can be adjusted by varying the number of X, Y or Z groups.

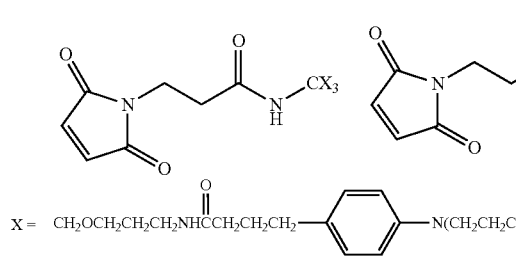

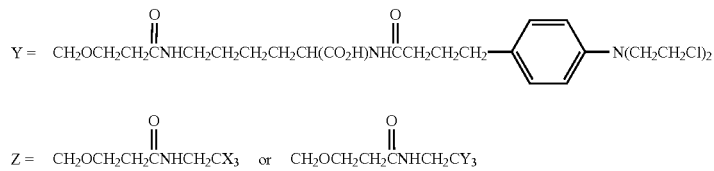

In some embodiments, a Spacer unit comprises branched, self-immolative 2,6-bis(hydroxymethyl)-p-cresol and 2,4,6-tris(hydroxymethyl)-phenol dendrimer units (WO 2004/01993; Szalai et al (2003) J. Amer. Chem. Soc. 125:15688-15689; Shamis et al (2004) J. Amer. Chem. Soc. 126:1726-1731; Amir et al (2003) Angew. Chem. Int. Ed. 42:4494-4499).

In some embodiments, all Drug units (D) connected to a dendritic or polymeric linker or Spacer unit are the same. In some embodiments, all Drug units (D) connected to a dendritic or polymeric linker or Spacer unit are not the same. In some embodiments, two or more types of drug units (D) are connected to the same copy of a dendritic or polymeric linker or Spacer unit.

Amino Acid Unit

In some embodiments, a linker unit comprises amino acid residues. In some embodiments, the Amino Acid unit (—$W_w$—), when present, links the drug units (D) to M, for example, an antibody, optionally through one or more Stretcher unit.

In some embodiments, —$W_w$— is a dipeptide, tripeptide, tetrapeptide, pentapeptide, hexapeptide, heptapeptide, octapeptide, nonapeptide, decapeptide, undecapeptide or dodecapeptide unit. Exemplary suitable amino acid residues for W include those occurring naturally, as well as non-naturally occurring amino acid analogs, such as citrulline. In some embodiments, each —W-unit independently has the structure of:

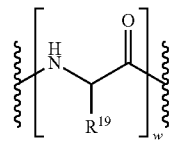

wherein w is an integer ranging from 0 to 12, $R^{19}$ is -$L^{19}$-$R^L$, $L^{19}$ is an optionally substituted CO, bivalent aliphatic chain or heteroalkylene, and $R^L$ is hydrogen or an optionally substituted group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur. In some embodiments, $R^{19}$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

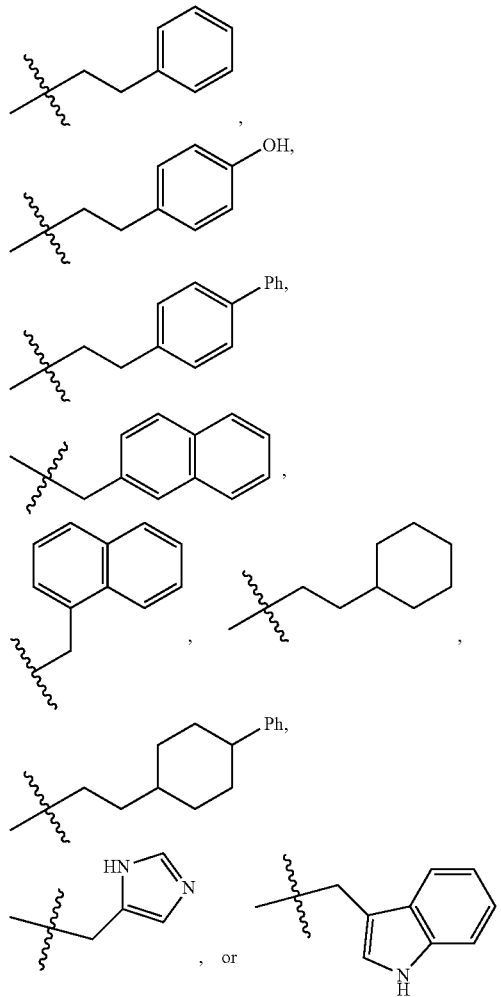

In some embodiments, an Amino Acid unit can be enzymatically cleaved by one or more enzymes, including a tumor-associated protease, to liberate a Drug moiety (D), or an active unit comprising the Drug and part of the Linker unit (L).

Useful —W$_w$-units can be designed and optimized in their selectivity for enzymatic cleavage by a particular enzymes, for example, a tumor-associated protease. In some embodiments, a —W$_w$— unit is that whose cleavage is catalyzed by cathepsin B, C and D, or a plasmin protease.

Exemplary —W$_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly).

When R$^{19}$ is other than hydrogen, the carbon atom to which R$^{19}$ is attached is chiral. In some embodiments, each carbon atom to which R$^{19}$ is attached is independently in the (S) or (R) configuration, or a racemic mixture. In some embodiments, the amino acid units are stereochemically pure. In some embodiments, the amino acid units are enantiomerically pure. In some embodiments, the amino acid unites are racemic. In some embodiments, the amino acid units are diastereomerically pure. In some embodiments, the amino acid units contain a plurality of stereoisomers. In some embodiments, the amino acid units contain a plurality of enantiomers. In some embodiments, the amino acid units contain a plurality of multiple diastereomers. In some embodiments, the amino acid units contain a plurality of stereoisomers, wherein the amount of each of the stereoisomers is pre-determined.

Spacer Unit

In some embodiments, the Spacer units (—Y$_y$—), when present (y=1 or 2), link an Amino Acid unit (—W—) to the drug moiety (D) when an Amino Acid unit is present (w=1-12). In some embodiments, the Spacer units link the Stretcher unit to the Drug moiety when the Amino Acid unit is absent. In some embodiments, the Spacer units link the drug moiety to the antibody unit when both the Amino Acid unit and Stretcher unit are absent (w, y=0). In some embodiments, a Spacer unit is of two general types: self-immolative and non self-immolative. In some embodiments, a Spacer unit is self-immolative. In some embodiments, a Spacer unit is non self-immolative. In some embodiments, an ADC compound has a non self-immolative Spacer unit, and part or all of the Spacer unit remains bound to the Drug moiety after cleavage, for example enzymatic cleavage, of the linker unit (L). When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from the ADC. In some embodiments, an independent hydrolysis reaction takes place within the target cell, cleaving the glycine-Drug moiety bond and liberating the Drug.

In some embodiments, —Y$_y$— is a p-aminobenzylcarbamoyl (PAB) unit whose phenylene portion is substituted with Q$_{m'}$ wherein Q is optionally substituted —C$_1$-C$_8$ alkyl, optionally substituted —O—(C$_1$-C$_8$ alkyl), -halogen, -nitro or —CN; and m' is an integer ranging from 0-4.

Exemplary non self-immolative Spacer units (—Y—) include -Gly-Gly-, -Gly-, -Ala-Phe-, and -Val-Cit-.

In some embodiments, y is 0 and L has no space unit.

In some embodiments, an ADC containing a self-immolative Spacer unit can release D. In one embodiment, —Y— is a PAB group that is linked to —W$_w$— via the amino nitrogen atom of the PAB group, and connected directly to D via a carbonate, carbamate or ether group, wherein a compound of formula II has the structure of:

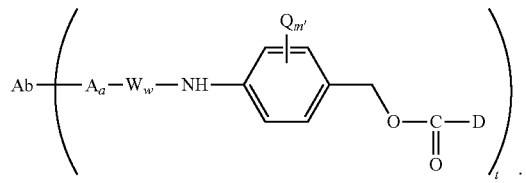

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

In some embodiments, a Spacer unit is a branched bis (hydroxymethyl)styrene (BHMS), which can be used to incorporate and release multiple drugs, having the structure:

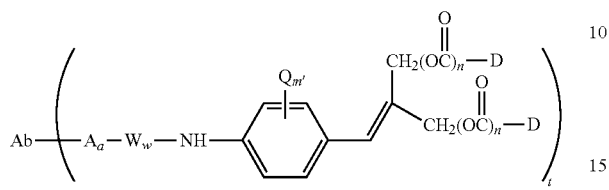

comprising a 2-(4-aminobenzylidene)propane-1,3-diol dendrimer unit (WO 2004/043493; de Groot et al (2003) Angew. Chem. Int. Ed. 42:4490-4494), wherein n is 0 or 1. In some embodiments, t is 0-4.

In some embodiments, the Spacer units (—$Y_y$—) are selected from formula (L-X)-(L-XII):

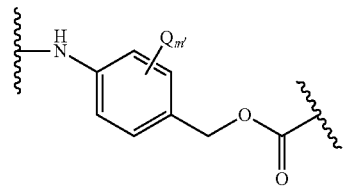

L-X

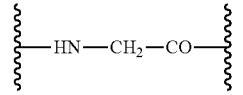

L-XI

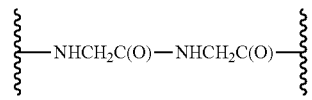

L-XII

Exemplary ADCs of formula II include those depicted in formula L-XIIIa (val-cit), L-XIIIb (MC-val-cit), and L-XIIIc (MC-val-cit-PAB):

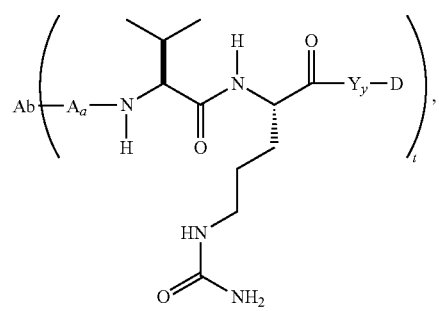

L-XIIIa

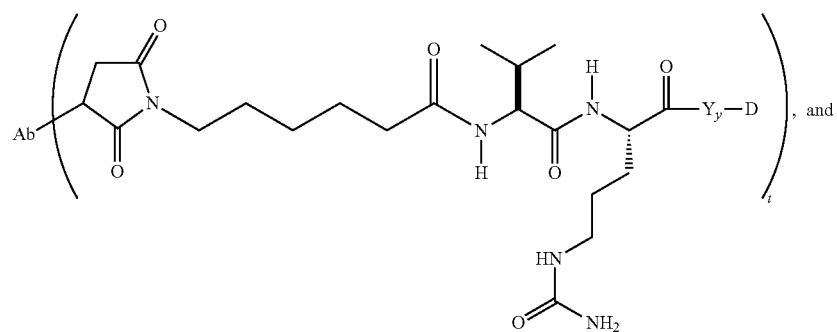

L-XIIIb

, and

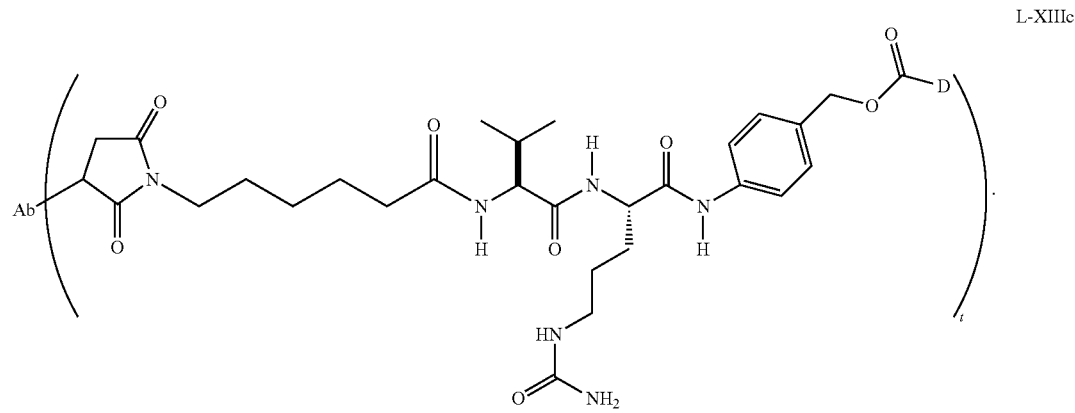

L-XIIIc

Other exemplary ADCs of formula II include:

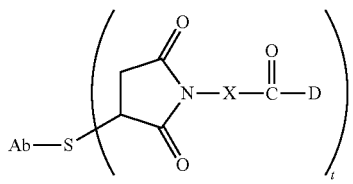
L-XIVa

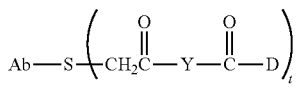
L-XIVb

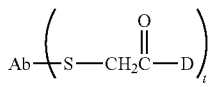
L-XIVc

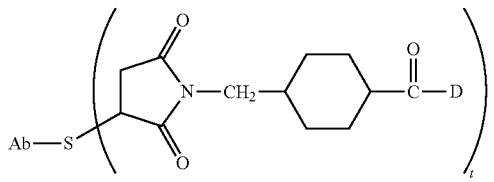
L-XIVd

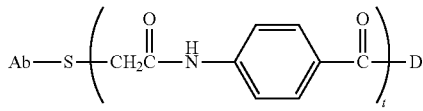
L-XIVe wherein X is: —CH$_2$-1,4-cyclohexylene-, —(CH$_2$)$_{n'}$—, —(CH$_2$CH$_2$O)$_{n'}$—, —CH$_2$-1,4-cyclohexylene-C(O)—N(R)—CH$_2$)$_{n'}$—, phenylene, -phenylene-(CH$_2$)$_{n'}$—, or —(CH$_2$)—C(O)—N(R)—CH$_2$)$_{n'}$—; Y is —N(R)-phenylene- or —N(R)—CH$_2$)$_{n'}$—; and n' is 1 to 12. In some embodiments, R is independently hydrogen or C$_{1-6}$ alkyl.

In some embodiments, a Linker has a reactive functional group which has a nucleophilic group that is reactive to an electrophilic group present on M, such as an antibody. Useful electrophilic groups include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry.

Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to:

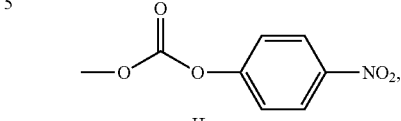

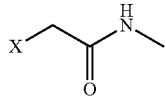

where X is a leaving group, e.g. O-mesyl, O-tosyl, —Cl, —Br, —I; or maleimide.

In some other embodiments, a Linker may be substituted with groups which modulate solubility or reactivity. For example, a charged substituent such as sulfonate (—SO$_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

In some embodiments, a provided compound of formula II is an ADC prepared with a linker reagent selected from: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, SVSB (succinimidyl-(4-vinylsulfone)benzoate), and bis-maleimide reagents: DTME, BMB, BMDB, BMH, BMOE, BM(PEO)$_3$, and BM(PEO)$_4$. Such reagents are widely described and used, and are commercially available from, for example, Pierce Biotechnology, Inc., Customer Service Department, P.O. Box 117, Rockford, Ill. 61105 U.S.A., U.S.A. 1-800-874-3723, International +815-968-0747. See pages 467-498, 2003-2004 Applications Handbook and Catalog. Bis-maleimide reagents allow the attachment of the thiol group of an antibody, such as a cysteine engineered antibody, to a thiol-containing drug moiety, label, or linker intermediate, in a sequential or concurrent fashion. Other functional groups besides maleimide, which are reactive with thiol groups of an M, L or D unit or intermediate, include iodoacetamide, bromoacetamide, vinyl pyridine, disulfide, pyridyl disulfide, isocyanate, and isothiocyanate.

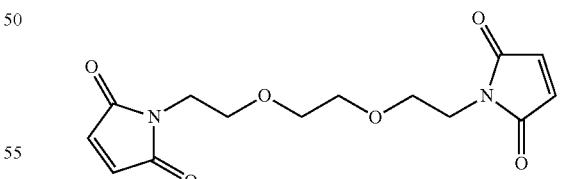

BM(PEO)$_3$

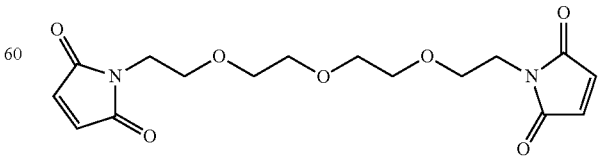

BM(PEO)$_4$

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Stretchers of formula L-IIIa can be introduced into a Linker by reacting the following linker reagents with the N-terminus of an Amino Acid unit:

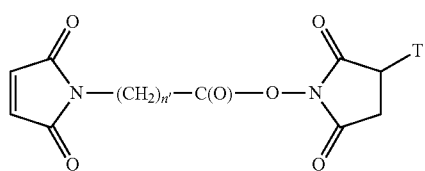

where n' is an integer ranging from 1-10 and T is —H or —SO₃Na; or

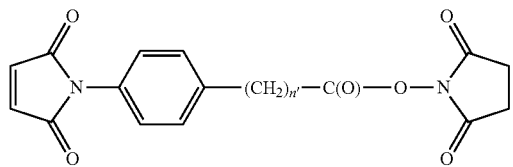

where n' is an integer ranging from 0-3;

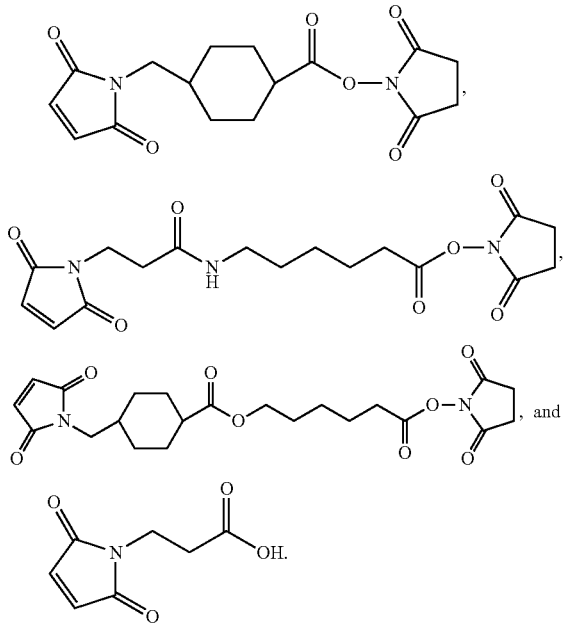

Among others, Stretcher units can also be introduced into a Linker by reacting the following bifunctional reagents with the N-terminus of an Amino Acid unit:

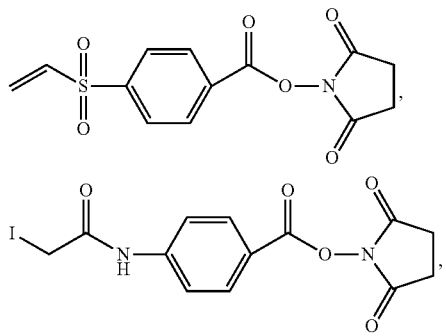

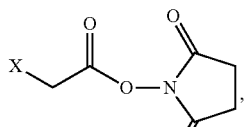

wherein X is —Br or —I,

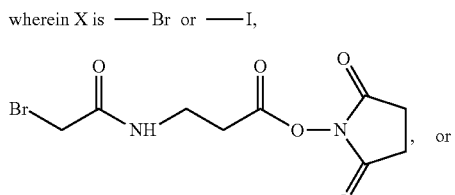

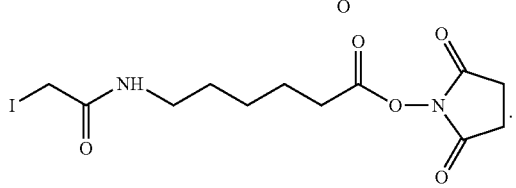

Stretcher units of formula can also be introduced into a Linker by reacting the following bifunctional reagents with the N-terminus of an Amino Acid unit:

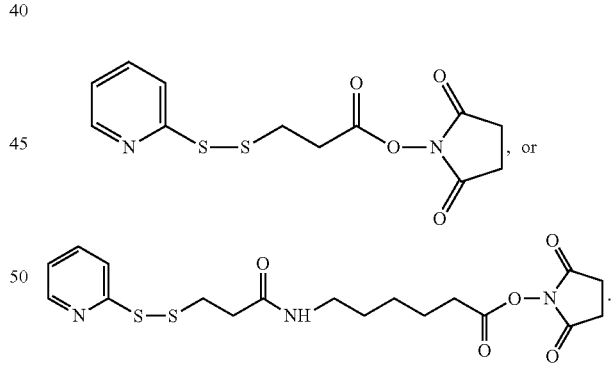

In some embodiments, an Stretcher unit is introduced into a Linker by reacting the following intermediates with the N-terminus of an Amino Acid unit:

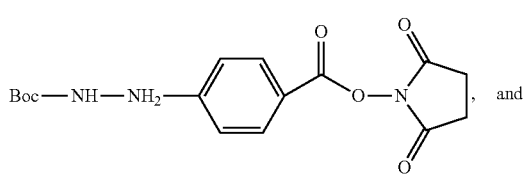

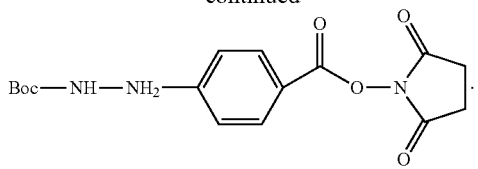

Isothiocyanate Stretchers of the formula shown below may be prepared from isothiocyanatocarboxylic acid chlorides as described in Angew. Chem., (1975) 87(14), 517.

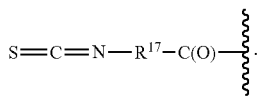

An exemplary valine-citrulline (val-cit or vc) dipeptide linker reagent having a maleimide Stretcher and a para-aminobenzylcarbamoyl (PAB) self-immolative Spacer has the structure:

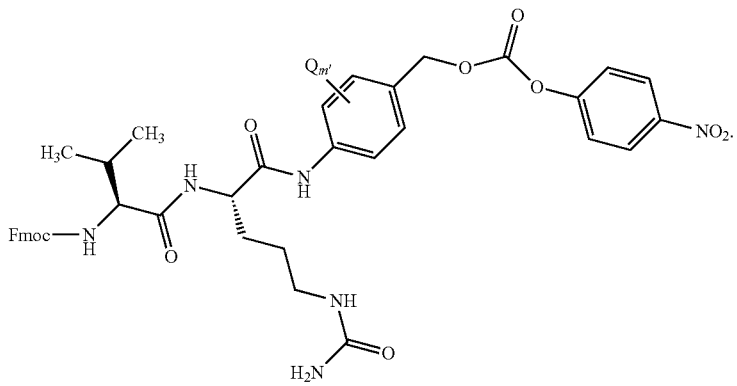

An exemplary phe-lys(Mtr) dipeptide linker reagent having a maleimide Stretcher unit and a p-aminobenzyl self-immolative Spacer unit can be prepared according to Dubowchik, et al. (1997) Tetrahedron Letters, 38:5257-60, and has the structure:

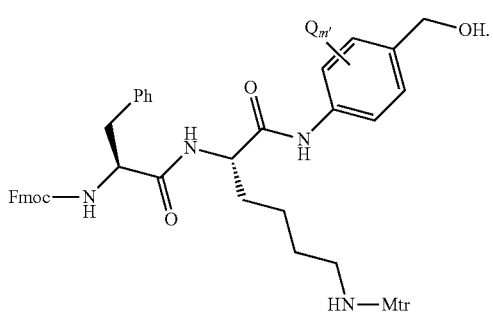

where Mtr is mono-4-methoxytrityl.

In some embodiments, a linker unit is a heterocycle self-immolative linker. Exemplary heterocyclic self-immolative linkers are widely known, including those described in U.S. Pat. No. 7,989,434, the entirety of which is hereby incorporated by reference.

In some embodiments, a heterocyclic linker reagents having the structure of formula LL-Ia, LL-IIa, or LLL-IIIa:

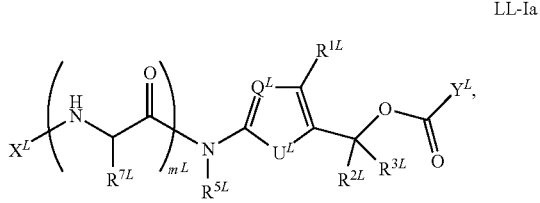

LL-Ia

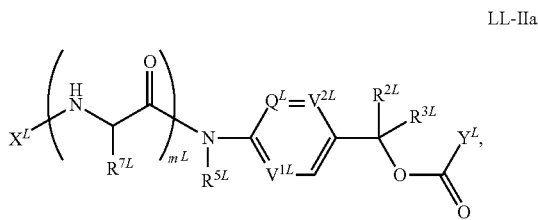

LL-IIa

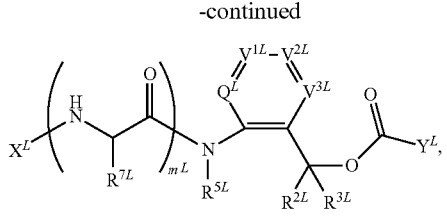

LL-IIIa wherein:
$U^L$ is O, S or $NR^{6L}$;
$Q^L$ is $CR^{4L}$ or N;
$V^{1L}$, $V^{2L}$ and $V^{3L}$ are independently $CR^{4L}$ or N provided that for

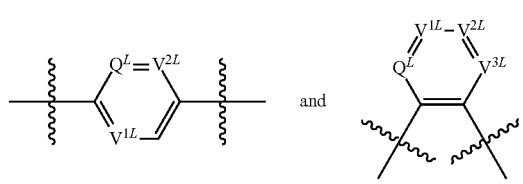

at least one of $Q^L$, $V^1$ and $V^2$ is N;
T is NH, $NR^6$, O or S pending from said drug moiety;

$R^{1L}$, $R^{2L}$, $R^{3L}$ and $R^{4L}$ are independently selected from H, F, Cl, Br, I, OH, —N($R^{5L}$)$_2$, —N($R^{5L}$)$_3^+$, $C_1$-$C_8$ alkylhalide, carboxylate, sulfate, sulfamate, sulfonate, —SO$_2R^{5L}$, —S(=O)$R^{5L}$, —SR$^{5L}$, —SO$_2$N($R^{5L}$)$_2$, —C(=O)$R^{5L}$, —CO$_2R^{5L}$, —C(=O)N($R^{5L}$)$_2$, —CN, —N$_3$, —NO$_2$, $C_1$-$C_8$ alkoxy, $C_1$-$C_8$ halosubstituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^{2L}$ and $R^{3L}$ form a carbonyl (=O), or spiro carbocyclic ring of 3 to 7 carbon atoms; and $R^{5L}$ and $R^{6L}$ are independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —N($R^{5L}$), —N($R^{5L}$)$_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2R^5$, —S(=O)$R^{5L}$, —SR$^S$, —SO$_2$N($R^{5L}$)$_2$, —C(=O)$R^{5L}$, —CO$_2R^{5L}$, —C(=O)N($R^{5L}$)$_2$, —CN, —N$_3$, —NO$_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate.

$R^{7L}$ is the side chain of an amino acid and is optionally protected with a protecting group;

$X^L$ and $Y^L$ independently: are H, form a protecting group or form a reactive functional group.

$m^L$ is 1, 2, 3, 4, 5, or 6.

In some embodiments, $X^L$ and $Y^L$ independently: are H, form a protecting group selected from Fmoc, Boc, triphenylmethyl, or form a reactive functional group selected from N-hydroxysuccinimide, para-nitrophenyl carbonate, para-nitrophenyl carbamate, pentafluorophenyl, haloacetamide, and maleimide.

In some embodiments, a linker unit L comprises a heterocyclic self-immolating moiety selected from formulae LL-I, LL-II, LL-III:

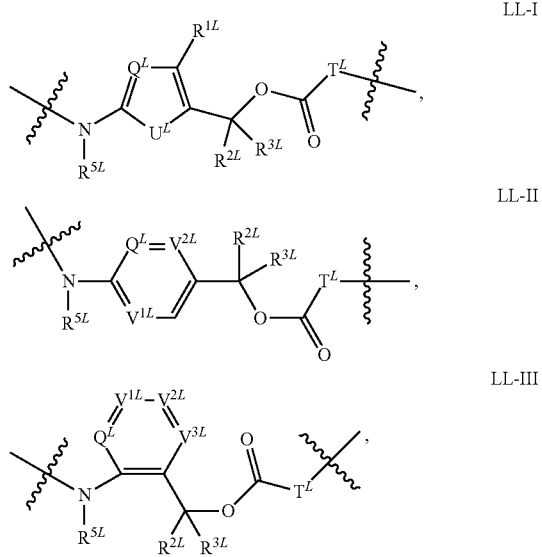

wherein each $T^L$ is independently NH, NR$^{6L}$, O or S pending from said drug moiety, and each other variable is independently as defined above and described herein.

In some embodiments, a linker moiety comprises a heterocyclic "self-immolating moiety" of formula LL-I, LL-II, or LL-III bound to the drug and incorporates an amide group that upon hydrolysis by an intracellular protease initiates a reaction that ultimately cleaves the self-immolative moiety from the drug such that the drug is released from the conjugate in an active form. In some embodiments, a linker moiety further comprises a peptide sequence adjacent to the self-immolative moiety that is a substrate for an intracellular enzyme, for example a cathepsin such as cathepsin B, that cleaves the peptide at the amide bond shared with the self-immolative moiety. In some embodiments, a drug moiety is connected to the self-immolative moiety of the linker via a chemically reactive functional group pending from the drug such as a primary or secondary amine, hydroxyl, sulfhydryl or carboxyl group.

In some embodiments, L has the structure of —$Y_y$—$W_w$—$X^s$—, and a provided compound of formula II has the structure of formula LL-IV:

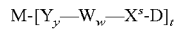

$$M\text{-}[Y_y\text{—}W_w\text{—}X^s\text{-}D]_t \qquad \text{LL-IV}$$

wherein $X^s$ is a heterocyclic self-immolating group having the structure of LL-I, LL-II, or LL-III.

In some embodiments, M is a cell-specific ligand capable of specifically targeting a selected cell population, D is a compound of formula I-c or I-d covalently connected to $X^s$ and —$Y_y$—$W_w$—$X^s$— is a linker wherein Y is optionally present as a spacer unit (y is 0 or 1), —$W_w$— is an enzymatically cleavable peptide (amino acid) sequence (w is 1, 2, 3, 4, 5 or 6), and $X^s$ is a heterocyclic self-immolating group connecting the drug moiety D and the enzymatically cleavable peptide sequence —$W_w$—. In some embodiments, the number of drug moieties per ligand, i.e. drug loading value t, is 1 to about 8.

Heterocyclic Self-Immolative Moiety ($X^s$)

In some embodiments, the drug-ligand conjugates of the invention employ a heterocyclic self-immolative moiety ($X^s$) covalently linked to the drug moiety and the cleavable peptide sequence moiety. In some embodiments, a self-immolative moiety is a bifunctional chemical group which is capable of covalently linking together two spaced chemical moieties into a normally stable molecule, releasing one of said spaced chemical moieties from the molecule by means of enzymatic cleavage; and following said enzymatic cleavage, spontaneously cleaving from the remainder of the bifunctional chemical group to release the other of said spaced chemical moieties. In some embodiments, a self-immolative moiety is covalently linked at one of its ends, directly or indirectly through a Spacer unit, to the ligand by an amide bond and covalently linked at its other end to a chemical reactive site (functional group) pending from the drug. In some embodiments, the derivatization of the drug with the self-immolative moiety may render the drug less pharmacologically active (e.g. less toxic) or not active at all until the drug is cleaved.

In some embodiments, the conjugate is stable extracellularly, or in the absence of an enzyme capable of cleaving the amide bond of the self-immolative moiety. Upon entry into a cell, or exposure to a suitable enzyme, the amide bond is cleaved initiating a spontaneous self-immolative reaction resulting in the cleavage of the bond covalently linking the self-immolative moiety to the drug, to thereby effect release of the drug in its underivatized or pharmacologically active form. In one embodiment, the self-immolative linker is coupled to the ligand, through an enzymatically cleavable peptide sequence that provides a substrate for an intracellular enzyme to cleave the amide bond to initiate the self-immolative reaction.

In some embodiments, a self-immolative moiety in a provided compound either incorporate one or more heteroatoms and thereby provides improved solubility, improves the rate of cleavage and decreases propensity for aggregation of the conjugate.

In some embodiments, when $T^L$ is NH, it is derived from a primary amine (—$NH_2$) pending from the drug moiety (prior to coupling to the self-immolative moiety). In some embodiments, when $T^L$ is N, it is derived from a secondary amine (—NH—) from the drug moiety (prior to coupling to the self-immolative moiety). In some embodiments, when $T^L$ is O or S, it is derived from a hydroxyl (—OH) or sulfhydryl (—SH) group respectively pending from the drug moiety prior to coupling to the self-immolative moiety.

Not to be limited by theory or a particular mechanism, the presence of electron-withdrawing groups on the heterocyclic ring of formula LL-I, LL-II or LL-III linkers may moderate the rate of cleavage.

In some embodiments, a self-immolative moiety is the group of formula LL-I in which $Q^L$ is N, and $U^L$ is O or S. In some embodiments, such group has a non-linearity structural feature which improves solubility of the conjugates. In this context, in some embodiments, $R^{1L}$ may be H, methyl, nitro, or $CF_3$ while $T^L$ is N or NH pending from the drug moiety D. In one embodiment, $Q^L$ is N and $U^L$ is O thereby forming an oxazole ring and $R^{1L}$ is H. In another embodiment, $Q^L$ is N and $U^L$ is S thereby forming a thiazole ring optionally substituted at $R^{1L}$ with an Me or $CF_3$ group and $T^L$ is N or NH pending from drug moiety D. It will be understood that when $T^L$ is NH, it is derived from a primary amine (—$NH_2$) pending from the drug moiety (prior to coupling to the self-immolative moiety) and when $T^L$ is N, it is derived from a secondary amine (—NH—) from the drug moiety (prior to coupling to the self-immolative moiety). Similarly, when $T^L$ is O or S, it is derived from a hydroxyl (—OH) or sulfhydryl (—SH) group respectively pending from the drug moiety prior to coupling to the self-immolative moiety.

In another exemplary embodiment, the self-immolative moiety is the group of formula LL-II in which $Q^L$ is N and $V^{1L}$ and $V^{2L}$ are independently N or CH and $T^L$ is N or NH.

In another embodiment, $Q^L$, $V^{1L}$ and $V^{2L}$ are each N. In another embodiment, $Q^L$ and $V^{1L}$ are N while $V^{2L}$ is CH. In another embodiment, $Q^L$ and $V^{2L}$ are N while $V^{1L}$ is CH.

In another embodiment, Q and $V^{1L}$ are both CH and $V^{2L}$ is N. In another embodiment, $Q^L$ is N while $V^{1L}$ and $V^{2L}$ are both CH.

In another embodiment, the self-immolative moiety is the group of formula LL-III in which $Q^L$, $V^{1L}$, $V^{2L}$ and $V^{3L}$ are each independently N or CH and $T^L$ is N or NH. In another embodiment $Q^L$ is N while $V^{1L}$, $V^{2L}$ and $V^{3L}$ are each N. In another embodiment, $Q^L$, $V^{1L}$, and $V^{2L}$ are each CH while $V^{3L}$ is N. In another embodiment $Q^L$, $V^{2L}$ and $V^{3L}$ are each CH while $V^{1L}$ is N. In another embodiment, $Q^L$, $V^{1L}$ and $V^{3L}$ are each CH while $V^{2L}$ is N. In another embodiment, $Q^L$ and $V^{2L}$ are both N while $V^{1L}$ and $V^{3L}$ are both CH. In another embodiment, $Q^L$ and $V^{2L}$ are both CH while $V^{1L}$ and $V^{3L}$ are both N. In another embodiment, $Q^L$ and $V^{3L}$ are both N while $V^{1L}$ and $V^{2L}$ are both CH.

Cleavable Peptide Sequence ($Z_M$)

In the conjugate of Formula IV, each m is independently 1, 2, 3, 4, 5 or 6. In exemplary embodiments, m may be 1, 2 or 3, to form single amino acid, dipeptide, and tripeptide amino acid units, respectively Amino acid units Z are selected from natural and non-natural amino acids. The side chain-bearing carbon may be in either D or L (R or S) configuration Amino acid unit Z may be alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit) Amino acid unit Z optionally includes protected forms of amino acids where reactive functionality of the side chains are protected. Protected amino acid reagents and intermediates are well known, including lysine-protected with acetyl, formyl, triphenylmethyl (trityl), and monomethoxytrityl (MMT). Other protected amino acid units include arginine-protected tosyl or nitro group, ornithine-protected with acetyl or formyl groups.

Each $Z_m$ unit independently has the formula denoted below in the square brackets, where m is an integer ranging from 0 to 6:

In some embodiments, —$W_w$— is a cleavable peptide sequence.

In some embodiments, in the conjugate of formula LL-IV, each w is independently 1, 2, 3, 4, 5 or 6. In exemplary embodiments, m may be 1, 2 or 3, to form single amino acid, dipeptide, and tripeptide amino acid units, respectively. Amino acid units W are selected from natural and non-natural amino acids. A side chain-bearing carbon may be in either D or L (R or S) configuration. An amino acid unit W may be alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit). Suitable amino acid unit W optionally includes protected forms of amino acids where reactive functionality of the side chains are protected. Protected amino acid reagents and intermediates are well known, including lysine-protected with acetyl, formyl, triphenylmethyl (trityl), and monomethoxytrityl (MMT). Other protected amino acid units include arginine-protected with tosyl or nitro group, ornithine-protected with acetyl or formyl groups, etc.

In some embodiments, each —W-unit independently has the structure of:

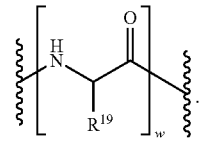

In some embodiments, w is 0-6.

The peptide unit sequence —$W_w$— is specifically tailored so that it will be selectively enzymatically cleaved from the drug moiety by one or more of the cellular proteases. The amino acid residue chain length of the peptide linker ranges from that of a single amino acid to about eight amino acid residues. Exemplary enzymatically-cleavable peptide sequences include Gly-Gly, Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Ala-Phe, Gly-Gly-Gly, Gly-Ala-Phe, Gly-Val-Cit, Gly-Phe-Leu-Gly (SEQ ID NO: 1), Ala-Leu-Ala-Leu (SEQ ID NO: 2), Phe-N 9-tosyl-Arg, and Phe-N 9-Nitro-Arg, in either orientation. Numerous specific cleavable peptide sequences suitable for use can be designed and optimized in their selectivity for enzymatic cleavage by a particular intracellular enzyme e.g. a tumor-associated protease. Cleavable peptides for use also include those which are optimized toward the proteases, cathepsin B, C and D, such as Phe-Lys, Ala-Phe, and Val-Cit. In some embodiments, a peptide sequence for use is tripeptide D-Ala-Phe-Lys, which is selectively recognized by the tumor-associated protease plasmin, which may be involved in tumor invasion and metastasis (de Groot, et al (2002) Molecular Cancer Therapeutics 1(11):901-911; de Groot, et al (1999) J. Med. Chem. 42(25):5277-5283).

In some embodiments, conjugates of formula LL-IV optionally incorporate a spacer unit Y (i.e. y is not 0). In some embodiments, Y is a divalent moiety that couples the N-terminus of the cleavable peptide (—$W_w$—) to the ligand M. In some embodiments, the spacer unit is of a length that enables the cleavable peptide sequence to be contacted by the cleaving enzyme (e.g. cathepsin B) and the hydrolysis of the amide bond coupling the cleavable peptide to the self-immolative moiety $X^s$. In some embodiments, a Spacer unit Y is covalently bound to $W_w$ via an amide bond. In some embodiments, a spacer unit is a bond and ligand M is directly and covalently attached to the self-immolative moiety $X^s$. In this case, the ligand M and the self-immolative moiety $X^s$ form an amide bond that upon proteolytic cleavage initiates the self-immolative reaction and the ultimate release of the drug D.

In some embodiments, a spacer unit Y is covalently bound to a functional group pending from the ligand M such as an amine (e.g. —$NH_2$ from a Lys residue), a carboxyl (—COOH from an Asp or Glu residue) or a sulfhydryl (e.g. —SH from a Cys residue) which forms an amide or a thioether or disulfide group. Spacer units may comprise a divalent radical such as alkyldiyl, aryldiyl, heteroaryldiyl, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Conjugates of the invention in which the spacer unit Y is reacted with a sulfhydryl functional group of ligand M (for example when M is Cys containing peptide or a reduced antibody) to form a thioether linkage include those represented by formulae LL-Va-Ve), in which spacer unit Y is the compound in brackets.

In some embodiments, Y has the structure of

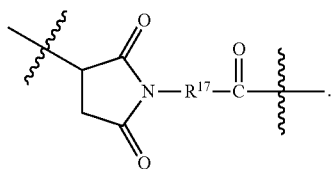

In some embodiments, a provided compound of formula II has the structure of formula LL-Va:

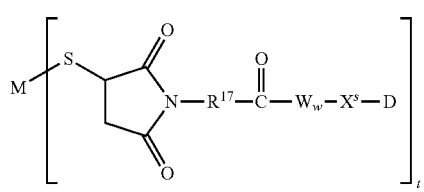

LL-Va

In some embodiments, Y is maleimidocaproyl (MC) (where $R^{17}$ is —$(CH_2)_5$—; e.g., made from maleimidocaproyl-N-hydroxysuccinimide (MC-NHS)):

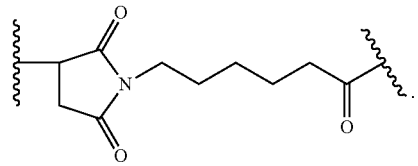

MC

In some embodiments, Y is maleimido-propanoyl (MP):

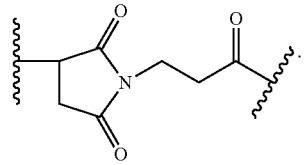

MP

In some embodiments, $R^{17}$ is —$(CH_2CH_2O)_r$—$CH_2$— and r is 2, and Y is

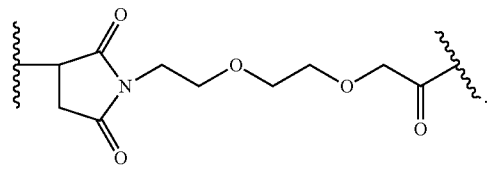 [SMILES: *C(=O)COCCOCCN1C(=O)CC(*)C1=O]

In some embodiments, $R^{17}$ is —$(CH_2)_rC(O)NR^b(CH_2CH_2O)_r$—$CH_2$— where $R^b$ is H and each r is 2, and Y is

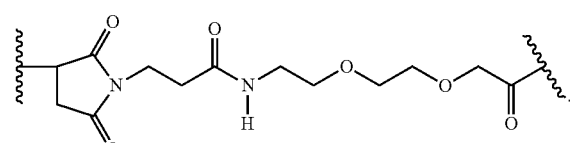

MPEG

In some embodiments, Y is SMCC (for example, made from succinimidyl 4-(N-maleimidomethyl)-cyclohexane-1-carboxylate):

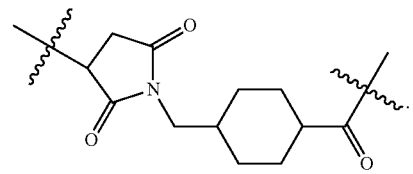 [SMILES: *C(=O)C1CCC(CN2C(=O)CC(*)C2=O)CC1]

In some embodiments, a compound of formula II has the structure of

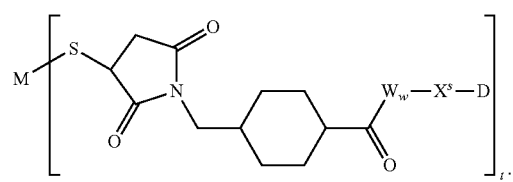

In some embodiments, Y has the structure of

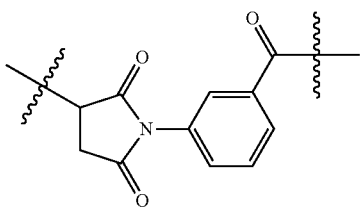 [SMILES: *C(=O)c1cccc(N2C(=O)CC(*)C2=O)c1]

(In some embodiments, made from m-maleimidobenzoyl-N-hydroxysuccinimide este (MBS)). In some embodiments, a compound of formula II has the structure of

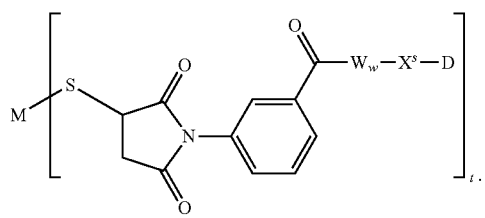

In some embodiments, Y has the structure of

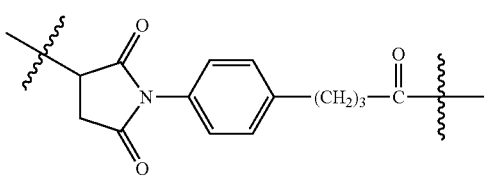

(In some embodiments, made from succinimidyl 4-(p-maleimidophenyl)butyrate (SMPB)). In some embodiments, a compound of formula II has the structure of

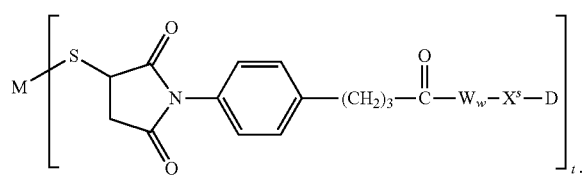

In some embodiments, Y has the structure of

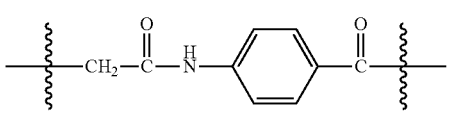 [SMILES: *CC(=O)Nc1ccc(C(*)=O)cc1]

(In some embodiments, made from made from N-succinimidyl(4-iodoacetyl)aminobenzoate (SIAB)). In some embodiments, a compound of formula II has the structure of

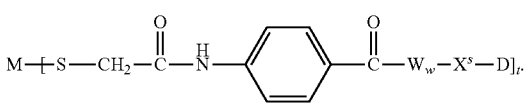

In some other embodiments, spacer unit Y and ligand M are linked via a thioether group. In some embodiments, such a compound may be prepared by reacting a sulfhydryl functional group pending from ligand M with an activated disulfide-containing precursor of spacer unit Y. Exemplary conjugates of this type include

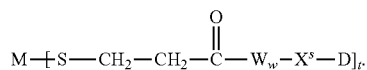

In some embodiments, Y has the structure of

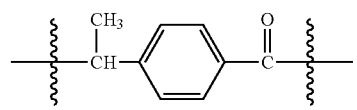 [SMILES: *C(=O)c1ccc(C(*)C)cc1]

(In some embodiments, made from made from 4-succinimidyloxycarbonyl-α-methyl-α-(2-pyridyldithio)toluene (SMPT)). In some embodiments, a compound of formula II has the structure of

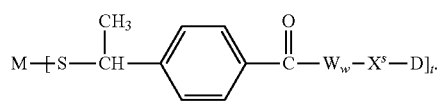

In some embodiments, Y has the structure of

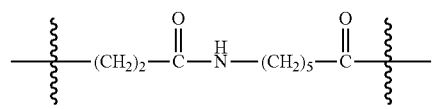

(In some embodiments, made from succinimidyl 6-[3-(2-pyridyldithio)-propionamide]hexanoate (LC-SPDP). In some embodiments, a compound of formula II has the structure of

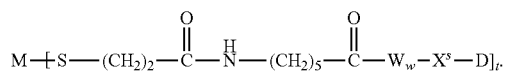

In some embodiments, Y has the structure of

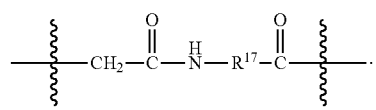

In some embodiments, a compound of formula II has the structure of

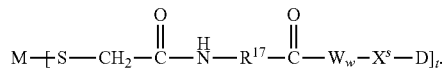

In some embodiments, Y has the structure of

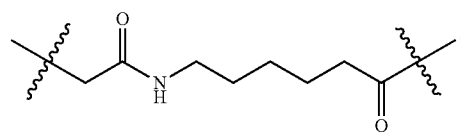

In some embodiments, Y, and/or a provided conjugate, is prepared with a cross-linking reagent selected from BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, SVSB (succinimidyl-(4-vinylsulfone) benzoate), and bis-maleimide reagents DTME, BMB, BMDB, BMH, BMOE, BM(PEO)$_3$, and BM(PEO)$_4$. Many cross-linking reagents are commercially available, for example, from Pierce Biotechnology, Inc., Customer Service Department, P.O. Box 117, Rockford, Ill. 61105 USA, 1-800-874-3723, International+815-968-0747. See pages 467-498, 2003-2004 of the Applications Handbook and Catalog. In some embodiments, bis-maleimide reagents allow the attachment of a thiol group of a cysteine residue of an M unit, such as an antibody, to a thiol-containing drug moiety or linker intermediate, in a sequential or concurrent fashion. Other functional groups besides maleimide, which are reactive with a thiol group of M (e.g., an antibody), drug moiety, or linker intermediate include iodoacetamide, bromoacetamide, vinyl pyridine, disulfide, pyridyl disulfide, isocyanate, and isothiocyanate.

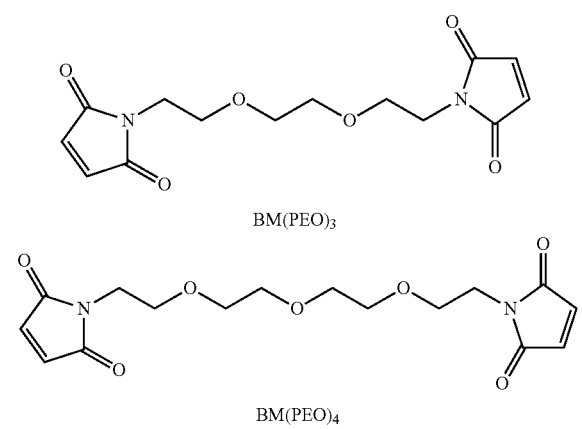

Useful spacer reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

A provided compound in which the spacer unit Y is coupled to ligand M via an amide group may be prepared by reacting a free amine functional group on ligand M with an active ester containing precursor of spacer unit Y. For example, a carboxyl group on spacer unit may be activated by reacting with N-hydroxysuccinimide and then reacted with M-NH$_2$ to form a conjugate in which M and Y or coupled by way of an amide group.

Useful functional groups on an antibody for linking to the spacer unit, either naturally or via chemical manipulation include, but are not limited to, sulfhydryl (—SH), amino, hydroxyl, the anomeric hydroxyl group of a carbohydrate, and carboxyl. In some embodiments, the reactive functional groups on the antibody are sulfhydryl and amino. Sulfhydryl groups can be generated by reduction of an intramolecular cysteine disulfide bond of an antibody, or can be generated by reaction of an amino group of a lysine moiety of an antibody using 2-iminothiolane (Traut's reagent) or another sulfhydryl generating reagent. In some embodiments, a sulfhydryl group is generated by modifying an antibody's amino acid sequence, for example, by replacing an amino acid residue with a cysteine residue. In some embodiments, an antibody is a cysteine engineered antibody.

In some embodiments, the Spacer unit is linked to the antibody unit via a disulfide bond between a sulfur atom of the Antibody unit and a sulfur atom of the Spacer unit, for example, as in

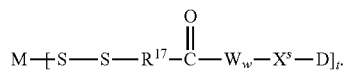

In some embodiments, t, the average number of drug moieties per antibody unit is from 1 to about 8.

In some other embodiments, the reactive group of the Spacer contains a reactive site that can form a bond with a primary or secondary amino group of an antibody. Examples of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Exemplary such Spacer units are depicted in ADCs having the structure of

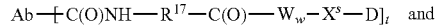

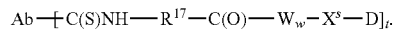

In some embodiments, a reactive group of the Spacer reacts with an electrophilic group, such as an aldehyde, ketone, acetal, or ketal group of an antibody, or a sugar (carbohydrate) of a glycosylated antibody. In some embodiments, a carbohydrate can be mildly oxidized using a reagent such as sodium periodate and the resulting (—CHO) unit of the oxidized carbohydrate can be condensed with a Spacer that contains a functionality such as a hydrazide, an oxime, a primary or secondary amine, a hydrazine, a thiosemicarbazone, a hydrazine carboxylate, and an arylhydrazide such as those described by Kaneko, T. et al (1991) Bioconjugate Chem 2:133-41. In some embodiments, an electrophilic group, such as an aldehyde or ketone group, is introduced through incorporation of an unnatural amino acid. For example, US Patent Application Publication US20100210543 and US20120183566 describes proteins, including antibodies, bearing at least one aldehyde groups, and preparation methods and processes thereof. Exemplary such Spacer units are depicted in compounds having the structure of

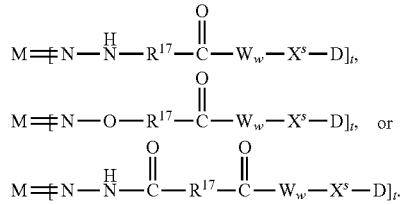

In some embodiments, L comprises an —S—S— moeity.
In some embodiments, a linker unit (L) comprises one of the following moieties (Singh et al, Recent Trends in Targeted Anticancer Prodrug and Conjugate Design, Curr Med Chem. 2008; 15(18): 1802-1826):

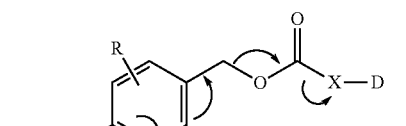

1,6-Benzyl elimination

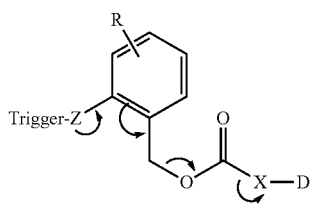

1,4-Benzyl elimination

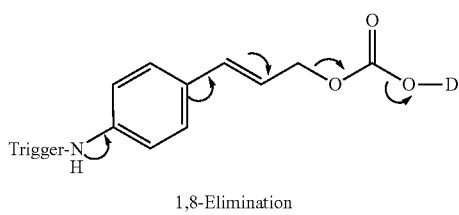

1,8-Elimination

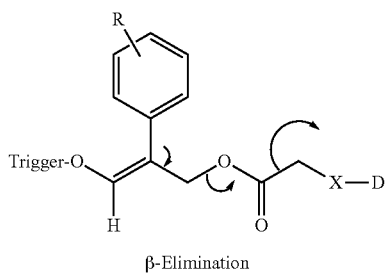

β-Elimination

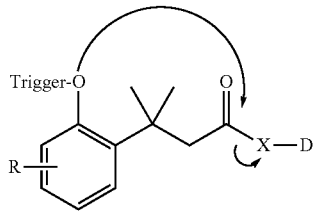

Cyclization/Lactonization

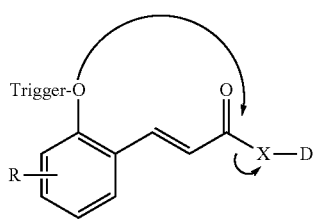

Cyclization/Lactolization

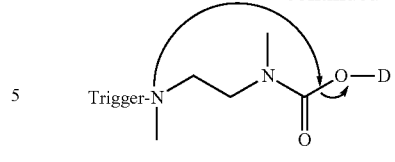

Cyclization

D = Drug
X & Z = O, NH
The self-immolative mechanism shown starts after the trigger group is removed by tumor specific cleavage In some embodiments, L comprises a group of

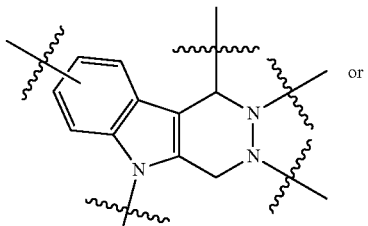

or

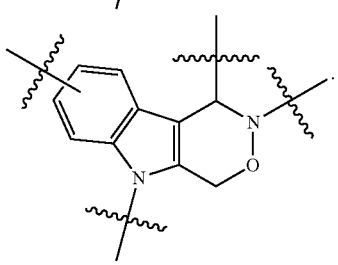

Exemplary M embodiments (ligand, e.g., antibodies) and/or L embodiments (linker units, e.g., moieties linking a drug or an active unit to a ligand, for example, an antibody) also include those described in U.S. Pat. Nos. 5,475,092, 6,214,345, 7,659,241, 7,223,837, 7,705,045, 8,158,590, 8,012,978, 8,337,856, 7,750,116, 7,659,241, 7,989,434, 7,851,437, 7,829,531, 7,754,681, 7,714,016, 7,585,834, 7,553,816, 7,091,186, 6,855,689, 6,759,509, 6,677,435, 6,268,488, 5,877,158, 7,375,078, 7,547,768, 7,754,441, 7,803,915, 7,749,504, 7,662,936, 7,855,275, 7,521,541, 7,479,544, 7,723,485, 7,989,595, 7,304,032, 6,897,034, 7,858,759, 7,842,789, 7,507,405, 7,214,776, 7,122,636, 7,834,154, 7,723,485, 7,183,076, 7,018,809, 6,582,928, 5,929,211, 7,087,840, 7,964,567, 7,964,566, 7,745,394, 7,256,257, 7,427,399, 7,494,646, 7,541,442, 7,595,379, 7,968,090, 7,811,565, 6,103,236, 7,696,313, 7,214,663, 7,115,573, 7,691,962, 7,893,023, 7,816,317, 7,319,139, and 6,870,033; US Patent Application Publications US 2011/0137017, US 2011/0195021, US 2011/0195022, US 2008/0050310, US 2009/0068202, US 2009/0280056, US 2010/0215669, US 2011/0142859, US 2011/0135667, and US 2008/0267981; and International Patent Application Publications WO 2007/089149, WO 2009/017394, WO 2010/062171, WO 2011/133039, WO 2012/177837, WO 2012/149412, WO 2012/145112, WO 2012/138749, WO 2012/135675, WO 2012/138537, WO 2012/135740, WO 2012/135517, WO 2012/135522, WO 2012/128868, WO 2012/112687, WO 2012/112708, WO 2012/078868, WO 2012/061590, WO 2012/058592, WO 2012/019024, WO 2011/162933, WO 2011/112978, WO 2011/106528, WO 2011/100403, WO 2011/

100398, WO 2011/091286, WO 2011/050180, WO 2010/126551, WO 2010/141566, WO 2010/128087, WO 2010/126552, WO 2009/134870, WO 2010/008726, WO 2009/134952, WO 2009/134976, WO 2009/134977, WO 2009/080830, WO 2009/080832, WO 2009/080831, WO 2007/024536, WO 2006/086733, WO 2007/024222, WO 2007/019232, WO 2005/037992, WO 2004/110498, WO 2005/009369, WO 2004/043344, WO 2004/016801, WO 2004/013093, WO 2004/005470, WO 2003/106621, WO 2003/068144, WO 2002/098883, WO 2001/024763, WO 2013055993, WO 2013055990, WO 2013049410, WO 2012/078688, WO 2012/054748, WO 2012/047724, WO 2011/130613, WO 2011/038159, WO 2010/111018, WO 2010/081004, WO 2009/135181, WO 2009/117531, WO 2009/052431, WO 2009/048967, WO 2008/070593, WO 2008/025020, WO 2007/137170, WO 2007/103288, WO 2007/075326, WO 2007/062138, WO 2007/030642, WO 2007/011968, WO 2007/008848, WO 2007/008603, WO 2006/128103, WO 2006/113909, WO 2006/065533, WO 2006/132670, WO 2006/044643, WO 2005/084390, WO 2005/082023, WO 2005/077090, WO 2005/070026, WO 2005/081711, WO 2005/001038, WO 2004/010957, WO 2002/043661, WO 2004/090113, WO 2004/050867, and WO 2004/032828. In some embodiments, M is an antibody described in one of the above-referenced patents and/or patent applications. In some embodiments, L is a moiety described in one of the above-referenced patents and/or patent applications that links a ligand (e.g., an antibody) to a drug unit (or other active unit, such as a cytotoxic unit). In some embodiments, L is a moiety described in one of the above-referenced patents and/or patent applications that links an antibody to a drug unit.

In some embodiments, L is a polymer unit. In some embodiments, L is a polyalkylene glycol linker. In some embodiments, L is a PEG linker. In some embodiments, L is a monodispersed PEG linker. Exemplary polymeric moieties, including PEG moieties, that can be used as linker units include those described in U.S. Pat. Nos. 7,119,162, 7,030,082, 6,858,580, 6,835,802, 6,815,530, 7,888,536, 6,620,976, 7,846,893, and US Patent Application Publications US 20110124844, US 20110118480, and US 20090203584.

In some embodiments, the present invention recognizes the challenges for preparing ETP or thiodiketopiperazine alkaloids or derivatives or analogs thereof. In some embodiments, the present invention provides a method for preparing ETP or thiodiketopiperazine alkaloids or derivatives or analogs thereof. In some embodiments, the present invention provides a method for preparing a provide compound. In some embodiments, the present invention provides new reagents for preparing ETP or thiodiketopiperazine alkaloids or derivatives or analogs thereof. In some embodiments, the present invention provides new reagents for preparing a provided compound. In some embodiments, a provided method and/or reagent provides unexpectedly high synthetic efficiency, for example, in terms of product yield and/or purity.

In some embodiments, the present invention provides methods for flexible and scalable synthesis of ETP or thiodiketopiperazine alkaloids or derivatives or analogs thereof, for example, a provided compound of formula I-a, I-b, I-c, I-d, II, or III. In some embodiments, the present invention provides a method for scalable synthesis, e.g., >5 g, >6 g, >7 g, >8 g, >9 g, >10 g, >11 g, >12 g, >13 g, >14 g, >15 g, >16 g, >17 g, >18 g, >19 g, or >20 g, >15 g or >20 g scale, of an erythro-β-hydroxytryptophan compound, an intermediate useful for the preparation of ETP or thiodiketopiperazine compounds, or derivatives or analogs thereof. In some embodiments, the present invention provides a method for scalable synthesis of an erythro-β-hydroxytryptophan compound, comprising step S-I-1:

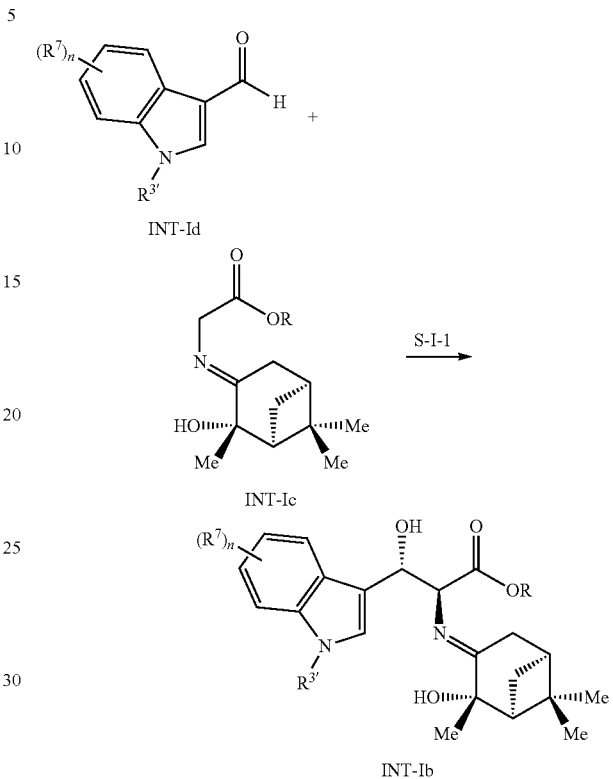

wherein each variable is independently as defined above and described herein. In some embodiments, INT-Ib is enantiomerically pure. In some embodiments, INT-1b is racemic. In some embodiments, INT-1b contains more of one enantiomer than the other. In some embodiments, the stereochemistry of the

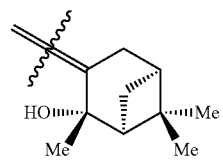

moiety remains essentially the same during step S-I-1. It is understood by a person of ordinary skill in the art that among other methods, enantiomeric purity of INT-1b can be controlled by selectively using one of the two enantiomers, or adjusting the relative amounts of the two enantiomers of INT-Ic.

In some embodiments, step S-I-1 comprises the use of a metal salt. In some embodiments, step S-I-1 is mediated by a titanium salt. In some embodiments, a titanium salt is TiCl(OEt)$_3$. In some embodiments, step S-I-1 is conducted at a temperature below room temperature. In some embodiments, step S-I-1 is conducted at about 0° C. In some embodiments, step S-I-1 comprises the use of a base. In some embodiments, a base is NEt$_3$. An exemplary condition is TiCl(OEt)$_3$, NEt$_3$, CH$_2$Cl$_2$, 0° C.

In some embodiments, a provided method for scalable synthesis of an erythro-β-hydroxytryptophan compound further comprises step S-I-2, which comprises removing the auxiliary group

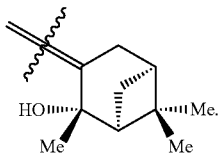

In some embodiments, the auxiliary group is recovered, e.g., as

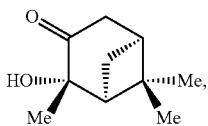

and re-used. In some embodiments, the auxiliary group is removed under acid conditions. In some embodiments, an acid is HCl. An exemplary acidic condition for step S-I-2 is 2 N HCl, THF.

In some embodiments, step S-I-2 further comprises protection of the hydroxyl group in formula INT-Ib. In some embodiments, a protection group is —OSi(R)$_3$. In some embodiments, a protection group is -TBS. An exemplary condition for introducing the protection group is: TBSOTf, 2,6-lutide, CH$_2$Cl$_2$, 23° C. In some embodiments, step S-I-2 provides a compound having the structure of formula INT-Ia:

INT-Ia

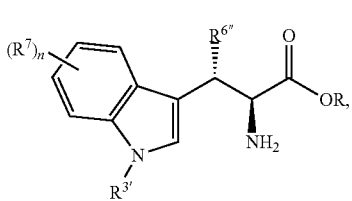

wherein R$^{6"}$ is —OR or —OSi(R)$_3$, and each other variable is independently as defined above and described herein. In some embodiments, INT-Ia is enantiomerically pure. In some embodiments, INT-Ia has an ee value greater than 0. In some embodiments, INT-Ia is racemic.

In some embodiments, an erythro-β-hydroxytryptophan compound is prepared according to scheme I set forth below:

Scheme I

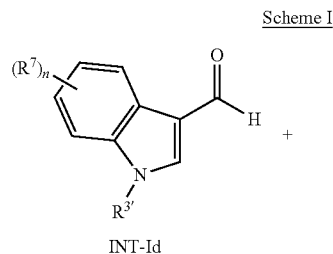

INT-Id

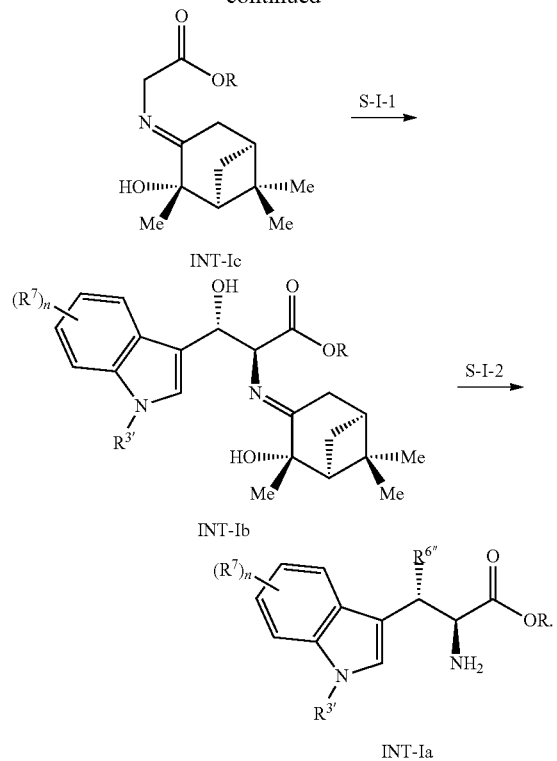

In some embodiments, each of INT-Ia, INT-1b and INT-1c is enantiomerically pure. It is understood by a person of ordinary skill in the art that in Scheme I, INT-Ic can be either of its enantiomers, and the configurations of the chiral centers in INT-Ic can remain essentially the same during the transformation.

In some embodiments, n is 0. In some embodiments, R$^{3'}$ is R$^3$. In some embodiments, R$^{3'}$ is —SO$_2$Ph. In some embodiments, R is ethyl. In some embodiments, R$^{6"}$ is —OH. In some embodiments, R$^{6"}$ is —OTBS.

In some embodiments, one of R$^6$ and R$^{6'}$ is —OR or —OSi(R)$_3$. Without wishing to be limited by theory, Applicants note that in some embodiments such compounds cannot be prepared efficiently using intermolecular Friedel-Crafts indolylation at the C3 position possibly due to, for example, the inductive and steric effects of the C-12-hydroxyl group:

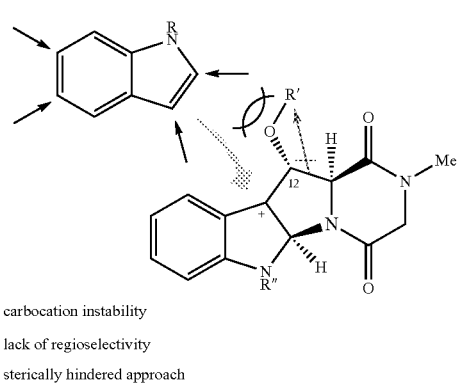

▓ carbocation instability
■ lack of regioselectivity
░ sterically hindered approach In some embodiments, the present invention provides methods for preparation of a compound having the structure of formula I-c, wherein one of $R^6$ and $R^{6'}$ is —OR or —OSi(R)$_3$. In some embodiments, a compound of I-c is a compound of I-a. In some embodiments, $R^4$ is an optionally substituted group selected from phenyl, an 8-14 membered bicyclic or polycyclic aryl ring, a 5-6 membered monocyclic heteroaryl ring having 1-4 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur. In some embodiments, ⇌ is a single bond.

In some embodiments, the present invention provides a method for preparing a compound of formula I-e:

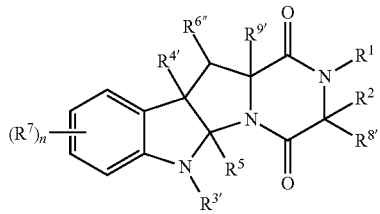

I-e comprising steps of:

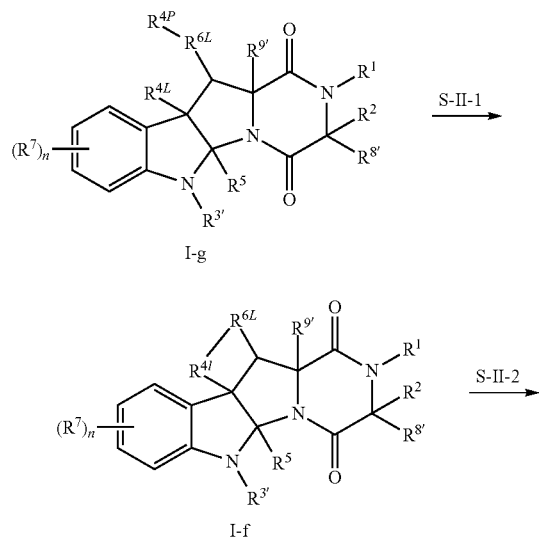

sulfur, or an 8-14 membered bicyclic or polycyclic heteroaryl ring having 1-5 heteroatoms independently selected from nitrogen, oxygen, or sulfur;

$R^{4I}$ is an optionally substituted bivalent group selected from phenylene, an 8-14 membered bicyclic or polycyclic arylene ring, a 5-6 membered monocyclic heteroarylene ring having 1-4 heteroatoms independently selected from nitrogen, oxygen, or sulfur, or an 8-14 membered bicyclic or polycyclic heteroarylene ring having 1-5 heteroatoms independently selected from nitrogen, oxygen, or sulfur, $R^{4L}$ is a leaving group;

$R^{4P}$ is an optionally substituted group selected from phenyl, an 8-14 membered bicyclic or polycyclic aryl ring, a 5-6 membered monocyclic heteroaryl ring having 1-4 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur;

$R^{6''}$ is —OR or —OSi(R)$_3$;

$R^{6L}$ is —Si(R)$_2$—O—;

$R^{8'}$ is hydrogen or $R^8$;

$R^{9'}$ is hydrogen or $R^9$; and each other variable is independently as defined above and described herein;

In some embodiments, each of $R^{4'}$, $R^{4P}$ and $R^{4I}$ is electron-rich. In some embodiments, each of $R^{4'}$ and $R^{4P}$ is independently an optionally substituted indolyl group. In some embodiments, $R^{4'}$ is optionally substituted 3-indolyl. In some embodiments, $R^{4'}$ is substituted 3-indolyl. In some embodiments, $R^{4'}$ is substituted 3-indolyl comprising N-substitution. In some embodiments, $R^{4P}$ is optionally substituted 2-indolyl. In some embodiments, $R^{4P}$ is substituted 2-indolyl. In some embodiments, $R^{4P}$ is substituted 2-indolyl comprising N-substitution. In some embodiments, $R^{4I}$ is an optionally substituted bivalent indole ring moiety. In some embodiments, $R^{4I}$ is an optionally substituted bivalent 2,3-indole ring moiety. In some embodiments, $R^{8'}$ is hydrogen. In some embodiments, $R^{9'}$ is hydrogen. In some embodiments, $R^{6L}$ is —Si(Me)$_2$-O—. In some embodiments, $R^{6L}$ is —Si(Et)$_2$-O—.

Exemplary leaving group are widely known and used in organic synthesis. In some embodiments, $R^{4L}$ is halogen. In some embodiments, $R^{4L}$ is —Cl. In some embodiments, $R^{4L}$ is —Br. In some embodiments, $R^{4L}$ is —I. In some embodiments, $R^{4L}$ is —OS(O)$_2$R.

In some embodiments, a compound of formula I-e has the structure of formula I-e-1:

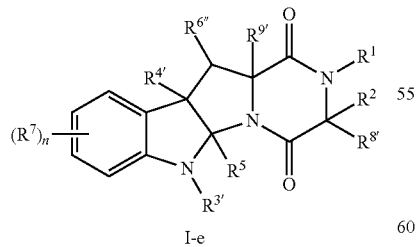

I-e wherein:

$R^{4'}$ is an optionally substituted group selected from phenyl, an 8-14 membered bicyclic or polycyclic aryl ring, a 5-6 membered monocyclic heteroaryl ring having 1-4 heteroatoms independently selected from nitrogen, oxygen, or

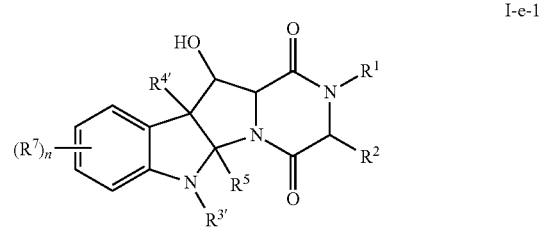

I-e-1 or a pharmaceutically acceptable salt thereof, wherein each variable is independently as described in classes and subclasses herein, both singly and in combination.

In some embodiments, a compound of formula I-f has the structure of formula I-f-1:

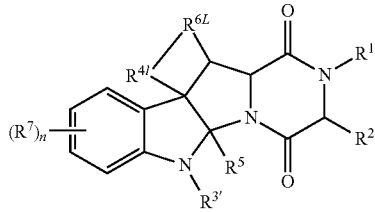

I-f-1 or a pharmaceutically acceptable salt thereof, wherein each variable is independently as described in classes and subclasses herein, both singly and in combination.

In some embodiments, a compound of formula I-g has the structure of formula I-g-1:

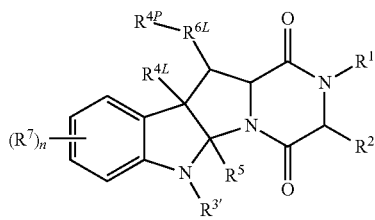

I-g-1 or a pharmaceutically acceptable salt thereof, wherein each variable is independently as described in classes and subclasses herein, both singly and in combination.

In some embodiments, step S-II-1 comprises an intramolecular Friedel-Crafts reaction. In some embodiments, an intramolecular Friedel-Crafts reaction is mediated by a silver salt. In some embodiments, a silver salt is AgBF$_4$. In some embodiments, an intramolecular Friedel-Crafts reaction is conducted at a temperature below room temperature. In some embodiments, an intramolecular Friedel-Crafts reaction is conducted at about 0° C. In some embodiments, step S-II-1 comprises the use of a base. In some embodiments, a base is 2,6-di-tert-butyl-4-methylpyridine (DTBMP). An exemplary condition is AgBF$_4$, DTBMP, EtNO$_2$, 0° C.

In some embodiments, step S-II-2 comprises breaking one or more bonds of $R^{6L}$. In some embodiments, step S-II-2 comprises the remove of $R^{6L}$, i.e, $R^{6L}$ is replaced with two —H. In some embodiments, a compound of I-f is converted to a compound of I-e under acidic conditions. In some embodiments, a compound of I-f is converted to a compound of I-e at a temperature higher than room temperature. In some embodiments, a compound of I-f is converted to a compound of I-e under acidic conditions and at a temperature higher than room temperature. An exemplary condition is 6 N HCl, THF, 80° C.

In some embodiments, step S-II-2 is carried out subsequently to step S-II-1. In some embodiments, step S-II-2 is conducted concurrently with step S-II-1. In some embodiments, steps S-II-1 and S-II-2 are carried out in one pot.

In some embodiments, the present invention provides a method for preparing triketopiperazine. In some embodiments, a provided method comprises use of a permanganate reagent. In some embodiments, a permanganate reagent is bis(pyridine)silver(I) permanganate.

In some embodiments, the present invention provides a method for preparing a triketopiperazine having the structure of formula I-h:

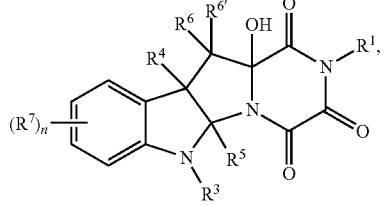

I-h or a pharmaceutically acceptable salt thereof, wherein each variable is independently as described in classes and subclasses herein, both singly and in combination, comprising providing a permanganate reagent.

In some embodiments, the present invention provides a method for preparing a triketopiperazine having the structure of formula I-h, further comprising providing a compound having the structure of 1-i:

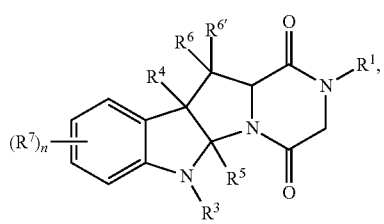

I-i wherein each variable is independently as described in classes and subclasses herein, both singly and in combination.

In some embodiments, in a provided method $R^6$ is —H and $R^{6'}$ is —OH or —OR. In some embodiments, in a provided method $R^4$ is optionally substituted, N-substituted indolyl, $R^6$ is —H and $R^{6'}$ is —OH or —OR. In some embodiments, an N-substituent is an electron-withdrawing group. In some embodiments, in a provided method $R^6$ is —H, $R^{6'}$ is —OH or —OR, and the newly installed —OH in formula I-h is trans to $R^{6'}$. In some embodiments, in a provided method $R^6$ is —H, $R^{6'}$ is —OH or —OR, and the newly installed —OH in formula I-h has inverted stereochemistry of the originating C—H stereochemistry (hydroxylation with inversion of the originating C—H stereochemistry). An exemplary transformation is illustrated below:

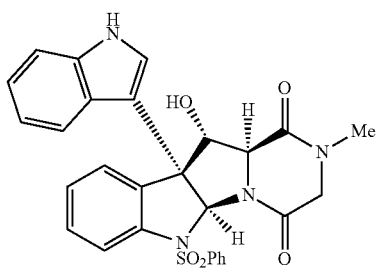

E2-24

-continued

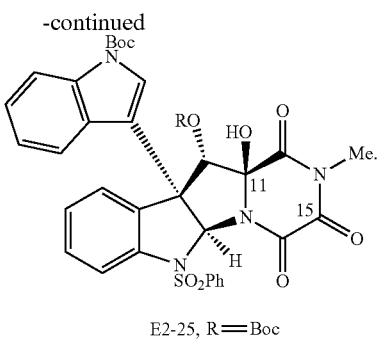

E2-25, R═Boc

In some embodiments, the present invention provides new reagents and methods for sulfidation. In some embodiments, a provided reagent is a product of the addition of thiols to enones. In some embodiments, a provided reagent has the structure of $HSC(R)_2C(R)_2C(O)R$. In some embodiments, a provided reagent has the structure of $HSCH_2CH_2C(O)R$. In some embodiments, a provided reagent is $HSCH_2CH_2C(O)Me$. In some embodiments, a provided reagent is $HSCH_2CH_2C(O)Ph$.

In some embodiments, the present invention provides a method comprising steps of:
(i) providing a first compound comprising at least one hydroxyl group or protected hydroxyl group;
(ii) providing a second compound having the structure of $HSC(R)_2C(R)_2C(O)R$;
(iii) replacing at least one hydroxyl group or protected hydroxyl group or derivatives thereof in the first compound with —$SC(R)_2C(R)_2C(O)R$ of the second compound to provide a third compound; and
(iv) optionally removing the —$C(R)_2C(R)_2C(O)R$ group from the third compound.

In some embodiments, a provided method is a method for sulfidation. In some embodiments, a first compound comprises a diketopiperazine moiety. In some embodiments, a first compound comprises a diketopiperazine moiety and two hydroxyl groups, wherein each of the hydroxyl groups is independently bonded to an α-carbon of an carbonyl group of the diketopiperazine moiety. In some embodiments, a first compound comprising a moiety having the structure of

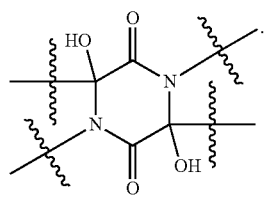 [SMILES: *N1C(=O)C(*)(O)N(*)C(=O)C1(*)O]

In some embodiments, a first compound comprising a moiety having the structure of

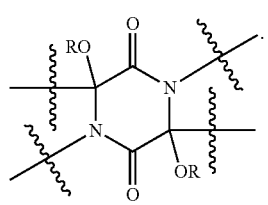

In some embodiments, a first compound comprising a moiety having the structure of

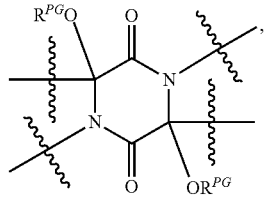

wherein $R^{PG}$ is a protecting group for hydroxyl. In some embodiments, a first compound comprising a moiety having the structure of

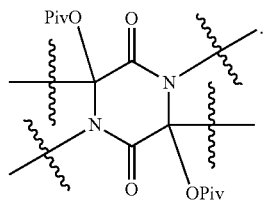

In some embodiments, a first compound has the structure of

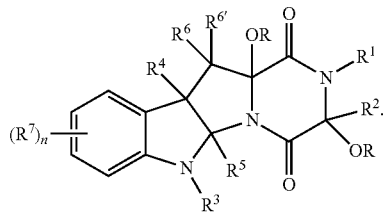

In some embodiments, a first compound has the structure of

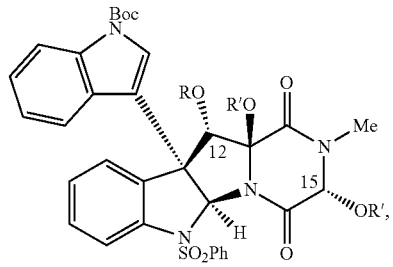

wherein R is Boc and R' is Piv. In some embodiments, a second compound has the structure of $HSCH_2CH_2C(O)R$. In some embodiments, a second compound is $HSCH_2CH_2C(O)Me$. In some embodiments, a second compound is $HSCH_2CH_2C(O)Ph$. In some embodiments, a third compound comprises a moiety having the structure of

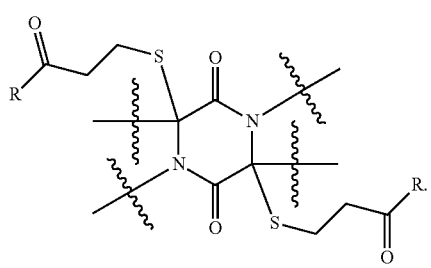

In some embodiments, a third compound has the structure of

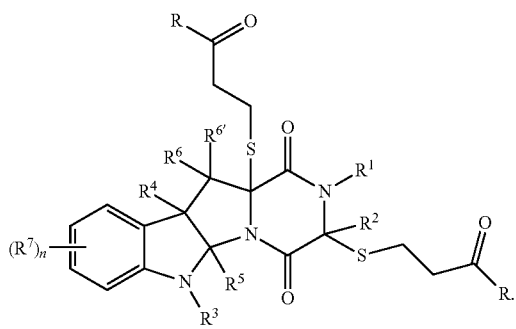

In some embodiments, a third compound is

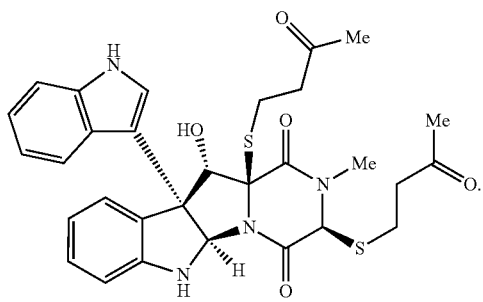 [SMILES: CC(=O)CCS[C@H]1C(=O)N2[C@H]3Nc4ccccc4[C@@]3(c3c[nH]c4ccccc34)[C@H](O)[C@]2(SCCC(C)=O)C(=O)N1C]

In some embodiments, step (iii) comprises use of nitromethane as a solvent. In some embodiments, step (iii) is stereoselective. In some embodiments, step (iii) is diastereoselective. In some embodiments, step (iv) comprises the use of an amine. In some embodiments, an amine has the structure of $HN(R)_2$. In some embodiments, an amine has the structure of $HN(R)_2$, wherein the two R groups are taken together to form an optionally substituted 5-6 membered saturated ring. In some embodiments, an amine is pyrrolidine. In some embodiments, step (iv) comprises a β-elimination reaction facilitated by enamine catalysis. In some embodiments, step (iv) comprises use of free thiol. In some embodiments, step (iv) is conducted under a mild condition that does not disrupt an N-protecting group of an indolyl moiety. In some embodiments, step (iv) is conducted under a mild condition that does not disrupt an N-protecting group of an indolyl moiety, wherein the protecting group is $—S(O)_2R$. In some embodiments, step (iv) is conducted under a mild condition that does not disrupt an N-protecting group of an indolyl moiety, wherein the protecting group is $—S(O)_2Ph$.

In some embodiments, a provided compound of formula I-a, I-b, I-c or I-d is a compound selected from Table 1, below, or a pharmaceutically acceptable salt thereof. Table 1. Exemplary compounds.

TABLE 1

Exemplary compounds.

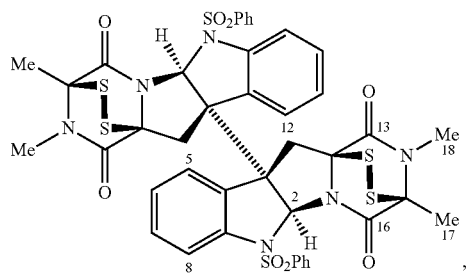

TABLE 1-continued

Exemplary compounds.

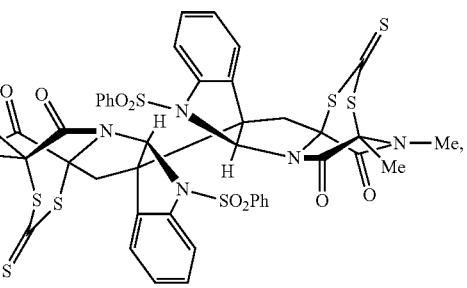

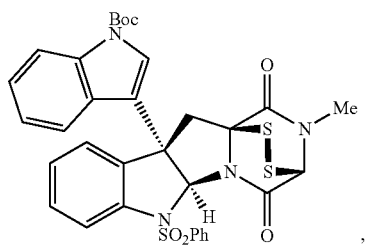

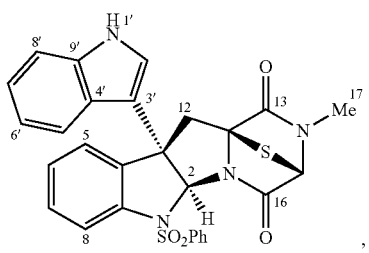

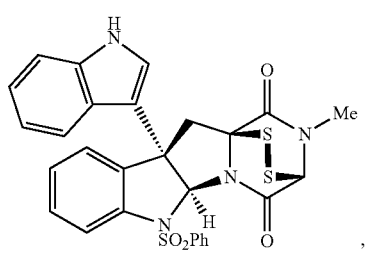

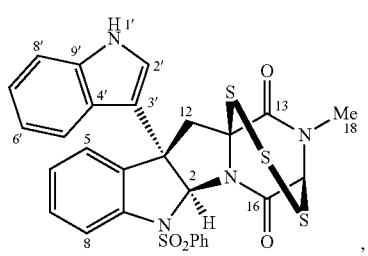

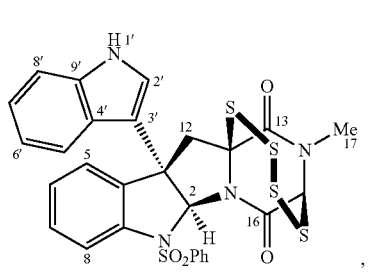

TABLE 1-continued
Exemplary compounds.
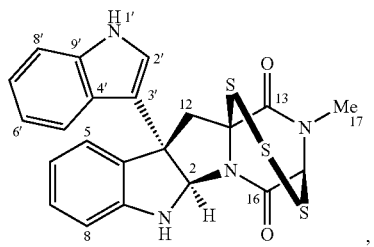
,
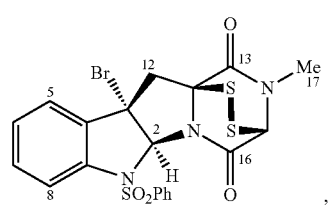
,
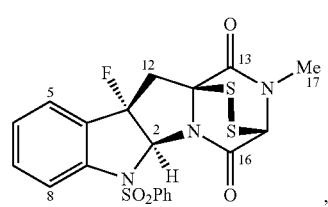
,
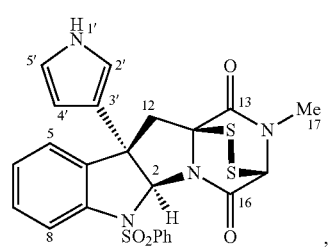
,
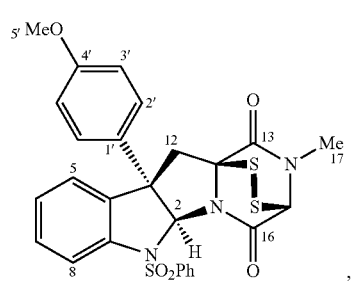
,
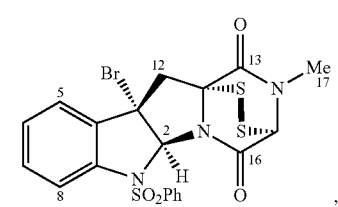
,
TABLE 1-continued
Exemplary compounds.
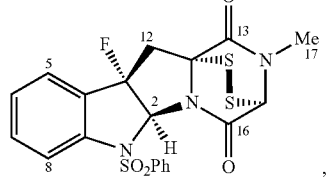
,
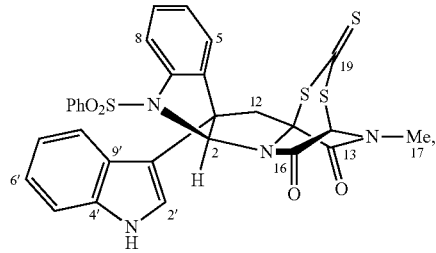
,
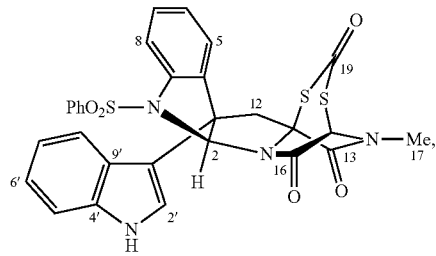
,
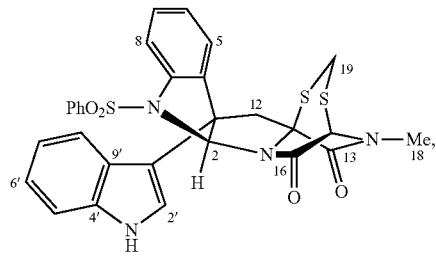
,
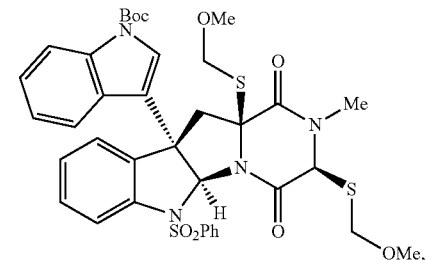
,
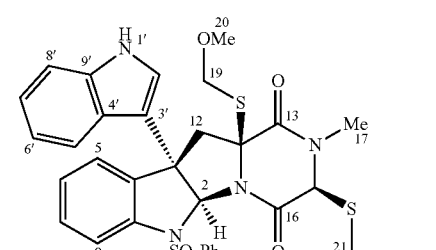
,

TABLE 1-continued
Exemplary compounds.
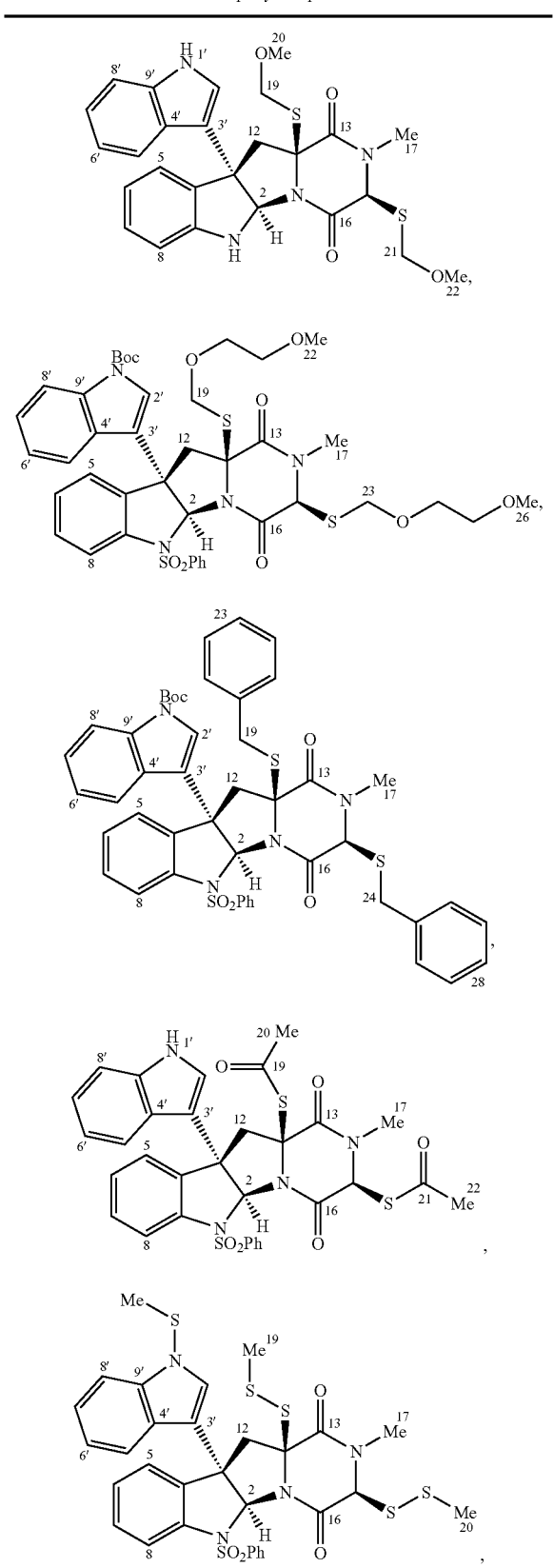
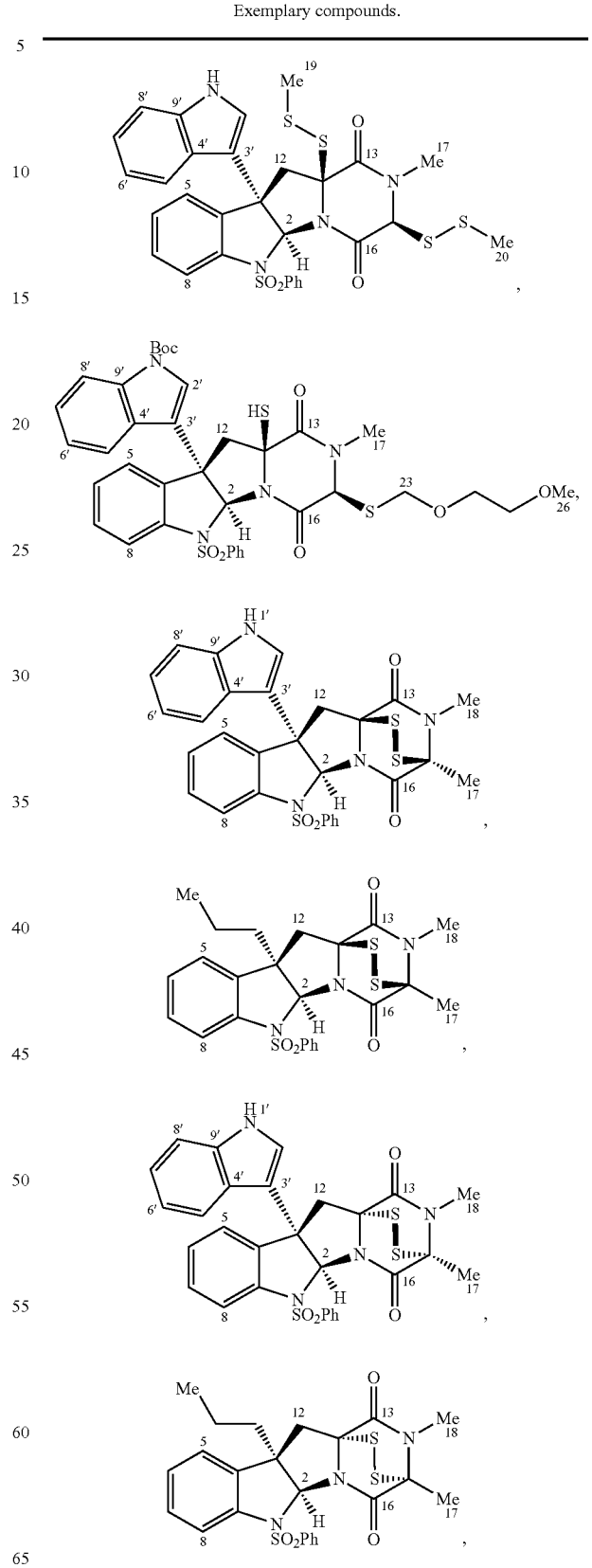

TABLE 1-continued
Exemplary compounds.
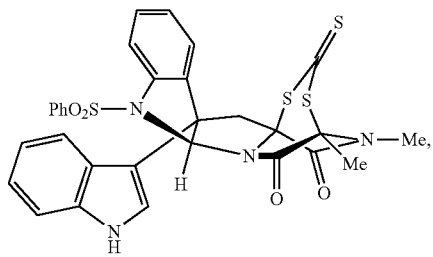
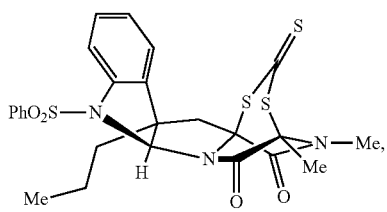
TABLE 1-continued
Exemplary compounds.
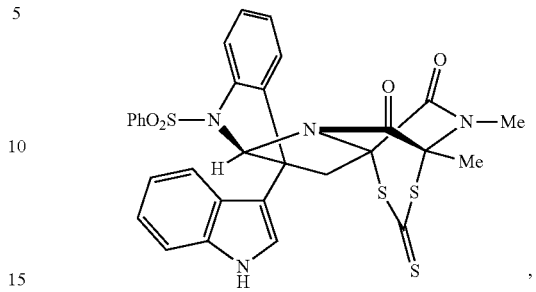
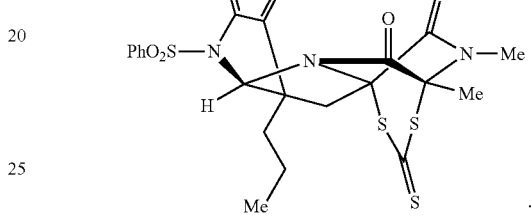
In some embodiments, a provided of formula I-a, I-b, I-c or I-d is a compound selected from Table 2, below, or a pharmaceutically acceptable salt thereof:
TABLE 2
Exemplary compounds.
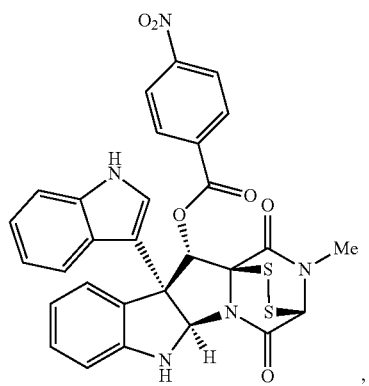 [SMILES: CN1C(=O)[C@]23SS[C@H]1C(=O)N2[C@H]1Nc2ccccc2[C@@]1(c1c[nH]c2ccccc12)[C@@H]3OC(=O)c1ccc([N+](=O)[O-])cc1]
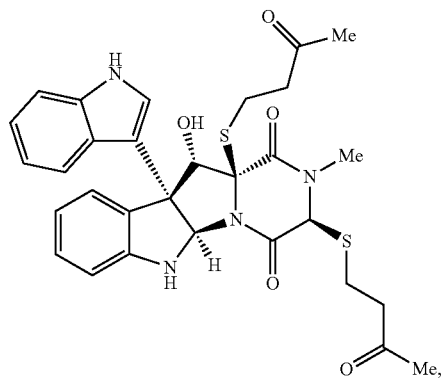 [SMILES: CC(=O)CCS[C@H]1C(=O)N2[C@H]3Nc4ccccc4[C@@]3(c3c[nH]c4ccccc34)[C@H](O)[C@]2(SCCC(C)=O)C(=O)N1C]

TABLE 2-continued
Exemplary compounds.
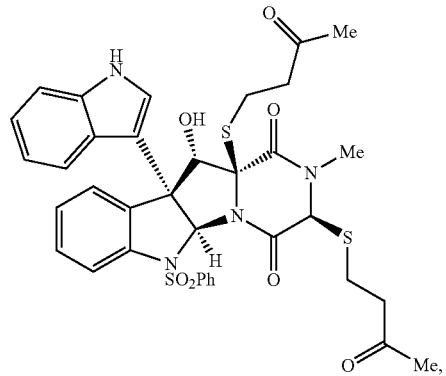
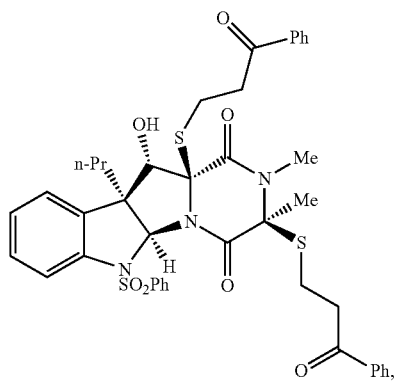
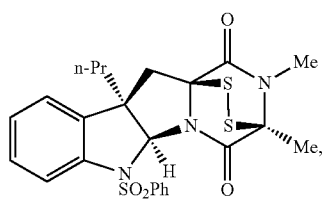
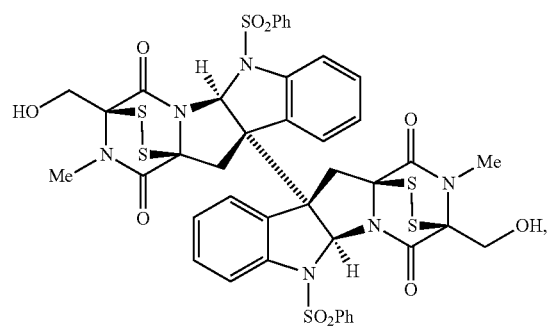

TABLE 2-continued
Exemplary compounds.
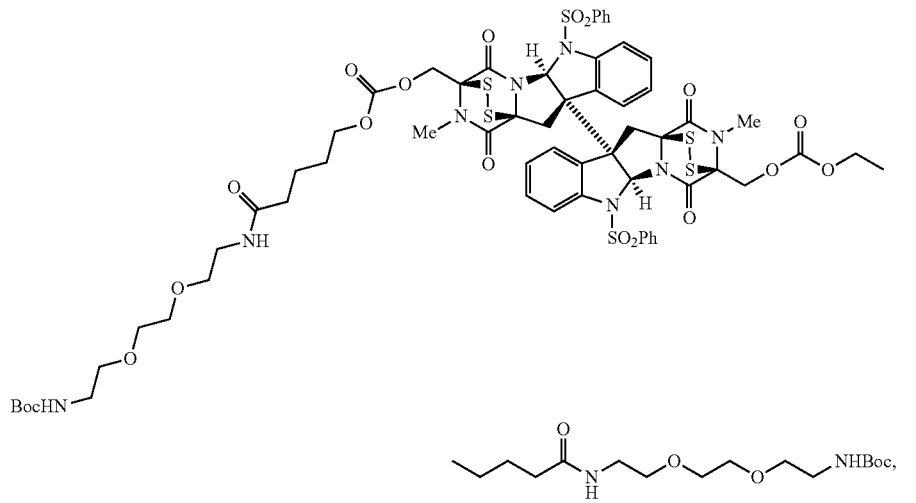
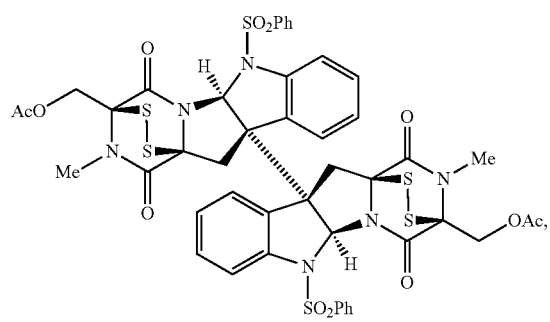
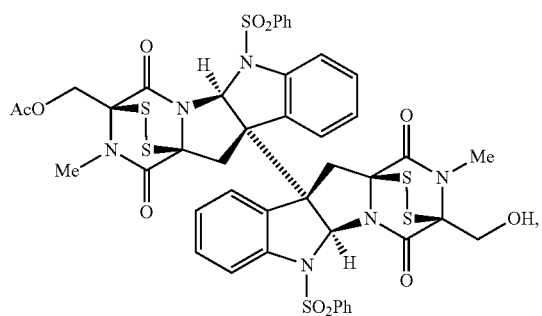
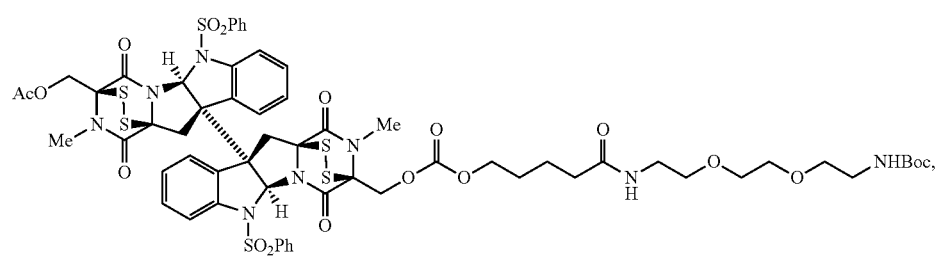

TABLE 2-continued
Exemplary compounds.
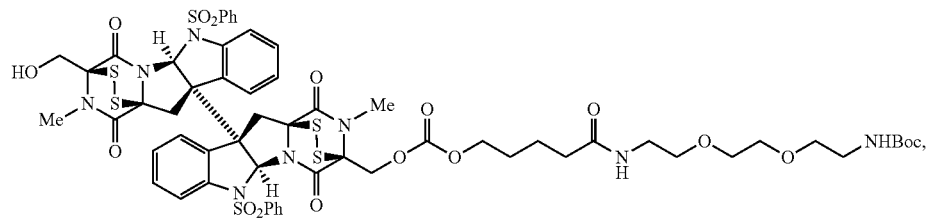
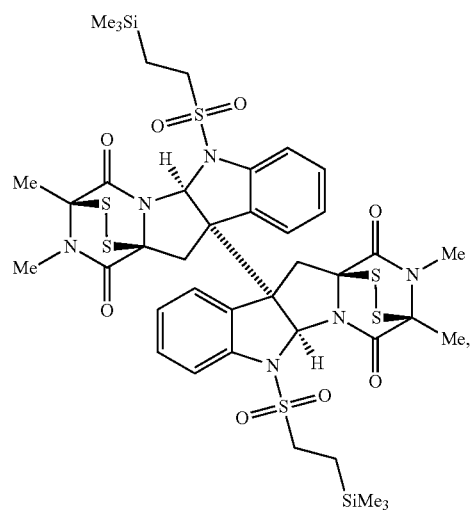 [SMILES: CN1C(=O)[C@@]23CC4([C@]56C[C@@]78SS[C@@](C)(C(=O)N7[C@H]5N(S(=O)(=O)CC[Si](C)(C)C)c5ccccc56)N(C)C8=O)c5ccccc5N(S(=O)(=O)CC[Si](C)(C)C)[C@@H]4N2C(=O)[C@]1(C)SS3]
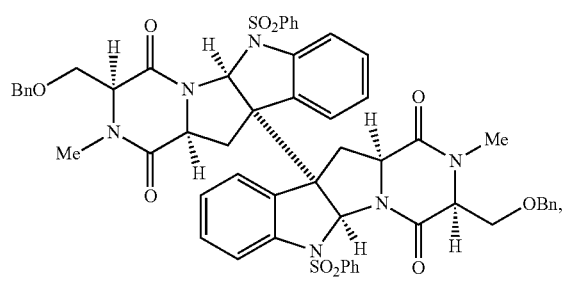
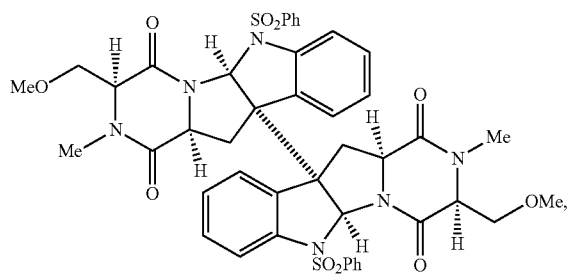
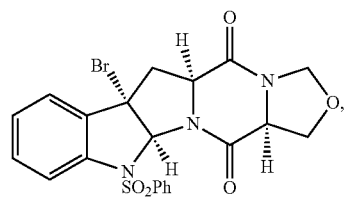

TABLE 2-continued
Exemplary compounds.
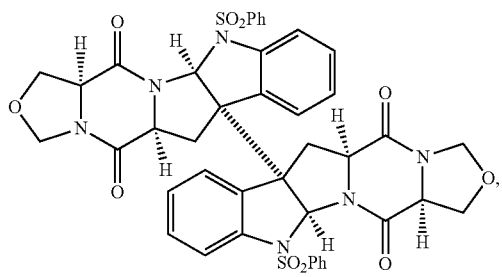
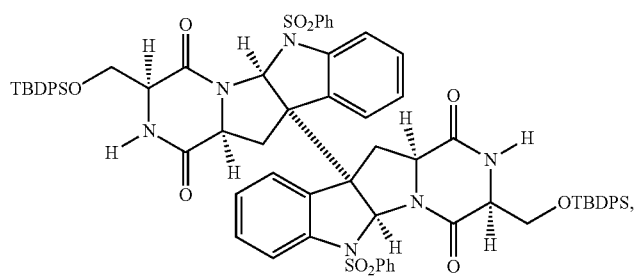
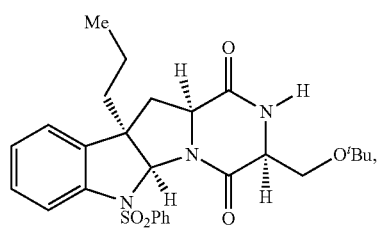
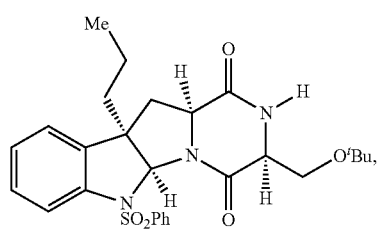
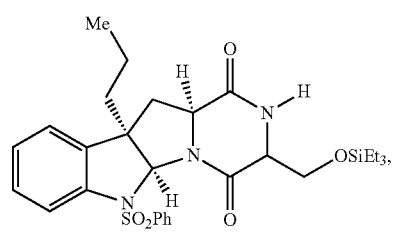

TABLE 2-continued

Exemplary compounds.

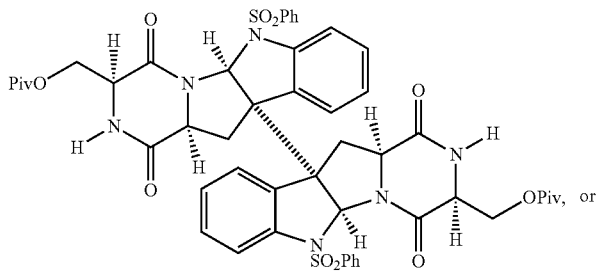

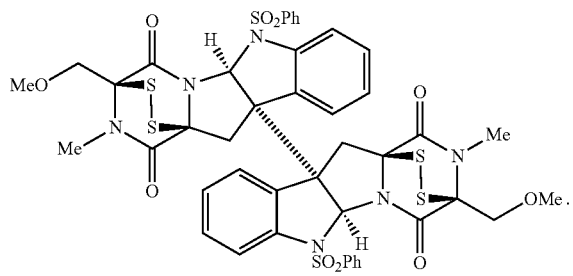

In some embodiments, a provided compound of formula I-c or I-d or D has the structure of those illustrated in Table 3:

TABLE 3

Exemplary structures.

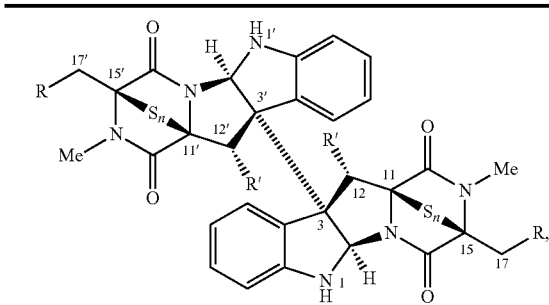

R = H, R' = OH, n = 2 Verticillin A (2)
R = H, R' = H, n = 2 12,12'-Dideoxyverticillin A (3)
R = OH, R' = H, n = 2 Chaetocin A (4)
R = OH, R' = H, n = 3 Chaetocin C (5)
R = OH, R' = H, n = 4 12,12'-Dideoxychetracin A (6)

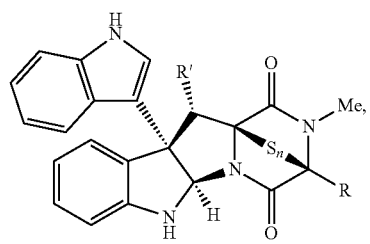

R = H, R' = OH, n = 2 Bionectin A (9)
R = H, R' = H, n = 2 12-Deoxybionectin A (10)
R = i-Pr, R' = OH, n = 3 Leptosin E (11)
R = Me, R' = H, n = 2 Glioclatine (12)
R = Me, R' = OH, n = 4 Gliocladine E (13)

TABLE 3-continued

Exemplary structures.

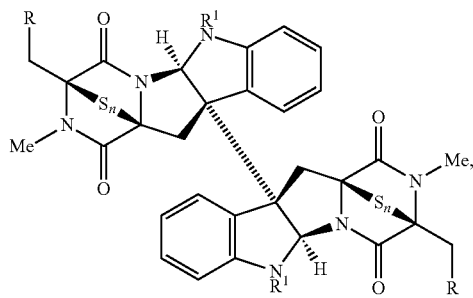

14, n = 2, R = H, R$^1$ = SO$_2$Ph
3, n = 2, R = H, R$^1$ = H
4, n = 2, R = OH, R$^1$ = H
15, n = 2, R = OAc, R$^1$ = H
5, n = 3, R = OH, R$^1$ = H
16, n = 3, R = OAc, R$^1$ = H
17, n = 3, R = OAc, R$^1$ = COCF$_3$
6, n = 4, R = OH, R$^1$ = H

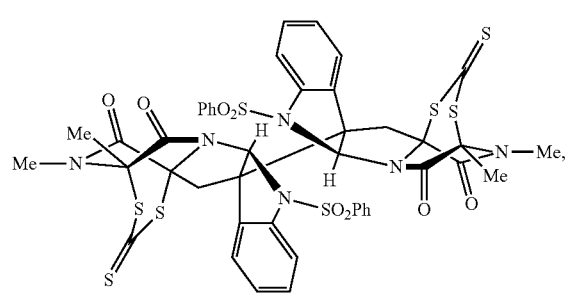

TABLE 3-continued

Exemplary structures.

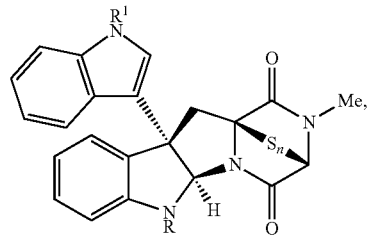

24, n = 2, R = SO$_2$Ph, R$^1$ = Boc
25, n = 1, R = SO$_2$Ph, R$^1$ = H
26, n = 2, R = SO$_2$Ph, R$^1$ = H
27, n = 3, R = SO$_2$Ph, R$^1$ = H
28, n = 4, R = SO$_2$Ph, R$^1$ = H
10, n = 2, R = H, R$^1$ = H
29, n = 3, R = H, R$^1$ = H

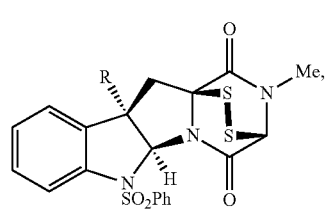

30, R = Br
31, R = F
32, R = pyrrol-3'-yl
33, R = p-MeOPh

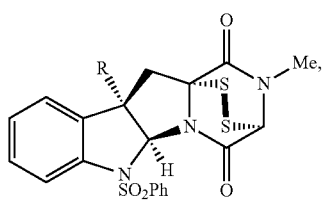

34, R = Br
35, R = F

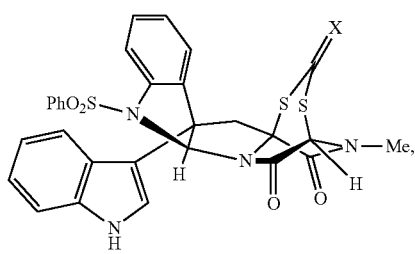

36, X = S
37, X = O
38, X = H,H

TABLE 3-continued

Exemplary structures.

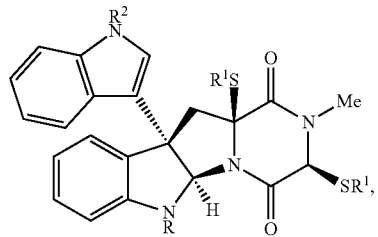

7, R = H, R$^1$ = Me, R$^2$ = H
39, R = SO$_2$Ph, R$^1$ = Me, R$^2$ = H
40, R = SO$_2$Ph, R$^1$ = MOM, R$^2$ = H
41, R = H, R$^1$ = MOM, R$^2$ = H
42, R = SO$_2$Ph, R$^1$ = MEM, R$^2$ = Boc
43, R = SO$_2$Ph, R$^1$ = Bn, R$^2$ = Boc
44, R = SO$_2$Ph, R$^1$ = Ac, R$^2$ = H
45, R = SO$_2$Ph, R$^1$ = SMe, R$^2$ = SMe
46, R = SO$_2$Ph, R$^1$ = SMe, R$^2$ = H

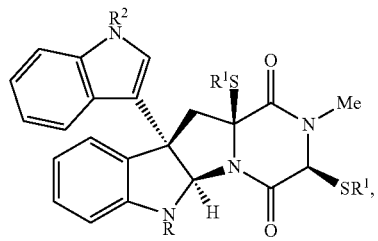

44, R = SO$_2$Ph, R$^1$ = Ac, R$^2$ = H
45, R = SO$_2$Ph, R$^1$ = SMe, R$^2$ = SMe
46, R = SO$_2$Ph, R$^1$ = SMe, R$^2$ = H

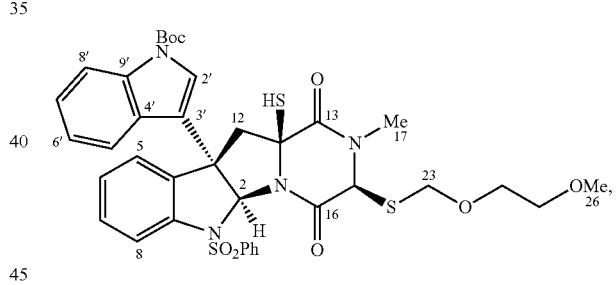

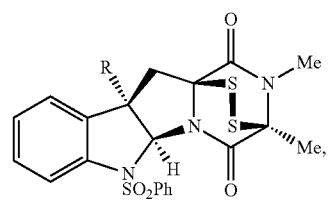

60, R = indol-3'-yl
61, R = n-Pr

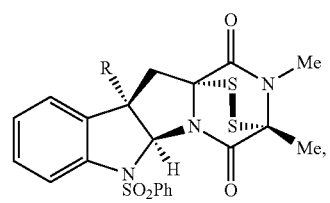

62, R = indol-3'-yl
63, R = n-Pr

TABLE 3-continued
Exemplary structures.
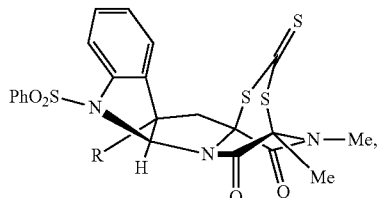
64, R = indol-3'-yl
65, R = n-Pr
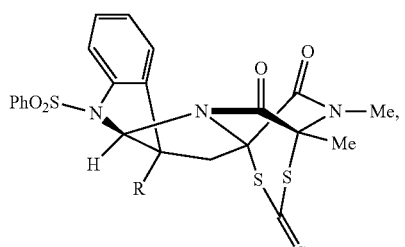
66, R = indol-3'-yl
67, R = n-Pr
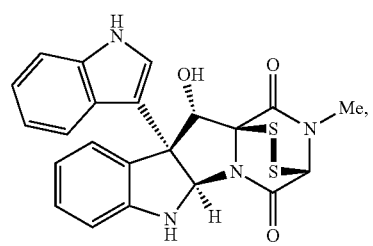
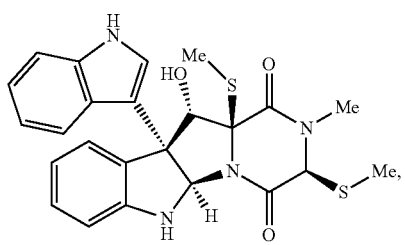 [SMILES: CS[C@H]1C(=O)N2[C@H]3Nc4ccccc4[C@@]3(c3c[nH]c4ccccc34)[C@H](O)[C@]2(SC)C(=O)N1C]
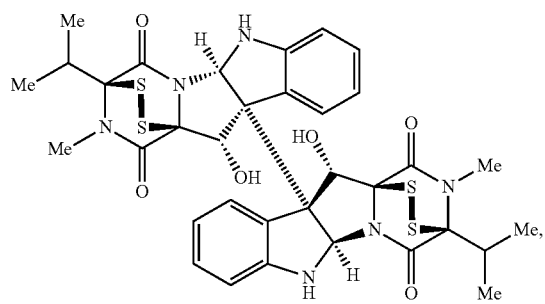
TABLE 3-continued
Exemplary structures.
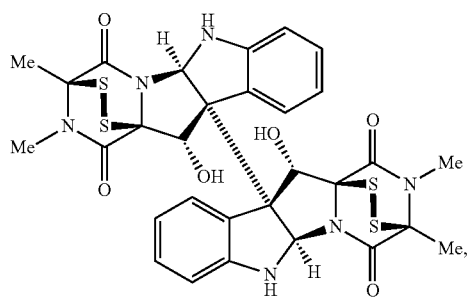
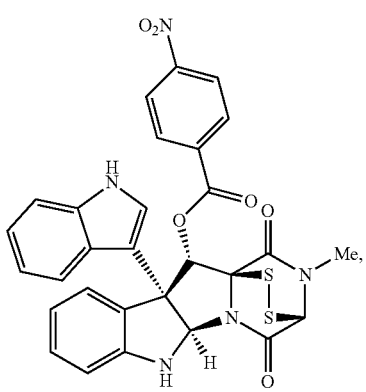 [SMILES: CN1C(=O)[C@]23SS[C@H]1C(=O)N2[C@H]1Nc2ccccc2[C@@]1(c1c[nH]c2ccccc12)[C@@H]3OC(=O)c1ccc([N+](=O)[O-])cc1]
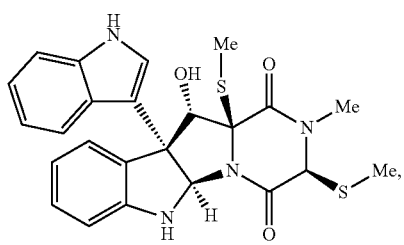 [SMILES: CS[C@H]1C(=O)N2[C@H]3Nc4ccccc4[C@@]3(c3c[nH]c4ccccc34)[C@H](O)[C@]2(SC)C(=O)N1C]
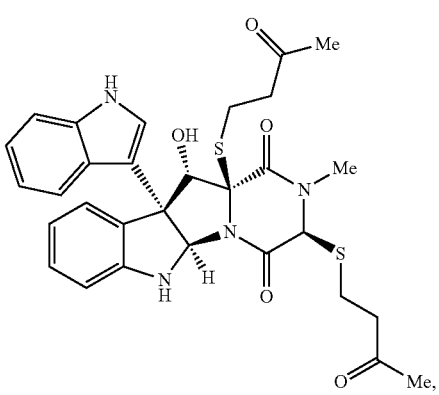 [SMILES: CC(=O)CCS[C@H]1C(=O)N2[C@H]3Nc4ccccc4[C@@]3(c3c[nH]c4ccccc34)[C@H](O)[C@]2(SCCC(C)=O)C(=O)N1C]

TABLE 3-continued

Exemplary structures.

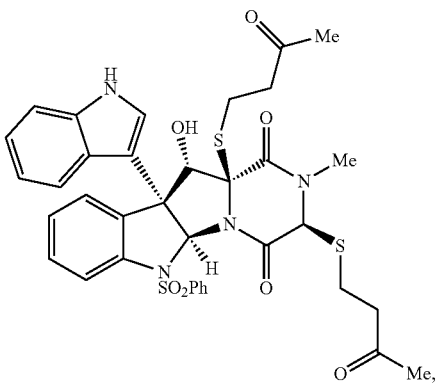

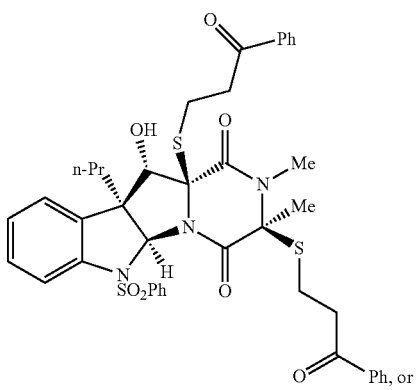

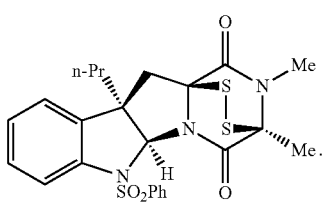

In some embodiments, the present invention provides an antibody-drug conjugate, wherein the drug unit is selected from a structure in Table 1, 2 or 3. In some embodiments, the present invention provides an antibody-drug conjugate, wherein the drug unit is selected from a structure in Table 1. In some embodiments, the present invention provides an antibody-drug conjugate, wherein the drug unit is selected from a structure in Table 2. In some embodiments, the present invention provides an antibody-drug conjugate, wherein the drug unit is selected from a structure in Table 3. In some embodiments, the present invention provides an antibody-drug conjugate, wherein the drug unit has the structure of formula I-a or I-b. In some embodiments, the drug unit has the structure of formula I-a-1. In some embodiments, the drug unit has the structure of formula I-a-2. In some embodiments, the drug unit has the structure of formula I-a-3. In some embodiments, the drug unit has the structure of formula I-a-4. In some embodiments, the drug unit has the structure of formula I-a-5. In some embodiments, the drug unit has the structure of formula I-b-1. In some embodiments, the drug unit has the structure of formula I-b-2. In some embodiments, the drug unit has the structure of formula I-b-3. In some embodiments, the drug unit has the structure of formula I-b-4. In some embodiments, the drug unit has the structure of formula I-b-5.

In some embodiments, D is a structure selected from Table 1, 2 or 3. In some embodiments, D is a structure selected from Table 1. In some embodiments, D is a structure selected from Table 2. In some embodiments, D is a structure selected from Table 3.

In some embodiments, the two

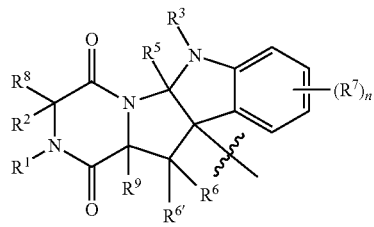

units of

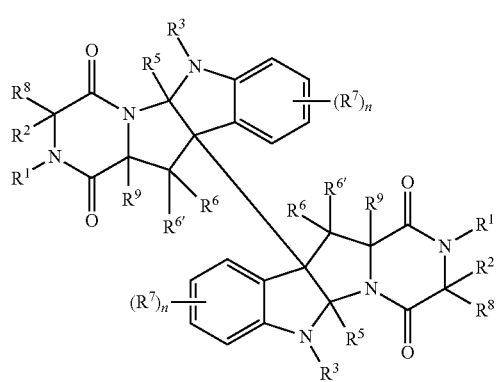

are the same. In some embodiments, the two

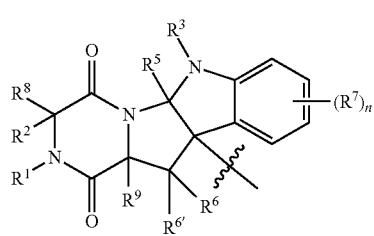

units of

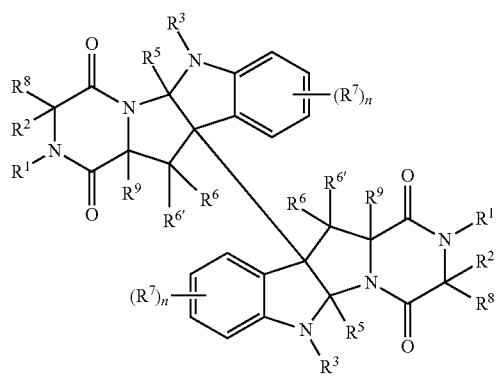

are different. In some embodiments, the two

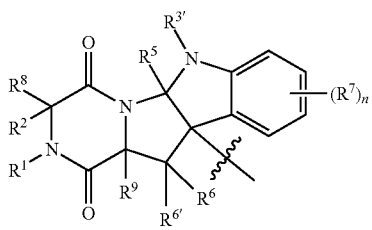

units of

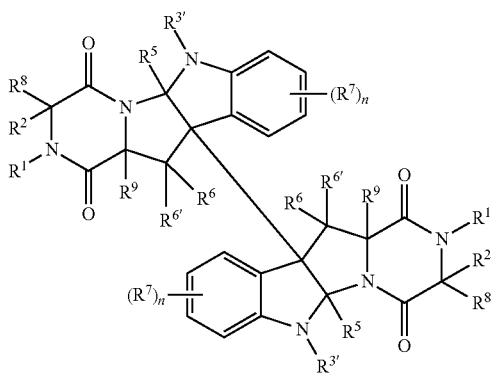

are different. In some embodiments, the two

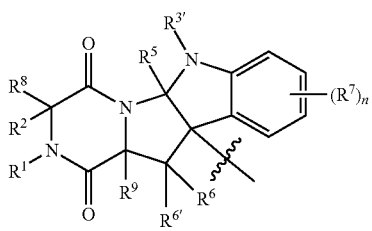

units of

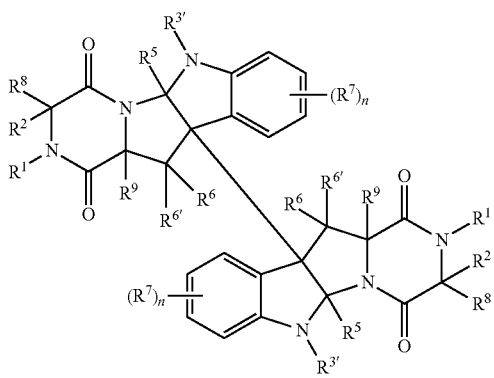

are different.

Also falling within the scope of this invention are the in vivo metabolic products of compound conjugates described herein, e.g., compounds of formula II. Such products may result for example from the oxidation, reduction, hydrolysis, amidation, esterification, enzymatic cleavage, and the like, of the administered compound. Accordingly, the invention includes compounds produced by a process comprising contacting a provided compound, e.g., a compound of formulae I-a, I-b, II, or III, with a subject for a period of time sufficient to yield a metabolic product thereof.

In some embodiments, metabolite products are identified by preparing a radiolabelled (e.g. $^{14}C$ or $^{3}H$) compound, administering it parenterally in a detectable dose (e.g. greater than about 0.5 mg/kg) to a subject such as a rat, mouse, guinea pig, monkey, or a human being, allowing sufficient time for metabolism to occur (typically about 30 seconds to 30 hours), and isolating its conversion products from the urine, blood or other biological samples. The metabolite structures are determined in conventional fashion, e.g. by MS, LC/MS or NMR analysis. In general, analysis of metabolites is done in the same way as conventional drug metabolism studies well-known to those skilled in the art. In some embodiments, conversion products, for example, those not otherwise found in vivo, are useful in diagnostic assays for therapeutic dosing of a provided compound such as an ADC having the structure of formula II.

In some embodiments, a provided compound generates reactive oxygen species (ROS). Exemplary ROS includes superoxide radical anion, hydroxyl radical and hydrogen peroxide. In some embodiments, the present invention provides a method for generating reactive oxygen species in a subject, comprising providing a compound of formula I-a, I-b, I-c, I-d, II, or III. In some embodiments, a provided compound conjugates with and/or inhibits cellular proteins by forming mixed disulfides between cysteine residues. In some embodiments, a provided compound conjugates with and/or inhibits cellular proteins by catalytic formation of intramolecular disulfide bonds between cysteine residues. In some embodiments, the present invention provides a method for conjugating with and/or inhibiting cellular proteins, comprising providing a compound of formula I-a, I-b, I-c, I-d, II, or III. In some embodiments, a provided compound disrupts tertiary structure of proteins containing a $Zn^{2+}$-binding cysteine-histidine rich protein domain. In some embodiments, the present invention provides a method for disrupting tertiary structures of proteins containing a $Zn^{2+}$-binding cysteine-histidine rich protein domain, comprising providing a compound of formula I-a, I-b, I-c, I-d, II, or III. In some embodiments, a provided compound ejects $Zn^{2+}$ ions from a protein. In some embodiments, the present invention provides a method for ejecting a $Zn^{2+}$ ion from a protein, comprising providing a compound of formula I-a, I-b, I-c, I-d, II, or III. In some embodiments, a provided compound induces caspase-dependent apoptosis. In some embodiments, the present invention provides a method for inducing apoptosis, comprising providing a compound of formula I-a, I-b, I-c, I-d, II, or III. In some embodiments, the present invention provides a method for inducing caspase-dependent apoptosis, comprising providing a compound of formula I-a, I-b, I-c, I-d, II, or III.

In some embodiments, the present invention provides compositions of provided compounds or pharmaceutically acceptable salts thereof. In some embodiments, a provided composition comprises an effective amount of a provided compound, or pharmaceutically acceptable salt thereof, for treatment of a disease, for example, cancer. In some embodiments, a composition is a pharmaceutical composition. In some embodiments, a provided composition is suitable for veterinary or human administration.

A provided composition can be in any form that allows for the composition to be administered to a subject. For example, a composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In some embodiments, a provided compound is administered parenterally. In some embodiments, a provided compound is administered parenterally. In some embodiments, a provided composition is administered intravenously. In some embodiments, a provided composition is administered intravenously.

Pharmaceutical compositions can be formulated so as to allow a provided compound to be bioavailable upon administration of the composition to a patient. Compositions can take the form of one or more dosage units, where for example, a tablet can be a single dosage unit, a vial may contain a single dose for intravenous administration, and a container of a provided compound in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of a provided compound or composition, the manner of administration, and the composition employed.

A pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration. When intended for oral administration, a composition is preferably in solid or liquid form, where semi-solid, semi-liquid, suspension and gel forms are included within the forms considered herein as either solid or liquid.

As a solid composition for oral administration, a composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When a composition is in the form of a capsule, e.g., a gelatin capsule, it can contain, in addition to materials of the above type, a liquid carrier such as polyethylene glycol, cyclodextrin or a fatty oil.

A composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a provided compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

Provided compositions comprise an effective amount of a provided compound such that a suitable dosage will be obtained. In some embodiments, this amount is at least about 0.01% of a provided compound by weight of the composition. When intended for oral administration, this amount can be varied to range from about 0.1% to about 80% by weight of the composition. In one aspect, oral compositions can comprise from about 4% to about 50% of a provided compound by weight of the composition. In yet another aspect, a provided composition is prepared so that a parenteral dosage unit contains from about 0.01% to about 2% by weight of a provided compound or composition.

For intravenous administration, a provided composition can comprise from about 0.01 to about 100 mg of a provided compound per kg of a subject's body weight. In one aspect, the composition can include from about 1 to about 100 mg of a provided compound per kg of a subject's body weight. In another aspect, the amount administered will be in the range from about 0.1 to about 25 mg/kg of body weight of a provided compound.

Generally, dosage of a provided compound administered to a patient is typically about 0.001 mg/kg to about 2000 mg/kg of a subject body weight. In one aspect, a dosage administered to a patient is between about 0.01 mg/kg to about 10 mg/kg of a subject's body weight, in another aspect, a dosage administered to a subject is between about 0.1 mg/kg and about 250 mg/kg of a subject's body weight, in yet another aspect, a dosage administered to a patient is between about 0.1 mg/kg and about 20 mg/kg of a subject's body weight, in yet another aspect a dosage administered is between about 0.1 mg/kg to about 10 mg/kg of a subject's body weight, and in yet another aspect, a dosage administered is between about 1 mg/kg to about 10 mg/kg of a subject's body weight. In some embodiments, a daily dosage might range from about 1 µg/kg to 100 mg/kg or more, depending on the factors mentioned above. An exemplary dosage of ADC to be administered to a patient is in the range of about 0.1 to about 10 mg/kg of patient weight.

A provided compound can be administered by any convenient mute, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a provided compound or composition. In certain embodiments, more than one provided compound or composition is administered to a patient.

In some embodiments, it is desirable to administer one or more provided compounds or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more provided compounds or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In some embodiments, a provided compound or compositions can be delivered in a controlled release system, such as but not limited to, a pump or various polymeric materials can be used. In yet another embodiment, a controlled-release system can be placed in proximity of a target of a provided compound or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

In some embodiments, a carrier is a diluent, adjuvant or excipient, with which a provided compound is administered. Such pharmaceutical carriers can be liquids, such as water and oils, including those of petroleum, animal, vegetable or synthetic origin, such as peanut oil, soybean oil, mineral oil, sesame oil and the like. Carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, provided compounds or compositions and pharmaceutically acceptable carriers are sterile. Water is an exemplary carrier when a provided compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Provided compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

In some embodiments, a provided compound or composition is formulated in accordance with routine procedures as a pharmaceutical composition adapted for intravenous administration to a subject particularly a human being. In some embodiments, carriers or vehicles for intravenous administration are sterile isotonic aqueous buffer solutions. Where necessary, a provided composition can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a provided compound is to be administered by infusion, it can be dispensed, for example, with an infusion bottle containing sterile pharmaceutical grade water or saline. Where a provided compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. In some embodiments, where in tablet or pill form, a provided composition can be coated to delay disintegration and absorption in the gastrointestinal tract thereby providing a sustained action over an extended period of time. Selectively permeable membranes surrounding an osmotically active driving compound are also suitable for orally administered compounds. For example, in these later platforms, fluid from the environment surrounding a capsule is imbibed by a driving compound, which swells to displace an agent or agent composition through an aperture. In some embodiments, a delivery platform can provide an essentially zero order delivery profile as opposed to the spiked profiles of immediate release formulations. A time-delay material such as glycerol monostearate or glycerol stearate can also be used.

A provided composition can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of a provided compound of from about 0.05% to about 50% w/v (weight per unit volume of composition), in another aspect, from 0.1% to 10% w/v.

A provided composition can be intended for rectal administration, in the form, e.g., of a suppository which will melt in the rectum and release a provided compound.

A provided composition can include various materials that modify the physical form of a solid or liquid dosage unit. For example, a provided composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. In some embodiments, an aerosol is used to denote a variety of systems ranging from those of colloidal nature to systems consisting of pressurized packages. Delivery can be by a liquefied or compressed gas or by a suitable pump system that dispenses the active ingredients.

Whether in solid, liquid or gaseous form, a provided composition can include a pharmacological agent used in the treatment of cancer, an autoimmune disease or an infectious disease.

Provided compounds and compositions are useful for treating various diseases, for example, cancer, an autoimmune disease or an infectious disease in a patient.

In some embodiments, a provided compound is an antibody-drug conjugate (ADC). Antibody-drug conjugates, e.g., a compound of formula II wherein M is an antibody or fragment thereof, may be administered by any route appropriate to the condition to be treated. In some embodiments, an ADC is administered parenterally, i.e. infusion, subcutaneous, intramuscular, intravenous, intradermal, intrathecal and epidural.

In some embodiments, provided pharmaceutical formulations of provided antibody-drug conjugates are typically prepared for parenteral administration, i.e. bolus, intravenous, intratumor injection with a pharmaceutically acceptable parenteral vehicle and in a unit dosage injectable form. In some embodiments, an antibody-drug conjugate having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

A provided pharmaceutical composition of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In some embodiments, the present invention provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

A provided compound or composition of the present invention may be used to treat various diseases or disorders, e.g. characterized by the overexpression of an antigen such as a cancer antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In some embodiments, the present invention provides a method for killing or inhibiting proliferation of cells comprising treating the cells with an amount of a provided compound, or a pharmaceutically acceptable salt thereof, being effective to kill or inhibit proliferation of the cells. In some embodiments, the cells are tumor cells or cancer cells. In some embodiments, the present invention provides a method of treating a disease, comprising administering to a subject in need an effective amount of a provided compound or a pharmaceutically acceptable salt thereof. In some embodiments, the present invention provides a method of treating a disease, comprising administering to a subject suffering therefrom or susceptible thereto an effective amount of a provided compound or pharmaceutically salt thereof. In some embodiments, a disease is a cancer, autoimmune disease or infectious disease. In some embodiments, a disease is cancer. In some embodiments, a disease is an autoimmune disease. In some embodiments, a disease is an infectious disease. In some embodiments, a provided is a compound of formula I-a. In some embodiments, a provided is a compound of formula I-b. In some embodiments, a provided is a compound of formula II.

A provided compound of the invention may be combined in a pharmaceutical combination formulation, or dosing regimen as combination therapy, with a second compound having therapeutic properties. A second compound of the pharmaceutical combination formulation or dosing regimen preferably has complementary activities to a provided compound of the combination such that they do not adversely affect each other.

In some embodiments, a second compound is a chemotherapeutic agent, cytotoxic agent, cytokine, growth inhibitory agent, anti-hormonal, a drug for an autoimmune disease, a drug for an infectious disease, and/or cardioprotectant. Such molecules are suitably present in combination in amounts that are effective for the purpose intended.

A combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for co-administered agents are those presently used and may be lowered due to the combined action (synergy) of the newly identified agent and other chemotherapeutic agents or treatments.

A provided combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In some embodiments, the present invention provides methods of treating cancer. In some embodiments, the present invention provides a method of treating cancer in a subject suffering therefrom, comprising administering to the subject a therapeutically effective amount of a provided compound. In some embodiments, a provided compound has the structure of formula I-a. In some embodiments, a provided compound has the structure of formula I-b. In some embodiments, a provided compound has the structure of formula II. In some embodiments, a provided compound has the structure of formula II-a. In some embodiments, a provided compound has the structure of formula II-b.

Provided compounds and/or compositions are useful for inhibiting the multiplication of a tumor cell or cancer cell, causing apoptosis in a tumor or cancer cell, or for treating cancer in a subject. Provided compounds and compositions can be used in a variety of settings for the treatment of cancers. A provided conjugate compound, e.g., a compound of formula II, can be used to deliver a drug to a tumor cell or cancer cell. Without being bound by theory, in one embodiment, the ligand unit (M) of a provided compound binds to or associates with a cancer-cell or a tumor-cell-associated antigen, and a provided compound can be taken up inside a tumor cell or cancer cell through receptor-mediated endocytosis. An antigen can be attached to a tumor cell or cancer cell or can be an extracellular matrix protein associated with the tumor cell or cancer cell. In some embodiments, once inside the cell, a conjugate compound is cleaved, for example, one or more specific peptide sequences within a linker unit (L) are hydrolytically cleaved by one or more tumor-cell or cancer-cell-associated proteases, resulting in release of a drug comprising part or all of the drug unit and optionally part or all of the linker unit. A released drug is then free to migrate within the cell and induce cytotoxic or cytostatic activities. In some other embodiments, a provided conjugate compound is cleaved outside a tumor cell or cancer cell, and a drug or drug-linker compound subsequently penetrates the cell.

In some embodiments, a ligand unit binds to a tumor cell or cancer cell. In some embodiments, a ligand unit binds to a tumor cell or cancer cell antigen which is on the surface of the tumor cell or cancer cell. In some embodiments, a ligand unit binds to a tumor cell or cancer cell antigen which is an extracellular matrix protein associated with a tumor cell or cancer cell.

In some embodiments, the specificity of a ligand unit for a particular tumor cell or cancer cell can be important for determining those tumors or cancers that are most effectively treated. For example, a provided conjugate compound having a BR96 Ligand unit can be useful for treating antigen positive carcinomas including those of the lung, breast, colon, ovaries, and pancreas. In some embodiments, a provided conjugate compound having an Anti-CD30 or an anti-CD40 Ligand unit can be useful for treating hematologic malignancies.

Other particular types of cancers that can be treated with provided compounds and/or compositions include, but are not limited to, those listed below:

Solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma ultiforme, astrocytoma, medulloblastoma, craniopharyngioma, ependymoma, pinealoma, emangioblastoma, acoustic neuroma, oligodendroglioma, meningioma, skin cancer, melanoma, neuroblastoma, retinoblastoma. Blood-borne cancers, including but not limited to: acute lymphoblastic leukemia "ALL", acute lymphoblastic B-cell leukemia, acute lymphoblastic T-cell leukemia, acute myeloblastic leukemia AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, lymphoblastic, myelogenous, lymphocytic and myelocytic leukemias. Lymphomas: Hodgkin's disease, non-Hodgkin's Lymphoma, Multiple myeloma, Waldenström's macroglobulinemia, Heavy chain disease, and Polycythemia vera.

In some embodiments, a cancer being treated is carcinoma, lymphoma, blastoma, sarcoma, leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In some embodiments, a provided conjugate compound provides conjugation-specific tumor or cancer targeting, thus reducing general toxicity of these compounds. In some embodiments, a linker unit stabilizes a provided compound in blood, yet are cleavable by tumor-specific proteases within the cell, liberating a drug unit optionally comprising part of the linker unit.

Cancers, including, but not limited to, a tumor, metastasis, or other disease or disorder characterized by uncontrolled cell growth, can be treated or prevented by administration of a provided compound or composition. In some embodiments, a provided compound or composition is administered with another cancer treatment.

In some embodiments, methods for treating or preventing cancer are provided, comprising administering to a subject in need thereof an effective amount of a provided compound or composition. In some embodiments, a provided compound is administered prior to, concurrently with, or subsequent to, a chemotherapeutic agent. In some embodiments, a chemotherapeutic agent is that with which treatment of the cancer has not been found to be refractory. In some embodiments, a chemotherapeutic agent is that with which the treatment of cancer has been found to be refractory. In some embodiments, a provided compound is administered to a patient that has also undergone surgery as treatment for the cancer.

In some embodiments, an additional method of treatment is radiation therapy. In some embodiments, a provided compound or composition is administered prior to, concurrently with or subsequent to radiation.

In some embodiments, a provided compound or composition is administered concurrently with a chemotherapeutic agent or with radiation therapy. In some embodiments, a chemotherapeutic agent or radiation therapy is administered prior or subsequent to administration of a provided compound or composition. In some embodiments, a chemotherapeutic agent or radiation therapy is administered concurrently with administration of a provided compound or composition. In some embodiments, a provided compound or composition is administered at least one hour, five hours, 12 hours, a day, a week, a month, or several months (e.g., up to three months), prior or subsequent to administration of a provided compound or composition.

A chemotherapeutic agent can be administered over a series of sessions. Any one or a combination of the chemotherapeutic agents can be administered. Exemplary chemotherapy drugs are widely known in the art, including but not limited to tubulin-binding drugs, kinase inhibitors, alkylating agents, DNA topoisomerase inhibitors, anti-folates, pyrimidine analogs, purine analogs, DNA antimetabolites, hormonal therapies, retinoids/deltoids, photodynamic therapies, cytokines, angiogenesis inhibitors, histone modifying enzyme inhibitors, and antimitotic agents. Examples are extensively described in the art, including but not limited to those in PCT Application Publication No. WO2010/025272. In some embodiments, a "tubulin-binding drug" refers to a ligand of tubulin or to a compound capable of binding α or β-tubulin monomers or oligomers thereof, αβ-tubulin heterodimers or oligomers thereof, or polymerized microtubules. Exemplary tubulin-binding drugs include, but are not limited to:

a) Combretastatins or other stilbene analogs (e.g., described in Pettit et al, Can. J. Chem., 1982; Pettit et al, J. Org. Chem., 1985; Pettit et al, J. Nat. Prod., 1987; Lin et al, Biochemistry, 1989; Singh et al, J. Org. Chem., 1989; Cushman et al, J. Med. Chem., 1991; Getahun et al, J. Med. Chem., 1992; Andres et al, Bioorg. Med. Chem. Lett., 1993; Mannila, Liebigs. Ann. Chem., 1993; Shirai et al, Bioorg. Med. Chem. Lett., 1994; Medarde et al., Bioorg. Med. Chem. Lett., 1995; Pettit et al, J. Med. Chem., 1995; Wood et al, Br. J. Cancer., 1995; Bedford et al, Bioorg. Med. Chem. Lett., 1996; Dorr et al, Invest. New Drugs, 1996; Jonnalagadda et al., Bioorg. Med. Chem. Lett., 1996; Shirai et al, Heterocycles, 1997; Aleksandrzak K, Anticancer Drugs, 1998; Chen et al, Biochem. Pharmacal., 1998; Ducki et al, Bioorg. Med. Chem. Lett., 1998; Hatanaka et al, Bioorg. Med. Chem. Lett., 1998; Medarde, Eur. J. Med. Chem., 1998; Medina et al, Bioorg. Med. Chem. Lett., 1998; Ohsumi et al, Bioorg. Med. Chem. Lett., 1998; Ohsumi et al., J. Med. Chem., 1998; Pettit G R et al., J. Med. Chem., 1998; Shirai et al, Bioorg. Med. Chem. Lett., 1998; Banwell et al, Aust. J. Chem., 1999; Medarde et al, Bioorg. Med. Chem. Lett., 1999; Shan et al, PNAS, 1999; Combeau et al, Mol. Pharmacal, 2000; Pettit et al, J. Med Chem, 2000; Pettit et al, Anticancer Drug Design, 2000; Pinney et al, Bioorg. Med. Chem. Lett., 2000; Flynn et al., Bioorg. Med. Chem. Lett., 2001; Gwaltney et al, Bioorg. Med. Chem. Lett., 2001; Lawrence et al, 2001; Nguyen-Hai et al, Bioorg. Med. Chem. Lett., 2001; Xia et al, J. Med. Chem., 2001; Tahir et al., Cancer Res., 2001; Wu-Wong et al., Cancer Res., 2001; Janik et al, Bioorg. Med. Chem. Lett., 2002; Kim et al., Bioorg Med Chem. Lett., 2002; Li et al, Bioorg. Med. Chem. Lett., 2002; Nam et al, Bioorg. Med. Chem. Lett., 2002; Wang et al, J. Med. Chem. 2002; Hsieh et al, Bioorg. Med. Chem. Lett., 2003; Hadimani et al., Bioorg. Med. Chem. Lett., 2003; Mu et al, J. Med. Chem., 2003; Nam, Curr. Med. Chem., 2003; Pettit et al, J. Med. Chem., 2003; WO 02/50007, WO 02/22626, WO 02/14329, WO 01/81355, WO 01/12579, WO 01/09103, WO 01/81288, WO 01/84929, WO 00/48591, WO 00/48590, WO 00/73264, WO 00/06556, WO 00/35865, WO 00/48590, WO 99/51246, WO 99/34788, WO 99/35150, WO 99/48495, WO 92/16486, U.S. Pat. Nos. 6,433,012, 6,201,001, 6,150,407, 6,169,104, 5,731,353, 5,674,906, 5,569,786, 5,561,122, 5,430,062, 5,409,953, 5,525,632, 4,996,237 and 4,940,726 and U.S. patent application Ser. No. 10/281,528);

b) 2,3-substituted Benzo[b]thiophenes (e.g., described in Pinney et al, Bioorg. Med. Chem. Lett., 1999; Chen et al, J. Org. Chem., 2000; U.S. Pat. Nos. 5,886,025; 6,162,930, and 6,350,777; WO 98/39323);

c) 2,3-disubstituted Benzo[b]furans (e.g., described in WO 98/39323, WO 02/060872);

d) Disubstituted Indoles (e.g., described in Gastpar R, J. Med. Chem., 1998; Bacher et al, Cancer Res., 2001; Flynn et al, Bioorg. Med. Chem. Lett, 2001; WO 99/51224, WO 01/19794, WO 01/92224, WO 01/22954; WO 02/060872, WO 02/12228, WO 02/22576, and U.S. Pat. No. 6,232,327);

e) 2-Aroylindoles (e.g., described in Mahboobi et al, J. Med. Chem., 2001; Gastpar et al., J. Med. Chem., 1998; WO 01/82909);

f) 2,3-disubstituted Dihydronaphthalenes (e.g., described in WO 01/68654, WO 02/060872);

g) Benzamidazoles (e.g., described in WO 00/41669);

h) Chalcones (e.g., described in Lawrence et al, Anti-Cancer Drug Des, 2000; WO 02/47604);

i) Colchicine, Allocolchicine, Thiocolcichine, Halichondrin B, and Colchicine derivatives (e.g., described in WO 99/02166, WO 00/40529, WO 02/04434, WO 02/08213, U.S. Pat. Nos. 5,423,753. 6,423,753) in particular the N-acetyl colchinol prodrug, ZD-6126;

j) Curacin A and its derivatives (e.g., described in Gerwick et al, J. Org. Chem., 1994, Blokhin et al, Mol. Phamacol., 1995; Verdier-Pinard, Arch. Biochem. Biophys., 1999; WO 02/06267);

k) Dolastatins such as Dolastatin-10, Dolastatin-15, and their analogs (e.g., described in Pettit et al, J. Am. Chem. Soc., 1987; Bai et al, Mol. Pharmacal, 1995; Pettit et al, Anti-Cancer Drug Des., 1998; Poncet, Curr. Pharm. Design, 1999; WO 99/35164; WO 01/40268; U.S. Pat. No. 5,985,837);

l) Epothilones such as Epothilones A, B, C, D, and Desoxyepothilones A and B, Fludelone (e.g., described in Chou et al. Cancer Res. 65:9445-9454, 2005, the entirety of which is hereby incorporated by reference), 9,10-dehydro-desoxyepothilone B (dehydelone), iso-oxazole-dehydelone (17-isooxazole-dehydelone), fludelone, iso-oxazolefludelone (17-isooxazole-fludelone), (Danishefsky, et al., PNAS, v.

105, 35:13157-62, 2008; WO 99/02514, U.S. Pat. No. 6,262, 094, Nicolau et al., Nature, 1997, Pub. No. US2005/ 0143429);

m) Inadones (e.g., described in Leoni et al., J. Natl. Cancer Inst., 2000; U.S. Pat. No. 6,162,810);

n) Lavendustin A and its derivatives (Mu F et al, J. Med. Chem., 2003, the entirety of which is hereby incorporated by reference);

o) 2-Methoxyestradiol and its derivatives (e.g., described in Fotsis et al, Nature, 1994; Schumacher et al, Clin. Cancer Res., 1999; Cushman et al, J. Med. Chem., 1997; Verdier-Pinard et al, Mol. Pharmacal, 2000; Wang et al, J. Med. Chem., 2000; WO 95/04535, WO 01/30803, WO 00/26229, WO 02/42319 and U.S. Pat. Nos. 6,528,676, 6,271,220, 5,892,069, 5,661,143, and 5,504,074);

p) Monotetrahydrofurans (e.g., "COBRAs"; Uckun, Bioorg. Med. Chem. Lett., 2000; U.S. Pat. No. 6,329,420);

q) Phenylhistin and its derivatives (e.g., described in Kanoh et al, J. Antibiot., 1999; Kano et al, Bioorg. Med. Chem., 1999 and U.S. Pat. No. 6,358,957);

r) Podophyllotoxins such as Epidophyllotoxin (e.g., described in Hammonds et al, J. Med. Microbial, 1996; Coretese et al, J. Biol. Chem., 1977);

s) Rhizoxins (e.g., described in Nakada et al, Tetrahedron Lett., 1993; Boger et al, J. Org. Chem., 1992; Rao, et al, Tetrahedron Lett., 1992; Kobayashi et al, Pure Appl. Chem., 1992; Kobayashi et al, Indian J. Chem., 1993; Rao et al, Tetrahedron Lett., 1993);

t) 2-strylquinazolin-4(3H)-ones (e.g., "SQOs", Jiang et al, J. Med. Chem., 1990, the entirety of which is hereby incorporated by reference);

u) Spongistatin and Synthetic spiroketal pyrans (e.g., "SPIKETs"; Pettit et al, J. Org. Chem., 1993; Uckun et al, Bioorgn. Med. Chem. Lett., 2000; U.S. Pat. No. 6,335,364, WO00/00514);

v) Taxanes such as Paclitaxel (TAXOL®), Docetaxel (TAXOTERE®), and Paclitaxel derivatives (e.g., described in U.S. Pat. No. 5,646,176, WIPO Publication No. WO 94/14787, Kingston, J. Nat. Prod., 1990; Schiff et al, Nature, 1979; Swindell et al, J. Cell Biol., 1981);

x) Vinca Alkaloids such as Vinblastine, Vincristine, Vindesine, Vinflunine, Vinorelbine (NAVELBINE®) (e.g., described in Owellen et al, Cancer Res., 1976; Lavielle et al, J. Med. Chem., 1991; Holwell et al, Br. J. Cancer., 2001); and y) Welwistatin (e.g., described in Zhang et al, Molecular Pharmacology, 1996, the entirety of which is hereby incorporated by reference).

Exemplary specific examples of tubulin-binding drugs include, but are not limited to, allocolchicine, amphethinile, chelidonine, colchicide, colchicine, combrestatin AI, combretastin A4, combretastain A4 phosphate, combrestatin 3, combrestatin 4, cryptophycin, curacin A, deo-dolastatin 10, desoxyepothilone A, desoxyepothilone B, dihydroxypentamethoxyflananone, docetaxel, dolastatin 10, dolastatin 15, epidophyllotoxin, epothilone A, epothilone B, epothilone C, epothilone D, etoposide, 9,10-dehydro-desoxyepothilone B (dehydelone), iso-oxazole-dehydelone (17-isooxazole-dehydelone), fludelone, iso-oxazolefludelone (17-isooxazolefludelone), griseofulvin, halichondrin B, isocolchicine, lavendustin A, methyl-3,5-diiodo-4-(4'-methoxyphenoxy) benzoate, N-acetylcolchinol, N-acetylcolchinol-O-phosphate, N-[2-[(4-hydroxyphenyl)amino]-3-pyridyl]-4-methoxybenzenesulfonamide, nocodazole, paclitaxel, phenstatin, phenylhistin, piceid, podophyllotoxin, resveratrol, rhizoxin, sanguinarine, spongistatin 1, steganacin, TAXOL, teniposide, thiocolchicine, vincristine, vinblastine, welwistatin, (Z)-2-methoxy-5-[2-(3,4,5-trimethoxyphenyl) vinyl]phenylamine, (Z)-3,5,4'-trimethoxystilbene (R3), 2-aryl-1,8-naphthyridin-4(1H)-one, 2-(41-methoxyphenyl)-3-(31,41,51-rimethoxybenzoyl)-6-methoxybenzo[b] thiophene, 2-methoxy estradiol, 2-strylquinazolin-4(3H)-one, 5,6-dihydroindolo(2,1-a)isoquinoline, and 10-deacetylbaccatin III.

In some other embodiments, exemplary chemotherapy drugs include but are not limited to nitrogen mustards, nitrosoureas, alkylsulphonates, triazenes, platinum complexes, epipodophyllins, mitomycins, DHFR inhibitors, IMP dehydrogenase inhibitors, ribonucleotide reductase inhibitors, uracil analogs, cytosine analogs, purine analogs, receptor antagonists (for example, anti-estrogen, LHRH agonists, anti-androgens), vitamin derivative or analogs, isoprenylation inhibitors, dopaminergic neurotoxins, cell cycle inhibitors, actinomycins, bleomycins, anthracyclines, MDR inhibitors, $Ca^{2+}$ ATPase inhibitors, and anti-metastatis agents. In some embodiments, exemplary specific examples of tubulin-binding drugs include, but are not limited to, Cyclophosphamide, Ifosfamide, Trofosfamide, Chlorambucil, Carmustine, Lomustine, Busulfan, Treosulfan, Dacarbazine, Procarbazine, Temozolomide, Cisplatin, Carboplatin, Aroplatin, Oxaliplatin, Topotecan, Irinotecan, 9-aminocamptothecin, Camptothecin, Crisnatol, Mitomycin C, Methotrexate, Trimetrexate, Mycophenolic acid, Tiazofurin, Ribavirin, 5-Ethynyl-1-beta-D-ribofuranosylimidazole-4-carboxamide (EICAR), Hydroxyurea, Deferoxamine, 5-Fluorouracil, Fluoxuridine, Doxifluridine, Ralitrexed, Cytarabine, Cytosine arabinoside, Fludarabine, Gemcitabine, Capecitabine, Mercaptopurine, Thioguanine, O-6-benzylguanine, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, inosine glycodialdehyde, macebecin II, Pyrazoloimidazole, Tamoxifen, Raloxifene, Megestrol, Goserelin, Leuprolide acetate, Flutamide, Bicalutamide, Cis-retinoic acid, All-trans retinoic acid (ATRA-IV), EB 1089, CB 1093, KH 1060, Vertoporfin, Phthalocyanine, Photosensitizer Pc4, Demethoxy-hypocrellin A, ABT-627, Bay 12-9566, Benefin, BMS-275291, cartilage-derived inhibitor, CAI, CEP-7055, Col 3, Halofuginone, Heparin hexasaccharide fragment, IM-862, Marimastat, Metalloproteinase inhibitors, 2-Methoxyestra diol, MMI 270, Neovastat, NM-3, Panzem, PI-88, Placental ribonuclease inhibitor, Plasminogen activator inhibitor, Prinomastat, Retinoids, Solimastat, Squalamine, SS 3304, SU 5416, SU 6668, SU 11248, Tetrahydrocortisol-S, Tetrathiomolybdate, Thalidomide, TNP-470, ZD 6126, ZD 6474, farnesyl transferase inhibitors, Bisphosphonates, trityl cysteine, 1-methyl-4-phenylpyridinium ion, Staurosporine, Actinomycin D, Dactinomycin, Bleomycin A2, Bleomycin B2, Peplomycin, Daunorubicin, Doxorubicin, Idarubicin, Epirubicin, Pirarubicin, Zorubicin, Mitoxantrone, Verapamil, Ardeemin, Ningalin, Thapsigargin, Metastatin, GLiY-SD-ME-1, Sorafenib, Imatinib, Gefinitib, Lapatinib, Dasatinib, Nilotinib, Temsirolimus, Erlotinib, Pomalidomide, Regorafenib, Paclitaxel Protein-Bound Particles For Injectable Suspension, Everolimus, Bosutinib, Cabozantinib, Cabozantinib, Ponatinib, Axitinib, Carfilzomib, Ingenol Mebutate, Regorafenib, Fentanyl, Omacetaxine Mepesuccinate, Cephalotaxine, Pazopanib, Enzalutamide, Fentanyl Citrate, Sunitinib, Vandetanib, Crizotinib, Vemurafenib, Abiraterone Acetate, Eribulin Mesylate, Cabazitaxel, Ondansetron, Pralatrexate, Romidepsin, Plerixafor, Granisetron, Bendamustine Hydrochloride, Raloxifene Hydrochloride, Topotecan, Ixabepilone, Nilotinib, Temsirolimus, Lapatinib, Nelarabine, Sorafenib, Clofarabine, Cinacalcet, Erlotinib, Palonosetron, Tositumomab, Aprepitant, Gefitinib, Abarelix, Conjugated Estrogens, Alfuzosin, Bortezomib, Leucovorin, Fulvestrant, Ibritumomab Tiuxetan, Zoledronic Acid, Triptorelin Pamoate, Arsenic Trioxide, Aromasin, Busulfan, Amifostine, Temozolomide, Odansetron, Dolasetron, Irinotecan, Gemcitabine, Porfimer Sodium, Valrubicin, Capecitabine, Zofran, Bromfenac, Letrozole, Leuprolide, Samarium ($^{153}$sm) Lexidronam, Pamidronate, Anastrozole, Levoleucovorin, Flutamide And Goserelin.

In some embodiments, a provided compound or composition is administered prior to, concurrently with or subsequent to another polypeptide or protein. In some embodiments, a polypeptide or protein is a recombinant polypeptide or protein. Exemplary polypeptides or proteins include but are not limited to cytokines, interferon alfa-2b, interleukin 2, filgrastim, rasburicase, secretin, asparaginase *Erwinia chrysanthemi*, and ziv-aflibercept. In some embodiments, a polypeptide or protein comprises an antibody or a fragment of an antibody. In some embodiments, a polypeptide or protein is an antibody or a fragment of an antibody. Examples include but are not limited to rituximab, trastuzumab, tositumomab, alemtuzumab, bevacizumab, cetuximab, panitumumab, ofatumumab, denosumab, ipilimumab, pertuzumab. In some embodiments, a polypeptide or protein is chemically modified. In some embodiments, a polypeptide or protein is conjugated to a drug. In some embodiments, an antibody or an antibody fragment is conjugated to a payload drug, forming an antibody-drug conjugate. In some embodiments, a payload drug is cytotoxic. Exemplary antibody-drug conjugates include but are not limited to gemtuzumab ozogamicin, brentuximab vedotin, and ado-trastuzumab emtansine. In some embodiments, a cancer treatment comprises the use of a vaccine. Exemplary vaccines for cancer treatment are well known in the art, for example but not limited to sipuleucel-T.

A provided compound may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, a provided compound (and optionally other agents as described herein) may be administered to the patient. In some embodiments, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

With respect to radiation, any radiation therapy protocol can be used depending upon the type of cancer to be treated. For example, but not by way of limitation, X-ray radiation can be administered; in some embodiments, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In some embodiments, methods of treatment of cancer with a provided compound or composition are provided as an alternative to chemotherapy or radiation therapy where the chemotherapy or the radiation therapy has proven or can prove too toxic, e.g., results in unacceptable or unbearable side effects, for a subject being treated. A subject being treated can, optionally, be treated with another cancer treatment such as surgery, radiation therapy or chemotherapy, depending on which treatment is found to be acceptable or bearable.

In some embodiments, a provided compound or composition can be used in an in vitro or ex vivo fashion, such as for the treatment of certain cancers, including, but not limited to leukemias and lymphomas. In some embodiments, such a treatment involves autologous stem cell transplants. In some embodiments, this can involve a multi-step process in which a subject's autologous hematopoietic stem cells are harvested and purged of all cancer cells, a subject's remaining bone-marrow cell population is then eradicated via the administration of a high dose of a provided compound or composition with or without accompanying high dose radiation therapy, and the stem cell graft is infused back into the animal. Supportive care is then provided while bone marrow function is restored and a subject recovers.

In some embodiments, the present invention provides methods for treating an autoimmune disease, comprising administering to a subject suffering therefrom or susceptible thereto an effective amount of a provided compound or a pharmaceutically acceptable salt thereof. In some embodiments, a subject is suffering from an autoimmune disease. In some embodiments, a provided compound is useful for killing or inhibiting replication of a cell that produces an autoimmune disease or for treating an autoimmune disease. A provided compound or composition can be used in a variety of settings for the treatment of an autoimmune disease in a patient. A provided compound can be used to deliver a Drug to a target cell. Without being bound by theory, in some embodiments, a provided conjugate compound associates with an antigen on the surface of a target cell, and a provided conjugate compound is then taken up inside a target-cell through receptor-mediated endocytosis. Once inside the cell, a provided conjugate compound can be cleaved. In some embodiments, one or more specific peptide sequences within the linker unit are enzymatically or hydrolytically cleaved, resulting in release of a drug comprising all or part of the drug unit and optionally part or all of the linker unit. A released drug is then free to migrate in the cytosol and induce cytotoxic or cytostatic activities. In an alternative embodiment, a conjugate compound is cleaved and a drug is released outside the target cell, and the drug subsequently penetrates the cell.

In some embodiments, a ligand unit binds to an autoimmune antigen. In some embodiments, an antigen is on the surface of a cell involved in an autoimmune condition. In some embodiments, a ligand unit binds to an autoimmune antigen which is on the surface of a cell. In some embodiments, a ligand binds to activated lymphocytes that are associated with the autoimmune disease state. In some embodiments, a provided compound kills or inhibits the multiplication of cells that produce an autoimmune antibody associated with a particular autoimmune disease.

Exemplary types of autoimmune diseases that can be treated with provided compounds or compositions include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those listed below:
Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird- Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibritis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, and Wegener's Granulomatosis.

In some embodiments, an autoimmune disease being treated is selected from rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

In some embodiments, the present invention provides methods for treating an autoimmune disease, comprising administering to a subject suffering therefrom an effective amount of a provided compound or composition. In some embodiments, a provided method comprises administering an effective amount of a provided compound or composition and another therapeutic agent known for treatment of an autoimmune disease. Exemplary therapeutic agents are widely known in the art, including but not limited to cyclosporine, cyclosporine A, mycophenylate mofetil, sirolimus, tacrolimus, enanercept, prednisone, azathioprine, methotrexate cyclophosphamide, prednisone, aminocaproic acid, chloroquine, hydroxychloroquine, hydrocortisone, dexamethasone, chlorambucil, DHEA, danazol, bromocriptine, meloxicam and infliximab.

In some embodiments, the present invention provides methods for treating an infectious disease, comprising administering to a subject suffering therefrom or susceptible thereto an effective amount of a provided compound or a pharmaceutically acceptable salt thereof. In some embodiments, a provided compound or composition is useful for killing or inhibiting the multiplication of a cell that produces an infectious disease or for treating an infectious disease. A provided compound can be used in a variety of settings for the treatment of an infectious disease in a subject. In some embodiments, a provided conjugate compound is used to deliver a drug to a target cell. In one embodiment, a ligand unit binds to the infectious disease cell. In one embodiment, a provided compound kills or inhibits the multiplication of cells that produce a particular infectious disease.

Exemplary types of infectious diseases that can be treated with a provided compound include, but are not limited to: Bacterial Diseases such as Diphtheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Eethyma, Pneumonia, Endocarditis, Septic Arthritis, Pneumococcal, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, Salmonella, Typhoid Fever, Dysentery, Conjunctivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, Chlamydia, Chlamydial Pneumonia, Trachoma and Inclusion Conjunctivitis; Systemic Fungal Diseases such as Histoplamosis, Coccidiodomycosis, Blastomycosis, Sporotrichosis, Cryptococcsis, Systemic Candidiasis, Aspergillosis, Mucormycosis, Mycetoma and Chromomycosis; Rickettsial Diseases such as Typhus, Rocky Mountain Spotted Fever, Ehrlichiosis, Eastern Tick-Borne Rickettsioses, Rickettsialpox, Q Fever and Bartonellosis; Parasitic Diseases such as Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease and Alveolar Hydatid Disease; Viral Diseases such as Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Human Immunodeficiency Virus (HIV), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simplex Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections and Smallpox.

In some embodiments, the present invention provides methods for treating an infectious disease, comprising administering to a subject suffering therefrom an effective amount of a provided compound or composition. In some embodiments, a provided method comprises administering an effective amount of a provided compound or composition and another therapeutic agent known for treatment of an infectious disease.

In some embodiments, a provided method for treating an infectious disease includes administering to a patient in need thereof a provided compound and another therapeutic agent that is an anti-infectious disease agent. Exemplary anti-infectious disease agents are widely known in the art, including but not limited to β-Lactam Antibiotics such as Penicillin G, Penicillin V, Cloxacilliin, Dicloxacillin, Methicillin, Nafcillin, Oxacillin, Ampicillin, moxicillin, Bacampicillin, Azlocillin, Carbenicillin, Mezlocillin, Piperacillin and Ticarcillin; Aminoglycosides: Amikacin, Gentamicin, Kanamycin, Neomycin, Netilmicin, Streptomycin and Tobramycin; Macrolides such as Azithromycin, Clarithromycin, Erythromycin, Lincomycinand Clindamycin; Tetracyclines such as Demeclocycline, Doxycycline, Minocycline, Oxytetracycline and Tetracycline; Quinolones such as Cinoxacin and Nalidixic Acid; Fluoroquinolones such as Ciprofloxacin, Enoxacin, Grepafloxacin, Levofloxacin, Lomefloxacin, Norfloxacin, Ofloxacin, Sparfloxacin and Trovafloxicin; Polypeptides such as Bacitracin, Colistin and Polymyxin B; Sulfonamides such as Sulfisoxazole, Sulfamethoxazole, Sulfadiazine, Sulfamethizole and Sulfacetamide; Miscellaneous Antibacterial Agents such as Trimethoprim, Sulfamethazole, Chloramphenicol, Vancomycin, Metronidazole, Quinupristin, Dalfopristin, Rifampin, Spectinomycin, Nitrofurantoin; General Antiviral Agents such as Idoxuradine, Vidarabine, Trifluridine, Acyclovir, Famcicyclovir, Pencicyclovir, Valacyclovir, Gancicyclovir, Foscarnet, Ribavirin, Amantadine, Rimantadine, Cidofovir, Antisense Oligonucleotides, Immunoglobulins and Inteferons; Drugs for HIV infection such as Tenofovir, Emtricitabine, Zidovudine, Didanosine, Zalcitabine, Stavudine, Lamivudine, Nevirapine, Delavirdine, Saquinavir, Ritonavir and Indinavir, Nelfinavir.

Conditions

Suitable conditions for performing provided methods or preparing provided compounds generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane and chloroform, or polar aprotic solvents, such as ethereal solvents including ether, tetrahydrofuran (THF), or dioxanes, or protic solvents, such as alcohols, or mixtures thereof. In some embodiments, a solvent is substituted hydrocarbons. In some embodiments, a solvent is $MeNO_2$. In some embodiments, a solvent is $EtNO_2$. In certain embodiments, one or more solvents are deuterated. In some embodiments, a single solvent is used. In certain embodiments, a solvent is benzene. In certain embodiments, a solvent is ether. In some embodiments, a solvent is a nitrile. In some embodiments, a solvent is acetonitrile.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent: hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

In some embodiments, a solvent is water. In some embodiments, a solvent is water. In some embodiments, a mixture of water with one or more other solvents is used.

Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C. In certain embodiments, a suitable temperature is about 20° C., 21° C., 22° C., 23° C., 24° C., or 25° C.

In certain embodiments, a provided method is performed at elevated temperature. In some embodiments, a suitable temperature is from about 25° C. to about 11° C. In certain embodiments, a suitable temperature is from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable temperature is about 80° C. In some embodiments, a suitable temperature is about 30° C. In some embodiments, a suitable temperature is about 40° C. In some embodiments, a suitable temperature is about 50° C. In some embodiments, a suitable temperature is about 60° C. In some embodiments, a suitable temperature is about 70° C. In some embodiments, a suitable temperature is about 80° C. In some embodiments, a suitable temperature is about 90° C. In some embodiments, a suitable temperature is about 100° C. In some embodiments, a suitable temperature is about 11° C.

In certain embodiments, a provided method is performed at temperature lower than ambient temperatures. In some embodiments, a suitable temperature is from about −100° C. to about 10° C. In certain embodiments, a suitable temperature is from about −80° C. to about 0° C. In certain embodiments, a suitable temperature is from about −70° C. to about 1° C. In certain embodiments, a suitable temperature is from about −60° C. to about 10° C. In certain embodiments, a suitable temperature is from about −50° C. to about 10° C. In certain embodiments, a suitable temperature is from about −40° C. to about 10° C. In certain embodiments, a suitable temperature is or from about −30° C. to about 10° C. In some embodiments, a suitable temperature is below 0° C. In some embodiments, a suitable temperature is about −100° C. In some embodiments, a suitable temperature is about −90° C. In some embodiments, a suitable temperature is about −80° C. In some embodiments, a suitable temperature is about −70° C. In some embodiments, a suitable temperature is about −60° C. In some embodiments, a suitable temperature is about −50° C. In some embodiments, a suitable temperature is about −40° C. In some embodiments, a suitable temperature is about −30° C. In some embodiments, a suitable temperature is about −20° C. In some embodiments, a suitable temperature is about −10° C. In some embodiments, a suitable temperature is about 0° C. In some embodiments, a suitable temperature is about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C. In some embodiments, a provided method comprises temperature increase from about −30° C. to 22° C. In some embodiments, a provided method comprises temperature decrease from a higher suitable temperature to a lower suitable temperature. In some embodiments, a provided method comprises temperature increase from about 110° C., about 100° C., about 90° C., about 80° C., about 70° C., about 60° C., about 50° C., about 40° C., about 30° C., about 25° C., about 22° C., ambient temperature, about 20° C., about 10° C., and about 0° C. to about 0° C., about −10° C., about −20° C., about −30° C., about −40° C., about −50° C., about −60° C., about −70° C., about −80° C., about −90° C., and about −100° C.

Suitable conditions typically involve reaction times of about 1 minute to about one or more days. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1, 2, 3, 4, 5, 6, 7, 8, 9, 10, 11, or 12, 24, 48, 96 or 120 hours. In certain embodiments, the reaction time is about 1 hour. In certain embodiments, the reaction time is about 2 hours. In certain embodiments, the reaction time is about 3 hours. In certain embodiments, the reaction time is about 4 hours. In certain embodiments, the reaction time is about 5 hours. In certain embodiments, the reaction time is about 6 hours. In some embodiments, the reaction time is about 12 hours. In some embodiments, the reaction time is about 24 hours. In some embodiments, the reaction time is about 48 hours. In some embodiments, the reaction time is about 96 hours. In some embodiments, the reaction time is about 120 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 5 minutes. In some embodiments, the reaction time is about 10 minutes. In some embodiments, the reaction time is about 15 minutes. In some embodiments, the reaction time is about 20 minutes. In some embodiments, the reaction time is about 25 minutes. In some embodiments, the reaction time is about 30 minutes. In some embodiments, the reaction time is about 35 minutes. In some embodiments, the reaction time is about 40 minutes. In some embodiments, the reaction time is about 100 minutes. In some embodiments, the reaction time is about 110 minutes. In some embodiments, the reaction time is about 200 minutes. In some embodiments, the reaction time is about 300 minutes. In some embodiments, the reaction time is about 400 minutes.

Some embodiments provide the ability to selectively synthesize products having a Z or E configuration about a double bond. In some embodiments, a method of the present invention provides the ability to synthesize compounds comprising a Z-olefin. In some embodiments, such methods are useful when applied to a wide range of olefin substrates, including those having sterically small or large groups adjacent the olefin. In some embodiments, the substrate olefins are terminal olefins. In some embodiments, a provided method produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced has a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

Some embodiments provide the ability to selectively synthesize products having a Z or E configuration about a double bond. In some embodiments, a method of the present invention provides the ability to synthesize compounds comprising an E-olefin. In some embodiments, such methods are useful when applied to a wide range of olefin substrates, including those having sterically small or large groups adjacent the olefin. In some embodiments, the substrate olefins are terminal olefins. In some embodiments, a provided method produces a double bond in a E:Z ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced has an E configuration. The E or trans selectivity may also be expressed as a percentage of product formed. In some cases, the product may be greater than about 50% E, greater than about 60% E, greater than about 70% E, greater than about 80% E, greater than about 90% E, greater than about 95% E, greater than about 96% E, greater than about 97% E, greater than about 98% E, greater than about 99% E, or, in some cases, greater than about 99.5% E.

In some embodiments, a provided method requires an amount of a compound which promotes a reaction, such that the loading is from about 0.001 mol % to about 20 mol % of the compound relative to substrate. In certain embodiments, the compound is used in an amount of between about 0.001 mol % to about 10 mol %. In certain embodiments, the compound is used in an amount of between about 0.001 mol % to about 6 mol %. In certain embodiments, the compound is used in an amount of between about 0.001 mol % to about 5 mol %. In certain embodiments, the compound is used in an amount of between about 0.001 mol % to about 4 mol %. In certain embodiments, the compound is used in an amount of between about 0.001 mol % to about 3 mol %. In certain embodiments, the compound is used in an amount of between about 0.001 mol % to about 1 mol %. In certain embodiments, the compound is used in an amount of between about 0.001 mol % to about 0.5 mol %. In certain embodiments, the compound is used in an amount of between about 0.001 mol % to about 0.2 mol %. In certain embodiments, the compound is used in an amount of about 0.001 mol %, 0.002 mol %, 0.005 mol %, 0.0 mol %, 0.02 mol %, 0.03 mol %, 0.04 mol %, 0.05 mol %, 0.1 mol %, 0.2 mol %, 0.5 mol %, 1 mol %, 2 mol %, 3 mol %, 4 mol %, 5 mol %, 6 mol %, 7 mol %, 8 mol %, 9 mol %, or 10 mol %. In some embodiments, the compound is used in an amount of about 0.0002% mol. In some embodiments, the compound is used in an amount of about 0.01% mol. In some embodiments, the compound is used in an amount of about 3% mol.

In some embodiments, a method of the present invention requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr.

In some embodiments, a method of the present invention is performed at increased pressure. In some embodiments, a method of the present invention is performed at greater than about 1 atm. In some embodiments, a method of the present invention is performed at greater than about 2 atm. In some embodiments, a method of the present invention is performed at greater than about 3 atm. In some embodiments, a method of the present invention is performed at greater than about 5 atm. In some embodiments, a method of the present invention is performed at greater than about 10 atm. In some embodiments, a method of the present invention is performed at about 2 atm. In some embodiments, a method of the present invention is performed at about 3 atm. In some embodiments, a method of the present invention is performed at about 5 atm. In some embodiments, a method of the present invention is performed at about 10 atm.

In some embodiments, a provided method provides chemoselectivity. In some embodiments, a desired product is produced in greater than about 50%, 55%, 60%, 65%, 70%, 75%, 80%, 85%, 90%, 91%, 92%, 93%, 94%, 95%, 96%, 97% 98%, 99% or 99.5% selectivity.

In some embodiments, a provided method provides stereoselectivity. In some embodiments, a desired stereoisomer is produced in greater than about 50%, 55%, 60%, 65%, 70%, 75%, 80%, 85%, 90%, 91%, 92%, 93%, 94%, 95%, 96%, 97% 98%, 99% or 99.5% selectivity. In some embodiments, a provided method provides diastereoselectivity. In some embodiments, a provided method provides diastereoselectivity. In some embodiments, a desired diastereomer is produced in greater than about 50%, 55%, 60%, 65%, 70%, 75%, 80%, 85%, 90%, 91%, 92%, 93%, 94%, 95%, 96%, 97% 98%, 99% or 99.5% selectivity. In some embodiments, a provided method provides enantioselectivity. In some embodiments, a desired enantiomer is produced in greater than about 50%, 55%, 60%, 65%, 70%, 75%, 80%, 85%, 90%, 91%, 92%, 93%, 94%, 95%, 96%, 97% 98%, 99% or 99.5% selectivity.

It will be appreciated that, in certain embodiments, each variable recited is as defined above and described in embodiments, herein, both singly and in combination.

EXEMPLIFICATION

The present invention recognizes, among other things, that there is a continuing demand for compounds, compositions and methods for treating various diseases, for example, cancer. In some embodiments, the present invention provides such compounds, compositions and methods. In some embodiments, the present invention provides methods and uses for such compounds and compositions. Exemplary but non-limiting examples are described herein.

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

The epipolythiodiketopiperazine (ETP) alkaloids are a highly complex class of compounds. In some embodiments, the present invention provides methods for flexible and scalable synthesis of ETP alkaloids or thiodiketopiperazines, or derivatives and analogs thereof, for example, a provided compound of formula I-a, I-b, I-c or I-d.

Epipolythiodiketopiperazine (ETP; for reviews on epipolythiodiketopiperazines, see: (a) T. W. Jordan and S. J. Cordiner, *Trends Pharmacol. Sci.*, 1987, 8, 144; (b) P. Waring, R. D. Eichner and A. Müllbacher, *Med. Res. Rev.*, 1988, 8, 499; (c) D. M. Gardiner, P. Waring and B. J. Howlett, *Microbiology*, 2005, 151, 1021; (d) N. J. Patron, R. F. Waller, A. J. Cozijnsen, D. C. Straney, D. M. Gardiner, W. C. Nierman and B. J. Howlett, *BMC Evol. Biol.*, 2007, 7, 174; (e) R. Huang, X. Zhou, T. Xu, X. Yang and Y. Liu, *Chem. Biodiv.*, 2010, 7, 2809; (f) E. Iwasa, Y. Hamashima and M. Sodeoka, *Isr. J. Chem.*, 2011, 51, 420) alkaloids constitute a large (ca. 120 members) and diverse family of biologically active secondary metabolites produced by a number of filamentous fungi including those from the *Chaetomium*, *Leptosphaeria*, *Aspergillus*, *Verticillium*, *Penicillium*, and *Pithomyces* genera. These compounds are characterized by the incorporation of an intramolecular polysulfide bridge at the α,α'-positions of a cyclo-dipeptide (or diketopiperazine—DKP). Although mono-, di-, tri-, and tetrasulfide members are naturally occurring, the disulfides are the most prevalent (For reviews about pharmacologically active sulfur-containing compounds, see: (a) T. Řezanka, M. Sobotka, J. Spížek and K. Sigler, *Anti-Infect. Agents Med. Chem.*, 2006, 5, 187; (b) C.-S. Jiang, W. E. G. Müller, H. C. Schröder and Y.-W. Guo, *Chem. Rev.*, 2012, 112, 2179). In some embodiments, ETP alkaloids containing one or two ETP rings, or derivatives or analogs thereof, possesses a wide spectrum of biological activities (T. W. Jordan and S. J. Cordiner, *Trends Pharmacol. Sci.*, 1987, 8, 144; C.-J. Zheng, C.-J. Kim, K. S. Bae, Y.-H. Kim and W.-G. Kim, *J. Nat. Prod.*, 2006, 69, 1816), including antibacterial ((a) P. Waring and J. Beaver, *Gen. Pharmac.*, 1996, 27, 1311; (b) A. L. Kung, S. D. Zabludoff, D. S. France, S. J. Freedman, E. A. Tanner, A. Vieira, S. Cornell-Kennon, J. Lee, B. Wang, J. Wang, K. Memmert, H.-U. Naegeli, F. Petersen, M. J. Eck, K. W. Bair, A. W. Wood and D. M. Livingston, *Cancer Cell*, 2004, 6, 33; (c) D. M. Vigushin, N. Mirsaidi, G. Brooke, C. Sun, P. Pace, L. Inman, C. J. Moody and R. C. Coombes, *Med. Oncol.*, 2004, 21, 21; (d) D. Greiner, T. Bonaldi, R. Eskeland, E. Roemer and A. Imhof, *Nat. Chem. Biol.*, 2005, 1, 143; (e) M. Yanagihara, N. Sasaki-Takahashi, T. Sugahara, S. Yamamoto, M. Shinomi, I. Yamashita, M. Hayashida, B. Yamanoha, A. Numata, T. Yamori and T. Andoh, *Cancer Sci.*, 2005, 96, 816; (f) C. R. Isham, J. D. Tibodeau, W. Jin, R. Xu, M. M. Timm and K. C. Bible, *Blood*, 2007, 109, 2579; (g) Y. Chen, H. Guo, Z. Du, X.-Z. Liu, Y. Che and X. Ye, *Cell Prolif*, 2009, 42, 838; (h) Y.-M. Lee, J.-H. Lim, H. Yoon, Y.-S. Chun and J.-W. Park, *Hepatology*, 2011, 53, 171; (i) F. Liu, Q. Liu, D. Yang, W. B. Bollag, K. Robertson, P. Wu and K. Liu, *Cancer Res.*, 2011, 71, 6807; (j) K. Yano, M. Horinaka, T. Yoshida, T. Yasuda, H. Taniguchi, A. E. Goda, M. Wakada, S. Yoshikawa, T. Nakamura, A. Kawauchi, T. Miki and T. Sakai, *Int. J. Oncol.*, 2011, 38, 365; (k) N. Zhang, Y. Chen, R. Jiang, E. Li, X. Chen, Z. Xi, Y. Guo, X. Liu, Y. Zhou, Y. Che and X. Jiang, *Autophagy*, 2011, 7, 598; (l) H. Chaib, A. Nebbioso, T. Prebet, R. Castellano, S. Garbit, A. Restouin, N. Vey, L. Altucci and Y. Collette, *Leukemia*, 2012, 26, 662; (m) C. R. Isham, J. D. Tibodeau, A. R. Bossou, J. R. Merchan and K. C. Bible, Br. J. Cancer, 2012, 106, 314; (n) M. Takahashi, Y. Takemoto, T. Shimazu, H. Kawasaki, M. Tachibana, Y. Shinkai, M. Takagi, K. Shin-ya, Y. Igarashi, A. Ito and M. Yoshida, *J. Antiobiot.*, 2012, 65, 263; (o) C.-S. Jiang and Y.-W. Guo, *Mini Rev. Med. Chem.*, 2011, 11, 728), antiviral (W. A. Rightsel, H. G. Schneider, B. J. Sloan, P. R. Graf, F. A. Miller, Q. R. Bartz, J. Ehrlich and G. J. Dixon, *Nature*, 1964, 204, 1333; P. A. Miller, K. P. Milstrey and P. W. Trown, *Science*, 1968, 159, 431), antiparasitic, antifungal ((a) J. J. Coleman, S. Ghosh, I. Okoli and E. Mylonakis, *PLoS ONE*, 2011, 6, e25321; (b) C. Speth, C. Kupfahl, K. Pfaller, M. Hagleitner, M. Deutinger, R. Würzner, I. Mohsenipour, C. Lass-Flörl and G. Rambach, *Mol. Immunol.*, 2011, 48, 2122), antimalarial, immunosuppressive, immunomodulatory ((a) A. Müllbacher, P. Waring, U. Tiwari-Palni and R. D. Eichner, *Molec. Immunol.*, 1986, 23, 231 (b) H. L. Pahl, B. Krauss, K. Schulze-Osthoff, T. Decker, E. B.-M. Traenckner, M. Vogt, C. Myers, T. Parks, P. Waring, A. Mühlbacher, A. P. Czernilofsky and P. A. Baeuerle, *J. Exp. Med.*, 1996, 183, 1829; (c) S, Nishida, L. S. Yoshida, T. Shimoyama, H. Nunoi, T. Kobayashi and S. Tsunawaki, *Infect. Immun.*, 2005, 73, 235; (d) P. Waring, R. D. Eichner and A. Müllbacher, *Med. Res. Rev.*, 1988, 8, 499; (e) P. Waring and J. Beaver, *Gen. Pharmac.*, 1996, 27, 1311), phytotoxic (M. Soledade, C. Pedras, G. Séguin-Swartz and S. R. Abrams, *Phytochem.*, 1990, 29, 777), nematicidal (J.-Y. Dong, H.-P. He, Y.-M. Shen and K.-Q. Zhang, *J. Nat. Prod.*, 2005, 68, 1510), antiplatelet (A. Bertling, S, Niemann, A. Uekötter, W. Fegeler, C. Lass-Flörl, C. von Eiff and B. E. Kehrel, *Thromb. Haemost.*, 2010, 104, 270), and anti-inflammatory effects (E. Iwasa, Y. Hamashima and M. Sodeoka, Isr. J. Chem., 2011, 51, 420). In some embodiments, a provided compound is antibacterial. In some embodiments, a provided compound is anticancer. In some embodiments, a provided compound is antiviral. In some embodiments, a provided compound is antiparasitic. In some embodiments, a provided compound is antifungal. In some embodiments, a provided compound is antimalarial. In some embodiments, a provided compound is immunosuppressive. In some embodiments, a provided compound is immunomodulatory. In some embodiments, a provided compound is phytotoxic. In some embodiments, a provided compound is nematicidal. In some embodiments, a provided compound is antiplatelet. In some embodiments, a provided compound is anti-inflammatory.

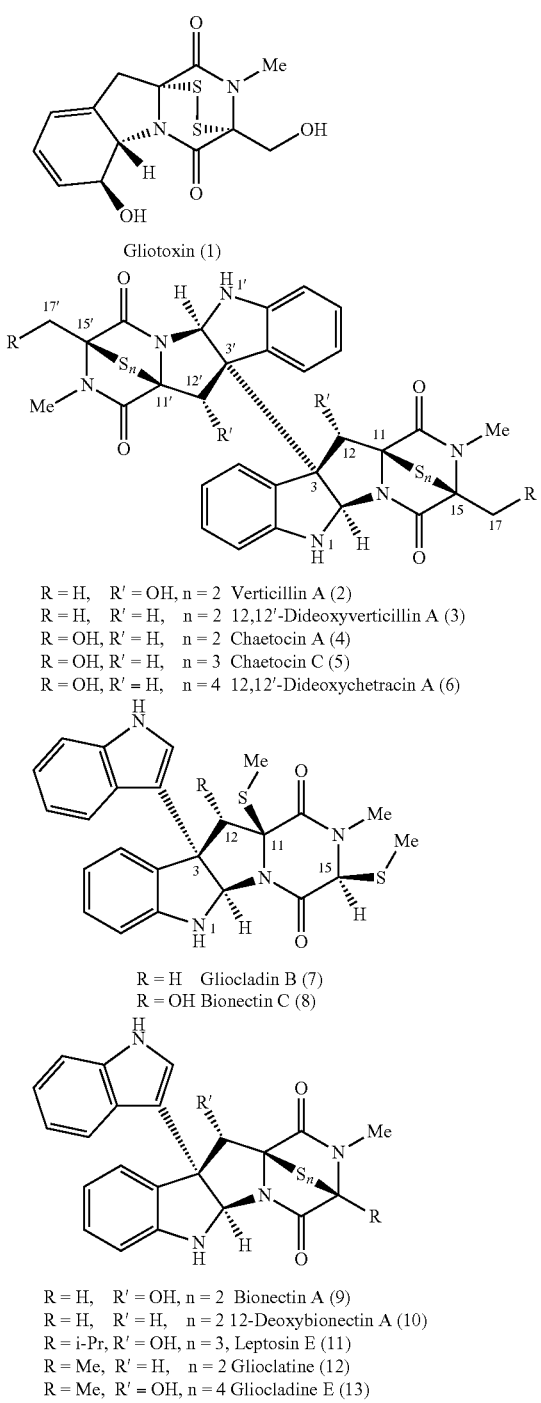

Representative Thiodiketopiperazines

A considerable number of synthetic efforts have been directed toward the synthesis of ETP compounds (For approaches to epipolythiodiketopiperazines, see: (a) P. W. Trown, *Biochem. Biophys. Res. Commun.*, 1968, 33, 402; (b) T. Hino and T. Sato, *Tetrahedron Lett.*, 1971, 12, 3127; (c) H. Poisel and U. Schmidt, *Chem. Ber.*, 1971, 104, 1714; (d) H. Poisel and U. Schmidt, *Chem. Ber.*, 1972, 105, 625; (e) E. Öhler, F. Tataruch and U. Schmidt, *Chem. Ber.*, 1973, 106, 396; (f) H. C. J. Ottenheijm, J. D. M. Herscheid, G. P. C. Kerkhoff and T. F. Spande, *J. Org. Chem.*, 1976, 41, 3433; (g) D. L. Coffen, D. A. Katonak, N. R. Nelson and F. D. Sancilio, *J. Org. Chem.*, 1977, 42, 948; (h) J. D. M. Herscheid, R. J. F. Nivard, M. W. Tijhuis, H. P. H. Scholten and H. C. J. Ottenheijm, *J. Org. Chem.*, 1980, 45, 1885; (i) R. M. Williams, R. W. Armstrong, L. K. Maruyama, J.-S. Dung and O. P. Anderson, *J. Am. Chem. Soc.*, 1985, 107, 3246; (j) C. J. Moody, A. M. Z. Slawin and D. Willows, *Org. Biomol. Chem.*, 2003, 1, 2716; (k) A. E. Aliev, S. T. Hilton, W. B. Motherwell and D. L. Selwood, *Tetrahedron Lett.*, 2006, 47, 2387; (1) L. E. Overman and T. Sato, *Org. Lett.*, 2007, 9, 5267; (m) N. W. Polaske, R. Dubey, G. S, Nichol and B. Olenyuk, *Tetrahedron: Asym.*, 2009, 20, 2742; (n) B. M. Ruff, S. Zhong, M. Nieger and S. Bräse, *Org. Biomol. Chem.*, 2012, 10, 935; (O) K. C. Nicolaou, D. Giguère, S. Totokotsopoulos and Y.-P. Sun, *Angew. Chem. Int. Ed.*, 2012, 51, 728; (p) P. Waring, R. D. Eichner and A. Müllbacher, *Med. Res. Rev.*, 1988, 8, 499). However, due to the synthetic challenges posed by the complex molecular architecture, only very few structures could be made, and even for those that have been synthesized, only very limited amounts have been provided. Therefore, although various ETP alkaloids have been assessed in a diverse array of biological tests, the non-uniformity of these studies precludes comparative analysis and the inference of meaningful conclusions. In some embodiments, among other things, the present invention recognizes that access to greater quantities of ETP alkaloids or thiodiketopiperazines and their analogs and derivatives is highly desired. In some embodiments, the present invention provides methods for synthesizing ETP alkaloids or thiodiketopiperazines and analogs and derivatives thereof. In some embodiments, the present invention provides methods for synthesizing ETP alkaloids or thiodiketopiperazines and analogs and derivatives thereof, wherein the methods produce ETP alkaloids or thiodiketopiperazines or analogs and derivatives thereof in quantities large enough to enable uniform biological studies. In some embodiments, the present invention provides new ETP or thiodiketopiperazine compounds and compositions thereof. In some embodiments, the present invention provides ETP or thiodiketopiperazine compounds and compositions thereof in quantities enough to enable uniform biological studies. In some embodiments, with the provided compounds and compositions in large enough quantities, the present invention analyzes the structural features of the ETP or thiodiketopiperazine compounds and their analogs and derivatives in relation to the biological activities. In some embodiments, the present invention provides evaluation of one or more of the following structural factors in relation to biological activities of ETP or thiodiketopiperazine compounds and derivatives and analogs thereof: polysulfide; the number of sulfur atoms, for example, in the polysulfide; the stereochemical configurations of the sulfurated centers; and dimerization state. In some embodiments, the present invention recognizes that investigation of the impact of each of these structural features is crucial to elucidating the mode of action of these compounds, to designing highly potent structures with suitable physicochemical and biopharmaceutical properties, and to their translation in vivo in clinical applications (e.g., biological probes and chemotherapeutic agents).

In some embodiments, the present provides a method for optimizing a ETP or thiodiketopiperazine compound or derivative or analog thereof, comprising:

(i) maintaining the polysulfide, or modifying the polysulfide to groups that can be converted to polysulfide when administered to a subject;

(ii) maintaining the stereochemistry of the sulfurated centers; and
(iii) optionally introducing an electron-withdrawing group to N1, if N1 is present.

In some embodiments, an electron-withdrawing group is $R^3$. In some embodiments, an electron-withdrawing group is —S(O)$_2$R. In some embodiments, an electron-withdrawing group is —S(O)$_2$Ph.

Exemplary structurally diverse ETP or thiodiketopiperazine alkaloids (and analogs and derivatives thereof) are depicted below:

A. Dimeric ETP derivatives from N-methyl-L-alanine/serine and L-tryptophan cyclo-dipeptide epipolysulfide bridge

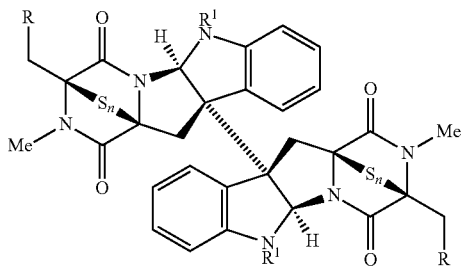

14, n = 2, R = H, $R^1$ = SO$_2$Ph
3, n = 2, R = H, $R^1$ = H
4, n = 2, R = OH, $R^1$ = H
15, n = 2, R = OAc, $R^1$ = H
5, n = 3, R = OH, $R^1$ = H
16, n = 3, R = OAc, $R^1$ = H
17, n = 3, R = OAc, $R^1$ = COCF$_3$
6, n = 4, R = OH, $R^1$ = H sulfur containing bridge

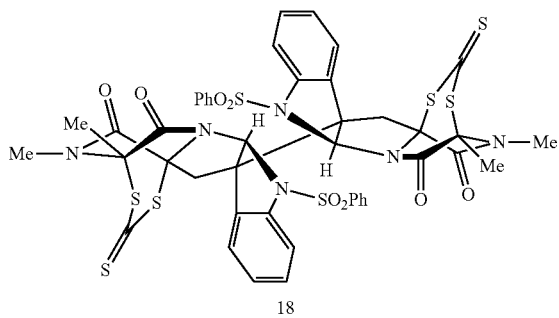

18 non-bridging trisulfane

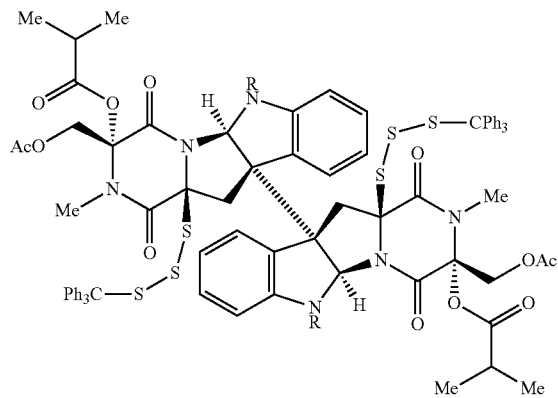

19, R = SO$_2$Ph
20, R = H

-continued
| no sulfur |
|---|
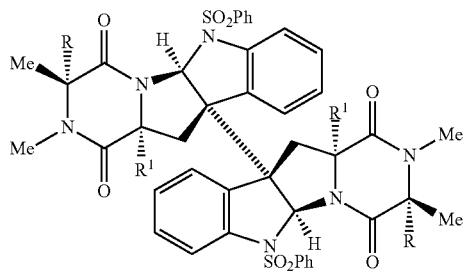
21, R = H, R¹ = H
22, R = OH, R¹ = OH
23, R = OTBS, R¹ = OH
| B. Monomeric ETP derivatives from sarcosine and L-tryptophan cyclo-dipeptide |
|---|
| epipolysulfide bridge |
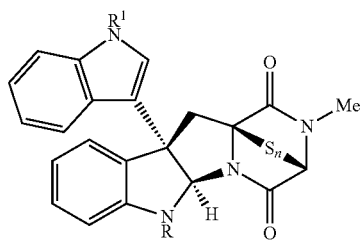
24, n = 2, R = SO₂Ph, R¹ = Boc
25, n = 1, R = SO₂Ph, R¹ = H
26, n = 2, R = SO₂Ph, R¹ = H
27, n = 3, R = SO₂Ph, R¹ = H
28, n = 4, R = SO₂Ph, R¹ = H
10, n = 2, R = H, R¹ = H
29, n = 3, R = H, R¹ = H
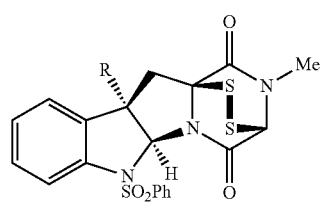
30, R = Br
31, R = F
32, R = pyrrol-3'-yl
33, R = p-MeOPh
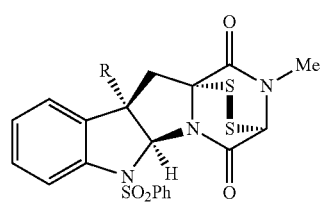
34, R = Br
35, R = F sulfur containing bridge

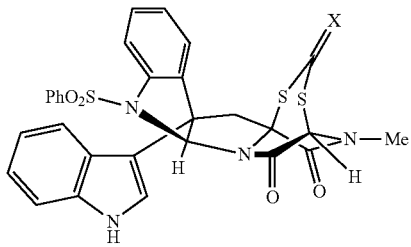

36, X = S
37, X = O
38, X = H,H non-bridging sulfur

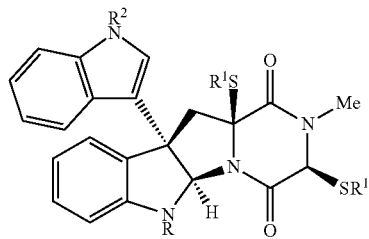

7, R = H, R$^1$ = Me, R$^2$ = H
39, R = SO$_2$Ph, R$^1$ = Me, R$^2$ = H
40, R = SO$_2$Ph, R$^1$ = MOM, R$^2$ = H
41, R = H, R$^1$ = MOM, R$^2$ = H
42, R = SO$_2$Ph, R$^1$ = MEM, R$^2$ = Boc
43, R = SO$_2$Ph, R$^1$ = Bn, R$^2$ = Boc
44, R = SO$_2$Ph, R$^1$ = Ac, R$^2$ = H
45, R = SO$_2$Ph, R$^1$ = SMe, R$^2$ = SMe
46, R = SO$_2$Ph, R$^1$ = SMe, R$^2$ = H

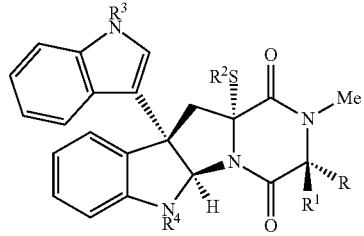

47, R = H, R$^1$ = SMEM, R$^2$ = H, R$^3$ = Boc, R$^4$ = SO$_2$Ph
48, R = OH, R$^1$ = H, R$^2$ = H, R$^3$ = H, R$^4$ = SO$_2$Ph
49, R = H, R$^1$ = H, R$^2$ = MOM, R$^3$ = Boc, R$^4$ = SO$_2$Ph
50, R = OCOi-Pr, R$^1$ = H, R$^2$ = COi-Pr, R$^3$ = H, R$^4$ = SO$_2$Ph
51, R = OCOi-Pr, R$^1$ = H, R$^2$ = COi-Pr, R$^3$ = H, R$^4$ = H no sulfur

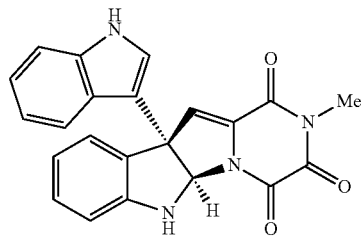

52

-continued
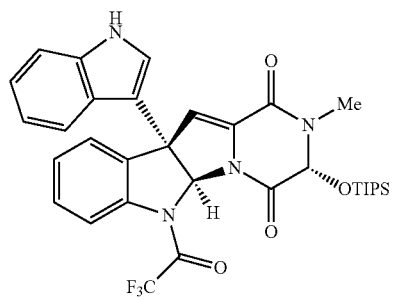
53
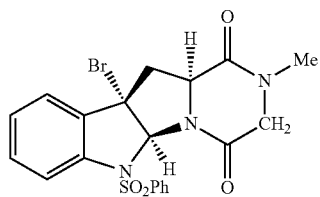
54
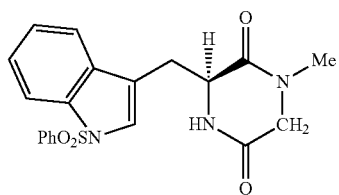
55
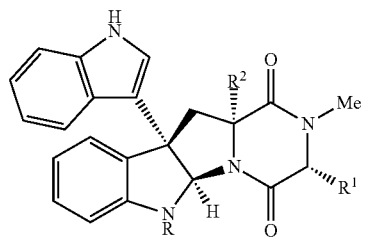
56, R = SO$_2$Ph, R$^1$ = OH, R$^2$ = OH
57, R = SO$_2$Ph, R$^1$ = OTIPS, R$^2$ = OH
58, R = H, R$^1$ = OTIPS, R$^2$ = OH
59, R = SO$_2$Ph, R$^1$ = H, R$^2$ = H
C. Monomeric ETP derivatives from N-methyl-L-alanine and L-tryptophan cyclo-dipeptide
epidisulfide bridge
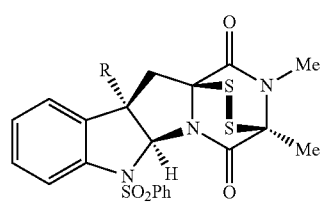
60, R = indol-3'-yl
61, R = n-Pr -continued

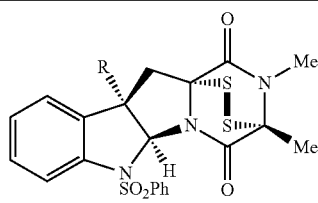

62, R = indol-3'-yl
63, R = n-Pr sulfur containing bridge

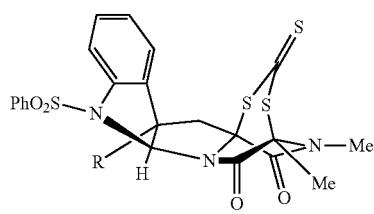

64, R = indol-3'-yl
65, R = n-Pr

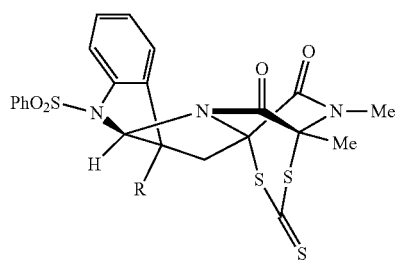

66, R = indol-3'-yl
67, R = n-Pr

Compounds that were differentially substituted at the C3-quaternary stereogenic center were constructed and then elaborated with different types of sulfur motifs. For example, compounds 3-7, 10, and 14-67 were concisely and efficiently accessed as described in Schemes E1-1-E1-3 or according to experimental procedures previously reported by our group.

endo-Tetracyclic bromide 54, prepared from sarcosine 1-tryptophan cyclo-dipeptide (N. Boyer and M. Movassaghi, Chem. Sci., 2012, 3, 1798), was used to access epidithiodiketopiperazines bearing different C3-substituents (Scheme E1-I). Electrophilic activation using silver(I) tetrafluoroborate in nitroethane and trapping of the transient tertiary benzylic carbocation with the desired nucleophile (i.e., fluoride, N-TIPS-pyrrole (E. M. Beck, N. P. Grimster, R. Hatley and M. J. Gaunt, J. Am. Chem. Soc., 2006, 128, 2528), anisole, 5-Br—N-TIPS-indole) afforded the C3-substituted endo-tetracycles 59 and 68-70 in high yields and excellent levels of regio- and stereoselection (N. Boyer and M. Movassaghi, Chem. Sci., 2012, 3, 1798). Dihydroxylation of 59 and 68-70 at the C11-methine and C15-methylene positions was achieved with tetra-n-butylammonium permanganate (n-Bu$_4$NMnO$_4$, 4 equiv) in dichloromethane to provide the corresponding diols in moderate to good yields as single diastereomers. The direct double cis-thiolation was accomplished in a single step and in good to high yields (47-80%) by exposure of the bis-hemiaminals to trifluoroacetic acid (TFA) in hydrogen sulfide-saturated dichloromethane solution followed by mild aerobic oxidation to access the bridgehead disulfides as β-epimers 26, 30-33 and α-epimers 34-35. The relative stereochemistry of the α-epimers 26, 30-33 of the epidisulfide bridges has been confirmed by key NOESY cross-peaks on the corresponding bis(thiomethylether). In some embodiments, the diastereoselectivities are consistent with the steric bias imposed by the C3-substituents {β:α ratio=2:1 (C3-F); 4:1 (C3-Br); >5:1 (C3-pyrrol-3'-yl); >7:1 (C3-indol-3'-yl); >10:1 (C3-p-MeOPh)}.

Scheme E1-1. Sarcosine-derived monomeric epidithiodiketopiperazines: modulation of the C3-substituent.

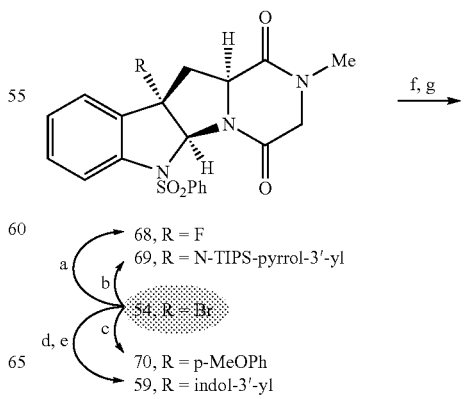

-continued

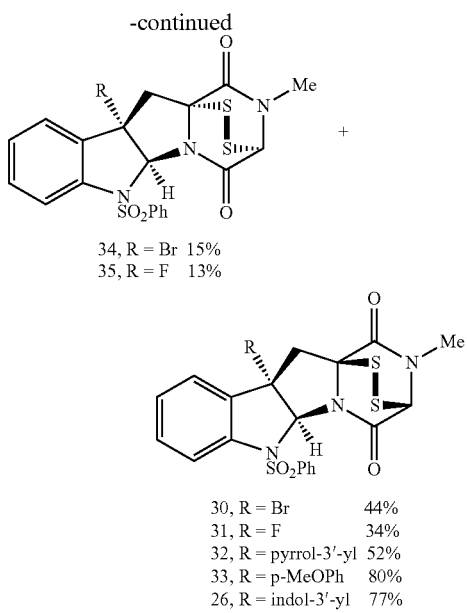

34, R = Br  15%
35, R = F   13%

30, R = Br          44%
31, R = F           34%
32, R = pyrrol-3'-yl  52%
33, R = p-MeOPh     80%
26, R = indol-3'-yl  77%

Reagents and conditions: (a) AgBF$_4$, DTBMP, EtNO$_2$, 23° C., 1 h, 90%; (b) N-TIPS-pyrrole, AgBF$_4$, DTBMP, EtNO$_2$, 0° C., 1 h, 72%; (c) Anisole, AgBF$_4$, DTBMP, EtNO$_2$, 0° C., 1 h, 99%; (d) 5-Br—N-TIPS-indole, AgBF$_4$, DTBMP, EtNO$_2$, 0° C., 1 h; 83%; (e) H$_2$, Pd/C, NEt$_3$, MeOH-EtOAc (2:3 v/v), 23° C., 8 h; Et$_3$N.3HF, 23° C., 13 h, quant.; (f) n-Bu$_4$NMnO$_4$, CH$_2$Cl$_2$, 23° C., 2 h, 25-52%; (g) H$_2$S, TFA-EtNO$_2$ (2:3 v/v), 0 to 23° C., 4 h; O$_2$, EtOAc, 23° C., 47-80%; TIPS=triisopropylsilyl; DTBMP=2,6-di-tert-butyl-4-methylpyridine; TFA=trifluoroacetic acid.

As exemplified in Scheme E1-2, a set of compounds with a modified sulfur motif within the DKP core were prepared. Chemo- and stereoselective thiolation of diol 56 by treatment with TFA in hydrogen sulfide-saturated dichloromethane solution at 0° C. generated the corresponding thiohemiaminal 48 in 90% yield and in a highly diastereoselective fashion (>10:1 dr). Masking of both alcohol and thiol groups as isobutyrates and photoinduced reductive removal of the benzenesulfonyl group gave 51. The desired degree of sulfidation was eventually accomplished by hydrazinolysis, chemoselective S-sulfenylation with chloro(triphenylmethane) sulfane or disulfane followed by hafnium triflate-mediated cyclization to afford (+)-12-deoxybionectin A (10) and its epitrithiodiketopiperazine congener 29 in 65 and 47% yield (3-steps), respectively. A similar two-step approach was employed to access benzenesulfonyl-protected epitri- and epitetrathiodiketopiperazines 27 and 28 in 42% and 44% yield, respectively. Ultimately, reduction of the bridgehead disulfide with NaBH$_4$ followed by in situ S-methylation afforded (+)-gliocladin B (7) and bis(methylthioether) 39 in high yields.

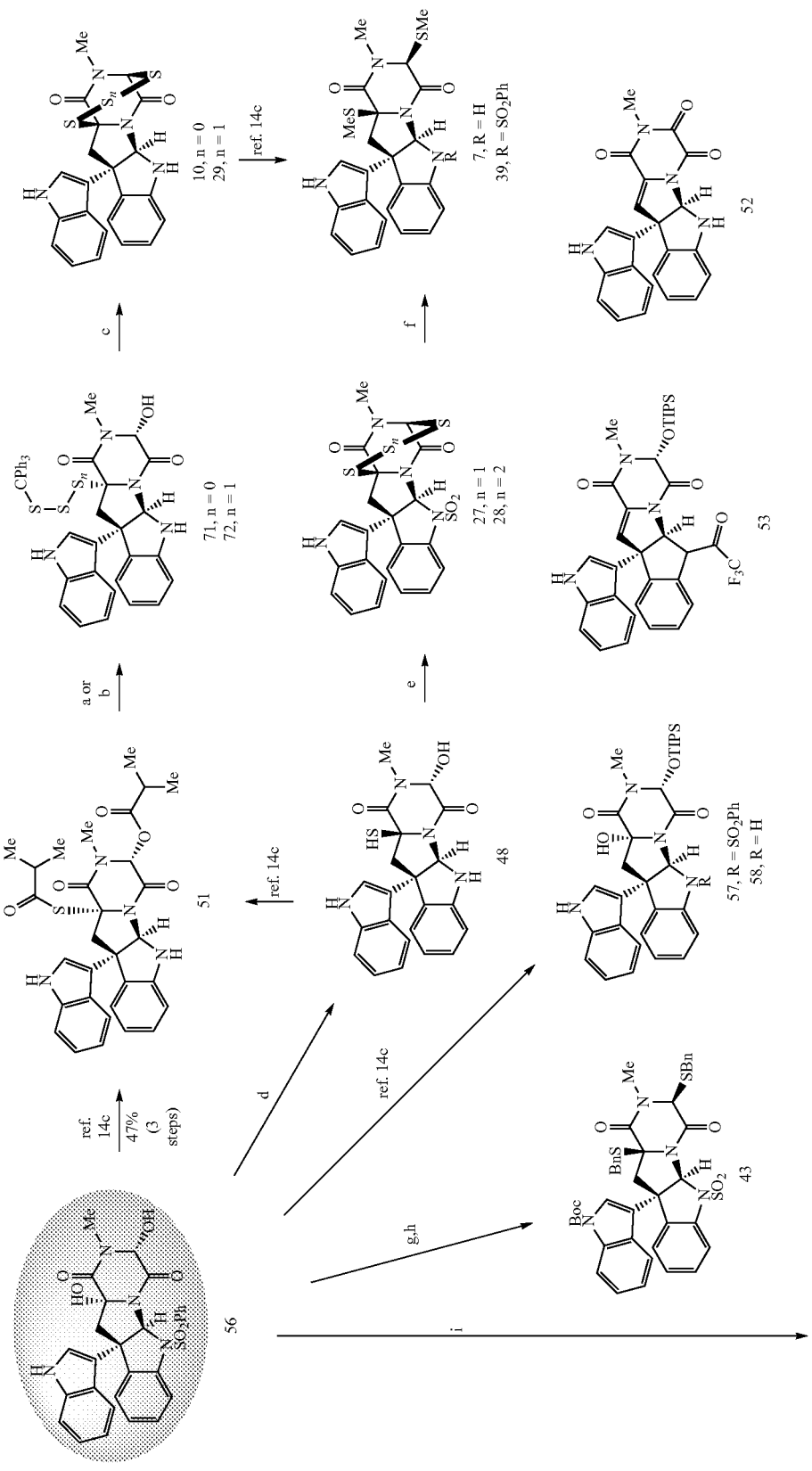
Scheme E1-2. Sarcosine-derived monomeric polythiodiketopiperazines: modulation of the sulfur bridge.

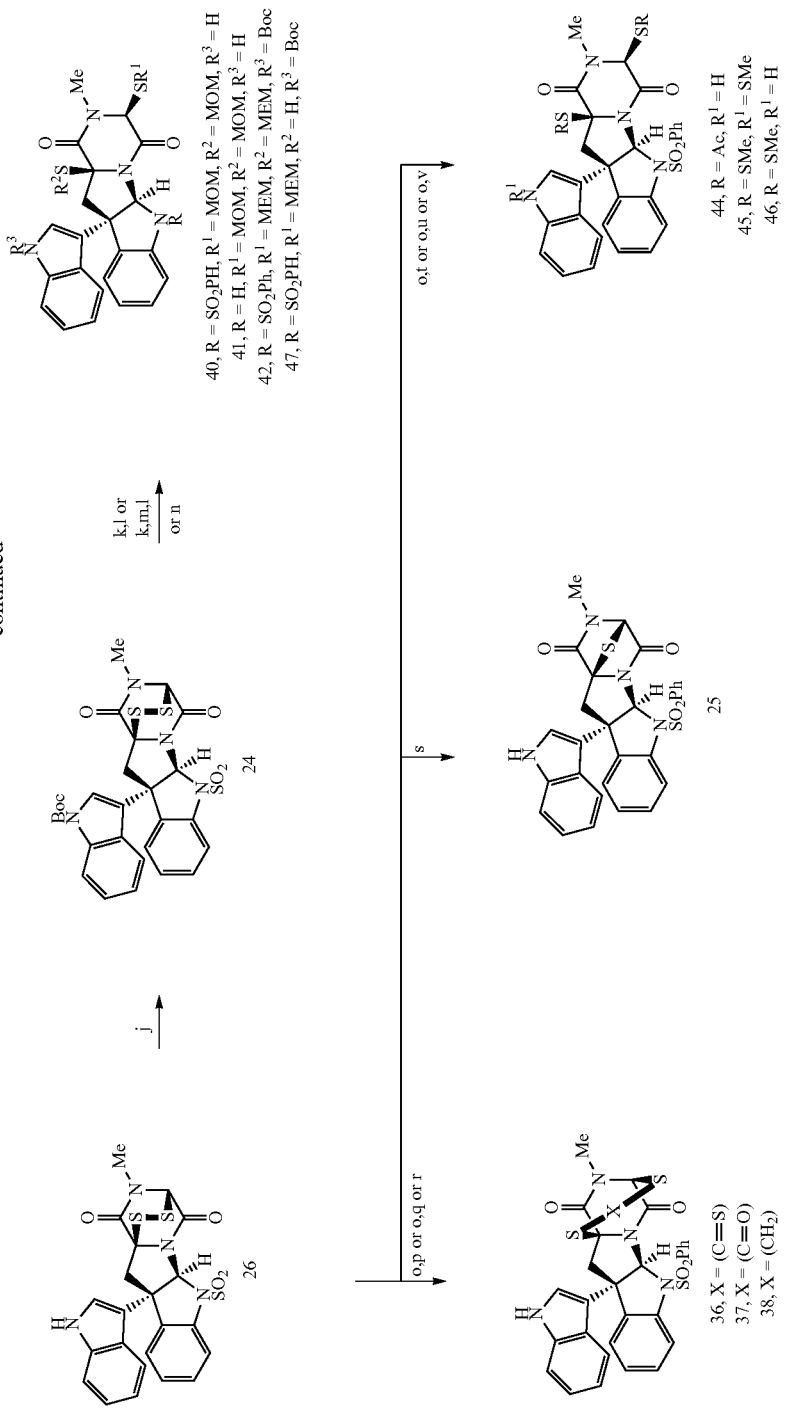

Reagents and conditions: (a) N$_2$H$_4$, THF, 0° C. 1 h; Ph$_3$CSCl, NEt$_3$, THF, 0° C., 90 min, 81% (2-steps); (b) N$_2$H4, THF, 0° C., 1 h; Ph$_3$CSSCl, Hünig's base, THF, 0° C., 25 min; (c) Hf(OTf)$_4$, MeCN, 23° C., 15 min, n=0: 80%, n=1: 47% (3-steps); (d) H$_2$S, TFA-CH$_2$Cl$_2$ (1:9 v/v), 0 to 23° C., 2 h, 90%, >10:1 dr; (e) Ph$_3$CSS$_m$Cl, Hünig's base, THF, 0° C., 25 min; Hf(OTf)$_4$, MeCN, 23° C., 50 min, m=s: 42% (2-steps), m=2: 44% (2-steps); (f) MeI, NaBH$_4$, Pyr, THF, MeOH, 23° C., 45 min, 80%; (g) BnSH, TFA-EtNO$_2$ (2:3 v/v), 23° C., 3 h, 80%, 17:3 dr, (h) Boc$_2$O, DMAP, MeCN, 23° C., 3 h, 69%; (i) H$_2$S, TFA-EtNO$_2$ (3:4 v/v), 0 to 23° C., 2 h; O$_2$, EtOAc, 23° C., 77%, >7:1 dr, (j) Boc$_2$O, DMAP, CH$_2$Cl$_2$, 23° C., 7 h, 81%; (k) NaBH$_4$, THF, MeOH, 23° C., 2 h; MOMCl, NEt$_3$, 23° C., 5 h, 73%; (l) TFA, CH$_2$Cl$_2$, 0 to 23° C., 3 h, 81-91%; (m) hv (350 nm), 1,4-dimethoxynaphthalene, ascorbic acid, sodium ascorbate, H$_2$O-MeCN (1:4 v/v), 25° C., 2.5 h, 82%; (n) NaBH$_4$, THF, MeOH, 23° C., 80 min; MEMCl, NEt$_3$, 23° C., 12 h, 80% (42) and 19% (47); (O) NaBH$_4$, THF, MeOH, 23° C., 45 min; (p) TCDI, CH$_2$Cl$_2$, 23° C., 22 h, 34% (2-steps); (q) CDI, CH$_2$Cl$_2$, 23° C., 24 h, 8% (2-steps); (r) CH$_2$I$_2$, NaBH$_4$, Pyr, THF, MeOH, 0 to 23° C., 1 h, 46%; (s) P(OEt)$_3$, THF, 23° C., 6 h, 63%; (t) AcCl, Pyr, CH$_2$Cl$_2$, 23° C., 4 h, 63% (2-steps); (u) MeSCl, Pyr, CH$_2$Cl$_2$, 0 to 23° C., 2 h, 49% (2-steps); (v) (MeS)$_2$, THF, 23° C., 19 h, 41% (2-steps); TFA=trifluoroacetic acid; Pyr=pyridine; Boc$_2$O=di-tert-butyl dicarbonate; DMAP=4-(dimethylamino)pyridine; TCDI=1,1'-thiocarbonyldiimidazole; CDI=1,1'-carbonyldiimidazole; MOMCl=chloromethyl methyl ether, MEMCl=2-methoxyethoxymethyl chloride.

(+)-Gliocladin C (52, Y. Usami, J. Yamaguchi and A. Numata, *Heterocycles*, 2004, 63, 1123) and several C11-hydroxylated (57-58) and C11,C12-dehydrogenated (53) intermediates were prepared following the procedures previously reported for the synthesis of this atypical non-thiolated triketopiperazine (N. Boyer and M. Movassaghi, *Chem. Sci.*, 2012, 3, 1798).

Exposure of hemiaminal 56 to benzyl mercaptan and TFA in nitroethane resulted in the formation of the corresponding bis(benzylthioether) (C15β:C15α=5.7:1) in 80% yield (single diastereomer, C15β). Further derivatization of the indole nitrogen with a t-butoxycarbonyl group gave 43 in 69% yield. After masking the indole substituent of the key ETP intermediate 26, the bridgehead disulfide was reduced with NaBH$_4$ and S-methoxymethylated in a single flask. Subsequent t-butoxycarbonyl removal with TFA in dichloromethane afforded bis(thioether) 40 in 66% yield over two steps. A similar strategy including the photoinduced reductive removal of the N1-benzenesulfonyl group provided 41 in 55% over three steps. Reduction of the sulfur bridge of ETP 24 with NaBH$_4$ in a mixture of THF and methanol and in situ trapping of the resulting thiolates with 2-methoxyethoxymethyl chloride (MEMCl) led to thioether 47 and bis(thioether) 42 in 19% and 80% yield, respectively.

Further modifications to the sulfur bridge were accomplished by treatment of the corresponding dithiol (obtained from NaBH$_4$ reduction of ETP 26) with 1,1'-thiocarbonyldiimidazole (TCDI) or 1,1'-carbonyldiimidazole (CDI) to afford di- and trithiocarbonates 36 and 37, respectively. Similarly, thioacetal 38 was accessed directly by double alkylation using diiodomethane. Desulfurization of epidithiodiketopiperazine 26 was realized by treatment with triethylphosphite in THF to give epimonosulfide 25 in 63% yield (F. Cherblanc, Y.-P. Lo, E. De Gussem, L. Alcazar-Fuoli, E. Bignell, Y. He, N. Chapman-Rothe, P. Bultinck, W. A. Herrebout, R. Brown, H. S. Rzepa and M. J. Fuchter, *Chem.-Eur. J.*, 2011, 17, 11868). The sulfur atoms were also capped with the S-acetyl and S-methylsulfane functional groupings to afford compounds that are potentially more labile under intracellular conditions. After reduction of the sulfur bridge of epidisulfide 26, its treatment with an excess of acetyl chloride, methanesulfenyl chloride, or dimethyldisulfide afforded compounds 44, 45 and 46, respectively, in good yields.

Compounds with substituent at the C15 position were also prepared, for example, compounds derived from N-methyl-1-alanine 1-tryptophan cyclo-dipeptide. As exemplified in Scheme E1-3, synthesis of these derivatives commenced with endo-tetracyclic bromide 73. Tertiary benzylic bromide 73 also proved to be an excellent substrate for the desired regio- and stereoselective Friedel-Crafts-type coupling with 5-bromo-1-triisopropylsilylindole (67% over 2 steps) to afford C3-indolyl tetracycle 74. Allylation of the C3-tertiary benzylic halide using allyltributylstannane under radical conditions (K. M. Depew, S. P. Marsden, D. Zatorska, A. Zatorski, W. G. Bornmann and S. J. Danishefsky, *J. Am. Chem. Soc.*, 1999, 121, 11953) followed by hydrogenation of the terminal olefin afforded C3-n-propyl tetracycle 75. These two C3-substituted tetracyclic monomers were subsequently subject to hydroxylation conditions using bis(pyridine) silver(I) permanganate (Pyr$_2$AgMnO$_4$) in pyridine. Treatment of the resultant diols with potassium trithiocarbonate and TFA in dichloromethane resulted in rapid formation of the desired monomeric dithiepanethiones 64 and 66 in 63% yield as a 5:1 isomeric mixture, as well as 65 and 67 in 52% and 17% yield, respectively. Exposure of these compounds to ethanolamine in acetone followed by oxidative workup using potassium triiodide yielded the corresponding epidithiodiketopiperazine analogs 60-63.

Scheme E1-3. Exemplary synthesis: alanine-derived monomeric polythiodiketopiperazines - modulation of the C3-substituent.

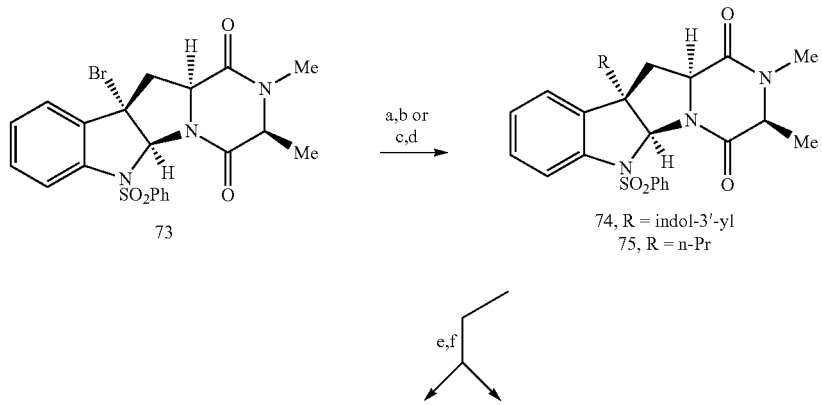

74, R = indol-3'-yl
75, R = n-Pr

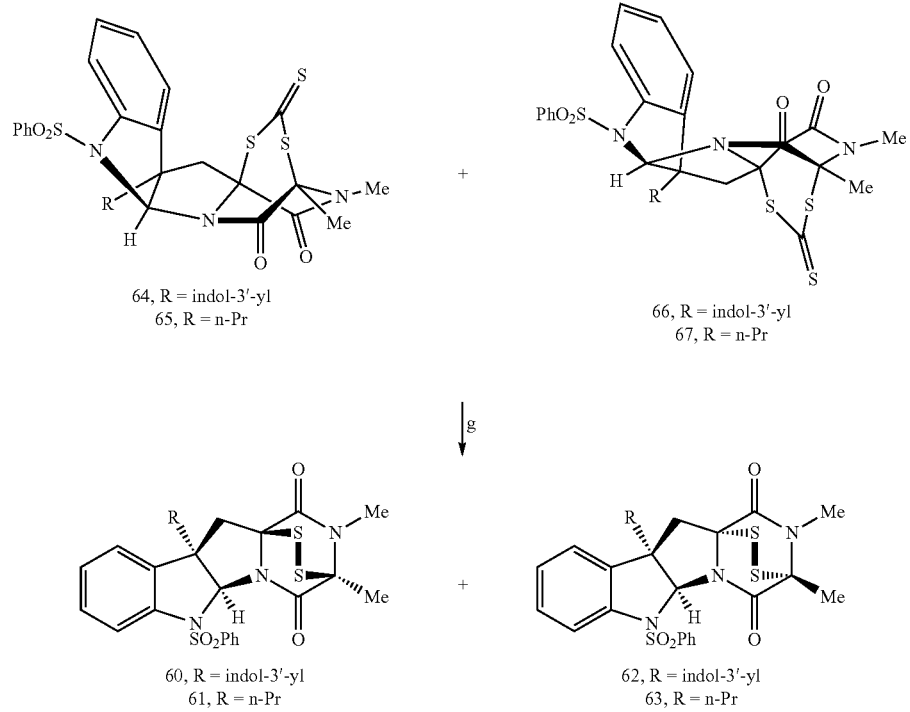

64, R = indol-3'-yl
65, R = n-Pr

66, R = indol-3'-yl
67, R = n-Pr

↓g

60, R = indol-3'-yl
61, R = n-Pr

62, R = indol-3'-yl
63, R = n-Pr

Reagents and conditions: (a) 5-Br—N-TIPS-indole, AgBF$_4$, DTBMP, EtNO$_2$, 0° C., 1 h, 67%; (b) H$_2$, Pd/C, NEt$_3$, MeOH-EtOAc (2:3 v/v), 23° C., 8 h; Et$_3$N.3HF, 23° C., 13 h, quant.; (c) AllylSnBu$_3$, AIBN, PhH, 80° C., 5 h, 61%; (d) H$_2$, Pd/C (5 mol %), CH$_2$Cl$_2$, 2 h, 100%; (e) Pyr$_2$AgMnO$_4$, Pyr, 23° C., 4 h, 37% (R=indol-3'-yl), 68% (R=n-Pr); (f) K$_2$CS$_3$, TFA-CH$_2$Cl$_2$ (1:2 v/v), 23° C., 2.5 h, 63%, 5:1 dr (64:66), 52% (65), 15% (67); (g) ethanolamine, acetone, 23° C., 45 min; KI$_3$, Pyr, CH$_2$Cl$_2$, 23° C., 48%, 5:1 dr (60:62), 70% (61), 78% (63); TIPS=triisopropyl-silyl; DTBMP=2,6-di-tert-butyl-4-methyl-pyridine; AIBN=α,α'-azoisobutyronitrile; Pyr$_2$AgMnO$_4$=bis(pyridine) silver(I) permanganate; Pyr=pyridine; TFA=trifluoroacetic acid.

Synthesis of exemplary dimeric DKP and ETP derivatives (Schemes S1 and S2) were described below. The diacetate forms of these epidi- and epitrithiodiketopiperazines (15-16) were also synthesized. A variety of derivatives (14, 18-19, 21-23) possessing the sulfonyl group were also prepared.

Certain synthesized compounds were screened for their ability to induce death in two human cancer cell lines: U-937 (leukemic monocyte lymphoma) and HeLa (cervical cancer). Compounds that demonstrated anticancer activity at 1 μM or below were retested in triplicate at a range of compound concentrations to generate logistical dose-response curves from which IC$_{50}$ values were derived. The results are presented in Table E1-1.

TABLE E1-1

Assessment of exemplary ETPs and DKPs for anticancer activity against U-937 (hystiocytic lymphoma) and HeLa (cervical carcinoma) human cancer cell lines after a 72-hour exposure.[a]

| Cmpd | U-937 | HeLa |
|---|---|---|
| Dimers with epipolysulfide bridges | | |
| 3 | 15.5 ± 2.9 | 7.2 ± 3.0 |
| 4 | 0.81 ± 0.15 | 6.9 ± 2.0 |
| 5 | 0.75 ± 0.13 | 6.3 ± 0.6 |
| 6 | 1.3 ± 0.5 | 5.6 ± 1.0 |
| 14 | 0.18 ± 0.06 | 0.09 ± 0.06 |
| 15 | 4.7 ± 1.3 | 14.1 ± 7.4 |
| 16 | 9.7 ± 2.1 | 70 ± 20 |
| 17 | 8.9 ± 2.3 | 28.1 ± 2.2 |
| 18 | 2.9 ± 2.1 | 1.1 ± 0.8 |
| Sulfur-containing dimers | | |
| 19 | >10,000 | >10,000 |
| 20 | >10,000 | >10,000 |
| Dimers without sulfur | | |
| 21 | >1,000 | >10,000 |
| 22 | >1,000 | >10,000 |
| 23 | >1,000 | >10,000 |
| Sarcosine-derived monomers with sulfur-containing bridge | | |
| 10 | 17.4 ± 1.1 | 117 ± 26 |
| 24 | 5.9 ± 1.4 | 75 ± 10 |
| 25 | 710 ± 134 | 1476 ± 182 |
| 26 | 2.8 ± 0.3 | 41.7 ± 5.7 |
| 27 | 36.6 ± 2.4 | 27.5 ± 9.2 |
| 28 | 8.3 ± 3.3 | 137 ± 86 |
| 29 | 24.5 ± 7.4 | 123 ± 29 |
| 30 | 5.0 ± 1.3 | 44.9 ± 1.3 |
| 31 | 20.7 ± 6.4 | 1530 ± 440 |
| 32 | 14.8 ± 3.1 | 26.8 ± 4.8 |
| 33 | 5.0 ± 2.1 | 22.2 ± 10.9 |
| 34 | 59 ± 23 | 550 ± 33 |
| 35 | 21.3 ± 8.7 | 56 ± 21 |
| 36 | 3.8 ± 0.9 | 33 ± 13 |
| 37 | 5.5 ± 1.3 | 37 ± 15 |
| 38 | 82 ± 28 | 465 ± 37 |

TABLE E1-1-continued

Assessment of exemplary ETPs and DKPs for anticancer activity
against U-937 (hystiocytic lymphoma) and HeLa (cervical carcinoma)
human cancer cell lines after a 72-hour exposure.[a]

| Cmpd | U-937 | HeLa |
|---|---|---|
| Sarcosine-derived monomers with non-bridging sulfur | | |
| 7 | >10,000 | >10,000 |
| 39 | >10,000 | >10,000 |
| 40 | >1,000 | >1,000 |
| 41 | >10,000 | >10,000 |
| 42 | >10,000 | >10,000 |
| 43 | >10,000 | >10,000 |
| 44 | 4.1 ± 0.5 | 17.3 ± 4.5 |
| 45 | 14.5 ± 9.1 | 13.7 ± 2.3 |
| 46 | 20.4 ± 9.0 | 36.6 ± 3.9 |
| Sarcosine-derived monomers without sulfur | | |
| 47 | >10,000 | >10,000 |
| 48 | >10,000 | >10,000 |
| 49 | >10,000 | >10,000 |
| 50 | >1,000 | >1,000 |
| 51 | >10,000 | >1,000 |
| 52 | >10,000 | >10,000 |
| 53 | >10,000 | >10,000 |
| 54 | >10,000 | >10,000 |
| 55 | >10,000 | >10,000 |
| 56 | >10,000 | >10,000 |
| 57 | >10,000 | >10,000 |
| 58 | >10,000 | >10,000 |
| 59 | >10,000 | >10,000 |
| N-Methylalanine-derived monomers with sulfur-containing bridge | | |
| 60 | 56 ± 23 | 67 ± 11 |
| 61 | >1,000 | >1,000 |
| 62 | >1,000 | >1,000 |
| 63 | >1,000 | >1,000 |
| 64 | 24 ± 12 | 25.3 ± 2.0 |
| 65 | >1,000 | >1,000 |
| 66 | >1,000 | >1,000 |
| 67 | >1,000 | >1,000 |

| ≤1 nM | <x≤ 1 10 nM | 10<x≤ 50 nM | 50<x≤ 150 nM | 150< x ≤ 1,000 | >1,000 nM |

[a]72-hour $IC_{50}$ values (in nM) as determined by MTS (U-937) and SRB (HeLa). Error is standard deviation of the mean n ≥ 3.; Cmpd = compound; DKP = diketopiperazine; ETP = epipolythiodiketopiperazine; $IC_{50}$ = half maximal inhibitory concentration; MTS = 3-(4,5-dimethylthiazol-2-yl)-5-(3-carboxymethoxyphenyl)-2-(4-sulfophenyl)-2H-tetrazolium; SRB = sulforhodamine B.

Among tested compounds, in both U-937 and HeLa cells, the homodimers are the most potent compounds {$IC_{50}$ (U-937)≥0.18 nM; $IC_{50}$ (HeLa)≥0.09 nM}, with the N1,N1'-benzenesulfonylated analog (14) of (+)-12,12'-dideoxyverticillin A (3) showing the best activity {$IC_{50}$ (U-937): 0.18 nM; $IC_{50}$ (HeLa): 0.09 nM}. Monomeric ETP derivatives also show good activity in both HeLa ($IC_{50}$≥5.9 nM) and U-937 ($IC_{50}$≥2.8 nM) human cancer cell lines. Within the N1-benzenesulfonyl monomeric class, various aromatic substituents (indol-3'-yl 26, N-Boc-indol-3'-yl 24, pyrrol-3'-yl 32, p-MeO-phenyl 33) are well tolerated at the C3-position and their $IC_{50}$'s are of the same order of magnitude {$IC_{50}$ (U-937): 2.8-14.8 nM; $IC_{50}$ (HeLa): 22-75 nM}. Halide substitution at C3 (bromide 30, fluorides 31 and 35) results in intermediately good activity. While not wishing to be limited by theory, Applicant notes that in some embodiments, the steric environment of the C3 position may be crucial for biological activity: n-alkyl groups at that position (n-propyl analogs 61 and 65) lead to substantially lower potencies than more sterically hindered (hetero)aryl and halide substituents or the C3' quaternary carbon of a second monomeric subunit, and the dimers in some embodiments have better activity than (hetero)arylated monomers. In some embodiments, dimers containing two sulfur bridge groups are one order of magnitude more potent than monomeric C3-(3'-indolyl) analogs and 2 to 3 orders of magnitude more potent than heterodimers bearing a single sulfur bridge. This non-linear increase of biological activity between mono- and dimeric ETP compounds was also observed in other families. While not wishing to be limited by theory, Applicant notes that the observation may suggest a synergistic effect; pharmacokinetic properties could also play a role.

Comparing homodimers (+)-12,12'-dideoxyverticillin A (3), (+)-chaetocin A (4), (+)-chaetocin C (5), and (+)-12,12'-dideoxychetracin A (6) head-to-head reveals that, in some embodiments, the chaetocin-type ETP derivatives are more potent than their non-C15-hydroxylated counterparts {$IC_{50}$ (U-937): 0.75-1.3 nM vs. 15.5 nM; $IC_{50}$ (HeLa): 5.6-6.9 nM vs. 7.2 nM}. In some embodiments, acetylation of the 17,17'-hydroxyl groups (15-16) also results in a reduction of potency (5.8- to 12.9-fold for U-937; 2.0- to 11.1-fold for HeLa). Methyl substitution at C15 in monomeric alkaloids (Trp-Ala cyclo-dipeptides 60 vs. 26 and 64 vs. 36) affects the potency of the compounds moderately in the test. Without the intention to be limited by theory, Applicant notes that the difference in potency between the different types of substituents at C15 may be generally minimal, although it could be sensitive to variations of the steric environment. In some embodiments, the present invention provides a method of optimizing an ETP compound or a derivative of an analog thereof, comprising modifying substituents at the C15 position. In some embodiments, a provided method is used to optimize the pharmacokinetic parameters during drug development. In some embodiments, a compound of formula I-a, I-b, I-c, or I-d is connected to L through C15 or a substituent on C15.

In some embodiments, the present invention discovered that substitution at N1 and N1' with electron-withdrawing groups, such as benzenesulfonyl (14) or trifluoroacetyl (17) groups, enhanced the anticancer activity of the alkaloids. For example, sulfonyl group (14) dramatically increased the potency {2 orders of magnitude more potent than the corresponding secondary aniline (+)-12,12'-dideoxyverticillin A (3)}. The trifluoroacetamide at N1 and N1' (17 vs. 16) also enhanced the anticancer activity. For the monomeric ETP-containing analogs, the N1-benzenesulfonyl substitution also amplifies the anticancer effect in U-937 cell line (epidisulfide: 26 vs. 10; epitrisulfide: 27 vs. 29). Without the intention to be limited by theory, Applicant notes that the N1 group could confer significantly higher chemical stability, and may also affect the pharmacodynamic properties of these ETP compounds.

In some embodiments, the present invention demonstrated that sulfuration at only the tryptophan $C_\alpha$-position is not sufficient for potent activity {bis(trisulfanes) (19 and 20), C11-thioesters (50-51), C11-thioether (49), and C11-thiols (47-48)}. In some embodiments, a provided method for optimizing an ETP compound, or derivatives or analogs, thereof comprises maintaining or installing sulfurization at both $C_\alpha$-position of the diketopiperazine ring (e.g., C11 and C15). In some embodiments, both amino acid $C_\alpha$ positions have sulfuration by separate sulfur atoms.

In some embodiments, sulfur derivatives possessing nonlabile alkyl groups {S-methylthioethers (7 and 39), S-(methoxymethyl)thioethers (40-41), S-(2-ethoxyethoxymethyl) thioether (42 and 47), S-benzylthioether (43)} did not display any anticancer activity ($IC_{50}$>10 μM). Thioacetal 38 were active. In some embodiments, the degree of sulfuration of the polysulfide bridge {dimers: (+)-chaetocin A (4) vs. (+)-chaetocin C (5) vs. (+)-12,12'-dideoxychetracin A (6) or 15 vs. 16; monomers: 10 vs. 29, 26 vs. 27 vs. 28} has no substantial impact on cell death induction; in some embodiments, the $IC_{50}$ values are within the margin of error of each other.

In addition to ETP-containing compounds, several monomeric or dimeric derivatives provided by the present invention possessing modifications directly on the sulfur bridge are competent anticancer agents. Exemplary derivative compounds include thioacetate (44), dithiocarbonate (37), trithiocarbonates (18, 36, 64), and alkyl disulfides (45-46). Without the intention to be limited by theory, Applicant notes that certain derivatives could be readily converted to the thiols; for example, the methyl disulfides would readily be converted to the thiols through reduction or nucleophilic displacement. While not wishing to be limited by theory, Applicant notes that the data could suggest a mode of action that involves a common intermediate; in the presence of a reducing cytoplasmic environment combined with the presence of enzymes-hydrolases, carboxylesterases, and lipases (W. Kroutil, A. A. Stämpfli, R. Dahinden, M. Jörg, U. Miller and J. P. Pachlatko, *Tetrahedron*, 2002, 58, 2589)—methyl disulfides, thioacetates, and thiocarbonates could play the role of prodrugs ((a) C. A. Fink, J. E. Carlson, P. A. McTaggart, Y. Qiao, R. Webb, R. Chatelain, A. Y. Jeng and A. J. Trapani, *J. Med. Chem.*, 1996, 39, 3158; (b) B. Testa and J. M. Mayer, *Hydrolysis in Drug and Prodrug Metabolism*; Wiley-VCH: Weinheim, 2003; (c) J. Rautio, H. Kumpulainen, T. Heimbach, R. Oliyai, D. Oh, T. Järvinen and J. Savolainen, *Nature Rev. Drug Disc.*, 2008, 7, 255). Without the intention to be limited by theory, Applicant notes that these compounds may be converted to their corresponding epidisulfide pharmacophores, which could be potentially actively concentrated within the cell via a glutathione-dependent uptake mechanism ((a) P. H. Bernardo, N. Brasch, C. C. L. Chai and P. Waring, *J. Biol. Chem.*, 2003, 278, 46549; and (b) C. S. Sevier and C. A. Kaiser, *Nature Rev. Mol. Cell. Biol.*, 2002, 3, 836). In some embodiments, compounds with the sulfur bridge on the α-face of the DKP (34, 62-63, 66-67) are inactive.

Certain provided compounds were tested in culture against a panel of three supplementary human cancer cell lines representing three additional tumor histologies (H460, lung carcinoma; 786-O, renal carcinoma; MCF-7, breast carcinoma). As shown in Table E1-2, the ETPs retain their potency across the cell lines. In some embodiments, a provided compound is active in all cell lines. In some embodiments, a provide compound can be used to selectively target certain cells and/or cancers. For example, compound 14 retains high levels of activity in all of the cell lines, while compound 17 is more active toward some of the cell lines. Without the intention to be limited, Applicant notes that certain cell lines could be more sensitive to provided compounds; for example, U-937 and HeLa are slightly more sensitive to the ETPs than the other three cell lines.

TABLE E1-2

Assessment of exemplary compounds for cytotoxicity in five human cell lines {U-937 (hystiocytic lymphoma), HeLa (cervical carcinoma), H460 (lung carcinoma), 786-O (renal carcinoma), and MCF-7 (breast carcinoma)} after a 72-hour exposure.[a]

| Compound | U-937 | HeLa | H460 | 786-O | MCF-7 |
|---|---|---|---|---|---|
| Dimers with epipolysulfide bridges | | | | | |
| 3 | 15.5 ± 2.9 | 7.2 ± 3.0 | 42 ± 15 | 33.5 ± 12.6 | 28.4 ± 4.5 |
| 4 | 0.81 ± 0.15 | 6.9 ± 2.0 | 53 ± 23 | 26.5 ± 7.7 | 50 ± 16 |
| 5 | 0.75 ± 0.13 | 6.3 ± 0.6 | 26.0 ± 9.3 | 14.6 ± 0.8 | 27 ± 11 |
| 6 | 1.3 ± 0.5 | 5.6 ± 1.0 | 39.3 ± 41 | 16.0 ± 2.4 | 22.5 ± 6.0 |
| 14 | 0.18 ± 0.06 | 0.09 ± 0.06 | 1.53 ± 0.85 | 1.55 ± 0.77 | 1.65 ± 0.51 |
| 15 | 4.7 ± 1.3 | 14.1 ± 7.4 | 140 ± 82 | 95 ± 23 | 77 ± 36 |
| 16 | 9.7 ± 2.1 | 70 ± 20 | 187 ± 79 | 204 ± 40 | 263 ± 98 |
| 17 | 8.9 ± 2.3 | 28.1 ± 2.2 | 179 ± 88 | 189 ± 26 | >333 |
| 18 | 2.9 ± 2.1 | 1.1 ± 0.8 | 18.5 ± 2.7 | 14.9 ± 4.4 | 10.7 ± 8.1 |
| Sarcosine-derived monomers with sulfur-containing bridge | | | | | |
| 10 | 17.4 ± 1.1 | 117 ± 26 | 215 ± 100 | 181 ± 26 | 156 ± 18 |
| 26 | 2.8 ± 0.3 | 41.7 ± 5.7 | 66 ± 19 | 62.7 ± 7.6 | 67 ± 19 |
| 27 | 36.6 ± 2.4 | 27.5 ± 9.2 | 146.4 ± 6.9 | 145 ± 10 | 151 ± 31 |
| 28 | 8.3 ± 3.3 | 137 ± 86 | 277 ± 43 | 344 ± 20 | 309 ± 31 |
| 29 | 24.5 ± 7.4 | 123 ± 29 | 348 ± 110 | 168 ± 34 | 217 ± 35 |
| 30 | 5.0 ± 1.3 | 44.9 ± 1.3 | 277 ± 44 | 162 ± 35 | 152 ± 42 |
| 31 | 20.7 ± 6.4 | 1530 ± 440 | >1000 | 368 ± 78 | 218 ± 97 |
| 32 | 14.8 ± 3.1 | 26.8 ± 4.8 | 31.8 ± 2.5 | 66 ± 23 | 61 ± 11 |
| 33 | 5.0 ± 2.1 | 22.2 ± 10.9 | 46.7 ± 5.3 | 83 ± 18 | 63 ± 16 |
| 35 | 21.3 ± 8.7 | 56 ± 21 | 123 ± 50 | 64 ± 20 | 93 ± 34 |
| 36 | 3.8 ± 0.9 | 33 ± 13 | 190 ± 61 | 133 ± 10 | 163 ± 7 |
| 37 | 5.5 ± 1.3 | 37 ± 15 | 119 ± 25 | 139 ± 3 | 145 ± 18 |
| Sarcosine-derived monomers with non-bridging sulfur | | | | | |
| 44 | 4.1 ± 0.5 | 17.3 ± 4.5 | 149 ± 59 | 151 ± 7 | 103 ± 37 |
| 45 | 14.5 ± 9.1 | 13.7 ± 2.3 | 252 ± 37 | 376 ± 120 | 373 ± 75 |
| N-Methylalanine-derived monomers with sulfur-contaning bridge | | | | | |
| 60 | 56 ± 23 | 67 ± 11 | 165 ± 65 | 907 ± 48 | 327 ± 36 |
| 64 | 24 ± 12 | 25.3 ± 2.0 | 222 ± 72 | 266 ± 85 | 210 ± 73 |
| ≤1 nM | 1 < x ≤ 10 nM | 10 < x ≤ 50 nM | 50 < x ≤ 150 nM | >150 nM | |

[a]72-hour IC$_{50}$ values (in nM) as determined by MTS (U-937) and SRB (HeLa, H460, 786-O, and MCF-7). Error is standard deviation of the mean, n ≥ 3; Cmpd = compound; IC$_{50}$ = half maximal inhibitory concentration; MTS = 3-(4,5-dimethylthiazol-2-yl-5-(3-carboxymethoxyphenyl)-2-(4-sulfophenyl)-2H-tetrazolium; SRB = sulforhodamine B.

The polysulfide dimers (+)-12,12'-dideoxyverticillin A (3), (+)-chaetocins A (4) and C (5), (+)-12,12'-dideoxychetracin A (6), 14, and bisdithiepanethione 18 are active across the board. In the case of the N1,N1'-benzenesulfonylated analog of (+)-12,12'-dideoxyverticillin A (14), the potency is dramatically increased (2 orders of magnitude more potent than with the addition of the benzenesulfonyl group.

In some embodiments, the degree of sulfuration has a larger impact in some of the adherent cell lines tested (H460, 786-O, and MCF-7), especially in the case of 26-28. In some embodiments, this set of compounds shows a 2-fold decrease in activity with each additional sulfur atom in the polysulfide bridge. Without the intention to be limited by theory, Applicant notes that lack of substitution at N1 (10 and 29, and dimers 4-6) mitigates this effect.

Bisthioacetate 44, trithiocarbonate 36 and dithiocarbonate 37 display lower activity than the corresponding epidisulfide 26, but are active toward the cell lines. These compounds show consistently lower $IC_{50}$ values than epidisulfide 10 (up to 6.7-fold more potent). In some embodiments, a provided compound displayed different activity across cell lines. C3-pyrrolyl 32 and C3-p-methoxyphenyl 33 epidisulfides displayed a consistent potency (4-fold change in activity, as compared to 6- to 40-fold changes for other derivatives) in addition to good relative potency in H460 cells.

Figure 2:
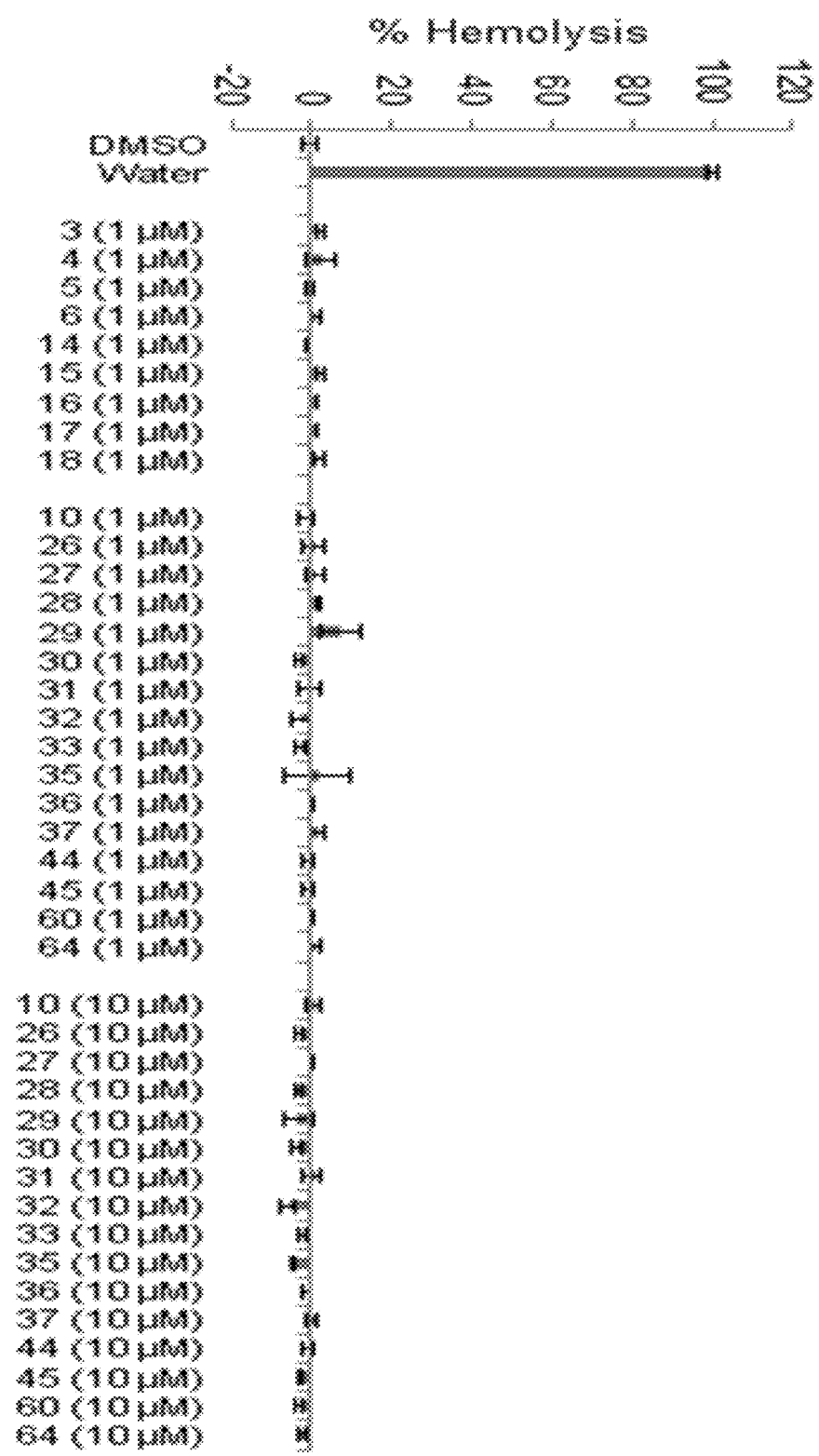
FIG. 2. Percent hemolysis following treatment with ETPs from Table E1-2. Error bars represent standard error of the mean, n≥3.
Figure 3:
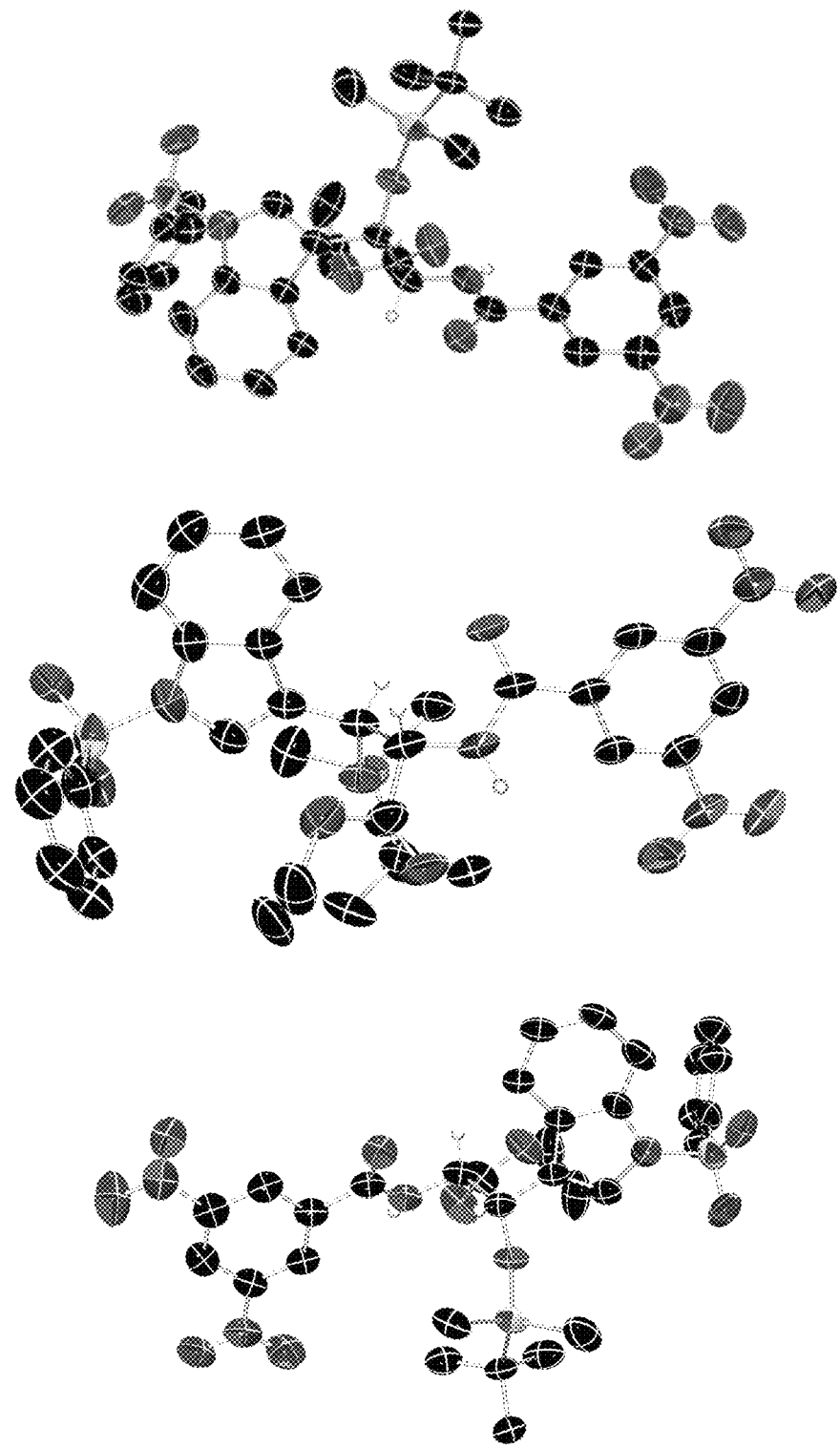
FIG. 3. Crystal Structure of 12-Hydroxytryptophan 3,5-Dinitrobenzamide (+)-E2-14 (3 views).
Figure 4:
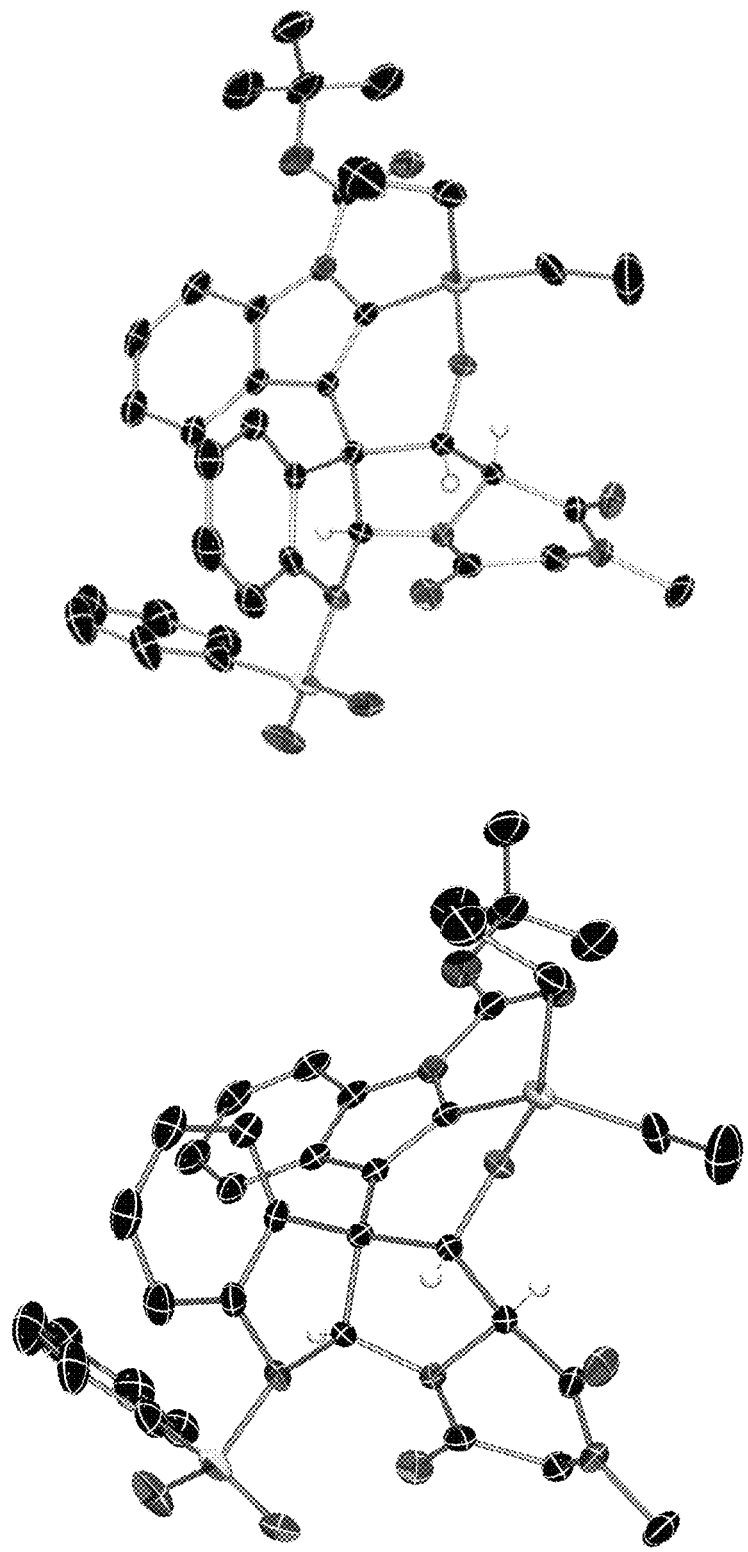
FIG. 4. Crystal Structure of Silacyclic Tetracycle E2-23 (3 views).
Figure 4:
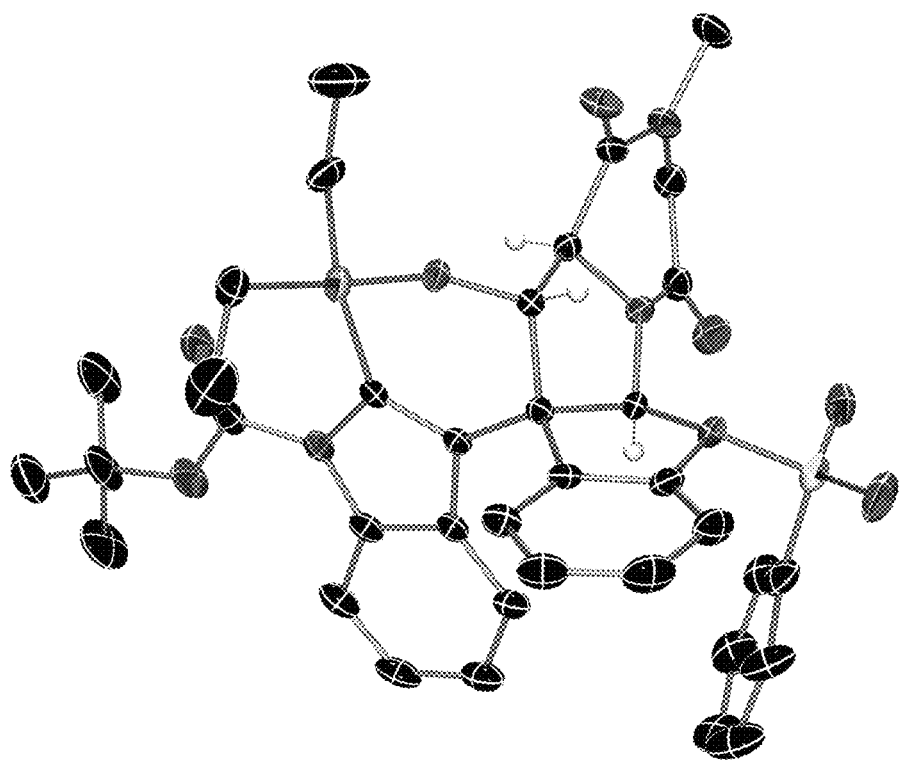
Figure 5:
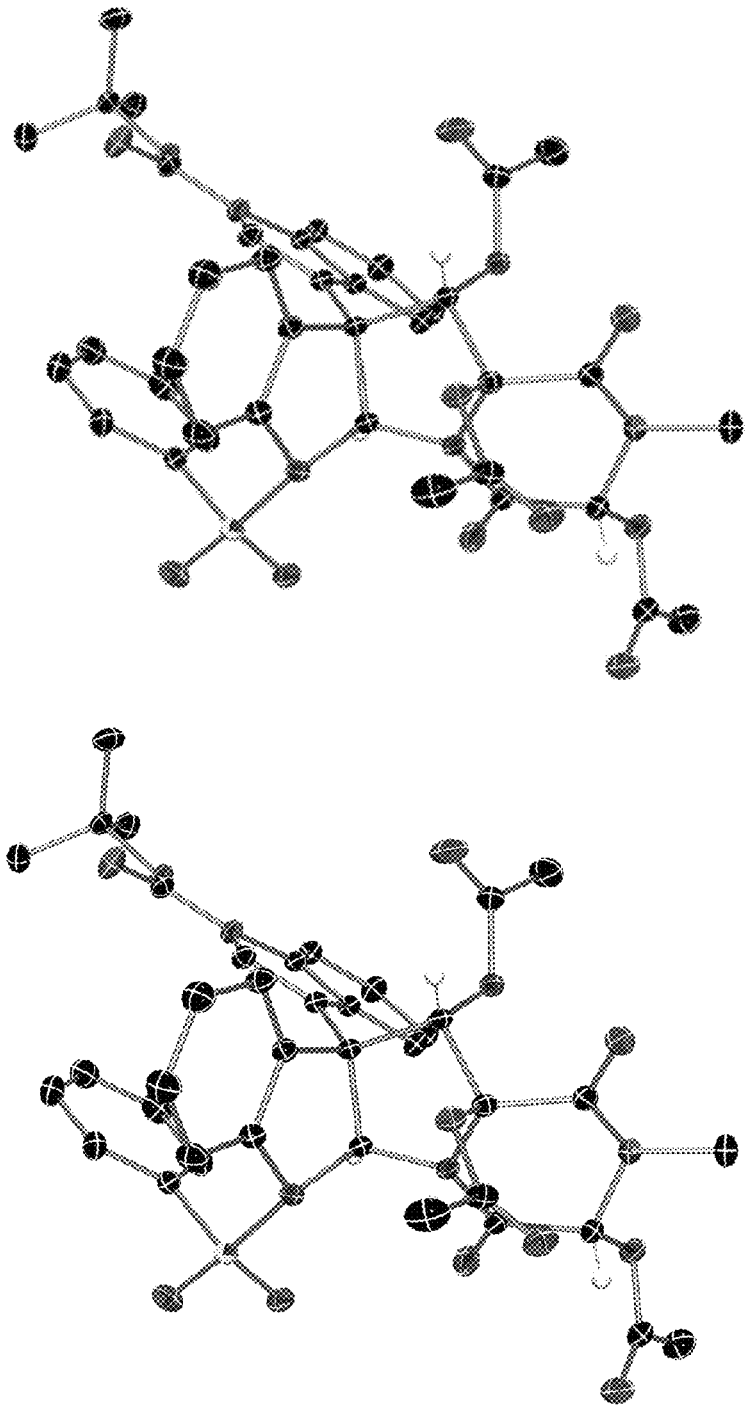
FIG. 5. Crystal Structure of Tetracyclic Triacetate E2-28 (3 views).
Figure 5:
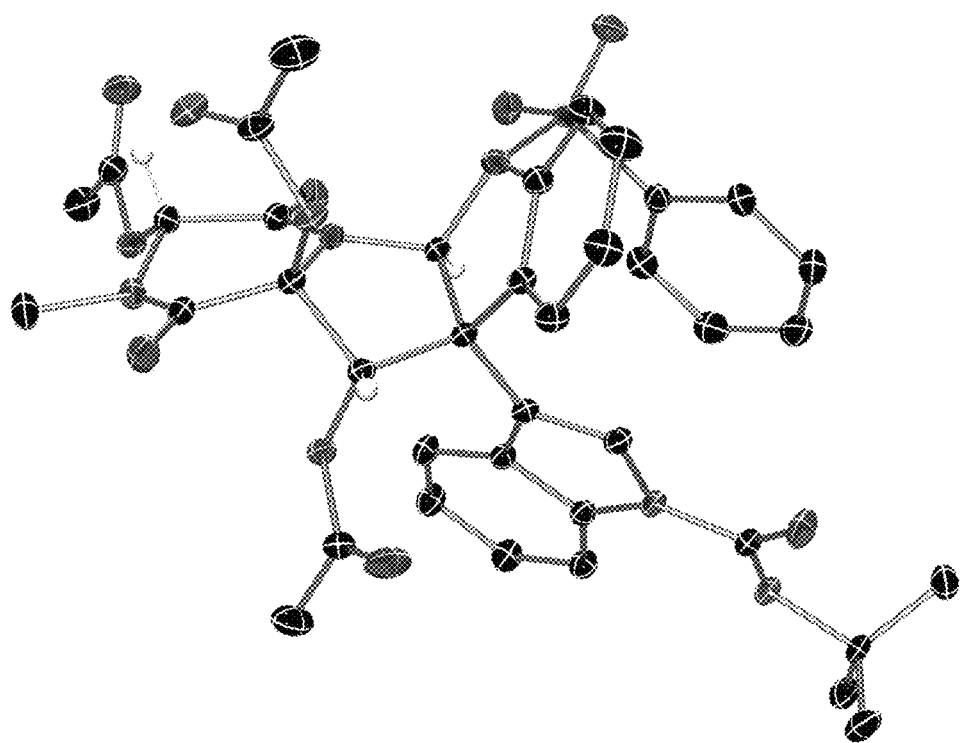
Figure 6:
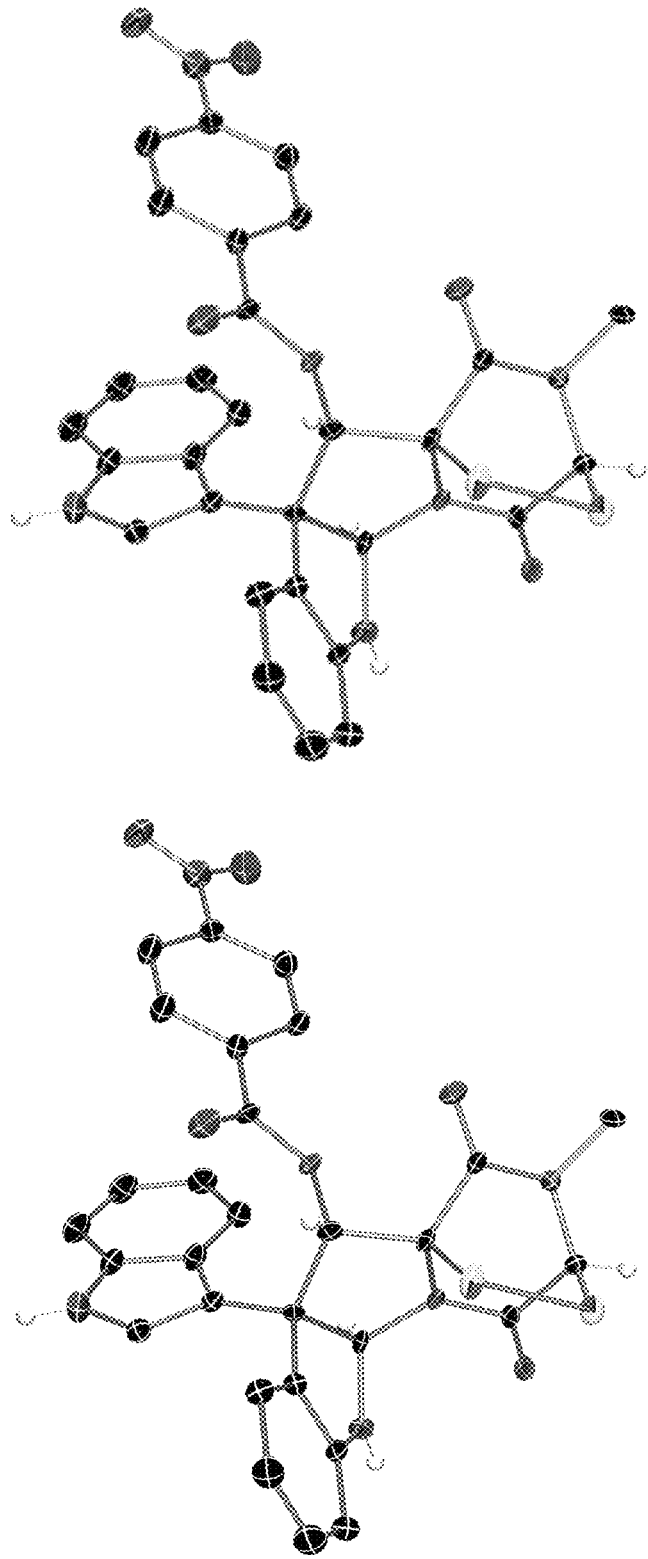
FIG. 6. Crystal Structure of (+)-Bionectin A p-Nitrobenzoate E2-38 (3 views).
Figure 6:
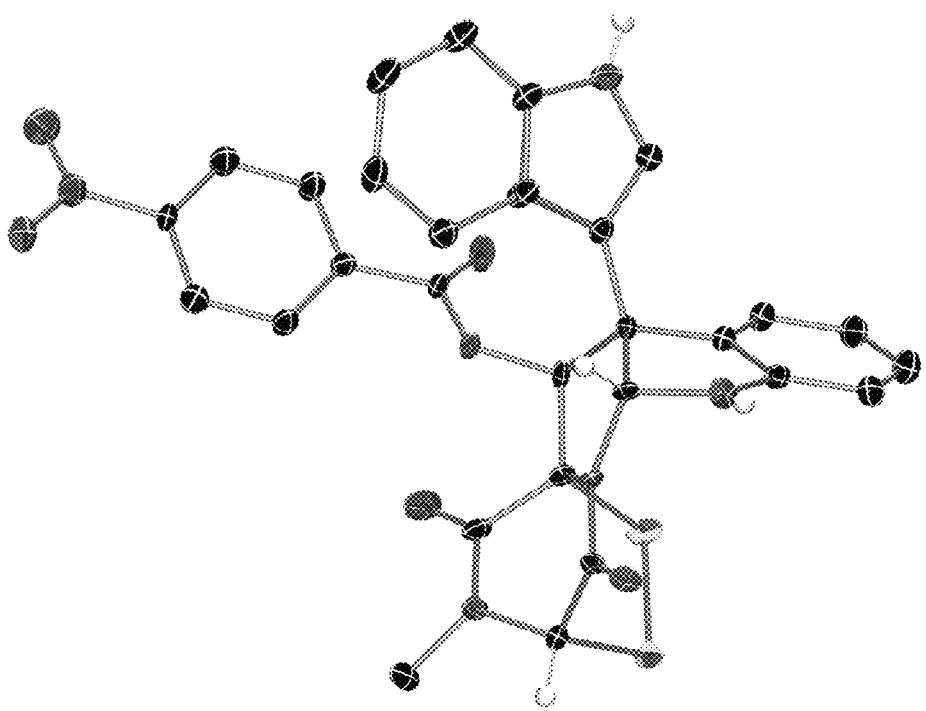

The exemplary compounds were evaluated for their ability to induce hemolysis in human erythrocytes at concentrations well above their anticancer IC50 values. As shown in FIG. 2 the compounds show no hemolytic activity. The concentrations at which hemolytic activity was assessed (1 and 10 μM) are, in some cases, over 1000-fold higher than the IC50 values for cancer cells.

Compounds 5, 14, 26 and 33 were examined for their ability to induce caspase-dependent apoptotic pathway on U-937 cells. The induction of apoptosis was first evaluated by the level of phosphatidylserine externalization (detected by FITC-conjugated Annexin V (AnnV)) that occurs prior to the disruption of cell membrane integrity (detected by propidium iodide (PI)). The progression of cells through the AnnV+/PI− quadrant (lower right, FIG. 1a) demonstrates the ability of both monomeric and dimeric ETP-containing derivatives to induce apoptosis.

Another marker of apoptosis is the cleavage patterns of various intracellular proteins. Caspase-3, one of the key apoptotic executioner caspases, is activated from its low-Page activity zymogen (procaspase-3) at an early stage of apoptosis. This activation was visualized by Western blot (FIG. 1b) by the cleavage of procaspase-3 (35 kDa) to caspase-3 (12 and 17 kDa). Caspase-3 in turn cleaves one of its cellular substrates, PARP-1. Treating cells with the four ETP derivatives, followed by Western blotting for procaspase-3/caspase-3 and PARP-1 revealed that all these compounds induce cleavage of procaspase-3 and PARP-1. Without the intention to be limited by theory, Applicant notes that data in FIG. 1 indicate that these ETP derivatives may induce caspase-dependent apoptotic cell death.

The present invention provides methods and compounds that enable structural-activity relationship study. Some of the results were presented below in Scheme E1-4.

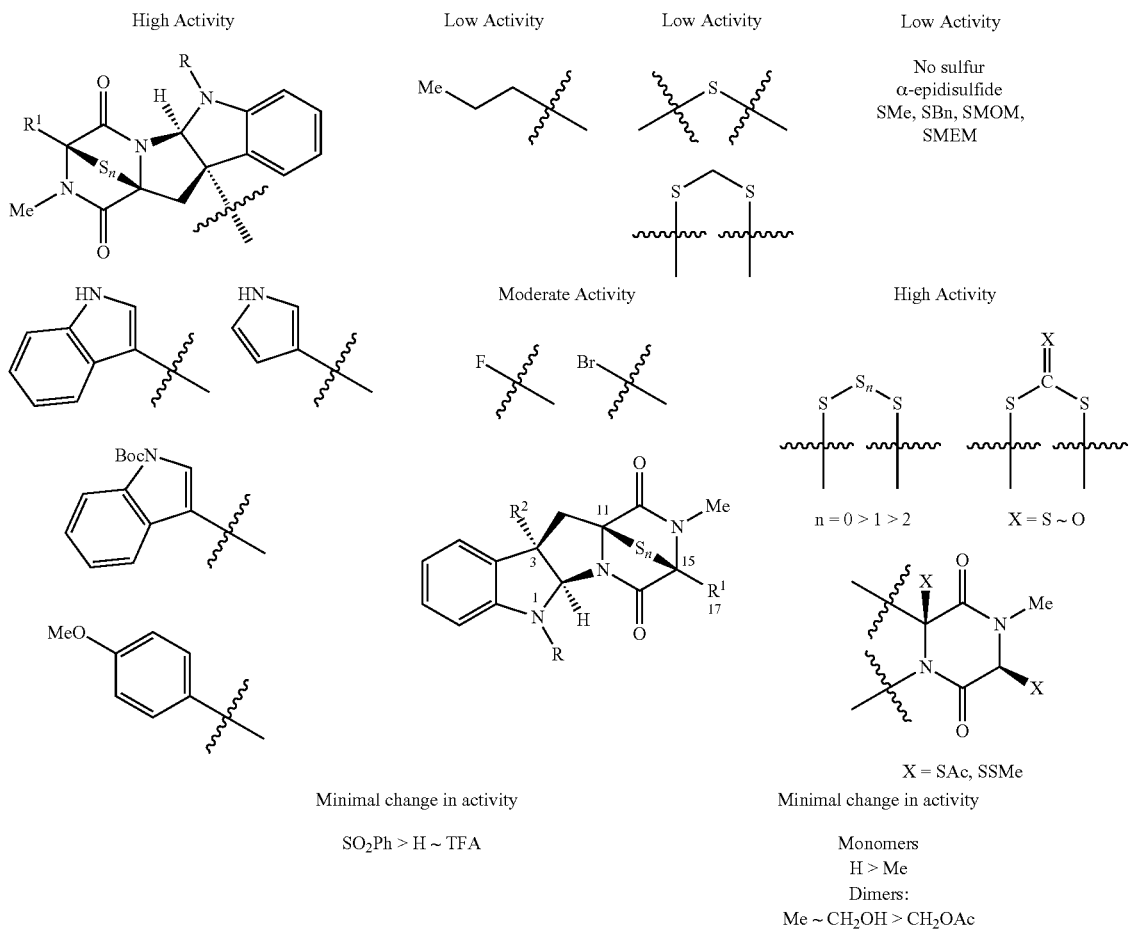

Scheme E1-4. Exemplary results of ETP structure-activity relationship.

Without the intention to be limited by theory, Applicant notes that some human cancer cell lines were most responsive to variations in functionalization at the C3 and C11/C15 centers while displaying a more modest response to modification at the N1 and $C_{17}$ positions. Again, without the intention to be limited by theory, Applicant notes that compounds may be highly potent if the diketopiperazines were sulfurated at the C11/C15 sites in a manner consistent with a species capable of being converted to an epidisulfide on the same face of the hexahydropyrrolo[1,2-a]pyrazine-1,4-dione moiety as N1 in the biological milieu. In some embodiments, the anticancer potencies of this collection of compounds correlate positively with the steric environment at the C3 position, rendering the dimeric ETP alkaloids, in certain cases, the most potent with (sub)nanomolar $IC_{50}$'s against a range of human cancer cell lines. Without the intention to be limited by theory, Applicant notes that the muted sensitivity of these cell lines to variations in N1 and $C_{17}$ substitution make these ideal sites for compound optimization. In some embodiments, despite their attenuated activity, a lower molecular-weight monomers may prove to have more optimal pharmacokinetic properties and provide further avenues for molecular modification in the optimization and development of small-molecule drugs.

General Procedures.

All reactions were performed in oven-dried or flame-dried round-bottom flasks. The flasks were fitted with rubber septa, and reactions were conducted under a positive pressure of argon. Cannulae or gas-tight syringes with stainless steel needles were used to transfer air- or moisture-sensitive liquids. Where necessary (so noted), solutions were deoxygenated by sparging with argon for a minimum of 10 min. Flash column chromatography was performed as described by Still et al. using granular silica gel (60-Å pore size, 40-63 μm, 4-6% $H_2O$ content, Zeochem) (Still, W. C.; Kahn, M.; Mitra, A. *J. Org. Chem.* 1978, 43, 2923). Analytical thin layer chromatography (TLC) was performed using glass plates pre-coated with 0.25 mm 230-400 mesh silica gel impregnated with a fluorescent indicator (254 nm). TLC plates were visualized by exposure to short wave ultraviolet light (254 nm), reversibly stained with iodine ($I_2$ absorbed on silica) vapor, and irreversibly stained by treatment with an aqueous solution of ceric ammonium molybdate (CAM) followed by heating (~1 min) on a hot plate (~250° C.). Organic solutions were concentrated at 29-30° C. on rotary evaporators capable of achieving a minimum pressure of ~2 torr. The benzenesulfonyl photodeprotection was accomplished by irradiation in a Rayonet RMR-200 photochemical reactor (Southern New England Ultraviolet Company, Branford, Conn., USA) equipped with 16 lamps (RPR-3500, 24 W, $\lambda_{max}$=350 nm, bandwidth ~20 nm).

Materials.

Commercial reagents and solvents were used as received with the following exceptions: dichloromethane, acetonitrile, tetrahydrofuran, methanol, pyridine, toluene, and triethylamine were purchased from J. T. Baker (Cycletainer™) and were purified by the method of Grubbs et al. under positive argon pressure (Pangborn, A. B.; Giardello, M. A.; Grubbs, R. H.; Rosen, R. K.; Timmers, F. J. *Organometallics* 1996, 15, 1518). Nitromethane and nitroethane (from Sigma-Aldrich) were purified by fractional distillation over calcium hydride and were stored over Linde 3 Å molecular sieves in Schlenk flasks sealed with septa and Teflon tape under argon atmosphere (Armarego, W. L. F.; Chai, C. L. L. *Purification of Laboratory Chemicals*, 5th ed.; Butterworth-Heinemann: London, 2003). Hünig's base and benzene were dried by distillation from calcium hydride under an inert argon atmosphere and used directly. 1,4-Dimethoxynaphthalene, hafnium (IV) trifluoromethanesulfonate hydrate, and iodomethane were purchased from Alfa Aesar; 1-(triisopropylsilyl)-1H-pyrrole was purchased from Combi-Block; triphenylmethanesulfenyl chloride was purchased from TCI America, Inc; 2,6-di-tert-butyl-4-methylpyridine (DTBMP) was purchased from OChem. Incorporation. All other solvents and chemicals were purchased from Sigma-Aldrich. Silver tetrafluoroborate (≥99.99% trace metals basis) and hydrogen sulfide (≥99.5%) were purchased from Sigma-Aldrich. 1,4-Dimethoxynaphthalene was purified by crystallization from absolute ethanol.

Instrumentation.

Proton nuclear magnetic resonance ($^1H$ NMR) spectra were recorded with a Bruker AVANCE-600 NMR spectrometer (with a Magnex Scientific superconducting actively-shielded magnet) or a Varian inverse probe 500 INOVA spectrometer, are reported in parts per million on the δ scale, and are referenced from the residual protium in the NMR solvent ($CDCl_3$: δ 7.26 ($CHCl_3$), acetone-$d_6$: δ 2.05 (acetone-$d_5$), acetonitrile-$d_3$: δ 2.13 (acetonitrile-$d_2$), DMSO-$d_6$: δ 2.50 (DMSO-$d_5$), methanol-$d_4$: δ 3.31 (methanol-$d_3$)) (Fulmer, G. R.; Miller, A. J. M.; Sherden, N. H.; Gottlieb, H. E.; Nudelman, A.; Stoltz, B. M.; Bercaw, J. E.; Goldberg, K. I. *Organometallics* 2010, 29, 2176). Data are reported as follows: chemical shift [multiplicity (br=broad, s=singlet, d=doublet, t=triplet, q=quadruplet, sp=septet, m=multiplet), coupling constant(s) in Hertz, integration, assignment]. Carbon-13 nuclear magnetic resonance ($^{13}C$ NMR) spectra were recorded with a Bruker AVANCE-600 NMR spectrometer (with a Magnex Scientific superconducting actively-shielded magnet), a Bruker AVANCE-400 NMR spectrometer (with a Magnex Scientific superconducting magnet), or a Varian 500 INOVA spectrometer, are reported in parts per million on the δ scale, and are referenced from the carbon resonances of the solvent ($CDCl_3$: δ 77.23, acetone-$d_6$: δ 29.84, acetonitrile-$d_3$: δ 118.26, DMSO-$d_6$: δ 39.52). Data are reported as follows: chemical shift (multiplicity (given if applicable), coupling constant in Hertz (given if applicable), assignment). Fluorine-19 nuclear magnetic resonance ($^{19}F$ NMR) spectra were recorded with a Varian Mercury 300 spectrometer, are reported in parts per million on the δ scale, and are referenced from the fluorine resonance of neat trichlorofluoromethane ($CFCl_3$: δ0). Data are reported as follows: chemical shift. Infrared data (IR) were obtained with a Perkin-Elmer 2000 FTIR and are reported as follows: frequency of absorption ($cm^{-1}$), intensity of absorption (s=strong, m=medium, w=weak, br=broad). Optical Rotations were recorded on a Jasco P-1010 Polarimeter (chloroform, Aldrich, Chromasolv Plus 99.9%; acetone, Aldrich, Chromasolv Plus 99.9%) and specific rotations are reported as follows: [wavelength of light, temperature (° C.), specific rotation, concentration in grams/100 mL of solution, solvent]. Preparative HPLC was performed on a Waters system with the 1525 Binary HPLC Pump, 2489 UV/Vis Detector, 3100 Mass Detector, System Fluidics Organizer, and 2767 Sample Manager components. We are grateful to Dr. Li Li and Deborah Bass for obtaining the mass spectrometric data at the Department of Chemistry's Instrumentation Facility, Massachusetts Institute of Technology. High-resolution mass spectra (HRMS) were recorded on a Bruker Daltonics APEXIV 4.7 Tesla FT-ICR-MS using an electrospray (ESI) ionization source.

Positional Numbering System.

At least three numbering systems for dimeric diketopiperazine alkaloids exist in the literature ((a) Von Hauser, D.; Weber, H. P.; Sigg, H. P. *Helv. Chim. Acta* 1970, 53, 1061. (b) Barrow, C. J.; Cai, P.; Snyder, J. K.; Sedlock, D. M.; Sun, H.

H.; Cooper, R. *J. Org. Chem.* 1993, 58, 6016. (c) Springer, J. P.; Büchi, G.; Kobbe, B.; Demain, A. L.; Clardy, J. *Tetrahedron Lett.* 1977, 28, 2403). In assigning the $^1$H and $^{13}$C NMR data of all intermediates en route to our different naturally occurring ETPs and their synthetic analogs, a uniform numbering scheme was to employed. For ease of direct comparison, particularly between early intermediates, non-thiolated diketopiperazines, and advanced compounds, the numbering system used by Barrow for (+)-WIN-64821 (using positional numbers 1-21) is optimal and used throughout this report. In key instances, the products are accompanied by the numbering system as shown below.

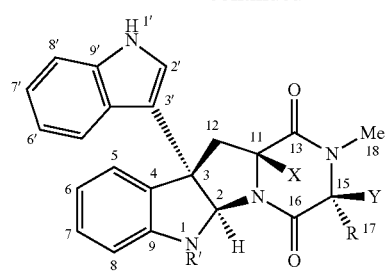

The numbering system used for all C3-(indol-3'-yl) diketopiperazines in this report

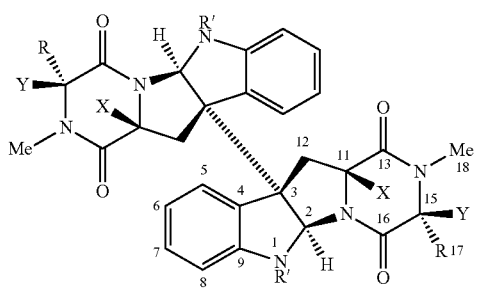

The numbering system used for all dimeric diketopiperazines in this report

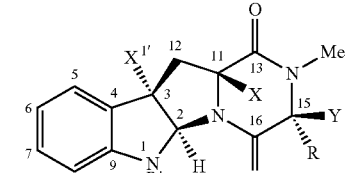

The numbering system used for all C3-substituted diketopiperazines in this report

| Exemplary dimeric epipolythiodiketopiperazines and diketopiperazines |
| --- |
| A. Dimeric ETP derivatives from N-methyl-L-alanine/serine and L-tryptophan cyclo-dipeptide |
| epipolysulfide bridge |

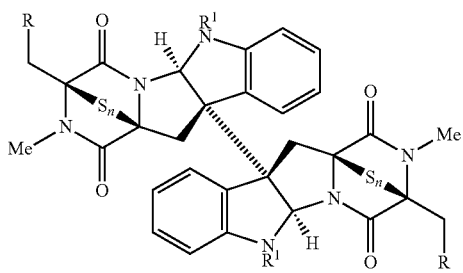

14, n = 2, R = H, R$^1$ = SO$_2$Ph
3$^7$, n = 2, R = H, R$^1$ = H
4$^8$, n = 2, R = OH, R$^1$ = H
15$^8$, n = 2, R = OAc, R$^1$ = H
5$^8$, n = 3, R = OH, R$^1$ = H
16$^8$, n = 3, R = OAc, R$^1$ = H
17$^8$, n = 3, R = OAc, R$^1$ = COCF$_3$
6$^8$, n = 4, R = OH, R$^1$ = H sulfur containing bridge

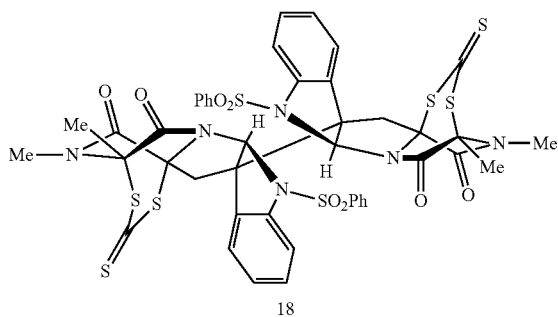

18

Exemplary dimeric epipolythiodiketopiperazines and diketopiperazines non-bridging trisulfane

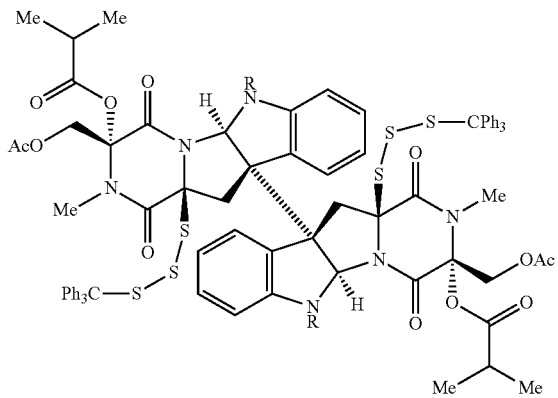

19, R = SO₂Ph
20⁸, R = H no sulfur

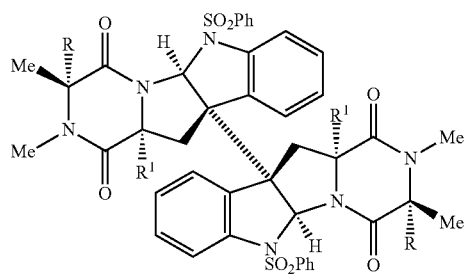

21⁷, R = H, R¹ = H
22⁷, R = OH, R¹ = OH
23⁷, R = OTBS, R¹ = OH

B. Monomeric ETP derivatives from sarcosine and L-tryptophan cyclo-dipeptide epipolysulfide bridge

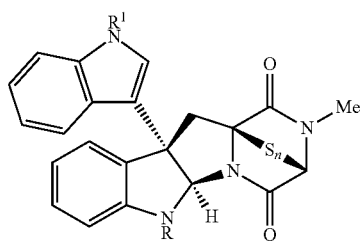

24, n = 2, R = SO₂Ph, R¹ = Boc
25, n = 1, R = SO₂Ph, R¹ = H
26, n = 2, R = SO₂Ph, R¹ = H
27, n = 3, R = SO₂Ph, R¹ = H
28, n = 4, R = SO₂Ph, R¹ = H
10⁹, n = 2, R = H, R¹ = H
29, n = 3, R = H, R¹ = H

Exemplary dimeric epipolythiodiketopiperazines and diketopiperazines
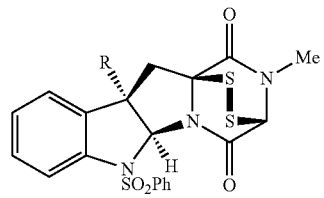
30, R = Br
31, R = F
32, R = pyrrol-3'-yl
33, R = p-MeOPh
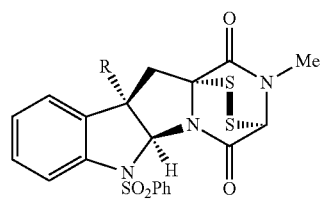
34, R = Br
35, R = F
sulfur containing bridge
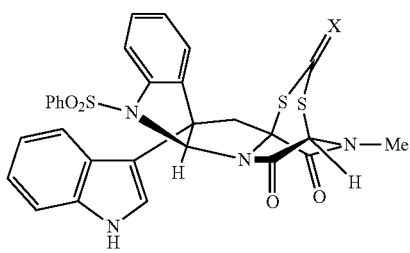
36, X = S
37, X = O
38, X = H,H
non-bridging sulfur
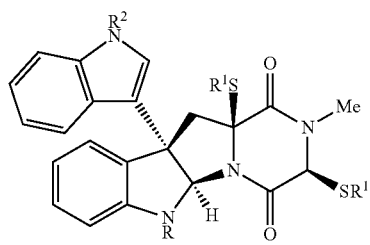
7[9], R = H, R[1] = Me, R[2] = H
39[9], R = SO$_2$Ph, R[1] = Me, R[2] = H
40, R = SO$_2$Ph, R[1] = MOM, R[2] = H
41, R = H, R[1] = MOM, R[2] = H
42, R = SO$_2$Ph, R[1] = MEM, R[2] = Boc
43, R = SO$_2$Ph, R[1] = Bn, R[2] = Boc
44, R = SO$_2$Ph, R[1] = Ac, R[2] = H
45, R = SO$_2$Ph, R[1] = SMe, R[2] = SMe
46, R = SO$_2$Ph, R[1] = SMe, R[2] = H Exemplary dimeric epipolythiodiketopiperazines and diketopiperazines
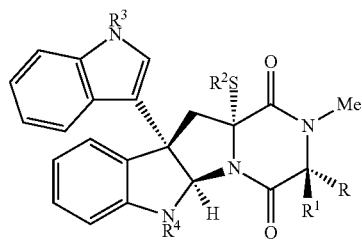
47, R = H, R$^1$ = SMEM, R$^2$ = H, R$^3$ = Boc, R$^4$ = SO$_2$Ph
48[9], R = OH, R$^1$ = H, R$^2$ = H, R$^3$ = H, R$^4$ = SO$_2$Ph
49, R = H, R$^1$ = H, R$^2$ = MOM, R$^3$ = Boc, R$^4$ = SO$_2$Ph
50[9], R = OCOi-Pr, R$^1$ = H, R$^2$ = COi-Pr, R$^3$ = H, R$^4$ = SO$_2$Ph
51[9], R = OCOi-Pr, R$^1$ = H, R$^2$ = COi-Pr, R$^3$ = H, R$^4$ = H
no sulfur
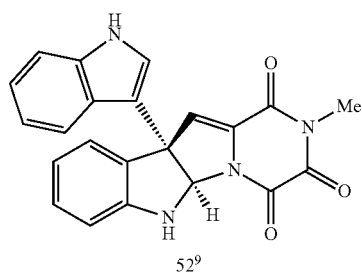 [SMILES: CN1C(=O)C(=O)N2C(=C[C@]3(c4c[nH]c5ccccc45)c4ccccc4N[C@H]23)C1=O]
52[9]
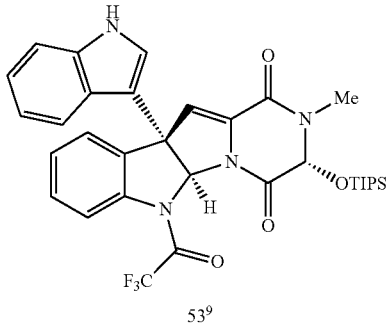
53[9]
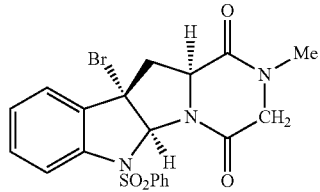
54[9]
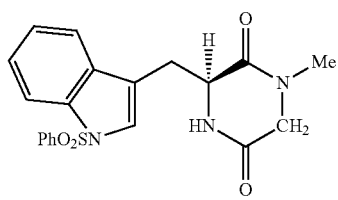
55[9]

Exemplary dimeric epipolythiodiketopiperazines and diketopiperazines

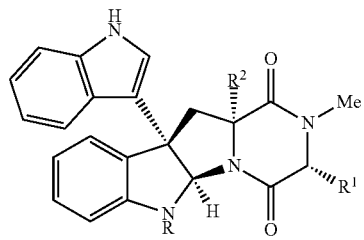

56[9], R = SO$_2$Ph, R$^1$ = OH, R$^2$ = OH
57[9], R = SO$_2$Ph, R$^1$ = OTIPS, R$^2$ = OH
58[9], R = H, R$^1$ = OTIPS, R$^2$ = OH
59[9], R = SO$_2$Ph, R$^1$ = H, R$^2$ = H

C. Monomeric ETP derivatives from N-methyl-L-alanine and L-tryptophan cyclo-dipeptide epidisulfide bridge

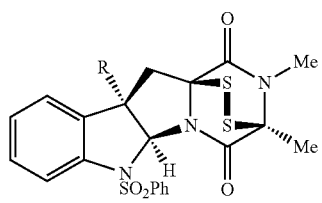

60, R = indol-3'-yl
61[7], R = n-Pr

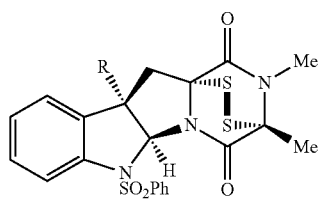

62, R = indol-3'-yl
63[7], R = n-Pr sulfur containing bridge

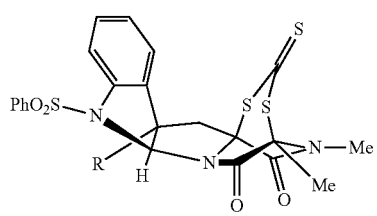

64, R = indol-3'-yl
65, R = n-Pr

| Exemplary dimeric epipolythiodiketopiperazines and diketopiperazines |
|---|
| 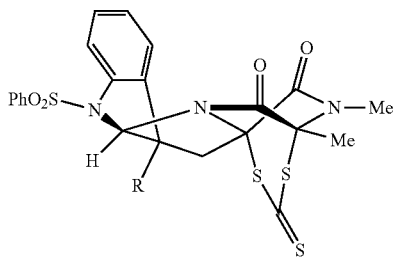 |
| 66, R = indol-3'-yl<br>67, R = n-Pr |

(Certain experimental procedures and characterization data are described in [7] Kim, J.; Ashenhurst, J. A.; Movassaghi, M. *Science* 2009, 324, 238; and [8] Kim, J.; Movassaghi, M. *J. Am. Chem. Soc.* 2010, 132, 14376).

Exemplary C3-substituted epipolythiodiketopiperazines and diketopiperazines (Certain experimental procedure and characterization data are described in [9] Boyer, N.; Movassaghi, M. *Chem. Sci.* 2012, 3, 1798).

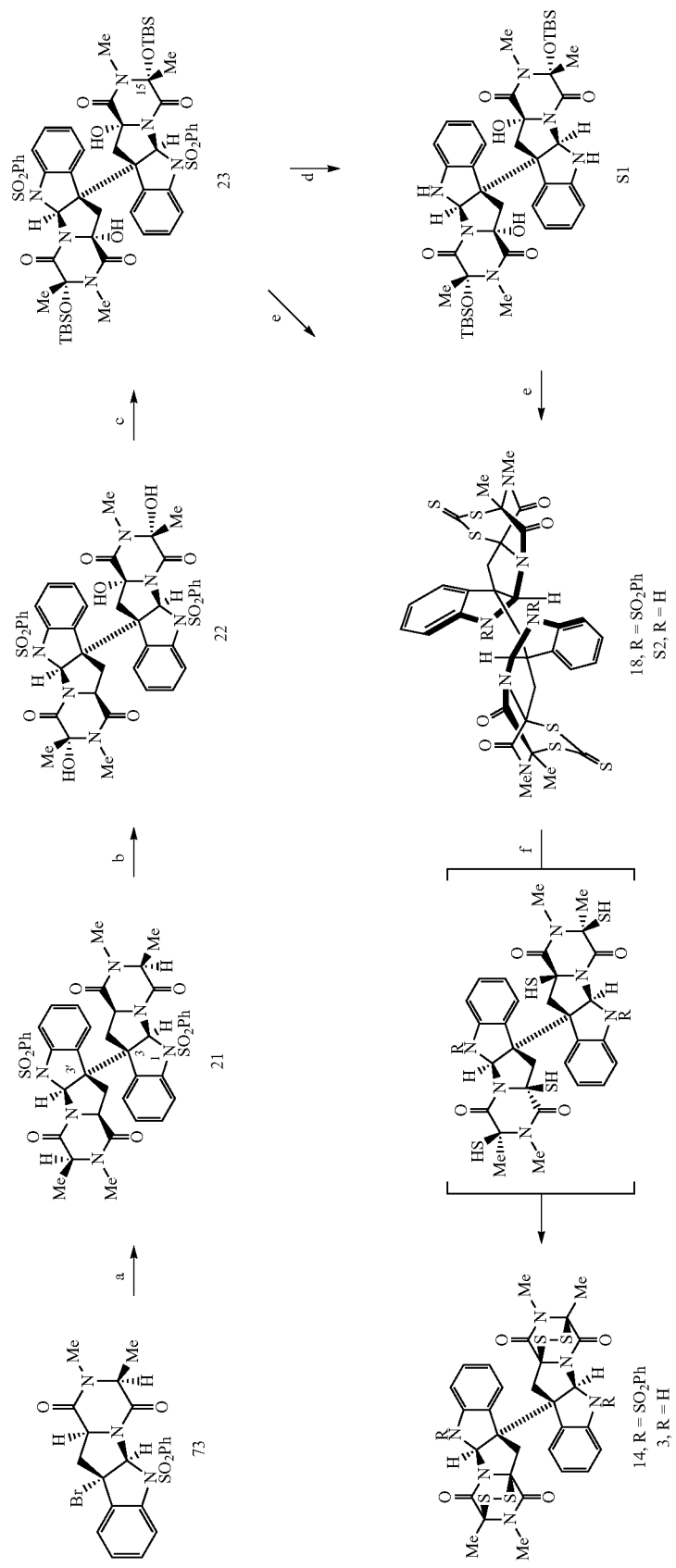

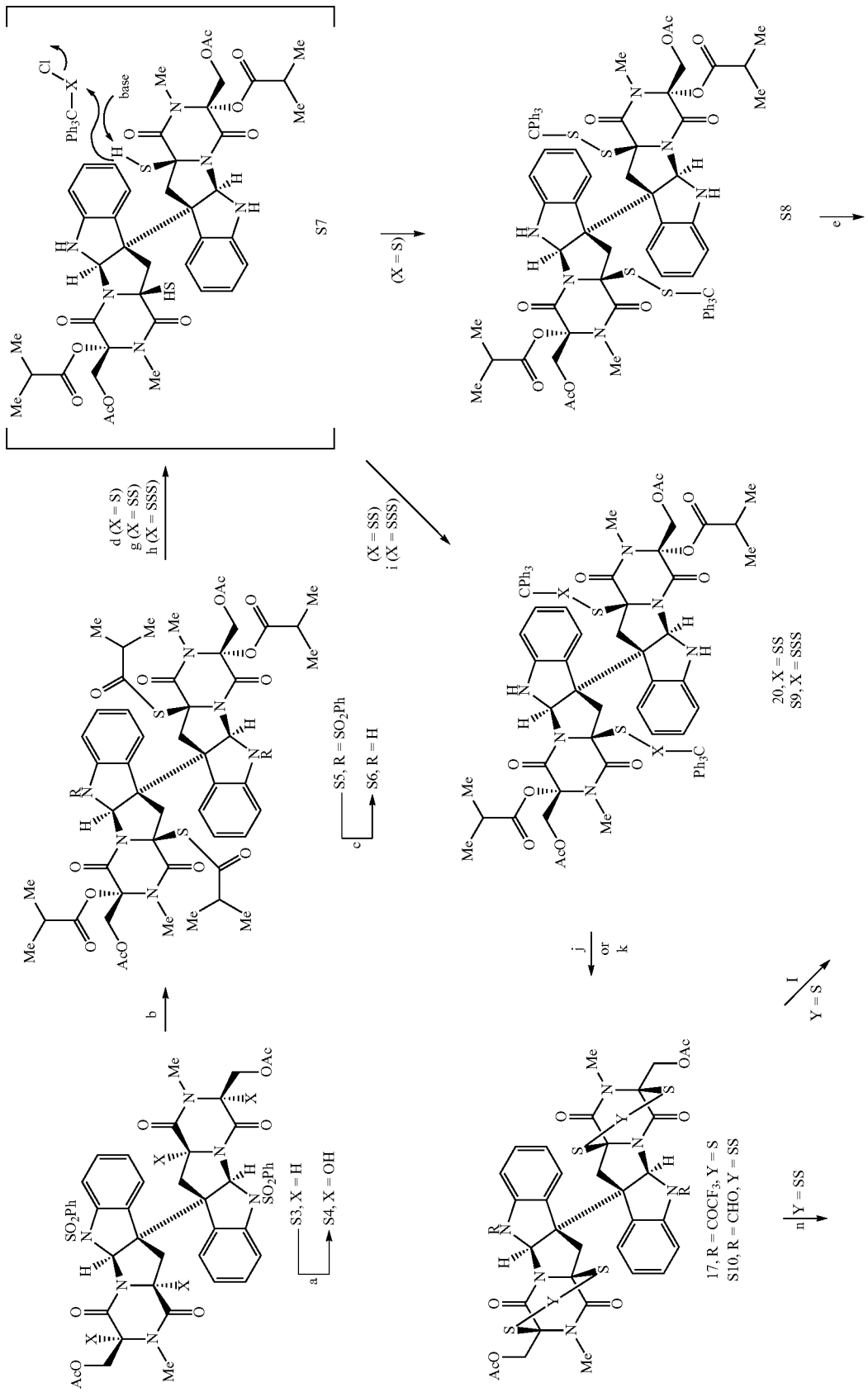
Scheme 2. Synthesis of (+)-chaetocins A (4) and C (5), (+)-12,12'-dideoxychetracin A (6) and other dimeric derivatives (15-17, 20).

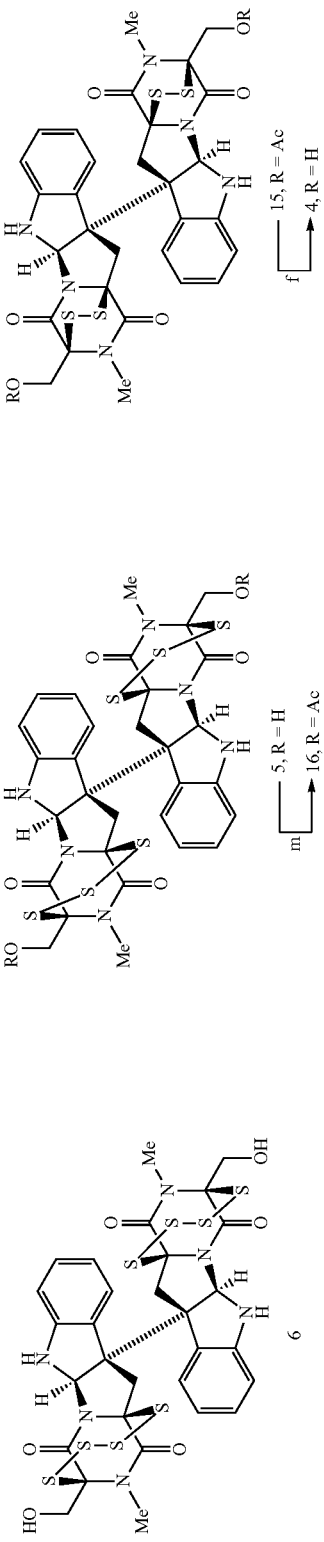

General Reagents and Methods for Biological Assays.

For biological assays, propidium iodide and phenazine methosulfate were purchased from Sigma-Aldrich. The 3-(4,5-dimethylthiazol-2-yl)-5-(3-carboxymethoxyphenyl)-2-(4-sulfophenyl)-2H-tetrazolium salt was obtained from Promega. Human erythrocytes were purchased from Bioreclamation and used within three days of receipt. Optical densities were recorded on a Spectramax Plus 384 (Molecular Devices, Sunnyvale, Calif.). Flow cytometry was performed on a BD Biociences LSR II (San Jose, Calif.) and the data was analyzed as described using FACSDiva software (San Jose, Calif.).

Cell Culture Information.

Cells were grown in media supplemented with fetal bovine serum (FBS) and antibiotics (100 µg/mL penicillin and 100 U/mL streptomycin). Specifically, experiments were performed using the following cell lines and media compositions: U-937, HeLa, H460, and 786-O (RPMI-1640+10% FBS), and MCF7 (EMEM+10% FBS). Cells were incubated at 37° C. in a 5% $CO_2$, 95% humidity atmosphere.

$IC_{50}$ Value Determination for Adherent Cells Using Sulforhodamine B (SRB).

Adherent cells (HeLa, H460, 786-O, and MCF7) were added into 96-well plates (5,000 cells/well for HeLa cell line; 2,000 cells/well for H460, 786-O, and MCF7 cell lines) in 100 µL media and were allowed to adhere for 2-3 hours. Compounds were solubilized in DMSO as 100× stocks, added directly to the cells (100 µL final volume), and tested over a range of concentrations in triplicate (1% DMSO final) on a half-log scale. Concentrations tested ranged from 1 µM to 10 µM, depending on the potency of the compound. DMSO and cell-free wells served as the live and dead control, respectively. After 72 hours of continuous exposure, the plates were evaluated using the SRB colorimetric assay as described previously (Vichai, V.; Kirtikara, K. *Nature Prot.* 2006, 1, 1112). Briefly, media was removed from the plate, and cells were fixed by the addition of 100 µL cold 10% trichloroacetic acid in water. After incubating at 4° C. for an hour, the plates were washed in water and allowed to dry. Sulforhodamine B was added as a 0.057% solution in 1% acetic acid (100 µL), and the plates were incubated at room temperature for 30 minutes, washed in 1% acetic acid, and allowed to dry. The dye was solubilized by adding 10 mM Tris base solution (pH 10.5, 200 µL) and incubating at room temperature for 30 minutes. Plates were read at $\lambda$=510 nm. $IC_{50}$ values were determined from three or more independent experiments using Table-Curve (San Jose, Calif.).

$IC_{50}$ Value Determination for Non-Adherent Cells Using MTS.

In a 96-well plate, compounds were pre-added as DMSO stocks in triplicate to achieve a final concentration of 1%. DMSO and cell-free wells served as the live and dead control, respectively. U-937 (5,000 cells/well) cells were distributed in 100 µL media to the compound-containing plate. After 72 hours, cell viability was assessed by adding 20 µL of a PMS/MTS solution (Cory, A. H.; Owen, T. C.; Barltrop, J. A.; Cory, J. G. *Cancer Commun.* 1991, 3, 207) to each well, allowing the dye to develop at 37° C. until the live control had processed MTS, and reading the absorbance at $\lambda$=490 nm. $IC_{50}$ values were determined from three or more independent experiments using TableCurve (San Jose, Calif.).

Hemolysis Assay Using Human Erythrocytes.

To prepare the erythrocytes, 0.1 mL of human blood was centrifuged (10,000 g, 2 min). The pellet was washed three times with saline (0.9% NaCl) via gentle re-suspension and centrifugation (10,000 g, 2 min). Following the final wash, the erythrocytes were re-suspended in 0.8 mL red blood cell (RBC) buffer (10 mM $Na_2HPO_4$, 150 mM NaCl, 1 mM $MgCl_2$, pH 7.4).

DMSO stocks of compounds were added to 0.5 mL tubes in singlicate (1 µL, 3.3% DMSO final). The stocks were diluted with 19 µL RBC buffer. Positive control tubes contained DMSO in water, and negative control tubes contained DMSO in RBC buffer. A suspension of washed erythrocytes (10 µL) was added to each tube, and samples were incubated at 37° C. for 2 hours. Samples were centrifuged (10,000 g, 2 min), and the supernatant was transferred to a clear, sterile 384-well plate. The absorbance of the supernatants was measured at $\lambda$=540 nm, and percent hemolysis was calculated relative to the average absorbance values measured for the controls.

Apoptosis in U-937 Cells with Annexin V-FITC and Propidium Iodide (AnnV/PI).

DMSO stocks of compounds were added to a 24-well plate in singlicate (0.2% DMSO final). After compound addition, 0.5 mL of a U-937 cell suspension (250,000 cells/mL) was added and allowed to incubate for 24 hours. Following treatment, the cell suspensions were transferred to flow cytometry tubes and pelleted (500 g, 3 min). The media was removed by aspiration, and cells were re-suspended in 200 µL AnnV binding buffer (10 mM HEPES, pH 7.4, 140 mM NaCl, 2.5 mM $CaCl_2$) with 5 µg/mL PI and 1:90 dilution of AnnV. Samples were analyzed using flow cytometry.

Apoptosis in U-937 Cells by Western Blot Analysis.

In a 24-well plate, compounds were added as DMSO stocks (0.2% DMSO final) in singlicate. After compound addition, 1.5 mL of a U-937 cell suspension (250,000 cells/mL) was added and allowed to incubate for 24 hours. The cell suspensions were transferred to 1.5 mL tubes and pelleted (600 g, 3 min). The media was removed via aspiration, and the cells were lysed by adding 40 µL of RIPA buffer (50 mM Tris, pH 8.0, 150 mM NaCl, 1% TX-100, 0.5% sodium deoxycholate, 0.1% SDS) with 1% Protease Inhibitor Cocktail Set III. Each sample was then vigorously vortexed twice for 15 seconds, with a 15-minute incubation on ice following each agitation. The cellular debris was pelleted (16,100 g, 5 min), and then 33 µL of the protein suspension was transferred to fresh 0.5 mL tubes. The protein levels were quantified using a standard BCA (Thermo Scientific), after which the samples were diluted with deionized water to achieve equal protein concentrations for all samples.

Prior to analyzing the samples, 6× Laemmli sample buffer (350 mM Tris, pH 6.8, 12% SDS, 0.012% bromophenol blue, 47% glycerol) with 5% β-mercaptoethanol was added to each sample to achieve a final 1× concentration, after which the samples were incubated at 95° C. for 5 minutes to denature the protein samples. 20-30 µg of protein was added to a 15-well 4-20% Tris-HCl gel and run for 1 hour at 120 V. The gel was equilibrated PBS (pH 7.4) for 5 minutes, and then transferred to a PVDF membrane for 2 hours at 45 V.

Generally, blots were probed as follows. The blot was blocked overnight at 4° C. with a blocking agent in 0.05% Tris-Buffered Saline Tween-20 (TBST) and then probed for the primary antibody at a 1:1000 dilution with a blocking agent in TBST overnight at 4° C. The blot was washed with TBST, and then probed with a secondary rabbit HRP antibody (1:10,000, Cell Signaling) in TBST for 1 hour at room temperature. The blot was washed with TBST and PBS, and then visualized with Pico luminescent substrate kit (Thermo Scientific). Caspase 3 and PARP were blocked in 5% milk, and actin was blocked in 5% BSA.

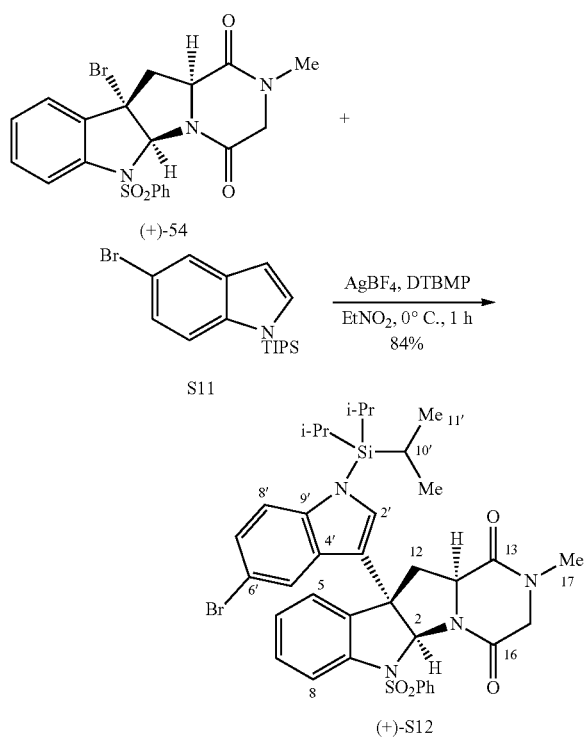

C3-(5-Bromo-1-TIPS-indol-3'-yl)-pyrrolidinoindoline (+)-S12

A round-bottom flask was charged with endo-tetracyclic bromide (+)-54 (5.00 g, 10.5 mmol, 1 equiv), 2,6-di-tert-butyl-4-methylpyridine (DTBMP, 2.59 g, 12.6 mmol, 1.20 equiv), and 5-bromo-1-triisopropylsilyl-1H-indole (S11, 14.8 g, 42.0 mmol, 4.00 equiv. 5-Bromo-1-triisopropylsilyl-1H-indole S11 was prepared in quantitative yield by silylation of commercially available 5-bromoindole using triisopropylsilyl chloride and sodium hydride in tetrahydrofuran. For preparation and characterization, see: Brown, D. A.; Mishra, M.; Zhang, S.; Biswas, S.; Parrington, I.; Antonio, T.; Reith, M. E. A.; Dutta, A. K. *Bioorg. Med. Chem.* 2009, 17, 3923), and the mixture was dried azeotropically (concentration of a benzene solution, 2×30 mL) under reduced pressure and placed under an argon atmosphere. Anhydrous nitroethane (120 mL) was introduced via syringe, and the mixture was cooled to 0° C. in an ice-water bath. A solution of silver(I) tetrafluoroborate (6.30 g, 32.4 mmol, 3.09 equiv) in anhydrous nitroethane (40 mL) at 0° C. was introduced via cannula to the solution containing the tetracyclic bromide (+)-54 over 20 min. After 5 min, a white precipitate was observed in the clear yellow reaction solution. The reaction flask was covered in aluminum foil, and the suspension was maintained at 0° C. After 1 h, saturated aqueous sodium chloride solution (25 mL) was introduced, and the resulting biphasic mixture was vigorously stirred for 30 min at 0° C. The reaction mixture was diluted with ethyl acetate (150 mL), was filtered through a Celite pad, and the solid was washed with ethyl acetate (3×50 mL). The combined filtrates were washed with 5% aqueous citric acid solution (2×100 mL), water (3×100 mL), and saturated aqueous sodium chloride solution (75 mL). The organic layer was dried over anhydrous sodium sulfate, was filtered, and was concentrated under reduced pressure. The resulting orange residue was purified by flash column chromatography (eluent: gradient, 2→10% acetone in dichloromethane) to afford the indole adduct (+)-S12 (6.56 g, 83.6%) as a white foam. Structural assignments were made with additional information from gCOSY, HSQC, gHMBC, and NOESY data. $^1$H NMR (600 MHz, CDCl$_3$, 20° C.): δ 8.04 (app-d, J=7.4, 2H, SO$_2$Ph-o-H), 7.77 (d, J=8.3, 1H, C$_8$H), 7.56 (app-t, J=7.5, 1H, SO$_2$Ph-p-H), 7.42 (app-dd, J=7.8, 8.0, 2H, SO$_2$Ph-m-H), 7.30 (d, J=8.9, 1H, C$_{8'}$H), 7.29 (app-dt, J=1.1, 7.9, 1H, C$_7$H), 7.15 (app-dd, J=1.8, 8.8, 1H, C$_{7'}$H), 6.98 (app-t, J=7.5, 1H, C$_6$H), 6.94 (s, 1H, C$_{2'}$H), 6.84 (d, J=7.4, 1H, C$_5$H), 6.55 (d, J=1.3, 1H, C$_{5'}$H), 6.28 (s, 1H, C$_2$H), 4.47 (dd, J=8.0, 9.5, 1H, C$_{11}$H), 4.07 (d, J=17.8, 1H, C$_{15}$H$_a$), 3.94 (d, J=17.8, 1H, C$_{15}$H$_b$), 3.03 (dd, J=7.6, 13.8, 1H, C$_{12}$H$_a$), 3.00 (s, 3H, C$_{17}$H$_3$), 2.86 (dd, J=10.0, 13.9, 1H, C$_{12}$H$_b$), 1.59 (app-sp, J=7.5, 3H, C$_{10'}$H), 1.08 (app-d, J=8.5, 18H, C$_{11'H}$). $^{13}$C NMR (100 MHz, CDCl$_3$, 20° C.): δ 167.7 (C$_{13}$), 166.8 (C$_{16}$), 141.3 (C$_{9'}$), 139.7 (C$_9$), 137.1 (SO$_2$Ph-ipso-C), 134.2 (SO$_2$Ph-p-C), 134.0 (C$_4$), 130.9 (C$_{2'}$), 130.3 (C$_{4'}$), 129.6 (C$_7$), 129.3 (SO$_2$Ph-m-C), 127.9 (SO$_2$Ph-o-C), 125.4 (C$_{7'}$), 124.6 (C$_6$), 124.0 (C$_5$), 121.9 (C$_{5'}$), 116.0 (C$_{8'}$), 115.7 (C$_8$), 115.1 (C$_{3'}$), 113.5 (C$_{6'}$), 82.7 (C$_2$), 59.5 (C$_{11}$), 55.4 (C$_3$), 54.6 (C$_{15}$), 37.6 (C$_{12}$), 33.8 (C$_{17}$), 18.2 (C$_{11'}$), 12.9 (C$_{10'}$). FTIR (thin film) cm$^{-1}$: 2949 (m), 2869 (m), 1681 (s), 1447 (m), 1396 (m), 1366 (m), 1178 (s), 1092 (w), 987 (w), 732 (m), 690 (w). HRMS (ESI) (m/z): calc'd for C$_{37}$H$_{44}$BrN$_4$O$_4$SSi [M+H]$^+$: 747.2030. found: 747.2025. [α]$_D^{24}$: +93.6 (c=0.26, CHCl$_3$). TLC (10% acetone in dichloromethane), Rf: 0.67 (UV, CAM).

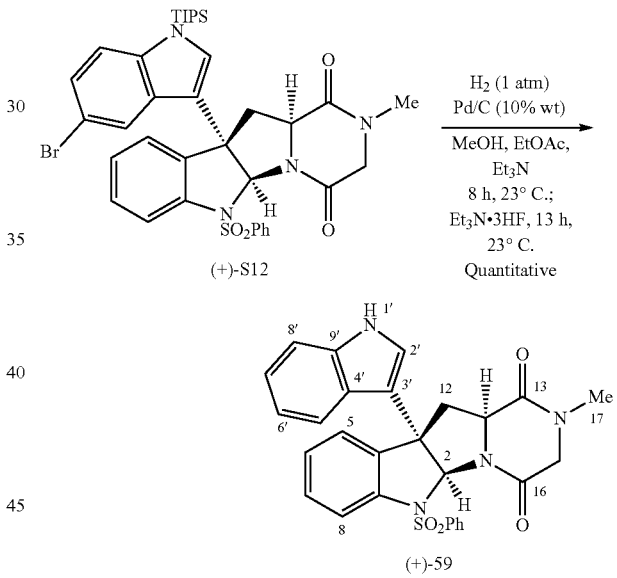

C3-(indol-3'-yl)-pyrrolidinoindolne (+)-59

A mixture of anhydrous methanol and ethyl acetate (3:2 v/v, 160 mL) was introduced into a round-bottom flask charged with the indole adduct (+)-S12 (6.56 g, 8.77 mmol, 1 equiv) and palladium on activated charcoal (10% w/w, 0.50 g, 0.47 mmol, 0.05 equiv). The flask was purged by three cycles of vacuum and dihydrogen and sealed under an atmosphere of hydrogen gas (15 psi). Triethylamine (1.50 mL, 10.7 mmol, 1.22 equiv) was introduced to the flask via syringe, and the resulting suspension was vigorously stirred at 23° C. Upon completion of the reaction (ca 8 h) as monitored by TLC, the flask was purged by three cycles of vacuum and argon and sealed under argon atmosphere. Neat triethylamine trihydrofluoride (3.00 mL, 18.4 mmol, 2.15 equiv, McClinton, M. A. *Aldrichimica Acta* 1995, 28, 31) was introduced to the flask via syringe and the resulting suspension was stirred at 23° C. After 13 h, the reaction mixture was filtered through a pad of Celite. The solids were washed with ethyl acetate (3×50 mL).

The combined filtrates were concentrated under reduced pressure. The resulting pale yellow solid was diluted in ethyl acetate (400 mL) and washed sequentially with an aqueous hydrochloric acid solution (1 N, 2×100 mL), water (2×100 mL), and saturated aqueous sodium chloride solution (50 mL). The organic layer was dried over anhydrous sodium sulfate, was filtered, and was concentrated under reduced pressure. The resulting residue was purified by flash column chromatography (eluent: 15% acetone in dichloromethane) to afford the indole adduct (+)-59 (4.59 g, 99.9%) as a white solid. Structural assignments were made with additional information from gCOSY, HSQC, gHMBC, and NOESY data.

$^1$H NMR (600 MHz, CDCl$_3$, 20° C.): δ 8.03 (br-s, 1H, N$_1$H), 7.75 (d, J=8.2, 1H, C$_8$H), 7.50 (d, J=7.6, 2H, SO$_2$Ph-o-H), 7.38 (t, J=7.5, 1H, SO$_2$Ph-p-H), 7.35 (d, J=8.2, 1H, C$_8$H), 7.30 (app-dt, J=1.1, 7.8, 1H, C$_7$H), 7.19 (app-t, J=7.6, 1H, C$_7$H), 7.10 (app-t, J=7.9, 2H, SO$_2$Ph-m-H), 7.09-7.06 (m, 1H, C$_5$H), 7.06 (app-t, J=7.4, 1H, C$_6$H), 6.93 (app-t, J=7.4, 1H, C$_6$H), 6.89 (d, J=7.9, 1H, C$_5$H), 6.37 (s, 1H, C$_2$H), 6.16 (d, J=2.3, 1H, C$_2$H), 4.56 (app-t, J=8.1, 1H, C$_{11}$H), 4.13 (d, J=17.5, 1H, C$_{15}$H$_a$), 3.85 (d, J=17.5, 1H, C$_{15}$H$_b$), 3.09 (dd, J=8.9, 14.1, 1H, C$_{12}$H$_a$), 3.03 (dd, J=7.2, 14.1, 1H, C$_{12}$H$_b$), 2.90 (s, 3H, C$_{17}$H$_3$). $^{13}$C NMR (150 MHz, CDCl$_3$, 20° C.): δ 167.5 (C$_{13}$), 165.9 (C$_{16}$), 139.6 (C$_9$), 137.6 (SO$_2$Ph-ipso-C), 137.4 (C$_{9'}$), 135.9 (C$_4$), 133.1 (SO$_2$Ph-p-C), 129.3 (C$_7$), 128.6 (SO$_2$Ph-m-C), 127.6 (SO$_2$Ph-o-C), 125.2 (C$_6$), 124.8 (C$_5$), 124.6 (C$_{4'}$), 123.6 (C$_{2'}$), 122.9 (C$_{7'}$), 120.3 (C$_{6'}$), 119.0 (C$_{5'}$), 117.1 (C$_8$), 115.0 (C$_{3'}$), 112.0 (C$_{8'}$), 83.8 (C$_2$), 58.8 (C$_{11}$), 55.4 (C$_3$), 54.6 (C$_{15}$), 36.1 (C$_{12}$), 33.8 (C$_{17}$). FTIR (thin film) cm$^{-1}$: 3384 (br-m), 3013 (w), 2925 (w), 1681 (s), 1457 (m), 1399 (m), 1355 (m), 1169 (m), 1091 (w), 751 (m). HRMS (ESI) (m/z): calc'd for C$_{27}$H$_{24}$N$_4$NaO$_4$S [M+Na]$^+$: 535.1410. found: 535.1413. [α]$_D$23: +70.0 (c=0.15, CHCl$_3$). TLC (25% acetone in dichloromethane), Rf: 0.41 (UV, CAM).

C3-(Indol-3'-yl) hexacyclic Diol (−)-56

Freshly prepared tetra-n-butylammonium permanganate (Sala, T.; Sargent, M. V. *J. Chem. Soc., Chem. Commun.* 1978, 253. Tetra-n-butylammonium permanganate was prepared according to a literature procedure (Karaman, H.; Barton, R. J.; Robertson, B. E.; Lee, D. G. *J. Org. Chem.* 1984, 49, 4509) and dried under reduced pressure at room temperature. (a) Gardner, K. A.; Mayer, J. M. *Science* 1995, 269, 1849. (b) Strassner, T.; Houk, K. N. *J. Am. Chem. Soc.* 2000, 122, 7821. (c) Shi, S.; Wang, Y.; Xu, A.; Wang, H.; Zhu, D.; Roy, S. B.; Jackson, T. A.; Busch, D. H.; Yin, G. *Angew. Chem. Int. Ed.* 2011, 50, 7321) (767 mg, 2.12 mmol, 3.79 equiv) was added as a solid to a solution of the indole adduct (+)-59 (287 mg, 0.56 mmol, 1 equiv) in dichloromethane (20 mL) at 23° C. After 30 min, the dark purple solution was diluted with saturated aqueous sodium sulfite solution (20 mL) and then with ethyl acetate (160 mL). The resulting mixture was washed sequentially with saturated aqueous sodium hydrogenocarbonate solution (50 mL), water (2×50 mL), and saturated aqueous sodium chloride solution (30 mL). The aqueous layer was extracted with ethyl acetate (2×100 mL), and the combined organic layers were dried over anhydrous sodium sulfate, were filtered, and were concentrated under reduced pressure. The resulting yellow residue was purified by flash column chromatography (eluent: gradient, 10-+25% acetone in dichloromethane) to afford the diol (−)-56 (127 mg, 41.6%) as a white solid (Analytically pure samples of polar diol (−)-56 could be obtained by trituration with minimal amount of chloroform). Structural assignments were made with additional information from gCOSY, HSQC, gHMBC, and NOESY data. $^1$H NMR (600 MHz, acetone-d$_6$, 20° C.): δ 9.85 (br-s, 1H, N$_1$H), 8.01 (d, J=8.2, 1H, C$_5$H), 7.56 (d, J=8.1, 1H, C$_8$H), 7.49 (d, J=8.1, 1H, C$_8$H), 7.41 (d, J=7.5, 1H, C$_5$H), 7.35 (app-t, J=7.5, 1H, SO$_2$Ph-p-H), 7.35 (app-t, J=7.5, 1H, C$_7$H), 7.24 (app-t, J=7.6, 1H, C$_7$H), 7.20 (app-t, J=7.5, 1H, C$_6$H), 7.17 (app-t, J=7.5, 1H, C$_6$H), 7.04 (d, J=7.5, 2H, SO$_2$Ph-o-H), 6.98 (app-t, J=7.8, 2H, SO$_2$Ph-m-H), 6.80 (d, J=6.2, 1H, C$_{15}$OH), 6.66 (s, 1H, C$_2$H), 6.22 (s, 1H, C$_{11}$OH), 5.65 (d, J=2.5, 1H, C$_2$H), 5.15 (d, J=6.0, 1H, C$_{15}$H), 3.64 (d, J=15.1, 1H, C$_{12}$H$_a$), 3.01 (d, J=15.1, 1H, C$_{12}$H$_b$), 2.95 (s, 3H, C$_{17}$H$_3$). $^{13}$C NMR (150 MHz, acetone-d$_6$, 20° C.): δ 168.1 (C$_{13}$), 165.7 (C$_{16}$), 140.4 (C$_9$), 139.3 (SO$_2$Ph-ipso-C), 138.8 (C$_4$), 138.6 (C$_{9'}$), 133.7 (SO$_2$Ph-p-C), 129.8 (C$_7$), 128.9 (SO$_2$Ph-m-C), 127.5 (SO$_2$Ph-o-C), 126.3 (C$_5$), 126.2 (C$_6$), 125.7 (C$_{2'}$), 125.2 (C$_{4'}$), 122.9 (C$_{7'}$), 120.4 (C$_{6'}$), 119.6 (C$_{5'}$), 118.2 (C$_8$), 115.7 (C$_{3'}$), 113.0 (C$_{8'}$), 88.6 (C$_{11}$), 85.3 (C$_2$), 83.9 (C$_{15}$), 55.3 (C$_3$), 45.1 (C$_{12}$), 31.8 (C$_{17}$). FTIR (thin film) cm$^{-1}$: 3392 (br-m), 1700 (s), 1460 (w), 1400 (w), 1360 (m), 1169 (m), 1091 (w), 750 (w). HRMS (ESI) (m/z): calc'd for C$_{28}$H$_{24}$N$_4$NaO$_6$S [M+Na]$^+$: 567.1309. found: 567.1315. [α]$_D^{24}$: −71.4 (c=0.114, acetone). m.p.: 212° C. TLC (20% acetone in dichloromethane), Rf: 0.24 (UV, CAM).

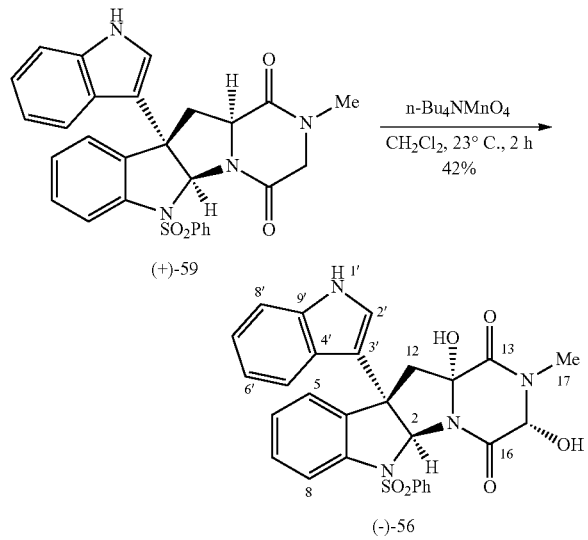

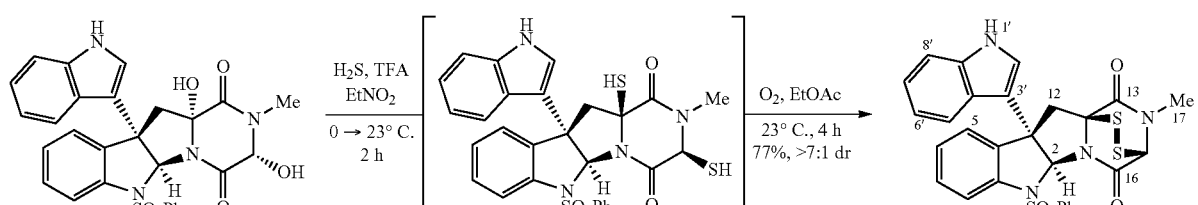

C3-(Indol-3'-yl) epidithiodiketopiperazine 26

A slow stream of hydrogen sulfide gas was introduced into a solution of diol (−)-56 (254 mg, 466 μmol, 1 equiv) in anhydrous nitroethane (20 mL) at 0° C., providing a saturated hydrogen sulfide solution. After 20 min, trifluoroacetic acid (TFA, 15 mL) was added slowly via syringe, and the slow introduction of hydrogen sulfide into the mixture was maintained for another 20 min. The reaction mixture was left under an atmosphere of hydrogen sulfide. The ice-water bath was removed, and the yellow solution was allowed to warm to 23° C. After 2 h, a slow stream of argon gas was introduced into the solution. After 15 min, the reaction mixture was diluted with ethyl acetate (150 mL) and slowly poured into saturated aqueous sodium hydrogenocarbonate solution (70 mL) at 23° C. The organic layer was sequentially washed with water (3×40 mL) and saturated aqueous sodium chloride solution (25 mL), was dried over anhydrous sodium sulfate, was filtered, and was concentrated under reduced pressure to afford the corresponding bisthiol S13 that was used in the next step without further purification. The orange residue was dissolved in ethyl acetate (120 mL). A slow stream of dioxygen gas was introduced into the solution. After 4 h, the yellow solution was concentrated under reduced pressure. The orange residue was purified by flash column chromatography on silica gel (eluent: gradient, 5→15% ethyl acetate in dichloromethane) to afford the epidithiodiketopiperazine 26 (205 mg, 76.7%) as a white solid. Structural assignments were made with additional information from gCOSY, HSQC, and gHMBC data. $^1$H NMR (600 MHz, acetone-$d_6$, 20° C.): δ 10.05 (br-s, 1H, $N_1$H), 7.65 (d, J=8.1, 1H, $C_8$H), 7.55 (d, J=7.5, 1H, $C_5$H), 7.50 (d, J=8.0, 1H, $C_5$H), 7.48 (d, J=8.8, 1H, $C_8$H), 7.46 (app-dt, J=1.0, 7.5, 1H, $C_7$H), 7.39 (t, J=7.4, 1H, SO$_2$Ph-p-H), 7.30 (app-t, J=0.8, 7.5, 1H, $C_6$H), 7.22 (dd, J=7.2, 8.0, 1H, $C_7$H), 7.12 (app-dd, J=1.0, 8.4, 2H, SO$_2$Ph-o-H), 7.10 (dd, J=7.3, 7.9, 1H, $C_6$H), 7.00 (dd, J=7.5, 8.2, 2H, SO$_2$Ph-m-H), 6.63 (s, 1H, $C_2$H), 5.98 (d, J=2.6, 1H, $C_2$H), 5.80 (s, 1H, $C_{15}$H), 3.95 (d, J=15.6, 1H, $C_{12}H_a$), 3.17 (s, 3H, $C_{17}H_3$), 2.92 (d, J=15.7, 1H, $C_{12}H_b$). $^{13}$C NMR (150 MHz, acetone-$d_6$, 20° C.): δ 165.9 ($C_{13}$), 161.0 ($C_{16}$), 141.5 ($C_9$), 138.7 (SO$_2$Ph-ipso-C), 138.5 ($C_{9'}$), 138.1 ($C_4$), 134.0 (SO$_2$Ph-p-C), 130.1 ($C_7$), 129.0 (SO$_2$Ph-m-C), 127.7 (SO$_2$Ph-o-C), 126.6 ($C_6$), 125.9 ($C_5$), 125.8 ($C_{2'}$), 125.0 ($C_{4'}$), 123.0 ($C_{7'}$), 120.6 ($C_{6'}$), 119.2 ($C_8$), 119.1 ($C_{5'}$), 114.1 ($C_{3'}$), 113.1 ($C_{8'}$), 85.7 ($C_2$), 75.5 ($C_{11}$), 69.1 ($C_{15}$), 56.4 ($C_3$), 42.6 ($C_{12}$), 31.8 ($C_{17}$). FTIR (thin film) cm$^{-1}$: 3392 (w), 3060 (w), 2990 (w), 1693 (s), 1447 (w), 1358 (m), 1234 (w), 1169 (m), 1089 (w), 1052 (w), 964 (w), 736 (m), 587 (m). HRMS (ESI) (m/z): calc'd for $C_{28}H_{23}N_4O_4S_3$ [M+H]$^+$: 575.0876. found 575.0885; calc'd for $C_{28}H_{22}N_4NaO_4S_3$ [M+Na]$^+$: 597.0695. found 597.0704. TLC (20% ethyl acetate in dichloromethane), Rf: 0.62 (UV, CAM).

General Procedure for the Friedel-Crafts Nucleophilic Substitution.

A round-bottom flask was charged with endo-tetracyclic bromide (+)-54 (1 equiv, Boyer, N.; Movassaghi, M. *Chem. Sci.* 2012, 3, 1798), 2,6-di-tert-butyl-4-methylpyridine (DTBMP, 2.10 equiv), and the nucleophile (for 68: tetrafluoroborate as nucleophilic fluorine source; for 69: 1-(triisopropylsilyl)-1H-pyrrole; for 70: anisole), and the mixture was dried azeotropically (concentration of an anhydrous benzene solution, 2×10 mL) under reduced pressure and placed under an argon atmosphere. Anhydrous nitroethane (4 mL) was introduced via syringe, and the mixture was cooled to 0° C. in an ice-water bath. A solution of silver(I) tetrafluoroborate (2.30 equiv) in anhydrous nitroethane (1 mL) at 0° C. was introduced via syringe to the solution containing the tetracyclic bromide (+)-54 over 1 min. The reaction flask was covered in aluminum foil. The ice-water bath was removed, and the reaction mixture was allowed to warm to 23° C. After 1 h, saturated aqueous sodium chloride solution (10 mL) was introduced, and the resulting biphasic mixture was vigorously stirred for 30 min at 23° C. The reaction mixture was diluted with ethyl acetate (50 mL), was filtered through a Celite pad, and the solids were washed with ethyl acetate (3×15 mL). The combined filtrates were washed with 5% aqueous citric acid solution (2×20 mL), water (3×20 mL), and saturated aqueous sodium chloride solution (15 mL). The organic layer was dried over anhydrous sodium sulfate, was filtered, and was concentrated under reduced pressure.

C3-Fluoro Friedel-Crafts adduct 68: $^1$H NMR (600 MHz, CDCl$_3$, 20° C.): δ 7.79 (app-dd, J=0.9, 8.2, 2H, SO$_2$Ph-o-H), 7.56 (d, J=8.2, 1H, $C_8$H), 7.50 (t, J=7.5, 1H, SO$_2$Ph-p-H), 7.39-7.35 (m, 1H, $C_7$H), 7.38 (dd, J=7.9, 8.3, 2H, SO$_2$Ph-m-H), 7.34 (d, J=7.7, 1H, $C_5$H), 7.15 (dd, J=7.5, 7.6, 1H, $C_6$H), 6.07 (d, J=14.5, 1H, $C_2$H), 4.53 (dd, J=8.2, 8.4, 1H, $C_{11}$H), 4.17 (d, J=17.6, 1H, $C_{15}H_a$), 3.86 (d, J=17.6, 1H, $C_{15}H_b$), 3.06-2.97 (m, 1H, $C_{12}H_a$), 2.93-2.83 (m, 1H, $C_{12}H_b$), 2.90 (s, 3H, $C_{17}H_3$). $^{19}$F NMR (282.4 MHz, CDCl$_3$, 20° C.): δ −133.3. MS (ESI) (m/z): [M+H]$^+$: 416.22, [M+Na]$^+$: 438.25, [2M+H]$^+$: 833.73, [2M+Na]$^+$: 853.59. TLC (20% acetone in dichloromethane), Rf: 0.46 (UV, CAM).

C3-(N-TIPS-Pyrrol-3'-yl) Friedel-Crafts adduct 69: $^1$H NMR (600 MHz, CDCl$_3$, 20° C.): δ 8.03 (app-dd, J=1.0, 7.3, 2H, SO$_2$Ph-o-H), 7.63 (d, J=7.7, 1H, $C_8$H), 7.54 (app-dt, J=1.5, 7.5, 1H, SO$_2$Ph-p-H), 7.43 (app-t, J=7.6, 2H, SO$_2$Ph-m-H), 7.16-7.11 (m, 1H, $C_7$H), 7.05-6.99 (m, 2H, $C_5$H+$C_6$H), 6.69-6.65 (m, 1H, $C_5$H), 6.53-5.49 (m, 1H, $C_4$H), 6.09 (s, 1H, $C_2$H), 5.83-5.79 (m, 1H, $C_2$H), 4.33 (dd, J=8.2, 8.9, 1H, $C_{11}$H), 4.10 (d, J=17.8, 1H, $C_{15}H_a$), 3.95 (app-dd, J=2.0, 17.6, 1H, $C_{15}H_b$), 2.99 (s, 3H, $C_{17}H_3$), 2.84 (dd, J=7.4, 13.3, 1H, $C_{12}H_a$), 2.73 (dd, J=10.0, 13.3, 1H, $C_{12}H_b$), 1.40 (app-dsp, J=1.6, 7.5, 3H, SiCH(CH$_3$)$_2$), 1.08 (d, J=7.6, 9H, SiCH(CH$_3$)$_2$), 1.07 (d, J=6.3, 9H, SiCH(CH$_3$)$_2$). $^{13}$C NMR (150 MHz, CDCl$_3$, 20° C.): δ 167.7 ($C_{13}$), 166.8 ($C_{16}$), 139.5 ($C_9$), 137.6 (SO$_2$Ph-ipso-C), 135.9 ($C_4$), 133.4 (SO$_2$Ph-p-C), 129.0 (SO$_2$Ph-m-C), 128.9 ($C_7$), 128.2 (SO$_2$Ph-o-C), 125.7 ($C_{5'}$), 125.0 ($C_{3'}$), 124.6 ($C_6$), 124.0 ($C_5$), 121.2 ($C_{2'}$), 115.6 ($C_8$), 109.4 ($C_{4'}$), 84.8 ($C_2$), 59.5 ($C_{11}$), 55.3 ($C_3$), 54.5 ($C_{15}$), 39.6 ($C_{12}$), 33.6 ($C_{17}$), 17.9 (SiCH(CH$_3$)$_2$), 11.7 (SiCH(CH$_3$)$_2$). MS (ESI) (m/z): [M+H]: 619.49, [M+Na]$^+$: 641.49, [2M+Na]$^+$: 1261.37. TLC (20% acetone in dichloromethane), Rf: 0.48 (UV, CAM).

C3-(p-Methoxyphenyl) Friedel-Crafts adduct 70: $^1$H NMR (600 MHz, CDCl$_3$, 20° C.): δ 7.60 (app-dd, J=0.7, 8.1, 1H, $C_8$H), 7.46 (app-dd, J=1.1, 8.4, 2H, SO$_2$Ph-o-H), 7.34 (app-dt, J=1.1, 7.5, 1H, SO$_2$Ph-p-H), 7.30-7.26 (m, 1H, $C_7$H), 7.14-7.11 (m, 2H, $C_5$H+$C_6$H), 7.11 (app-t, J=7.5, 2H, SO$_2$Ph-m-H), 6.67 (d, J=8.9, 2H, $C_2$H), 6.63 (d, J=8.9, 1H, $C_{3'}$H), 6.15 (s, 1H, $C_2$H), 4.42 (dd, J=7.6, 8.2, 1H, $C_{11}$H), 4.12 (d, J=17.5, 1H, $C_{15}H_b$), 3.84 (d, J=17.5, 1H, $C_{15}H_a$), 3.78 (s, 3H, $C_5$H$_3$), 3.10 (dd, J=6.8, 14.2, 1H, $C_{12}H_a$), 2.91-2.85 (m, 1H, $C_{12}H_b$), 2.90 (s, 3H, $C_{17}H_3$). MS (ESI) (m/z): [M+Na]$^+$: 526.31, [2M+Na]$^+$: 1029.94. TLC (20% acetone in dichloromethane), Rf: 0.37 (UV, CAM).

General Procedure for the Regio- and Stereoselective Hydroxylation.

Freshly prepared tetra-n-butylammonium permanganate (4.0 equiv) was added as a solid to a solution of the corresponding diketopiperazine (54, 68-70) (1 equiv) in dichloromethane (0.05 M) at 23° C. After 2 h, the dark purple solution was diluted with saturated aqueous sodium sulfite solution (20 mL) and then with ethyl acetate (120 mL). The resulting mixture was washed sequentially with saturated aqueous sodium hydrogenocarbonate solution (20 mL), water (4×20 mL), and saturated aqueous sodium chloride solution (20 mL). The organic layer was dried over anhydrous sodium sulfate, was filtered, and was concentrated under reduced pressure.

1055 (w), 756 (s). HRMS (ESI) (m/z): calc'd for $C_{20}H_{16}BrN_3NaO_4S_3$ [M+Na]$^+$: 559.9379. found 559.9392. TLC (20% ethyl acetate in dichloromethane), Rf: 0.47 (UV, $I_2$, CAM). The relative stereochemistry of the epidisulfide bridge of the β-epimer 30 has been confirmed by key NOESY

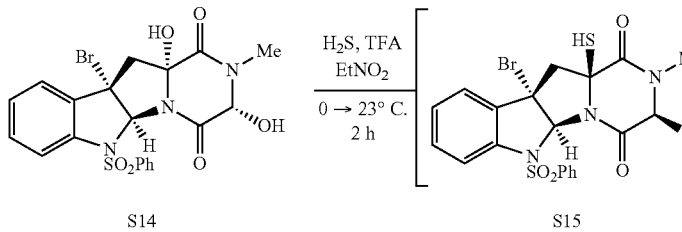

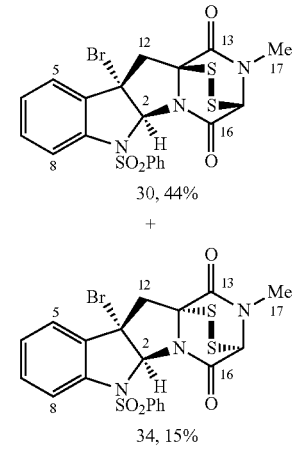

C3-Bromo epidithiodiketopiperazines 30 and 34

This compound was prepared in two steps starting from bishemiaminal S14 (13.5 mg, 26.6 μmol) using the methodology developed to access the corresponding C3-(indol-3'-yl) epidithiodiketopiperazine 26. The orange residue was purified by flash column chromatography on silica gel (eluent: gradient, 15→40% ethyl acetate in dichloromethane) to afford the β-epimer of epidithiodiketopiperazine 30 (6.3 mg, 44%) as a colorless oil and its α-epimer 34 (2.1 mg, 15%) as a colorless oil. Structural assignments were made with additional information from gCOSY, HSQC, and gHMBC data.

S14:

$^1$H NMR (600 MHz, MeOD-d$_4$, 20° C.): δ 7.89 (app-dd, J=0.8, 8.2, 2H, $SO_2$Ph-o-H), 7.56 (t, J=7.5, 1H, $SO_2$Ph-p-H), 7.47 (d, J=8.3, 1H, $C_8$H), 7.44 (dd, J=7.5, 8.2 2H, $SO_2$Ph-m-H), 7.38 (d, J=7.7, 1H, $C_5$H), 7.33 (app-dt, J=1.0, 7.7, 1H, $C_7$H), 7.16 (app-dt, J=0.6, 7.5, 1H, $C_6$H), 6.55 (s, 1H, $C_2$H), 4.99 (s, 1H, $C_{15}$H), 3.71 (d, J=15.4, 1H, $C_{12}H_a$), 3.09 (d, J=15.4, 1H, $C_{12}H_b$), 2.86 (s, 3H, $C_{17}H_3$). MS (ESI) (m/z): [2M+Na]$^+$: 1039.24. TLC (20% acetone in dichloromethane), Rf: 0.40 (UV, CAM).

β-Epimer 30:

$^1$H NMR (600 MHz, CDCl$_3$, 20° C.): δ 7.82 (d, J=8.0, 2H, $SO_2$Ph-o-H), 7.60 (d, J=8.2, 1H, $C_8$H), 7.52 (app-dd, J=7.4, 7.6, 1H, $SO_2$Ph-p-H), 7.42-7.38 (m, 1H, $C_7$H), 7.40 (app-t, J=7.7, 2H, $SO_2$Ph-m-H), 7.35 (d, J=7.7, 1H, $C_5$H), 7.25 (app-t, J=7.6, 1H, $C_6$H), 6.47 (s, 1H, $C_2$H), 5.22 (s, 1H, $C_{15}$H), 3.82 (d, J=15.4, 1H, $C_{12}H_a$), 3.19 (d, J=15.4, 1H, $C_{12}H_b$), 3.11 (s, 3H, $C_{17}H_3$). $^{13}$C NMR (150 MHz, CDCl$_3$, 20° C.): δ 164.3 ($C_{13}$), 159.6 ($C_{16}$), 140.2 ($C_9$), 138.1 ($SO_2$Ph-ipso-C), 135.1 ($C_4$), 134.1 ($SO_2$Ph-p-C), 131.5 ($C_7$), 129.2 ($SO_2$Ph-m-C), 128.3 ($SO_2$Ph-o-C), 127.1 ($C_6$), 124.3 ($C_5$), 118.9 ($C_8$), 87.4 ($C_2$), 74.0 ($C_{11}$), 68.3 ($C_{15}$), 58.2 ($C_3$), 46.7 ($C_{12}$), 32.3 ($C_{17}$). FTIR (thin film) cm$^{-1}$: 2926 (m), 2857 (w), 1771 (m), 1697 (s), 1551 (w), 1449 (m), 1368 (s), 1170 (s), 1090 (w), cross-peaks on the corresponding bis(methylthioether). Assignment is supported by key NOESY signals ($^1$H,$^1$H) in ppm: (1.86, 3.40), (3.40, 7.36), (3.11, 6.68). This derivatized compound was prepared in one step using the methodology developed to access (+)-gliocladin B (Boyer, N.; Movassaghi, M. *Chem. Sci.* 2012, 3, 1798). {$^1$H NMR (600 MHz, CDCl$_3$, 20° C.): δ 7.82 (d, J=8.1, 2H, $SO_2$Ph-o-H), 7.59 (d, J=8.2, 1H, $C_8$H), 7.55 (app-dd, J=7.3, 7.6, 1H, $SO_2$Ph-p-H), 7.45 (dd, J=7.7, 7.8, 2H, $SO_2$Ph-m-H), 7.39 (app-t, J=7.9, 1H, $C_7$H), 7.36 (d, J=7.8, 1H, $C_5$H), 7.19 (app-t, J=7.6, 1H, $C_6$H), 6.68 (s, 1H, $C_2$H), 4.52 (s, 1H, $C_{15}$H), 3.40 (d, J=14.5, 1H, $C_{12}H_a$), 3.11 (d, J=14.5, 1H, $C_{12}H_b$), 3.06 (s, 3H, $C_{17}H_3$), 2.27 (s, 3H, $C_{15}SCH_3$), 1.86 (s, 3H, $C_{11}SCH_3$). $^{13}$C NMR (150 MHz, CDCl$_3$, 20° C.): δ 164.0 ($C_{13}$), 163.5 ($C_{16}$), 140.5 ($C_9$), 138.8 ($SO_2$Ph-ipso-C), 137.2 ($C_4$), 133.6 ($SO_2$Ph-p-C), 131.1 ($C_7$), 129.3 ($SO_2$Ph-m-C), 127.6 ($SO_2$Ph-o-C), 125.9 ($C_6$), 123.8 ($C_5$), 117.9 ($C_8$), 86.8 ($C_2$), 69.7 ($C_{11}$), 67.3 ($C_{15}$), 58.0 ($C_3$), 49.9 ($C_{12}$), 32.7 ($C_{17}$), 17.2 ($C_{15}SCH_3$), 15.4 ($C_{11}SCH_3$).}

α-Epimer 34:

$^1$H NMR (600 MHz, CDCl$_3$, 20° C.): δ 7.91 (d, J=8.1, 2H, $SO_2$Ph-o-H), 7.53-7.51 (m, 1H, $SO_2$Ph-p-H), 7.52 (d, J=7.9, 1H, $C_8$H), 7.41 (app-t, J=7.7, 2H, $SO_2$Ph-m-H), 7.38 (d, J=7.9, 1H, $C_5$H), 7.32 (dd, J=7.6, 8.0, 1H, $C_7$H), 7.17 (app-t, J=7.6, 1H, $C_6$H), 6.61 (s, 1H, $C_2$H), 5.16 (s, 1H, $C_{15}$H), 4.25 (d, J=15.0, 1H, $C_{12}H_a$), 3.09 (d, J=15.0, 1H, $C_{12}H_b$), 2.95 (s, 3H, $C_{17}H_3$). $^{13}$C NMR (150 MHz, CDCl$_3$, 20° C.): δ 164.1 ($C_{13}$), 160.9 ($C_{16}$), 138.8 ($C_9$), 138.2 ($SO_2$Ph-ipso-C), 134.1 ($SO_2$Ph-p-C), 133.6 ($C_4$), 131.5 ($C_7$), 129.2 ($SO_2$Ph-m-C), 128.4 ($SO_2$Ph-o-C), 126.8 ($C_6$), 125.2 ($C_5$), 117.7 ($C_8$), 87.7 ($C_2$), 73.8 ($C_{11}$), 68.9 ($C_{15}$), 58.2 ($C_3$), 45.0 ($C_{12}$), 31.9 ($C_{17}$). FTIR (thin film) cm$^{-1}$: 3296 (w), 3008 (m), 2925 (s), 2855 (s), 1771 (m), 1699 (s), 1552 (m), 1463 (s), 1447 (s), 1368 (s), 1171 (s), 1091 (s), 1057 (m), 757 (s). HRMS (ESI) (m/z): calc'd for $C_{20}H_{16}BrN_3NaO_4S_3$ [M+Na]$^+$: 559.9379. found 559.9396. TLC (20% ethyl acetate in dichloromethane), Rf: 0.56 (UV, $I_2$, CAM).

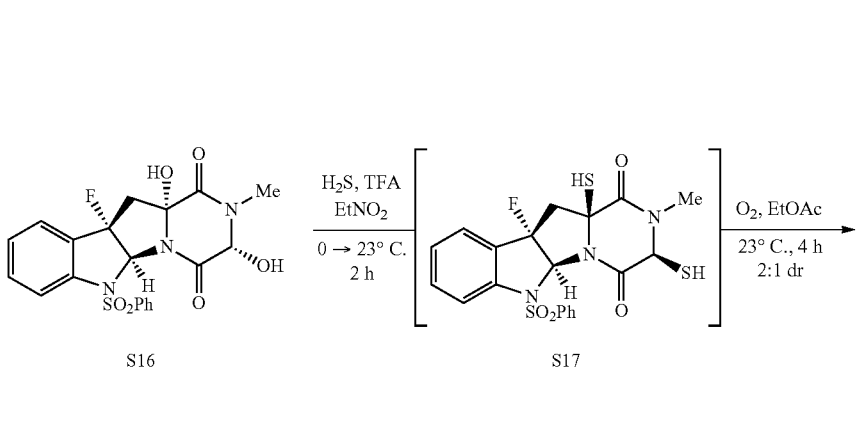
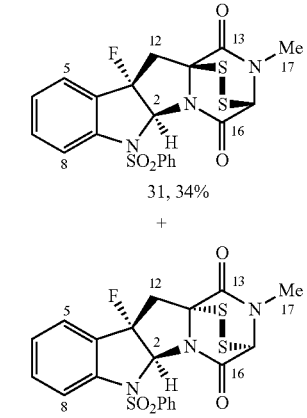

31, 34%

+

35, 13%

C3-Fluoro epidithiodiketopiperazines 31 and 35

This compound was prepared in two steps starting from bishemiaminal S16 (15.1 mg, 33.7 μmol) using the methodology developed to access the corresponding C3-(indol-3'-yl) epidithiodiketopiperazine 26. The orange residue was purified by flash column chromatography on silica gel (eluent: gradient, 15→40% ethyl acetate in dichloromethane) to afford the β-epimer of epidithiodiketopiperazine 31 (5.4 mg, 34%) as a colorless oil and its α-epimer 35 (2.1 mg, 13%) as a colorless oil. Structural assignments were made with additional information from gCOSY, HSQC, and gHMBC data.

S16:
$^1$H NMR (600 MHz, CDCl$_3$, 20° C.): δ 7.68 (d, J=7.6, 2H, SO$_2$Ph-o-H), 7.56 (d, J=8.2, 1H, C$_8$H), 7.50 (t, J=8.2, 1H, SO$_2$Ph-p-H), 7.43 (dd, J=7.6, 8.2, 1H, C$_7$H), 7.36 (app-t, J=7.9, 2H, SO$_2$Ph-m-H), 7.36-7.33 (m, 1H, C$_5$H), 7.18 (app-t, J=7.5, 1H, C$_6$H), 6.44 (d, J=13.2, 1H, C$_2$H), 5.75 (br-s, 2H, C$_{11}$OH+C$_{15}$OH), 5.13 (s, 1H, C$_{15}$H), 3.49 (dd, J=8.6, 15.6, 1H, C$_{12}$H$_a$), 3.02 (s, 3H, C$_{17}$H$_3$), 2.97 (dd, J=15.6, 20.8, 1H, C$_{12}$H$_b$). $^{13}$C NMR (100 MHz, CDCl$_3$, 20° C.): δ 166.7 (C$_{13}$), 166.4 (C$_{16}$), 141.8 (d, J=4.6, C$_9$), 136.8 (SO$_2$Ph-ipso-C), 134.0 (SO$_2$Ph-p-C), 132.2 (d, J=3.2, C$_7$), 130.6 (d, J=23.5, C$_4$), 129.2 (SO$_2$Ph-m-C), 128.0 (SO$_2$Ph-o-C), 126.8 (C$_6$), 125.5 (C$_5$), 118.5 (C$_8$), 101.7 (d, J=202.3, C$_3$), 88.5 (d, J=4.1, C11), 83.1 (d, J=33.0, C$_2$), 83.0 (C$_{15}$), 42.9 (d, J=29.7, C$_{12}$), 32.6 (C$_{17}$). $^{19}$F NMR (282.4 MHz, CDCl$_3$, 20° C.): δ-133.2. FTIR (thin film) cm$^{-1}$: 3365 (br-m), 1695 (br-s), 1447 (m), 1402 (m), 1365 (m), 1342 (m), 1173 (m), 1087 (w), 1023 (w), 912 (w), 729 (m), 600 (m). HRMS (ESI) (m/z): calc'd for C$_{20}$H$_{19}$FN$_3$O$_6$S [M+H]$^+$: 448.0973. found 448.0963; calc'd for C$_{20}$H$_{15}$FN$_3$NaO$_6$S [M+Na]$^+$: 470.0793. found 470.0780. TLC (20% acetone in dichloromethane), Rf: 0.29 (UV, CAM).

β-Epimer 31:
$^1$H NMR (600 MHz, CDCl$_3$, 20° C.): δ 7.68 (app-dd, J=1.1, 7.4, 2H, SO$_2$Ph-o-H), 7.64 (d, J=8.2, 1H, C$_8$H), 7.51 (t, J=7.5, 1H, SO$_2$Ph-p-H), 7.50 (app-dt, J=1.1, 6.7, 1H, C$_7$H), 7.38 (dd, J=7.6, 8.1, 2H, SO$_2$Ph-m-H), 7.40-7.36 (m, 1H, C$_6$H), 7.28 (d, J=7.6, 1H, C$_5$H), 6.31 (d, J=11.8, 1H, C$_2$H), 5.23 (s, 1H, C$_{15}$H), 3.65 (app-t, J=15.2, 1H, C$_{12}$H$_a$), 3.13 (s, 3H, C$_{17}$H$_3$), 2.89 (app-d, J=15.1, 1H, C$_{12}$H$_b$). $^{13}$C NMR (150 MHz, CDCl$_3$, 20° C.): δ 164.5 (C$_{13}$), 160.0 (C$_{16}$), 143.2 (d, J=4.8, C$_9$), 137.3 (SO$_2$Ph-ipso-C), 133.8 (SO$_2$Ph-p-C), 132.8 (d, J=3.4, C$_7$), 129.9 (d, J=23.3, C$_4$), 129.1 (SO$_2$Ph-m-C), 127.9 (SO$_2$Ph-o-C), 126.8 (d, J=2.8, C$_6$), 124.8 (C$_5$), 119.4 (d, J=2.2, C$_8$), 102.3 (d, J=205.5, C$_3$), 82.7 (d, J=31.8, C$_2$), 74.4 (d, J=6.2, C11), 68.4 (C$_{15}$), 39.2 (d, J=32.3, C$_{12}$), 32.3 (C$_{17}$). $^{19}$F NMR (282 MHz, CDCl$_3$, 20° C.): δ-137.7. FTIR (thin film) cm$^{-1}$: 2999 (w), 2920 (w), 1693 (s), 1447 (w), 1368 (m), 1173 (m), 1088 (w), 1040 (w), 914 (w), 719 (w). HRMS (ESI) (m/z): calc'd for C$_{20}$H$_{17}$FN$_3$O$_4$S$_3$ [M+H]$^+$: 478.0360. found 478.0375; calc'd for C$_{20}$H$_{16}$FN$_3$NaO$_4$S$_3$ [M+Na]$^+$: 500.0179. found 500.0198. TLC (20% ethyl acetate in dichloromethane), Rf: 0.27 (UV, I$_2$, CAM). The relative stereochemistry of the epidisulfide bridge of the β-epimer 31 has been confirmed by key NOESY cross-peaks on the corresponding bis(methylthioether). Assignment is supported by key NOESY signals ($^1$H, $^1$H) in ppm: (1.93, 3.11), (3.11, 7.41), (2.94, 6.45). This derivatized compound was prepared in one step using the methodology developed to access (+)-gliocladin B (Boyer, N.; Movassaghi, M. *Chem. Sci.* 2012, 3, 1798). {$^1$H NMR (600 MHz, CDCl$_3$, 20° C.): δ 7.94 (d, J=8.0, 2H, SO$_2$Ph-o-H), 7.72 (d, J=8.3, 1H, C$_8$H), 7.56 (app-dd, J=7.4, 7.5, 1H, SO$_2$Ph-p-H), 7.49-7.45 (m, 1H, C$_7$H), 7.47 (app-t, J=7.7, 2H, SO$_2$Ph-m-H), 7.41 (d, J=7.7, 1H, C$_5$H), 7.20 (app-t, J=7.5, 1H, C$_6$H), 6.45 (d, J=17.5, 1H, C$_2$H), 4.58 (s, 1H, C$_{15}$H), 3.11 (app-t, J=14.3, 1H, C$_{12}$H$_a$), 3.09 (s, 3H, C$_{17}$H$_3$), 2.94 (dd, J=14.3, 20.1, 1H, C$_{12}$H$_b$), 2.30 (s, 3H, C$_{19}$H$_3$), 1.93 (s, 3H, C$_{20}$H$_3$). $^{13}$C NMR (150 MHz, CDCl$_3$, 20° C.): δ 164.3 (C$_{13}$), 160.2 (C$_{16}$), 144.1 (d, J=5.1, C$_9$), 138.3 (SO$_2$Ph-ipso-C), 133.6 (SO$_2$Ph-p-C), 132.4 (d, J=3.2, C$_7$), 129.3 (SO$_2$Ph-m-C), 128.8 (d, J=23.9, C$_4$), 127.5 (SO$_2$Ph-o-C), 125.3 (d, J=2.7, C$_6$), 124.2 (C$_5$), 117.1 (d, J=1.8, C$_8$), 102.8 (d, J=200.8, C$_3$), 82.0 (d, J=32.5, C$_2$), 70.6 (d, J=6.5, C$_{11}$), 67.1 (C$_{15}$), 45.5 (d, J=31.8, C$_{12}$), 32.8 (C$_{17}$), 16.9 (C$_{15}$SCH$_3$), 15.2 (C$_{11}$SCH$_3$). $^{19}$F NMR (282.4 MHz, CDCl$_3$, 20° C.): δ-135.0. MS (ESI) (m/z): [M+Na]$^+$: 530.52, [2M+Na]$^+$: 1038.00.}

α-Epimer 35:
$^1$H NMR (600 MHz, CDCl$_3$, 20° C.): δ 7.74 (d, J=8.5, 2H, SO$_2$Ph-o-H), 7.59 (d, J=8.2, 1H, C$_8$H), 7.51 (app-dt, J=1.1, 7.6, 1H, SO$_2$Ph-p-H), 7.43 (dd, J=7.5, 7.6, 1H, C$_7$H), 7.40 (d, J=7.5, 1H, C$_5$H), 7.39 (app-t, J=7.6, 2H, SO$_2$Ph-m-H), 7.20 (dd, J=7.5, 7.6, 1H, C$_6$H), 6.43 (d, J=11.5, 1H, C$_2$H), 5.21 (s, 1H, C$_{15}$H), 3.89 (dd, J=5.2, 15.2, 1H, C$_{12}$H$_a$), 3.01 (s, 3H, C$_{17}$H$_3$), 2.85 (app-ddd, J=0.5, 15.9, 16.6, 1H, C$_{12}$H$_b$). $^{13}$C NMR (150 MHz, CDCl$_3$, 20° C.): δ 164.2 (C$_{13}$), 161.6 (C$_{16}$), 141.9 (d, J=3.7, C$_9$), 137.0 (SO$_2$Ph-ipso-C), 134.0 (SO$_2$Ph-p-C), 132.8 (d, J=2.8, C$_7$), 129.2 (SO$_2$Ph-m-C), 128.6 (d, J=19.5, C$_4$), 128.0 (SO$_2$Ph-o-C), 126.8 (C$_6$), 125.4 (C$_5$), 118.5 (C$_5$), 101.8 (d, J=170.3, C$_3$), 83.1 (d, J=26.9, C$_2$), 74.0

(d, J=4.0, $C_{11}$), 68.6 ($C_{15}$), 39.2 (d, J=26.4, $C_{12}$), 31.9 ($C_{17}$). $^{19}$F NMR (282 MHz, CDCl$_3$, 20° C.): δ −134.1. FTIR (thin film) cm$^{-1}$: 3069 (w), 2991 (w), 1699 (s), 1448 (w), 1367 (m), 1335 (m), 1173 (m), 1089 (w), 908 (w), 730 (m), 720 (m). HRMS (ESI) (m/z): calc'd for $C_{20}H_{17}FN_3O_4S_3$ [M+H]$^+$: 478.0360. found 478.0372; calc'd for $C_{20}H_{16}FN_3NaO_4S_3$ [M+Na]$^+$: 500.0179. found 500.0199. TLC (20% ethyl acetate in dichloromethane), Rf: 0.16 (UV, I$_2$, CAM).

C), 137.5 ($C_4$), 132.8 (SO$_2$Ph-p-C), 128.9 (SO$_2$Ph-m-C), 128.8 ($C_7$), 127.1 (SO$_2$Ph-o-C), 125.7 ($C_{3'}$), 124.9 ($C_6$), 123.5 ($C_5$), 119.3 ($C_{5'}$), 117.0 ($C_8$), 115.6 ($C_{2'}$), 106.3 ($C_{4'}$), 86.0 ($C_2$), 69.7 ($C_{11}$), 67.7 ($C_{15}$), 53.1 ($C_3$), 45.7 ($C_{12}$), 32.5 ($C_{17}$), 17.3 ($C_{15}$SCH$_3$), 15.5 ($C_{11}$SCH$_3$).} $^1$H NMR (600 MHz, CDCl$_3$, 20° C.): δ 7.86 (br-s, 1H, N$_1$H), 7.57 (d, J=8.1, 1H, C$_8$H), 7.49 (d, J=8.4, 2H, SO$_2$Ph-o-H), 7.36 (app-dt, J=1.1, 7.6, 1H, SO$_2$Ph-p-H), 7.35 (app-t, J=8.2, 1H, C$_7$H), 7.23 (d,

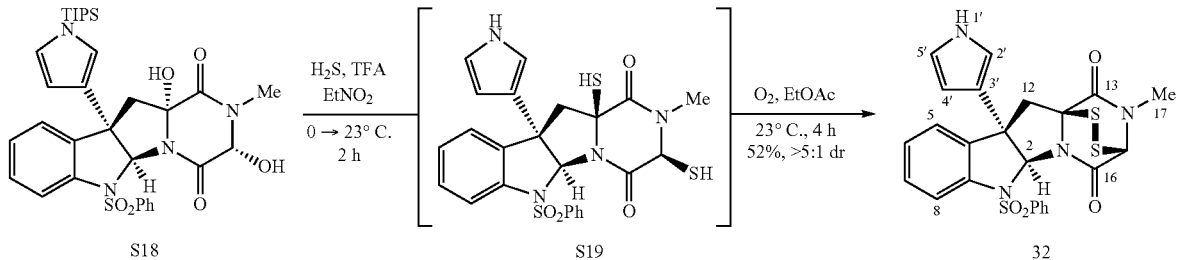

S18    S19    32

C3-(Pyrrol-3'-yl) epidithiodiketopiperazine 32

This compound was prepared in two steps starting from bishemiaminal S18 (308 mg, 473 μmol) using the methodology developed to access the corresponding C3-(indol-3'-yl) epidithiodiketopiperazine 26. The orange residue was purified by flash column chromatography on silica gel (eluent: gradient, 10→40% ethyl acetate in dichloromethane) to afford the epidithiodiketopiperazine 32 (128 mg, 51.5%) as a pale yellow solid. Structural assignments were made with additional information from gCOSY, HSQC, and gHMBC data. The relative stereochemistry of the epidisulfide bridge 32 has been confirmed by key NOESY cross-peaks on the corresponding bis(methylthioether). Assignment is supported by key NOESY signals ($^1$H,$^1$H) in ppm: (1.89, 3.06), (2.91, 5.86-5.82), (2.91, 6.07-6.04), (2.91, 6.47). This derivatized compound was prepared in one step using the methodology developed to access (+)-gliocladin B (Boyer, N.; Movassaghi, M. Chem. Sci. 2012, 3, 1798). {$^1$H NMR (600 MHz, CDCl$_3$, 20° C.): δ 8.07 (br-s, 1H, N$_1$H), 7.84 (d, J=7.5, 2H, SO$_2$Ph-o-H), 7.50 (d, J=8.2, 1H, C$_8$H), 7.47 (t, J=7.5, 1H, SO$_2$Ph-p-H), 7.35 (app-t, J=7.9, 2H, SO$_2$Ph-m-H), 7.28 (app-dt, J=1.1, 7.8, 1H, C$_7$H), 7.19 (d, J=7.4, 1H, C$_5$H), 7.09 (dd, J=7.4, 7.5, 1H, C$_6$H), 6.65-6.62 (m, 1H, C$_5$H), 6.47 (s, 1H, C$_2$H), 6.07-6.04 (m, 1H, C$_{2'}$H), 5.86-5.82 (m, 1H, C$_{4'}$H), 4.50 (s, 1H, C$_{15}$H), 3.06 (d, J=14.4, 1H, C$_{12}$H$_a$), 3.06 (s, 3H, C$_{18}$H$_3$), 2.91 (d, J=14.4, 1H, C$_{12}$H$_b$), 2.23 (s, 3H, C$_{15}$SCH$_3$), 1.89 (s, 3H, C$_{11}$SCH$_3$). $^{13}$C NMR (150 MHz, CDCl$_3$, 20° C.): δ 165.3 ($C_{13}$), 162.6 ($C_{16}$), 142.1 ($C_9$), 140.0 (SO$_2$Ph-ipso- J=7.5, 1H, C$_5$H), 7.19 (dd, J=7.4, 7.5, 1H, C$_6$H), 7.15 (app-dt, J=0.9, 7.4, 2H, SO$_2$Ph-m-H), 6.72-6.69 (m, 1H, C$_{5'}$H), 6.28 (s, 1H, C$_{2'}$H), 6.03-5.99 (m, 1H, C$_{4'}$H), 5.58-5.54 (m, 1H, C$_{2'}$H), 5.22 (s, 1H, C$_{15}$H), 3.60 (d, J=15.5, 1H, C$_{12}$H$_a$), 3.13 (s, 3H, C$_{17}$H$_3$), 2.82 (d, J=15.5, 1H, C$_{12}$H$_b$). $^{13}$C NMR (150 MHz, CDCl$_3$, 20° C.): δ 165.4 ($C_{13}$), 160.3 ($C_{16}$), 140.9 ($C_9$), 138.6 (SO$_2$Ph-ipso-C), 137.2 ($C_4$), 132.9 (SO$_2$Ph-p-C), 129.5 ($C_7$), 128.5 (SO$_2$Ph-m-C), 127.6 (SO$_2$Ph-o-C), 126.0 ($C_6$), 124.5 ($C_5$), 123.5 ($C_{3'}$), 119.6 ($C_{5'}$), 118.5 ($C_8$), 117.1 ($C_{2'}$), 106.4 ($C_{4'}$), 87.1 ($C_2$), 74.4 ($C_{11}$), 68.4 ($C_{15}$), 55.4 ($C_3$), 44.2 ($C_{12}$), 32.2 ($C_{17}$). FTIR (thin film) cm$^{-1}$: 3391 (w), 2925 (w), 1699 (s), 1458 (m), 1360 (m), 1169 (m), 1090 (w), 749 (m). HRMS (ESI) (m/z): calc'd for $C_{24}H_{20}N_4NaO_4S_3$ [M+Na]$^+$: 547.0539. found 547.0560. TLC (20% ethyl acetate in dichloromethane), Rf: 0.33 (UV, I$_2$, CAM).

S18:

$^1$H NMR (600 MHz, acetone-d$_6$, 20° C.): δ 7.75 (app-dd, J=0.8, 7.5, 2H, SO$_2$Ph-o-H), 7.54 (app-dt, J=0.9, 7.5, 1H, SO$_2$Ph-p-H), 7.37 (app-dt, J=0.7, 7.6, 2H, SO$_2$Ph-m-H), 7.30 (d, J=7.6, 1H, C$_8$H), 7.26 (app-dd, J=0.4, 7.7, 1H, C$_5$H), 7.22 (app-dt, J=1.1, 7.6, 1H, C$_6$H), 7.12 (app-dt, J=1.1, 7.4, 1H, C$_7$H), 6.72-6.69 (m, 1H, C$_{5'}$H), 6.66-6.63 (m, 1H, C$_{4'}$H), 6.39 (s, 1H, C$_{2'}$H), 6.25 (br-s, 1H, C$_{11}$OH), 6.09 (br-s, 1H, C$_{15}$OH), 5.71-5.68 (m, 1H, C$_{2'}$H), 5.05 (s, 1H, C$_{15}$H), 3.35 (d, J=14.7, 1H, C$_{12}$H$_a$), 2.92 (s, 3H, C$_{17}$H$_3$), 2.85 (d, J=14.7, 1H, C$_{12}$H$_b$), 1.46 (sp, J=7.5, 3H, SiCH(CH$_3$)$_2$), 1.08 (d, J=7.5, 18H, SiCH(CH$_3$)$_2$). MS (ESI) (m/z): [M+Na]$^+$: 547.0539. TLC (20% acetone in dichloromethane), Rf: 0.44 (UV, I$_2$, CAM).

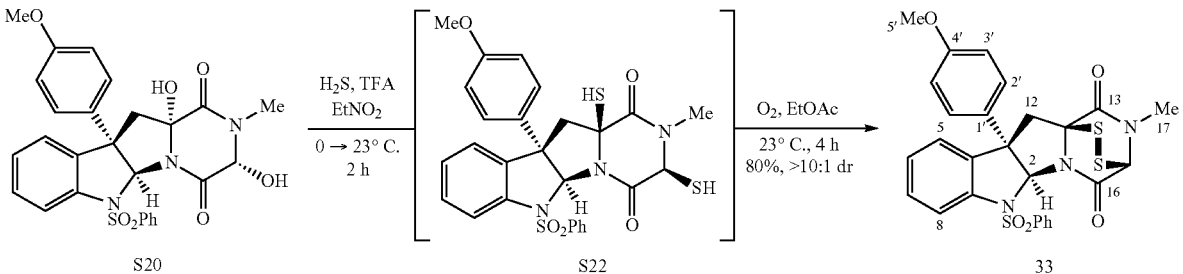

S20    S22    33

C3-(p-Methoxyphenyl)epidithiodiketopiperazine 33

This compound was prepared in two steps starting from bishemiaminal S20 (380 mg, 709 mmol) using the methodology developed to access the corresponding C3-(indol-3'-yl) epidithiodiketopiperazine 26. The orange residue was purified by flash column chromatography on silica gel (eluent: gradient, 5→25% ethyl acetate in dichloromethane) to afford the epidithiodiketopiperazine 33 (321 mg, 80.0%) as a pale yellow solid. Structural assignments were made with additional information from gCOSY, HSQC, and gHMBC data. The relative stereochemistry of the epidisulfide bridge 33 has been confirmed by key NOESY cross-peaks on the corresponding bis(methylthioether). Assignment is supported by key NOESY signals ($^1$H,$^1$H) in ppm: (1.89, 3.13), (3.13, 7.13-7.07), (2.98, 6.89), (2.98, 6.47). This derivatized compound was prepared in one step using the methodology developed to access (+)-gliocladin B (Boyer, N.; Movassaghi, M. *Chem. Sci.* 2012, 3, 1798). {$^1$H NMR (600 MHz, CDCl$_3$, 20° C.): δ 7.85 (app-dd, J=0.7, 7.7, 2H, SO$_2$Ph-o-H), 7.54 (d, J=8.1, 1H, C$_8$H), 7.48 (t, J=7.3, 1H, SO$_2$Ph-p-H), 7.35 (app-t, J=7.8, 2H, SO$_2$Ph-m-H), 7.30 (app-dt, J=1.4, 7.5, 1H, C$_7$H), 7.13-7.07 (m, 2H, C$_5$H+C$_6$H), 6.89 (d, J=8.8, 2H, C$_2$·H), 6.70 (d, J=8.8, 2H, C$_3$·H), 6.64 (s, 1H, C$_{15}$H), 4.48 (s, 1H, C$_2$H), 3.75 (s, 3H, C$_{5'}$H$_3$), 3.13 (d, J=14.3, 1H, C$_{12}$H$_a$), 3.06 (s, 3H, C$_{17}$H$_3$), 2.98 (d, J=14.3, 1H, C$_{12}$H$_b$), 2.20 (s, 3H, C$_{15}$SCH$_3$), 1.89 (s, 3H, C$_{11}$SCH$_3$). $^{13}$C NMR (150 MHz, CDCl$_3$, 20° C.): δ 165.1 (C$_{13}$), 162.3 (C$_{16}$), 158.8 (C$_{4'}$), 142.3 (C$_9$), 140.1 (SO$_2$Ph-ipso-C), 136.7 (C$_4$), 134.2 (C$_{1'}$), 132.9 (SO$_2$Ph-p-C), 129.1 (SO$_2$Ph-m-C), 127.1 (C$_{2'}$), 127.1 (C$_7$), 127.0 (SO$_2$Ph-o-C), 124.9 (C$_6$), 123.8 (C$_5$), 117.1 (C$_8$), 114.4 (C3'), 85.8 (C$_2$), 69.8 (C$_{11}$), 67.6 (C$_{15}$), 57.0 (C$_3$), 55.5 (C$_{5'}$), 45.7 (C$_{12}$), 32.5 (C$_{17}$), 17.2 (C$_{15}$SCH$_3$), 15.5 (C$_{11}$SCH$_3$).} $^1$H NMR (600 MHz, CDCl$_3$, 20° C.): δ 7.64 (d, J=8.0, 1H, C$_8$H), 7.40 (app-dt, J=1.4, 7.0, 1H, C$_7$H), 7.33 (d, J=8.0, 2H, SO$_2$Ph-o-H), 7.29 (t, J=7.5, 1H, SO$_2$Ph-p-H), 7.28-7.23 (m, 2H, C$_5$H+C$_6$H), 7.02 (dd, J=7.6, 7.8, 2H, SO$_2$Ph-m-H), 6.76 (d, J=8.7, 2H, C$_{2'}$H), 6.62 (d, J=8.7, 1H, C$_{3'}$H), 6.39 (s, 1H, C$_2$H), 5.28 (s, 1H, C$_{15}$H), 3.78 (s, 3H, C$_{5'}$H$_3$), 3.63 (d, J=15.6, 1H, C$_{12}$H$_a$), 3.13 (s, 3H, C$_{17}$H$_3$), 2.87 (d, J=15.6, 1H, C$_{12}$H$_b$). $^{13}$C NMR (150 MHz, CDCl$_3$, 20° C.): δ 165.2 (C$_{13}$), 160.2 (C$_{16}$), 158.9 (C$_{4'}$), 141.3 (C$_9$), 138.3 (SO$_2$Ph-ipso-C), 135.8 (C$_4$), 133.1 (SO$_2$Ph-p-C), 131.2 (C$_{1'}$), 129.9 (C$_7$), 128.6 (SO$_2$Ph-m-C), 128.0 (C$_{2'}$), 127.3 (SO$_2$Ph-o-C), 126.2 (C$_5$), 125.8 (C$_5$), 119.1 (C$_8$), 114.5 (C$_{3'}$), 87.8 (C$_2$), 74.6 (C$_{11}$), 68.4 (C$_{15}$), 59.5 (C$_3$), 55.5 (C$_{5'}$), 45.6 (C$_{12}$), 32.2 (C$_{17}$). FTIR (thin film) cm$^{-1}$: 3065 (w), 3006 (w), 2931 (w), 2839 (w), 1698 (s), 1512 (m), 1459 (m), 1363 (m), 1255 (m), 1170 (m), 1035 (w), 755 (m). HRMS (ESI) (m/z): calc'd for C$_{27}$H$_{23}$N$_3$NaO$_5$S$_3$ [M+Na]$^+$: 588.0692. found 588.0694. TLC (20% ethyl acetate in dichloromethane), Rf: 0.42 (UV, I$_2$, CAM).

S20:

$^1$H NMR (600 MHz, DMSO-d$_6$, 20° C.): δ 7.44 (t, J=7.5, 1H, SO$_2$Ph-p-H), 7.38 (d, J=7.8, 1H, C$_8$H), 7.34 (app-t, J=8.8, 1H, C$_7$H), 7.26 (d, J=7.4, 2H, SO$_2$Ph-o-H), 7.21 (app-dt, J=0.6, 7.3, 1H, C$_6$H), 7.14 (dd, J=7.6, 8.1, 2H, SO$_2$Ph-m-H), 7.01 (d, J=7.5, 1H, C$_5$H), 6.76 (d, J=8.8, 2H, C$_{2'}$H), 6.66 (d, J=8.8, 1H, C$_{3'}$H), 6.22 (s, 1H, C$_2$H), 5.00 (d, J=7.4, 1H, C$_{15}$H), 3.74 (s, 3H, C$_5$H$_3$), 3.19 (d, J=15.0, 1H, C$_{12}$H$_a$), 2.77 (s, 3H, C$_{17}$H$_3$), 2.67 (d, J=15.0, 1H, C$_{12}$H$_b$). $^{13}$C NMR (100 MHz, DMSO-d$_6$, 20° C.): δ 166.6 (C$_{13}$), 165.8 (C$_{16}$), 158.0 (C$_{4'}$), 139.4 (C$_9$), 138.0 (SO$_2$Ph-ipso-C), 137.8 (C$_4$), 133.4 (C$_{1'}$), 133.2 (SO$_2$Ph-p-C), 128.9 (C$_7$), 128.7 (SO$_2$Ph-m-C), 128.0 (C$_{2'}$), 126.7 (SO$_2$Ph-o-C), 126.7 (C$_5$), 125.7 (C$_6$), 117.0 (C$_8$), 114.0 (C$_{3'}$), 87.3 (C$_2$), 86.0 (C$_{11}$), 80.9 (C$_{15}$), 57.4 (C$_3$), 55.1 (C$_{5'}$), 49.7 (C$_{12}$), 30.5 (C$_{17}$). MS (ESI) (m/z): [M+H]$^+$: 537.39, [M+Na]$^+$: 558.43, [2M+Na]$^+$: 1094.13. TLC (20% acetone in dichloromethane), Rf: 0.50 (UV, CAM).

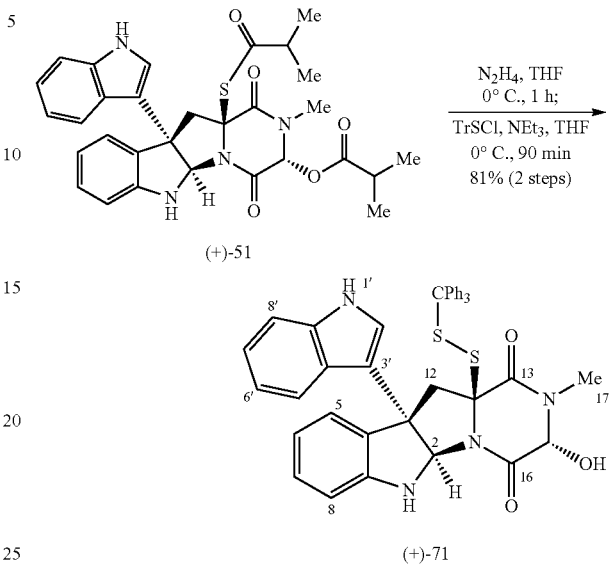

(+)-51

Hexacyclic triphenylmethandisulfide (+)-71

(Boyer, N.; Movassaghi, M. *Chem. Sci.* 2012, 3, 1798) Anhydrous hydrazine (150 µL, 4.77 mmol, 11.1 equiv) was added via syringe to a solution of aminothioisobutyrate (+)-51 (240 mg, 428 µmol, 1 equiv, Boyer, N.; Movassaghi, M. *Chem. Sci.* 2012, 3, 1798) in anhydrous tetrahydrofuran (50 mL) at 0° C. After 1 h, the reaction mixture was diluted sequentially with saturated aqueous ammonium chloride solution (20 mL) and ethyl acetate (120 mL). The organic layer was sequentially washed with saturated aqueous ammonium chloride solution (50 mL), water (2×50 mL), and saturated aqueous sodium chloride solution (30 mL). The aqueous layer was extracted with ethyl acetate (2×50 mL). The combined organic layers were dried over anhydrous sodium sulfate, were filtered, and were concentrated under reduced pressure to afford the hexacyclic aminothiol that was used in the next step without further purification. The hexacyclic aminothiol can be purified by flash column chromatography on silica gel (eluent: gradient, 1→3% methanol in dichloromethane). $^1$H NMR (600 MHz, CDCl$_3$, 20° C.): δ 8.16 (br-s, 1H, N$_1$H), 7.40 (d, J=8.1, 1H, C$_5$H), 7.31 (d, J=8.2, 1H, C$_8$H), 7.23 (d, J=7.4, 1H, C$_5$H), 7.19 (app-dt, J=1.0, 7.7, 1H, C$_7$H), 7.17 (app-t, J=7.4, 1H, C$_7$H), 7.02 (app-t, J=7.6, 1H, C$_6$H), 6.89 (d, J=2.6, 1H, C$_{2'}$H), 6.85 (app-t, J=7.0, 1H, C$_6$H), 6.77 (d, J=7.8, 1H, C$_8$H), 5.92 (s, 1H, C$_2$H), 5.36 (s, 1H, C$_{15}$H), 5.20 (br-s, 1H, N$_1$H), 3.76 (d, J=14.3, 1H, C$_{12}$H$_a$), 3.75 (br-s, 1H, C$_{15}$OH), 3.30 (d, J=14.3, 1H, C$_{12}$H$_b$), 3.09 (s, 3H, C$_{14}$H$_3$), 2.57 (br-s, 1H, C$_{11}$SH). $^{13}$C NMR (150 MHz, CDCl$_3$, 20° C.): δ 166.6 (C$_{13}$), 166.6 (C$_{16}$), 148.2 (C$_9$), 137.4 (C$_{9'}$), 131.8 (C$_4$), 129.4 (C$_7$), 125.0 (C$_{4'}$), 125.0 (C$_5$), 122.7 (C$_{7'}$), 122.2 (C$_{2'}$), 120.4 (C$_6$), 120.2 (C$_{6'}$), 119.7 (C$_{5'}$), 117.3 (C$_{3'}$), 111.8 (C$_{8'}$), 110.4 (C$_8$), 82.5 (C$_2$), 77.2 (C$_{15}$), 69.0 (C$_{11}$), 54.2 (C$_3$), 50.9 (C$_{12}$), 29.3 (C$_{18}$). TLC (5% methanol in dichloromethane), Rf: 0.27 (UV, CAM).

Triethylamine (600 µL, 4.27 mmol, 10.0 equiv) and solid triphenylmethanesulfenyl chloride (665 mg, 2.14 mmol, 5.00 equiv) were sequentially added to a solution of hexacyclic aminothiol in anhydrous tetrahydrofuran (60 mL) at 0° C. under an argon atmosphere. After 90 min, the solution was partitioned between saturated aqueous ammonium chloride (50 mL) and ethyl acetate (130 mL). The aqueous layer was extracted with diethyl ether (2×50 mL), and the combined organic layers were washed sequentially with water (2×50 mL) and saturated aqueous sodium chloride solution (30 mL), were dried over anhydrous sodium sulfate, were filtered, and were concentrated under reduced pressure. The residue was purified by flash column chromatography on silica gel (eluent: gradient, 10→30% ethyl acetate in dichloromethane) to afford triphenylmethanedisulfide (+)-71 (242 mg, 81.4%) as a white solid. This sequence can also be combined as a sequential single-flask two-step process to afford (+)-71 in 74% yield. Structural assignments were made with additional information from gCOSY, HSQC, and gHMBC data. $^1$H NMR (600 MHz, acetonitrile-$d_3$, 20° C.): δ 9.16 (br-s, 1H, $N_1$.H), 7.37 (d, J=7.4, 1H, $C_8$.H), 7.36 (d, J=7.6, 1H, $C_5$.H), 7.34-7.30 (m, 6H, C(Ph-o-H)$_3$), 7.34-7.30 (m, 3H, C(Ph-p-H)$_3$), 7.18-7.15 (m, 6H, C(Ph-m-H)$_3$), 7.15-7.11 (m, 1H, $C_7$H), 7.10 (app-dt, J=0.8, 7.6, 1H, $C_7$.H), 6.97 (d, J=2.7, 1H, $C_2$.H), 6.96 (app-t, J=8.0, 1H, $C_6$.H), 6.68 (d, J=7.9, 1H, $C_8$H), 6.64-6.60 (m, 1H, $C_5$H), 6.64-6.60 (m, 1H, $C_6$H), 5.75 (d, J=1.0, 1H, $C_2$H), 5.60 (br-s, 1H, $N_1$H), 5.11 (s, 1H, $C_{15}$H), 4.59 (br-s, 1H, $C_{15}$OH), 3.32 (d, J=14.5, 1H, $C_{12}H_a$), 2.89 (s, 3H, $C_{17}H_3$), 2.70 (d, J=14.5, 1H, $C_{12}H_b$). $^{13}$C NMR (150 MHz, acetonitrile-$d_3$, 20° C.): δ 166.9 ($C_{13}$), 164.1 ($C_{16}$), 149.2 ($C_9$), 145.0 (C(Ph-ipso-C)$_3$), 138.1 ($C_9$.), 133.3 ($C_4$), 131.2 (C(Ph-m-C)$_3$), 129.4 ($C_7$), 128.8 (C(Ph-o-C)$_3$), 128.4 (C(Ph-p-C)$_3$), 125.8 ($C_4$.), 125.4 ($C_5$), 122.8 ($C_7$.), 122.7 ($C_2$.), 120.3 ($C_6$), 120.3 ($C_5$.), 120.1 ($C_6$.), 118.6 ($C_3$.), 112.7 ($C_8$.), 110.6 ($C_8$), 83.1 ($C_2$), 78.4 (CPh$_3$), 78.4 ($C_{15}$), 73.1 ($C_{11}$), 54.3 ($C_3$), 49.4 ($C_{12}$), 29.1 ($C_{18}$). FTIR (thin film) cm$^{-1}$: 3345 (br-m), 3056 (w), 2926 (w), 1674 (s), 1483 (m), 1459 (m), 1442 (m), 1388 (m), 745 (s), 700 (s). HRMS (ESI) (m/z): calc'd for $C_{41}H_{35}N_4O_3S_2$[M+H]$^+$: 695.2145. found: 695.2147. [α]$_D$24: +165.2 (c=0.12, CHCl$_3$). TLC (5% methanol in dichloromethane), Rf: 0.44 (UV, CAM). Triphenylmethanedisulfide (+)-71 has also been characterized by NMR in CDCl$_3$: $^1$H NMR (600 MHz, CDCl$_3$, 20° C.): δ 8.00 (br-s, 1H, $N_1$.H), 7.31 (d, J=7.8, 1H, $C_5$.H), 7.30 (d, J=7.8, 1H, $C_8$.H), 7.29-7.26 (m, 6H, C(Ph-o-H)$_3$), 7.29-7.26 (m, 3H, C(Ph-p-H)$_3$), 7.20-7.17 (m, 6H, C(Ph-m-H)$_3$), 7.16 (app-t, J=7.7, 1H, $C_7$H), 7.15 (app-t, J=8.1, 1H, $C_7$.H), 7.02 (app-t, J=7.5, 1H, $C_6$.H), 6.83 (d, J=2.5, 1H, $C_2$.H), 6.74-6.68 (m, 1H, $C_5$H), 6.74-6.68 (m, 1H, $C_6$H), 6.74-6.68 (m, 1H, $C_8$H), 5.82 (s, 1H, $C_2$H), 5.24 (d, J=3.6, 1H, $C_{15}$H), 4.99 (br-s, 1H, $N_1$H), 4.07 (d, J=3.6, 1H, $C_{15}$OH), 3.43 (d, J=14.7, 1H, $C_{12}H_a$), 3.00 (s, 3H, $C_{17}H_3$), 2.57 (d, J=14.7, 1H, $C_{12}H_b$). $^{13}$C NMR (150 MHz, CDCl$_3$, 20° C.): δ 167.3 ($C_{16}$), 163.7 ($C_{13}$), 147.6 ($C_9$), 143.9 (C(Ph-ipso-C)$_3$), 137.3 ($C_9$.), 131.6 ($C_4$), 130.8 (C(Ph-m-C)$_3$), 129.5 ($C_7$), 127.9 (C(Ph-o-C)$_3$), 127.5 (C(Ph-p-C)$_3$), 125.2 ($C_5$), 125.1 ($C_4$.), 122.6 ($C_7$.), 122.0 ($C_2$.), 120.2 ($C_6$.), 120.0 ($C_5$.), 119.9 ($C_6$), 117.5 (CO$_3$.), 111.6 ($C_8$.), 110.1 ($C_8$), 82.6 ($C_2$), 77.6 (CPh$_3$), 72.9 ($C_{15}$), 69.7 ($C_{11}$), 54.0 ($C_3$), 48.0 ($C_{12}$), 29.4 ($C_{18}$).

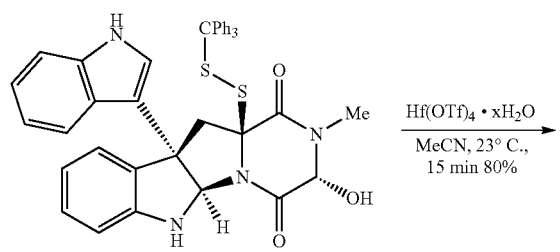

(+)-71

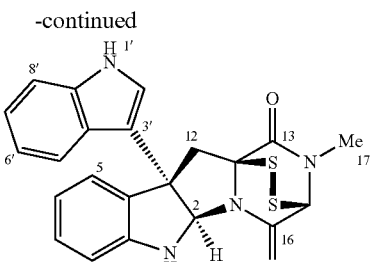

(+)-12-deoxybionectin A (10)

(+)-71 (+)-12-Deoxybionectin A (10)

(Zheng, C.-J.; Kim, C.-J.; Bae, K. S.; Kim, Y.-H.; Kim, W.-G. J. Nat. Prod. 2006, 69, 1816; Boyer, N.; Movassaghi, M. Chem. Sci. 2012, 3, 1798) Hafnium(IV) trifluoromethanesulfonate hydrate (800 mg) was added as a solid to a colorless solution of hexacyclic triphenylmethanedisulfide (+)-71 (100 mg, 144 μmol, 1 equiv) in anhydrous acetonitrile (40 mL) at 23° C. A bright yellow coloration was observed immediately after the addition. The suspension was stirred at 23° C. under an argon atmosphere. After 15 min, the reaction mixture was partitioned between saturated aqueous sodium bicarbonate (60 mL) and ethyl acetate (100 mL). The aqueous layer was extracted with ethyl acetate (2×50 mL). The combined organic layers were washed sequentially with water (3×50 mL) and saturated aqueous sodium chloride solution (30 mL), were dried over anhydrous sodium sulfate, were filtered, and were concentrated under reduced pressure. The residue was purified by flash column chromatography on silica gel (eluent: gradient, 1→6% acetone in dichloromethane) to afford (+)-12-deoxybionectin A (10) (50.2 mg, 80.3%) as a colorless oil. Structural assignments were made with additional information from gCOSY, HSQC, and gHMBC data. $^1$H NMR (600 MHz, CDCl$_3$, 20° C.): δ 8.07 (br-s, 1H, $N_1$.H), 7.48 (d, J=8.0, 1H, $C_5$.H), 7.37 (d, J=8.2, 1H, $C_8$.H), 7.25 (d, J=8.3, 1H, $C_5$H), 7.20 (app-dt, J=0.7, 7.7, 1H, $C_7$.H), 7.20 (app-dt, J=0.7, 7.7, 1H, $C_7$H), 7.09 (app-t, J=7.6, 1H, $C_6$.H), 6.95 (d, J=2.5, 1H, $C_2$.H), 6.88 (app-t, J=7.4, 1H, $C_6$H), 6.76 (d, J=7.9, 1H, $C_8$H), 5.95 (s, 1H, $C_2$H), 5.30 (br-s, 1H, $N_1$H), 5.21 (s, 1H, $C_{15}$H), 4.10 (d, J=15.4, 1H, $C_{12}H_a$), 3.15 (s, 3H, $C_{17}H_3$), 2.95 (d, J=15.4, 1H, $C_{12}H_b$). $^{13}$C NMR (150 MHz, CDCl$_3$, 20° C.): δ 165.8 ($C_{13}$), 162.2 ($C_{16}$), 148.2 ($C_9$), 137.5 ($C_9$.), 132.0 ($C_4$), 129.4 ($C_7$), 125.1 ($C_4$.), 124.3 ($C_5$), 122.9 ($C_7$.), 122.9 ($C_2$.), 120.4 ($C_6$.), 120.1 ($C_6$), 119.6 ($C_5$.), 116.7 ($C_3$.), 111.9 ($C_8$.), 110.4 ($C_8$), 83.0 ($C_2$), 74.8 ($C_{11}$), 68.4 ($C_{15}$), 56.1 ($C_3$), 43.6 ($C_{12}$), 32.2 ($C_{17}$). FTIR (thin film) cm$^{-1}$: 3358 (br-w), 3006 (w), 2926 (w), 1684 (s), 1609 (w), 1460 (w), 1383 (w), 1232 (m), 748 (m). HRMS (ESI) (m/z): calc'd for $C_{22}H_{19}N_4O_2S_2$ [M+H]$^+$: 435.0944. found: 435.0943. [α]$_D^{24}$: +387.3 (c=0.10, CHCl$_3$). TLC (10% acetone in dichloromethane), Rf: 0.54 (UV, CAM). The relative stereochemistry of the epidisulfide bridge 10 has been confirmed by key NOESY signals ($^1$H,$^1$H) in ppm: (1.99, 3.31), (3.31, 7.16), (3.20, 6.06) on the corresponding bis(methylthioether)—i.e., (+)-gliocladin B (7, see Boyer, N.; Movassaghi, M. Chem. Sci. 2012, 3, 1798).

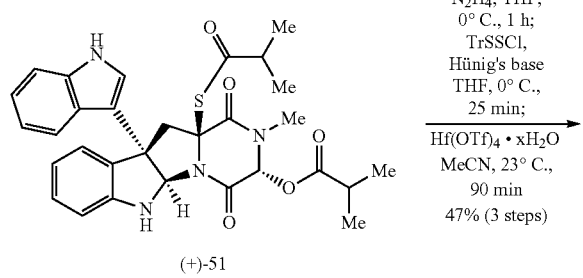

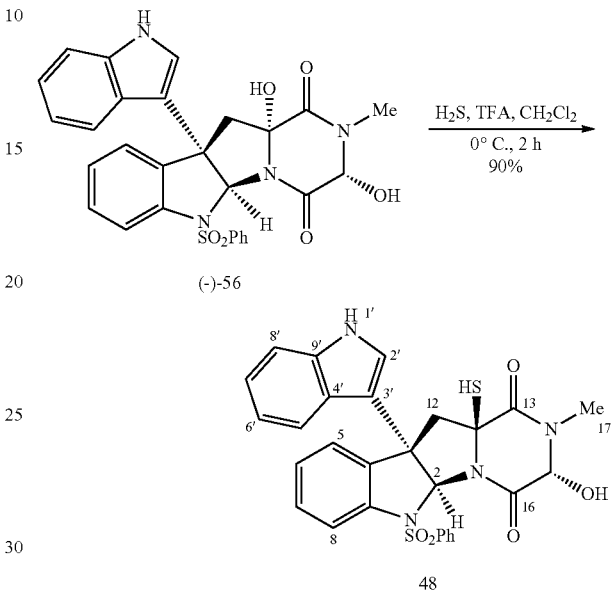

C3-(Indol-3'-yl) epitrithiodiketopiperazine 29

This compound was prepared in two steps starting from aminothioisobutyrate (+)-51 (26.5 mg, 47.3 μmol, Boyer, N.; Movassaghi, M. *Chem. Sci.* 2012, 3, 1798) using the methodology developed to access the corresponding C3-(indol-3'-yl) epidithiodiketopiperazine (+)-12-deoxybionectin A (10). The residue was purified by flash column chromatography on silica gel (eluent: gradient, 2→10% acetone in dichloromethane) to afford epitrithiodiketopiperazine 29 (10.3 mg, 46.7%) as a colorless oil. Structural assignments were made with additional information from gCOSY, HSQC, and gHMBC data. Without the intention to be limited by theory, Applicant notes that in some embodiments, upon concentration or in concentrated solution, the epitrithiodiketopiperazine 29 tends to degrade, thus rendering its isolation and characterization particularly arduous. $^1$H NMR (600 MHz, CDCl$_3$, 20° C.): Major conformer: δ 8.10 (br-s, 1H, N$_1$H), 7.46 (d, J=8.1, 1H, C$_5$H), 7.35 (d, J=8.0, 1H, C$_8$H), 7.21 (app-dt, J=0.7, 6.9, 1H, C$_7$H), 7.18 (app-t, J=7.6, 1H, C$_7$H), 7.14 (d, J=7.3, 1H, C$_5$H), 7.06 (app-t, J=7.5, 1H, C$_6$H), 6.92 (d, J=2.4, 1H, C$_2$H), 6.81 (d, J=8.3, 1H, C$_8$H), 6.80 (app-t, J=7.5, 1H, C$_6$H), 5.85 (s, 1H, C$_2$H), 4.87 (s, 1H, C$_{15}$H), 3.80 (d, J=14.6, 1H, C$_{12}$H$_a$), 3.20 (s, 3H, C$_{17}$H$_3$), 3.16 (d, J=14.6, 1H, C$_{12}$H$_b$). The resonance for N$_1$H was not observed. Minor conformer: δ 8.11 (br-s, 1H, N$_1$H), 7.54 (d, J=8.1, 1H, C$_5$H), 7.36 (d, J=7.9, 1H, C$_8$H), 7.22-7.18 (m, 1H, C$_7$H), 7.12 (d, J=7.4, 1H, C$_5$H), 7.11 (dd, J=7.6, 7.7, 1H, C$_7$H), 7.09 (app-t, J=7.6, 1H, C$_6$H), 6.94 (d, J=2.4, 1H, C$_2$H), 6.78 (app-t, J=7.5, 1H, C$_6$H), 6.71 (d, J=7.7, 1H, C$_8$H), 6.19 (s, 1H, C$_2$H), 5.21 (s, 1H, C$_{15}$H), 3.70 (d, J=14.7, 1H, C$_{12}$H$_a$), 3.09 (d, J=14.7, 1H, C$_{12}$H$_b$), 3.02 (s, 3H, C$_{17}$H$_3$). The resonance for N$_1$H was not observed. $^{13}$C NMR (150 MHz, CDCl$_3$, 20° C.): Major conformer: δ 168.9 (C$_{13}$), 164.5 (C$_{16}$), 149.6 (C$_9$), 137.3 (C$_{9'}$), 130.8 (C$_4$), 129.9 (C$_7$), 125.0 (C$_{4'}$), 124.8 (C$_5$), 122.8 (C$_{7'}$), 122.5 (C$_{2'}$), 120.3 (C$_{6'}$), 120.0 (C$_6$), 119.7 (C$_{5'}$), 116.5 (C$_{3'}$), 111.8 (C$_{8'}$), 110.6 (C$_8$), 82.1 (C$_2$), 79.3 (C$_{11}$), 67.2 (C$_{15}$), 54.2 (C$_3$), 49.2 (C$_{12}$), 31.2 (C$_{17}$). Minor conformer: δ 167.4 (C$_{13}$), 163.2 (C$_{16}$), 148.2 (C$_9$), 137.4 (C$_{9'}$), 131.4 (C$_4$), 129.2 (C$_7$), 125.1 (C$_{4'}$), 124.3 (C$_5$), 122.8 (C$_{7'}$), 122.5 (C$_{2'}$), 120.3 (C$_{6'}$), 120.2 (C$_6$), 119.7 (C$_{5'}$), 116.7 (CO$_{3'}$), 111.9 (C$_{8'}$), 109.8 (C$_8$), 83.7 (C$_2$), 74.8 (C$_{11}$), 71.2 (C$_{15}$), 54.3 (C$_3$), 46.8 (C$_{12}$), 32.5 (C$_{17}$). FTIR (thin film) cm$^{-1}$: 3397 (br-m), 3061 (w), 2922 (w), 2852 (w), 1693 (s), 1458 (m), 1382 (m), 1265 (w), 1170 (m), 1092 (w), 1026 (w), 737 (m). HRMS (ESI) (m/z): calc'd for C$_{22}$H$_{19}$N$_4$O$_2$S$_3$ [M+H]$^+$: 467.0665. found: 467.0669. TLC (10% acetone in dichloromethane), Rf: 0.61 (UV, I$_2$, CAM).

C3-(Indol-3'-yl) C11-thiohemiaminal 48

A slow stream of hydrogen sulfide gas was introduced into a solution of diol (−)-56 (185 mg, 340 μmol, 1 equiv) in anhydrous dichloromethane (30 mL) at 0° C., providing a saturated hydrogen sulfide solution. After 20 min, trifluoroacetic acid (6 mL) was added via syringe over 10 min, and the slow introduction of hydrogen sulfide into the mixture was maintained for another 10 min. The reaction mixture was left under an atmosphere of hydrogen sulfide for an additional 2 h at 0° C. A slow stream of argon gas was introduced into the solution. After 15 min, the reaction mixture was diluted with ethyl acetate (150 mL) and slowly poured into saturated aqueous sodium hydrogenocarbonate solution (50 mL). The organic layer was sequentially washed with water (3×40 mL) and saturated aqueous sodium chloride solution (40 mL). The organic layer was dried over anhydrous sodium sulfate, was filtered, and was concentrated under reduced pressure. The residue was purified by flash column chromatography on silica gel (eluent: gradient, 5→25% acetone in dichloromethane) to afford thiohemiaminal 48 (171 mg, 89.8%) as an orange solid. Structural assignments were made with additional information from gCOSY, HSQC, and gHMBC data. $^1$H NMR (600 MHz, CDCl$_3$, 20° C.): δ 7.89 (br-s, 1H, N$_1$H), 7.87 (d, J=8.2, 1H, C$_8$H), 7.45 (d, J=7.7, 2H, SO$_2$Ph-o-H), 7.44-7.39 (m, 1H, C$_7$H), 7.34 (t, J=7.4, 1H, SO$_2$Ph-p-H), 7.31 (d, J=8.2, 1H, C$_8$H), 7.21-7.18 (m, 2H, C$_5$H+C$_6$H), 7.17 (dd, J=7.4, 7.8, 1H, C$_7$H), 7.03 (app-t, J=7.8, 2H, SO$_2$Ph-m-H), 6.92 (dd, J=7.5, 7.6, 1H, C$_6$H), 6.73 (d, J=8.0, 1H, C$_5$H), 6.61 (s, 1H, C$_2$H), 6.22 (d, J=2.3, 1H, C$_2$H), 5.42 (s, 1H, C$_{15}$H), 4.53 (br-s, 1H, C$_{15}$OH), 3.82 (d, J=14.9, 1H, C$_{12}$H$_a$), 3.11 (s, 3H, C$_{17}$H$_3$), 2.99 (d, J=14.9, 1H, C$_{12}$H$_b$), 2.61 (s, 1H, C$_{11}$SH). $^{13}$C NMR (150 MHz, CDCl$_3$, 20° C.): δ 166.2 (C$_{13}$), 165.8 (C$_{16}$), 140.9 (C$_9$), 137.3 (SO$_2$Ph-ipso-C), 136.8 (C$_{9'}$), 135.9 (C$_4$), 133.3 (SO$_2$Ph-p-C), 129.4 (C$_7$), 128.6 (SO$_2$Ph-m-C), 127.5 (SO$_2$Ph-o-C), 126.0 (C$_6$), 125.0 (C$_5$), 124.1 (C$_{4'}$), 123.9 (C$_{2'}$), 122.9 (C$_{7'}$), 120.5 (C$_{6'}$), 118.7 (C$_{5'}$), 118.4 (C$_8$), 114.2 (C$_{3'}$), 111.9 (C$_{8'}$), 84.5 (C$_2$), 77.3 (C$_{15}$), 69.5 (C$_{11}$), 53.8 (C$_3$), 51.8 (C$_{12}$), 29.3 (C$_{17}$). FTIR (thin film) cm$^{-1}$: 3394 (br-w), 2926 (w), 2547 (w), 1700 (s), 1662 (s), 1457 (m), 1359 (m), 1168 (s), 1090 (m), 1024 (w), 734 (m). HRMS (ESI) (m/z): calc'd for C$_{28}$H$_{24}$N$_4$NaO$_5$S$_2$ [M+Na]$^+$: 583.1080. found: 583.1095. TLC (20% ethyl acetate in dichloromethane), Rf: 0.09 (UV, CAM).

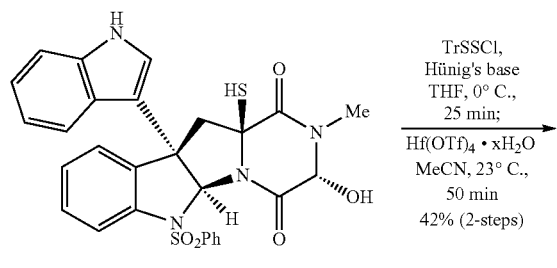

C3-(Indol-3'-yl) epitrithiodiketopiperazine 27

This compound was prepared in two steps starting from thiohemiaminal 48 (25.0 mg, 44.6 μmol) using the methodology developed to access the corresponding C3-(indol-3'-yl) epidithiodiketopiperazine (+)-12-deoxybionectin A (10). The residue was purified by flash column chromatography on silica gel (eluent: gradient, 5→30% ethyl acetate in dichloromethane) to afford epitrithiodiketopiperazine 27 (11.3 mg, 41.8%) as a white solid. Structural assignments were made with additional information from gCOSY, HSQC, and gHMBC data. Based on $^1$H NMR analysis at 20° C. in CDCl$_3$, the product exists as a 3:7 mixture of minor:major conformers. Without the intention to be limited by theory, Applicant notes that in some embodiments, upon concentration or in concentrated solution, the epitrithiodiketopiperazine 27 tends to degrade, thus rendering its isolation and characterization particularly arduous; one of the by-products has been identified as the corresponding epidithiodiketopiperazine 26. $^1$H NMR (600 MHz, CDCl$_3$, 20° C.): Major conformer: δ 7.89 (br-s, 1H, N$_1$H), 7.81 (d, J=8.1, 1H, C$_8$H), 7.53 (d, J=7.5, 2H, SO$_2$Ph-o-H), 7.41 (app-ddd, J=2.3, 6.5, 8.1, 1H, C$_7$H), 7.37 (t, J=7.7, 1H, SO$_2$Ph-p-H), 7.33 (d, J=8.1, 1H, C$_8$H), 7.19 (dd, J=6.9, 7.9, 1H, C$_7$H), 7.16-7.12 (m, 2H, C$_5$H+C$_6$H), 7.09 (dd, J=7.8, 8.0, 2H, SO$_2$Ph-m-H), 6.96 (dd, J=7.4, 7.7, 1H, C$_6$H), 6.89 (d, J=8.0, 1H, C$_5$H), 6.56 (s, 1H, C$_2$H), 6.25 (d, J=2.5, 1H, C$_{15}$H), 3.83 (d, J=15.2, 1H, C$_{12}$H$_a$), 3.21 (s, 3H, C$_{17}$H$_3$), 2.84 (d, J=15.2, 1H, C$_{12}$H$_b$). Minor conformer: δ 7.77 (br-s, 1H, N$_1$H), 7.68 (d, J=8.0, 1H, C$_8$H), 7.38-7.34 (m, 2H, C$_5$H+C$_8$H), 7.34-7.32 (m, 1H, C$_7$H), 7.27-7.22 (m, 2H, C$_5$H+SO$_2$Ph-p-H), 7.22-7.19 (m, 2H, SO$_2$Ph-o-H), 7.19-7.16 (m, 1H, C$_6$H), 7.15-7.12 (m, 1H, C$_6$H), 6.98-6.94 (m, 1H, C$_7$H), 6.95 (s, 1H, C$_2$H), 6.92-6.86 (m, 2H, SO$_2$Ph-m-H), 5.88 (d, J=2.6, 1H, C$_2$H), 5.26 (s, 1H, C$_{15}$H), 3.62 (d, J=15.1, 1H, C$_{12}$H$_a$), 3.03 (s, 3H, C$_{17}$H$_3$), 2.85 (d, J=15.1, 1H, Cl$_2$H$_b$). $^{13}$C NMR (150 MHz, CDCl$_3$, 20° C.): Major conformer: δ 168.2 (C$_{13}$), 162.6 (C$_{16}$), 142.0 (C$_9$), 137.7 (SO$_2$Ph-ipso-C), 137.3 (C$_{9'}$), 135.3 (C$_4$), 133.1 (SO$_2$Ph-p-C), 130.2 (C$_7$), 128.6 (SO$_2$Ph-m-C), 127.5 (SO$_2$Ph-o-C), 125.8 (C$_6$), 124.9 (C$_5$), 124.2 (C$_{4'}$), 124.0 (C$_{2'}$), 123.0 (C$_{7'}$), 120.5 (C$_{6'}$), 118.9 (C$_{5'}$), 118.8 (C$_8$), 113.8 (C$_{3'}$), 112.0 (C$_{8'}$), 84.4 (C$_2$), 79.5 (C$_{11}$), 67.2 (C$_{15}$), 53.7 (C$_3$), 48.8 (C$_{12}$), 32.8 (C$_{17}$). Minor conformer: δ 169.9 (C$_{13}$), 161.5 (C$_{16}$), 141.2 (C$_9$), 138.1 (SO$_2$Ph-ipso-C), 137.1 (C$_{9'}$), 136.6 (C$_4$), 132.9 (SO$_2$Ph-p-C), 129.7 (C$_7$), 128.2 (SO$_2$Ph-m-C), 127.4 (SO$_2$Ph-o-C), 126.5 (C$_6$), 124.7 (C$_5$), 124.2 (C$_{2'}$), 123.9 (C$_{4'}$), 123.2 (C$_{7'}$), 120.8 (C$_{6'}$), 119.4 (C$_8$), 118.7 (C$_{5'}$), 114.2 (CO$_{3'}$), 112.0 (C$_{8'}$), 85.4 (C$_2$), 75.0 (C$_{11}$), 71.4 (C$_{15}$), 54.1 (C$_3$), 46.3 (C$_{12}$), 33.2 (C$_{17}$). FTIR (thin film) cm$^{-1}$: 3394 (br-m), 3017 (w), 2922 (w), 2852 (w), 1699 (s), 1460 (m), 1364 (m), 1236 (w), 1169 (m), 1082 (m), 1049 (w), 750 (m). HRMS (ESI) (m/z): calc'd for C$_{28}$H$_{23}$N$_4$O$_4$S$_4$[M+H]$^+$: 607.0597. found 607.0611; calc'd for C$_{28}$H$_{22}$N$_4$NaO$_4$S$_4$ [M+Na]$^+$: 629.0416. found 629.0435. TLC (10% ethyl acetate in dichloromethane), Rf: 0.46 (UV, CAM).

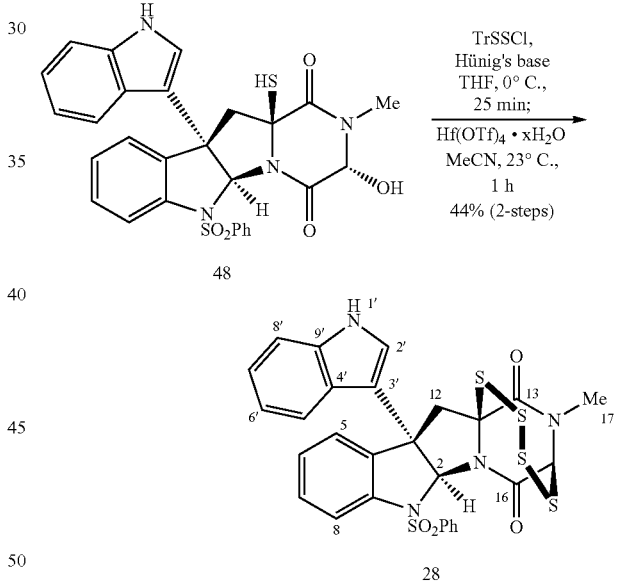

C3-(Indol-3'-yl) epitetrathiodiketopiperazine 28

The compound was prepared in two steps starting from thiohemiaminal 48 (49.3 mg, 88.0 μmol) using the methodology developed to access the corresponding C3-(indol-3'-yl) epidithiodiketopiperazine (+)-12-deoxybionectin A (10). The residue was purified by flash column chromatography on silica gel (eluent: gradient, 5→30% acetate in dichloromethane) to afford epitetrathiodiketopiperazine 28 (25.0 mg, 44.4%) as a white solid. Structural assignments were made with additional information from gCOSY, HSQC, and gHMBC data. Without the intention to be limited by theory, Applicant notes that in some embodiments, the isolation and purification of epitetrathiodiketopiperazine 28 were complicated by its instability in solution. $^1$H NMR (600 MHz, CDCl$_3$, 20° C.): δ 7.92 (br-s, 1H, N$_1$,H), 7.69 (d, J=7.8, 2H, SO$_2$Ph-o-H), 7.58 (d, J=8.1, 1H, C$_8$H), 7.40 (t, J=7.4, 1H, SO$_2$Ph-p-H), 7.34 (d, J=8.2, 1H, C$_8$H), 7.31 (app-t, J=7.8, 1H, C$_7$H), 7.22-7.16 (m, 4H, C$_5$H+C$_6$H+SO$_2$Ph-m-H), 7.11 (app-t, J=7.4, 1H, C$_6$H), 7.04 (d, J=7.8, 1H, C$_5$H), 7.01 (dd, J=7.1, 7.7, 1H, C$_6$H), 6.95 (s, 1H, C$_2$H), 6.45 (d, J=2.2, 1H, C$_{2'}$H), 5.23 (s, 1H, C$_{15}$H), 3.47 (d, J=14.8, 1H, C$_{12}$H$_a$), 3.06 (s, 3H, C$_{17}$H$_3$), 3.03 (d, J=14.8, 1H, C$_{12}$H$_b$). $^{13}$C NMR (150 MHz, CDCl$_3$, 20° C.): δ 168.2 (C$_{13}$), 162.8 (C$_{16}$), 141.8 (C$_9$), 138.5 (SO$_2$Ph-ipso-C), 137.3 (C$_{9'}$), 136.4 (C$_4$), 133.2 (SO$_2$Ph-p-C), 129.7 (C$_7$), 128.8 (SO$_2$Ph-m-C), 127.7 (SO$_2$Ph-o-C), 125.7 (C$_6$), 124.6 (C$_5$), 124.3 (C$_{4'}$), 123.0 (C$_{2'}$), 123.0 (C$_{7'}$), 120.7 (C$_{6'}$), 118.8 (C$_{5'}$), 117.3 (C$_8$), 115.8 (C$_{3'}$), 112.0 (C$_{8'}$), 85.2 (C$_2$), 76.0 (C$_{11}$), 68.3 (C$_{15}$), 53.6 (C$_3$), 49.1 (C$_{12}$), 32.5 (C$_{17}$). FTIR (thin film) cm$^{-1}$: 3395 (br-w), 3061 (w), 2924 (w), 2853 (w), 1690 (s), 1458 (w), 1382 (m), 1240 (w), 1170 (m), 1023 (w), 734 (m), 591 (m). HRMS (ESI) (m/z): calc'd for C$_{28}$H$_{22}$N$_4$NaO$_4$S$_5$ [M+Na]$^+$: 661.0137. found 661.0120. TLC (10% ethyl acetate in dichloromethane), Rf: 0.30 (UV, I$_2$, CAM).

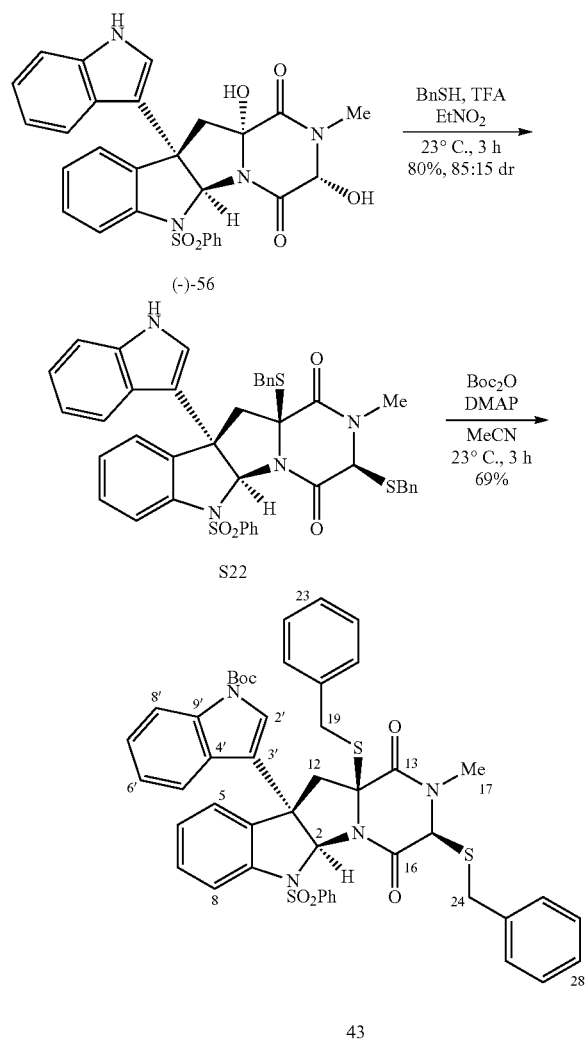

43

C3-(N-Boc-indol-3'-yl)bis(benzylthioether) 43

Trifluoroacetic acid (4 mL) was slowly added via syringe to a stirred solution of diol (−)-56 (70.0 mg, 128.6 μmol, 1 equiv) and benzyl mercaptan (BnSH, 600 μL, 5.12 mmol, 39.7 equiv) in anhydrous nitroethane (5 mL) at 23° C. After 3 h, the reaction mixture was diluted with ethyl acetate (100 mL) and slowly poured into saturated aqueous sodium hydrogenocarbonate solution (40 mL) at 23° C. The organic layer was sequentially washed with water (3×40 mL) and saturated aqueous sodium chloride solution (25 mL). The combined aqueous layers were extracted with ethyl acetate (2×30 mL). The combined organic layers were dried over anhydrous sodium sulfate, were filtered, and were concentrated under reduced pressure. The residue was purified by flash column chromatography on silica gel (eluent: gradient, 10→40% ethyl acetate in hexanes) to afford the bis(benzylthioether) S22 (77.8 mg, 79.9%) as a pale yellow oil. {A minor diastereomer was also isolated from this reaction (13.0 mg, 13.3%)}.

S22:

$^1$H NMR (600 MHz, CDCl$_3$, 20° C.): δ 7.85 (d, J=8.0, 1H, C$_8$H), 7.75 (d, J=7.4, 1H, C$_8$H), 7.41 (t, J=7.5, 1H, SO$_2$Ph-p-H), 7.38-7.27 (m, 7H), 7.27-7.23 (m, 1H), 7.22-7.15 (m, 4H), 7.18 (app-t, J=7.5, 2H, SO$_2$Ph-m-H), 7.14-7.10 (m, 2H, C$_6$H+C$_{6'}$H), 7.10-7.05 (m, 2H), 6.80-6.76 (m, 2H), 6.71 (s, 1H, C$_2$H), 6.41 (d, J=2.5, 1H, C$_{2'}$H), 4.48 (s, 1H, C$_{15}$H), 4.06 (d, J=12.9, 1H, C$_{19}$H$_a$), 3.81 (d, J=13.6, 1H, C$_{24}$H$_a$), 3.79 (d, J=12.8, 1H, C$_{19}$H$_b$), 3.76 (d, J=13.7, 1H, C$_{24}$H$_b$), 3.39 (d, J=14.4, 1H, C$_{12}$H$_a$), 2.83 (d, J=14.4, 1H, C$_{12}$H$_b$), 2.53 (s, 3H, C$_{17}$H$_3$). MS (ESI) (m/z): [M+H]$^+$: 757.56, [M+Na]$^+$: 779.60, [M+H]$^+$: 795.55. TLC (50% ethyl acetate in hexanes), Rf: 0.40 (UV, CAM).

4-Dimethylaminopyridine (DMAP, 8.0 mg, 65.5 μmol, 0.83 equiv) was added as a solid to a solution of bis(benzylthioether) S22 (60.0 mg, 79.3 μmol, 1 equiv) and di-tert-butyl dicarbonate (Boc$_2$O, 60.0 mg, 275 μmol, 3.47 equiv) in anhydrous acetonitrile (4 mL) at 23° C. After 2 h, another portion of DMAP (2.5 mg, 20.5 μmol, 0.26 equiv) was added. After 1 h, the reaction mixture was diluted with ethyl acetate (60 mL). The resulting mixture was sequentially washed with aqueous 5% citric acid solution (30 mL), water (2×20 mL), and saturated aqueous sodium chloride solution (20 mL). The organic layer was dried over anhydrous sodium sulfate, was filtered, and was concentrated under reduced pressure. The resulting residue was purified by flash column chromatography (eluent: gradient, 10→50% ethyl acetate in hexanes) to afford the N-Boc-indole adduct 43 (47.0 mg, 69.2%) as a colorless oil. Structural assignments were made with additional information from gCOSY, HSQC, gHMBC, and NOESY data. $^1$H NMR (600 MHz, CDCl$_3$, 20° C.): δ 8.03 (br-s, 1H, C$_8$,H), 7.79 (d, J=8.2, 1H, C$_8$H), 7.47 (d, J=7.4, 2H, C$_{21}$H), 7.45-7.39 (m, 3H, C$_7$H+SO$_2$Ph-o-H), 7.37 (dd, J=7.5, 7.6, 2H, C$_{22}$H), 7.32-7.28 (m, 2H, C$_7$H+C$_{21}$H), 7.24 (dd, J=7.4, 7.5, 1H, C$_{28}$H), 7.22-7.17 (m, 3H, C$_{26}$H+SO$_2$Ph-p-H), 7.17 (app-t, J=7.5, 1H, C$_6$H), 7.11 (app-t, J=7.6, 1H, C$_6$H), 7.01 (d, J=7.5, 1H, C$_5$H), 7.00-6.92 (m, 5H, C$_5$H+C$_{27}$H+SO$_2$Ph-m-H), 6.68 (s, 1H, C$_2$H), 6.51 (br-s, 1H, C$_{2'}$H), 4.47 (s, 1H, C$_{15}$H), 3.96 (d, J=14.0, 1H, C$_{19}$H$_a$), 3.85 (d, J=14.0, 1H, C$_{19}$H$_b$), 3.70 (d, J=12.1, 1H, C$_{24}$H$_a$), 3.51 (d, J=12.1, 1H, C$_{24}$H$_b$), 3.17 (d, J=14.7, 1H, C$_{12}$H$_a$), 2.86 (d, J=14.7, 1H, C$_{12}$H$_b$), 2.57 (s, 3H, C$_{17}$H$_3$), 1.66 (s, 9H, OC(CH$_3$)$_3$). $^{13}$C NMR (150 MHz, CDCl$_3$, 20° C.): δ 165.2 (C$_{13}$), 163.4 (C$_{16}$), 140.9 (C$_{carbamate}$), 142.1 (C$_9$), 138.3 (C$_{9'}$), 137.3 (SO$_2$Ph-ipso-C), 136.0 (C$_4$), 136.0 (C$_{25}$), 135.7 (C$_{20}$), 132.7 (SO$_2$Ph-p-C), 129.9 (C$_{21}$), 129.7 (C$_{26}$), 129.7 (SO$_2$Ph-m-C), 129.5 (C$_7$), 128.9 (C$_{22}$), 128.5 (SO$_2$Ph-o-C), 128.4 (C$_{27}$), 127.8 (C$_{23}$), 127.4 (C$_{4'}$), 127.2 (C$_{28}$), 126.0 (C$_6$), 125.1 (C$_{7'}$), 124.7 (C$_{2'}$), 124.1 (C$_5$), 123.3 (C$_{6'}$), 120.0 (C$_{3'}$), 119.2 (C$_5$), 119.1 (C$_8$), 115.9 (C$_{8'}$), 84.4 (OC(CH$_3$)$_3$), 83.6 (C$_2$), 70.6 (C$_{11}$), 63.4 (C$_{15}$), 53.2 (C$_3$), 45.5 (C$_{12}$), 37.5 (C$_{19}$), 37.0 (C$_{24}$), 31.5

($C_{17}$), 28.4 (OC(CH$_3$)$_3$). FTIR (thin film) cm$^{-1}$: 3214 (br-w), 3062 (w), 3027 (w), 2979 (w), 2930 (w), 2856 (w), 1734 (s), 1696 (s), 1668 (s), 1476 (m), 1454 (s), 1373 (s), 1270 (s), 1235 (s), 1171 (s), 1158 (s), 1097 (m), 1026 (m), 754 (s), 703 (m). HRMS (ESI) (m/z): calc'd for C$_{47}$H$_{44}$N$_4$NaO$_6$S$_3$ [M+Na]$^+$: 879.2315. found 879.2303. TLC (30% ethyl acetate in hexanes), Rf: 0.33 (UV, CAM).

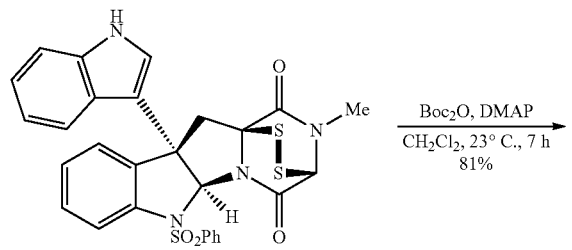

26

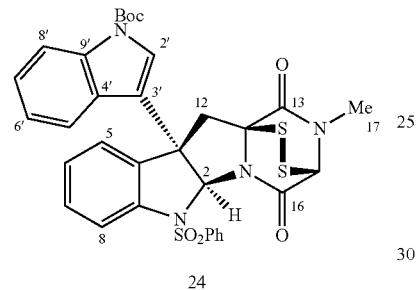

24

C3-(N-Boc-indol-3'-yl) epidithiodiketopiperazine 24

A solution of DMAP in anhydrous dichloromethane (0.17 M, 25 µL, 2.5 mol %) was added via syringe to a solution of epidithiodiketopiperazine 26 (98.3 mg, 171 µmol, 1 equiv) and di-tert-butyl dicarbonate (77.6 mg, 355 µmol, 2.08 equiv) in anhydrous dichloromethane (20 mL) at 23° C. After 2 h, another portion of DMAP solution (25 µL, 2.5 mol %) was added. After 5 h, the reaction mixture was diluted with ethyl acetate (100 mL). The resulting mixture was sequentially washed with aqueous 5% citric acid solution (50 mL), water (2×50 mL), and saturated aqueous sodium chloride solution (30 mL). The organic layer was dried over anhydrous sodium sulfate, was filtered, and was concentrated under reduced pressure. The resulting residue was purified by flash column chromatography (eluent: gradient, 30→60% ethyl acetate in hexanes) to afford the N-Boc-epidithiodiketopiperazine 24 (93.3 mg, 80.9%) as a pale yellow oil. Structural assignments were made with additional information from gCOSY, HSQC, and gHMBC data. $^1$H NMR (600 MHz, CDCl$_3$, 20° C.): δ 8.05 (br-s, 1H, C$_8$·H), 7.85 (d, J=8.1, 1H, C$_8$H), 7.48 (app-dt, J=4.5, 8.1, 1H, C$_7$H), 7.38 (app-dt, J=1.3, 7.7, 1H, SO$_2$Ph-p-H), 7.55 (d, J=7.1, 1H, C$_5$H), 7.34-7.30 (m, 2H, C$_5$H+C$_6$H), 7.28 (dd, J=7.1, 7.3, 1H, C$_7$·H), 7.17 (app-t, J=7.4, 1H, C$_6$H), 7.13 (d, J=7.6, 2H, SO$_2$Ph-o-H), 6.82 (dd, J=7.6, 8.1, 2H, SO$_2$Ph-m-H), 6.55 (s, 1H, C$_2$·H), 6.18 (br-s, 1H, C$_2$·H), 5.29 (s, 1H, C$_{15}$H), 3.88 (d, J=15.6, 1H, C$_{12}$H$_a$), 3.17 (s, 3H, C$_{17}$H$_3$), 2.67 (d, J=15.6, 1H, C$_{12}$H$_b$), 1.66 (s, 9H, OC(CH$_3$)$_3$). $^{13}$C NMR (150 MHz, CDCl$_3$, 20° C.): δ 165.1 (C$_{13}$), 160.3 (C$_{16}$), 149.2 (C$_{carbamate}$), 141.0 (C$_9$), 137.5 (SO$_2$Ph-ipso-C), 137.5 (C$_9$·), 135.9 (C$_4$), 132.8 (SO$_2$Ph-p-C), 130.3 (C$_7$), 128.1 (SO$_2$Ph-m-C), 127.1 (SO$_2$Ph-o-C), 126.7 (C$_6$), 125.6 (C$_4$·), 125.4 (C$_5$), 124.5 (C$_2$·), 123.6 (C$_7$·), 123.6 (C$_6$·), 120.1 (C$_5$·), 119.0 (C$_8$), 118.5 (C$_3$·), 116.0 (C$_8$·), 84.6 (OC(CH$_3$)$_3$), 84.1 (C$_2$), 74.4 (C$_{11}$), 68.5 (C$_{15}$), 55.2 (C$_3$), 42.2 (C$_{12}$), 32.3 (C$_{17}$), 28.4 (OC(CH$_3$)$_3$). FTIR (thin film) cm$^{-1}$: 2978 (w), 2929 (w), 1733 (s), 1677 (m), 1454 (m), 1371 (s), 1256 (m), 1157 (s), 1092 (m), 751 (s). HRMS (ESI) (m/z): calc'd for C$_{33}$H$_{30}$N$_4$NaO$_6$S$_3$ [M+Na]$^+$: 697.1220. found 697.1231. TLC (50% ethyl acetate in hexanes), Rf: 0.39 (UV, I$_2$, CAM).

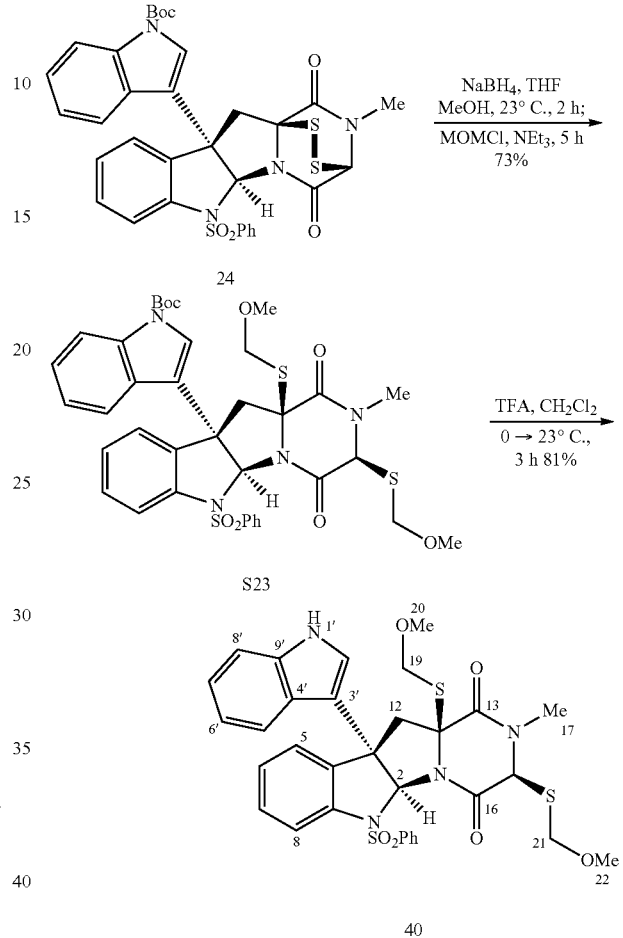

40

C3-(N-Boc-Indol-3'-yl)bis(S-MOM)ether 40

Sodium borohydride (50.0 mg, 1.32 mmol, 6.06 equiv) was added as a solid to a solution of epidithiodiketopiperazine 24 (147 mg, 218 µmol, 1 equiv) in anhydrous tetrahydrofuran (15 mL) and anhydrous methanol (60.0 µL) at 23° C. After 2 h, chloromethyl methyl ether (MOMCl, 500 µL, 1.42 mmol, 30.4 equiv) was added to the reaction mixture. After 1 h, triethylamine (200 µL, 1.42 mmol, 6.53 equiv) was added to the reaction mixture. After 4 h, the white reaction mixture was diluted with ethyl acetate (100 mL) and washed with saturated aqueous ammonium chloride solution (30 mL). The aqueous layer was extracted with ethyl acetate (2×20 mL). The combined organic layers were washed sequentially with water (2×30 mL) and saturated aqueous sodium chloride solution (20 mL), were dried over anhydrous sodium sulfate, were filtered, and were concentrated under reduced pressure. The residue was purified by flash column chromatography on silica gel (eluent: gradient, 30→70% ethyl acetate in hexanes) to afford the bis(S-MOM) derivative S23 (123 mg, 73.4%) as a colorless oil.

S23:

$^1$H NMR (600 MHz, CDCl$_3$, 20° C.): δ 8.03 (br-s, 1H, C$_8$·H), 7.84 (app-dd, J=0.5, 8.2, 1H, C$_8$H), 7.53 (br-d, J=7.4, 2H, SO$_2$Ph-o-H), 7.38 (app-ddd, J=1.5, 7.4, 8.2, 1H, C$_7$H), 7.30 (app-t, J=7.6, 1H, C$_7$H), 7.27 (app-dt, J=0.9, 8.3, 1H, C$_6$H), 7.19 (app-dd, J=0.8, 7.5, 1H, C$_5$H), 7.15 (app-dt, J=0.9, 7.4, 1H, C$_6$H), 7.05 (dd, J=7.7, 7.8, 2H, SO$_2$Ph-m-H), 7.00 (dd, J=7.4, 7.6, 2H, SO$_2$Ph-p-H), 6.73 (d, J=7.8, 1H, C$_5$H), 6.72 (s, 1H, C$_2$H), 6.65 (s, 1H, C$_{2'}$H), 5.21 (d, J=11.8, 1H, C$_{21}$H$_a$), 5.08 (app-d, J=12.7, 1H, C$_{19}$H$_a$), 4.95 (s, 1H, C$_{15}$H), 4.46 (d, J=11.8, 1H, C$_{21}$H$_b$), 4.30 (d, J=12.7, 1H, C$_{19}$H$_b$), 3.46 (s, 3H, C$_{22}$H$_3$), 3.39 (d, J=14.7, 1H, C$_{12}$H$_a$), 3.23 (d, J=14.7, 1H, C$_{12}$H$_b$), 3.08 (s, 3H, C$_{17}$H$_3$), 2.92 (s, 3H, C$_{20}$H$_3$), 1.66 (s, 9H, OC(CH$_3$)$_3$). TLC (50% ethyl acetate in hexanes), Rf: 0.49 (UV, CAM).

Trifluoroacetic acid (2 mL) was added to a solution of the N-Boc-indole S23 (6.1 mg, 7.8 µmol, 1 equiv) in anhydrous dichloromethane (5 mL) at 0° C. After 30 min, the ice-water bath was removed, and the solution was allowed to warm to 23° C. After 3 h, the reaction mixture was diluted with ethyl acetate (50 mL) and slowly poured into saturated aqueous sodium hydrogenocarbonate solution (25 mL). The organic layer was sequentially washed with water (3×15 mL) and saturated aqueous sodium chloride solution (15 mL). The combined aqueous layers were extracted with ethyl acetate (2×20 mL). The combined organic layers were dried over anhydrous sodium sulfate, were filtered, and were concentrated under reduced pressure. The residue was purified by flash column chromatography on silica gel (eluent: gradient, 10→40% ethyl acetate in hexanes) to afford the bis(S-MOM) ether 40 (4.3 mg, 81%) as a pale yellow oil. Structural assignments were made with additional information from gCOSY, HSQC, gHMBC, and NOESY data. $^1$H NMR (600 MHz, CDCl$_3$, 20° C.): δ 7.87 (br-s, 1H, C$_{1'}$H), 7.79 (d, J=8.2, 1H, C$_8$H), 7.72 (d, J=7.7, 2H, SO$_2$Ph-o-H), 7.41 (app-dd, J=7.4, 7.5, 1H, SO$_2$Ph-p-H), 7.32 (app-dt, J=0.9, 7.8, 1H, C$_7$H), 7.29 (d, J=8.1, 1H, C$_{8'}$H), 7.19 (dd, J=7.7, 8.0, 2H, SO$_2$Ph-m-H), 7.14 (app-t, J=7.5, 1H, C$_{7'}$H), 7.14 (d, J=7.4, 1H, C$_5$H), 7.08 (dd, J=7.4, 7.7, 1H, C$_6$H), 6.83 (dd, J=7.4, 7.8, 1H, C$_{6'}$H), 6.70 (d, J=8.0, 1H, C$_{5'}$H), 6.68 (s, 1H, C$_2$H), 6.51 (d, J=2.5, 1H, C$_{2'}$H), 5.17 (d, J=11.8, 1H, C$_{21}$H$_a$), 5.11 (d, J=12.7, 1H, Cl$_{19}$H), 4.91 (s, 1H, C$_{15}$H), 4.44 (d, J=11.8, 1H, C$_{21}$H$_b$), 4.35 (d, J=12.7, 1H, C$_{19}$H$_b$), 3.51 (d, J=14.7, 1H, C$_{12}$H$_a$), 3.45 (s, 3H, C$_{22}$H$_3$), 3.29 (d, J=14.7, 1H, C$_{12}$H$_b$), 3.07 (s, 3H, C$_{17}$H$_3$), 2.93 (s, 3H, C$_{20}$H$_3$). $^{13}$C NMR (150 MHz, CDCl$_3$, 20° C.): δ 165.7 (C$_{13}$), 163.2 (C$_{16}$), 141.6 (C$_9$), 138.4 (SO$_2$Ph-ipso-C), 137.3 (C$_{9'}$), 136.4 (C$_4$), 133.0 (SO$_2$Ph-p-C), 129.0 (C$_7$), 128.8 (SO$_2$Ph-m-C), 127.5 (SO$_2$Ph-o-C), 125.2 (C$_6$), 125.0 (C$_5$), 124.5 (C$_{4'}$), 122.9 (C$_{2'}$), 122.7 (C$_{7'}$), 120.4 (C$_{6'}$), 119.1 (C$_{5'}$), 117.0 (C$_8$), 116.5 (C3'), 111.7 (C$_{8'}$), 84.6 (C$_2$), 76.5 (C$_{21}$), 75.5 (C$_{15}$), 70.5 (C$_{11}$), 64.9 (C$_{15}$), 56.8 (C$_{20}$), 56.6 (C$_{22}$), 53.7 (C$_3$), 49.2 (C$_{12}$), 32.3 (C$_{17}$). FTIR (thin film) cm$^{-1}$: 3390 (w), 3004 (w), 2927 (w), 2823 (w), 1693 (s), 1666 (s), 1461 (m), 1392 (s), 1364 (s), 1312 (m), 1265 (w), 1235 (w), 1181 (s), 1084 (s), 751 (s). HRMS (ESI) (m/z): calc'd for C$_{32}$H$_{32}$N$_4$NaO$_6$S$_3$ [M+Na]$^+$: 687.1376. found: 687.1378. TLC (50% ethyl acetate in hexanes), Rf: 0.38 (UV, CAM).

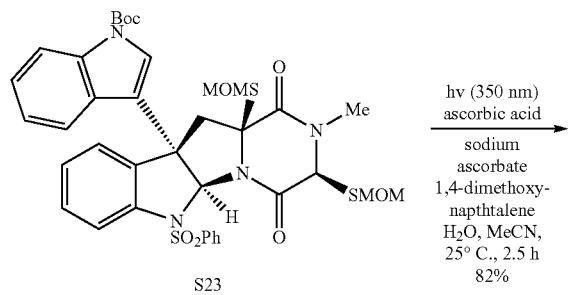

S23

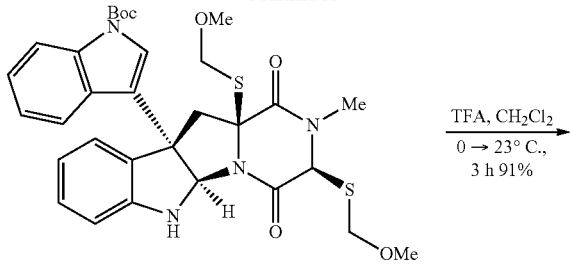

S24

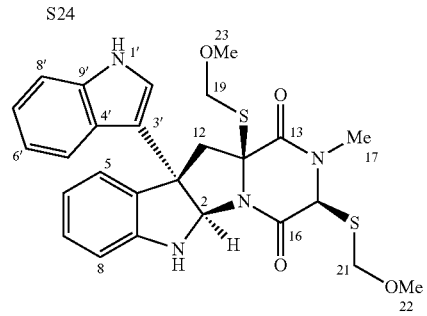

41

C3-(Indol-3'-yl)bis(S-MOM)ether 41

A 20×150 mm Pyrex tube was sequentially charged with bis(S-MOM)ether S23 (92.2 mg, 121 µmol, 1 equiv), 1-ascorbic acid (310 mg, 1.76 mmol, 14.6 equiv), sodium 1-ascorbate (380 mg, 1.92 mmol, 15.9 equiv), and 1,4-dimethoxynaphthalene (1.25 g, 6.64 mmol, 55.1 equiv), and the mixture was placed under an argon atmosphere. A solution of water in acetonitrile (20% v/v, 24 mL) that was purged with argon for 15 min at 23° C. was transferred to the flask via cannula. The system was vigorously stirred under an argon atmosphere and irradiated with a Rayonet photoreactor equipped with 16 lamps emitting at 350 nm at 25° C. After 2.5 h, the lamps were turned off, and the reaction mixture was diluted with ethyl acetate (100 mL) and diethyl ether (50 mL). The resulting solution was sequentially washed with saturated aqueous sodium hydrogenocarbonate solution (50 mL), water (2×40 mL), and saturated aqueous sodium chloride solution (40 mL). The aqueous layer was extracted with ethyl acetate (2×50 mL). The combined organic layers were dried over anhydrous sodium sulfate, were filtered, and were concentrated under reduced pressure. The residue was purified by flash column chromatography on silica gel (eluent: gradient, 20→60% ethyl acetate in hexanes) to afford aniline S24 (61.7 mg, 81.9%) as a pale yellow oil.

S24:
$^1$H NMR (600 MHz, CDCl$_3$, 20° C.): δ 8.11 (br-s, 1H, N$_1$H), 7.46 (br-s, 1H, C$_{8'}$H), 7.37 (d, J=7.9, 1H, C$_5$H), 7.26 (app-t, J=7.6, 1H, C$_7$H), 7.10 (d, J=7.2, 1H, C$_5$H), 7.13-7.08 (m, 3H, C$_6$H+C$_7$H+C$_8$H), 6.74-6.67 (m, 2H, C$_{2'}$H+C$_6$H), 6.04 (s, 1H, C$_2$H), 5.19 (d, J=11.7, 1H, C$_{21}$H$_a$), 5.16 (d, J=12.6, 1H, C$_{19}$H$_a$), 4.90 (s, 1H, C$_{15}$H), 4.52 (d, J=11.7, 1H, C$_{21}$H$_b$), 4.31 (d, J=12.6, 1H, C$_{19}$H$_b$), 3.55 (d, J=14.1, 1H, C$_{12}$H$_a$), 3.45 (d, J=14.1, 1H, C$_{12}$H$_b$), 3.47 (s, 3H, C$_{22}$H$_3$), 3.06 (s, 3H, C$_{17}$H$_3$), 2.91 (s, 3H, C$_{20}$H$_3$), 1.65 (s, 9H, OC(CH$_3$)). HRMS (ESI) (m/z): calc'd for C$_{31}$H$_{36}$N$_4$NaO$_6$S$_2$ [M+Na]$^+$: 647.1968. found: 647.1976. TLC (50% ethyl acetate in hexanes), Rf: 0.74 (UV, CAM).

Trifluoroacetic acid (2 mL) was added to a solution of the N-Boc-indole S24 (6.0 mg, 9.6 µmol, 1 equiv) in anhydrous dichloromethane (5 mL) at 0° C. After 30 min, the ice-water bath was removed, and the solution was allowed to warm to 23° C. After 3 h, the reaction mixture was diluted with ethyl acetate (50 mL) and slowly poured into saturated aqueous sodium hydrogenocarbonate solution (25 mL) at 23° C. The organic layer was sequentially washed with water (3×15 mL) and saturated aqueous sodium chloride solution (15 mL). The combined aqueous layers were extracted with ethyl acetate (2×20 mL). The combined organic layers were dried over anhydrous sodium sulfate, were filtered, and were concentrated under reduced pressure. The residue was purified by flash column chromatography on silica gel (eluent: gradient, 20→60% ethyl acetate in hexanes) to afford the bis(S-MOM) ether 41 (4.6 mg, 91%) as a colorless oil. Structural assignments were made with additional information from gCOSY, HSQC, gHMBC, and NOESY data. $^1$H NMR (600 MHz, CDCl$_3$, 20° C.): δ 7.98 (br-s, 1H, N$_1$H), 7.38 (d, J=8.0, 1H, C$_5$H), 7.32 (d, J=8.2, 1H, C$_8$H), 7.16 (app-t, J=7.2, 1H, C$_7$H), 7.14 (d, J=6.9, 1H, C$_5$H), 7.10 (app-dt, J=1.0, 7.8, 1H, C$_7$H), 7.02 (app-t, J=7.2, 1H, C$_6$H), 7.01 (d, J=2.7, 1H, C$_2$H), 6.73 (dd, J=7.3, 7.5, 1H, C$_6$H), 6.71 (d, J=7.8, 1H, C$_8$H), 6.05 (s, 1H, C$_2$H), 5.22 (d, J=11.7, 1H, C$_{21}$H$_a$), 5.13 (d, J=12.6, 1H, C$_{19}$H$_a$), 4.93 (s, 1H, C$_{15}$H), 4.53 (d, J=11.7, 1H, C$_{21}$H$_b$), 4.34 (d, J=12.6, 1H, C$_{19}$H$_b$), 3.48 (s, 2H, C$_{12}$H), 3.48 (s, 3H, C$_{22}$H$_3$), 3.07 (s, 3H, C$_{17}$H$_3$), 2.95 (s, 3H, C$_{20}$H$_3$). The resonance for N$_1$H was not observed. $^{13}$C NMR (150 MHz, CDCl$_3$, 20° C.): δ 166.1 (C$_{13}$), 165.4 (C$_{16}$), 148.5 (C$_9$), 137.4 (C$_{9'}$), 132.8 (C$_4$), 128.6 (C$_7$), 125.3 (C$_{4'}$), 124.9 (C$_5$), 122.6 (C$_{7'}$), 121.6 (C$_{2'}$), 120.2 (C$_{6'}$), 119.9 (C$_{5'}$), 119.6 (C$_6$), 119.4 (C3'), 111.6 (C$_{8'}$), 109.3 (C$_8$), 82.6 (C$_2$), 77.0 (C$_{21}$), 75.7 (C$_{19}$), 69.3 (C$_{11}$), 65.1 (C$_{15}$), 57.0 (C$_{20}$), 56.5 (C$_{22}$), 54.3 (C$_3$), 48.0 (C$_{12}$), 32.0 (C$_{17}$). FTIR (thin film) cm$^{-1}$: 3394 (br-w), 3013 (w), 2928 (w), 2823 (w), 1693 (s), 1669 (s), 1461 (m), 1393 (m), 1363 (m), 1265 (w), 1180 (s), 752 (s). HRMS (ESI) (m/z): calc'd for C$_{26}$H$_{28}$N4NaO$_4$S$_2$ [M+Na]$^+$: 547.1444. found: 547.1434. TLC (50% ethyl acetate in hexanes), Rf: 0.43 (UV, CAM).

C3-(N-Boc-Indol-3'-yl)bis(S-MEM)ether 42 and C3-(N-Boc-indol-3'-yl) S15-MEM ether 47

Sodium borohydride (9.8 mg, 250 μmol, 3.6 equiv) was added as a solid to a solution of epidithiodiketopiperazine 24 (47.0 mg, 69.6 μmol, 1 equiv) in anhydrous tetrahydrofuran (8 mL) and anhydrous methanol (50 μL) at 23° C. After 80 min, 2-methoxyethoxymethyl chloride (MEMCl, 300 μL, 2.63 mmol, 37.7 equiv) followed by triethylamine (400 μL, 2.85 mmol, 40.9 equiv) were added to the reaction mixture. After 12 h, the yellow reaction mixture was partitioned between aqueous 5% citric acid solution (30 mL) and ethyl acetate (80 mL). The isolated organic layer was washed sequentially with water (2×30 mL) and saturated aqueous sodium chloride solution (20 mL), was dried over anhydrous sodium sulfate, was filtered, and was concentrated under reduced pressure. The residue was purified by flash column chromatography on silica gel (eluent: gradient, 10→25% ethyl acetate in dichloromethane) to afford the bis(S-MEM) ether adduct 42 (57.6 mg, 80.2%) and the S15-MEM-adduct 47 (10.0 mg, 18.8%) as colorless oils. Structural assignments were made with additional information from gCOSY, HSQC, gHMBC, and NOESY data.

C3-(N-Boc-indol-3'-yl)bis(S-MEM)ether 42

$^1$H NMR (600 MHz, CDCl$_3$, 20° C.): δ 8.02 (br-s, 1H, C$_8$H), 7.83 (d, J=8.2, 1H, C$_8$H), 7.56 (br-d, J=6.2, 2H, SO$_2$Ph-o-H), 7.36 (dd, J=7.7, 8.0, 1H, C$_7$H), 7.32 (t, J=7.3, 1H, SO$_2$Ph-p-H), 7.24 (d, J=7.8, 1H, C$_5$H), 7.16 (d, J=7.4, 1H, C$_5$H), 7.10 (app-t, J=7.6, 1H, C$_6$H), 7.08 (app-t, J=7.5, 2H, SO$_2$Ph-m-H), 6.96 (app-t, J=7.5, 1H, C$_6$H), 6.76 (s, 1H, C$_2$H), 6.67-6.61 (m, 1H, C$_7$H), 6.62 (s, 1H, C$_2$H), 5.21 (d, J=12.0, 1H, C$_{23}$H$_a$), 5.13 (d, J=12.8, 1H, C$_{19}$H$_a$), 5.00 (s, 1H, C$_{15}$H), 4.63 (d, J=12.0, 1H, C$_{23}$H$_b$), 4.47 (d, J=12.8, 1H, C$_{19}$H$_b$), 4.00-3.94 (m, 1H, C$_{24}$H$_a$), 3.67-3.64 (m, 2H, C$_{24}$H$_b$+C$_{25}$H$_a$), 3.61-3.56 (m, 1H, C$_{25}$H$_b$), 3.41 (d, J=14.9, 1H, C$_{12}$H$_a$), 3.39 (s, 3H, C$_{26}$H$_3$), 3.38-3.33 (m, 2H, C$_{21}$H), 3.31 (s, 3H, C$_{22}$H$_3$), 3.28-3.23 (m, 1H, C$_{20}$H$_a$), 3.23 (d, J=14.9, 1H, C$_{12}$H$_b$), 3.20-3.14 (m, 1H, C$_{20}$H$_b$), 3.09 (s, 3H, C$_{17}$H$_3$),

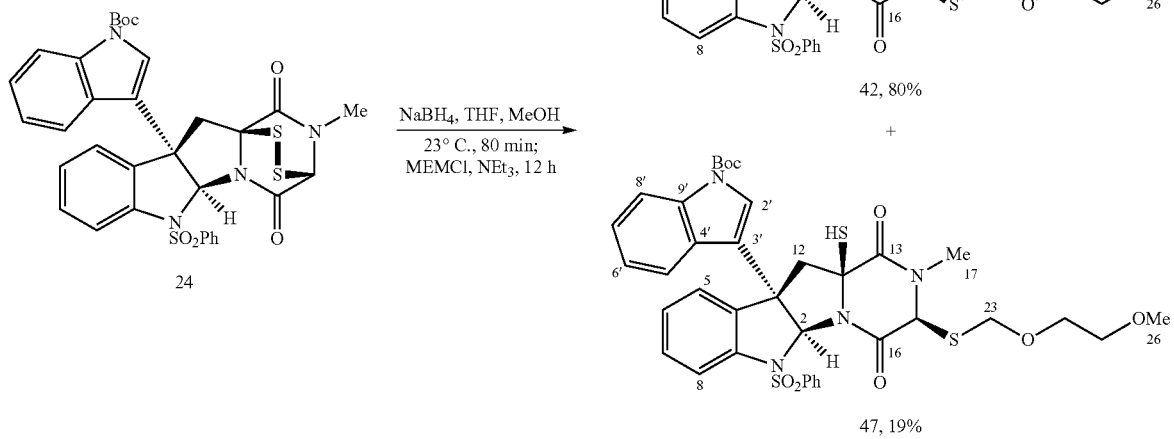

1.69 (s, 9H, OC(CH$_3$)$_3$). $^{13}$C NMR (150 MHz, CDCl$_3$, 20° C.): δ 165.3 (C$_{13}$), 163.1 (C$_{16}$), 149.3 (C$_{carbamate}$), 141.7 (C$_9$), 137.9 (SO$_2$Ph-ipso-C), 136.3 (C$_{9'}$), 135.7 (C$_4$), 133.0 (SO$_2$Ph-p-C), 129.3 (C$_7$), 128.6 (SO$_2$Ph-m-C), 127.4 (SO$_2$Ph-o-C), 127.2 (C$_{4'}$), 125.5 (C$_6$), 125.0 (C$_{5'}$), 124.9 (C$_{7'}$), 124.5 (C$_{7'}$), 123.2 (C$_{6'}$), 120.3 (C$_3$), 119.1 (C$_{2'}$), 117.9 (C$_8$), 115.7 (C$_{8'}$), 84.4 (OC(CH$_3$)$_3$), 83.8 (C$_2$), 75.2 (C$_{23}$), 74.0 (C$_{19}$), 71.6 (C$_{25}$), 71.6 (C$_{21}$), 70.3 (C$_{11}$), 68.2 (C$_{20}$), 68.1 (C$_{24}$), 64.9 (C$_{15}$), 59.3 (C$_{22}$), 59.2 (C$_{26}$), 53.3 (C$_3$), 48.6 (C$_{12}$), 32.2 (C$_{17}$), 28.4 (OC(CH$_3$)$_3$). FTIR (thin film) cm$^{-1}$: 2920 (m), 2851 (m), 1734 (s), 1699 (s), 1668 (s), 1454 (s), 1373 (s), 1310 (m), 1272 (m), 1158 (s), 1088 (s), 1025 (m), 752 (s). HRMS (ESI) (m/z): calc'd for C$_{41}$H$_{48}$N$_4$NaO$_{10}$S$_3$ [M+Na]$^+$: 875.2425. found: 875.2411. TLC (20% ethyl acetate in dichloromethane), Rf: 0.44 (UV, I$_2$, CAM).

C3-(N-Boc-indol-3'-yl) S15-MEM ether 47

$^1$H NMR (600 MHz, CDCl$_3$, 20° C.): δ 8.04 (br-s, 1H, C$_8$H), 7.85 (d, J=8.1, 1H, C$_8$H), 7.45 (app-dt, J=1.0, 8.0, 1H, C$_7$H), 7.38 (br-d, J=6.2, 2H, SO$_2$Ph-o-H), 7.31 (app-t, J=7.8, 1H, C$_7$H), 7.29-7.21 (m, 3H, C$_5$H+C$_6$H+SO$_2$Ph-p-H), 7.12 (dd, J=7.4, 7.6, 1H, C$_6$H), 6.95 (app-t, J=7.7, 2H, SO$_2$Ph-m-H), 6.91 (d, J=7.8, 1H, C$_5$H), 6.67 (s, 1H, C$_2$H), 6.53 (s, 1H, C$_2$H), 5.25 (d, J=11.9, 1H, C$_{23}$H$_a$), 5.09 (s, 1H, C$_{15}$H), 4.71 (d, J=11.9, 1H, C$_{23}$H$_b$), 4.00-3.96 (m, 1H, C$_{24}$H$_a$), 3.70-3.62 (m, 2H, C$_{24}$H$_b$+C$_{25}$H$_a$), 3.62-3.58 (m, 1H, C$_{25}$H$_b$), 3.43 (d, J=14.6, 1H, C$_{12}$H$_a$), 3.40 (s, 3H, C$_{26}$H$_3$), 3.13 (s, 3H, C$_{17}$H$_3$), 2.87 (d, J=14.6, 1H, C$_{12}$H$_b$), 1.66 (s, 9H, OC(CH$_3$)$_3$). $^{13}$C NMR (150 MHz, CDCl$_3$, 20° C.): δ 167.5 (C$_{13}$), 162.2 (C$_{16}$), 149.2 (C$_{carbamate}$), 142.2 (C$_9$), 137.8 (SO$_2$Ph-ipso-C), 135.6 (C$_{9'}$), 135.6 (C$_4$), 132.8 (SO$_2$Ph-p-C), 129.9 (C$_7$), 128.3 (SO$_2$Ph-m-C), 127.3 (SO$_2$Ph-o-C), 126.9 (C$_{4'}$), 126.3 (C$_6$), 125.2 (C$_{7'}$), 124.9 (C$_5$), 124.8 (C$_{2'}$), 123.4 (C$_{6'}$), 119.6 (CO$_3$), 119.3 (C$_8$), 119.0 (C$_{5'}$), 115.9 (C$_{8'}$), 84.5 (OC(CH$_3$)$_3$), 83.8 (C$_2$), 74.0 (C$_{23}$), 71.6 (C$_{25}$), 68.4 (C$_{24}$), 68.1 (C$_{11}$), 64.3 (C$_{15}$), 59.3 (C$_{26}$), 53.4 (C$_3$), 51.2 (C$_{12}$), 32.7 (C$_{17}$), 28.4 (OC(CH$_3$)$_3$). FTIR (thin film) cm$^{-1}$: 2978 (w), 2922 (w), 1734 (m), 1697 (m), 1454 (m), 1372 (s), 1272 (w), 1235 (w), 1157 (m), 1091 (m), 752 (s). HRMS (ESI) (m/z): calc'd for C$_{37}$H$_{40}$N$_4$NaO$_5$S$_3$ [M+Na]$^+$: 787.1900. found: 787.1897. TLC (20% ethyl acetate in dichloromethane), Rf: 0.24 (UV, I$_2$, CAM).

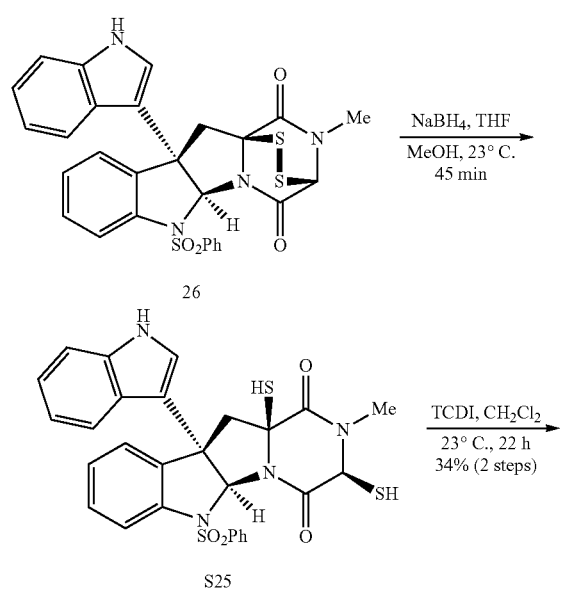

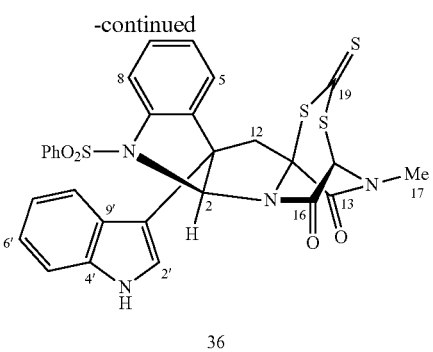

C3-(Indol-3'-yl)dithiepanethione 36

Sodium borohydride (4.9 mg, 0.13 mmol, 3.4 equiv) was added as a solid to a solution of epidithiodiketopiperazine 26 (22.0 mg, 38.3 μmol, 1 equiv) in anhydrous tetrahydrofuran (5 mL) and anhydrous methanol (50 μL) at 23° C. After 45 min, the reaction mixture was diluted with ethyl acetate (40 mL) and washed with saturated aqueous ammonium chloride solution (20 mL). The aqueous layer was extracted with ethyl acetate (2×20 mL) and the combined organic layers were washed sequentially with water (2×20 mL) and saturated aqueous sodium chloride solution (20 mL), were dried over anhydrous sodium sulfate, were filtered, and were concentrated under reduced pressure to afford the hexacyclic bisthiol S25 that was used in the next step without further purification. 1,1'-Thiocarbonyldiimidazole (TCDI, 108 mg, 606 μmol, 15.8 equiv) was added as a solid to the solution of bisthiol S25 in anhydrous dichloromethane (6 mL) at 23° C. After 22 h, the volatiles were removed under reduced pressure. The residue was purified by flash column chromatography on silica gel (eluent: gradient, 5→25% ethyl acetate in dichloromethane) to afford the dithiepanethione 36 (8.4 mg, 34%) as a pale yellow oil. Structural assignments were made with additional information from gCOSY, HSQC, and gHMBC data. Without the intention to be limited by theory, Applicant notes that in some embodiments, upon concentration or in concentrated solution, the dithiepanethione 36 tends to degrade, thus rendering its isolation and characterization particularly arduous. $^1$H NMR (600 MHz, CDCl$_3$, 20° C.): δ 7.86 (br-s, 1H, N$_1$H), 7.75 (d, J=8.2, 1H, C$_8$H), 7.49 (app-dd, J=1.0, 8.3, 2H, SO$_2$Ph-o-H), 7.43-7.36 (m, 2H, C$_7$H+SO$_2$Ph-p-H), 7.35 (d, J=8.1, 1H, C$_8$H), 7.23-7.17 (m, 3H, C$_5$H+C$_6$H+C$_7$H), 7.10 (dd, J=7.6, 8.1, 2H, SO$_2$Ph-m-H), 6.98 (app-dt, J=0.5, 7.5, 1H, C$_6$H), 6.89 (d, J=8.0, 1H, C$_5$H), 6.64 (s, 1H, C$_2$H), 6.36 (d, J=2.5, 1H, C$_2$H), 5.05 (s, 1H, C$_{15}$H), 3.96 (d, J=15.6, 1H, C$_{12}$H$_a$), 3.18 (s, 3H, C$_{17}$H$_3$), 2.80 (d, J=15.6, 1H, C$_{12}$H$_b$). $^{13}$C NMR (150 MHz, CDCl$_3$, 20° C.): δ 214.3 (C$_{19}$), 164.3 (C$_{13}$), 159.4 (C$_{16}$), 140.9 (C$_9$), 137.5 (SO$_2$Ph-ipso-C), 137.3 (C$_{9'}$), 135.1 (C$_4$), 133.2 (SO$_2$Ph-p-C), 130.2 (C$_7$), 128.7 (SO$_2$Ph-m-C), 127.4 (SO$_2$Ph-o-C), 126.2 (C$_6$), 124.6 (C$_6$), 124.2 (C$_{4'}$), 124.1 (C$_{2'}$), 123.2 (C$_{7'}$), 120.7 (C$_{6'}$), 118.8 (C$_{5'}$), 118.5 (C$_8$), 113.8 (C$_3$), 112.0 (C$_{8'}$), 85.3 (C$_2$), 75.3 (C$_{11}$), 69.5 (C$_{15}$), 54.6 (C$_3$), 45.8 (C$_{12}$), 32.7 (C$_{17}$). FTIR (thin film) cm$^{-1}$: 3393 (br-w), 2921 (m), 2851 (w), 1703 (s), 1459 (m), 1361 (m), 1168 (m), 1089 (w), 1016 (w), 907 (w), 733 (m). HRMS (ESI) (m/z): calc'd for C$_{29}$H$_{23}$N$_4$O$_4$S$_4$ [M+H]$^+$: 619.0597. found 619.0609; calc'd for C$_{29}$H$_{22}$N4NaO$_4$S$_4$ [M+Na]$^+$: 641.0416. found 641.0424. TLC (20% ethyl acetate in dichloromethane), Rf: 0.68 (UV, I$_2$, CAM).

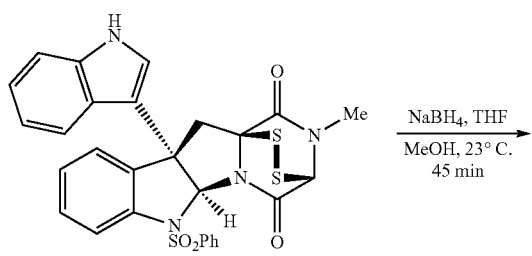

26

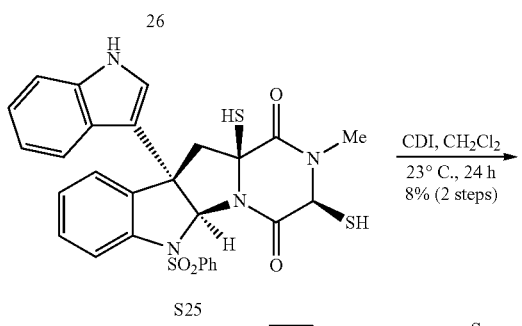

S25

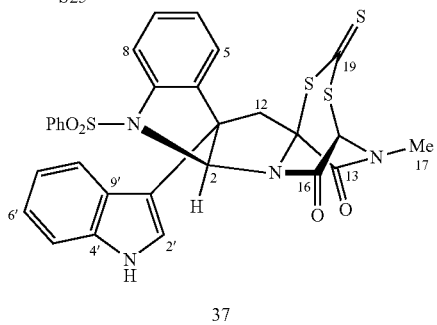

37

C3-(Indol-3'-)dithiocarbonate 37

Sodium borohydride (4.9 mg, 0.13 mmol, 3.3 equiv) was added as a solid to a solution of epidithiodiketopiperazine 26 (22.6 mg, 39.3 μmol, 1 equiv) in anhydrous tetrahydrofuran (5 mL) and anhydrous methanol (50 μL) at 23° C. After 45 min, the reaction mixture was diluted with ethyl acetate (40 mL) and washed with saturated aqueous ammonium chloride solution (20 mL). The aqueous layer was extracted with ethyl acetate (2×20 mL) and the combined organic layers were washed sequentially with water (2×20 mL) and saturated aqueous sodium chloride solution (20 mL), were dried over anhydrous sodium sulfate, were filtered, and were concentrated under reduced pressure to afford the hexacyclic bisthiol S25 that was used in the next step without further purification. 1,1'-Carbonyldiimidazole (CDI, 80.0 mg, 493 μmol, 12.0 equiv) was added as a solid to the solution of bisthiol S25 in anhydrous dichloromethane (10 mL) at 23° C. After 24 h, the volatiles were removed under reduced pressure. The residue was purified by flash column chromatography on silica gel (eluent: gradient, 5→20% ethyl acetate in dichloromethane) to afford the dithiocarbonate 37 along with epidithiodiketopiperazine 26. Both compounds were separated by preparative HPLC [Waters X-Bridge preparative HPLC column, C18, 5 nm, 19×250 mm; 20.0 mL/min; gradient, 20→90% acetonitrile in water, 20 min; $t_R$(37)=15.35 min, $t_R$(26)=14.50 min] to afford 37 (2.0 mg, 8%) as a pale yellow oil. Epidithiodiketopiperazine 26 was also recovered (2.9 mg, 12%). Structural assignments were made with additional information from gCOSY, HSQC, and gHMBC data. $^1$H NMR (600 MHz, CDCl$_3$, 20° C.): δ 7.84 (br-s, 1H, N$_1$,H), 7.78 (d, J=8.2, 1H, C$_8$H), 7.45 (d, J=8.4, 2H, SO$_2$Ph-o-H), 7.41 (app-ddd, J=1.6, 7.3, 7.7, 1H, C$_7$H), 7.37 (app-dt, J=1.0, 6.4, 1H, SO$_2$Ph-p-H), 7.35 (d, J=8.2, 1H, C$_8$H), 7.21 (app-ddd, J=0.8, 7.2, 7.6, 1H, C$_7$H), 7.19 (app-dt, J=0.9, 7.3, 1H, C$_6$H), 7.16 (app-dd, J=1.1, 7.6, 1H, C$_5$H), 7.06 (dd, J=7.6, 8.3, 2H, SO$_2$Ph-m-H), 6.99 (app-dt, J=0.7, 7.5, 1H, C$_6$H), 6.90 (d, J=7.9, 1H, C$_5$H), 6.64 (s, 1H, C$_2$H), 6.26 (d, J=2.6, 1H, C$_2$,H), 5.17 (s, 1H, C$_{15}$H), 3.92 (d, J=15.5, 1H, C$_{12}$H$_a$), 3.20 (s, 3H, C$_{17}$H$_3$), 2.78 (d, J=15.5, 1H, C$_{12}$H$_b$). $^{13}$C NMR (150 MHz, CDCl$_3$, 20° C.): δ 185.4 (C$_{19}$), 165.0 (C$_{13}$), 160.0 (C$_{16}$), 141.0 (C$_9$), 137.3 (SO$_2$Ph-ipso-C), 137.3 (C$_9$'), 135.2 (C$_4$), 133.2 (SO$_2$Ph-p-C), 130.2 (C$_7$), 128.7 (SO$_2$Ph-m-C), 127.5 (SO$_2$Ph-o-C), 126.2 (C$_6$), 124.6 (C$_5$), 124.1 (C$_4$'), 124.1 (C$_2$'), 123.2 (C$_7$'), 120.7 (C$_6$'), 118.7 (C$_5$'), 118.7 (C$_8$), 113.8 (C$_3$'), 112.0 (C$_8$'), 85.3 (C$_2$), 72.6 (C$_{11}$), 66.6 (C$_{15}$), 54.5 (C$_3$), 46.5 (C$_{12}$), 32.6 (C$_{17}$). FTIR (thin film) cm$^{-1}$: 3396 (br-m), 2924 (m), 2853 (w), 1696 (m), 1460 (m), 1383 (m), 1169 (m), 1091 (w), 1051 (w), 735 (m). HRMS (ESI) (m/z): calc'd for C$_{29}$H$_{22}$N$_4$NaO$_5$S$_3$ [M+Na]$^+$: 625.0645. found 625.0652. TLC (20% ethyl acetate in dichloromethane), Rf: 0.57 (UV, I$_2$, CAM).

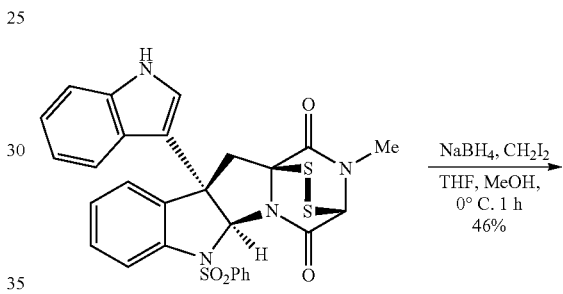

26

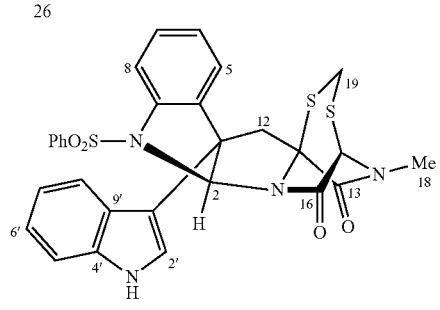

38

C3-(Indol-3'-yl)dithioacetal 38

Sodium borohydride (15.0 mg, 0.400 mmol, 9.88 equiv) was added as a solid to a solution of epidithiodiketopiperazine 26 (23.1 mg, 40.2 μmol, 1 equiv) in anhydrous THF (5 mL) and diiodomethane (0.2 mL) at 0° C. under an argon atmosphere ((a) Cook, K. M.; Hilton, S. T.; Mecinović, J.; Motherwell, W. B.; Figg, W. D.; Schofield, C. J. *J. Biol. Chem.* 2009, 284, 26831. (b) Poisel, H.; Schmidt, U. *Chem. Ber.* 1971, 104, 1714). After 5 min, anhydrous methanol (50 μL) was added. After 50 min, the reaction mixture was partitioned between aqueous hydrochloric acid solution (1 N, 25 mL) and ethyl acetate (80 mL). The aqueous layer was extracted with ethyl acetate (2×20 mL), and the combined organic layers were washed sequentially with water (2×30 mL) and saturated aqueous sodium chloride solution (30 mL), were dried over anhydrous sodium sulfate, were filtered, and were concentrated under reduced pressure. The residue was purified by flash column chromatography on silica gel (eluent: gradient, 5→20% ethyl acetate in dichloromethane) to afford dithioacetal 38 (10.8 mg, 45.6%) as a colorless oil. Structural assignments were made with additional information from gCOSY, HSQC, and gHMBC data. Based on $^1$H NMR analysis at 20° C. in CDCl$_3$, the product exists as a 1:4 mixture of minor: major conformers. $^1$H NMR (600 MHz, CDCl$_3$, 20° C.): Major conformer: δ 7.89 (br-s, 1H, N$_1$,H), 7.87 (d, J=8.2, 1H, C$_8$H), 7.65 (d, J=7.7, 2H, SO$_2$Ph-o-H), 7.43 (app-dd, J=7.4, 7.5, 1H, SO$_2$Ph-p-H), 7.37 (app-ddd, J=1.3, 7.4, 8.2, 1H, C$_7$H), 7.31 (d, J=8.2, 1H, C$_8$,H), 7.15 (dd, J=7.7, 7.9, 2H, SO$_2$Ph-m-H), 7.14 (app-t, J=7.3, 1H, C$_7$,H), 7.10 (app-t, J=7.5, 1H, C$_6$H), 7.02 (app-dd, J=0.4, 7.4, 1H, C$_5$H), 6.81 (app-dd, J=7.4, 7.7, 1H, C$_6$,H), 6.57 (s, 1H, C$_2$H), 6.51 (d, J=8.0, 1H, C$_5$,H), 6.43 (d, J=2.4, 1H, C$_2$,H), 4.86 (s, 1H, C$_{15}$H), 4.55 (d, J=14.8, 1H, C$_{19}$H$_a$), 3.86 (d, J=14.9, 1H, C$_{12}$H$_a$), 3.71 (d, J=14.8, 1H, C$_{19}$H$_b$), 3.08 (s, 3H, C$_{17}$H$_3$), 2.70 (d, J=14.9, 1H, C$_{12}$H$_b$). Minor conformer: δ 7.78 (d, J=8.3, 1H, C$_8$H), 7.78 (br-s, 1H, N$_1$,H), 7.44-7.40 (m, 1H, C$_7$H), 7.35 (d, J=7.7, 2H, SO$_2$Ph-o-H), 7.32-7.29 (m, 1H, C$_7$,H), 7.28 (d, J=8.3, 1H, C$_5$H), 7.27-7.21 (m, C$_8$,H SO$_2$Ph-p-H), 7.20 (d, J=8.0, 1H, C$_5$,H), 7.12-7.07 (m, 2H, C$_6$H+C$_6$,H), 6.93 (dd, J=7.7, 8.0, 2H, SO$_2$Ph-m-H), 6.57 (s, 1H, C$_2$H), 5.97 (d, J=2.5, 1H, C$_2$,H), 5.26 (s, 1H, C$_{15}$H), 4.01 (d, J=15.6, 1H, C19H$_a$), 3.56 (d, J=14.9, 1H, C$_{19}$H$_b$), 3.16 (s, 3H, C$_{17}$H$_3$), 3.11 (d, J=15.8, 1H, C$_{12}$H$_a$), 2.72 (d, J=15.8, 1H, C$_{12}$H$_b$). $^{13}$C NMR (150 MHz, CDCl$_3$, 20° C.): Major conformer: δ 167.5 (C$_{13}$), 161.7 (C$_{16}$), 140.5 (C$_9$), 137.3 (C$_{9'}$), 136.6 (SO$_2$Ph-ipso-C), 136.1 (C$_4$), 133.4 (SO$_2$Ph-p-C), 129.5 (C$_7$), 128.8 (SO$_2$Ph-m-C), 128.0 (SO$_2$Ph-o-C), 125.7 (C$_6$), 124.6 (C$_5$), 124.4 (C$_{4'}$), 124.1 (C$_{2'}$), 122.9 (C$_{7'}$), 120.4 (C$_{6'}$), 119.0 (C$_{5'}$), 117.8 (C$_8$), 113.9 (C$_{3'}$), 111.8 (C$_{8'}$), 85.4 (C$_2$), 70.6 (C$_{11}$), 65.2 (C$_{15}$), 54.4 (C$_3$), 48.1 (C$_{12}$), 32.7 (C$_{17}$), 31.7 (C$_{19}$). Minor conformer: δ 165.3 (C$_{13}$), 160.5 (C$_{16}$), 140.8 (C$_9$), 137.6 (C$_{9'}$), 137.2 (SO$_2$Ph-ipso-C), 136.6 (C$_4$), 133.0 (SO$_2$Ph-p-C), 129.9 (C$_7$), 128.4 (SO$_2$Ph-m-C), 127.3 (SO$_2$Ph-o-C), 126.1 (C$_6$), 124.8 (C$_5$), 124.4 (C$_{4'}$), 124.2 (C$_{2'}$), 123.2 (C$_{7'}$), 120.8 (C$_{6'}$), 119.1 (C$_{5'}$), 118.8 (C$_8$), 114.2 (C$_{3'}$), 111.9 (C$_{8'}$), 84.8 (C$_2$), 74.5 (C$_{11}$), 68.5 (C$_{15}$), 55.7 (C$_3$), 42.6 (C$_{12}$), 32.7 (C$_{17}$), 32.3 (C$_{19}$). FTIR (thin film) cm$^{-1}$: 3392 (br-m), 3059 (w), 2977 (w), 1690 (s), 1451 (w), 1361 (m), 1266 (w), 1170 (m), 1090 (w), 1022 (m), 736 (m). HRMS (ESI) (m/z): calc'd for C$_{29}$H$_{24}$N$_4$NaO$_4$S$_3$ [M+Na]$^+$: 611.0852. found 611.0850. TLC (10% ethyl acetate in dichloromethane), Rf: 0.40 (UV, I$_2$, CAM).

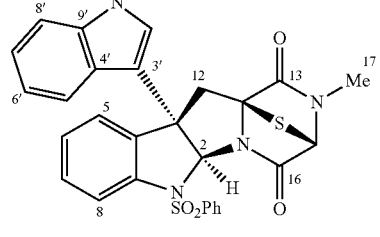

25

C3-(Indol-3'-yl)epimonothiodiketopiperazine 25

(Cherblanc, F.; Lo, Y.-P.; De Gussem, E.; Alcazar-Fuoli, L.; Bignell, E.; He, Y.; Chapman-Rothe, N.; Bultinck, P.; Herrebout, W. A.; Brown, R.; Rzepa, H. S.; Fuchter, M. J. *Chem.—Eur. J.* 2011, 17, 11868): Triethylphosphite (10.0 µL, 58.4 µmol, 21.4 equiv) was added to the solution of epidithiodiketopiperazine 26 (8.6 mg, 15 µmol, 1 equiv) in anhydrous tetrahydrofuran (4 mL) at 23° C. After 6 h, the reaction mixture was diluted sequentially with saturated aqueous ammonium chloride solution (20 mL) and ethyl acetate (60 mL). The organic layer was washed with water (2×15 mL) and saturated aqueous sodium chloride solution (15 mL), was dried over anhydrous sodium sulfate, was filtered, and was concentrated under reduced pressure. The residue was purified by flash column chromatography on silica gel (eluent: gradient, 2→8% ethyl acetate in dichloromethane) to afford the epimonothiodiketopiperazine 25 (5.1 mg, 63%) as a white solid. Structural assignments were made with additional information from gCOSY, HSQC, and gHMBC data. Limited solubility of epimonothiodiketopiperazine 25 was observed in CH$_2$Cl$_2$, CHCl$_3$, EtOAc, MeOH, DMSO. $^1$H NMR (600 MHz, acetone-d$_6$, 20° C.): δ 9.95 (br-s, 1H, N$_1$,H), 7.64 (d, J=8.1, 1H, C$_8$H), 7.59 (d, J=7.8, 1H, C$_5$,H), 7.52 (d, J=7.3, 1H, C$_5$H), 7.48 (d, J=8.0, 1H, C$_8$,H), 7.44 (app-dt, J=1.1, 7.8, 1H, C$_7$H), 7.32 (app-tt, J=0.9, 7.4, 1H, SO$_2$Ph-p-H), 7.28 (app-dt, J=0.9, 7.6, 1H, C$_6$H), 7.26 (app-dt, J=0.9, 7.6, 1H, C$_7$,H), 7.20 (app-dt, J=0.8, 7.5, 1H, C$_6$,H), 6.98 (app-dd, J=1.0, 8.3, 2H, SO$_2$Ph-o-H), 6.90 (app-t, J=7.5, 2H, SO$_2$Ph-m-H), 6.19 (s, 1H, C$_2$H), 5.67 (d, J=2.6, 1H, C$_2$,H), 5.17 (s, 1H, C$_{15}$H), 3.70 (d, J=15.4, 1H, C$_{12}$H$_a$), 3.11 (s, 3H, C$_{17}$H$_3$), 2.84 (d, J=15.4, 1H, C$_{12}$H$_b$). $^{13}$C NMR (150 MHz, acetone-d$_6$, 20° C.): δ 173.9 (C$_{13}$), 171.6 (C$_{16}$), 141.4 (C$_9$), 138.7 (SO$_2$Ph-ipso-C), 138.7 (C$_{9'}$), 137.9 (C$_4$), 133.9 (SO$_2$Ph-p-C), 130.2 (C$_7$), 129.0 (SO$_2$Ph-m-C), 127.2 (SO$_2$Ph-o-C), 126.4 (C$_6$), 125.7 (C$_5$), 125.3 (C$_{2'}$), 124.9 (C$_{4'}$), 123.0 (C$_{7'}$), 120.6 (C$_{6'}$), 119.0 (C$_{5'}$), 118.6 (C$_8$), 115.3 (C$_{3'}$), 113.1 (C$_{8'}$), 83.3 (C$_2$), 81.9 (C$_{11}$), 73.0 (C$_{15}$), 59.4 (C$_3$), 35.3 (C$_{12}$), 31.4 (C$_{17}$). FTIR (thin film) cm$^{-1}$: 3357 (br-w), 3059 (w), 2919 (w), 2851 (w), 1740 (s), 1713 (s), 1457 (m), 1358 (m), 1261 (w), 1169 (m), 1086 (w), 971 (w), 737 (s), 685 (m). HRMS (ESI) (m/z): calc'd for C$_{28}$H$_{22}$N$_4$NaO$_4$S$_2$ [M+Na]$^+$: 565.0975. found 565.0971. TLC (10% ethyl acetate in dichloromethane), Rf: 0.76 (UV, I$_2$, CAM).

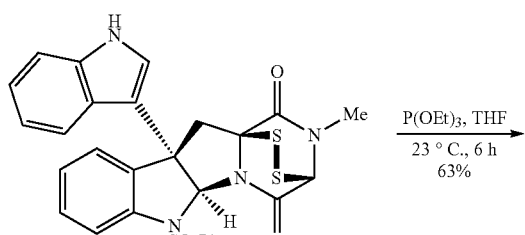

26

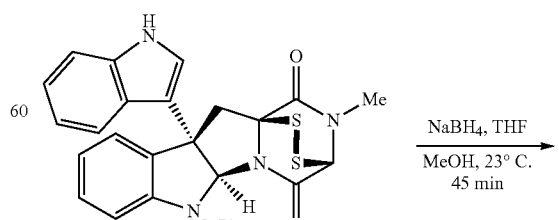

26

-continued

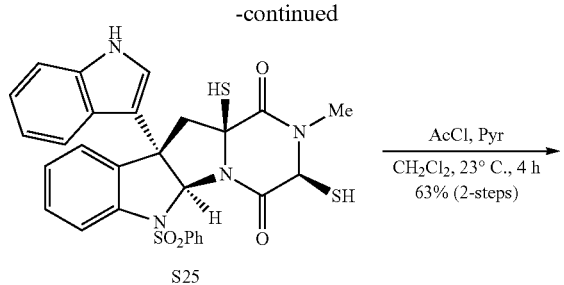

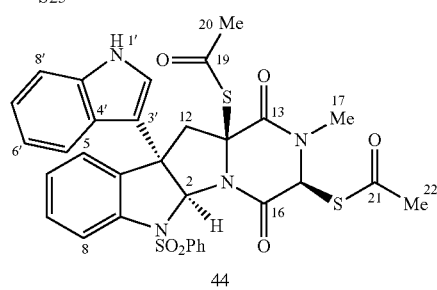

C3-(Indol-3'-yl)bisthloaeetate 44

Sodium borohydride (4.9 mg, 0.13 mmol, 3.3 equiv) was added as a solid to a solution of epidithiodiketopiperazine 26 (22.6 mg, 39.3 µmol, 1 equiv) in anhydrous tetrahydrofuran (5 mL) and anhydrous methanol (50 µL) at 23° C. After 45 min, the reaction mixture was diluted with ethyl acetate (40 mL) and washed with saturated aqueous ammonium chloride solution (20 mL). The aqueous layer was extracted with ethyl acetate (2×20 mL), and the combined organic layers were washed sequentially with water (2×20 mL) and saturated aqueous sodium chloride solution (20 mL), were dried over anhydrous sodium sulfate, were filtered, and were concentrated under reduced pressure to afford the hexacyclic bisthiol S25 that was used in the next step without further purification. Acetyl chloride (200 µL, 2.80 mmol, 71.3 equiv) was added to the solution of bisthiol S25 in anhydrous dichloromethane (6 mL) and anhydrous pyridine (300 µL, 3.72 mmol, 94.7 equiv) at 23° C. After 4 h, the reaction mixture was diluted with ethyl acetate (60 mL) and washed with aqueous 5% citric acid solution (2×20 mL). The aqueous layer was extracted with ethyl acetate (2×20 mL), and the combined organic layers were washed sequentially with water (2×20 mL), saturated aqueous sodium hydrogenocarbonate solution (20 mL), water (20 mL), and saturated aqueous sodium chloride solution (20 mL), were dried over anhydrous sodium sulfate, were filtered, and were concentrated under reduced pressure. The residue was purified by flash column chromatography on silica gel (eluent: gradient, 5→20% ethyl acetate in dichloromethane) to afford bisthioacetate 44 (17.0 mg, 62.7%) as a pale yellow oil. Structural assignments were made with additional information from gCOSY, HSQC, and gHMBC data. $^1$H NMR (600 MHz, CDCl$_3$, 20° C.): δ 8.01 (br-s, 1H, N$_1$,H), 7.78 (d, J=8.1, 1H, C$_8$H), 7.75 (d, J=8.2, 2H, SO$_2$Ph-o-H), 7.42 (app-dt, J=1.0, 7.5, 1H, SO$_2$Ph-p-H), 7.37-7.33 (m, 1H, C$_7$H), 7.29 (d, J=8.2, 1H, C$_8$,H), 7.21 (dd, J=7.6, 8.3, 2H, SO$_2$Ph-m-H), 7.12 (dd, J=7.4, 8.0, 1H, C$_7$,H), 7.08-7.03 (m, 2H, C$_5$H+C$_6$H), 6.81 (dd, J=7.2, 7.9, 1H, C$_6$,H), 6.72 (s, 1H, C$_2$H), 6.58 (d, J=8.0, 1H, C$_5$,H), 6.55 (d, J=2.5, 1H, C$_2$,H), 6.09 (s, 1H, C$_{15}$H), 3.44 (d, J=14.7, 1H, C$_{12}$H$_a$), 3.26 (d, J=14.7, 1H, C$_{12}$H$_b$), 2.98 (s, 3H, C$_{17}$H$_3$), 2.48 (s, 3H, C$_{22}$H$_3$), 2.06 (s, 3H, C$_{20}$H$_3$). $^{13}$C NMR (150 MHz, CDCl$_3$, 20° C.): δ 194.0 (C$_{21}$), 193.9 (C19), 165.1 (C$_{13}$), 161.9 (C$_{16}$), 142.0 (C$_9$), 137.7 (SO$_2$Ph-ipso-C), 137.3 (C$_9$—), 135.2 (C$_4$), 133.3 (SO$_2$Ph-p-C), 129.6 (C$_7$), 129.0 (SO$_2$Ph-m-C), 127.5 (SO$_2$Ph-o-C), 125.1 (C$_6$), 124.9 (C$_5$), 124.4 (C$_4$,), 122.9 (C$_2$,), 122.8 (C$_7$,), 120.4 (C$_6$,), 118.7 (C$_5$,), 116.6 (C$_8$), 115.7 (C$_3$,), 111.9 (C$_8$,), 84.8 (C$_2$), 73.3 (C$_{11}$), 63.5 (C$_{15}$), 53.6 (C$_3$), 49.3 (C$_{12}$), 32.3 (C$_{17}$), 30.6 (C$_{20}$), 30.5 (C$_{22}$). FTIR (thin film) cm$^{-1}$: 3395 (br-m), 3063 (w), 2923 (m), 2852 (w), 1699 (br-s), 1459 (m), 1368 (m), 1311 (w), 1172 (m), 1121 (m), 1093 (m), 1025 (w), 954 (w), 734 (m). HRMS (ESI) (m/z): calc'd for C$_{32}$H$_{28}$N4NaO$_6$S$_3$ [M+Na]$^+$: 683.1063. found 683.1047. TLC (20% ethyl acetate in dichloromethane), Rf: 0.52 (UV, I$_2$, CAM).

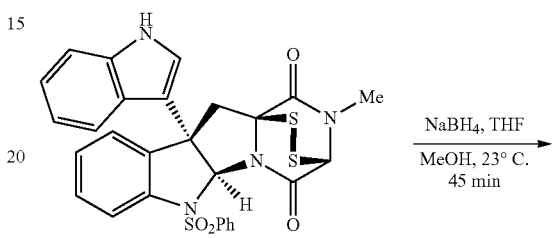

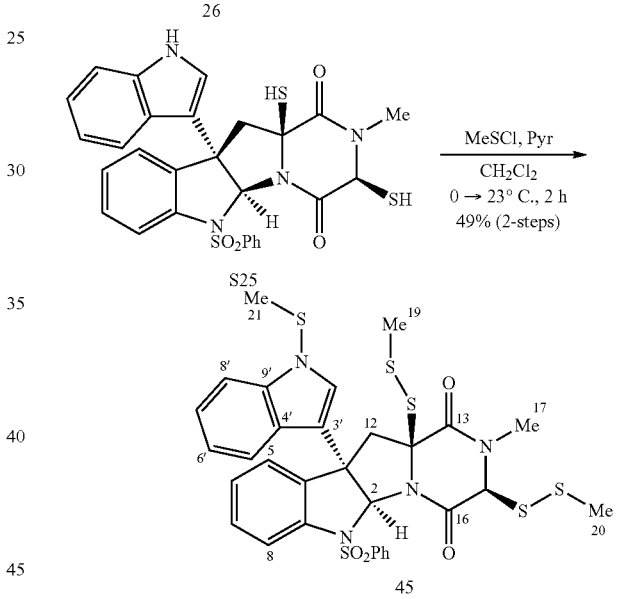

C3-(Indol-3'-yl) N-(thiomethyl)bis(methyldisulfane) 45

((a) Gilow, H. M.; Brown, C. S.; Copeland, J. N.; Kelly, K. E. *J. Heterocyclic Chem.* 1991, 28, 1025. (b) Kim, J. K.; Caserio, M. C. *J. Org. Chem.* 1979, 44, 1897. (c) Kharasch, N.; Parker, A. J. *J. Org. Chem.* 1959, 24, 1029): Sodium borohydride (3.7 mg, 0.10 mmol, 5.2 equiv) was added as a solid to a solution of epidithiodiketopiperazine 26 (10.8 mg, 18.8 µmol, 1 equiv) in anhydrous tetrahydrofuran (5 mL) and anhydrous methanol (50 µL) at 23° C. After 45 min, the reaction mixture was diluted with ethyl acetate (40 mL) and washed with saturated aqueous ammonium chloride solution (20 mL). The aqueous layer was extracted with ethyl acetate (2×20 mL), and the combined organic layers were washed sequentially with water (2×20 mL) and saturated aqueous sodium chloride solution (20 mL), were dried over anhydrous sodium sulfate, were filtered, and were concentrated under reduced pressure to afford the hexacyclic bisthiol S25 that was used in the next step without further purification. A solution of methanesulfinyl chloride (Douglass, I. B.; Norton, R. V.; Farah, B. S. *Org. Synth.* 1960, 40, 62) in dichloromethane (1.6 M, 250 μL, 402 μmol, 21.4 equiv) was added to the solution of bisthiol S25 in anhydrous dichloromethane (5 mL) and anhydrous pyridine (100 μL, 1.24 mmol, 66.0 equiv) at 0° C. After 10 min, the ice-water bath was removed, and the yellow solution was allowed to warm to 23° C. After 2 h, the reaction mixture was diluted sequentially with saturated aqueous ammonium chloride solution (20 mL) and ethyl acetate (60 mL). The organic layer was sequentially washed with saturated aqueous ammonium chloride solution (20 mL), water (2×15 mL), and saturated aqueous sodium chloride solution (15 mL). The aqueous layer was extracted with ethyl acetate (2×20 mL). The combined organic layers were dried over anhydrous sodium sulfate, were filtered, and were concentrated under reduced pressure. The residue was purified by flash column chromatography on silica gel (eluent: gradient, 5→30% ethyl acetate in hexanes) to afford the N-thiomethyl bis(methyldisulfane) 45 (6.5 mg, 49%) as a colorless oil. Structural assignments were made with additional information from gCOSY, HSQC, and gHMBC data. $^{1}$H NMR (600 MHz, CDCl$_3$, 20° C.): δ 7.74 (d, J=8.1, 1H, C$_8$H), 7.57 (d, J=8.2, 1H, C$_{8'}$H), 7.42-7.37 (m, 1H, C$_7$H), 7.39 (d, J=8.2, 2H, SO$_2$Ph-o-H), 7.35 (app-dt, J=1.0, 7.4, 1H, SO$_2$Ph-p-H), 7.31 (app-dt, J=0.8, 7.7, 1H, C$_{7'}$H), 7.27 (app-dt, J=1.0, 7.6, 1H, C$_5$H), 7.21 (app-dt, J=0.8, 7.5, 1H, C$_6$H), 7.09 (app-dt, J=0.7, 7.5, 1H, C$_{6'}$H), 7.01 (d, J=7.9, 1H, C$_{5'}$H), 6.97 (dd, J=7.6, 8.2, 2H, SO$_2$Ph-m-H), 6.71 (s, 1H, C$_2$H), 6.08 (s, 1H, C$_{2'}$H), 5.02 (s, 1H, C$_{15}$H), 3.29 (d, J=15.0, 1H, C$_{12}$H$_a$), 3.25 (d, J=15.0, 1H, C$_{12}$H$_b$), 3.17 (s, 3H, C$_{17}$H$_3$), 2.67 (s, 3H, C$_{20}$H$_3$), 2.50 (s, 3H, C$_{21}$H$_3$), 2.29 (s, 3H, C$_{19}$H$_3$). $^{13}$C NMR (150 MHz, CDCl$_3$, 20° C.): δ 165.3 (C$_{13}$), 162.5 (C$_{16}$), 142.0 (C$_9$), 141.2 (C$_{9'}$), 137.8 (SO$_2$Ph-ipso-C), 136.0 (C$_4$), 133.0 (C$_{2'}$), 132.9 (SO$_2$Ph-p-C), 129.7 (C$_7$), 128.4 (SO$_2$Ph-m-C), 127.3 (SO$_2$Ph-o-C), 125.9 (C$_6$), 125.8 (C$_{4'}$), 124.6 (C$_5$), 123.7 (C$_{7'}$), 121.6 (C$_{6'}$), 119.1 (C$_{5'}$), 118.8 (C$_{20}$), 117.6 (C$_{3'}$), 111.7 (C$_{8'}$), 84.8 (C$_2$), 79.2 (C$_{15}$), 73.9 (C$_{11}$), 53.5 (C$_3$), 46.0 (C$_{12}$), 32.7 (C$_{17}$), 24.4 (C$_{20}$), 24.0 (C$_{21}$), 23.3 (C$_{19}$). FTIR (thin film) cm$^{-1}$: 2925 (w), 1699 (s), 1458 (m), 1359 (m), 1231 (w), 1168 (m), 1091 (w), 749 (m). HRMS (ESI) (m/z): calc'd for C$_{31}$H$_{30}$N$_4$NaO$_4$S$_6$ [M+Na]$^+$: 737.0484. found 737.0469. TLC (50% ethyl acetate in hexanes), Rf: 0.60 (UV, I$_2$, CAM).

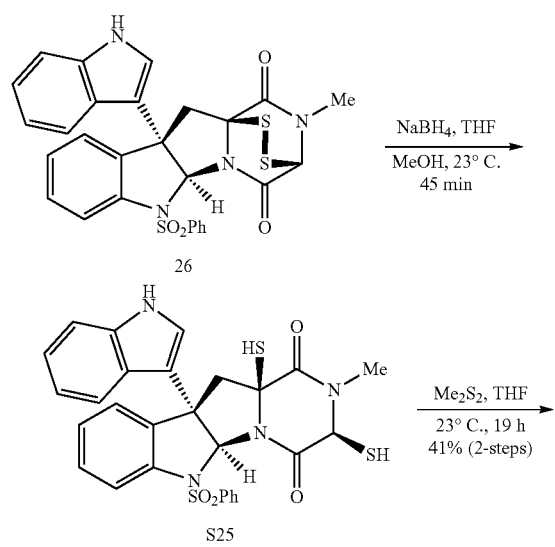

-continued

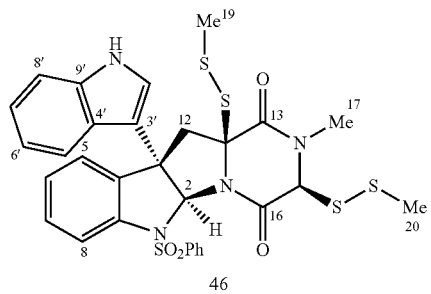

46

C3-(Indol-3'-yl)bis(methyldlsulfane) 46

Sodium borohydride (4.8 mg, 0.13 mmol, 3.7 equiv) was added as a solid to a solution of epidithiodiketopiperazine 26 (19.5 mg, 33.9 μmol, 1 equiv) in anhydrous tetrahydrofuran (5 mL) and anhydrous methanol (50 μL) at 23° C. After 45 min, the reaction mixture was diluted with ethyl acetate (40 mL) and washed with saturated aqueous ammonium chloride solution (20 mL). The aqueous layer was extracted with ethyl acetate (2×20 mL), and the combined organic layers were washed sequentially with water (2×20 mL) and saturated aqueous sodium chloride solution (20 mL), were dried over anhydrous sodium sulfate, were filtered, and were concentrated under reduced pressure to afford the hexacyclic bisthiol S25 that was used in the next step without further purification. Dimethyldisulfide (200 μL, 2.23 mmol, 65.7 equiv) (Dubs, P.; Stuessi, R. *Helv. Chim. Acta* 1976, 59, 1307) was added to the solution of bisthiol S25 in anhydrous tetrahydrofuran (6 mL) at 23° C. After 19 h, the volatiles were removed under reduced pressure. The residue was purified by flash column chromatography on silica gel (eluent: gradient, 5→10% ethyl acetate in dichloromethane) to afford the bis(methyldisulfane) 46 (9.3 mg, 41%) as a colorless oil. Structural assignments were made with additional information from gCOSY, HSQC, and gHMBC data. $^{1}$H NMR (600 MHz, CDCl$_3$, 20° C.): δ 7.85 (br-s, 1H, N$_1$,H), 7.70 (d, J=8.1, 1H, C$_8$H), 7.52 (d, J=7.4, 2H, SO$_2$Ph-o-H), 7.36 (app-dt, J=1.3, 7.8, 1H, C$_7$H), 7.33 (t, J=7.5, 1H, SO$_2$Ph-p-H), 7.32 (d, J=8.2, 1H, C$_{8'}$H), 7.24 (app-dd, J=0.8, 7.5, 1H, C$_5$H), 7.19 (app-ddd, J=2.4, 5.8, 8.2, 1H, C$_7$,H), 7.16 (app-dt, J=0.8, 7.5, 1H, C$_6$H), 7.07 (app-dt, J=0.5, 7.9, 2H, SO$_2$Ph-m-H), 7.01-6.96 (m, 2H, C$_{5'}$H+C$_{6'}$H), 6.76 (s, 1H, C$_2$H), 6.28 (d, J=2.6, 1H, C$_{2'}$H), 5.00 (s, 1H, C$_{15}$H), 3.38 (d, J=15.0, 1H, C$_{12}$H$_a$), 3.26 (d, J=15.0, 1H, C$_{12}$H$_b$), 3.17 (s, 3H, C$_{17}$H$_3$), 2.64 (s, 3H, C$_{20}$H$_3$), 2.29 (s, 3H, C$_{19}$H$_3$). $^{13}$C NMR (150 MHz, CDCl$_3$, 20° C.): δ 165.4 (C$_{13}$), 162.6 (C$_{16}$), 141.8 (C$_9$), 138.2 (SO$_2$Ph-ipso-C), 137.3 (C9), 136.4 (C$_4$), 133.0 (SO$_2$Ph-p-C), 129.5 (C$_7$), 128.6 (SO$_2$Ph-m-C), 127.4 (SO$_2$Ph-o-C), 125.7 (C$_6$), 124.6 (C$_5$), 124.2 (C$_{4'}$), 123.3 (C$_{2'}$), 122.9 (C$_{7'}$), 120.5 (C$_{6'}$), 118.9 (C$_{5'}$), 118.3 (C$_8$), 115.7 (C$_{3'}$), 111.9 (C$_{8'}$), 85.2 (C$_2$), 79.2 (C$_{15}$), 74.0 (C$_{11}$), 53.6 (C$_3$), 46.4 (C$_{12}$), 32.7 (C$_{17}$), 24.4 (C$_{20}$), 23.4 (C$_{19}$). FTIR (thin film) cm$^{-1}$: 3392 (br-m), 3060 (w), 2921 (w), 1685 (s), 1459 (m), 1391 (m), 1266 (w), 1169 (m), 1092 (w), 1022 (w), 736 (m). HRMS (ESI) (m/z): calc'd for C$_{30}$H$_{25}$N$_4$NaO$_4$S$_5$ [M+Na]$^+$: 691.0606. found 691.0613. TLC (20% ethyl acetate in dichloromethane), Rf: 0.67 (UV, I$_2$, CAM).

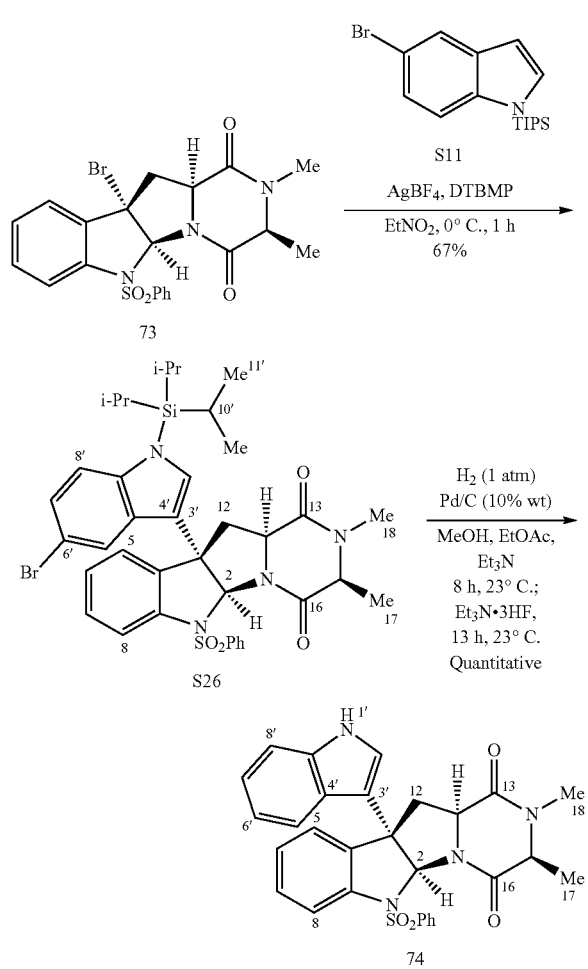

C3-(Indol-3'-yl)-pyrrolidinoindoline 74

This compound was prepared in two steps starting from endo-tetracyclic bromide (Kim, J.; Ashenhurst, J. A.; Movassaghi, M. *Science* 2009, 324, 238) (+)-73 (512.5 mg, 10.5 mmol, 1 equiv) using the methodology developed to access the corresponding C3-(5-bromo-N-TIPS-indol-3'-yl)-pyrrolidinoindoline (+)-S12 with DTBMP (339 mg, 1.65 mmol, 1.58 equiv), 5-bromo-1-triisopropylsilyl-1H-indole S11 (1.92 g, 5.45 mmol, 5.20 equiv) (5-Bromo-1-triisopropylsilyl-1H-indole S11 was prepared in quantitative yield by silylation of commercially available 5-bromoindole using triisopropylsilyl chloride and sodium hydride in tetrahydrofuran. For preparation and characterization, see: Brown, D. A.; Mishra, M.; Zhang, S.; Biswas, S.; Parrington, I.; Antonio, T.; Reith, M. E. A.; Dutta, A. K. *Bioorg. Med. Chem.* 2009, 17, 3923), and silver(I) tetrafluoroborate (600 mg, 3.08 mmol, 2.95 equiv) in anhydrous nitroethane (12 mL). After 1 h, saturated aqueous sodium chloride solution (20 mL) was introduced, and the resulting biphasic mixture was vigorously stirred for 30 min at 0° C. The reaction mixture was diluted with ethyl acetate (50 mL), was filtered through a Celite pad, and the solid was washed with ethyl acetate (3×15 mL). The combined filtrates were washed with 5% aqueous citric acid solution (2×25 mL), water (3×25 mL), and saturated aqueous sodium chloride solution (25 mL). The organic layer was dried over anhydrous sodium sulfate, was filtered, and was concentrated under reduced pressure. The resulting residue was purified by flash column chromatography (eluent: gradient, 1→10% acetone in dichloromethane) to afford the C3-(5-bromo-N-TIPS-indol-3'-yl)-pyrrolidinoindoline S26 (537 mg, 67.4%) as a white foam.

The free indole was accessed in a one-pot two-step procedure using the methodology developed to access the corresponding C3-(indol-3'-yl)-pyrrolidinoindoline (+)-59. The reaction mixture was filtered through a pad of Celite. The solids were washed with ethyl acetate (3×50 mL). The combined filtrates were concentrated under reduced pressure. The resulting pale yellow solid was diluted in ethyl acetate (150 mL) and washed sequentially with an aqueous hydrochloric acid solution (1 N, 2×50 mL), water (2×50 mL), and saturated aqueous sodium chloride solution (40 mL). The organic layer was dried over anhydrous sodium sulfate, was filtered, and was concentrated under reduced pressure to afford the C3-(indol-3'-yl)-pyrrolidinoindoline 74 (370 mg, 99.7%) as a white solid that was used in the next step without further purification.

S26:

$^1$H NMR (600 MHz, CDCl$_3$, 20° C.): δ 8.03 (d, J=7.8, 2H, SO$_2$Ph-o-H), 7.78 (d, J=8.4, 1H, C$_8$H), 7.54 (app-dd, J=7.2, 7.8, 1H, SO$_2$Ph-p-H), 7.40 (app-t, J=7.8, 2H, SO$_2$Ph-m-H), 7.30 (d, J=8.9, 1H, C$_8$,H), 7.28 (app-dt, J=1.0, 7.9, 1H, C$_7$H), 7.15 (app-dd, J=1.7, 8.8, 1H, C$_7$,H), 6.97 (dd, J=7.5, 7.6, 1H, C$_6$H), 6.95 (s, 1H, C$_2$,H), 6.82 (d, J=7.3, 1H, C$_5$H), 6.50 (br-s, 1H, Cr$_5$,H), 6.30 (s, 1H, C$_2$H), 4.44 (dd, J=7.8, 9.4, 1H, C$_{11}$H), 3.97 (q, J=7.1, 1H, C$_{15}$H), 3.03 (dd, J=7.5, 13.8, 1H, C$_{12}$H$_a$), 2.99 (s, 3H, C$_{15}$H$_3$), 2.88 (dd, J=9.8, 13.8, 1H, C$_{12}$H$_b$), 1.66 (d, J=7.1, 3H, C$_{17}$H), 1.59 (app-sp, J=7.5, 3H, C$_{10}$H), 1.07 (app-d, J=5.5, 18H, C$_{11}$H). $^{13}$C NMR (150 MHz, CDCl$_3$, 20° C.): δ 169.5 (C$_{13}$), 169.2 (C$_{16}$), 141.3 (C$_9$), 139.6 (C$_9$), 137.1 (SO$_2$Ph-ipso-C), 134.2 (SO$_2$Ph-p-C), 133.9 (C$_4$), 130.9 (C$_2$), 130.3 (C$_4$,), 129.5 (C$_7$), 129.2 (SO$_2$Ph-m-C), 127.9 (SO$_2$Ph-o-C), 125.3 (C$_7$,), 124.5 (C$_6$), 123.9 (C$_5$), 121.9 (C$_5$), 116.0 (C$_8$,), 115.6 (C$_8$), 115.1 (C$_3$,), 113.5 (C$_6$), 83.0 (C$_2$), 59.5 (C$_{11}$), 57.5 (C$_{15}$), 55.3 (C$_3$), 37.8 (C$_{12}$), 29.6 (C$_{18}$), 18.2 (C$_{11}$,), 14.8 (C$_{11}$,), 12.9 (C$_{10}$,). TLC (20% acetone in dichloromethane), Rf: 0.76 (UV, CAM).

74:

$^1$H NMR (600 MHz, CDCl$_3$, 20° C.): δ 8.94 (br-s, 1H, N$_1$,H), 7.74 (d, J=8.2, 1H, C$_8$H), 7.46 (d, J=8.2, 2H, SO$_2$Ph-o-H), 7.35 (app-dt, J=0.9, 7.5, 1H, SO$_2$Ph-p-H), 7.34 (d, J=8.3, 1H, C$_8$,H), 7.29 (dd, J=7.5, 8.1, 1H, C$_7$H), 7.19 (app-dt, J=4.1, 8.2, 1H, C$_7$,H), 7.12 (d, J=7.5, 1H, C$_5$H), 7.09-7.04 (m, 3H, SO$_2$Ph-m-H+C$_6$H), 6.95 (app-d, J=4.0, 2H, C$_5$,H+C$_6$,H), 6.40 (s, 1H, C$_2$H), 6.09 (d, J=2.0, 1H, C$_2$,H), 4.52 (app-t, J=7.8, 1H, C$_{11}$H), 4.07 (q, J=7.0, 1H, C$_{15}$H), 3.10 (app-d, J=7.8, 2H, C$_{12}$H), 2.90 (s, 3H, C$_{18}$H$_3$), 1.61 (d, J=7.1, 3H, C$_{17}$H$_3$). MS (ESI) (m/z): [M+H]$^+$: 527.25; [M+Na]$^+$: 549.21. TLC (20% acetone in dichloromethane), Rf: 0.27 (UV, CAM).

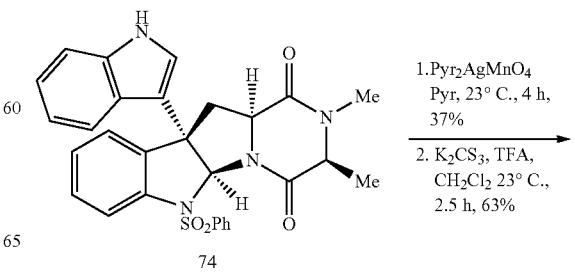

74

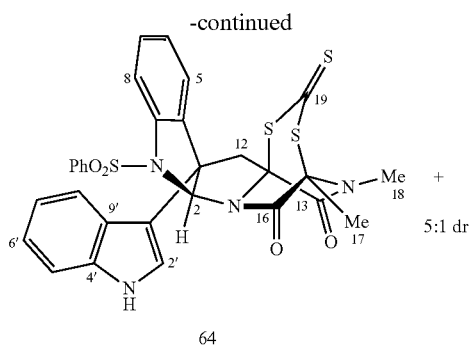

64

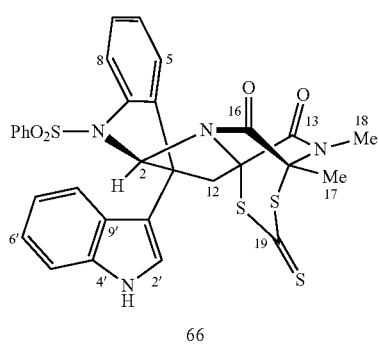

66

C3-(Indo-3'-v)dithiepanethiones 64 and 66

Freshly prepared bis(pyridine)silver(I) permanganate (Firouzabadi, H.; Vessal, B.; Naderi, M. *Tetrahedron Lett.* 1982, 23, 1847) (800 mg, 2.08 mmol, 5.45 equiv) was added as a solid to a solution of indole adduct 74 (201 mg, 382 µmol, 1 equiv) in anhydrous pyridine (5 mL) at 23° C. After 2 h, a second portion of bis(pyridine)silver(I) permanganate (600 mg, 1.56 mmol, 4.08 equiv) was added. After 2 h, the resulting thick brown suspension was diluted with saturated aqueous sodium sulfite solution (50 mL) and then with ethyl acetate (160 mL). The resulting mixture was washed sequentially with water (2×50 mL), aqueous 5% copper sulfate solution (3×50 mL), and saturated aqueous sodium chloride solution (30 mL). The combined aqueous layers were extracted with ethyl acetate (2×100 mL). The combined organic layers were dried over anhydrous sodium sulfate, were filtered, and were concentrated under reduced pressure. The resulting yellow residue was purified by flash column chromatography (eluent: gradient, 2→20% isopropanol in dichloromethane and hexanes (50%)) to afford the corresponding diols (78.0 mg, 36.5%) as a yellow oil (isolated as a mixture of isomers).

To a yellow solution of potassium trithiocarbonate (250 mg, 1.34 mmol, 9.63 equiv) (Stueber, D.; Patterson, D.; Mayne, C. L.; Orendt, A. M.; Grant, D. M.; Parry, R. W. *Inorg. Chem.* 2001, 40, 1902) in anhydrous dichloromethane (6 mL) and trifluoroacetic acid (4 mL) at 23° C. was added a solution of the diol (78.0 mg, 139 µmol, 1 equiv) in dichloromethane (1 mL). After 2.5 h, the reaction mixture was diluted with ethyl acetate (60 mL) and washed with saturated aqueous sodium bicarbonate (30 mL). The aqueous layer was extracted with ethyl acetate (2×20 mL) and the combined organic layers were dried over anhydrous sodium sulfate, were filtered, and were concentrated under reduced pressure. The resulting orange residue was purified by flash column chromatography on silica gel (eluent: gradient, 2→8% ethyl acetate in dichloromethane) to afford an inseparable mixture of isomeric monomeric dithiepanethiones 64 and 66 (55.7 mg, 63.3%, 64:66, 5:1) as a pale yellow solid. Isomers 64 and 66 were separated for the purpose of full and independent characterization by preparative HPLC [Waters X-Bridge preparative HPLC column, C18, 5 nm, 19×250 mm; 20.0 mL/min; gradient, 30→100% acetonitrile in water, 35 min; $t_R(6^4)$=21.3 min, $t_R(66)$=23.4 min]. Structural assignments were made using additional information from gCOSY, HSQC, and HMBC experiments.

β-Epimer 64:

$^1$H NMR (600 MHz, CDCl$_3$, 20° C.): δ 7.81 (br-s, 1H, $N_1$H), 7.74 (d, J=8.2, 1H, $C_8$H), 7.44-7.39 (m, 1H, $C_7$H), 7.37 (app-dd, J=0.7, 7.5, 2H, SO$_2$Ph-o-H), 7.35 (d, J=8.1, 1H, $C_8$H), 7.34 (t, J=7.5, 1H, SO$_2$Ph-p-H), 7.26-7.21 (m, 3H, $C_5$H+$C_6$H+$C_7$H), 7.08-7.04 (m, 2H, $C_5$H+$C_6$H), 7.02 (app-t, J=7.7, 2H, SO$_2$Ph-m-H), 6.74 (s, 1H, $C_2$H), 6.20 (d, J=2.5, 1H, $C_2$H), 3.91 (d, J=15.6, 1H, $C_{12}H_a$), 3.13 (s, 3H, $C_{18}H_3$), 2.86 (d, J=15.6, 1H, $C_{12}H_b$), 2.01 (s, 3H, $C_{17}H_3$). $^{13}$C NMR (100 MHz, CDCl$_3$, 20° C.): δ 215.9 ($C_{19}$), 165.0 ($C_{13}$), 161.0 ($C_{16}$), 141.1 ($C_9$), 137.8 (SO$_2$Ph-ipso-C), 137.3 ($C_9$—), 135.4 ($C_4$), 133.1 (SO$_2$Ph-p-C), 130.2 ($C_7$), 128.5 (SO$_2$Ph-m-C), 127.3 (SO$_2$Ph-o-C), 126.3 ($C_6$), 124.7 ($C_5$), 124.1 ($C_{4'}$), 124.0 ($C_{2'}$), 123.2 ($C_{7'}$), 120.8 ($C_{6'}$), 119.0 ($C_8$), 118.8 ($C_5$), 114.1 ($C_{3'}$), 112.0 ($C_{8'}$), 85.6 ($C_2$), 75.1 ($C_{11}$), 73.5 ($C_{15}$), 54.1 ($C_3$), 46.4 ($C_{12}$), 28.7 ($C_{18}$), 20.2 ($C_{17}$). FTIR (thin film) cm$^{-1}$: 3397 (br-m), 3061 (w), 1688 (s), 1459 (w), 1361 (s), 1241 (w), 1170 (s), 1108 (w), 1001 (m), 908 (w), 734 (m). HRMS (ESI) (m/z): calc'd for $C_{30}H_{25}N_4O_4S_4$[M+H]$^+$: 633.0753. found 633.0744. TLC (50% ethyl acetate in hexanes), Rf: 0.33 (UV, CAM).

α-Epimer 66:

$^1$H NMR (600 MHz, CDCl$_3$, 20° C.): δ 7.80 (app-dd, J=1.6, 6.8, 1H, $C_5$H), 7.72 (d, J=8.0, 1H, $C_8$H), 7.54 (br-s, 1H, $N_1$H), 7.40-7.34 (m, 3H, $C_5$H+$C_7$H+$C_8$H), 7.34-7.29 (m, 2H, $C_6$H+$C_7$H), 7.22 (app-t, J=7.5, 1H, $C_6$H), 7.20 (t, J=7.4, 1H, SO$_2$Ph-p-H), 7.06 (app-dd, J=0.9, 8.3, 2H, SO$_2$Ph-o-H), 6.81 (dd, J=7.6, 8.1, 2H, SO$_2$Ph-m-H), 6.79 (s, 1H, $C_2$H), 5.55 (d, J=2.5, 1H, $C_2$H), 4.04 (d, J=15.6, 1H, $C_2H_a$), 3.11 (d, J=15.6, 1H, $C_{12}H_b$), 2.98 (s, 3H, $C_1H_3$), 2.00 (s, 3H, $C_{17}H_3$). $^{13}$C NMR (100 MHz, CDCl$_3$, 20° C.): δ 209.5 ($C_{19}$), 164.5 ($C_{13}$), 161.1 ($C_{16}$), 139.3 ($C_9$), 138.3 (SO$_2$Ph-ipso-C), 137.3 ($C_{9'}$), 135.8 ($C_4$), 132.7 (SO$_2$Ph-p-C), 130.0 ($C_7$), 128.1 (SO$_2$Ph-m-C), 127.0 (SO$_2$Ph-o-C), 125.9 ($C_6$), 125.4 ($C_5$), 124.9 ($C_{2'}$), 123.7 ($C_{4'}$), 123.5 ($C_{7'}$), 121.3 ($C_{6'}$), 119.1 ($C_{5'}$), 118.2 ($C_8$), 114.4 ($C_{3'}$), 112.0 ($C_{8'}$), 85.4 ($C_2$), 74.9 ($C_{11}$), 73.6 ($C_{15}$), 54.9 ($C_3$), 42.0 ($C_{12}$), 28.8 ($C_{18}$), 21.3 ($C_{17}$). FTIR (thin film) cm$^{-1}$: 3396 (br-m), 2924 (w), 1698 (s), 1458 (m), 1364 (m), 1334 (m), 1251 (w), 1169 (m), 1091 (m), 1013 (m), 912 (w), 734 (m). HRMS (ESI) (m/z): calc'd for $C_{30}H_{25}N_4O_4S_4$[M+H]$^+$: 633.0753. found 633.0767. TLC (50% ethyl acetate in hexanes), Rf: 0.33 (UV, CAM).

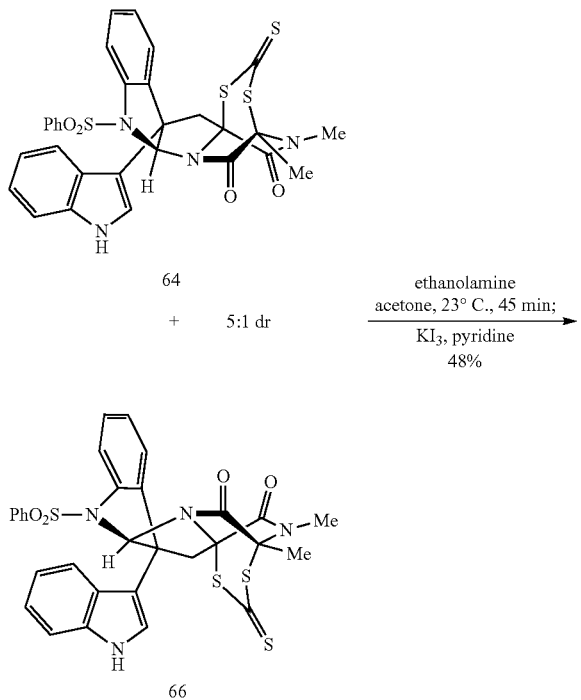

C3-(Indol-3'-yl) epidithiodiketopiperazines 60 and 62

Ethanolamine (4 mL) was added via syringe to a solution of the bisdithiepanethiones 64 and 66 (33.0 mg, 52.1 μmol, 1 equiv, 64:66, 5:1) in acetone (6 mL) at 23° C. After 45 min, the reaction mixture was partitioned between ethyl acetate (100 mL) and aqueous hydrochloric acid solution (1 N, 30 mL). The organic layer was collected, and the aqueous layer was extracted with ethyl acetate (2×15 mL). A solution of potassium triiodide in pyridine (2.5% w/v) was added dropwise to the combined organic layers until a persistent yellow color was observed. The resulting mixture was washed with aqueous hydrochloric acid (1 N, 20 mL), and saturated aqueous sodium chloride solution (20 mL). The organic layer was dried over anhydrous sodium sulfate, was filtered, and was concentrated under reduced pressure. The residue was purified by flash column chromatography on silica gel (eluent: gradient, 20→50% ethyl acetate in hexanes) to afford an inseparable mixture of isomeric monomeric epidithiodiketopiperazines 60 and 62 (14.8 mg, 48.2%, 60:62, 5:1) as a pale yellow solid. Isomers 60 and 62 were separated for the purpose of full and independent characterization by preparative HPLC [Waters X-Bridge preparative HPLC column, C18, 5 μm, 19×250 mm; 20.0 mL/min; gradient, 30→100% acetonitrile in water, 35 min; $t_R$(60)=18.0 min, $t_R$(62)=19.7 min]. Structural assignments were made using additional information from gCOSY, HSQC, and HMBC experiments.

β-Epimer 60

$^1$H NMR (600 MHz, CDCl$_3$, 20° C.): δ 8.01 (d, J=7.3, 1H, C$_5$,H), 7.73 (d, J=8.0, 1H, C$_8$H), 7.60 (br-s, 1H, N$_1$,H), 7.41 (d, J=6.6, 1H, C$_5$H), 7.39 (d, J=7.8, 1H, C$_8$,H), 7.43-7.38 (m, 1H, C$_7$H), 7.38-7.31 (m, 2H, C$_6$H+C$_7$H), 7.26-7.21 (m, 2H, C$_6$H+SO$_2$Ph-p-H), 7.11 (app-dd, J=0.9, 8.3, 2H, SO$_2$Ph-o-H), 6.85 (dd, J=7.6, 8.1, 2H, SO$_2$Ph-m-H), 6.84 (s, 1H, C$_2$H), 5.58 (d, J=2.5, 1H, C$_2$,H), 4.00 (d, J=15.1, 1H, C$_{12}$H$_a$), 3.19 (d, J=15.1, 1H, C$_{12}$H$_b$), 2.97 (s, 3H, C$_{18}$H$_3$), 2.04 (s, 3H, C$_{17}$H$_3$). $^{13}$C NMR (100 MHz, CDCl$_3$, 20° C.): δ 166.0 (C$_{13}$), 161.9 (C$_{16}$), 140.9 (C$_9$), 137.6 (SO$_2$Ph-ipso-C), 137.2 (C$_9$,), 136.9 (C$_4$), 133.0 (SO$_2$Ph-p-C), 129.8 (C$_7$), 128.3 (SO$_2$Ph-m-C), 127.2 (SO$_2$Ph-o-C), 126.1 (C$_6$), 124.5 (C$_4$), 124.3 (C$_4$,), 124.0 (C$_2$,), 123.1 (C$_7$,), 120.7 (C$_6$,), 119.3 (C$_8$), 118.7 (C$_5$,), 114.1 (C$_3$,), 112.1 (C$_8$,), 85.1 (C$_2$), 73.9 (C$_{15}$), 73.5 (C$_{11}$), 55.3 (C$_3$), 43.0 (C$_{12}$), 27.8 (C$_{18}$), 18.4 (C$_{17}$). FTIR (thin film) cm$^{-1}$: 3396 (br-m), 3061 (w), 2924 (w), 2851 (w), 1704 (s), 1447 (w), 1360 (m), 1332 (s), 1244 (w), 1169 (s), 1109 (m), 1090 (m), 910 (w), 735 (s). HRMS (ESI) (m/z): calc'd for C$_{29}$H$_{25}$N$_4$O$_4$S$_3$ [M+H]$^+$: 589.1032. found 589.1043. TLC (50% ethyl acetate in hexanes), Rf: 0.27 (UV, CAM).

α-Epimer 62:

$^1$H NMR (600 MHz, CDCl$_3$, 20° C.): δ 7.99 (d, J=7.4, 1H, C$_5$,H), 7.70 (d, J=8.0, 1H, C$_8$H), 7.57 (br-s, 1H, N$_1$,H), 7.40-7.34 (m, 3H, C$_5$H+C$_7$H+C$_5$,H), 7.34-7.28 (m, 2H, C$_7$H+C$_7$,H), 7.21 (app-dt, J=1.7, 7.6, 2H, C$_6$H+SO$_2$Ph-p-H), 7.08 (app-dd, J=0.9, 8.3, 2H, SO$_2$Ph-o-H), 6.82 (dd, J=7.6, 8.1, 2H, SO$_2$Ph-m-H), 6.82 (s, 1H, C$_2$H), 5.55 (d, J=2.5, 1H, C$_2$,H), 3.97 (d, J=15.1, 1H, C$_{12}$H$_a$), 3.16 (d, J=15.1, 1H, C$_{12}$H$_b$), 2.94 (s, 3H, C$_{18}$H$_3$), 2.01 (s, 3H, C$_{17}$H$_3$). $^{13}$C NMR (100 MHz, CDCl$_3$, 20° C.): δ 165.9 (C$_{13}$), 162.6 (C$_{16}$), 139.5 (C$_9$), 138.3 (SO$_2$Ph-ipso-C), 137.3 (C$_9$,), 135.6 (C$_4$), 132.6 (SO$_2$Ph-p-C), 129.8 (C$_7$), 128.1 (SO$_2$Ph-m-C), 127.1 (SO$_2$Ph-o-C), 125.9 (C$_6$), 125.4 (C$_5$), 124.6 (C$_2$,), 123.9 (C$_4$,), 123.4 (C$_7$,), 121.0 (C$_6$,), 119.2 (C$_5$,), 118.4 (C$_8$), 115.2 (C$_3$,), 111.9 (C$_8$,), 85.0 (C$_2$), 74.4 (C$_{11}$), 73.8 (C$_{15}$), 55.9 (C$_3$), 41.2 (C$_{12}$), 27.6 (C$_{18}$), 18.7 (C$_{17}$). FTIR (thin film) cm$^{-1}$: 3395 (br-m), 2923 (w), 1701 (s), 1460 (w), 1359 (m), 1332 (m), 1247 (w), 1168 (m), 1090 (w), 912 (w), 734 (m). HRMS (ESI) (m/z): calc'd for C$_{29}$H$_{25}$N$_4$O$_4$S$_3$ [M+H]$^+$: 589.1032. found 589.1037. TLC (50% ethyl acetate in hexanes), Rf: 0.27 (UV, CAM).

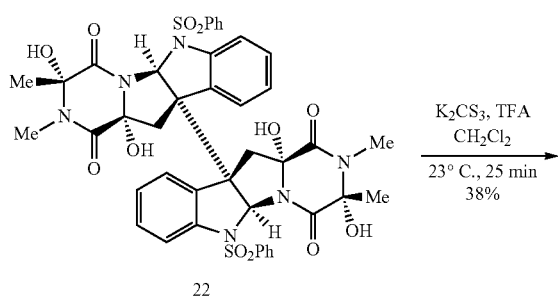

Dimeric bisdithiepanethione 18

Dimeric tetraol 22 (200 mg, 226 μmol, 1 equiv) was added as a solid to a yellow solution of potassium trithiocarbonate (632 mg, 3.39 mmol, 15.0 equiv) in anhydrous dichloromethane (5.1 mL) and trifluoroacetic acid (1.7 mL) at 23° C. After 25 min, the reaction mixture was diluted with dichloromethane (60 mL) and washed with saturated aqueous sodium bicarbonate (125 mL). The aqueous layer was extracted with dichloromethane (2×30 mL) and the combined organic layers were dried over anhydrous sodium sulfate, were filtered, and were concentrated under reduced pressure to afford a yellow powder. This powder was purified by flash column chromatography on silica gel (eluent: 5% acetone in dichloromethane) to afford dimeric bisdithiepanethione 18 (88.8 mg, 38.0%) as an orange-yellow solid. $^1$H NMR (500 MHz, CDCl$_3$, 20° C.): δ 7.75-7.65 (m, 2H, C$_8$H), 7.75-7.65 (m, 4H, SO$_2$Ph-o-H), 7.53 (app-t, J=7.4, 2H, SO$_2$Ph-p-H), 7.41 (app-t, J=8.0, 4H, SO$_2$Ph-m-H), 7.30-7.14 (m, 6H, C$_6$H, C$_7$H, C$_5$H), 6.86 (s, 2H, C$_2$H), 3.26 (d, J=14.9, 2H, C$_{12}$H$_a$), 3.09 (d, J=14.9, 2H, C$_{12}$H$_b$), 3.01 (s, 6H, C$_{18}$H), 1.68 (s, 6H, C$_{17}$H). $^{13}$C NMR (125.8 MHz, CDCl$_3$, 20° C.): δ 215.1 (C=S), 164.1 (C$_{13}$), 159.7 (C$_{16}$), 142.7 (C$_9$), 141.9 (SO$_2$Ph-ipso-C), 133.1 (SO$_2$Ph-p-C), 131.3 (C$_4$), 129.2 (SO$_2$Ph-m-C), 129.2 (C$_6$), 125.5 (SO$_2$Ph-o-C), 125.2 (C$_7$), 124.5 (C$_8$), 116.1 (C$_5$), 81.6 (C$_2$), 73.9 (C$_{11}$), 73.6 (C$_{15}$), 59.1 (C$_3$), 44.7 (C$_{12}$), 28.6 (C$_{18}$), 19.3 (C$_{17}$). FTIR (thin film) cm$^{-1}$: 1715 (s), 1691 (s), 1479 (m), 1462 (m), 1447 (m), 1359 (s), 1169 (s), 729 (m). HRMS (ESI) (m/z): calc'd for C$_{44}$H$_{36}$N$_6$NaO$_8$S$_8$ [M+Na]$^+$: 1055.0252. found 1055.0255. [α]$_D$24: +230 (c 0.19, CHCl$_3$). TLC (5% acetone in dichloromethane), Rf: 0.27 (UV, CAM). S$_2$Ph

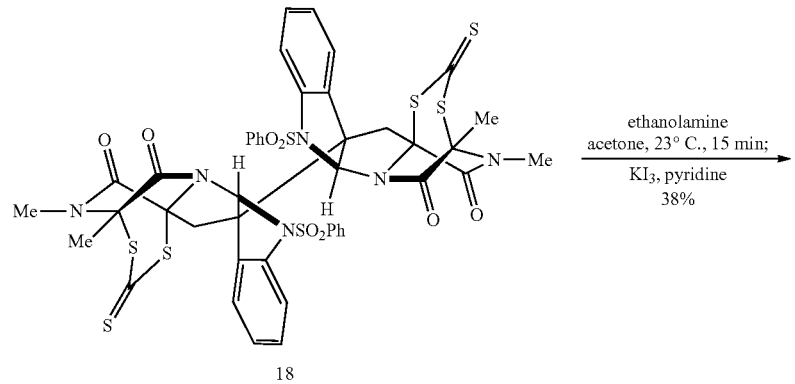

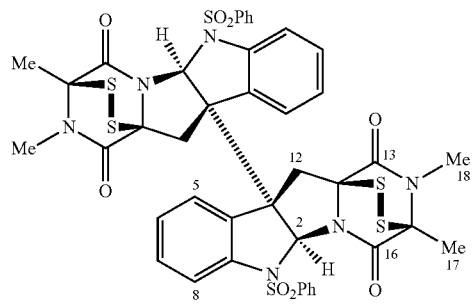

14

Dimeric epidithiodiketopiperazine 14

Ethanolamine (500 µL) was added via syringe to a solution of dimeric bisdithiepanethione 18 (11.2 mg, 10.8 µmol, 1 equiv) in acetone (500 µL) at 23° C. After 15 min, the reaction mixture was diluted with dichloromethane (30 mL) and aqueous hydrochloric acid solution (1 N, 30 mL). The organic layer was collected, and the aqueous layer was extracted with dichloromethane (2×5 mL). A solution of potassium triiodide in pyridine (2.5% w/v) was added dropwise to the combined organic layers until a persistent yellow color was observed. The resulting mixture was washed with aqueous hydrochloric acid (1 N, 30 mL) and the layers were separated. The aqueous layer was extracted with dichloromethane (2×5 mL), and the combined organic layers were dried over anhydrous sodium sulfate, were filtered, and were concentrated under reduced pressure. The residue was purified by flash column chromatography on silica gel (eluent: 5% acetone in dichloromethane) to afford dimeric epidithiodiketopiperazine 14 (3.9 mg, 38%) as a white solid. $^1$H NMR (500 MHz, CDCl$_3$, 20° C.): δ 7.85 (dd, J=1.4, 7.3, 4H, SO$_2$Ph-o-H), 7.68 (d, J=7.5, 2H, C$_8$H), 7.54 (tt, J=1.2, 7.5, 2H, SO$_2$Ph-p-H), 7.46 (app-t, J=8.0, 4H, SO$_2$Ph-m-H), 7.20 (app-dt, J=1.3, 7.5, 2H, C$_6$H), 7.16 (app-dt, J=1.2, 7.5, 2H, C$_7$H), 7.04 (dd, J=1.0, 7.6, 2H, C$_5$H), 6.83 (s, 2H, C$_2$H), 3.55 (d, J=15.2, 2H, C$_{12}$H$_a$), 2.97 (s, 6H, C$_{15}$H), 2.95 (d, J=15.2, 2H, C$_{12}$H$_b$), 1.62 (s, 6H, C$_{17}$H). $^{13}$C NMR (125.8 MHz, CDCl$_3$, 20° C.): δ 164.9 (C$_{13}$), 160.8 (C$_{16}$), 142.5 (C$_9$), 142.4 (SO$_2$Ph-ipso-C), 132.6 (SO$_2$Ph-p-C), 130.9 (C$_4$), 130.6 (C$_6$), 129.0 (SO$_2$Ph-m-C), 125.7 (SO$_2$Ph-o-C), 125.2 (C$_7$), 124.7 (C$_8$), 116.3 (C$_5$), 81.9 (C$_2$), 73.8 (C15), 73.4 (C$_{11}$), 60.5 (C$_3$), 41.9 (C$_{12}$), 27.8 (C$_{18}$), 17.9 (C$_{17}$). FTIR (thin film) cm$^{-1}$: 1716 (s), 1688 (s), 1480 (m), 1462 (m), 1447 (s), 1348 (s), 1168 (m). HRMS (ESI) (m/z): calc'd for C$_{42}$H$_{37}$N$_6$O$_8$S$_6$ [M+H]$^+$: 945.0992. found 945.0968. TLC (5% acetone in dichloromethane), Rf: 0.21 (UV, CAM).

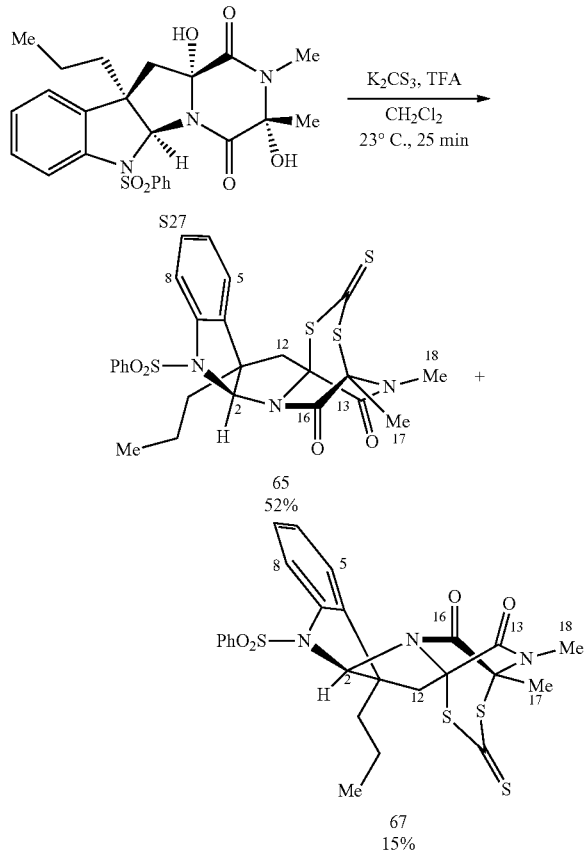

C3-Propyl dithiepanethiones 65 and 67

A solution of the tetracyclic diol S27 (228 mg, 470 µmol, 1 equiv) in dichloromethane (3.5 mL) was added to a yellow solution of potassium trithiocarbonate (438 mg, 2.35 mmol, 5.00 equiv) in anhydrous dichloromethane (7 mL) and trifluoroacetic acid (3 mL) at 23° C. An additional portion of trifluoroacetic acid (1.5 mL) was added to the reaction mixture via syringe. After 25 min, the reaction mixture was diluted with dichloromethane (60 mL) and washed with saturated aqueous sodium bicarbonate (125 mL). The aqueous layer was extracted with dichloromethane (2×30 mL) and the combined organic layers were dried over anhydrous sodium sulfate, were filtered, and were concentrated under reduced pressure to yield a yellow powder. This powder was purified by flash column chromatography on silica gel (eluent: 20% acetone in dichloromethane) to afford diastereomeric dithiepanethiones 65 (137 mg, 52.0%) and 67 (38.7 mg, 14.7%) as yellow films.

β-Epimer 65:
$^1$H NMR (500 MHz, CDCl$_3$, 20° C.): δ 7.72 (d, J=7.5, 2H, SO$_2$Ph-o-H), 7.52 (t, J=7.5, 1H, SO$_2$Ph-p-H), 7.40 (app-t, J=7.9, 2H, SO$_2$Ph-m-H), 7.35 (d, J=7.1, 1H, C$_8$H), 7.29 (app-dt, J=1.7, 8.2, 1H, C$_7$H), 7.19 (app-dt, J=0.9, 7.7, 1H, C$_6$H), 7.16 (dd, J=1.4, 7.6, 1H, C$_5$H), 6.29 (s, 1H, C$_2$H), 3.00 (s, 3H, C$_{15}$H), 2.98 (d, J=15.1, 1H, C$_{12}$H$_a$), 2.75 (d, J=15.1, 1H, C$_{12}$H$_b$), 1.79 (s, 3H, C$_{17}$H), 1.47-1.31 (m, 2H, CH$_2$CH$_2$CH$_3$), 1.47-1.31 (m, 1H, CH$_2$CH$_a$H$_b$CH$_3$), 1.19-1.06 (m, 1H, CH$_2$CH$_a$H$_b$CH$_3$), 0.78 (app-t, J=7.0, 3H CH$_2$CH$_2$CH$_3$). $^{13}$C NMR (125.8 MHz, CDCl$_3$, 20° C.): δ 215.9 (C=S), 164.7 (C$_{13}$), 160.5 (C$_{16}$), 141.6 (C$_9$), 140.4 (SO$_2$Ph-ipso-C), 135.4 (C$_4$), 133.3 (SO$_2$Ph-p-C), 129.7 (C$_7$), 129.2 (SO$_2$Ph-m-C), 126.5 (SO$_2$Ph-o-C), 125.9 (C$_6$), 123.6 (C$_5$), 117.6 (C$_8$), 83.7 (C$_2$), 74.6 (C$_{11}$), 73.5 (C$_{15}$), 54.5 (C$_3$), 46.1 (C$_{12}$), 40.5 (CH$_2$CH$_2$CH$_3$), 28.5 (C$_{18}$), 19.7 (C$_{17}$), 18.0 (CH$_2$CH$_2$CH$_3$), 14.3 (CH$_2$CH$_2$CH$_3$). FTIR (thin film) cm$^{-1}$: 1711 (s), 1686 (s), 1477 (m), 1461 (m), 1447 (m), 1365 (s), 1167 (s), 732 (m). HRMS (ESI) (m/z): calc'd for C$_{25}$H$_{25}$N$_3$NaO$_4$S$_4$ [M+Na]$^+$: 582.0620. found 582.0646. TLC (40% ethyl acetate in hexanes), Rf: 0.18 (UV, CAM).

α-Epimer 67:
$^1$H NMR (500 MHz, CDCl$_3$, 20° C.): δ 7.79 (dd, J=1.0, 7.3, 2H, SO$_2$Ph-o-H), 7.57 (d, J=8.0, 1H, C$_8$H), 7.53 (t, J=7.5, 1H, SO$_2$Ph-p-H), 7.40 (app-t, J=7.8, 2H, SO$_2$Ph-m-H), 7.27 (app-dt, J=1.4, 7.8, 1H, C$_7$H), 7.12 (app-dt, J=0.9, 7.6, 1H, C$_6$H), 7.06 (dd, J=0.8, 7.5, 1H, C$_5$H), 6.06 (s, 1H, C$_2$H), 3.42 (d, J=15.7, 1H, C$_{12}$H$_a$), 2.97 (s, 3H, C$_{18}$H), 2.44 (d, J=15.7, 1H, C$_{12}$H$_b$), 1.95 (s, 3H, C$_{17}$H), 1.37-1.26 (m, 1H, CH$_2$CH$_a$H$_b$CH$_3$), 1.26-1.14 (m, 1H, CH$_2$CH$_a$H$_b$CH$_3$), 0.97-0.83 (m, 2H, CH$_2$CH$_2$CH$_3$), 0.69 (app-t, J=6.8, 3H, CH$_2$CH$_2$CH$_3$). $^{13}$C NMR (125.8 MHz, CDCl$_3$, 20° C.): δ 216.8 (C=S), 164.3 (C$_{13}$), 161.4 (C$_{15}$), 139.3 (C$_9$), 138.9 (SO$_2$Ph-ipso-C), 138.3 (C$_4$), 133.8 (SO$_2$Ph-p-C), 129.3 (SO$_2$Ph-m-C), 129.3 (C$_7$), 127.7 (SO$_2$Ph-o-C), 126.3 (C$_6$), 124.4 (C$_5$), 118.3 (C$_8$), 84.5 (C$_2$), 74.8 (C$_{11}$), 74.1 (C$_{15}$), 55.0 (C$_3$), 42.4 (C$_{12}$), 40.0 (CH$_2$CH$_2$CH$_3$), 28.6 (C$_{18}$), 21.0 (C$_{17}$), 18.3 (CH$_2$CH$_2$CH$_3$), 14.2 (CH$_2$CH$_2$CH$_3$). FTIR (thin film) cm$^{-1}$: 1712 (s), 1691 (s), 1476 (m), 1461 (m), 1447 (m), 1368 (s), 1333 (s), 1172 (s), 727 (w). HRMS (ESI) (m/z): calc'd for C$_2$H$_{25}$N$_3$NaO$_4$S$_4$ [M+Na]$^+$: 582.0620. found 582.0636. TLC (40% ethyl acetate in hexanes), Rf: 0.50 (UV, CAM).

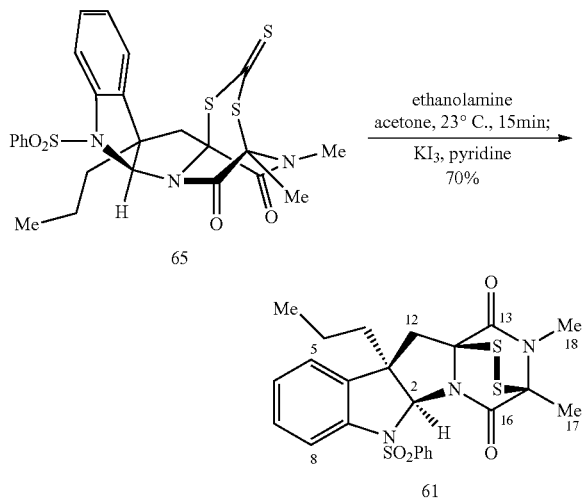

β-C3-Propyl epidithiodiketopiperazine 61

Ethanolamine (500 μL) was added via syringe to a solution of dithiepanethione 65 (13.3 mg, 23.8 μmol, 1 equiv) in acetone (500 μL) at 23° C. After 15 min, the reaction mixture was diluted with dichloromethane (30 mL) and aqueous hydrochloric acid solution (2 N, 30 mL). The organic layer was collected, and the aqueous layer was extracted with dichloromethane (2×2 mL). A solution of potassium triiodide in pyridine (2.5% w/v) was added dropwise to the combined organic layers until a persistent yellow color was observed. The resulting mixture was washed with aqueous hydrochloric acid (2 N, 30 mL) and the layers were separated. The aqueous layer was extracted with dichloromethane (2×5 mL), and the combined organic layers were dried over anhydrous sodium sulfate, were filtered, and were concentrated under reduced pressure. The residue was purified by flash column chromatography on silica gel (eluent: 1% acetone in dichloromethane) to afford epidithiodiketopiperazine 61 (8.6 mg, 70%) as a clear film. $^1$H NMR (500 MHz, CDCl$_3$, 20° C.): δ 7.80 (d, J=7.0, 2H, SO$_2$Ph-o-H), 7.53 (t, J=7.0, 1H, SO$_2$Ph-p-H), 7.46-7.37 (m, 1H, C$_8$H), 7.46-7.37 (m, 2H, SO$_2$Ph-m-H), 7.29 (app-dt, J=1.1, 7.7, 1H, C$_7$H), 7.16 (app-t, J=7.6, 1H, C$_6$H), 7.12 (d, J=7.6, 1H, C$_5$H), 6.09 (s, 1H, C$_2$H), 3.19 (d, J=15.2, 1H, C$_{12}$H$_a$), 2.98 (s, 3H, C$_{18}$H), 2.57 (d, J=15.2, 1H, C$_{12}$H$_b$), 1.87 (s, 3H, C$_{17}$H), 1.43-1.30 (m, 1H, CH$_2$CH$_a$H$_b$CH$_3$), 1.22-1.04 (m, 1H, CH$_2$CH$_a$H$_b$CH$_3$), 1.22-1.04 (m, 2H, CH$_2$CH$_2$CH$_3$), 0.77-0.68 (m, 3H, CH$_2$CH$_2$CH$_3$). $^{13}$C NMR (125.8 MHz, CDCl$_3$, 20° C.): δ 165.9 (C$_{13}$), 161.6 (C$_{16}$), 141.1 (C$_9$), 139.8 (SO$_2$Ph-ipso-C), 137.6 (C$_4$), 133.4 (SO$_2$Ph-p-C), 129.3 (C$_7$), 129.2 (SO$_2$Ph-m-C), 127.4 (SO$_2$Ph-o-C), 125.9 (C$_6$), 123.6 (C$_5$), 118.4 (C$_8$), 83.7 (C$_2$), 73.7 (C$_{11}$), 73.5 (C$_{15}$), 55.9 (C$_3$), 41.8 (C$_{12}$), 40.0 (CH$_2$CH$_2$CH$_3$), 27.7 (C$_{18}$), 18.3 (CH$_2$CH$_2$CH$_3$), 18.0 (C$_{17}$), 14.3 (CH$_2$CH$_2$CH$_3$). FTIR (thin film) cm$^{-1}$: 1713 (s), 1688 (s), 1478 (m), 1460 (m), 1447 (m), 1341 (s), 1172 (s), 719 (w). HRMS (ESI) (m/z): calc'd for C$_{24}$H$_{25}$N3NaO$_4$S$_3$ [M+Na]$^+$: 538.0899. found 538.0923. TLC (1% acetone in dichloromethane), Rf: 0.21 (UV, CAM).

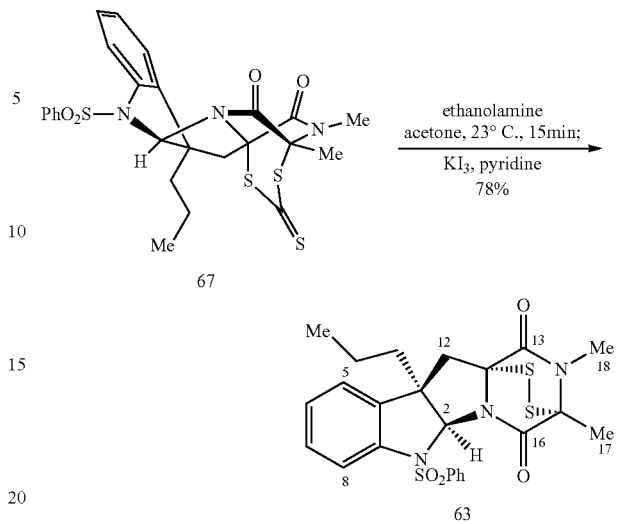

α-C3-Propyl epidithiodiketopiperazine 63

Ethanolamine (500 μL) was added via syringe to a solution of dithiepanethione 67 (13.3 mg, 23.8 μmol, 1 equiv) in acetone (500 μL) at 23° C. After 15 min, the reaction mixture was diluted with dichloromethane (30 mL) and aqueous hydrochloric acid solution (2 N, 30 mL). The organic layer was collected, and the aqueous layer was extracted with dichloromethane (2×5 mL). A solution of potassium triiodide in pyridine (2.5% w/v) was added dropwise to the combined organic layers until a persistent yellow color was observed. The resulting mixture was washed with aqueous hydrochloric acid (2 N, 30 mL) and the layers were separated. The aqueous layer was extracted with dichloromethane (2×5 mL), and the combined organic layers were dried over anhydrous sodium sulfate, were filtered, and were concentrated under reduced pressure. The residue was purified by flash column chromatography on silica gel (eluent: 30% ethyl acetate in dichloromethane) to afford epidithiodiketopiperazine 63 (9.6 mg, 78%) as a clear film. $^1$H NMR (500 MHz, CDCl$_3$, 20° C.): δ 7.83 (dd, J=0.8, 8.2, 2H, SO$_2$Ph-o-H), 7.53 (t, J=7.4, 1H, SO$_2$Ph-p-H), 7.51 (d, J=7.9, 1H, C$_8$H), 7.40 (app-t, J=8.1, 2H, SO$_2$Ph-m-H), 7.28-7.19 (m, 1H, C$_7$H), 7.13-7.05 (m, 1H, C$_6$H), 7.13-7.05 (m, 1H, C$_5$H), 6.14 (s, 1H, C$_2$H), 3.57 (d, J=14.9, 1H, C$_{12}$H$_a$), 2.89 (s, 3H, C$_{15}$H), 2.37 (d, J=14.9, 1H, C$_{12}$H$_b$), 1.93 (s, 3H, C$_{17}$H), 1.38-1.14 (m, 2H, CH$_2$CH$_2$CH$_3$), 1.00-0.85 (m, 2H, CH$_2$CH$_2$CH$_3$), 0.70 (app-t, J=7.2, 3H, CH$_2$CH$_2$CH$_3$). $^{13}$C NMR (125.8 MHz, CDCl$_3$, 20° C.): δ 165.7 (C$_{13}$), 162.9 (C$_{16}$), 139.3 (C$_9$), 139.1 (SO$_2$Ph-ipso-C), 137.4 (C$_4$), 133.7 (SO$_2$Ph-p-C), 129.3 (SO$_2$Ph-m-C), 129.3 (C$_7$), 127.7 (SO$_2$Ph-o-C), 126.1 (C$_6$), 124.5 (C$_5$), 118.1 (C$_8$), 84.3 (C$_2$), 74.6 (C$_{11}$), 73.9 (C$_1$s), 56.4 (C$_3$), 40.5 (C$_{12}$), 39.7 (CH$_2$CH$_2$CH$_3$), 27.5 (C$_{19}$), 18.7 (C$_7$), 18.1 (CH$_2$CH$_2$CH$_3$), 14.2 (CH$_2$CH$_2$CH$_3$). FTIR (thin film) cm$^{-1}$: 1694 (s), 1447 (m), 1366 (s), 1331 (m), 1172 (s), 722 (w). HRMS (ESI) (m/z): calc'd for C$_{24}$H$_{25}$N3NaO$_4$S$_3$ [M+Na]$^+$: 538.0899. found 538.0920. TLC (30% ethyl acetate in hexanes), Rf: 0.21 (UV, CAM).

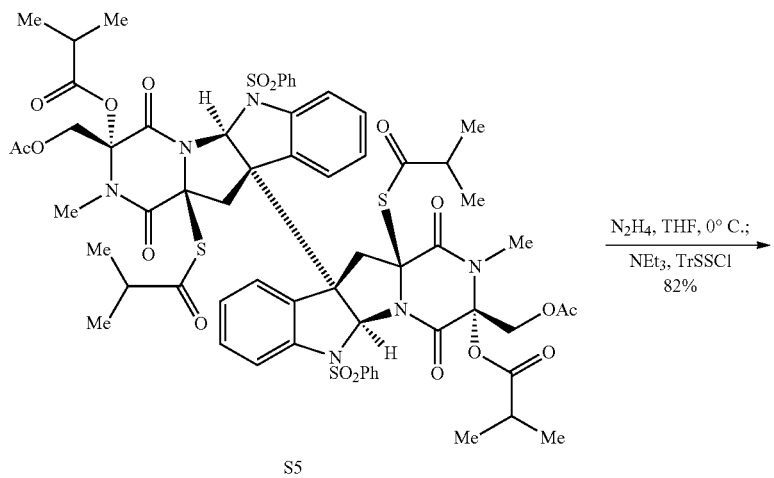

S5

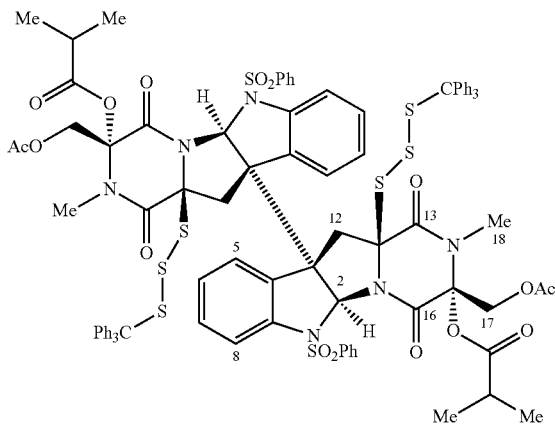

19

Dimeric bis(triphenylmethanetrisulfide) 19

Anhydrous hydrazine (0.8 μL, 25 μmol, 5.00 equiv) was added via syringe to a solution of diaminodithioisobutyrate (+)-S5 (6.6 mg, 5.0 μmol, 1 equiv) in tetrahydrofuran (2 mL) at 0° C. After 18 min, triethylamine (17.5 μL, 126 μmol, 25.0 equiv) and solid chloro(triphenylmethyl)disulfane (17.2 mg, 50.3 μmol, 10.0 equiv) were sequentially added to the reaction mixture under an inert atmosphere. After 13 min, saturated aqueous ammonium chloride (3 mL) was added to the reaction mixture. The solution was then poured into a separatory funnel containing saturated aqueous ammonium chloride (10 mL) and dichloromethane (15 mL). The aqueous layer was extracted with dichloromethane (2×5 mL), and the combined organic layers were dried over anhydrous sodium sulfate, were filtered, and were concentrated under reduced pressure. The residue was purified by flash column chromatography on silica gel (eluent: 35% ethyl acetate in hexanes) to afford dimeric bis(triphenylmethanetrisulfide) (+)-19 (7.4 mg, 82%) as a slightly off-white solid. $^1$H NMR (500 MHz, CDCl$_3$, 20° C.): δ 8.04 (d, J=7.5, 4H, SO$_2$Ph-o-H), 7.64 (t, J=7.5, 2H, SO$_2$Ph-p-H), 7.52 (app-t, J=7.9, 4H, SO$_2$Ph-m-H), 7.22-7.12 (m, 2H, C$_8$H), 7.22-7.12 (m, 18H, C(C$_6$H$_5$)$_3$), 6.99-6.90 (m, 12H, C(C$_6$H$_5$)$_3$), 6.80 (s, 2H, C$_2$H), 6.65 (br-s, 2H, C$_5$H), 6.57 (app-t, J=8.1, 2H, C$_7$H), 6.08 (app-t, J=7.0, 2H, C$_6$H), 4.43 (d, J=11.9, 2H, C$_{17}$H$_a$), 4.23 (d, J=11.7, 2H, C$_{17}$H$_b$), 3.31 (d, J=14.5, 2H, C$_{12}$H$_a$), 2.92 (d, J=14.4, 2H, C$_{12}$H$_b$), 2.71 (s, 6H, C$_{15}$H), 2.54 (app-sp, J=7.1, 2H, CH$_{isobutyrate}$), 1.79 (s, 6H, CH$_{3acetate}$), 1.11 (d, J=7.0, 6H, CH$_{3isobutyrate}$), 1.08 (d, J=7.1, 6H, CH$_{3isobutyrate}$). $^{13}$C NMR (125.8 MHz, CDCl$_3$, 20° C.): δ 174.1 (C=O$_{isobutyrate}$), 170.1 (C=O$_{acetate}$), 164.1 (C$_{13}$), 161.2 (C$_{16}$), 143.3 (C(C$_6$H$_5$)$_3$), 142.8 (C$_9$), 140.5 (SO$_2$Ph-ipso-C), 133.4 (SO$_2$Ph-p-C), 130.7 (C$_4$), 130.5 (C(C$_6$H$_5$)$_3$), 129.6 (SO$_2$Ph-m-C), 129.4 (C$_7$), 128.0 (C(C$_6$H$_5$)$_3$), 127.3 (C(C$_6$H$_5$)$_3$), 127.3 (SO$_2$Ph-o-C), 124.0 (C$_5$), 123.8 (C$_6$), 112.8 (C$_8$), 86.2 (C$_1$s), 80.9 (C$_2$), 75.2

($C_{11}$), 73.3 (C($C_6H_5$)$_3$), 64.7 ($C_{17}$), 60.7 ($C_3$), 42.8 ($C_{12}$), 33.6 ($CH_{isobutyrate}$), 28.7 ($C_{18}$), 21.4 ($CH_{3acetate}$), 18.8 ($CH_{3isobutyrate}$). FTIR (thin film) cm$^{-1}$: 1749 (s), 1708 (s), 1480 (m), 1462 (m), 1447 (m), 1380 (s), 1220 (m), 1173 (s), 729 (m), 699 (m). HRMS (ESI) (m/z): calc'd for $C_{92}H_{88}N_7O_6S_8$ [M+NH$_4$]$^+$: 1802.4048. found 1802.4073. [α]$_D$24: +287 (c 0.35, CHCl$_3$). TLC (35% ethyl acetate in hexanes), Rf: 0.23 (UV, CAM).

Among other things, the present invention recognizes that it is particularly challenging to prepare ETP or thiodiketopiperazine compounds wherein one of R$^6$ and R$^{6'}$ is —OR or —OSi(R)$_3$. In some embodiments, the present provides new methods for preparing a provided compounds, wherein one of R$^6$ and R$^{6'}$ is —OR or —OSi(R)$_3$. In some embodiments, such a compound, for example, a compound having the structure of formula I-c or I-d, is depicted below:

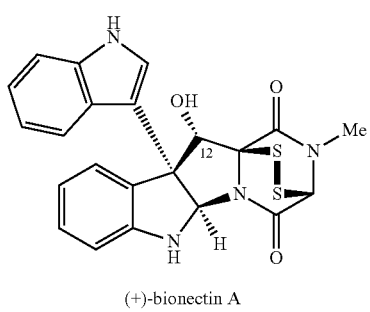

(E2-1)

(+)-bionectin A

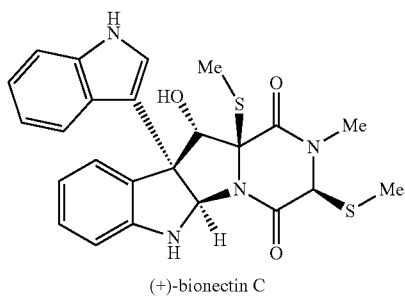

(E2-2)

(+)-bionectin C

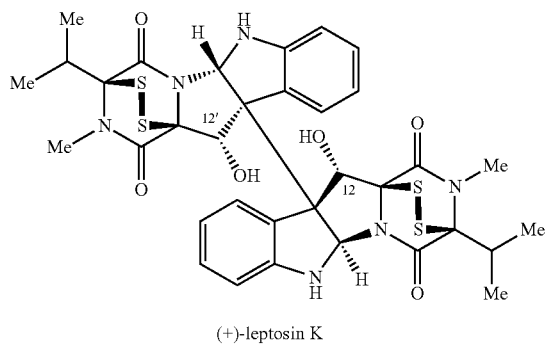

(E2-3)

(+)-leptosin K

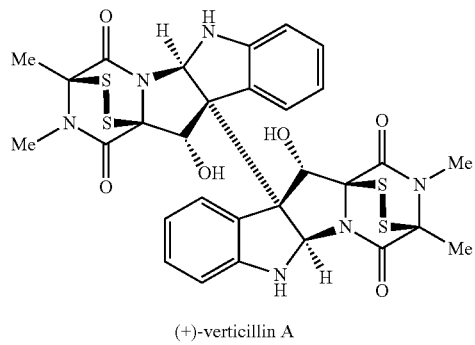

(E2-4)

(+)-verticillin A

Exemplary C12-hydroxylated epipolythiodiketopiperazines

In some embodiments, a provided new method comprises an intermolecular Friedel-Crafts reaction of a silyl-tethered indole moiety. In some embodiments, the present invention provides scalable methods for erythro-3-hydroxytryptophan amino acid synthesis. In some embodiments, the present invention provide new mercaptan reagent for synthesis of, for example, epipolythiodiketopiperazine (ETP) or thiodiketopiperazines compounds, and/or derivatives and analogs thereof. In some embodiments, a provided mercaptan reagent can be unraveled under a mild condition that does not disrupt an N-protecting group of an indolyl moiety. In some embodiments, a provided mercaptan reagent can be unraveled under a mild condition that does not disrupt an N-protecting group of an indolyl moiety, wherein the protecting group is —S(O)$_2$R. In some embodiments, a provided mercaptan reagent can be unraveled under a mild condition that does not disrupt an N-protecting group of an indolyl moiety, wherein the protecting group is —S(O)$_2$Ph. In some embodiments, the present invention provides a method of permanganate-mediated stereoinvertive hydroxylation of the α-stereocenters of diketopiperazines. In some embodiments, the present invention provides a method of direct triketopiperazine synthesis from cyclo-dipeptides. Non-limiting examples are described herein.

In some embodiments, the present invention provides a general method for preparing epidithiodiketopiperazine alkaloids, for example, a provided compound of formulae I-a, I-b, I-c and I-d, by using 3-hydroxytryptophan in lieu of tryptophan as our feedstock material.

An exemplary retrosynthetic analysis of (+)-bionectins A (E2-1) and C (E2-2) is outlined in Scheme E2-1.

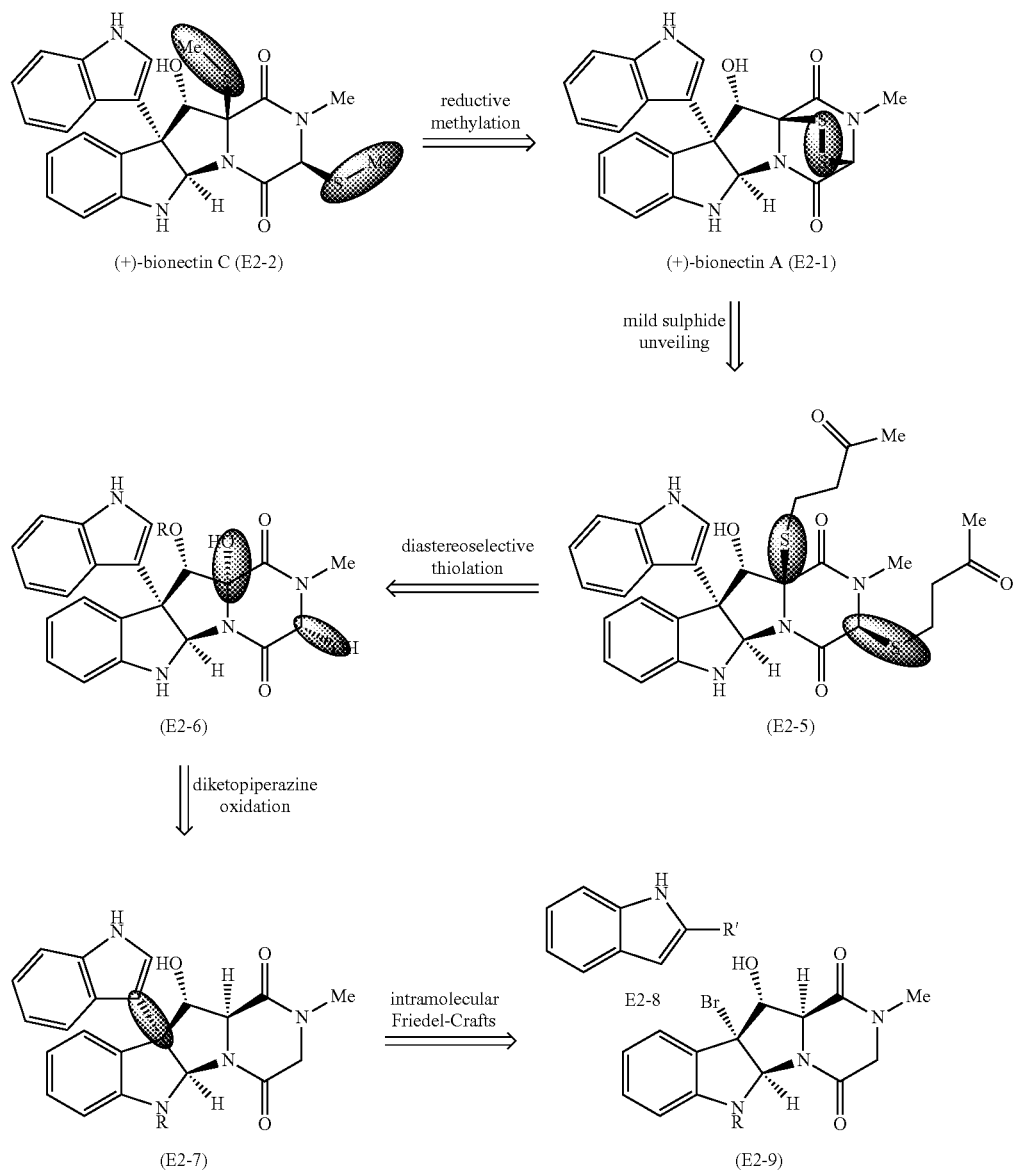

Scheme E2-1. Retrosynthetic analysis for (+)-bionectins A (E2-1) and C (E2-2).

In some embodiments, an exemplary synthesis of (+)-bionectins A and C commenced with the development of a concise and scalable route to erythro-β-hydroxytryptophan (Scheme E2-2). While several methods have been reported for the synthesis of the threo diastereomer ((a) H. Sugiyama, T. Shioiri and F. Yokokawa, *Tetrahedron Lett.*, 2002, 43, 3489; (b) S.-J. Wen, H.-W. Zhang and Z.-J. Yao, *Tetrahedron Lett.*, 2002, 43, 5291; (c) K. S. Feldman and A. G. Karatjas, *Org. Lett.*, 2004, 6, 2489; (d) S.-J. Wen and Z.-J. Yao, *Org. Lett.*, 2004, 6, 2721; (e) D. Crich and A. Banerjee, *J. Org. Chem.*, 2006, 71, 7106; (f) D. B. Hansen, A. S. Lewis, S. J. Gavalas and M. M. Joullié, *Tetrahedron: Asymmetry*, 2006, 17, 15; (g) J. Patel, G. Clavé, P.-Y. Renard and X. Franck, *Angew. Chem., Int. Ed.*, 2008, 47, 4224), there was no scalable available method to the desired tryptophan derivative. After extensive optimization it was surprisingly found that titanium (IV)-mediated anti-aldol reaction (A. Solladiè-Cavallo and J. L. Koessler, *J. Org. Chem.*, 1994, 59, 3240; (b) A. Solladie-Cavallo and T. Nsenda, *Tetrahedron Lett.*, 1998, 39, 2191; (c) A. Teniou and H. Alliouche, *Asian J. Chem.*, 2006, 18, 2487) to indole-3-carboxaldehyde E2-10 and (−)-pinanone-derived ethyl iminogylcinate E2-11 (T. Oguri, N. Kawai, T. Shioiri and S.-i. Yamada, *Chem. Pharm. Bull.*, 1978, 26, 803) efficiently afforded the aldol adducts, in some embodiments, in 81% yield on greater than 40 gram scale. Subsequent hydrolysis of the Schiff base then afforded greater than 20 grams of β-hydroxy-α-amino ester E2-13 in 94% ee along with recovery of the chiral auxiliary. The absolute and relative stereochemistry of the material were verified through single crystal X-ray diffraction analysis of its 3,5-dinitrobenzamide derivative E2-14.

Scheme E2-2.

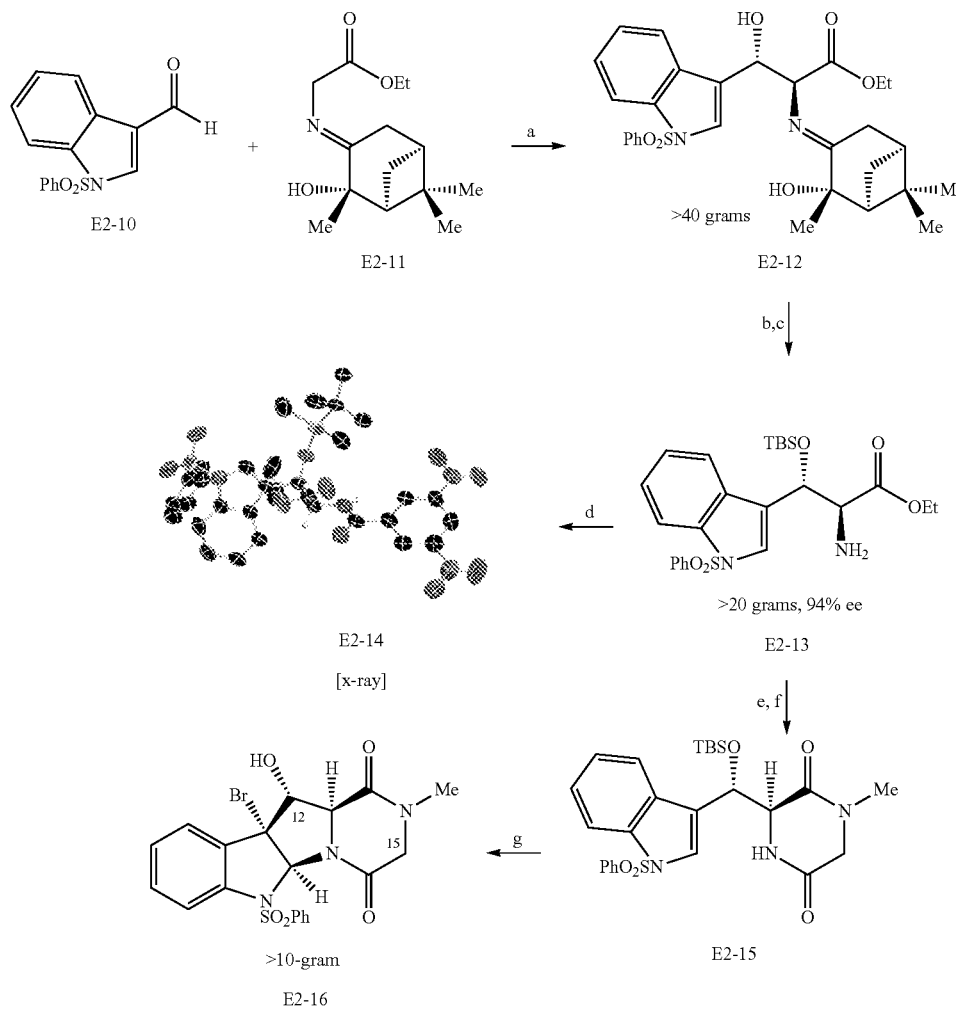

Asymmetric synthesis of a β-hydroxytryptophan derivative. Conditions: (a) TiCl(OEt)₃, NEt₃, CH₂Cl₂, 0° C., 81% (58% desired diastereomer);
(b) TBSOTf, 2,6-lutidine, CH₂Cl₂, 0° C., 72%; (c) 2N HCl, THF, 81%; (d) 3,5-dinitrobenzoyl chloride, NEt₃, CH₂Cl₂, 23° C., 94%;
(e) N-Boc-sarcosine, EDC•HCl, HOBt, CH₂Cl₂, 23° C., 98%; (f) TFA, CH₂Cl₂, 23° C.;

AcOH, morpholine, ᵗBuOH, 80° C., 97%; (g) Br₂, MeCN, 0° C.; anisole, 94%, 9:1 dr; X-ray structures are displayed as ORTEPs at 50% probability; TBSOTf=tert-butyldimethylsilyl trifluoromethanesulfonate, Boc=tert-butoxycarbonyl, EDC=1-ethyl-3-(3-dimethylamino propyl) carbodiimide, TFA=trifluoroacetic acid, DMAP=4-(dimethylamino)pyridine, DTBMP=2,6-di-tert-butyl-4-methylpyridine, THF=tetrahydrofuran.

With a rapid and scalable route to erythro-β-hydroxytryptophan available, we proceeded to the synthesis of the desired tetracycle E2-16. Dipeptide formation with N-Boc-scarcosine followed by unveiling of the amine and intramolecular cyclization with AcOH and morpholine in tert-butanol afforded diketopiperazine E2-15 in 97% yield. Exposure of diketopiperazine E2-15 to excess bromine in MeCN at 0° C. and subsequent addition of anisole led to a diastereoselective halocyclization with concomitant loss of the silyl ether. In some embodiments, in addition to preventing undesired ring-halogenation, quenching of excess bromine with anisole resulted in the in situ formation of hydrobromic acid, which was responsible for the desired removal of the silyl ether function. Under these optimized conditions, tetracyclic bromide E2-16 could be accessed in decagram quantities in 94% yield (9:1 dr, endo: exo) favoring the desired diastereomer. In some embodiments, we found that the C12 hydroxyl group favors the formation of the desired endo-cyclization product independent of the ancillary amino acid substituent at the C15 center.

Using the tetracyclic bromide, we tried to implement an intermolecular Friedel-Crafts indolylation at the C3 position in a manner akin to gliocladin synthesis; however, without the intention to be limited by theory, due to the inductive effects of the C12-hydroxyl group (Scheme E2-3), we found the C3-bromide proved recalcitrant toward ionization. Under more forcing conditions, C3-carbocation derivatives E2-18 could be formed, but their instability required rapid trapping, a feat in some embodiments hindered by the additional substitution at C12. Application of the conditions for intermolecular Friedel-Crafts reaction ((a) J. Kim and M. Movassaghi, *J. Am. Chem. Soc.*, 2011, 133, 14940; (b) N. Boyer and M. Movassaghi, *Chem. Sci.*, 2012, 3, 1798) resulted in regioisomeric and diastereomeric products (Scheme E2-3). In some embodiments, the geometry of the tricyclic substructure was insufficient in overcoming the steric pressures imposed by C12-hydroxylation, resulting in 10% undesired byproducts consistent with indole addition from the concave face.

Scheme E2-3. Considerations in design of a new intramolecular Friedel-Crafts chemistry for C12-hydroxylated diketopiperazines E2-18.

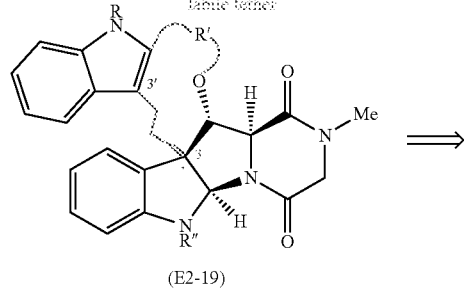

(E2-19)

- intramolecular C3-addition
- directed C3-C3' union

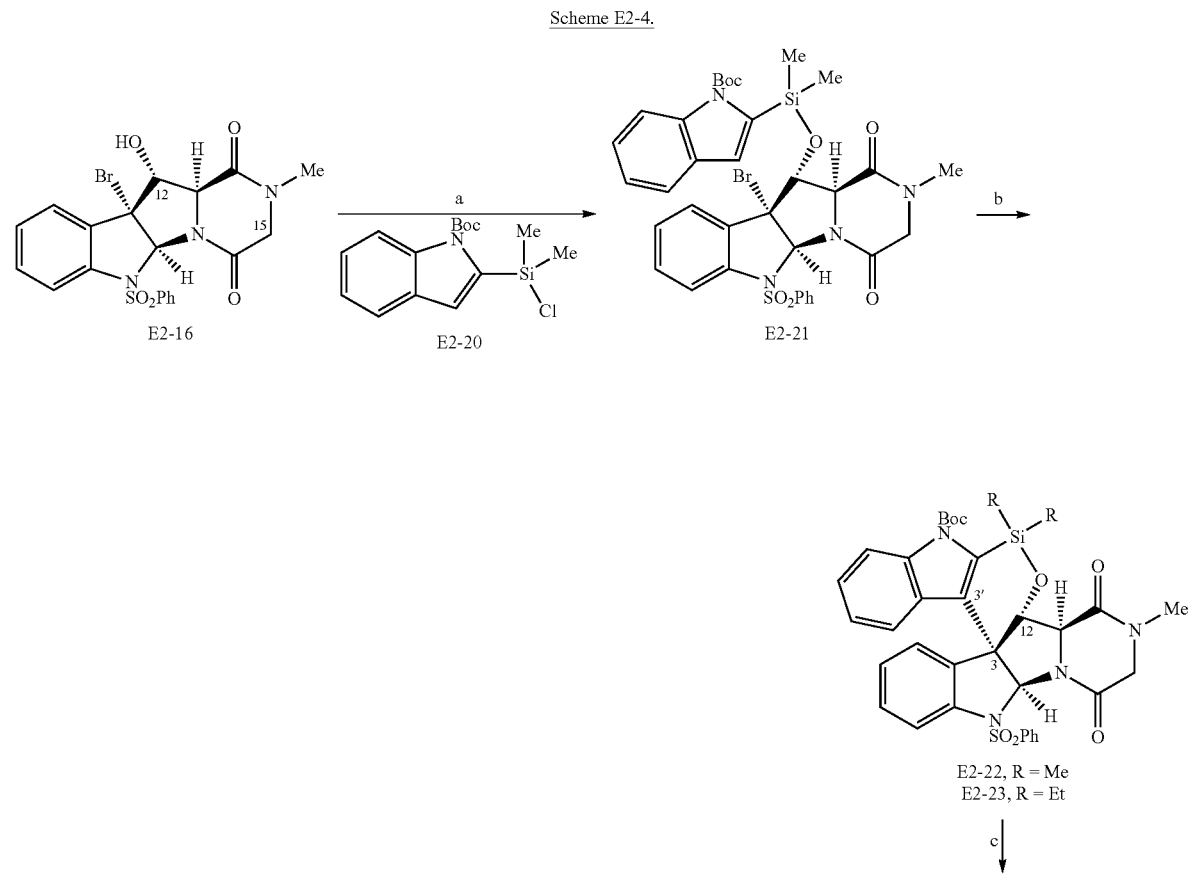

(E2-19)

- carbocation instability
- lack of regioselectivity
- sterically hindered approach After examining a variety of strategies, it was surprisingly found that an intramolecular delivery of the indole fragment provided the desired product efficiently. Silylation of tetracyclic alcohol with chlorodimethyl(N-Boc-2-indole)silane (E2-20, S. E. Denmark and J. D. Baird, *Org. Lett.*, 2004, 6, 3649) provided the desired silyl-tethered indole adduct E2-21 in 74% yield (Scheme E2-4). Surprisingly, a silver-mediated intramolecular Friedel-Crafts reaction proceeded smoothly in nitroethane at 0° C. to afford the C3-(3'-indolyl)-silacyclic product E2-22 in 68% yield. The structure of a diethyl silyl variant E2-23 was confirmed through X-ray analysis (Scheme E2-4). The desired C3-indolylated tetracycle E2-24 was accessed in 58% yield by treatment of silacyclic product E2-22 with aqueous hydrochloric acid.

Scheme E2-4.

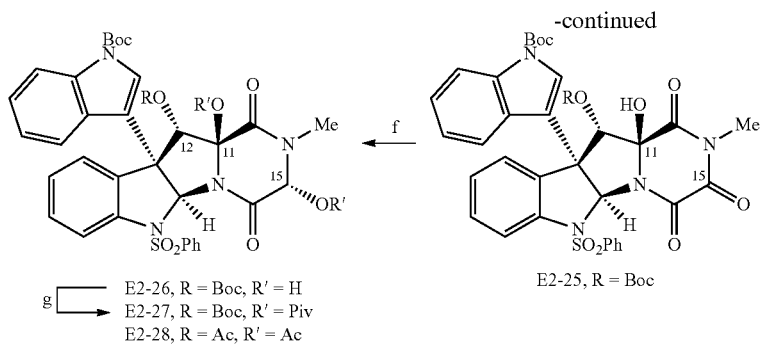

E2-26, R = Boc, R' = H
E2-27, R = Boc, R' = Piv
E2-28, R = Ac, R' = Ac

Intramolecular Friedel-Crafts reaction and elaboration of the tetracyclic core.
Conditions: (a) 20, DMAP, THF, 23° C., 74%; (b) AgBF$_4$, DTBMP, EtNO$_2$, 0° C., 68%; (c) 6N HCl, THF, 80° C., 58%; (d) Boc$_2$O, DMAP, CH$_2$Cl$_2$, 23° C., 92%; (e) Py$_2$AgMnO$_4$, CH$_2$Cl$_2$, 23° C., 45%; (f) NaBH$_4$, MeOH, -20° C., 75%, (g) PivCl, DMAP, CH$_2$Cl$_2$, 23° C., 83%.

The key indolylated intermediate E2-24 was subsequently bis(tert-butoxycarbonyl) protected in 92% yield using Boc$_2$O and DMAP in anticipation of our C—H hydroxylation chemistry. In some embodiments, the hydroxylation proceeded effectively in the presence of less electron-rich substructures (Scheme E2-4). In some embodiments, the oxidation was more efficient with the tert-butoxycarbonyl group on N1' on this system. Surprisingly, rather than providing the expected stereoretentive dihydroxylation product (Scheme E2-1), in some embodiments, oxidation of the tetracycle with excess bis(pyridine)silver(I) permanganate in dichloromethane afforded triketopiperazine 25 in 45% yield as a single diastereomer, representing an average of 77% yield per oxidation event. Direct access to a triketopiperazine motif is a highly enabling transformation, and can be used to preparation C-15 derivatives, for example, as described in J. E. DeLorbe, D. Home, R. Jove, S. M. Mennen, S, Nam, F.-L. Zhang and L. E. Overman, *J. Am. Chem. Soc.*, 2013, 135, 4117.

The C15 carbonyl group of triketopiperazine E2-25 was reduced in a highly diastereoselective fashion using sodium borohydride in methanol at −20° C. to afford the desired diol E2-27 in 75% yield (Scheme E2-4). The relative stereochemistries of the C11 and C15 alcohols were then verified by peracetylation of a C12-acetylated diol derivative followed by single crystal X-ray diffraction analysis of the resultant triacetate E2-28. Surprisingly, the C11 stereochemistry is consistent with hydroxylation with inversion of the originating C—H stereochemistry, an event unprecedented in other oxidations of diketopiperazines without C12-hydroxylation ((a) J. Kim, J. A. Ashenhurst and M. Movassaghi, *Science*, 2009, 324, 238; (b) J. Kim and M. Movassaghi, *J. Am. Chem. Soc.*, 2010, 132, 14376. (c) N. Boyer and M. Movassaghi, *Chem. Sci.*, 2012, 3, 1798). While not wishing to be limited by theory, Applicant notes that it is likely that the captodatively-stabilized radical resulting from permanganate-mediated C—H abstraction is sterically shielded by the C12-tert-butoxycarbonate group, preventing the subsequent hydroxylation step through a rapid rebound mechanism (K. A. Gardner and J. M. Mayer, *Science*, 1995, 269, 1849; (b) T. Strassner and K. N. Houk, *J. Am. Chem. Soc.*, 2000, 122, 7821); reaction of a permanganate molecule with the persistent, stereochemically labile carbon-centered radical on the opposite face of the diketopiperazine would afford the oxidation product.

In some embodiments, recognizing the C11 and C15 alcohols to be recalcitrant toward ionization by virtue of their proximity to an inductively withdrawing carbonate and their location on a secondary carbon, respectively, the hydroxyl groups were activated for ionization by acylation with pivaloyl chloride and DMAP in dichloromethane to provide dipivaloate E2-27 in 83% yield. Constraining our search to functional groups capable of withstanding conditions for the photoinduced reductive removal of a benzenesulfonyl group, we initially evaluated the use of thioacid and alkyl mercaptan nucleophiles. While thioacids resulted in categorically low levels of diastereoselection for the nucleophilic addition, alkyl mercaptans proved highly diastereoselective on this substrate in affording their bisthioether adduct. However, known thioether reagents such as 2-cyanoethyl and 2-trimethylsilylethyl mercaptans required intolerably harsh conditions for their conversion to the necessary thiols.

TABLE E2-1.

Stereoselective sulfidation of diketopiperazines.

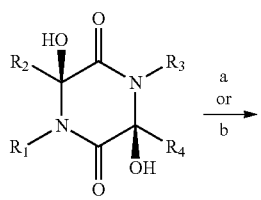

TABLE E2-1.-continued

| Bisulfide | yield[a] | ETP | yield |
|---|---|---|---|
| E2-31 | 70% | E2-34 | 65% |
| E2-32 | 78% | E2-34 | 60% |
| E2-33 | 75% | E2-35 | 57% |

Conditions: (a) E2-29, TFA, MeCN, 23° C.; (b) E2-30, TFA, MeCN, 23° C.; (c) pyrrolidine, $O_2$, MeCN, 23° C.
[a]Isolated as a single diastereomer.
$R_{Me}$ = $CH_2CH_2(CO)Me$,
$R_{Ph}$ = $CH_2CH_2(CO)Ph$.

In some embodiments, the present invention provides new sulphide surrogates, and new methods for sulfidation. We generated 4-mercaptobutan-2-one (E2-29) (N. C. Ross and R. Levine, J. Org. Chem., 1964, 29, 2346) by addition of hydrogen sulphide to methyl vinyl ketone and 3-mercaptopropiophenone (E2-30) by addition of thioacetic acid to 3-chloropropiophenone followed by hydrolysis. Exposure of several diketopiperazine-derived bishemiaminals to trifluoroacetic acid in acetonitrile gratifyingly resulted in diastereoselective cis-thioether adducts (Table E2-1). While the additions were highly diastereoselective using either of our thiol reagents on our bisproline substrate, in some embodiments, mercaptan E2-30 afforded superior diastereoselectivities to mercaptan E2-29 on other substrates including the diol presursor to bisthioether E2-33. In some embodiments, bisthioether adducts of methylketone-based mercaptan E2-29 underwent pyrrolidine-catalyzed sulfide-cleavage at a faster rate and was better suited for use with more sensitive compounds such as substrate E2-27.

Scheme E2-5.

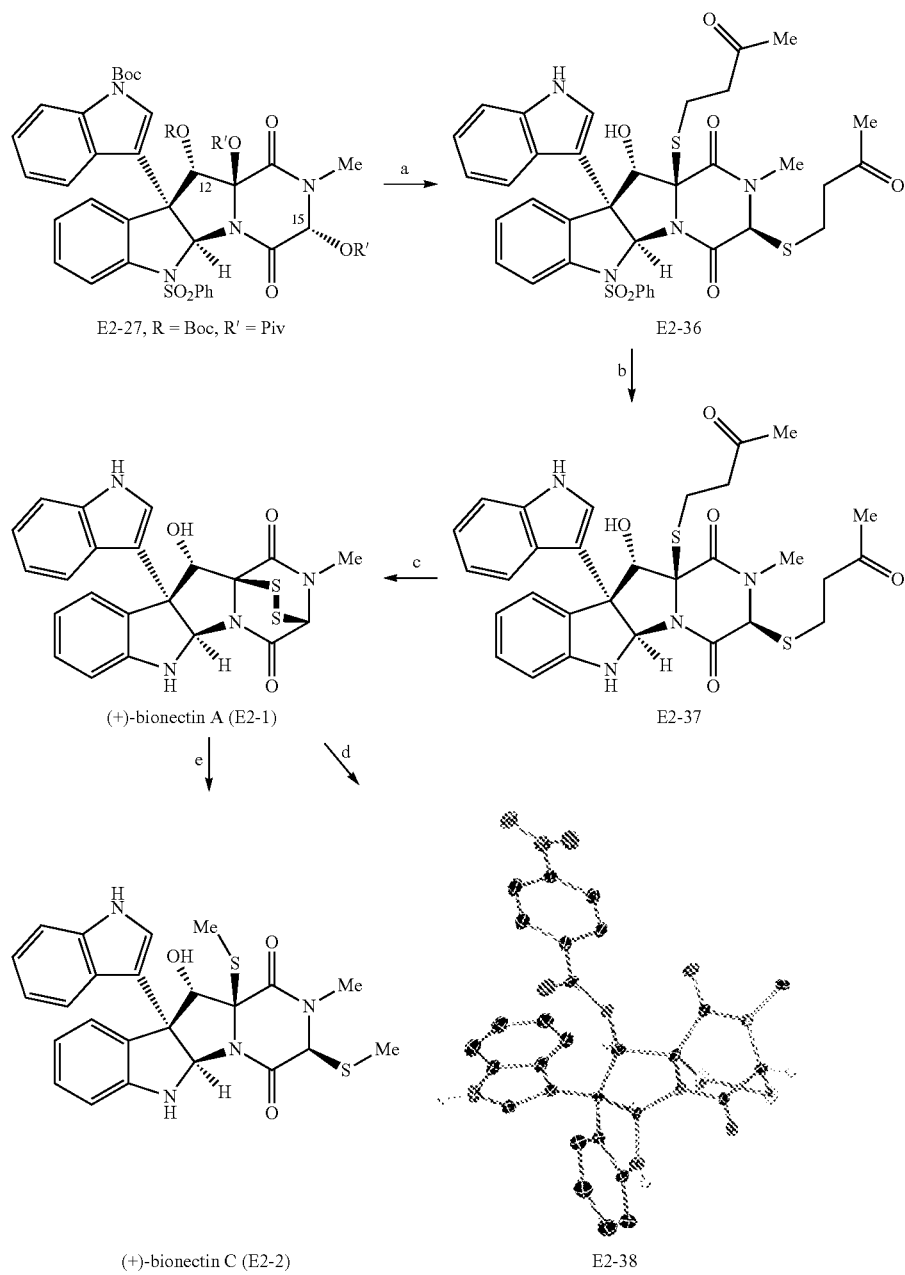

(+)-bionectin C (E2-2)   E2-38

Total synthesis of (+)-bionectins A (E2-1) and C (E2-2). Conditions: (a) 4-mercapto-2-butanone, TFA, MeNO₂, 80%, 3:1 dr; (b) 350 nm, 1,4-dimethoxynaphthalene, L-ascorbic acid, sodium L-ascorbate, H₂O, MeCN, 25° C., 56%; (c) pyrrolidine, EtSH, THF, 23° C.; KI₃, Py, CH₂Cl₂, 81%; (d) p-NO₂BzCl, DMAP, CH₂Cl₂, 0° c., 98%; (e) NaBH₄, MeI, Py, MeOH, 0° C., 97%. Py = pyridine, Piv = pivaloyl, Bz = benzoyl.

The bisthioethers generated using this new method could be converted to the corresponding epidithiodiketopiperazine under exceedingly mild conditions. Addition of pyrrolidine to a solution of the adducts in acetonitrile under an atmosphere of oxygen resulted in the direct conversion of substrates E2-31-E2-33 to their corresponding disulphides (Table E2-1). In the event that a dithiol cannot be oxidized readily with molecular oxygen to the disulphide in order to drive the β-addition/elimination equilibriation process toward product formation, a sacrificial thiol can be added to the reaction mixture to effect a transthioetherification.

Indeed, application of the provided new methodology for sulfidation of diketopiperazines proved critical in the synthesis of (+)-bionectins A and C. Treatment of a solution of dipivaloate E2-27 and ketomercaptan reagent E2-29 with trifluoroacetic acid in nitromethane at 23° C. yielded a diastereomeric mixture of bisthioethers E2-36 in 80% yield and 3:1 dr with concomitant removal of the tert-butoxycarbonyl groups at the N1' amine and C12 alcohol. While not wishing to be limited by theory, Applicant notes that ionization at C11 did not occur in acetonitrile likely due to the inductive effects of the C12-hydroxy group. The major diastereomer possessed the desired C11, C15-stereochemistry and could be isolated in 56% yield upon photoinduced electron transfer-mediated removal of the benzensulfonyl group (T. Hamada, A. Nishida and O. Yonemitsu, *J. Am. Chem. Soc.*, 1986, 108, 140). The bisthioethers were then removed with a mild enamine-mediated transthioetherification protocol employing pyrrolidine and ethanethiol in THF. The use of a sacrificial thiol was surprisingly found to be optimal in the unveiling of the thiols; exposure to an atmosphere of oxygen was insufficient in oxidizing the dithiol to a disulphide. Without the intention to be limited by theory, Applicant notes that the C15 thiol may prefer an equatorial disposition in its ground state and that conformation may not be as conducive to oxidation by molecular oxygen. Mild oxidation with $KI_3$ in pyridine then afforded the target compound (+)-bionectin A (E2-1) in 81% yield.

We treated the synthetic sample of (+)-E2-1 with p-nitrobenzoyl chloride and DMAP in $CH_2Cl_2$ at 0° C. to afford (+)-bionectin A-p-nitrobenzoate (E2-38) in 98% yield. Single crystal X-ray diffraction analysis of this C12-p-nitrobenzoate derivative confirmed its structure. Reductive methylation of (+)-bionectin A (E2-1) with sodium borohydride and MeI in pyridine and methanol afforded (+)-bionectin C (E2-2) in 97% yield (H. Poisel and U. Schmidt, *Chem. Ber.*, 1971, 104, 1714).

General Procedures.

All reactions were performed in oven-dried or flame-dried round-bottom flasks. The flasks were fitted with rubber septa and reactions were conducted under a positive pressure of argon. Cannulae or gas-tight syringes with stainless steel needles were used to transfer air- or moisture-sensitive liquids. Where necessary (so noted), solutions were deoxygenated by sparging with argon for a minimum of 10 min. Flash column chromatography was performed as described by Still et al. using granular silica gel (60-Å pore size, 40-63 μm, 4-6% $H_2O$ content, Zeochem) (Still, W. C.; Kahn, M.; Mitra, A. *J. Org. Chem.* 1978, 43, 2923). Analytical thin layer chromatography (TLC) was performed using glass plates pre-coated with 0.25 mm 230-400 mesh silica gel impregnated with a fluorescent indicator (254 nm). TLC plates were visualized by exposure to short wave ultraviolet light (254 nm) and an aqueous solution of ceric ammonium molybdate (CAM) followed by heating on a hot plate (~250° C.). Organic solutions were concentrated at 29-30° C. on rotary evaporators capable of achieving a minimum pressure of ~2 torr. The benzenesulfonyl photodeprotection was accomplished by irradiation in a Rayonet RMR-200 photochemical reactor (Southern New England Ultraviolet Company, Branford, Conn., USA) equipped with 16 lamps (RPR-3500, 24 W, $\lambda_{max}$=350 nm, bandwidth ~20 nm).

Materials.

Commercial reagents and solvents were used as received with the following exceptions: dichloromethane, acetonitrile, tetrahydrofuran, methanol, pyridine, toluene, and triethylamine were purchased from J. T. Baker (Cycletainer™) and were purified by the method of Grubbs et al. under positive argon pressure (Pangborn, A. B.; Giardello, M. A.; Grubbs, R. H.; Rosen, R. K.; Timmers, F. J. *Organometallics* 1996, 15, 1518). Nitromethane and nitroethane (from Sigma-Aldrich) were purified by fractional distillation over calcium hydride and were stored over Linde 4 Å molecular sieves in Schlenk flasks sealed with septa and teflon tape under argon atmosphere (Armarego, W. L. F.; Chai, C. L. L. *Purification of Laboratory Chemicals*, 5$^{th}$ ed.; Butterworth-Heinemann: London, 2003). Titanium (IV) ethoxide (99.99%-Ti) PURATREM and bromine were purchased from Strem Chemicals, Inc.; N-Boc-L-sarcosine, 1-ethyl-3-(3-dimethylaminopropyl) carbodiimide hydrochloride, N-hydroxybenzotriazole, tert-butyldimethylsilyl trifluoromethanesulfonate, trifluoroacetic acid, 4-(dimethylamino)pyridine, silver nitrate were purchased from Chem-Impex; 1,4-dimethoxynaphthalene and iodomethane were purchased from Alfa Aesar; di-tert-butyl dicarbonate was purchased from Oakwood Products, Inc.; 2,6-di-tert-butyl-4-methylpyridine (DTBMP) was purchased from OChem. Incorporation. All other solvents and chemicals were purchased from Sigma-Aldrich. 1,4-Dimethoxynaphthalene was purified by crystallization from absolute ethanol.

Instrumentation.

Proton nuclear magnetic resonance ($^1$H NMR) spectra were recorded with a Bruker AVANCE-600 NMR spectrometer (with a Magnex Scientific superconducting actively-shielded magnet) or with a Varian inverse probe 500 INOVA spectrometer, are reported in parts per million on the δ scale, and are referenced from the residual protium in the NMR solvent ($CDCl_3$: δ 7.26 ($CHCl_3$) or DMSO-$d_6$: δ 2.50 (DMSO-$d_5$)) (Fulmer, G. R.; Miller, A. J. M.; Sherden, N. H.; Gottlieb, H. E.; Nudelman, A.; Stoltz, B. M.; Bercaw, J. E.; Goldberg, K. I. *Organometallics* 2010, 29, 2176). Data are reported as follows: chemical shift [multiplicity (br=broad, s=singlet, d=doublet, t=triplet, sp=septet, m=multiplet), coupling constant(s) in Hertz, integration, assignment]. Carbon-13 nuclear magnetic resonance ($^{13}$C NMR) spectra were recorded with a Bruker AVANCE-600 NMR Spectrometer (with a Magnex Scientific superconducting actively-shielded magnet) or a Bruker AVANCE-400 NMR Spectrometer (with a Magnex Scientific superconducting magnet) or with a Varian 500 INOVA spectrometer, are reported in parts per million on the δ scale, and are referenced from the carbon resonances of the solvent ($CDCl_3$: δ 77.23 or DMSO-$d_6$: δ 39.52). Data are reported as follows: chemical shift (multiplicity, coupling constant(s) in Hertz, assignment). Infrared data (IR) were obtained with a Perkin-Elmer 2000 FTIR and are reported as follows: frequency of absorption ($cm^{-1}$), intensity of absorption (s=strong, m=medium, w=weak, br=broad). Optical rotations were measured on a Jasco-1010 polarimeter with a sodium lamp and are reported as follows: $[\alpha]_\lambda^{T° C.}$ (c=g/100 mL, solvent). We are grateful to Dr. Li Li and Deborah Bass for obtaining the mass spectrometric data at the Department of Chemistry's Instrumentation Facility, Massachusetts Institute of Technology. High resolution mass spectra (HRMS) were recorded on a Bruker Daltonics APEXIV 4.7 Tesla FT-ICR-MS using an electrospray (ESI) ionization source.

Positional Numbering System.

At least three numbering systems for dimeric diketopiperazine alkaloids exist in the literature ((a) Von Hauser, D.; Weber, H. P.; Sigg, H. P. *Helv. Chim. Acta* 1970, 53, 1061. (b) Barrow, C. J.; Cai, P.; Snyder, J. K.; Sedlock, D. M.; Sun, H. H.; Cooper, R. *J. Org. Chem.* 1993, 58, 6016. (c) Springer, J. P.; Büchi, G.; Kobbe, B.; Demain, A. L.; Clardy, J. *Tetrahedron Lett.* 1977, 28, 2403. (d) Zheng, C.-J.; Kim, C.-J.; Bae, K. S.; Kim, Y.-H.; Kim, W.-G *J. Nat. Prod.* 2006, 69, 1816. (e) DeLorbe, J. E.; Jabri, S. Y.; Mennen, S. M.; Overman, L. E.; Zhang, F.-L. *J. Am. Chem. Soc.* 2011, 133, 6549). In assigning the $^1$H and $^{13}$C NMR data of all intermediates en route to our total syntheses of (+)-bionectins A (E2-1) and C (E2-2), we wished to employ a uniform numbering scheme. For ease of direct comparison, particularly between early intermediates, non-thiolated diketopiperazines, and advanced compounds, the numbering system used by Barrow for (+)-WIN-64821

(using positional numbers 1-21) is optimal and used throughout this report. In key instances, the products are accompanied by the numbering system as shown below.

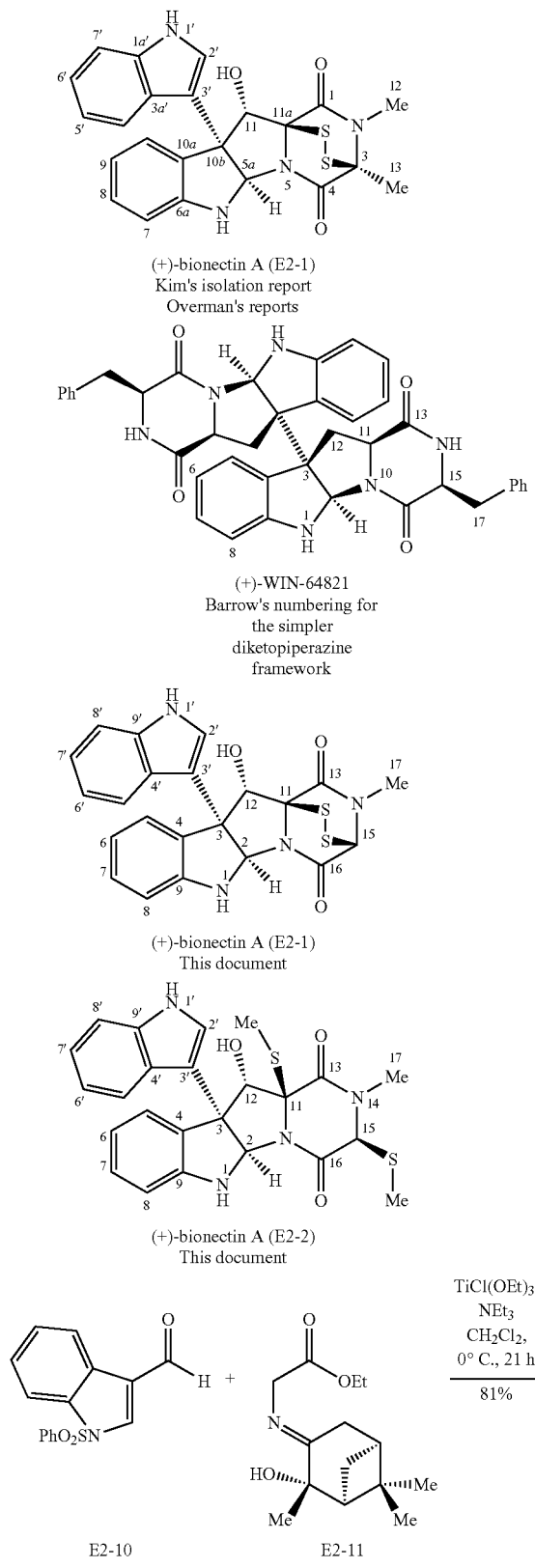

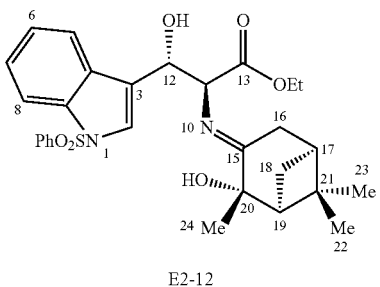

12-HydroxytrvytoDhan Alcohol E2-12

A solution of chlorotitanium (IV) triethoxide (22.5 g, 103 mmol, 1.05 equiv, Holoway, H. *Chem. Ind.* 1962, 3, 214) in dichloromethane (69 mL) was added via cannula to a solution of ethyl 2-((S,2S,5S)-2-hydroxypinan-3-imino)glybioncin C (E2-11, 24.8 g, 97.8 mmol, 1 equiv, (a) Oguri, T.; Kaway, N.; Yamada, S. *Chem. Pharm. Bull.* 1978, 26, 803. (b) Solladiè-Cavallo, A.; Simon, M. C. *Tetrahedron Lett.* 1989, 30, 6011. (c) Solladiè-Cavallo, A.; Simon-Wermeister, M. C.; Schwarz, J. *Organometallics* 1993, 12, 3743) in dichloromethane (300 mL) at 0° C. A fine powder of 1-(phenylsulfonyl)-1H-indole-3-carbaldehyde (E2-10, 29.3 g, 103 mmol, 1.05 equiv, Wenkert, E.; Moeller, P. D. R.; Piettre, S. R. *J. Am. Chem. Soc.* 1988, 110, 7188) was then added as a solid to the reaction mixture. Triethylamine (27.3 mL, 196 mmol, 2.00 equiv) was subsequently added dropwise via syringe and the reaction mixture was stirred at 0° C. After 21 h, brine (1 L) at 0° C. was added to the reaction mixture and the resulting bilayer suspension was filtered through Celite. The organic layer was separated, and the aqueous layer was extracted with dichloromethane (2×300 mL). The combined organic layers were dried over anhydrous sodium sulfate, were filtered, and were concentrated under reduced pressure. The resulting orange foam was purified by flash column chromatography on silica gel (eluent: gradient, 30→50% ethyl acetate in hexanes) to provide an inseparable mixture of diastereomeric aldol products (42.5 g, 80.6%) as a yellow foam. In some embodiments, the aldol products were highly prone to degradation through a retro-aldol pathway; thus, the mixture of diastereomers was quickly isolated and immediately used in the subsequent reaction. Structural assignments were made using additional information from gCOSY, HSQC, and gHMBC experiments.

$^1$H NMR (600 MHz, CDCl$_3$, 20° C.; only the peaks corresponding to the major diastereomer are tabulated): δ 7.96 (d, J=8.3, 1H, C$_8$H), 7.86 (d, J=8.6, 2H, SO$_2$Ph-o-H), 7.71 (s, 1H, C$_2$H), 7.67 (d, J=7.8, 1H, C$_8$H), 7.49 (t, J=7.6, 1H, SO$_2$Ph-p-H), 7.39 (app-t, J=8.1, 2H, SO$_2$Ph-m-H), 7.29 (app-t, J=7.3, 1H, C$_7$H), 7.23 (app-t, J=7.2, 1H, C$_6$H), 5.49 (d, J=6.9, 1H, C$_{12}$H), 4.46 (d, J=6.9, 1H, C$_{11}$H), 4.11-3.99 (m, 2H, CO$_2$CH$_2$CH$_3$), 3.90 (br-s, 1H, C$_{12}$OH), 2.42 (dd, J=2.0, 17.7, 1H, C$_{16}$H$_a$), 2.19 (dd, J=2.7, 18.0, 1H, C$_{16}$H$_b$), 2.11-2.05 (m, 1H, C$_{18}$H$_a$), 2.00 (br-s, 1H, C$_{20}$OH), 1.89 (app-t, J=5.8, 1H, C$_{19}$H), 1.87-1.83 (m, 1H, C$_{17}$H), 1.42 (s, 3H, C$_{24}$H), 1.23 (s, 3H, C$_{22/23}$H), 1.06 (app-t, J=7.4, 3H, CO$_2$CH$_2$CH$_3$), 1.02 (d, J=4.7, 1H, C$_{18}$H$_b$), 0.80 (s, 3H, C$_{22/23}$H). $^{13}$C NMR (150 MHz, CDCl$_3$, 20° C.): δ 180.6 (C$_{15}$), 169.5 (C$_{13}$), 138.0 (SO$_2$Ph-ipso-C), 134.5 (C$_9$), 133.6 (SO$_2$Ph-p-C), 129.9 (C$_4$), 129.2 (SO$_2$Ph-m-C), 126.7 (SO$_2$Ph-o-C), 124.9 (C$_7$), 124.7 (C$_2$), 123.1 (C$_6$), 122.3 (C$_3$), 120.2 (C$_5$), 113.5 (C$_8$), 76.8 (C$_{20}$), 67.7 (C$_{12}$), 67.4 (C$_{11}$), 61.1 (CO$_2$CH$_2$CH$_3$), 50.3 (C$_{19}$), 38.5 (C$_{21}$), 38.2 (C$_{17}$), 33.8 (C$_{16}$), 28.1 (C$_{24}$), 27.8 (C$_{18}$), 27.1

($C_{22/23}$), 22.6 ($C_{22/23}$), 13.7 ($CO_2CH_2CH_3$). FTIR (thin film) $cm^{-1}$: 3422 (br-m), 2926 (s), 1734 (s), 1649 (m), 1557 (w), 1448 (s), 1373 (s), 1273 (m), 1181 (s), 1126 (m), 1089 (m), 1022 (w), 978 (w), 920 (w), 751 (m). HRMS (ESI) (m/z): calc'd for $C_{29}H_{35}N_2O_6S$ $[M+H]^+$: 539.2210. found: 539.2198. TLC (50% ethyl acetate in hexanes), Rf: 0.49 (UV, CAM, $KMnO_4$).

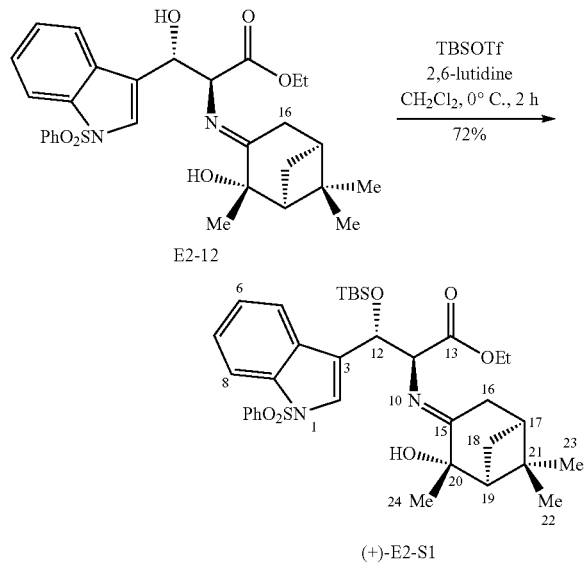

(+)-E2-S1

12-Hydroxytryptophan Silyl Ether (+)-E2-S1 t-Butyldimethylsilyl trifluoromethanesulfonate (21.8 mL, 94.7 mmol, 1.20 equiv) was added via syringe to a solution of 12-hydroxytryptophan alcohol E2-12 (42.5 g, 78.9 mmol, 1 equiv) and 2,6-lutidine (18.7 mL, 161 mmol, 2.04 equiv) in dichloromethane (900 mL) at 0° C. After 2 h, saturated aqueous ammonium chloride solution (750 mL) was added to the reaction mixture and the resulting solution was allowed to warm to 23° C. After 10 min, the layers were separated and the aqueous layer was further extracted with dichloromethane (2×200 mL). The combined organic layers were dried over anhydrous sodium sulfate, were filtered, and were concentrated under reduced pressure. The resulting orange foam was purified by flash column chromatography on silica gel (eluent: 20% ethyl acetate in hexanes) to provide the 12-hydroxytryptophan silyl ether (+)-E2-S1 (37.1 g, 72.0%) as a yellow oil. Structural assignments were made using additional information from gCOSY, HSQC, and gHMBC experiments.

$^1$H NMR (600 MHz, $CDCl_3$, 20° C.): δ 7.97 (d, J=8.3, 1H, $C_8H$), 7.84 (d, J=7.4, 2H, $SO_2$Ph-o-H), 7.77 (d, J=7.8, 1H, $C_5H$), 7.52 (s, 1H, $C_2H$), 7.50 (t, J=7.9, 1H, $SO_2$Ph-p-H), 7.39 (app-t, J=8.2, 2H, $SO_2$Ph-m-H), 7.30 (app-t, J=7.3, 1H, $C_7H$), 7.24 (app-t, J=7.1, 1H, $C_6H$), 5.53 (d, J=8.5, 1H, $C_{12}H$), 4.41 (d, J=8.6, 1H, $C_{11}H$), 4.23-4.14 (m, 2H, $CO_2CH_2CH_3$), 2.42 (app-dt, J=2.5, 18.1, 1H, $C_{16}H_a$), 2.00 (dd, J=2.9, 18.1, 1H, $C_{16}H_b$), 1.93-1.90 (m, 1H, $C_{18}H_a$), 1.80 (app-t, J=5.8, 1H, $C_{19}H$), 1.75-1.71 (m, 1H, $C_{17}H$), 1.42 (br-s, 1H, $C_{20}OH$), 1.31 (s, 3H, $C_{24}H$), 1.06 (app-t, J=7.2, 3H, $CO_2CH_2CH_3$), 1.18 (s, 3H, $C_{22/23}H$), 0.82 (s, 9H, $Si(CH_3)_2C(CH_3)_3$), 0.70 (d, J=5.2, 1H, $C_{18}H_b$), 0.69 (s, 3H, $C_{22/23}H$), 0.03 (s, 3H, $Si(CH_3)_2C(CH_3)_3$), −0.30 (s, 3H, $Si(CH_3)_2C(CH_3)_3$). $^{13}$C NMR (150 MHz, $CDCl_3$, 20° C.): δ 180.2 ($C_{15}$), 170.0 ($C_{13}$), 138.3 ($SO_2$Ph-ipso-C), 135.2 ($C_9$), 133.9 ($SO_2$Ph-p-C), 129.5 ($C_4$), 129.4 ($SO_2$Ph-m-C), 126.8 ($SO_2$Ph-o-C), 125.2 ($C_7$), 124.6 ($C_3$), 124.0 ($C_2$), 123.3 ($C_6$), 121.0 ($C_5$), 114.1 ($C_8$), 76.4 ($C_{20}$), 70.7 ($C_{11}$), 70.0 ($C_{12}$), 61.1 ($CO_2CH_2CH_3$), 49.8 (C19), 38.4 ($C_{21}$), 38.1 ($C_{17}$), 33.4 ($C_{16}$), 28.3 ($C_{24}$), 27.8 ($C_{81}$), 27.3 ($C_{22/23}$), 25.7 ($Si(CH_3)_2C(CH_3)_3$), 22.8 ($C_{22/23}$), 18.1 ($Si(CH_3)_2C(CH_3)_3$), 14.4 ($CO_2CH_2CH_3$), −4.6 ($Si(CH_3)_2C(CH_3)_3$), −5.3 ($Si(CH_3)_2C(CH_3)_3$). FTIR (thin film) $cm^{-1}$: 2929 (s), 1735 (s), 1652 (m), 1559 (w), 1494 (w), 1448 (s), 1372 (s), 1259 (m), 1179 (s), 1088 (s), 977 (w), 837 (m), 780 (m), 750 (m), 686 (m). HRMS (ESI) (m/z): calc'd for $C_{35}H_{49}N_2O_6SSi$ $[M+H]^+$: 653.3075. found: 653.3063. $[α]_D^{24}$: +3.1 (c=0.30, $CHCl_3$). TLC (33% ethyl acetate in hexanes), Rf: 0.42 (UV, CAM).

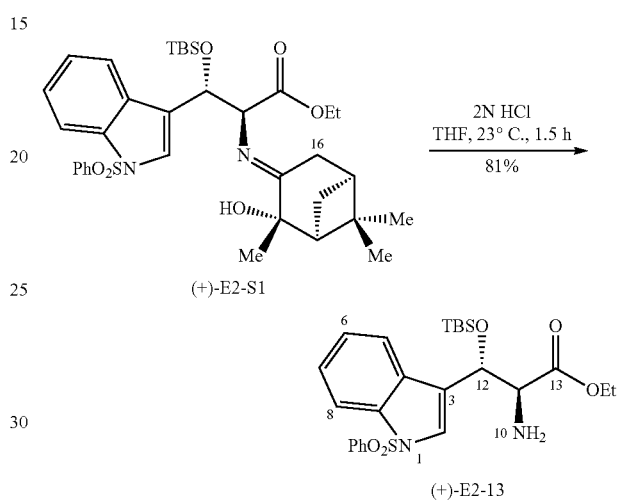

(+)-E2-13

12-Hydroxytroxytryptophan Amine (+)-E2-13

Aqueous hydrogen chloride solution (2 N, 520 mL) was added to a solution of 12-hydroxytryptophan silyl ether (+)-E2-S1 (37.1 g, 56.8 mmol, 1 equiv) in tetrahydrofuran (520 mL) at 23° C. After 1.5 h, the mixture was concentrated to remove the organic solvent. The resulting mixture was extracted with ethyl acetate (3×500 mL). The combined organic layers were dried over anhydrous sodium sulfate, were filtered, and were concentrated under reduced pressure. The resulting orange foam was purified by flash column chromatography on silica gel (eluent: gradient, 20→30→100% ethyl acetate in hexanes) to provide 12-hydroxytryptophan amine (+)-E2-13 (23.0 g, 80.5%) as a yellow foam. Structural assignments were made using additional information from gCOSY, HSQC, and gHMBC experiments. $^1$H NMR (600 MHz, $CDCl_3$, 20° C.): δ 8.00 (d, J=8.3, 1H, $C_8H$), 7.83 (d, J=7.4, 2H, $SO_2$Ph-o-H), 7.64 (d, J=7.9, 1H, $C_5H$), 7.52 (t, J=7.4, 1H, $SO_2$Ph-p-H), 7.49 (s, 1H, $C_2H$), 7.41 (app-t, J=8.2, 2H, $SO_2$Ph-m-H), 7.32 (app-t, J=7.4, 1H, $C_7H$), 7.22 (app-t, J=7.3, 1H, $C_6H$), 5.01 (d, J=6.5, 1H, $C_{12}H$), 4.10-3.98 (m, 2H, $CO_2CH_2CH_3$), 3.78 (d, J=6.5, 1H, $C_{11}H$), 1.13 (app-t, J=7.1, 3H, $CO_2CH_2CH_3$), 0.80 (s, 9H, $Si(CH_3)_2C(CH_3)_3$), 0.00 (s, 3H, $Si(CH_3)_2C(CH_3)_3$), −0.33 (s, 3H, $Si(CH_3)_2C(CH_3)_3$). $^{13}$C NMR (150 MHz, $CDCl_3$, 20° C.): δ 172.9 ($C_{13}$), 138.1 ($SO_2$Ph-ipso-C), 135.2 ($C_9$), 134.0 ($SO_2$Ph-p-C), 129.4 ($SO_2$Ph-m-C), 129.0 ($C_4$), 126.8 ($SO_2$Ph-o-C), 125.2 ($C_7$), 124.6 ($C_2$), 123.5 ($C_6$), 122.9 ($C_3$), 121.1 ($C_5$), 114.0 ($C_8$), 72.0 ($C_{12}$), 61.1 ($CO_2CH_2CH_3$), 60.8 ($C_{11}$), 25.7 ($Si(CH_3)_2C(CH_3)_3$), 18.2 ($Si(CH_3)_2C(CH_3)_3$), 14.1 ($CO_2CH_2CH_3$), −4.8 ($Si(CH_3)_2C(CH_3)_3$), −5.3 ($Si(CH_3)_2C(CH_3)_3$). FTIR (thin film) $cm^{-1}$: 2931 (s), 2858 (s), 1735 (s), 1560 (w), 1448 (m), 1372 (s), 1258 (m), 1180 (s), 1088 (m), 1023 (w), 976 (w), 838 (s), 751 (s), 686 (m). HRMS (ESI) (m/z): calc'd for $C_{25}H_{35}N_2O_5SSi$ [M+H]+: 503.2030. found: 503.2016. $[\alpha]_D^{24}$: +31 (C=0.45, CHCl$_3$). TLC (50% ethyl acetate in hexanes), Rf: 0.47 (UV, CAM, KMnO$_4$).

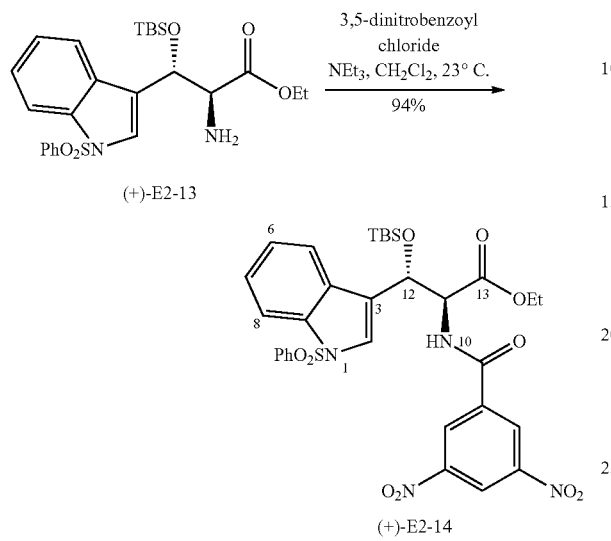

12-Hydroxytryptophan 3,5-Dinitrobenzamide
(+)-E2-14

Triethylamine (83.1 µL, 596 µmol, 2.00 equiv) was added to a solution of 12-hydroxytryptophan amine (+)-E2-13 (100 mg, 198 µmol, 1 equiv) and 3,5-dinitrobenzoyl chloride (68.7 mg, 298 µmol, 1.50 mmol) in dichloromethane (10 mL) at 23° C. After 1 h, saturated aqueous ammonium chloride solution was added (5 mL) to the reaction mixture. After 5 min, the layers were separated, and the aqueous layer was further extracted with ethyl acetate (2×5 mL). The combined organic layers were dried over anhydrous sodium sulfate, were filtered, and were concentrated under reduced pressure. The resulting orange foam was purified by flash column chromatography on silica gel (eluent: gradient, 20-40% ethyl acetate in hexanes) to provide 12-hydroxytryptophan 3,5-dinitrobenzamide (+)-E2-14 (129 mg, 93.9%) as a yellow solid. Structural assignments were made using additional information from gCOSY, HSQC, and gHMBC experiments. $^1$H NMR (600 MHz, CDCl$_3$, 20° C.): δ 9.20 (s, 1H, Bz-p-H), 8.95 (s, 2H, Bz-o-H), 8.05 (d, J=8.1, 1H, C$_8$H), 7.98 (d, J=7.6, 1H, C$_5$H), 7.86 (d, J=7.7, 2H, SO$_2$Ph-o-H), 7.54 (t, J=7.2, 1H, SO$_2$Ph-p-H), 7.47 (s, 1H, C$_2$H), 7.43 (app-t, J=7.5, 2H, SO$_2$Ph-m-H), 7.39 (app-t, J=7.7, 1H, C$_7$H), 7.35 (app-t, J=7.2, 1H, C$_6$H), 7.31 (d, J=6.5, 1H, N$_{10}$H), 5.48 (app-s, 1H, C$_{12}$H), 5.10 (d, J=5.0, 1H, C$_{11}$H), 4.16 (m, 1H, COCH$_{2a}$CH$_3$), 4.06 (m, 1H, CO$_2$CH$_{2b}$CH$_3$), 1.14 (app-t, J=7.0, 3H, CO$_2$CH$_2$CH$_3$), 0.93 (s, 9H, Si(CH$_3$)$_2$C(CH$_3$)$_3$), 0.00 (s, 3H, Si(CH$_3$)$_2$C(CH$_3$)$_3$), −0.15 (s, 3H, Si(CH$_3$)$_2$C(CH$_3$)$_3$). $^{13}$C NMR (150 MHz, CDCl$_3$, 20° C.): δ 168.8 (C$_{13}$), 162.4 (C=O$_{Bz}$), 148.9 (Bz-m-C), 138.2 (SO$_2$Ph-ipso-C), 137.2 (Bz-ipso-C), 135.5 (C$_9$), 134.1 (SO$_2$Ph-p-C), 129.4 (SO$_2$Ph-m-C), 128.6 (C$_4$), 127.3 (Bz-o-C), 126.8 (SO$_2$Ph-o-C), 125.4 (C$_7$), 124.2 (C$_2$), 123.9 (C$_6$), 122.7 (C$_3$), 121.7 (Bz-p-C), 120.5 (C$_5$), 114.0 (C$_8$), 70.1 (C$_{12}$), 62.3 (CO$_2$CH$_2$CH$_3$), 59.3 (C$_{11}$), 25.7 (Si(CH$_3$)$_2$C(CH$_3$)$_3$), 18.3 (Si(CH$_3$)$_2$C(CH$_3$)$_3$), 14.2 (CO$_2$CH$_2$CH$_3$), −4.6 (Si(CH$_3$)$_2$C(CH$_3$)$_3$), −5.1 (Si(CH$_3$)$_2$C(CH$_3$)$_3$). FTIR (thin film) cm$^{-1}$: 3394 (br), 2932 (w), 2362 (m), 1736 (m), 1674 (m), 1545 (s), 1448 (m), 1345 (s), 1253 (m), 1180 (s), 1119 (m), 1093 (m), 977 (w), 920 (w), 838 (m), 726 (m). HRMS (ESI) (m/z): calc'd for $C_{32}H_{40}N_5O_{10}SSi$ [M+NH$_4$]$^+$: 714.2260. found: 714.2251. $[\alpha]_D^{24}$: +20 (c=0.37, CHCl$_3$). TLC (20% ethyl acetate in hexanes), Rf: 0.21 (UV, CAM).

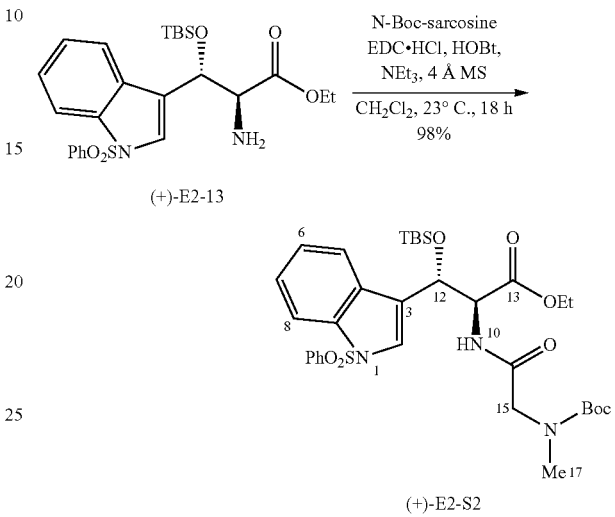

Dipeptide (+)-E2-S2

A round-bottom flask was charged sequentially with 12-hydroxytryptophan amine (+)-E2-13 (7.05 g, 14.0 mmol, 1 equiv), N-Boc-sarcosine (3.45 g, 18.2 mmol, 1.30 equiv), N-hydroxybenzotriazole (2.84 g, 21.0 mmol, 1.50 equiv), 1-ethyl-3-(3-dimethylaminopropyl) carbodiimide hydrogen chloride (5.37 g, 28.0 mmol, 2.00 equiv), and powdered 4 Å molecular sieves (4.00 g), and the contents were placed under an atmosphere of argon. Dichloromethane (100 mL) was introduced via cannula and the resulting solution was cooled to 0° C. Triethylamine (5.86 mL, 42.0 mmol, 3.00 equiv) was subsequently added dropwise via syringe and the reaction mixture was allowed to warm slowly to 23° C. After 18 h, saturated aqueous sodium bicarbonate solution (200 mL) was added, and the aqueous layer was extracted with ethyl acetate (3×250 mL). The combined organic layers were dried over anhydrous sodium sulfate, were filtered, and were concentrated under reduced pressure. The resulting orange foam was purified by flash column chromatography on silica gel (eluent: 50% ethyl acetate in hexanes) to provide dipeptide (+)-E2-S2 (9.05 g, 98%) as a yellow foam. Structural assignments were made using additional information from gCOSY, HSQC, and gHMBC experiments. $^1$H NMR (500 MHz, DMSO-d$_6$, 60° C.): δ 7.97 (d, J=7.7, 1H, N$_{10}$H), 7.89 (d, J=8.3, 1H, C$_8$H), 7.87 (d, J=7.7, 2H, SO$_2$Ph-o-H), 7.76 (d, J=7.7, 1H, C$_5$H), 7.67 (t, J=7.3, 1H, SO$_2$Ph-p-H), 7.64 (s, 1H, C$_2$H), 7.55 (app-t, J=7.7, 2H, SO$_2$Ph-m-H), 7.33 (app-t, J=7.7, 1H, C$_7$H), 7.26 (app-t, J=7.7, 1H, C$_6$H), 5.16 (d, J=7.7, 1H, C$_{12}$H), 4.75 (app-t, J=7.8, 1H, C$_{11}$H), 4.08 (q, J=7.1, 2H, CO$_2$CH$_2$CH$_3$), 3.85-3.65 (m, 1H, C$_{15}$H$_a$), 3.44 (d, J=17.0, 1H, C$_{15}$H$_b$), 3.14 (s, 3H, C$_{17}$H), 1.24 (br-s, 9H, CO$_2$C(CH$_3$)$_3$), 1.17 (t, J=7.1, 3H, CO$_2$CH$_2$CH$_3$), 0.74 (s, 9H, Si(CH$_3$)$_2$C(CH$_3$)$_3$), −0.04 (s, 3H, Si(CH$_3$)$_2$C(CH$_3$)$_3$), −0.39 (s, 3H, Si(CH$_3$)$_2$C(CH$_3$)$_3$). $^{13}$C NMR (125.8 MHz, DMSO-d$_6$, 60° C.): δ 171.0 (C$_{13}$), 169.4 (C$_{16}$), 156.2 (CO$_2$C(CH$_3$)$_3$), 138.5 (SO$_2$Ph-ipso-C), 136.1 (C$_9$), 135.6 (SO$_2$Ph-p-C), 130.9 (SO$_2$Ph-m-C), 129.6 (C$_4$), 127.6 (SO$_2$Ph-o-C), 126.1 (C$_7$), 126.1 (C$_2$), 124.5 (C$_6$), 123.6 (C$_3$), 122.1 (C$_5$), 114.4 (C$_8$), 80.3 (CO$_2$C(CH$_3$)$_3$), 70.2 (C$_{12}$), 61.8 (CO$_2$CH$_2$CH$_3$), 58.6 (C$_{11}$), 52.1 (C$_{15}$), 35.9 (C$_{17}$), 29.1 (CO$_2$C(CH$_3$)$_3$), 26.5 (Si(CH$_3$)$_2$C(CH$_3$)$_3$), 18.8 (Si(CH$_3$)$_2$C(CH$_3$)$_3$), 15.0 (CO$_2$CH$_2$CH$_3$), −4.1 (Si(CH$_3$)$_2$C(CH$_3$)$_3$), −4.4 (Si(CH$_3$)$_2$C(CH$_3$)$_3$). FTIR (thin film) cm$^{-1}$: 3414 (br-m), 2933 (s), 2859 (m), 1739 (m), 1699 (s), 1510 (m), 1450 (m), 1374 (s), 1252 (m), 1179 (s), 1120 (m), 1024 (w), 975 (w), 840 (w), 753 (w), 685 (w). HRMS (ESI) (m/z): calc'd for C$_{33}$H$_{45}$N$_3$O$_5$SSi [M+H]$^+$: 674.2926. found: 674.2926. [α]$_D^{24}$: +69 (c=0.24, CHCl$_3$). TLC (50% ethyl acetate in hexanes), Rf: 0.45 (UV, CAM).

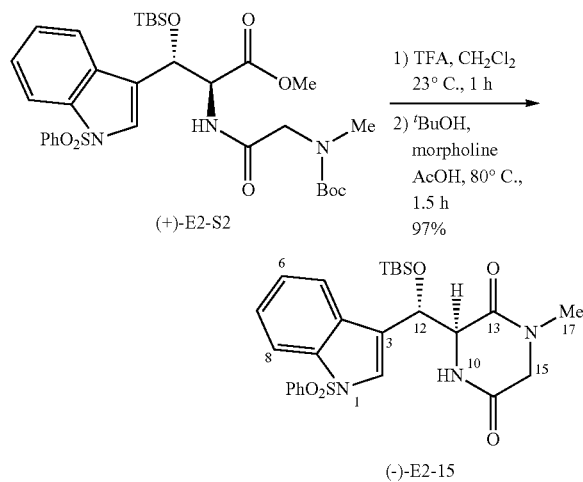

(+)-E2-S2

1) TFA, CH$_2$Cl$_2$
23° C., 1 h

2) $^t$BuOH, morpholine
AcOH, 80° C., 1.5 h
97%

(−)-E2-15

Diketopiperazine (−)-E2-15

Trifluoroacetic acid (27 mL) was introduced dropwise to a solution of dipeptide (+)-E2-S2 (14.6 g, 21.7 mmol, 1 equiv) in dichloromethane (140 mL) at 23° C. After 1 h, the reaction mixture was concentrated to dryness under reduced pressure. The crude residue was dissolved in tert-butanol (210 mL). Acetic acid (32 mL) and morpholine (32 mL) were successively added to the solution, and the resulting reaction mixture was warmed to 80° C. After 1.5 h, the reaction mixture was concentrated under reduced pressure and the solids were removed by vacuum filtration over a sintered funnel. The solids were extracted with ethyl acetate and the combined organic filtrates were concentrated under reduced pressure. The resulting orange oil was purified by flash column chromatography on silica gel (eluent: gradient, 50→100% ethyl acetate in hexanes) to provide diketopiperazine (−)-E2-15 (11.1 g, 97.0%) as a yellow foam. Structural assignments were made using additional information from gCOSY, HSQC, and gHMBC experiments. $^1$H NMR (600 MHz, CDCl$_3$, 20° C.): δ 7.97 (d, J=8.4, 1H, C$_8$H), 7.89 (d, J=7.8, 2H, SO$_2$Ph-o-H), 7.55 (s, 1H, C$_2$H), 7.54 (t, J=7.4, 1H, SO$_2$Ph-p-H), 7.51 (d, J=7.9, 1H, C$_5$H), 7.47 (app-t, J=7.7, 2H, SO$_2$Ph-m-H), 7.31 (app-t, J=7.6, 1H, C$_7$H), 7.22 (app-t, J=7.8, 1H, C$_6$H), 6.39 (br-s, 1H, NH), 5.51 (d, J=3.4, 1H, C$_{12}$H), 4.31 (app-s, 1H, C$_{11}$H), 3.19 (d, J=17.6, 1H, C$_{15}$H$_a$), 2.32 (s, 3H, C$_{14}$H), 2.17 (d, J=17.6, 1H, C$_{15}$H$_b$), 0.89 (s, 9H, Si(CH$_3$)$_2$C(CH$_3$)$_3$), 0.06 (s, 3H, Si(CH$_3$)$_2$C(CH$_3$)$_3$), −0.07 (s, 3H, Si(CH$_3$)$_2$C(CH$_3$)$_3$). $^{13}$C NMR (150 MHz, CDCl$_3$, 20° C.): δ 164.9 (C$_{13}$), 162.6 (C$_{16}$), 138.0 (SO$_2$Ph-ipso-C), 134.7 (C$_9$), 134.1 (SO$_2$Ph-p-C), 129.6 (SO$_2$Ph-m-C), 127.9 (C$_4$), 127.1 (SO$_2$Ph-o-C), 126.0 (C$_2$), 125.4 (C$_7$), 123.6 (C$_6$), 120.6 (C$_3$), 120.5 (C$_5$), 113.6 (C$_8$), 70.4 (C$_{12}$), 61.7 (C$_{11}$), 50.5 (C$_{15}$), 33.3 (C$_{17}$), 25.9 (Si(CH$_3$)$_2$C(CH$_3$)$_3$), 18.3 (Si(CH$_3$)$_2$C(CH$_3$)$_3$), −4.7 (Si(CH$_3$)$_2$C(CH$_3$)$_3$), −5.1 (Si(CH$_3$)$_2$C(CH$_3$)$_3$). FTIR (thin film) cm$^{-1}$: 3251 (br m), 2932 (m), 1676 (s), 1448 (m), 1371 (m), 1179 (s), 1122 (m), 979 (w), 838 (w), 751 (w), 686 (w). HRMS (ESI) (m/z): calc'd for C$_2$H$_{34}$N$_3$O$_5$SSi [M+H]$^+$: 528.1983. found: 528.1982. [α]$_D^{24}$: −21 (c=0.17, CHCl$_3$). TLC (50% ethyl acetate in hexanes), Rf: 0.32 (UV, CAM).

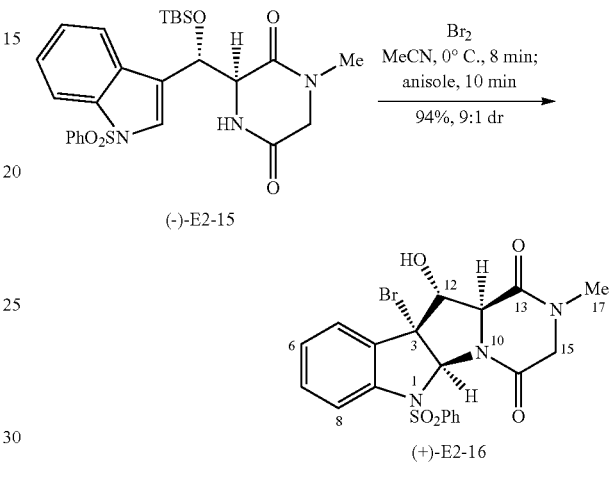

(−)-E2-15

Br$_2$
MeCN, 0° C., 8 min;
anisole, 10 min
94%, 9:1 dr (+)-E2-16

Tetracyclic Bromide (+)-E2-16

A solution of bromine (2 M, 61.0 mL, 122 mmol, 4.00 equiv) in acetonitrile that was pre-cooled to 0° C. was poured in one portion into a solution of diketopiperazine (−)-E2-15 (16.1 g, 30.5 mmol, 1 equiv) in acetonitrile (268 mL) at 0° C. The reaction progress was monitored by TLC analysis in 2 min interval. After 8 min, upon complete consumption of starting material, anisole (19.9 mL, 183 mmol, 6.00 equiv) that was pre-cooled to 0° C. was poured in one portion into the reaction mixture. After 10 min, a mixture of saturated aqueous sodium thiosulfate solution and saturated aqueous sodium bicarbonate solution (1:1, 500 mL) was added to the red solution. The reaction mixture was extracted with ethyl acetate (3×100 mL). The combined organic layers were dried over anhydrous sodium sulfate, were filtered, and were concentrated under reduced pressure. The resulting residue was purified by flash column chromatography on silica gel (eluent: gradient, 20→50% acetone in dichloromethane) to afford a mixture of the endo-tetracyclic bromide (+)-E2-16 and its minor exo-diastereomer (14.2 g, 94.5%, 8.7:1 dr) as a white foam. The mixture of diastereomers can be separated easily on smaller scales using the same purification conditions reported here. On decagram scales, in some embodiments, it could be more practical to carry the diastereomeric mixture to next step. Structural assignments were made with additional information using gCOSY, HSQC, gHMBC, and NOESY experiments. $^1$H NMR (600 MHz, CDCl$_3$, 20° C.): δ 7.98 (d, J=8.0, 2H, SO$_2$Ph-o-H), 7.54 (d, J=8.3, 1H, C$_8$H), 7.52 (t, J=7.6, 1H, SO$_2$Ph-p-H), 7.42 (app-t, J=7.8, 2H, SO$_2$Ph-m-H), 7.33 (d, J=7.6, 1H, C$_5$H), 7.28 (app-t, J=7.9, 1H, C$_7$H), 7.11 (app-t, J=7.6, 1H, C$_6$H), 6.25 (s, 1H, C$_2$H), 4.62 (d, J=5.9, 1H, C$_{12}$H), 4.23 (d, J=5.8, 1H, C$_{11}$H), 4.16 (d, J=17.6, 1H, C$_{15}$H), 3.91 (br-s, 1H, OH), 3.84 (d, J=17.5, 1H, C$_{15}$H$_b$), 2.88 (s, 3H, $C_{17}H$). $^{13}C$ NMR (150 MHz, $CDCl_3$, 20° C.): δ 165.8 ($C_{13}$), 164.9 ($C_{16}$), 139.2 ($C_9$), 137.4 ($SO_2Ph$-ipso-C), 134.0 ($SO_2Ph$-p-C), 131.8 ($C_4$), 131.2 ($C_7$), 129.1 ($SO_2Ph$-m-C), 128.4 ($SO_2Ph$-o-C), 125.9 ($C_6$), 125.3 ($C_5$), 116.8 ($C_8$), 85.1 ($C_2$), 74.2 ($C_{12}$), 68.0 ($C_3$), 63.4 ($C_{11}$), 54.0 ($C_{15}$), 33.5 ($C_{17'}$). FTIR (thin film) $cm^{-1}$: 3367 (br s), 2958 (s), 1677 (s), 1458 (m), 1399 (m), 1364 (m), 1170 (m), 1089 (w), 729 (w), 688 (w). HRMS (ESI) (m/z): calc'd for $C_{20}H_{19}BrN_3O_5S$ $[M+H]^+$: 492.0223. found: 492.0222. $[α]_D^{24}$: +56 (c=0.30, $CHCl_3$). TLC (33% acetone in dichloromethane), Rf: 0.35 (UV, CAM).

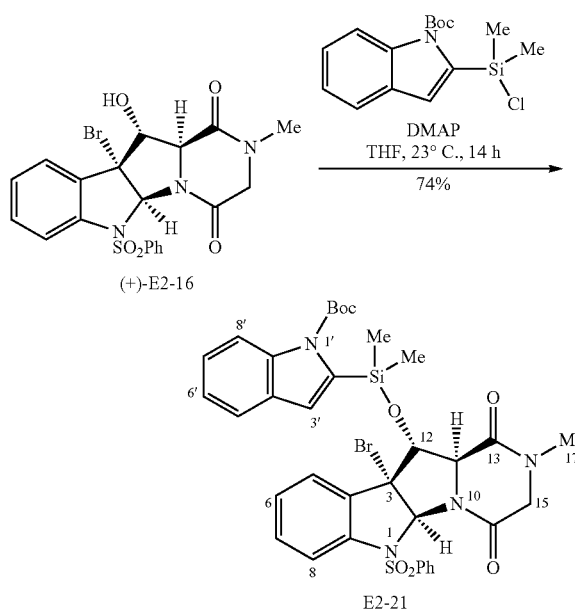

(+)-E2-16

Indole-Tethered Tetracycle E2-21

A solution of n-butyllithium (1.57 M, 18.3 mL, 28.7 mmol, 1.61 equiv) in hexanes was added dropwise to a solution of freshly distilled diisopropylamine (4.02 mL, 28.7 mmol, 1.61 equiv) in tetrahydrofuran (4.28 mL) at −78° C. After 5 min, the solution was allowed to warm to 0° C. After 35 min, the solution of lithium diisopropylamide was transferred via cannula to a solution of N-Boc-indole (6.24 g, 28.7 mmol, 1.61 equiv) and dimethyldichlorosilane (3.25 mL, 26.8 mmol, 1.50 equiv) in tetrahydrofuran (47.3 mL) at 0° C. After 8 h, the reaction mixture was transferred via cannula to a solution of tetracyclic bromide (+)-E2-16 (8.78 g, 17.83 mmol, 1 equiv) and 4-dimethylaminopyridine (4.68 g, 38.28 mmol, 2.15 equiv) in tetrahydrofuran (63.3 mL) at 23° C. After 14 h, the reaction mixture was diluted with ethyl acetate (300 mL) and washed with saturated aqueous sodium bicarbonate solution (500 mL). The aqueous layer was further extracted with ethyl acetate (2×200 mL). The combined organic layers were dried over anhydrous sodium sulfate, were filtered, and were concentrated under reduced pressure. The resulting orange foam was purified by flash column chromatography on silica gel (eluent: gradient, 33→50% ethyl acetate in hexanes) to provide the indole-tethered tetracycle E2-21 (10.1 g, 74.3%) as a white foam. Structural assignments were made using additional information from gCOSY, HSQC, and gHMBC experiments. $^1H$ NMR (600 MHz, $CDCl_3$, 20° C.): δ 8.03 (d, J=7.6, 2H, $SO_2Ph$-o-H), 7.96 (d, J=8.3, 1H, $C_8H$), 7.63 (d, J=7.7, 1H, $C_5H$), 7.57 (d, J=8.1, 1H, $C_8H$), 7.53 (t, J=7.4, 1H, $SO_2Ph$-p-H), 7.44 (app-t, J=7.9, 2H, $SO_2Ph$-m-H), 7.31 (app-t, J=7.4, 1H, $C_7H$), 7.27 (app-t, J=7.9, 1H, $C_7H$), 7.26-7.21 (m, 1H, $C_5H$), 7.26-7.21 (m, 1H, $C_6H$), 7.26-7.21 (m, 1H, $C_3H$), 7.00 (app-t, J=7.5, 1H, $C_6H$), 6.33 (s, 1H, $C_2H$), 5.13 (d, J=3.7, 1H, $C_{12}H$), 4.30 (d, J=3.6, 1H, $C_1H$), 4.11 (d, J=17.2, 1H, $C_{15}H_a$), 3.79 (d, J=17.2, 1H, $C_{15}H_b$), 2.82 (s, 3H, $C_{17}H$), 1.69 (s, 9H, $CO_2C(CH_3)_3$), 0.54 (s, 3H, $Si(CH_3)_2$), 0.50 (s, 3H, $Si(CH_3)_2$). $^{13}C$ NMR (150 MHz, $CDCl_3$, 20° C.): δ 165.5 ($C_{13}$), 165.2 ($C_{16}$), 151.7 (C=$O_{carbamate}$), 139.1 ($C_{2'}$), 138.9 ($C_9$), 137.8 ($SO_2Ph$-ipso-C), 137.3 ($C_{9'}$—), 133.8 ($SO_2Ph$-p-C), 131.4 ($C_{4'}$), 131.3 ($C_4$), 131.0 ($C_7$), 129.0 ($SO_2Ph$-m-C), 128.4 ($SO_2Ph$-o-C), 125.6 ($C_6$), 125.4 ($C_5$), 124.9 ($C_{7'}$), 122.7 ($C_{6'}$), 121.5 ($C_{5'}$), 121.1 ($C_{3'}$), 116.5 ($C_8$), 115.4 ($C_{8'}$), 85.5 ($C_2$), 84.6 ($CO_2C(CH_3)_3$), 74.6 ($C_{12}$), 69.6 ($C_3$), 66.5 ($C_{11}$), 54.3 ($C_{15}$), 33.6 ($C_{17}$), 28.3 ($CO_2C(CH_3)_3$), 0.5 ($Si(CH_3)_2$), −0.4 ($Si(CH_3)_2$). FTIR (thin film) $cm^{-1}$: 2957 (w), 1715 (s), 1466 (w), 1447 (w), 1373 (s), 1335 (m), 1251 (m), 1169 (s), 1072 (w), 922 (w), 834 (w), 751 (m), 689 (w). HRMS (ESI) (m/z): calc'd for $C_3H_3BrN_4O_7SSi$ $[M+H]^+$: 765.1408. found: 765.1441. TLC (50% ethyl acetate in hexanes), Rf: 0.44 (UV, CAM).

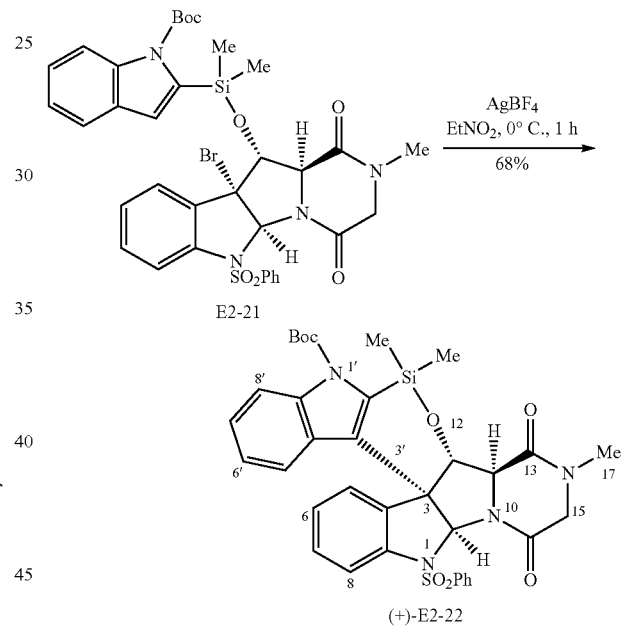

(+)-E2-22

Silacyclic Tetracycle (+)-E2-22

A round-bottom flask was charged with indole-tethered tetracycle E2-21 (6.85 g, 8.95 mmol, 1 equiv) and 2,6-di-tert-butyl-4-methylpyridine (3.69 g, 17.9 mmol, 2.00 equiv) and azeotropically dried with benzene (3×50 mL) under reduced pressure. The flask was left under reduced pressure for 12 h to ensure the complete removal of benzene then returned to atmospheric pressure by backfilling with argon. Anhydrous nitroethane (200 mL, distilled over $CaH_2$ and stored over 4 Å molecular sieves) was then introduced via cannula and the resulting solution was cooled to 0° C. A solution of silver (I) tetrafluoroborate (8.69 g, 44.8 mmol, 5.00 equiv) in nitroethane (30 mL) at 0° C. was introduced via cannula to the solution containing the indole-tethered tetracycle E2-21 over 1 min. The reaction mixture immediately changed color to a dark red then to brown. After 1 h, brine (150 mL) was added and the resulting biphasic mixture was vigorously stirred at 23° C. After 10 min, the reaction mixture was extracted with ethyl acetate (3×150 mL). The combined organic layers were dried over anhydrous sodium sulfate, were filtered, and were concentrated under reduced pressure. The resulting white residue was purified by flash column chromatography (eluent: gradient, 40→100% ethyl acetate in hexanes) to afford the silacyclic tetracycle (+)-E2-22 (4.20 g, 68.5%) as a white foam. Structural assignments were made using additional information from gCOSY, HSQC, gHMBC, and NOESY experiments. $^1$H NMR (500 MHz, CDCl$_3$, 20° C.): δ 8.25 (d, J=8.3, 2H, SO$_2$Ph-o-H), 7.96 (d, J=8.2, 1H, C$_8$H), 7.87 (d, J=8.4, 1H, C$_8$'H), 7.74 (t, J=7.5, 1H, SO$_2$Ph-p-H), 7.59 (app-t, J=7.8, 2H, SO$_2$Ph-m-H), 7.30 (app-t, J=7.6, 1H, C$_7$'H), 7.15 (app-t, J=7.5, 1H, C$_7$H), 6.91 (app-t, J=7.5, 1H, C$_6$H), 6.71 (d, J=7.4, 1H, C$_5$H), 6.50 (app-t, J=7.4, 1H, C$_6$'H), 6.39 (s, 1H, C$_2$H), 5.51 (d, J=8.0, 1H, C$_5$'H), 4.91 (d, J=9.5, 1H, C$_{12}$H), 4.32 (d, J=9.5, 1H, C$_{11}$H), 4.02 (d, J=18.2, 1H, C$_{15}$H$_a$), 3.95 (d, J=18.1, 1H, C$_{15}$H$_b$), 3.05 (s, 3H, C$_{17}$H), 1.70 (s, 9H, CO$_2$C(CH$_3$)$_3$), 0.54 (s, 3H, Si(CH$_3$)$_2$), 0.48 (s, 3H, Si(CH$_3$)$_2$). $^{13}$C NMR (125.8 MHz, CDCl$_3$, 20° C.): δ 167.7 (C$_{13}$), 166.5 (C$_{16}$), 151.6 (C=O$_{carbamate}$), 139.8 (C$_9$), 136.8 (C$_9$'), 136.3 (SO$_2$Ph-ipso-C), 136.0 (Cr), 133.8 (SO$_2$Ph-p-C), 132.0 (C$_4$), 129.8 (C$_7$), 129.6 (SO$_2$Ph-m-C), 129.5 (C$_4$'), 128.4 (SO$_2$Ph-o-C), 125.3 (C$_7$'), 125.1 (C$_3$'), 124.5 (C$_6$), 123.5 (C$_5$), 122.7 (C$_6$'), 119.3 (C$_5$'), 115.5 (C$_8$'), 115.2 (C$_8$), 85.6 (CO$_2$C(CH$_3$)$_3$), 80.5 (C$_{12}$), 79.1 (C$_2$), 61.4 (C$_{11}$), 56.6 (C$_3$), 54.2 (C$_{15}$), 33.5 (C$_{17}$), 28.3 (CO$_2$C(CH$_3$)$_3$), 1.7 (Si(CH$_3$)$_2$), 0.6 (Si(CH$_3$)$_2$). FTIR (thin film) cm$^{-1}$: 2927 (s), 1700 (m), 1652 (w), 1558 (m), 1494 (m), 1454 (w), 1373 (m), 1328 (w), 1258 (w), 1159 (w), 1050 (w), 876 (m), 825 (m), 751 (w). HRMS (ESI) (m/z): calc'd for C$_{35}$H$_3$N$_4$NaO$_7$SSi [M+Na]$^+$: 707.1966. found: 707.1986. [α]$_D$24: +203 (c=0.22, CHCl$_3$). TLC (33% acetone in hexanes), Rf: 0.25 (UV, CAM).

then sealed and heated to 80° C. After 40 min, the sealed tube was immediately immersed in an ice-water bath and rapidly cooled to 0° C. The cold solution was slowly poured into a saturated aqueous sodium bicarbonate solution (250 mL) at 0° C. and extracted with ethyl acetate (200 mL). The aqueous layer was further extracted with ethyl acetate (2×100 mL), and the combined organic layers were dried over anhydrous sodium sulfate, were filtered, and were concentrated under reduced pressure. The resulting residue was purified by flash column chromatography (eluent: gradient, 25→50% acetone in dichloromethane) to afford the 3-indolylated tetracycle (+)-E2-24 (456 mg, 57.9%) as a white solid. Structural assignments were made using additional information from gCOSY, HSQC, gHMBC, and NOESY experiments. $^1$H NMR (500 MHz, CDCl$_3$, 20° C.): δ 7.94 (br-s, 1H, N$_1$'H), 7.75 (d, J=8.1, 1H, C$_8$H), 7.44 (dd, J=1.2, 8.6, 2H, SO$_2$Ph-o-H), 7.37-7.27 (m, 1H, SO$_2$Ph-p-H), 7.37-7.27 (m, 1H, C$_8$'H), 7.37-7.27 (m, 1H, C$_7$H), 7.18-7.13 (m, 1H, C$_5$H), 7.18-7.13 (m, 1H, C$_7$'H), 7.09-7.01 (m, 2H, SO$_2$Ph-m-C), 7.09-7.01 (m, 1H, C$_6$H), 6.91-6.84 (m, 1H, C$_5$'H), 6.91-6.84 (m, 1H, C$_6$'H), 6.64 (d, J=2.7, 1H, C$_2$'H), 6.49 (s, 1H, C$_2$H), 4.92 (dd, J=3.3, 6.0, 1H, C$_{12}$H), 4.42 (d, J=5.7, 1H, C$_{11}$H), 4.09 (d, J=17.1, 1H, C$_{15}$H$_a$), 3.84 (d, J=17.5, 1H, C$_{15}$H$_b$), 2.88 (s, 3H, C$_{17}$H), 2.71 (d, J=3.2, 1H, OH). $^{13}$C NMR (125.8 MHz, CDCl$_3$, 20° C.): δ 166.9 (C$_{13}$), 165.4 (C$_{16}$), 139.6 (C$_9$), 137.4 (SO$_2$Ph-ipso-C), 136.9 (C$_9$'), 134.5 (C$_4$), 133.0 (SO$_2$Ph-p-C), 129.6 (C$_7$), 128.6 (SO$_2$Ph-m-C), 127.5 (SO$_2$Ph-o-C), 126.2 (C$_4$'), 125.8 (C$_2$'), 125.3 (C$_5$), 125.2 (C$_6$), 122.8 (C$_7$'), 120.5 (C$_5$'), 120.5 (C$_6$'), 117.3 (C$_8$), 111.7 (C$_8$'), 110.6 (C$_3$'), 82.3 (C$_2$), 77.4 (C$_{12}$), 64.6 (C$_{11}$), 59.8 (C$_3$), 54.3 (C$_{15}$), 33.5 (C$_{17}$). FTIR (thin film) cm$^{-1}$: 3388 (br-s), 3061 (m), 2923 (m), 1673 (s), 1458 (m), 1427 (m), 1402 (m), 1357 (m), 1260 (w), 1168 (m), 1109 (m), 735 (m), 687 (w). HRMS (ESI) (m/z): calc'd for C$_{28}$H$_{25}$N$_4$O$_5$S [M+H]$^+$: 529.1540. found: 529.1545. [α]$_D$$^{24}$: +11 (c=0.05, CHCl$_3$). TLC (50% acetone in dichloromethane), Rf: 0.41 (UV, CAM).

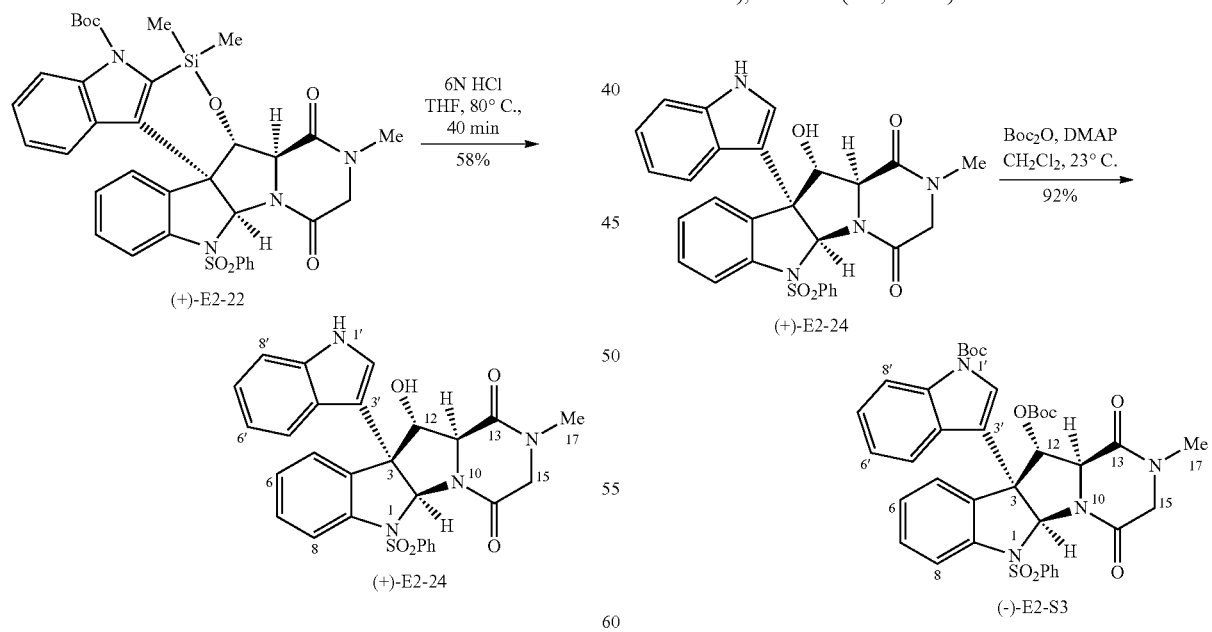

(+)-E2-22

3-Indolylated Tetracycle (+)-E2-24

(+)-E2-24

Bis(tert-butoxycarbonyl)Tetracycle (−)-E2-S3

Aqueous hydrogen chloride solution (6 N, 20 mL) was added in one portion to a sealed tube charged with a solution of silacyclic tetracycle (+)-E2-22 (1.02 g, 1.49 mmol, 1 equiv) in tetrahydrofuran (20 mL) at 23° C. The reaction flask was Di-tert-butyl dicarbonate (783 μL, 3.41 mmol, 4.00 equiv) was added via syringe to a solution of 3-indolylated tetracycle (+)-E2-24 (450 mg, 852 μmol, 1 equiv) and 4-dimethylaminopyridine (52.1 mg, 426 μmol, 0.500 equiv) in dichloromethane (10.0 mL) at 23° C. After 30 min, the crude reaction mixture was purified by flash column chromatography on silica gel (eluent: 8% acetone in dichloromethane) to afford bis(tert-butoxycarbonyl)tetracycle (−)-E2-S3 (568 mg, 91.5%) as a white solid. Structural assignments were made using additional information from gCOSY, HSQC, and HMBC experiments. $^1$H NMR (500 MHz, CDCl$_3$, 20° C.): δ 7.98 (d, J=7.3, 1H, C$_8$H), 7.73 (d, J=7.6, 1H, C$_8$H), 7.67 (d, J=8.1, 1H, C$_5$H), 7.58 (d, J=7.7, 1H, C$_8$H), 7.33 (app-t, J=7.9, 1H, C$_6$H), 7.30 (app-t, J=7.3, 1H, C$_7$H), 7.25 (app-t, J=8.0, 1H, C$_6$H), 7.20 (app-t, J=7.5, 1H, C$_7$H), 7.02 (t, J=7.4, 1H, SO$_2$Ph-p-H), 6.88 (d, J=7.3, 2H, SO$_2$Ph-o-H), 6.64 (app-t, J=7.5, 2H, SO$_2$Ph-m-H), 6.58 (s, 1H, C$_2$H), 5.99 (s, 1H, C$_2$H), 5.92 (d, J=4.0, 1H, C$_{12}$H), 4.53 (d, J=3.9, 1H, C$_{11}$H), 4.18 (d, J=17.4, 1H, C$_{15}$H$_a$), 3.79 (d, J=17.4, 1H, C$_{15}$H$_b$), 2.81 (s, 3H, C$_{17}$H), 1.50 (s, 9H, C(CH$_3$)$_{3carbamate}$), 0.80 (s, 9H, C(CH$_3$)$_{3carbonate}$). $^{13}$C NMR (125.8 MHz, CDCl$_3$, 20° C.): δ 164.8 (C$_{13}$), 164.5 (C$_{16}$), 151.4 (C=O$_{carbonate}$), 148.6 (C=O$_{carbamate}$), 139.2 (C$_4$), 137.8 (SO$_2$Ph-ipso-C), 135.8 (C$_9$), 133.8 (C$_9$), 132.2 (SO$_2$Ph-p-C), 130.1 (C$_6$), 128.1 (C$_4$'), 127.7 (SO$_2$Ph-o-C), 127.5 (C$_2$'), 126.8 (C$_8$), 126.5 (SO$_2$Ph-o-C), 126.2 (C$_7$), 124.7 (C$_7$'), 122.9 (C$_6$'), 121.5 (C$_5$'), 118.8 (C$_5$), 115.9 (C$_3$'), 115.1 (C$_8$'), 84.0 (C(CH$_3$)$_{3carbamate}$), 82.4 (C(CH$_3$)$_{3carbonate}$), 82.3 (C$_2$), 78.3 (C$_{12}$), 63.4 (C$_{11}$), 59.6 (C$_3$), 54.1 (C$_{15}$), 33.6 (C$_{17}$), 28.0 (C(CH$_3$)$_{3carbamate}$), 26.6 (C(CH$_3$)$_{3carbonate}$). FTIR (thin film) cm$^{-1}$: 2979 (w), 1740 (s), 1708 (s), 1686 (s), 1453 (m), 1371 (s), 1280 (s), 1258 (s), 1156 (s), 1100 (m), 750 (m). HRMS (ESI) (m/z): calc'd for C$_{38}$H$_{40}$N$_4$NaO$_9$S [M+Na]$^+$: 751.2408. found 751.2405. [α]$_D^{24}$: −22 (c=0.31, CHCl$_3$). TLC (8% acetone in dichloromethane), Rf: 0.28 (UV, CAM).

romethane (2×50 mL) and the combined organic layers were dried over anhydrous sodium sulfate, were filtered, and were concentrated under reduced pressure. The crude reaction mixture was purified by flash column chromatography on silica gel (eluent: 50% ethyl acetate in hexanes) to afford triketopiperazine (−)-E2-25 (105 mg, 45.1%) as a white solid. Structural assignments were made using additional information from gCOSY, HSQC, and HMBC experiments. $^1$H NMR (500 MHz, CDCl$_3$, 20° C.): δ 7.97 (d, J=8.2, 1H, C$_8$H), 7.86 (d, J=8.0, 1H, C$_8$H), 7.59-7.52 (m, 1H, C$_5$H), 7.59-7.52 (m, 1H, C$_7$H), 7.33 (app-t, J=7.6, 1H, C$_6$H), 7.32-7.26 (m, 1H, C$_7$H), 7.32-7.26 (m, 1H, C$_5$H), 7.22 (app-t, J=7.1, 1H, C$_6$H), 7.10 (d, J=7.5, 2H, SO$_2$Ph-o-H), 6.98 (t, J=7.5, 1H, SO$_2$Ph-p-H), 6.93 (s, 1H, C$_2$H), 6.61 (app-t, J=7.9, 2H, SO$_2$Ph-m-H), 6.53 (s, 1H, C$_2$H), 5.69 (s, 1H, C$_{12}$H), 4.45 (s, 1H, C$_{11}$OH), 3.34 (s, 3H, C$_{17}$H), 1.61 (s, 9H, C(CH$_3$)$_{3carbamate}$), 0.78 (s, 9H, C(CH$_3$)$_{3carbonate}$). $^{13}$C NMR (125.8 MHz, CDCl$_3$, 20° C.): δ 165.5 (C$_{15}$), 157.0 (C$_{13}$), 151.3 (C$_{16}$), 150.7 (C=O$_{carbonate}$), 149.0 (C=O$_{carbamate}$), 140.9 (C$_9$), 136.3 (C$_9$'), 136.2 (SO$_2$Ph-ipso-C), 133.7 (C$_4$), 132.7 (SO$_2$Ph-p-C), 130.5 (C$_7$), 128.0 (SO$_2$Ph-m-C), 127.4 (C$_2$'), 127.4 (C$_4$'), 127.0 (SO$_2$Ph-o-C), 126.5 (C$_6$), 125.3 (C$_5$), 124.9 (C$_5$'), 123.3 (C$_6$'), 121.8 (C$_7$'), 120.0 (C$_8$), 115.7 (CO$_3$'), 115.2 (C$_8$'), 90.5 (C$_{12}$), 85.3 (C$_{12}$), 84.4 (C(CH$_3$)$_{3carbamate}$), 83.5 (C(CH$_3$)$_{3carbonate}$), 82.2 (C$_2$), 57.8 (C$_3$), 28.3 (C(CH$_3$)$_{3carbamate}$), 28.1 (C$_{17}$), 26.8 (C(CH$_3$)$_{3carbonate}$). FTIR (thin film) cm$^{-1}$: 3386 (br-s), 2981 (w), 1738 (s), 1703 (s), 1453 (m), 1371 (s), 1274 (m), 1252 (m), 1156 (m), 751 (m). HRMS (ESI) (m/z): calc'd for C$_3$H$_{39}$N$_4$O$_S$ [M+H]$^+$: 759.2331. found 759.2302. [α]$_D^{24}$: −69 (c=0.15, CHCl$_3$). TLC (40% ethyl acetate in hexanes), Rf: 0.20 (UV, CAM).

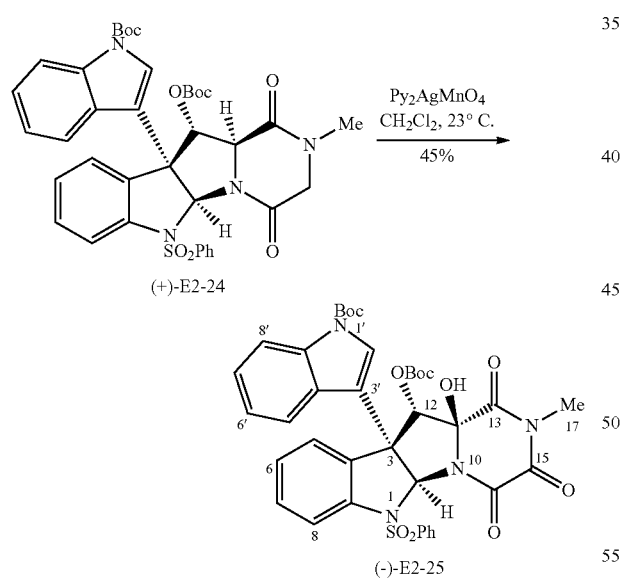

Triketopiperazine (−)-E2-25

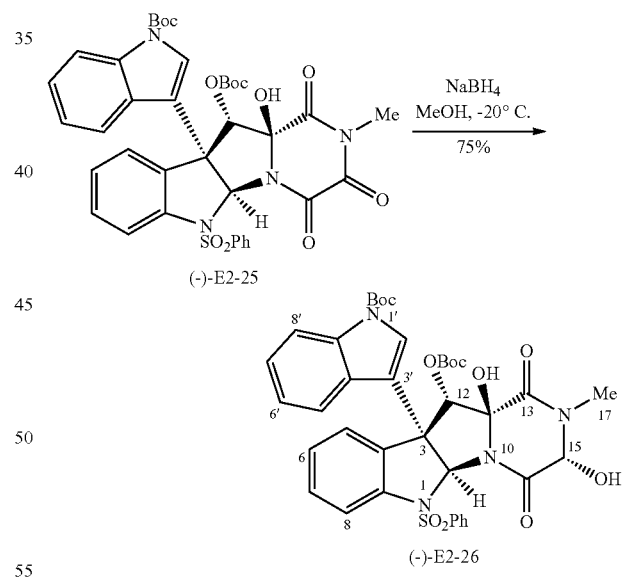

Tetracyclic Diol (−)-E2-26

Bis(pyridine)silver permanganate (945 mg, 2.45 mmol, 8.00 equiv) was added as a solid to a solution of bis(tert-butoxycarbonyl)tetracycle (−)-E2-S3 (224 mg, 307 μmol, 1 equiv) in dichloromethane (10.0 mL) at 23° C. After 1 h, the reaction mixture was diluted with dichloromethane (100 mL) and washed with aqueous sodium bisulfite solution (1 M, 125 mL). The resulting aqueous layer was extracted with dichlo- Sodium borohydride (17.3 mg, 457 μmol, 2.00 equiv) was added as a solid to a solution of triketopiperazine (−)-E2-25 (174 mg, 229 μmol, 1 equiv) in methanol at −20° C. After 20 min, saturated aqueous sodium bicarbonate solution (5 mL) was added to the reaction mixture. The solution was diluted with dichloromethane (60 mL) and washed with saturated aqueous sodium bicarbonate solution (60 mL). The mixture was extracted with dichloromethane (2×60 mL), and the combined organic layers were dried over anhydrous sodium sulfate, were filtered, and were concentrated under reduced pressure. The crude reaction mixture was purified by flash column chromatography on silica gel (eluent: 20% acetone in dichloromethane) to afford tetracyclic diol (−)-E2-26 (130 mg, 74.9%) as a white solid. Structural assignments were made using additional information from gCOSY, HSQC, and HMBC experiments. $^1$H NMR (500 MHz, CDCl$_3$, 20° C.): δ 7.97 (d, J=7.6, 1H, C$_8$H), 7.75 (d, J=8.1, 1H, C$_8$H), 7.52 (d, J=7.1, 1H, C$_5$H), 7.45 (d, J=7.9, 1H, C$_5$H), 7.36 (app-t, J=7.8, 1H, C$_7$H), 7.31 (app-t, J=7.3, 1H, C$_7$H), 7.26 (app-t, J=7.6, 1H, C$_6$H), 7.23 (app-t, J=7.5, 1H, C$_6$H), 7.01 (d, J=7.4, 2H, SO$_2$Ph-o-H), 6.97 (t, J=7.5, 1H, SO$_2$Ph-p-H), 6.94 (s, 1H, C$_2$H), 6.58 (app-t, J=8.1, 2'H, SO$_2$Ph-m-H), 6.43 (s, 1H, C$_2$H), 5.66 (s, 1H, C$_{12}$H), 5.39 (d, J=3.0, 1H, C$_{15}$H), 4.92 (d, J=2.8, 1H, C$_{15}$OH), 4.38 (br-s, 1H, C$_{11}$OH), 2.99 (s, 3H, C$_{17}$H), 1.59 (s, 9H, C(CH$_3$)$_{3carbamate}$), 0.80 (s, 9H, C(CH$_3$)$_{3carbonate}$). $^{13}$C NMR (125.8 MHz, CDCl$_3$, 20° C.): δ 165.4 (C$_{16}$), 163.7 (C$_{13}$), 151.2 (C=O$_{carbonate}$), 149.0 (C=O$_{carbamate}$), 140.7 (C$_9$), 136.8 (SO$_2$Ph-ipso-C), 136.3 (C$_{9'}$), 134.0 (C$_4$), 132.4 (SO$_2$Ph-p-C), 129.8 (C$_7$), 127.8 (SO$_2$Ph-m-C), 127.7 (C$_{4'}$), 127.3 (C$_{2'}$), 126.8 (SO$_2$Ph-o-C), 126.2 (C$_6$), 125.4 (C$_5$), 124.8 (C$_{7'}$), 123.1 (C$_{6'}$), 122.3 (C$_{5'}$), 119.7 (C$_8$), 116.0 (C$_{3'}$), 115.1 (C$_{8'}$), 90.5 (C$_{11}$), 84.9 (C$_{12}$), 84.2 (C(CH$_3$)$_{3carbamate}$), 83.0 (C(CH$_3$)$_{3carbonate}$), 81.4 (C$_2$), 77.1 (C$_{15}$), 57.3 (C$_3$), 29.6 (C$_{17}$), 28.3 (C(CH$_3$)$_{3carbamate}$), 26.9 (C(CH$_3$)$_{3carbonate}$). FTIR (thin film) cm$^{-1}$:3417 (br-s), 2980 (w), 1738 (s), 1687 (s), 1454 (m), 1371 (s), 1276 (m), 1252 (m), 1156 (s), 749 (w). HRMS (ESI) (m/z):calc'd for C$_{38}$H$_{41}$N$_4$O$_{11}$S [M+H]$^+$: 761.2487. found 761.2481. [α]$_D^{24}$:−19 (c=0.16, CHCl$_3$). TLC (20% acetone in dichloromethane), R$_f$: 0.23 (UV, CAM).

dichloromethane) to afford tetracyclic dipivaloate (+)-E2-27 (119 mg, 83.0%) as a white solid. Structural assignments were made using additional information from gCOSY, HSQC, and HMBC experiments. $^1$H NMR (500 MHz, CDCl$_3$, 20° C.): δ 7.96 (d. J=7.9, 1H, C$_8$H), 7.81 (d, J=8.1, 1H, C$_8$H), 7.60 (dd, J=0.7, 7.5, 1H, C$_5$H), 7.45 (br-s, 1H, C$_5$H), 7.39 (app-dt, J=1.2, 7.7, 1H, C$_7$H), 7.32-7.25 (m, 1H, C$_6$H), 7.32-7.25 (m, 1H, C$_7$H), 7.20-7.13 (m, 2H, SO$_2$Ph-o-H), 7.20-7.13 (m, 1H, C$_6$H), 6.99 (t, J=7.5, SO$_2$Ph-p-H), 6.91 (s, 1H, C$_2$H), 6.63 (app-t, J=7.9, 2H, SO$_2$Ph-m-H), 6.52 (br-s, 1H, C$_{15}$H), 6.44 (s, 1H, C$_2$H), 5.70 (s, 1H, C$_{12}$H), 2.91 (s, 3H, C$_{17}$H), 1.59 (s, 9H, C(CH$_3$)$_{3carbamate}$), 1.40 (s, 9H, C(CH$_3$)$_{3pivaloate}$), 0.79 (s, 9H, C(CH$_3$)$_{3carbonate}$), 0.68 (s, 9H, C(CH$_3$)$_{3pivaloate}$). $^{13}$C NMR (125.8 MHz, CDCl$_3$, 20° C.): δ 177.3 (C=O$_{pivaloate}$), 176.3 (C=O$_{pivaloate}$), 161.3 (C$_{16}$), 160.8 (C$_{13}$), 151.0 (C=O$_{carbonate}$), 149.0 (C=O$_{carbamate}$), 141.5 (C$_9$), 136.6 (SO$_2$Ph-ipso-C), 136.3 (C$_{9'}$), 133.1 (C$_4$), 132.6 (SO$_2$Ph-p-C), 130.0 (C$_7$), 127.9 (SO$_2$Ph-m-C), 127.5 (C$_{4'}$), 127.3 (C$_{2'}$), 127.0 (SO$_2$Ph-o-C), 126.0 (C$_6$), 125.7 (C$_5$), 124.7 (C$_{7'}$), 123.0 (C$_{6'}$), 122.3 (C$_{5'}$), 119.4 (C$_8$), 116.6 (C$_{3'}$), 115.0 (C$_{8'}$), 92.2 (C$_{11}$), 85.2 (C$_{12}$), 84.2 (C(CH$_3$)$_{3carbamate}$), 83.2 (C$_2$), 82.8 (C(CH$_3$)$_{3carbonate}$), 78.3 (C$_{15}$), 57.9 (C$_3$), 39.3 (C(CH$_3$)$_{3pivaloate}$), 38.7 (C(CH$_3$)$_{3pivaloate}$), 30.7 (C$_{17}$), 28.3 (C(CH$_3$)$_{3carbamate}$), 27.2 (C(CH$_3$)$_{3pivaloate}$), 26.8 (C(CH$_3$)$_{3carbonate}$), 26.3 (C(CH$_3$)$_{3pivaloate}$). FTIR (thin film) cm$^{-1}$: 2978 (m), 1742 (s), 1699 (m), 1454 (m), 1371 (s), 1276 (m), 1252 (m), 1155 (m), 1123 (s), 750 (m). HRMS (ESI) (m/z): calc'd for C$_{48}$H$_{56}$N$_4$NaO$_{13}$S [M+Na]$^+$: 951.3457. found 951.3451. [α]$_D^{24}$: +5.3 (c=0.095, CHCl$_3$). TLC (1% acetone in dichloromethane), R$_f$: 0.27 (UV, CAM).

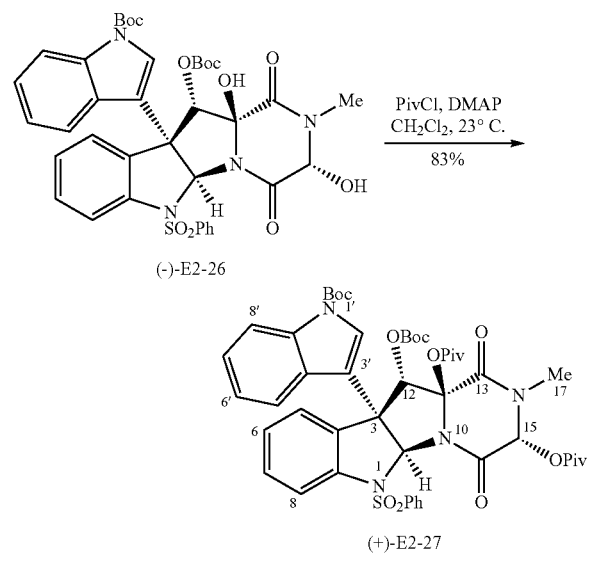

Tetracyclic Dipivaloate (+)-E2-27

Pivaloyl chloride (75.8 μL, 616 μmol, 4.00 equiv) was added via syringe to a solution of tetracyclic diol (−)-E2-26 (117 mg, 154 μmol, 1 equiv) and 4-dimethylaminopyridine (94.1 mg, 771 μmol, 5.00 equiv) in dichloromethane (4 mL) at 23° C. After 1 h 45 min, methanol (50 μL) was added to the reaction mixture, and the crude solution was purified by flash column chromatography on silica gel (eluent: 1% acetone in

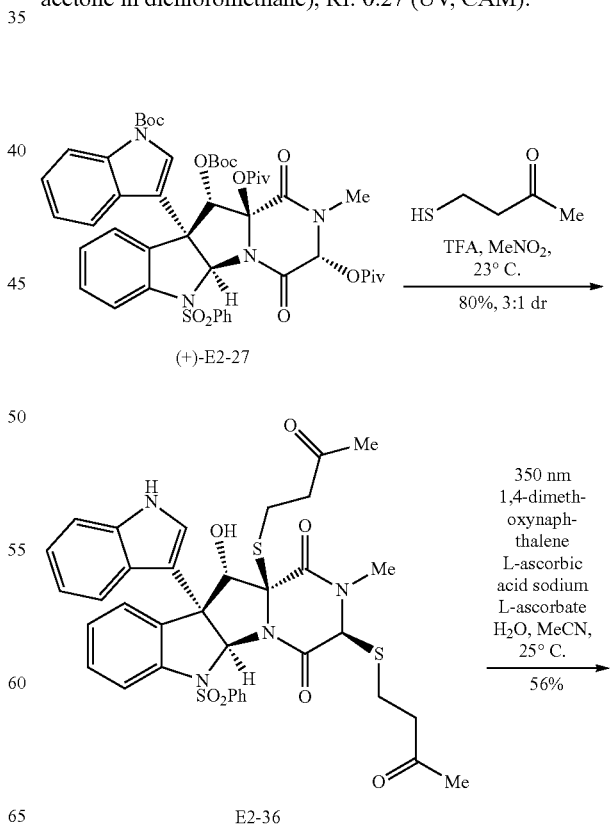

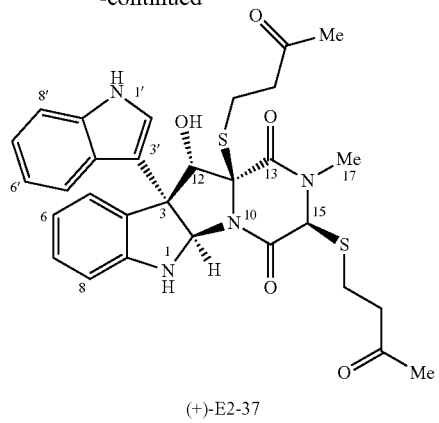

(+)-E2-37

Tetracyclic Bisthioether (+)-E2-37

Trifluoroacetic acid (3 mL) was added via syringe to a solution of tetracyclic dipivaloate (+)-E2-27 (109 mg, 117 μmol, 1 equiv) and 3-mercapto-2-butanone (366 mg, 3.51 mmol, 30.0 equiv, Ross, N. C.; Levine, R. *J. Org. Chem.* 1964, 29, 2346) in nitromethane (3 mL) at 23° C. After 45 min, the reaction mixture was diluted with dichloromethane (60 mL) and washed with saturated aqueous sodium bicarbonate solution (100 mL). The aqueous layer was extracted with dichloromethane (2×30 mL), and the combined organic layers were dried over anhydrous sodium sulfate, were filtered, and were concentrated under reduced pressure. The crude reaction mixture was purified by flash column chromatography on silica gel (eluent: 20% acetone in dichloromethane) to afford a diastereomeric mixture of bisthioethers (68.8 mg, 80.2%, 3:1 dr, major:minor) as a beige solid. A 25-mL Pyrex pear-shaped flask was sequentially charged with the diastereomeric mixture of bisthioethers (68.8 mg, 93.9 μmol, 1 equiv), L-ascorbic acid (165 mg, 939 μmol, 10.0 equiv), sodium L-ascorbate (186 mg, 939 μmol, 10.0 equiv), and 1,4-dimethoxynaphthalene (1.06 g, 5.63 mmol, 60.0 equiv), and the mixture was placed under an argon atmosphere. Acetonitrile (8 mL) and water (2 mL) were then sequentially introduced via syringe and the resulting solution was sparged with argon for 5 min at 23° C. The system was stirred vigorously and irradiated in a Rayonet photoreactor equipped with 16 radially distributed (r=12.7 cm) 25 W black light phosphor lamps ($\lambda_{max}$=350 nm) at 25° C. After 1.5 h, the lamps were turned off and the reaction mixture was diluted with dichloromethane (60 mL). The resulting solution was washed with saturated aqueous sodium bicarbonate solution (60 mL). The aqueous layer was extracted with dichloromethane (2×10 mL), and the combined organic layers were dried over anhydrous sodium sulfate, were filtered, and were concentrated under reduced pressure. The crude reaction mixture was purified by flash column chromatography on silica gel (eluent: gradient, 20→25% acetone in dichloromethane) to afford tetracyclic bisthioether (+)-E2-37 (31.0 mg, 55.7%) as a single diastereomer and as a clear film. Structural assignments were made using additional information from gCOSY, HSQC, and HMBC experiments. $^1$H NMR (500 MHz, CDCl$_3$, 20° C.): δ 8.00 (s, 1H, N$_1$H), 7.85 (d, J=7.4, 1H, C$_5$·H), 7.37 (d, J=7.3, 1H, C$_5$H), 7.31 (d, J=7.5, 1H, C$_8$·H), 7.17 (app-t, J=7.2, 1H, C$_7$H), 7.14 (app-t, J=7.2, 1H, C$_6$·H), 7.09 (d, J=2.5, 1H, C$_2$·H), 7.05 (app-t, J=7.5, 1H, C$_7$H), 6.69 (app-t, J=7.3, 1H, C$_6$H), 6.62 (d, J=7.7, 1H, C$_8$H), 6.29 (s, 1H, C$_2$H), 5.30 (d, J=1.8, 1H, C$_{12}$H), 5.07 (s, 1H, N$_1$H), 4.76 (s, 1H, C$_{15}$H), 3.34 (d, J=2.0, 1H, C$_{12}$OH), 3.10-3.02 (m, 2H, C$_{22}$H), 3.08 (s, 3H, C$_{17}$H), 2.98-2.86 (m, 2H, C$_{23}$H), 2.86-2.77 (m, 1H, C$_1$H$_a$), 2.75-2.67 (m, 1H, C$_{18}$H$_b$), 2.47-2.32 (m, 2H, C$_{19}$H), 2.20 (s, 3H, C$_{25}$H), 2.04 (s, 3H, C$_{21}$H). $^{13}$C NMR (125.8 MHz, CDCl$_3$, 20° C.): δ 206.9 (C$_{24}$), 206.3 (C$_{20}$), 165.4 (C$_{16}$), 165.1 (C$_{13}$), 147.5 (C$_9$), 137.1 (C$_9$·), 132.2 (C$_4$), 128.8 (C$_7$), 125.8 (C$_4$·), 123.7 (C$_5$), 123.2 (C$_2$·), 122.4 (C$_7$·), 121.2 (C$_5$·), 120.0 (C$_6$·), 119.3 (C$_6$), 114.9 (C$_3$·), 111.8 (C$_8$·), 110.2 (C$_8$), 81.6 (C$_2$), 81.5 (C$_{12}$), 73.5 (C$_{11}$), 66.9 (C$_{15}$), 59.3 (C$_3$), 44.1 (C$_{23}$), 42.6 (C19), 32.0 (C$_{17}$), 30.3 (C$_{25}$), 30.1 (C$_{21}$), 28.6 (C$_{22}$), 25.7 (C$_{18}$). FTIR (thin film) cm$^{-1}$: 3371 (br-s), 2930 (w), 1711 (m), 1661 (s), 1423 (m), 1397 (m), 1364 (w), 1238 (w), 743 (m). HRMS (ESI) (m/z): calc'd for C$_{30}$H$_{32}$N$_4$NaO$_5$S$_2$ [M+Na]$^+$: 615.1706. found 615.1693. [α]$_D^{24}$: +179 (c=0.075, CHCl$_3$). TLC (25% acetone in dichloromethane), Rf: 0.23 (UV, CAM).

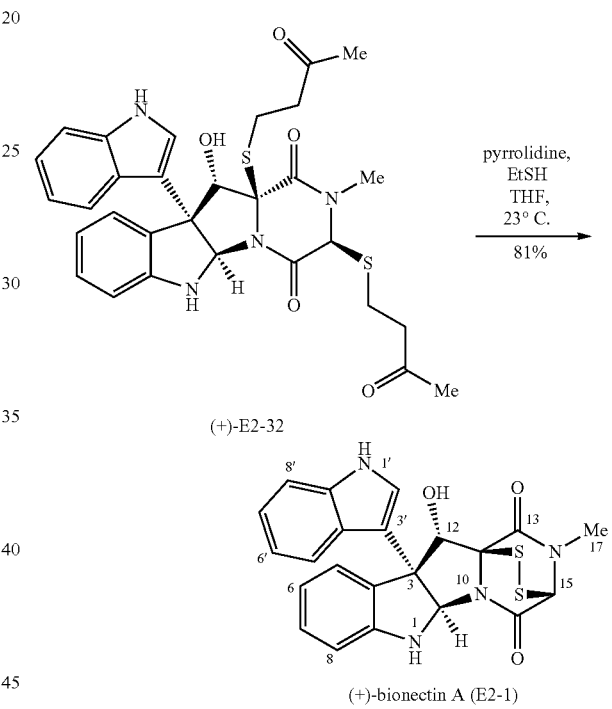

(+)-E2-32

(+)-bionectin A (E2-1)

(+)-Bionectin A (E2-1)

Pyrrolidine (20 μL, 242 μmol, 27.6 equiv) was added via syringe to a solution of tetracyclic bisthioether (+)-E2-37 (5.2 mg, 8.77 μmol, 1 equiv) and ethanethiol (20 μL, 270 μmol, 30.8 equiv) in tetrahydrofuran (1 mL) at 23° C. After 2 h, the reaction mixture was diluted with dichloromethane (10 mL) and washed with aqueous hydrochloric acid (1N, 10 mL). The aqueous layer was extracted with dichloromethane (2×5 mL), and the combined organic layers were dried over anhydrous sodium sulfate, were filtered, and were concentrated under reduced pressure. The crude reaction mixture was purified by flash column chromatography on silica gel (eluent: 10% acetone in dichloromethane) to afford (+)-bionectin A (E2-1) (3.2 mg, 81%) as a beige solid. Structural assignments were made using additional information from gCOSY, HSQC, HMBC, and NOESY experiments. $^1$H NMR (500 MHz, CDCl$_3$, 20° C.): δ 8.11 (br-s, 1H, N$_1$H), 7.91 (d, J=7.8, 1H, C$_5$·H), 7.44 (d, J=7.5, 1H, C$_5$H), 7.32 (d, J=8.1, 1H, C$_8$·H), 7.18 (app-t, J=6.9, 1H, C$_7$H), 7.16-7.11 (m, 1H, C$_6$H), 7.16-7.11 (m, 1H, C$_7$H), 7.06 (d, J=2.6, 1H, C$_2$H), 6.83 (app-t, J=7.5, 1H, C$_6$H), 6.69 (d, J=7.8, 1H, C$_8$H), 6.30 (s, 1H, C$_2$H), 5.36 (br-s, 1H, N$_1$H), 5.32 (s, 1H, C$_{12}$H), 5.19 (s, 1H, C$_{12}$OH), 5.17 (s, 1H, C$_{15}$H), 3.11 (s, 3H, C$_{17}$H). $^{13}$C NMR (125.8 MHz, CDCl$_3$, 20° C.): δ 166.2 (C$_3$), 161.9 (C$_{16}$), 147.3 (C$_9$), 137.1 (C$_{9'}$), 130.9 (C$_4$), 129.6 (C$_7$), 126.3 (C$_{4'}$), 124.7 (C$_5$), 123.5 (C$_{2'}$), 122.6 (C$_{7'}$), 121.6 (C$_{5'}$), 120.1 (C$_{6'}$), 120.1 (C$_6$), 113.4 (C$_{3'}$), 111.7 (C$_{8'}$), 110.9 (C$_8$), 82.5 (C$_2$), 81.0 (C$_{12}$), 77.0 (C$_{11}$), 67.7 (C$_{15}$), 61.6 (C$_3$), 32.0 (C$_{17}$). FTIR (thin film) cm$^{-1}$: 3402 (br-s), 2922 (w), 1677 (s), 1482 (w), 1458 (w), 1377 (m), 1237 (m), 1093 (w), 747 (m). HRMS (ESI) (m/z): calc'd for C$_{22}$H$_9$N$_4$O$_3$S$_2$ [M+H]$^+$: 451.0893. found 451.0891. [α]$_D^{24}$: +284 (c=0.11, CHCl$_3$). TLC (10% acetone in dichloromethane), Rf: 0.25 (UV, CAM).

3.10 (s, 3H, C$_{17}$H), 2.45 (s, 3H, C$_{15}$SCH$_3$), 2.06 (s, 3H, C$_{11}$SCH$_3$). $^{13}$C NMR (125.8 MHz, CDCl$_3$, 20° C.): δ 165.0 (C$_{16}$), 164.8 (C$_{13}$), 147.6 (C$_9$), 137.1 (C$_9$), 131.9 (C$_4$), 129.0 (C$_7$), 126.0 (C$_{4'}$), 123.4 (C$_5$), 123.1 (C$_{2'}$), 122.6 (C$_{7'}$), 121.3 (C$_{5'}$), 120.1 (C$_{6'}$), 119.3 (C$_6$), 115.1 (C$_{3'}$), 111.8 (C$_{8'}$), 110.1 (C$_8$), 81.8 (C$_2$), 80.5 (C$_{12}$), 73.4 (C$_{11}$), 67.8 (C$_{15}$), 59.1 (C$_3$), 32.4 (C$_{17}$), 18.3 (C$_{15}$SCH$_3$), 15.7 (C$_{11}$SCH$_3$). FTIR (thin film) cm$^{-1}$: 3399 (br-s), 2921 (w), 1661 (s), 1608 (w), 1483 (w), 1458 (w), 1424 (m), 1397 (m), 1238 (m), 1087 (w), 741 (m). HRMS (ESI) (m/z): calc'd for C$_{24}$H$_{25}$N$_4$O$_3$S$_2$[M+H]$^+$: 481.1363. found 481.1355. [α]$_D^{24}$: +270 (c=0.009, CHCl$_3$). TLC (10% acetone in dichloromethane), Rf: 0.08 (UV, CAM).

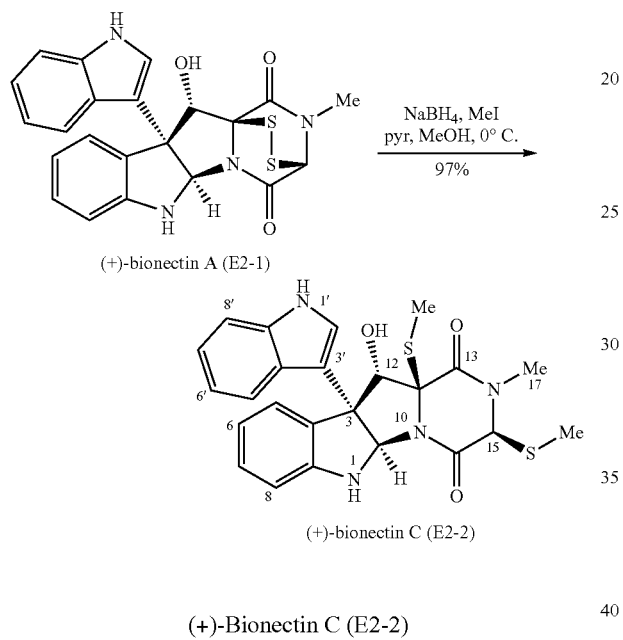

(+)-Bionectin C (E2-2)

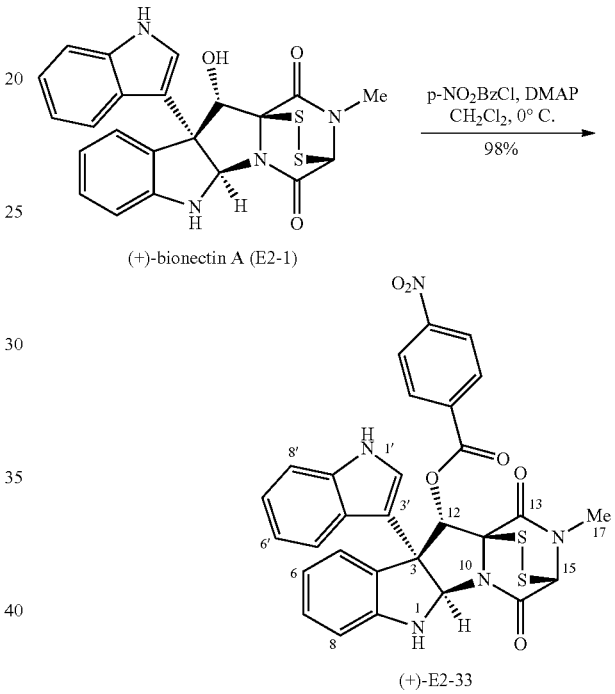

Bionectin A n-Nitrobenzoate (E2-38)

Sodium borohydride (2.2 mg, 57.7 μmol, 10.0 equiv) was added as a solid to a solution of (+)-bionectin A (E2-1) (2.6 mg, 5.77 μmol, 1 equiv) and methyl iodide (35.9 μL, 577 μmol, 100 equiv) in pyridine (100 μL) and methanol (200 μL) at 0° C. After 1 h, the reaction mixture was diluted with ethyl acetate (10 mL) and washed with saturated aqueous ammonium chloride solution (10 mL). The aqueous layer was extracted with ethyl acetate (2×10 mL), and the combined organic layers were dried over anhydrous sodium sulfate, were filtered, and were concentrated under reduced pressure. The crude reaction mixture was purified by flash column chromatography on silica gel (eluent: gradient, 10→15% acetone in dichloromethane) to afford (+)-bionectin C (E2-2) (2.7 mg, 97%) as a white solid. Structural assignments were made using additional information from gCOSY, HSQC, HMBC, and NOESY experiments. $^1$H NMR (500 MHz, CDCl$_3$, 20° C.): δ 8.00 (br-s, 1H, N$_1$H), 7.85 (d, J=7.9, 1H, C$_{5'}$H), 7.41 (d, J=7.5, 1H, C$_5$H), 7.31 (d, J=7.6, 1H, C$_{8'}$H), 7.17 (app-dt, J=1.0, 7.1, 1H, C$_7$H), 7.13 (app-dt, J=1.0, 7.1, 1H, C$_{6'}$H), 7.10 (d, J=2.7, 1H, C$_{2'}$H), 7.08 (app-dt, J=1.1, 7.6, 1H, C$_{7'}$H), 6.71 (ap-dt, J=0.7, 7.5, 1H, C$_6$H), 6.63 (d, J=7.8, 1H, C$_8$H), 6.34 (s, 1H, C$_2$H), 5.30 (d, J=2.1, 1H, C$_{12}$H), 5.09 (s, 1H, N$_1$H), 4.59 (s, 1H, C$_{15}$H), 3.24 (d, J=2.2, 1H, C$_{12}$OH), p-Nitrobenzoyl chloride (1.6 mg, 8.67 μmol, 1.50 equiv) was added to a solution of (+)-bionectin A (E2-1) (2.6 mg, 5.78 μmol, 1 equiv) and 4-dimethylaminopyridine (3.5 mg, 28.9 μmol, 5.00 equiv) in dichloromethane (1 mL) at 0° C. After 1 h, another portion of p-nitrobenzoyl chloride (1.5 mg, 8.08 μmol, 1.40 equiv) was added to the reaction. After 1 h 10 min, another portion of p-nitrobenzoyl chloride (2.2 mg, 11.9 μmol, 2.05 equiv) was added to the reaction. After 1 h 20 min, another portion of 4-dimethylaminopyridine (0.7 mg, 5.73 μmol, 0.99 equiv) was added to the reaction. After 1 h 10 min, p-nitrobenzoyl chloride (5.0 mg, 26.9 μmol, 4.66 equiv) was added to the reaction. After 38 min, methanol (50 μL) was added to the reaction. The crude reaction mixture was purified by flash column chromatography on silica gel (eluent: 2% acetone in dichloromethane) to afford (+)-bionectin A p-nitrobenzoate (E2-38) (3.4 mg, 98%) as a yellow solid. Crystals suitable for X-ray diffraction were obtained by slow evaporation of a saturated solution in chloroform at 23° C. $^1$H NMR (500 MHz, CDCl$_3$, 20° C.): δ 8.05 (br-s, 1H, N$_1$'H), 8.04 (d, J=8.8, 2H, p-NO$_2$Bz-m-H), 7.75 (d, J=8.2, 1H, C$_5$'H), 7.72 (d, J=8.9, 2H, p-NO$_2$Bz-o-H), 7.66 (d, J=7.4, C$_5$H), 7.21 (app-t, J=7.7, 1H, C$_7$H), 7.19 (d, J=8.1, 1H, C$_8$H), 7.04 (d, J=2.7, 1H, C$_2$'H), 7.00 (app-t, J=7.9, 1H, C$_7$'H), 6.95 (app-t, J=7.6, 1H, C$_6$H), 6.91 (app-t, J=7.3, 1H, C$_6$'H), 6.73 (d, J=7.8, 1H, C$_8$'H), 6.65 (s, 1H, C$_{12}$H), 6.55 (s, 1H, C$_2$H), 5.40 (br-s, 1H, N$_1$H), 5.26 (s, 1H, C$_{15}$H), 3.03 (s, 3H, C$_{17}$H). $^{13}$C NMR (125.8 MHz, CDCl$_3$, 20° C.): δ 163.7 (C=O$_{Bz}$), 163.1 (C$_{13}$), 161.7 (C$_{16}$), 150.4 (p-NO$_2$Bz-p-C), 147.7 (C$_9$), 137.1 (C$_9$'), 134.9 (p-NO$_2$Bz-ipso-C), 130.9 (p-NO$_2$Bz-m-C), 130.1 (C$_7$), 129.5 (C$_4$'), 125.7 (C$_4$), 125.0 (C$_5$), 124.7 (C$_2$'), 123.3 (p-NO$_2$Bz-o-C), 122.7 (C$_7$'), 121.1 (C$_5$'), 120.2 (C$_6$), 120.1 (C$_6$'), 111.8 (C$_8$'), 111.8 (C$_3$'), 110.9 (C$_8$), 81.3 (C$_2$), 80.6 (C$_{12}$), 75.8 (C$_{11}$), 68.7 (C$_{15}$), 60.9 (C$_3$), 32.3 (C$_{17}$). FTIR (thin film) cm$^{-1}$: 3406 (br-s), 1738 (w), 1691 (s), 1608 (w), 1526 (m), 1346 (w), 1263 (m), 1099 (m), 749 (m), 715 (w). HRMS (ESI) (m/z): calc'd for C$_{29}$H$_{21}$N$_5$NaO$_6$S$_2$ [M+Na]$^+$: 622.0825. found 622.0820. [α]$_D$24: +17 (c=0.12, CHCl$_3$). TLC (2% acetone in dichloromethane), Rf: 0.28 (UV, CAM).

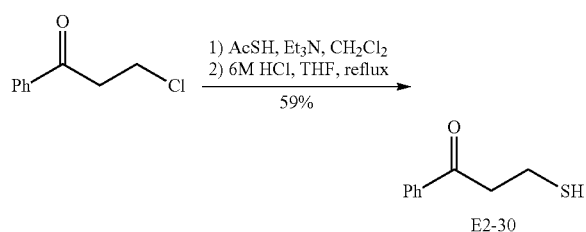

3-Mercaptopropiophenone (E2-30)

Triethylamine (1.49 mL, 10.7 mmol, 1.50 equiv) was added to a solution of 3-chloropropiophenone (1.20 g, 7.12 mmol, 1 equiv) in dichloromethane (100 mL) at 23° C. Thioacetic acid (602 μL, 8.54 mmol, 1.20 equiv) was then added dropwise to the solution. After 1 h, the reaction mixture was concentrated in vacuo. The crude residue was dissolved in tetrahydrofuran (50 mL) and aqueous hydrochloric acid (6 N, 50 mL) was added to the solution. Thee reaction mixture was then heated to reflux. After 36 h, the reaction was diluted with ethyl acetate (200 mL) and washed with saturated aqueous sodium bicarbonate solution (400 mL). The aqueous layer was extracted with ethyl acetate (3×200 mL), and the combined organic layers were dried over sodium sulfate, were filtered, and were concentrated under reduced pressure. The crude reaction mixture was purified by flash column chromatography on silica gel (eluent: 20% ethyl acetate in hexanes) to afford 3-mercaptopropiophenone (E2-30, 703 mg, 59.4%) as a colorless oil. $^1$H NMR (500 MHz, CDCl$_3$, 20° C.): δ 7.93 (d, J=7.5, 2H, COPh-o-H), 7.55 (t, J=7.5, 1H, COPh-p-H), 7.45 (app-t, J=7.5, 2H, COPh-m-H), 3.31 (t, J=7, 2H, CH$_2$CH$_2$SH, 2.89 (dt, J=8.5, 6.0, 2H, CH$_2$CH$_2$SH), 1.74 (t, J=8.5, 1H, SH). $^{13}$C NMR (125.8 MHz, CDCl$_3$, 20° C.): δ 198.2 (C=O), 136.8 (COPh-ipso-C), 133.6 (COPh-p-C), 128.9 (COPh-m-C), 128.2 (COPh-o-C), 42.7 (CH$_2$CH$_2$SH), 19.1 (CH$_2$CH$_2$SH). FTIR (thin film) cm$^{-1}$: 3061 (w), 2941 (w), 1683 (s), 1597 (m), 1580 (m) 1448 (m). HRMS (ESI) (m/z): calc'd for C$_9$H$_{11}$OS [M+H]$^+$: 167.0525. found 167.0526. TLC (20% ethyl acetate in hexanes), Rf: 0.28 (UV, CAM).

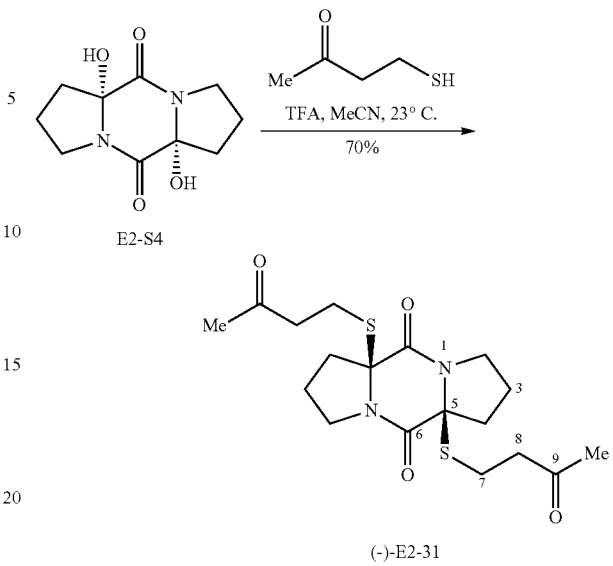

Bisproline Bis(ethylmethylketone thioether) (–)-E2-31

Trifluoroacetic acid (15 mL) was added via syringe to a solution of bisproline diol E2-S4 (397 mg, 1.76 mmol, 1 equiv) and 3-mercaptobutan-2-one (E2-29, 928 μL, 8.77 mmol, 5.00 equiv) in acetonitrile (15 mL) at 23° C. The clear solution immediately turned yellow. After 30 min, the reaction was diluted with ethyl acetate (50 mL) and washed with saturated aqueous sodium bicarbonate solution (50 mL). The aqueous layer was extracted with ethyl acetate (3×20 mL), and the combined organic layers were dried over sodium sulfate, were filtered, and were concentrated under reduced pressure. The crude reaction mixture was purified by flash column chromatography on silica gel (eluent: 3% acetone in dichloromethane) to afford the bisproline bis(ethylmethylketone thioether) (–)-E2-31 (490 mg, 70.2%) as a white solid. $^1$H NMR (500 MHz, CDCl$_3$, 20° C.): δ 3.68-3.62 (m, 2H, C$_2$H), 3.56-3.51 (m, 2H, C$_2$H), 2.90-2.87 (m, 4H, C$_8$H), 2.75-2.61 (m, 4H, C$_7$H), 2.46-2.42 (m, 2H, C$_4$H$_a$), 2.33-2.22 (m, 2H, C$_3$H$_a$), 2.12-2.04 (m, 2H, C$_4$H$_b$), 2.10 (s, 6H, COCH$_3$), 2.01-1.95 (m, 2H, C$_3$H$_b$). $^{13}$C NMR (125.8 MHz, CDCl$_3$, 20° C.): δ 206.4 (C$_9$), 165.3 (C$_6$), 71.7 (C$_5$), 45.4 (C$_2$), 43.2 (C$_7$), 35.4 (C$_4$), 30.0 (COCH$_3$), 25.2 (C$_8$), 20.0 (C$_3$). FTIR (thin film) cm$^{-1}$: 1715 (m), 1660 (s), 1409 (s), 1363 (w), 1158 (w). HRMS (ESI) (m/z): calc'd for C$_{18}$H$_{30}$N$_3$O$_4$S$_2$[M+NH$_4$]$^+$: 416.1672. found: 416.1679. [α]$_D$$^{24}$: –33 (c=0.28, CH$_2$Cl$_2$). TLC (10% acetone in dichloromethane), Rf: 0.39 (UV, CAM).

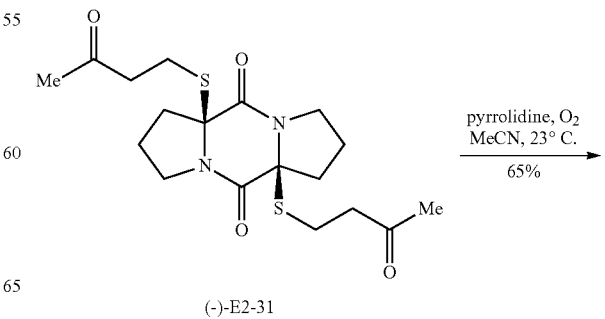

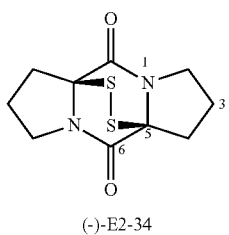

(−)-E2-34

Bisproline Epidithiodiketopiperazine (−)-E2-34

Pyrrolidine (70.0 μL, 852 μmol, 4.07 equiv) was added to a solution of bis(ethylmethylketone thioether) (−)-E2-31 (83.5 mg, 210 μmol, 1 equiv) in acetonitrile (250 μL) at 23° C., and the reaction was placed under a balloon of oxygen. The clear solution immediately turned orange. After 1 h, the reaction was diluted with dichloromethane (5 mL) and washed with saturated aqueous ammonium chloride solution (5 mL). The aqueous layer was extracted with ethyl acetate (3×3 mL), and the combined organic layers were dried over sodium sulfate, were filtered, and were concentrated under reduced pressure. The orange residue was purified by flash column chromatography on silica gel (eluent: 3% acetone in dichloromethane) to afford the bisproline epidithiodiketopiperazine (−)-E2-34 (34.8 mg, 64.8%) as a white solid. $^1$H NMR (500 MHz, CDCl$_3$, 20° C.): δ 3.88-3.84 (m, 2H, C$_2$H$_a$), 3.58-3.52 (m, 2H, C$_2$H$_b$), 3.02-2.94 (m, 2H, C$_4$H$_a$), 2.35-2.27 (m, 2H, C$_4$H$_b$), 2.35-2.27 (m, 2H, C$_3$H$_a$), 2.25-2.18 (m, 2H, C$_3$H$_b$). $^{13}$C NMR (125.8 MHz, CDCl$_3$, 20° C.): δ 164.1 (C$_6$), δ 78.1 (C$_5$), δ 46.6 (C$_2$), δ 32.9 (C$_4$), δ 24.4 (C$_3$). FTIR (thin film) cm$^{-1}$: 2921 (m), 1660 (s), 1405 (m), 1338 (w), 1097 (m). HRMS (ESI) (m/z): calc'd for C$_{10}$H$_{12}$N$_2$NaO$_2$S$_2$ [M+Na]$^+$: 279.0323. found: 279.0314. [α]$_D^{24}$: −144 (c=0.11, CH$_2$Cl$_2$). TLC (10% acetone in dichloromethane), Rf: 0.44 (UV, CAM).

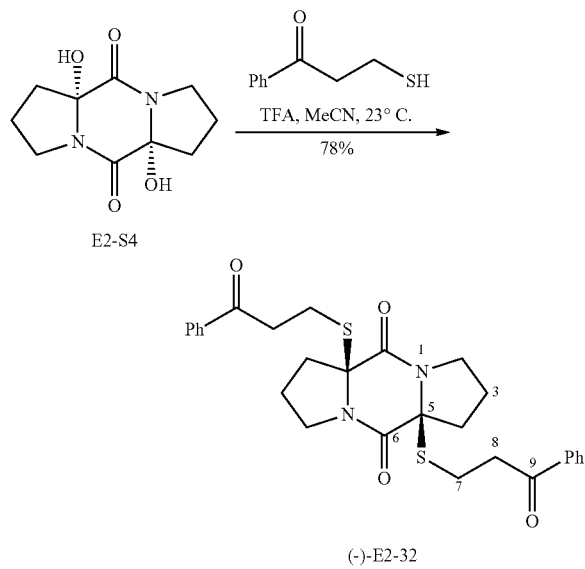

Bisproline bis(ethylphenylketone thioether) (−)-E2-32

Trifluoroacetic acid (1 mL) was added via syringe to a solution of bisproline diol E2-S4 (36.6 mg, 0.162 mmol, 1 equiv) and 3-mercaptopropiophenone (E2-30, 76.2 μL, 801 μmol, 5.00 equiv) in acetonitrile (1 mL) at 23° C. The clear solution immediately turned yellow. After 30 min, the reaction was diluted with ethyl acetate (5 mL) and washed with saturated aqueous sodium bicarbonate solution (5 mL). The aqueous layer was extracted with ethyl acetate (3×5 mL), and the combined organic layers were dried over sodium sulfate, were filtered, and were concentrated under reduced pressure. The crude reaction mixture was purified by flash column chromatography on silica gel (eluent: 3% acetone in dichloromethane) to afford the bisproline bis(ethylmethylketone thioether) (−)-E2-32 (65.9 mg, 77.5%) as a white solid. $^1$H NMR (500 MHz, CDCl$_3$, 20° C.): δ 7.89 (d, J=7.5, 4H, COPh-o-H), 7.53 (t, J=7.5, 2H, COPh-p-H), 7.42 (app-t, J=8.0, 4H, COPh-m-H), 3.73-3.67 (m, 2H, C$_2$H$_a$), 3.61-3.56 (m, 2H, C$_2$H$_b$), 3.33-3.27 (m, 2H, C$_7$H$_a$), 3.23-3.26 (m, 2H, C$_7$H$_b$), 3.12-3.09 (m, 4H, C$_8$H), 2.55-2.51 (m, 2H, C$_4$H$_a$), 2.38-2.28 (m, 2H, C$_3$H$_a$), 2.17-2.10 (m, 2H, C$_4$H$_b$), 2.05-1.99 (m, 2H, C$_3$H$_b$). $^{13}$C NMR (125.8 MHz, CDCl$_3$, 20° C.): δ 198.7 (C$_9$), 166.2 (C$_6$), 137.2 (COPh-ipso-C), 133.6 (COPh-p-C), 128.9 (COPh-m-C), 128.2 (COPh-o-C), 72.5 (C$_5$), 45.7 (C$_2$), 38.9 (C$_7$), 35.7 (C$_4$), 25.7 (C$_8$), 20.1 (C$_3$). FTIR (thin film) cm$^{-1}$: 2956 (w), 1683 (m), 1660 (m), 1597 (w), 1448 (w), 1406 (m), 1350 (w). HRMS (ESI) (m/z): calc'd for C$_{28}$H$_{34}$N$_3$O$_4$S$_2$ [M+NH$_4$]$^+$: 540.1925. found: 540.1925. [α]$_D^{24}$: −54 (c=0.17, CH$_2$Cl$_2$). TLC (10% acetone in dichloromethane), Rf: 0.43 (UV, CAM).

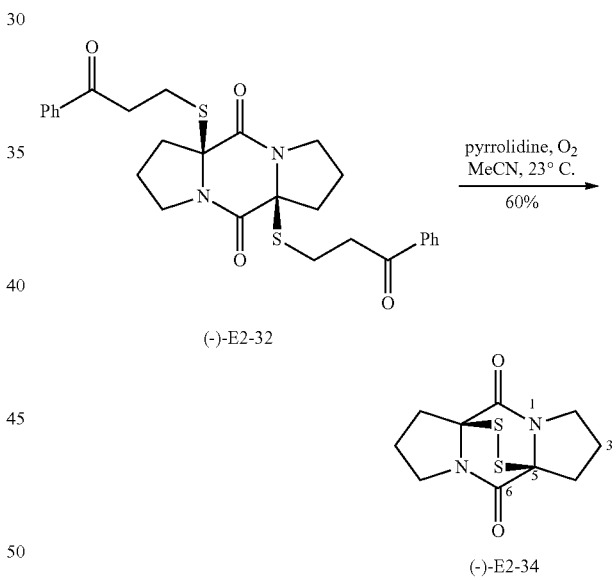

Bisproline Epidithiodiketopiperazine (−)-E2-34

Pyrrolidine (24.3 μL, 284 μmol, 3.79 equiv) was added to a solution of bis(ethylmethylketone thioether) (−)-E2-32 (39.2 mg, 75.0 μmol, 1 equiv) in acetonitrile (250 μL) at 23° C., and the reaction was placed under a balloon of oxygen. The clear solution immediately turned orange. After 1 h, the reaction was diluted with dichloromethane (5 mL) and washed with saturated aqueous ammonium chloride solution (5 mL). The aqueous layer was extracted with dichloromethane (3×3 mL), and the combined organic layers were dried over sodium sulfate, were filtered, and were concentrated under reduced pressure. The orange residue was purified by flash column chromatography on silica gel (eluent: 3% acetone in dichloromethane) to afford the bisproline epidithiodiketopiperazine (−)-E2-34 (11.5 mg, 59.8%) as a white solid.

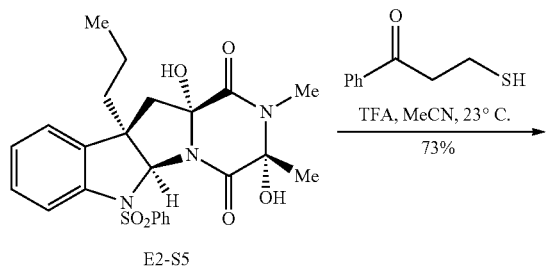

E2-S5

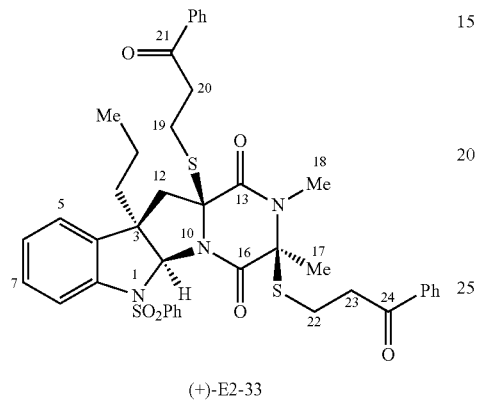

(+)-E2-33

3-Propyl Tetracyclic Bis(ethylphenylketone thioether) (+)-E2-33

Trifluoroacetic acid (1 mL) was added via syringe to a solution of 3-propyl tetracyclic diol E2-S5 (46.3 mg, 95.4 μmol, 1 equiv) and 3-mercaptopropiophenone (E2-30, 72.3 μL, 477 μmol, 5.00 equiv) in acetonitrile (1 mL) at 23° C. The clear solution immediately turned yellow. After 30 min, the reaction was diluted with ethyl acetate (5 mL) and washed with saturated aqueous sodium bicarbonate solution (2 mL). The aqueous layer was extracted with ethyl acetate (3×5 mL), and the combined organic layers were dried over sodium sulfate, were filtered, and were concentrated under reduced pressure. The crude reaction mixture was purified by flash column chromatography on silica gel (eluent: 3% acetone in dichloromethane) to afford the 3-propyl tetracyclic bis(ethylphenylketone thioether) (+)-E2-33 (54.5 mg, 73.1%) as a white solid. $^1$H NMR (500 MHz, CDCl$_3$, 20° C.): δ 8.00-7.97 (m, 4H, COPh-m-H), 7.81 (d, J=8.5, 2H, SO$_2$Ph-o-H), 7.67 (d, 1H, C$_8$H), (7.53-7.48, (m, 1H, SO$_2$Ph-p-H), 7.53-7.48 (m, 2H, SO$_2$Ph-m-H), 7.47-7.53 (m, 4H, COPh-o-H), 7.47-7.35 (m, 2H, COPh-p-H), 7.53-7.48 (m, 1H, SO$_2$Ph-p-H), 7.17 (app-dt, J=1.3, 7.0, 1H, C$_7$H), 7.06 (d, J=7.5, 1H, C$_5$H), 7.00 (app-t, J=7.5, 1H, C$_6$H), 6.26 (s, 1H, C$_2$H), 3.45-3.38 (m, 1H, C$_{19}$H$_a$), 3.30-3.23 (m, 1H, C$_{19}$H$_b$), 3.12-3.02 (m, 2H, C$_{20}$H), 3.07 (s, 3H, C$_{18}$H), 2.99-2.92 (m, 2H, C$_{22}$H), 2.81 (d, J=14, 1H, C$_{12}$H$_a$), 2.61-2.68 (m, 2H, C$_{23}$H), 2.30 (d, J=14, 1H, Cl$_2$H$_b$), 1.92 (s, 3H, C$_{17}$H), 1.44-1.37 (m, 2H, CH$_2$CH$_2$CH$_3$), 1.31-1.22 (m, 2H, CH$_2$CH$_2$CH$_3$), 0.56-0.52 (m, 3H, CH$_2$CH$_2$CH$_3$). $^{13}$C NMR (125 MHz, CDCl$_3$, 20° C.): δ 199.1 (C$_{21}$), 198.4 (C$_{24}$), 166.7 (C$_{16}$), 164.8 (C$_{13}$), 143.6 (C$_9$), 138.9 (SO$_2$Ph-ipso-C), 137.2 (COPh-ipso-C), 137.1 (COPh-ipso-C), 136.3 (C$_4$), 133.9 (SO$_2$Ph-p-C), 133.9 (COPh-p-C), 133.8 (COPh-p-C), 129.9 (C$_7$), 129.4 (SO$_2$Ph-o-C), 129.3 (SO$_2$Ph-m-C), 129.2 (COPh-o-C), 129.0 (COPh-o-C), 128.8 (COPh-m-C), 128.1 (COPh-m-C), 125.3 (C$_6$), 123.5 (C$_5$), 116.6 (C$_8$), 83.0 (C$_2$), 71.7 (C$_{11}$), 68.8 (C$_{15}$), 54.1 (C$_3$), 50.0 (C$_{12}$), 42.5 (CH$_2$CH$_2$CH$_3$), 39.6 (C$_{20}$), 38.8 (C$_{23}$), 30.1 (C$_{18}$), 27.1 (C$_{17}$), 25.9 (C$_{19}$), 25.3 (C$_{22}$), 38.4 (CH$_2$CH$_2$CH$_3$), 14.7 (CH$_2$CH$_2$CH$_3$). FTIR (thin film) cm$^{-1}$: 2924 (m), 2851 (m), 1682 (s), 1597 (w), 1448 (m), 1372 (m). HRMS (ESI) (m/z): calc'd for C$_{42}$H$_{47}$N$_4$O$_6$S$_3$ [M+NH$_4$]$^+$: 799.2652. found: 799.2658. [α]$_D$24: +124 (c=0.075). TLC (5% acetone in dichloromethane), Rf: 0.25 (UV, CAM).

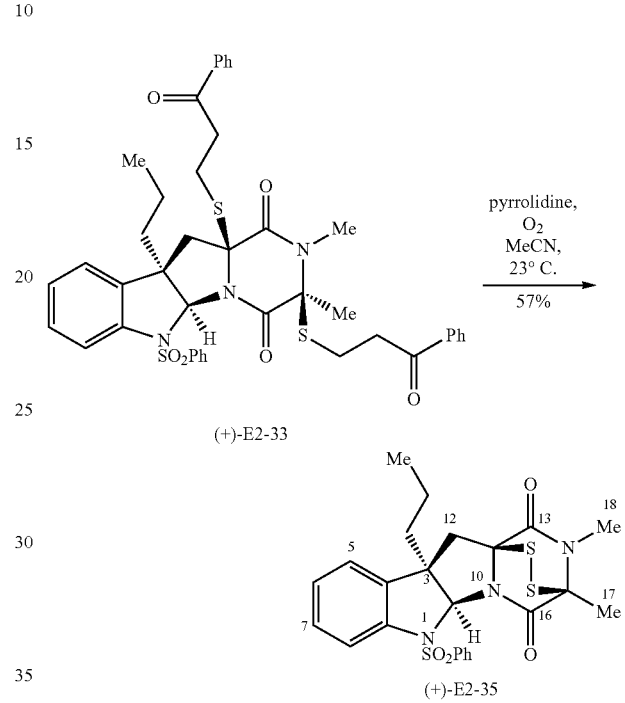

3-Propyl Pentacyclic Epidithiodiketopiperazine E2-35

Pyrrolidine (6.8 μL, 82.8 μmol, 4.16 equiv) was added to a solution of 3-propyl tetracyclic bis(ethylphenylketone thioether) (+)-E2-33 (15.6 mg, 19.9 μmol, 1 equiv) in acetonitrile (150 μL) at 23° C., and the reaction was placed under a balloon of oxygen. The clear solution immediately turned orange. After 1 h, the reaction was diluted with dichloromethane (3 mL) and washed with saturated aqueous ammonium chloride solution (3 mL). The aqueous layer was extracted with ethyl acetate (3×2 mL), and the combined organic layers were dried over sodium sulfate, were filtered, and were concentrated under reduced pressure. The orange residue was purified by flash column chromatography on silica gel (eluent: 3% acetone in dichloromethane) to afford the 3-propyl pentacyclic epidithiodiketopiperazine E2-35 (5.9 mg, 57.4%) as a white solid. $^1$H NMR (500 MHz, CDCl$_3$, 20° C.): δ 7.80 (d, J=7.0, 2H, SO$_2$Ph-o-H), 7.53 (app-t, J=7.0, 1H, SO$_2$Ph-p-H), 7.46-7.37 (m, 1H, C$_8$H), 7.46-7.37 (m, 2H, SO$_2$Ph-m-H), 7.29, (app-dt, J=1.1, 7.7, 1H, C$_7$H), 7.16 (app-t, J=7.7, 1H, C$_6$H), 7.12 (d, J=7.6, 1H, C$_5$H), 6.09 (s, 1H, C$_2$H), 3.19 (d, J=15.2, 1H, C$_{12}$H$_a$), 2.98 (s, 2H, C$_{18}$H), 2.57 (d, J=15.2, 1H, C$_{12}$H$_b$), 1.87 (s, 3H, C$_{17}$H), 1.43-1.30 (m, 1H, CH$_2$CH$_2$CH$_3$), 1.22-1.04 (m, 2H, CH$_2$CH$_2$CH$_3$), 0.77-0.68 (m, 1H, CH$_2$CH$_2$CH$_3$). $^{13}$C NMR (125.8 MHz, CDCl$_3$, 20° C.): δ 165.9 (C$_{13}$), 161.6 (C$_{16}$), 142.1 (C$_9$), 139.8 (SO$_2$Ph-ipso-C), 137.6 (C$_4$), 133.4 (SO$_2$Ph-p-C), 129.3 (C$_7$), 129.2 (SO$_2$Ph-m-C), 127.4 (SO$_2$Ph-o-C), 125.9 (C$_6$), 123.6 (C$_5$), 118.4 (C$_8$), 83.7 (C$_2$), 73.7 (C$_{11}$), 73.5 (C$_{15}$), 55.9 (C$_3$), 41.8 (C$_{12}$), 40.0 (CH$_2$CH$_2$CH$_3$), 27.7 (C$_{18}$), 18.3 (CH$_2$CH$_2$CH$_3$), 18.0 (C$_{17}$), 14.3 (CH$_2$CH$_2$CH$_3$). FTIR (thin film) cm$^{-1}$: 2960 (w), 1713 (s), 1688 (s), 1478 (w), 1460 (w), 1341 (m), 1172 (m), 1092 (w). HRMS (ESI) (m/z): calc'd for C$_{24}$H$_{25}$NaN$_3$O$_4$S$_3$ [M+Na]$^+$: 538.0899. found: 538.0923. TLC (1% acetone in dichloromethane), Rf: 0.21 (UV, CAM).

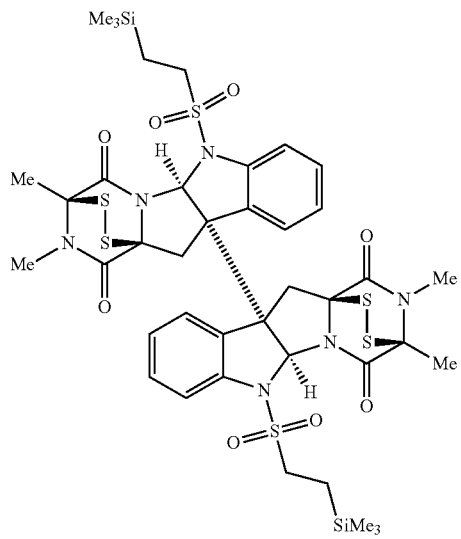 [SMILES: CN1C(=O)[C@@]23CC4([C@]56C[C@@]78SS[C@@](C)(C(=O)N7[C@H]5N(S(=O)(=O)CC[Si](C)(C)C)c5ccccc56)N(C)C8=O)c5ccccc5N(S(=O)(=O)CC[Si](C)(C)C)[C@@H]4N2C(=O)[C@]1(C)SS3]

The compound was prepared using similar procedures as described above. $^1$H NMR (500 MHz, CDCl$_3$, 20° C.): δ 7.52 (d, J=7.7, 1H), 7.17 (app-t, J=7.7, 1H), 7.05 (app-t, J=7.7, 2H), 6.73 (s, 1H), 3.82 (app-dt, J=3.5, 14.4, 1H), 3.48 (d, J=15.1, 1H), 3.30 (app-dt, J=3.5, 14.1, 1H), 2.99 (s, 3H), 2.82 (d, J=14.8, 1H), 1.93 (s, 3H), 1.25-1.13 (m, 1H), 0.98 (app-dt, J=3.9, 14.4, 1H), 0.05 (s, 9H).

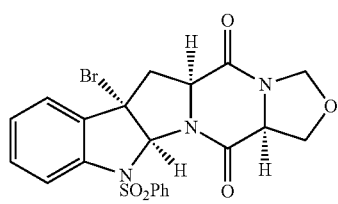

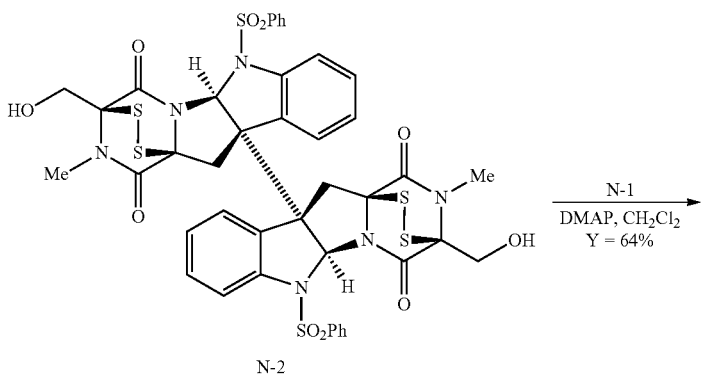

The compound was prepared using similar procedures as described above. $^1$H NMR (500 MHz, CDCl$_3$, 20° C.): δ 7.93 (d, J=7.5, 2H), 7.54 (d, J=8.3, 1H), 7.51 (t, J=7.3, 1H), 7.40 (app-t, J=7.9, 2H), 7.34 (d, J=7.5, 1H), 7.29 (app-t, J=7.7, 1H), 7.11 (app-t, J=7.5, 1H), 6.23 (s, 1H), 4.97 (d, J=5.0, 1H), 4.74 (d, J=5.1, 1H), 4.61 (dd, J=6.2, 9.0, 1H), 4.39-4.23 (m, 3H), 3.39 (dd, J=6.1, 14.3, 1H), 2.99 (dd, J=9.0, 14.3, 1H).

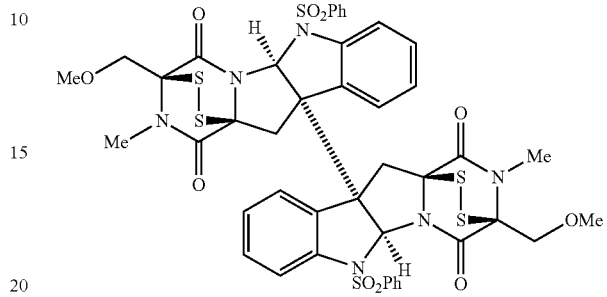

The compound was prepared using similar procedures as described above. $^1$H NMR (500 MHz, CDCl$_3$, 20° C.): δ 7.85 (d, J=7.2, 2H), 7.68 (d, J=6.4, 1H), 7.57-7.51 (m, 1H), 7.49-7.43 (m, 2H), 7.22-7.12 (m, 2H), 7.01 (d, J=7.7, 1H), 6.83 (s, 1H), 3.79 (d, J=11.6, 1H), 3.70 (d, J=11.7, 1H), 3.53 (d, J=15.0, 1H), 3.36 (s, 3H), 3.07 (s, 3H), 2.96 (d, J=15.2, 1H).

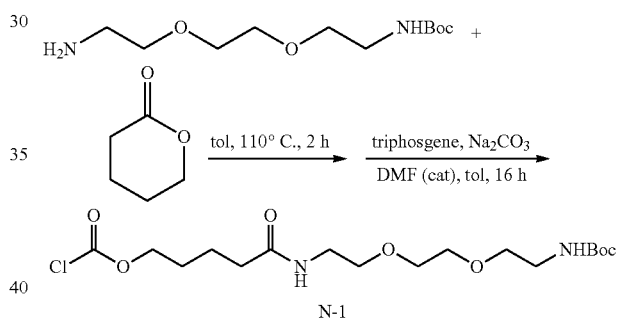

Compound N-1

Compound N-1 was prepared as illustrated above. After purification on silica column, compound N-1 was used for next step. $^1$H NMR (400 MHz, CDCl$_3$, 20° C.): δ 6.04 (br-s, 1H), 4.95 (br-s, 1H), 4.30 (m, 2H), 3.59-3.52 (m, 8H), 3.44 (m, 2H), 3.30 (br-s, 2H), 2.21 (m, 2H), 1.73 (m, 4H), 1.42 (s, 9H).

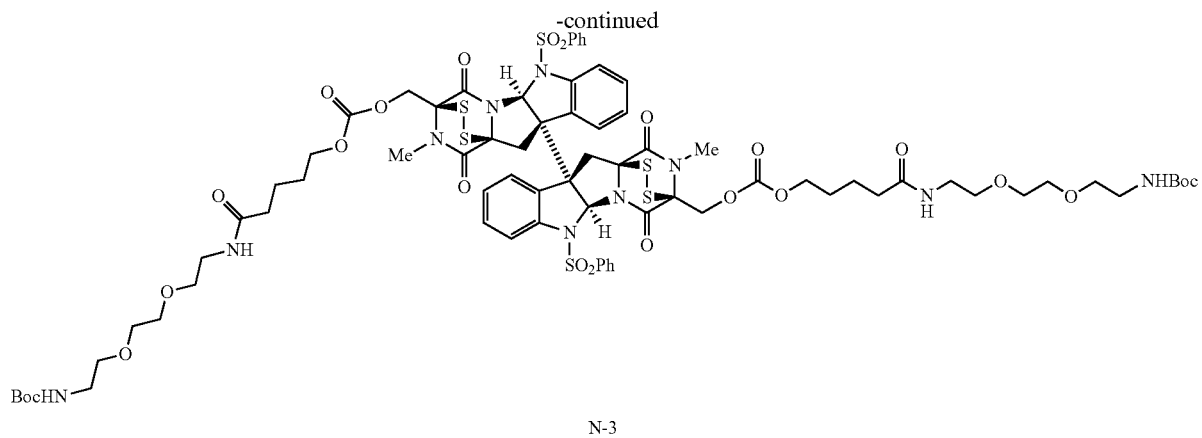

N-3

Compound N-2 was prepared using similar procedures as those described for other EPT compounds. Reaction of N-2 with N-1 provided compound N-3 in 64% yield. It is understood that based on the chemistry described herein, a person having ordinary skill in the art can readily prepare an antibody-drug conjugate from a provided compound, for example, N-2. It is also understood that compound N-3 is readily de-protected to provide a free amino group, which can be used for conjugation to provide antibody-drug conjugates. For example, a hydroxyl group or an amino group can be linked to L and/or M through reaction with an activated carbonyl group to form an ester, carbonate, amide or carbamate.

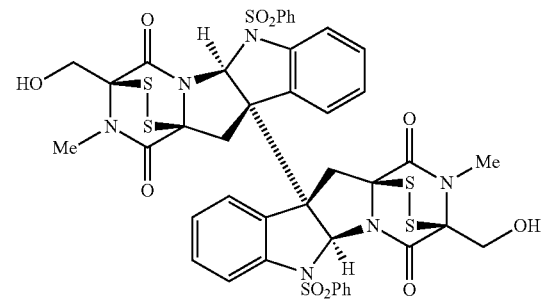

$^1$H NMR (400 MHz, CDCl$_3$, 20° C.): δ 7.85 (m, 4H), 7.67 (d, J=6.9, 2H), 7.56 (m, 2H), 7.48 (app-t, J=7.9, 4H), 7.23-7.16 (m, 4H), 7.06 (d, J=8.6, 2H), 6.83 (s, 2H), 4.12 (dd, J=4.2, 12.4, 2H), 3.84 (dd, J=4.9, 12.4, 2H), 3.57 (d, J=15.2, 2H), 3.03 (s, 6H), 2.96 (d, J=15.1, 2H), 2.73 (t, J=7.8, 2H).

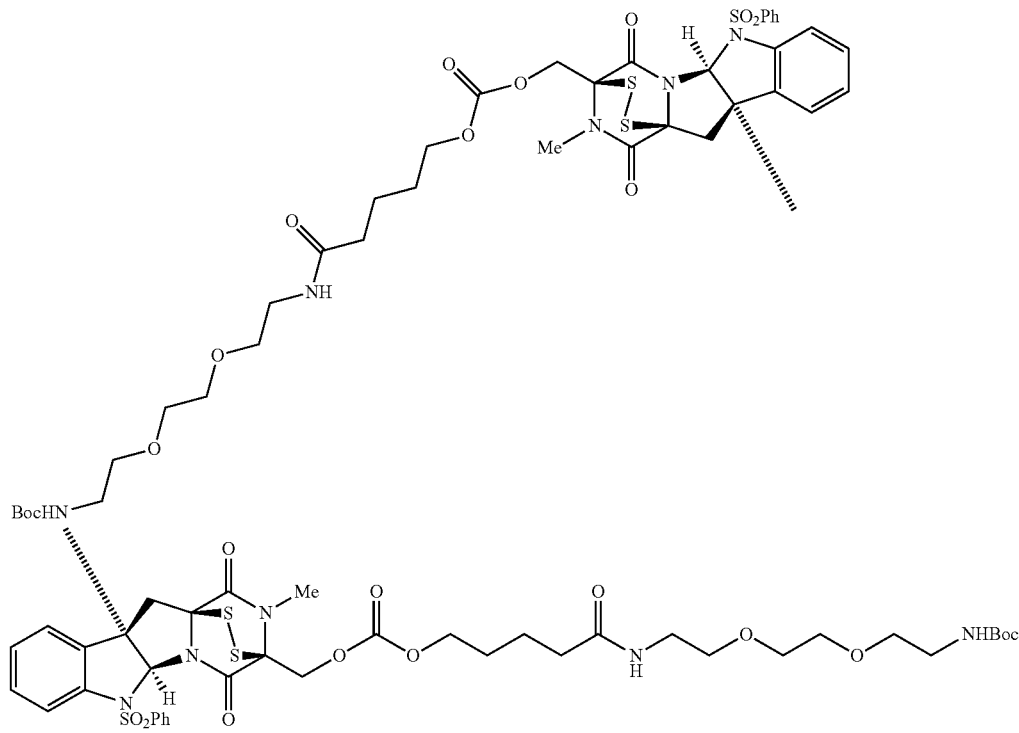

$^1$H NMR (400 MHz, CDCl$_3$, 20° C.): δ 7.86 (m, 4H), 7.64 (d, J=7.2, 2H), 7.57 (m, 2H), 7.48 (app-t, J=8.0, 4H), 7.24-7.14 (m, 4H), 7.03 (d, J=8.1, 2H), 6.84 (s, 2H), 6.04 (br-s, 2H), 4.98 (br-s, 2H), 4.50 (s, 4H), 4.16 (m, 4H), 3.59-3.52 (m, 18H), 3.44 (m, 4H), 3.30 (m, 4H), 3.06 (s, 6H), 2.92 (d, J=15.2, 2H), 2.21 (m, 4H), 1.71 (m, 8H), 1.42 (s, 18H).

In some embodiments, a compound such as N-2 or deprotected N3 has more than one functional group that can be used for conjugation. In some embodiments, a drug unit D is linked to two or more L and/or M units.

In some embodiments, a drug unit D is linked to one L and/or M unit. It is understood that single linkage to L can be achieved through, for example, selective protection/de-protection. An example is illustrated below:

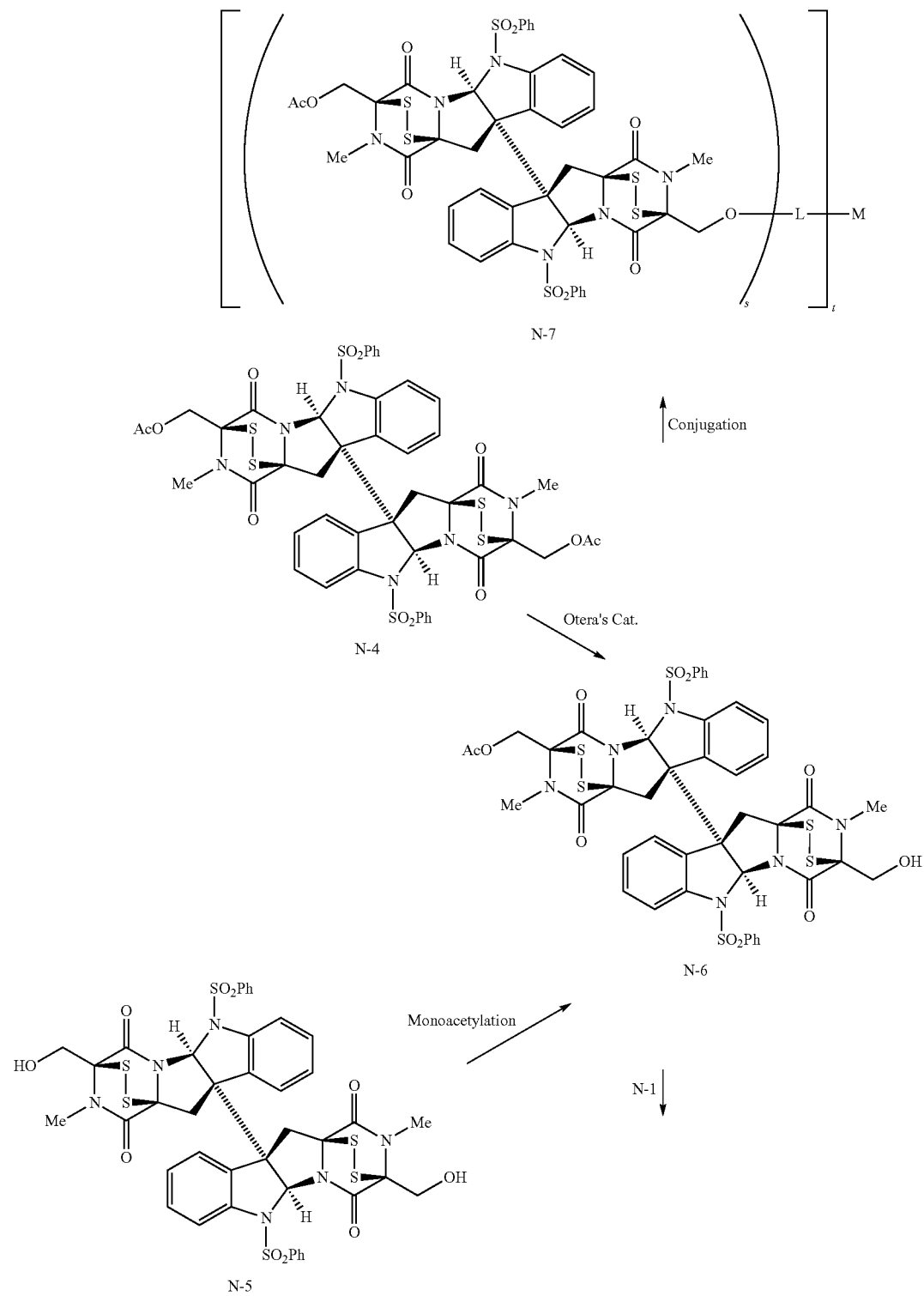

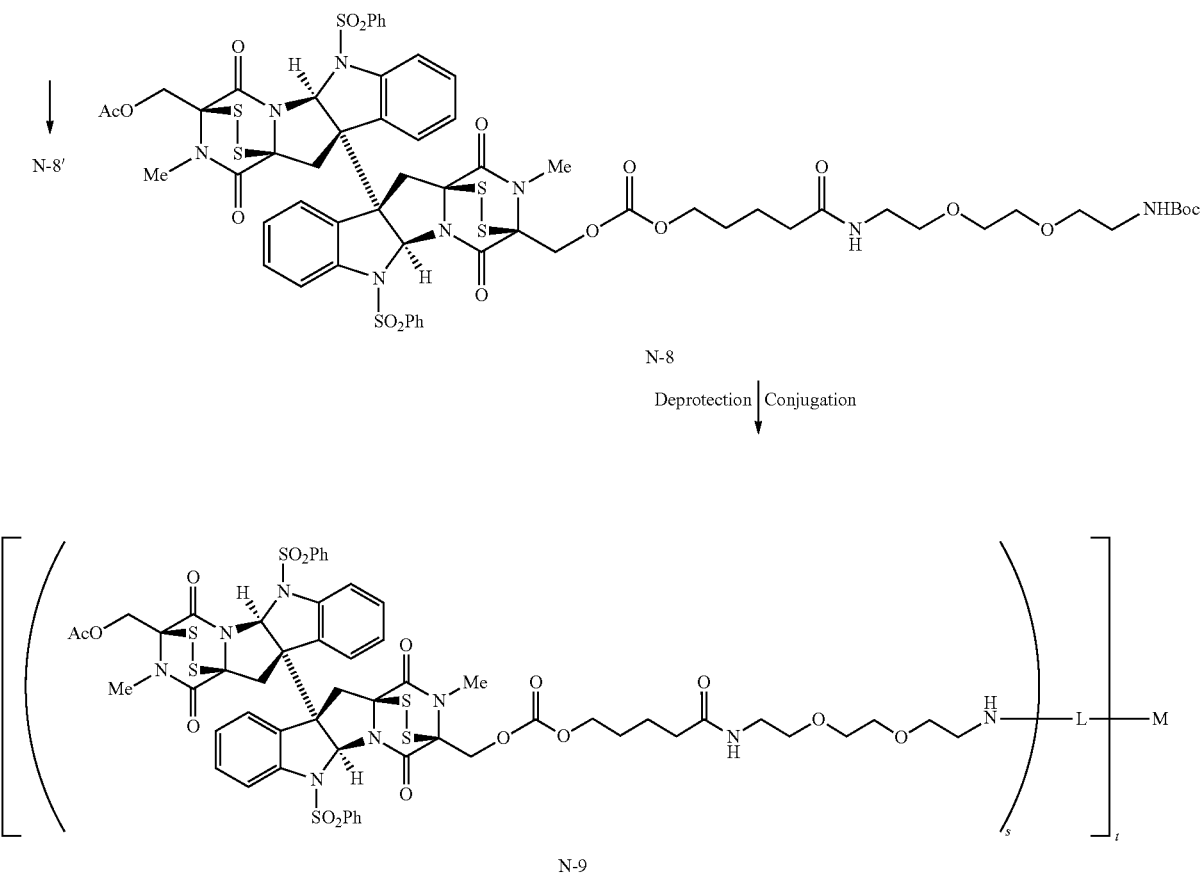
N-8
Deprotection | Conjugation
N-9
In the example above, N-4 is selectively deprotected, or N-5 is monoacetylated, to provide N-6. N-6 can be conjugated, for example, by reaction with activated carbonyl group, to form N-7. Alternatively, N-6 can be further modified to provide N-8, which can be subsequently conjugated to provide N-9. In an exemplary N-9, s is 1, L is
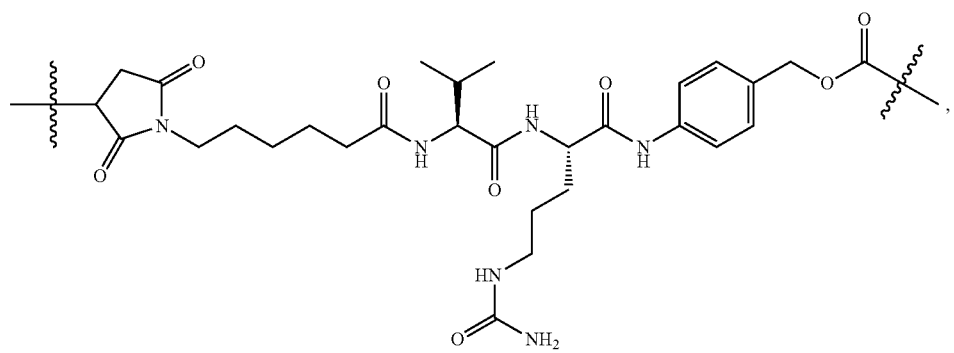 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

wherein the drug unit is connected to L through the —C(O)—O— group, and M is a chimeric IgG1 antibody cAC10 specific for human CD30. In some embodiments, the acetyl group of N-8 was removed, either through alternative synthesis pathway or through deprotection, providing N-8'. For example, in some embodiments, N-8' was prepared through direct mono-acylation of N-5. After removal of Boc, N-8' can be conjugated based on known chemistry to provide N-9', wherein the drug unit is N-8'. In an exemplary N-9', s is 1, L is

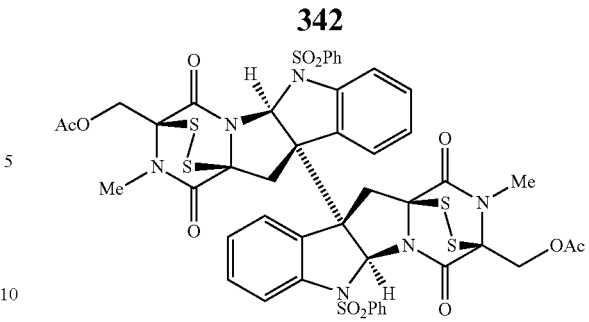

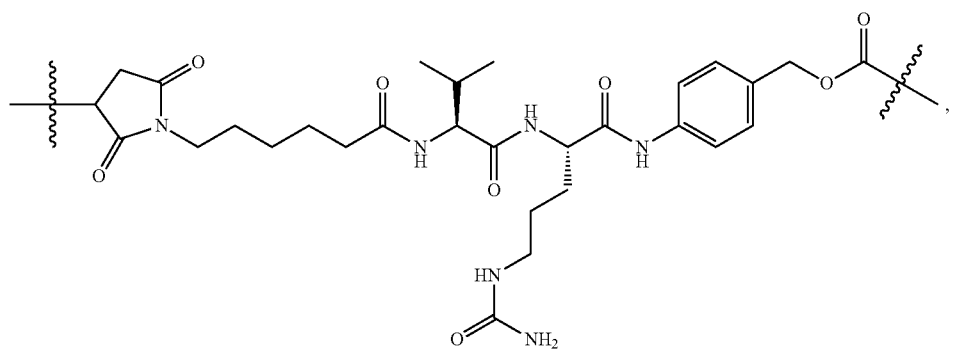 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

wherein the drug unit is connected to L through the —C(O)—O— group, and M is a chimeric IgG1 antibody cAC10 specific for human CD30.

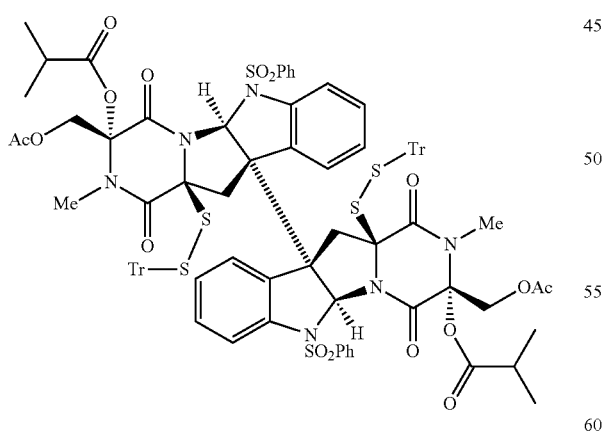

$^1$H NMR (400 MHz, CD$_2$Cl$_2$, 20° C.): δ 8.08 (d, J=7.4, 4H), 7.55 (t, J=7.4, 2H), 7.45 (t, J=8.0, 4H), 7.34-7.23 (m, 20H), 7.08 (t, J=7.4, 2H), 7.02 (d, J=7.4, 12H), 6.71 (m, 4H), 6.58 (t, J=7.4, 2H), 4.61 (d, J=11.4, 2H), 3.98 (d, J=11.4, 2H), 3.21 (d, J=14.4, 2H), 2.80 (d, J=14.5, 2H), 2.61-2.54 (m, 8H), 1.69 (s, 6H), 1.18 (d, J=7.0, 6H), 1.11 (d, J=7.0, 6H).

$^1$H NMR (400 MHz, CDCl$_3$, 20° C.): δ 7.87 (m, 4H), 7.64 (d, J=8.3, 2H), 7.56 (m, 2H), 7.47 (app-t, J=8.0, 4H), 7.24-7.16 (m, 4H), 7.03 (d, J=8.1, 2H), 6.85 (s, 2H), 4.42 (m, 4H), 3.58 (d, J=15.2, 2H), 3.04 (s, 6H), 2.92 (d, J=15.2, 2H), 2.12 (s, 6H).

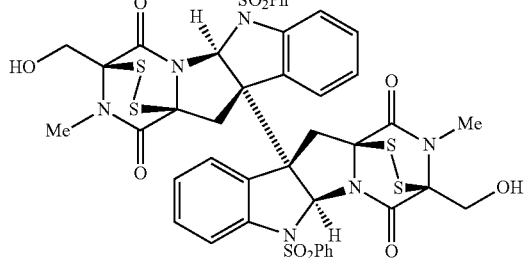

$^1$H NMR (400 MHz, CDCl$_3$, 20° C.): δ 7.85 (m, 4H), 7.67 (d, J=6.9, 2H), 7.56 (m, 2H), 7.48 (app-t, J=7.9, 4H), 7.23-7.16 (m, 4H), 7.06 (d, J=8.6, 2H), 6.83 (s, 2H), 4.12 (dd, J=4.2, 12.4, 2H), 3.84 (dd, J=4.9, 12.4, 2H), 3.57 (d, J=15.2, 2H), 3.03 (s, 6H), 2.96 (d, J=15.1, 2H), 2.73 (t, J=7.8, 2H).

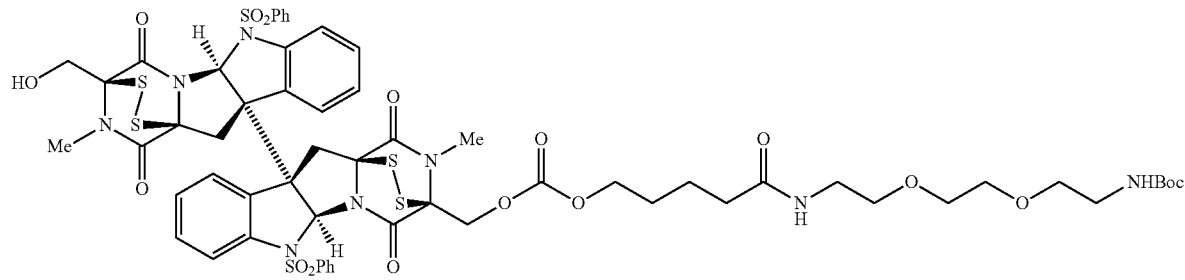

Compound N-8': $^1$H NMR (400 MHz, CDCl$_3$, 20° C.): δ 7.86 (m, 4H), 7.65 (app-t, J=7.0, 2H), 7.56 (m, 2H), 7.47 (m, 4H), 7.23-7.15 (m, 4H), 7.04 (m, 2H), 6.85 (s, 1H), 6.81 (s, 1H), 6.02 (br-s, 1H), 4.97 (br-s, 1H), 4.50 (m, 2H), 4.16-4.09 (m, 3H), 3.84 (dd, J=5.0, 12.5, 1H), 3.58-3.52 (m, 10H), 3.44 (m, 2H), 3.29 (m, 2H), 3.06 (s, 3H), 3.03 (s, 3H), 2.96-2.91 (m, 2H), 2.77 (t, J=7.8, 1H), 2.20 (m, 2H), 1.70 (m, 4H), 1.42 (s, 9H).

Among other things, the present invention provides ready synthetic access to ETP or thiodiketopiperazine compounds or derivatives and analogs thereof; the present invention also provides detailed knowledge of sites that can be modified without loss of activity, and that ETP or thiodiketopiperazine compounds or derivatives and analogs thereof do not have hemolytic activity. The present invention, among other things, recognizes that ETP or thiodiketopiperazine compounds or derivatives and analogs thereof can be used as drug units for ligand-drug conjugates. In some embodiments, the present invention provides ligand-drug conjugates ("conjugate compound"). In some embodiments, a ligand-drug conjugate is an antibody-drug conjugate. In some embodiments, a provided compound has the structure of formula II. In some embodiments, a provided compound has the structure of formula II-a or II-b. In some embodiments, a compound of formula II-a or II-b is an ADC. Chemistry for conjugating ETP or thiodiketopiperazine compounds or derivatives and analogs thereof to ligands such as antibodies are widely known and practiced in the art, including those described in the present specification. Combining with methods provided herein for synthesizing and modifying ETP or thiodiketopiperazine compounds (or derivatives or analogs thereof), a wide array of ADCs can be prepared, including those having the structure of formula II-a or II-b. Methods for assaying a provided compound, including a provided ADC, are also widely known and practiced in the art. In some embodiments, a provided compound is tested in cancer cell lines in culture and/or in in vivo tumor models, for example, those described above, and also in D. Greiner, T. Bonaldi, R. Eskeland, E. Roemer and A. Imhof, *Nat. Chem. Biol.*, 2005, 1, 143; C. R. Isham, J. D. Tibodeau, W. Jin, R. Xu, M. M. Timm and K. C. Bible, *Blood*, 2007, 109, 2579; Y. Chen, H. Guo, Z. Du, X.-Z. Liu, Y. Che and X. Ye, *Cell Prolif,* 2009, 42, 838; Y.-M. Lee, J.-H. Lim, H. Yoon, Y.-S. Chun and J.-W. Park, *Hepatology,* 2011, 53, 171; F. Liu, Q. Liu, D. Yang, W. B. Bollag, K. Robertson, P. Wu and K. Liu, *Cancer Res.*, 2011, 71, 6807; N. Zhang, Y. Chen, R. Jiang, E. Li, X. Chen, Z. Xi, Y. Guo, X. Liu, Y. Zhou, Y. Che and X. Jiang, *Autophagy,* 2011, 7, 598; H. Chaib, A. Nebbioso, T. Prebet, R. Castellano, S. Garbit, A. Restouin, N. Vey, L. Altucci and Y. Collette, *Leukemia,* 2012, 26, 662; C. R. Isham, J. D. Tibodeau, A. R. Bossou, J. R. Merchan and K. C. Bible, *Br. J. Cancer,* 2012, 106, 314; M. Takahashi, Y. Takemoto, T. Shimazu, H. Kawasaki, M. Tachibana, Y. Shinkai, M. Takagi, K. Shin-ya, Y. Igarashi, A. Ito and M. Yoshida, *J. Antiobiot.,* 2012, 65, 263; Y. Teng, K. Iuchi, E. Iwasa, S. Fujishiro, Y. Hamashima, K. Dodo and M. Sodeoka, *Bioorg. Med. Chem. Lett.,* 2010, 20, 5085; M. Sodeoka, K. Dodo, Y. Teng, K. Iuchi, Y. Hamashima, E. Iwasa and S. Fujishiro, *Pure Appl. Chem.,* 2012, 84, 1369; J. D. Tibodeau, L. M. Benson, C. R. Isham, W. G. Owen and K. C. Bible, *Antiox. Redox Signal.,* 2009, 11, 1097; and Beverly A. Teicher (Editor), Tumor Models in Cancer Research (Cancer Drug Discovery and Development), 2$^{nd}$ Ed, Humana Press, 2011 (Publication date, Dec. 2, 2010). In some embodiments, a provided compound demonstrates activities and efficacy for treating cancer.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A compound having the structure of formula I-a:

$$I\text{-}a$$

or a pharmaceutically acceptable salt thereof, wherein:
  ⸺ is a single bond or a double bond, as valency permits;
  $R^1$ is R, —C(O)R, —C(O)N(R)$_2$—S(O)R, —S(O)$_2$R, —S(O)$_2$OR, —C(R)$_2$OR, or —S(O)$_2$N(R)$_2$;
  each R is independently hydrogen or a group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered mono cyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:
  two R groups are optionally taken together with their intervening atoms to form a 3-14 membered, saturated, partially unsaturated, or aryl ring having, in addition to the intervening atoms, 0-4 heteroatoms independently selected from nitrogen, oxygen, or sulfur;
  $R^2$ is hydrogen, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$;
  each q is independently 0, 1, 2, 3, or 4;
  $R^3$ is —SO$_2$R or —COCF$_3$;
  $R^4$ is absent when ⸺ is a double bond or is R or halogen;
  $R^5$ is absent when ⸺ is a double bond or is hydrogen or a $C_{1-6}$ aliphatic group;
  each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or
  $R^6$ and $R^{6'}$ are taken together to form =O, =C(R)$_2$ or =NR;
  n is 0, 1, 2, 3, or 4;
  each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$—B(R)$_2$, —B(OR)$_2$, or —Si(R)$_3$;
  $R^8$ is —(S)$_m$—$R^x$ wherein m is 1, 2, or 3, and $R^x$ is R, —SR, —C(O)R, —C(O)OR, —C(O)N(R)$_2$, —C(S)R, —S(O)R, —S(O)$_2$R, or —S(O)$_2$N(R)$_2$; and
  $R^9$ is —(S)$_p$—$R^y$ wherein p is 1, 2, or 3, such that the sum of m and p is 2, 3, or 4, and $R^y$ is R, —SR, —C(O)R, —C(O)OR, —C(O)N(R)$_2$, —C(S)R, —S(O)R, —S(O)$_2$R, or —S(O)$_2$N(R)$_2$; or
  $R^8$ and $R^9$ are taken together to form —S—, —(S)$_m$—[C(R)$_2$]$_q$—(S)$_p$—, —(S)$_m$—(S)$_p$—, —(S)$_m$—C(O)—(S)$_p$—, —(S)$_m$—C(S)—(S)$_p$—, —(S)$_m$—S(O)—(S)$_p$—, or —(S)$_m$—S(O)$_2$—(S)$_p$—.

2. The compound of claim 1, wherein $R^3$ is —$SO_2Ph$.

3. The compound of claim 2, wherein $R^8$ and $R^9$ are taken together to form —S—, —$(S)_m$—$(CH_2)$—$(S)_p$—, —$(S)_m$—$(S)_p$—, —$(S)_m$—C(O)—$(S)_p$—, or —$(S)_m$—C(S)—$(S)_p$—.

4. The compound of claim 3, wherein each of $R^5$, $R^6$ and $R^{6'}$ is independently hydrogen.

5. The compound of claim 4, wherein $R^8$ and $R^9$ are taken together to form —S—S—.

6. A compound having the structure of formula I-b:

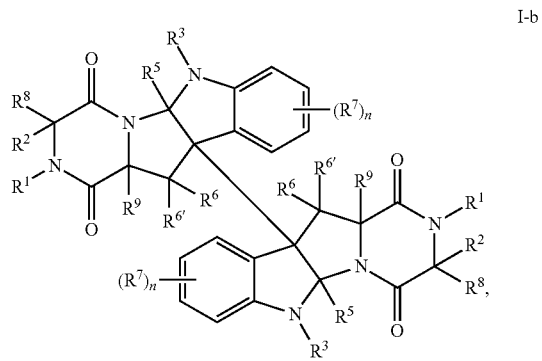

I-b or a pharmaceutically acceptable salt thereof, wherein:
  each $R^1$ is independently R, —C(O)R, —C(O)N(R)$_2$, —S(O)R, —S(O)$_2$R, —S(O)$_2$OR, —C(R)$_2$OR, or —S(O)$_2$N(R)$_2$;
  each R is independently hydrogen or a group selected from $C_{1-20}$ aliphatic, $C_{1-20}$ heteroalkyl, phenyl, a 3-7 membered saturated or partially unsaturated carbocyclic ring, an 8-14 membered bicyclic or polycyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; or:
  two R groups are optionally taken together with their intervening atoms to form a 3-14 membered, saturated, partially unsaturated, or aryl ring having, in addition to the intervening atoms, 0-4 heteroatoms independently selected from nitrogen, oxygen, or sulfur;
  each $R_2$ is independently R, —[C(R)$_2$]$_q$—OR, —[C(R)$_2$]$_q$—N(R)$_2$, —[C(R)$_2$]$_q$—SR, —[C(R)$_2$]$_q$—OSi(R)$_3$, —[C(R)$_2$]$_q$—OC(O)R, —[C(R)$_2$]$_q$—OC(O)OR, —[C(R)$_2$]$_q$—OC(O)N(R)$_2$, —[C(R)$_2$]$_q$—OC(O)N(R)—SO$_2$R or —[C(R)$_2$]$_q$—OP(OR)$_2$;
  each q is independently 0, 1, 2, 3, or 4;
  each $R^3$ is —SO$_2$R;
  each $R^5$ is independently hydrogen or a $C_{1-6}$ aliphatic group;
  each of $R^6$ and $R^{6'}$ is independently R, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, or —OSi(R)$_3$; or $R^6$ and $R^{6'}$ are taken together to form =O, =C(R)$_2$ or =NR;
  each n is independently 0, 1, 2, 3, or 4;
  each $R^7$ is independently R, halogen, —CN, —NO$_2$, —OR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;
  each $R^8$ is independently —$(S)_p$—$R^x$ wherein m is 1, 2, or 3, and $R^x$ is R, —SR, —C(O)R, —C(O)OR, —C(O)N(R)$_2$, —C(S)R, —S(O)R, —S(O)$_2$R, or —S(O)$_2$N(R)$_2$; and
  each $R^9$ is independently —$(S)_p$—$R^y$ wherein p is 1, 2, or 3, such that the sum of m and p is 2, 3, or 4, and $R^y$ is R, —SR, —C(O)R, —C(O)OR, —C(O)N(R)$_2$, —C(S)R, —S(O)R, —S(O)$_2$R, or —S(O)$_2$N(R)$_2$; or
  $R^8$ and $R^9$ are taken together to form —S—, —$(S)_m$—[C(R)$_2$]$_q$—$(S)_p$—, —$(S)_m$—$(S)_p$—, —$(S)_m$—C(O)—$(S)_p$—, —$(S)_m$—C(S)—$(S)_p$—, —$(S)_m$—S(O)—$(S)_p$—, or —$(S)_m$—S(O)$_2$—$(S)_p$—.

7. The compound of claim 6, wherein $R^3$ is —$SO_2Ph$.

8. The compound of claim 7, wherein $R^8$ and $R^9$ are taken together to form —S—, —$(S)_m$—$(CH_2)$—$(S)_p$—, —$(S)_m$—$(S)_p$—, —$(S)_m$—C(O)—$(S)_p$—, or —$(S)_m$—C(S)—$(S)_p$—.

9. The compound of claim 8, wherein each of $R^5$, $R^6$ and $R^{6'}$ is independently hydrogen.

10. The compound of claim 9, wherein $R^8$ and $R^9$ are taken together to form —S—S—.

11. A compound selected from the group consisting of:

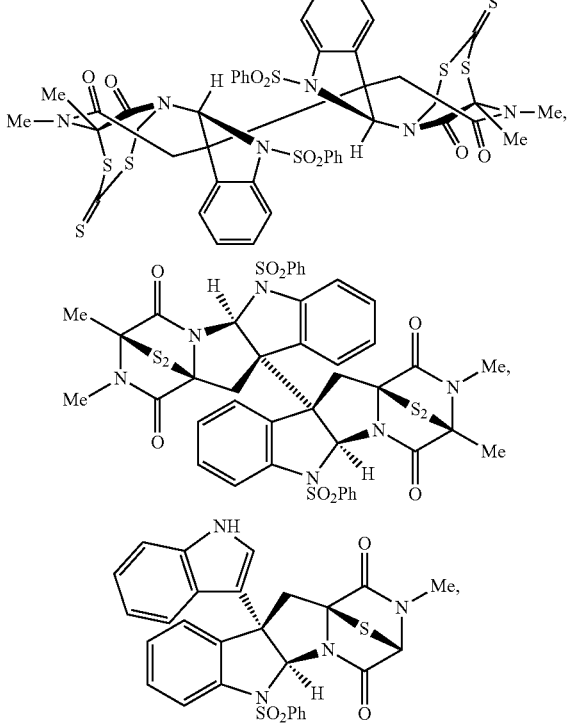

349
-continued
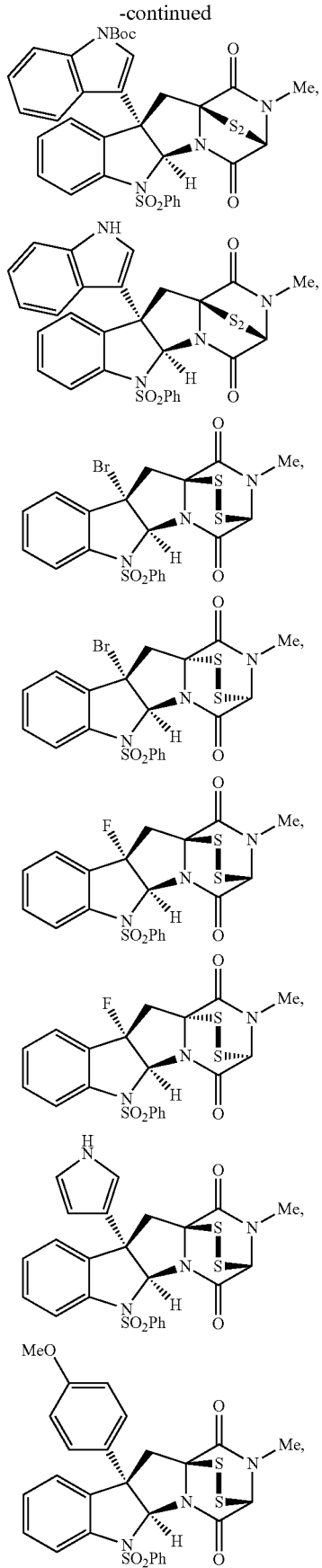
350
-continued
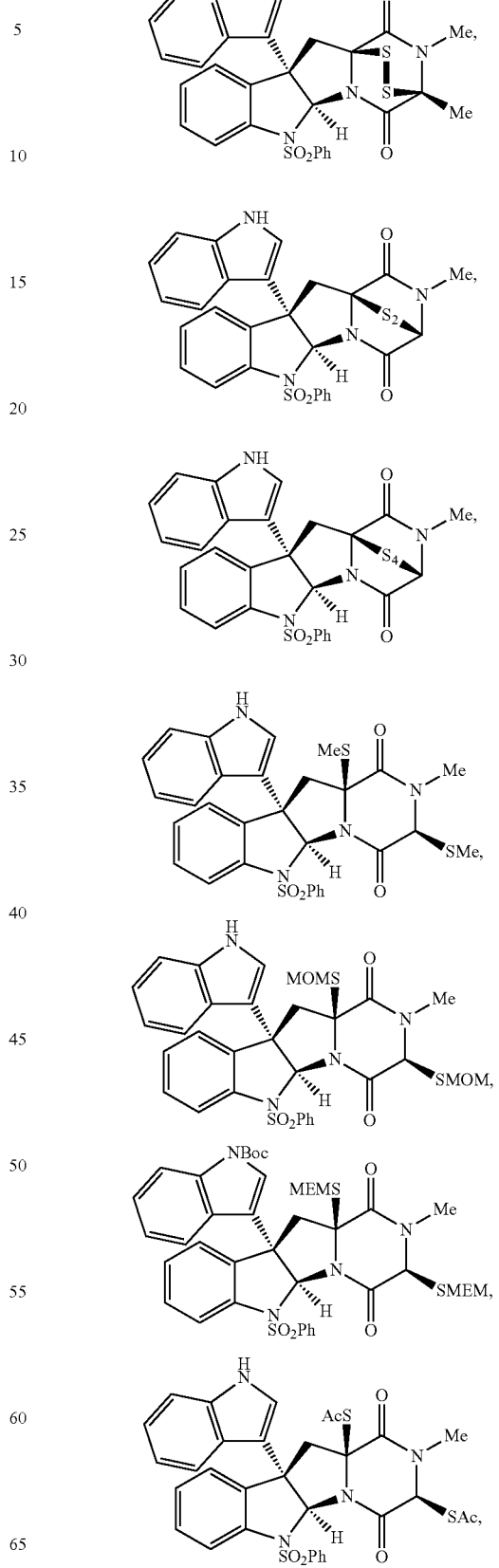

351
-continued
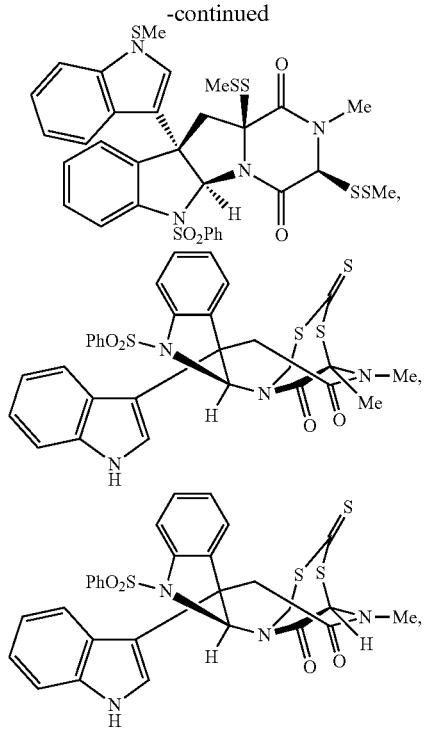
352
-continued
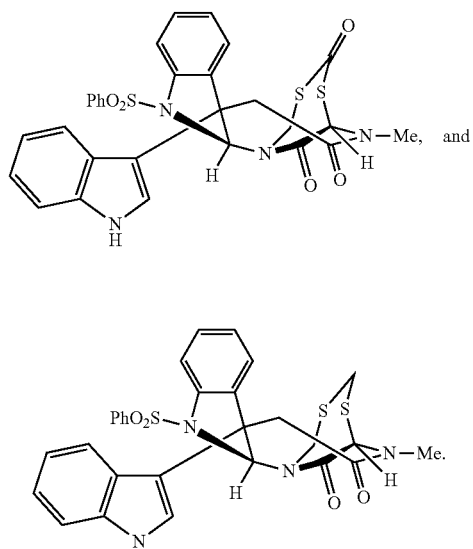
* * * * *

UNITED STATES PATENT AND TRADEMARK OFFICE
CERTIFICATE OF CORRECTION

PATENT NO. : 9,353,150 B2  
APPLICATION NO. : 14/096158  
DATED : May 31, 2016  
INVENTOR(S) : Mohammad Movassaghi et al.

Page 1 of 1

It is certified that error appears in the above-identified patent and that said Letters Patent is hereby corrected as shown below:

In the claims:

At column 350, claim number 11, line numbers 12-20, please replace the structure

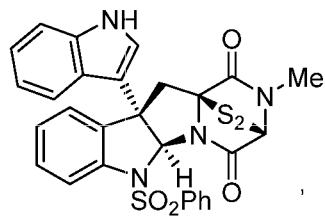

with the following structure:

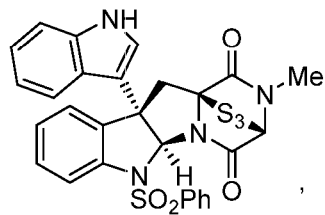

Signed and Sealed this
Second Day of August, 2016

Michelle K. Lee
*Director of the United States Patent and Trademark Office*

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Cleavable peptide sequence

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: Cleavable peptide sequence

<400> SEQUENCE: 2

Ala Leu Ala Leu
1